US012441691B2

(12) United States Patent
Morgan et al.

(10) Patent No.: US 12,441,691 B2
(45) Date of Patent: Oct. 14, 2025

(54) BICYCLIC 1,4-DIAZEPANONES AND THERAPEUTIC USES THEREOF

(71) Applicant: Cytokinetics, Inc., South San Francisco, CA (US)

(72) Inventors: Bradley P. Morgan, South San Francisco, CA (US); Chris Evans, South San Francisco, CA (US); Pu-Ping Lu, South San Francisco, CA (US); Makoto Yamasaki, South San Francisco, CA (US); Wenyue Wang, South San Francisco, CA (US); Scott Collibee, South San Francisco, CA (US); Takuya Makino, Tokyo (JP); Kazuyuki Tsuchiya, Tokyo (JP); Toshio Kurosaki, Tokyo (JP); Susumu Yamaki, Tokyo (JP); Eriko Honjo, Tokyo (JP); Yuka Koizumi, Tokyo (JP); Naoto Katoh, Tokyo (JP); Ryuichi Sekioka, Tokyo (JP); Ikumi Kuriwaki, Tokyo (JP)

(73) Assignee: CYTOKINETICS, INC., South San Francisco, CA (US)

( * ) Notice: Subject to any disclaimer, the term of this patent is extended or adjusted under 35 U.S.C. 154(b) by 0 days.

(21) Appl. No.: 18/623,812

(22) Filed: Apr. 1, 2024

(65) Prior Publication Data

US 2024/0368091 A1 Nov. 7, 2024

Related U.S. Application Data

(62) Division of application No. 17/453,761, filed on Nov. 5, 2021, now Pat. No. 11,981,644.
(Continued)

(51) Int. Cl.

| | |
|---|---|
| ***C07D 243/14*** | (2006.01) |
| ***C07D 401/12*** | (2006.01) |
| ***C07D 403/14*** | (2006.01) |
| ***C07D 405/14*** | (2006.01) |
| ***C07D 413/08*** | (2006.01) |
| ***C07D 413/12*** | (2006.01) |
| ***C07D 417/12*** | (2006.01) |
| ***C07D 471/04*** | (2006.01) |
| ***C07D 471/10*** | (2006.01) |
| ***C07D 487/04*** | (2006.01) |
| ***C07D 498/04*** | (2006.01) |
| ***C07D 519/00*** | (2006.01) |

(52) U.S. Cl.

CPC ......... *C07D 243/14* (2013.01); *C07D 401/12* (2013.01); *C07D 403/14* (2013.01); *C07D 405/14* (2013.01); *C07D 413/08* (2013.01); *C07D 413/12* (2013.01); *C07D 417/12* (2013.01); *C07D 471/04* (2013.01); *C07D 471/10* (2013.01); *C07D 487/04* (2013.01); *C07D 498/04* (2013.01); *C07D 519/00* (2013.01); *C07B 2200/13* (2013.01)

(58) Field of Classification Search

CPC .. C07D 243/14; C07D 401/12; C07D 403/14; C07D 405/14; C07D 413/08; C07D 413/12; C07D 417/12; C07D 471/04; C07D 487/04; C07D 498/04; C07D 519/00

USPC .................................................... 514/255.05

See application file for complete search history.

(56) References Cited

U.S. PATENT DOCUMENTS 5,846,514 A 12/1998 Foster
6,334,997 B1 1/2002 Foster
(Continued)

FOREIGN PATENT DOCUMENTS

CN 101522681 A 9/2009
EP 2653466 A1 10/2013
(Continued)

OTHER PUBLICATIONS

Berge, S.M. et al. (Jan. 1977). "Pharmaceuticals Salts," J. Pharmaceutical Sciences 66(1):1-19.
(Continued)

*Primary Examiner* — Kahsay Habte
(74) *Attorney, Agent, or Firm* — MORRISON & FOERSTER LLP

(57) ABSTRACT

Provided herein are compounds of formula (I):

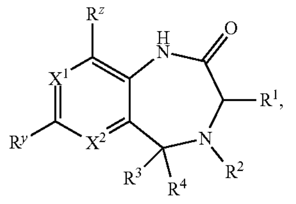

(I)

or a stereoisomer or tautomer thereof, or a pharmaceutically acceptable salt of any of the foregoing, wherein $X^1$, $X^2$, $R^y$, $R^z$, $R^1$, $R^2$, $R^3$, and $R^4$ are as defined herein.

Also provided herein is a pharmaceutically acceptable composition comprising a compound of formula (I), or a stereoisomer or tautomer thereof, or a pharmaceutically acceptable salt of any of the foregoing.

Also provided herein are methods of using a compound of formula (I), or a stereoisomer or tautomer thereof, or a pharmaceutically acceptable salt of any of the foregoing, to treat various diseases, disorders, and conditions responsive to the modulation of the contractility of the skeletal sarcomere.

27 Claims, 4 Drawing Sheets

Related U.S. Application Data

(60) Provisional application No. 63/110,776, filed on Nov. 6, 2020.

(56) References Cited

U.S. PATENT DOCUMENTS

| | | | |
|---|---|---|---|
| 6,410,254 | B1 | 6/2002 | Finer |
| 6,743,599 | B1 | 6/2004 | Finer |
| 7,202,051 | B1 | 4/2007 | Finer |
| 7,378,254 | B2 | 5/2008 | Finer |
| 7,598,248 | B2 | 10/2009 | Muci |
| 7,956,056 | B2 | 6/2011 | Muci |
| 8,293,761 | B2 | 10/2012 | Muci |
| 8,716,291 | B2 | 5/2014 | Hinken et al. |
| 8,962,632 | B2 | 2/2015 | Yang |
| 8,969,346 | B2 | 3/2015 | Ashcraft |
| 9,018,223 | B2 | 4/2015 | Warrington |
| 9,133,123 | B2 | 9/2015 | Ashcraft |
| 9,604,965 | B2 | 3/2017 | Ashcraft |
| 9,730,886 | B2 | 8/2017 | Yang |
| 9,914,741 | B2 | 3/2018 | Sato et al. |
| 9,987,279 | B2 | 6/2018 | Mori |
| 9,994,528 | B2 | 6/2018 | Ashcraft |
| 10,076,519 | B2 | 9/2018 | Ashcraft |
| 10,259,821 | B2 | 4/2019 | Sato et al. |
| 10,272,030 | B2 | 4/2019 | Yang |
| 10,689,393 | B2 | 6/2020 | Sato et al. |
| 10,765,624 | B2 | 9/2020 | Yang |
| 10,766,899 | B2 | 9/2020 | Morgan |
| 11,369,565 | B2 | 6/2022 | Yang et al. |
| 11,479,561 | B2 | 10/2022 | Sato et al. |
| 11,981,644 | B2 | 5/2024 | Morgan et al. |
| 2013/0261101 | A1 | 10/2013 | Combs et al. |
| 2015/0065525 | A1 | 3/2015 | Jasper |
| 2015/0250784 | A1 | 9/2015 | Malik |
| 2017/0042890 | A1 | 2/2017 | Shefner |
| 2017/0233402 | A1 | 8/2017 | Sato et al. |
| 2017/0266192 | A1 | 9/2017 | Jasper |
| 2019/0167676 | A1 | 6/2019 | Malik |
| 2020/0270266 | A1 | 8/2020 | Sato et al. |
| 2021/0045997 | A1 | 2/2021 | Yang et al. |
| 2023/0026651 | A1 | 1/2023 | Yang |
| 2023/0083960 | A1 | 3/2023 | Morgan et al. |
| 2023/0125280 | A1 | 4/2023 | Sato |

FOREIGN PATENT DOCUMENTS

| | | | |
|---|---|---|---|
| WO | 199528399 | A1 | 10/1995 |
| WO | 2004054584 | A1 | 7/2004 |
| WO | 2006089286 | A2 | 8/2006 |
| WO | 2007022638 | A1 | 3/2007 |
| WO | 2008016669 | A2 | 2/2008 |
| WO | 2008144483 | A2 | 11/2008 |
| WO | 2008016669 | A3 | 12/2008 |
| WO | 2009093269 | A1 | 7/2009 |
| WO | 2008144483 | A3 | 8/2012 |
| WO | 2014040077 | A1 | 3/2014 |
| WO | 2021013712 | A1 | 1/2021 |
| WO | 2022099011 | A1 | 5/2022 |
| WO | 2023215367 | A1 | 11/2023 |

OTHER PUBLICATIONS

Breslin, H.J. et al. (Jun. 5, 2017). Synthesis and Anti-HIV Activity of 1,3,4,5-Tetrahydro-2H-1,4-Benzodiazepin-2-One (TBO) Derivatives. Truncated 4,5,6,7-Tetrahydro-5-Methylimidazo[4,5,1-jk][1,4]Benzodiazepin-2(1H)-Ones (TIBO) Analogues, Bioorganic 7(11):2427-2436.

Cas Registration No. 1008253-78-8, entered Mar. 16, 2008, 1 page.

Cas Registration No. 1009235-41-9, entered Mar. 20, 2008, 1 page.

Dean, D. (2000). "Preface: Current Pharmaceutical Design," Curr. Pharm. Des. 6(10): Preface, 3 pages.

Evans, A.E. (Mar. 1981, e-pub. Jan. 9, 2007). "Synthesis of Radiolabelled Compounds," J Radio Anal. Chem. 64(1-2):9-32.

Herrmann, C. et al. (1993). "A Structural and Kinetic Study on Myofibrils Prevented from Shortening by Chemical Cross-Linking," Biochem. 32(28): 7255-7263.

International Preliminary Report on Patentability mailed on May 8, 2023, for PCT Application No. PCT/US2021/058260, filed on Nov. 5, 2021, 8 pages.

International Search Report and Written Opinion mailed on Aug. 10, 2023, for PCT Application No. PCT/US2023/020814, filed on May 3, 2023, 17 pages.

International Search Report and Written Opinion mailed on Feb. 7, 2022, for PCT Application No. PCT/US2021/058260, filed on Nov. 5, 2021, 19 pages.

Kabalka, G.W. et al. (1989). "The Synthesis of Radiolabeled Compounds via Organometallic Intermediates," Tetrahedron 45(21):6601-6621.

Mossetti, R. et al. (Nov. 9, 2011). "Exploiting the Acylating Nature of the Imida-Ugi Intermediate: A Straightforward Syntheiss of Tetrahydro-1, 4-Benzodiazepin-2-Ones," The Journal of Organic Chemistry 76 (24):10258-10262.

Tempest, P. et al. (2001). "Two-Step Solution-Phase Synthesis of Novel Benzimidazoles Utilizing a UDC (Ugi/de-Boc/Cyclize) Strategy," Tetrahedron Letters 42:4959-4962.

International Preliminary Report on Patentability mailed on Oct. 29, 2024, for PCT Application No. PCT/US2023/020814, filed on May 3, 2023, 9 pages.

U.S. Appl. No. 18/852,138, filed Dec. 31, 2024, for Chris Evans et al. (A copy of U.S. Patent Application is not submitted herewith pursuant to the waiver of 37 C.F.R. § 1.98(a)(2)(iii) issued by the Office on Sep. 21, 2004.).

Dietrich, J. et al. (2010, e-pub. Jun. 1, 2010). "Concise Two-Step Solution Phase Syntheses Of Four Novel Dihydroquinazoline Scaffolds," Tetrahedron Letters 51(30):3951-3955.

Hulme, C. et al. (2009, e-pub. Feb. 20, 2009). "An Efficient Solution Phase Synthesis Of Triazadibenzulenones: 'Designer Isonitrile Free' Methodology Enabled By Microwaves," Tetrahedron Letters 50 (17):1939-1942.

BICYCLIC 1,4-DIAZEPANONES AND THERAPEUTIC USES THEREOF

CROSS-REFERENCE TO RELATED APPLICATION

This application is a divisional of U.S. application Ser. No. 17/453,761, filed Nov. 5, 2021, which claims priority to and the benefit of U.S. Provisional Application No. 63/110,776, filed on Nov. 6, 2020, the disclosure of which is incorporated herein by reference in its entirety.

FIELD

Provided herein are bicyclic 1,4-diazepanone compounds, pharmaceutical compositions comprising such compounds, and methods of using such compounds and pharmaceutical compositions for treating various diseases, disorders, and conditions responsive to the modulation of the contractility of the skeletal sarcomere.

BACKGROUND

The cytoskeleton of skeletal and cardiac muscle cells is unique compared to that of all other cells. It consists of a nearly crystalline array of closely packed cytoskeletal proteins called the sarcomere. The sarcomere is elegantly organized as an interdigitating array of thin and thick filaments. The thick filaments are composed of myosin, the motor protein responsible for transducing the chemical energy of ATP hydrolysis into force and directed movement. The thin filaments are composed of actin monomers arranged in a helical array. There are four regulatory proteins bound to the actin filaments, which allows the contraction to be modulated by calcium ions. An influx of intracellular calcium initiates muscle contraction; thick and thin filaments slide past each other driven by repetitive interactions of the myosin motor domains with the thin actin filaments.

Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II forms homo-dimers resulting in two globular head domains linked together by a long alpha-helical coiled-coiled tail to form the core of the sarcomere's thick filament. The globular heads have a catalytic domain where the actin binding and ATPase functions of myosin take place. Once bound to an actin filament, the release of phosphate (cf. ADP-Pi to ADP) signals a change in structural conformation of the catalytic domain that in turn alters the orientation of the light-chain binding lever arm domain that extends from the globular head; this movement is termed the power stroke. This change in orientation of the myosin head in relation to actin causes the thick filament, of which it is a part, to move with respect to the thin actin filament, to which it is bound. Un-binding of the globular head from the actin filament ($Ca^{2+}$ regulated), coupled with return of the catalytic domain and light chain to their starting conformation/orientation completes the catalytic cycle, is responsible for intracellular movement and muscle contraction.

Tropomyosin and troponin mediate the calcium effect on the interaction on actin and myosin. The troponin complex is comprised of three polypeptide chains: troponin C, which binds calcium ions; troponin I, which binds to actin; and troponin T, which binds to tropomyosin. The skeletal troponin-tropomyosin complex regulates the myosin-binding sites extending over several actin units at once.

Troponin, a complex of the three polypeptides described above, is an accessory protein that is closely associated with actin filaments in vertebrate muscle. The troponin complex acts in conjunction with the muscle form of tropomyosin to mediate the $Ca^{2+}$ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponin I, troponin T, and tropomyosin inhibits the interaction of actin and myosin. Skeletal troponin C is capable of binding up to four calcium molecules. Studies suggest that when the level of calcium in the muscle is raised, troponin C exposes a binding site for troponin I, recruiting it away from actin. This causes the tropomyosin molecule to shift its position as well, thereby exposing the myosin binding sites on actin and stimulating myosin ATPase activity.

Human skeletal muscle is composed of different types of contractile fibers, classified by their myosin type and termed either slow or fast fibers. Table 1 summarizes the different proteins that make up these types of muscle.

TABLE 1

| | Muscle Fiber Type | |
|---|---|---|
| | Fast Skeletal | Slow Skeletal |
| Myosin Heavy Chain (MHC) | IIa, (IIb*), IIx/d | Cardiac β |
| Troponin I (TnI) | TnI fast Skeletal | TnI slow Skeletal |
| Troponin T (TnT) | TnT fast Skeletal | TnT slow Skeletal |
| Troponin C (TnC) | TnC fast Skeletal | TnC slow/cardiac |
| Tropomyosin (TM) | TM-β/TM-α/TPM3** | TM-β/TM-αs |

*MHC IIb is not expressed in human muscle but is present in rodents and other mammals.
**TPM3 represents tropomyosin 3

In healthy humans, most skeletal muscles are composed of both fast and slow fibers, although the proportions of each vary with muscle type. Slow skeletal fibers, often called type I fibers, have more structural similarity with cardiac muscle and tend to be used more for fine and postural control. They usually have a greater oxidative capacity and are more resistant to fatigue with continued use. Fast skeletal muscle fibers, often called type II fibers, are classified into fast oxidative (IIa) and fast glycolytic (type IIx/d) fibers. While these muscle fibers have different myosin types, they share many components, including the troponin and tropomyosin regulatory proteins. Fast skeletal muscle fibers tend to exert greater force but fatigue faster than slow skeletal muscle fibers and are functionally useful for acute, large scale movements such as rising from a chair or correcting falls.

Muscle contraction and force generation is controlled through nervous stimulation by innervating motor neurons. Each motor neuron may innervate many (approximately 100 to 380) muscle fibers as a contractile whole, termed a motor unit. When a muscle is required to contract, motor neurons send stimuli as nerve impulses (action potentials) from the brain stem or spinal cord to each fiber within the motor unit. The contact region between nerve and muscle fibers is a specialized synapse called the neuromuscular junction (NMJ). Here, membrane depolarizing action potentials in the nerve are translated into an impulse in the muscle fiber through release of the neurotransmitter acetylcholine (ACh).

ACh triggers a second action potential in the muscle that spreads rapidly along the fiber and into invaginations in the membrane, termed t-tubules. T-tubules are physically connected to $Ca^{2+}$ stores within the sarcoplasmic reticulum (SR) of muscle via the dihydropyridine receptor (DHPR). Stimulation of the DHPR activates a second $Ca^{2+}$ channel in the SR, the ryanodine receptor, to trigger the release of $Ca^{2+}$ from stores in the SR to the muscle cytoplasm where it can interact with the troponin complex to initiate muscle contraction. If muscle stimulation stops, calcium is rapidly taken back up into the SR through the ATP dependent $Ca^{2+}$ pump, sarco/endoplasmic reticulum $Ca^{2+}$-ATPase (SERCA).

Currently, there is limited treatment or no cure for most neuromuscular diseases. Thus, there is a need for the development of new compounds that modulate skeletal muscle contractility. There remains a need for agents that exploit new mechanisms of action and which may have better outcomes in terms of relief of symptoms, safety, and patient mortality, both short-term and long-term and an improved therapeutic index.

SUMMARY

The invention provides novel compounds that are expected to be used as an active ingredient in a pharmaceutical composition, and in particular, in a pharmaceutical composition for preventing or treating a disease or condition responsive to modulation of the contractility of the skeletal sarcomere. Modulation of the skeletal sarcomere may be modulation, for example, by modulation of the troponin complex of the fast skeletal muscle sarcomere through one or more of fast skeletal myosin, actin, tropomyosin, troponin C, troponin I, and troponin T, and fragments and isoforms thereof.

In one aspect, provided herein is a compound of formula (I):

(I)

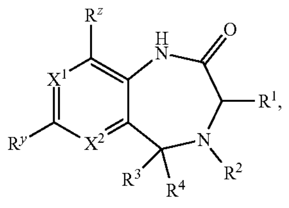

or a stereoisomer or tautomer thereof, or a pharmaceutically acceptable salt of any of the foregoing, wherein:

$X^1$ and $X^2$ are each independently N or C—$R^x$;

each $R^x$, $R^y$, and $R^z$ is independently H, halo, $C_{3-10}$cycloalkyl, $C_{3-10}$cycloalkenyl, or $C_{6-20}$aryl;

$R^1$ is $C_{3-12}$alkyl, $C_{2-12}$alkenyl, $C_{2-12}$alkynyl, $C_{3-10}$cycloalkyl, $C_{3-10}$cycloalkenyl, or

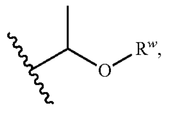

wherein $R^w$ is optionally substituted $C_{1-12}$alkyl;

$R^2$ is:

a) C(O)—$R^h$, wherein $R^h$ is (i) optionally substituted amino, optionally substituted $C_{1-3}$alkoxy, optionally substituted —C(O)$NH_2$, optionally substituted $C_{3-10}$cycloalkyl, optionally substituted $C_{3-10}$cycloalkenyl, optionally substituted $C_{6-20}$aryl, optionally substituted 3-15 membered heterocyclyl, or optionally substituted 5-20 membered heteroaryl, or (ii) $C_{1-12}$alkyl, wherein the $C_{1-12}$alkyl is unsubstituted or is substituted with one or more $R''$, wherein $R''$ is OH, oxo, halo, cyano, —C(O)$NH_2$, optionally substituted amino, optionally substituted sulfonyl, optionally substituted $C_{1-12}$alkoxy, optionally substituted $C_{6-20}$aryloxy, optionally substituted $C_{3-10}$cycloalkyl, optionally substituted $C_{3-10}$cycloalkenyl, optionally substituted 3-15 membered heterocyclyl, or optionally substituted 5-20 membered heteroaryl, or b) $C_{1-12}$alkyl, wherein the $C_{1-12}$alkyl is unsubstituted or is substituted with one or more $R''$, wherein $R'''$ is OH, halo, cyano, oxo, $C_{1-12}$alkyl, $C_{1-12}$alkoxy, $C_{6-20}$aryloxy, —C(O)$NH_2$, —C(O)NH($C_{1-12}$alkyl), —C(O)N($C_{1-12}$alkyl)$_2$, —C(O)OH, —C(O)—$C_{1-12}$alkoxy, —C(O)-(3-15 membered heterocyclyl), $NH_2$, —NH($C_{1-12}$alkyl), —N($C_{1-12}$alkyl)$_2$, —NHC(O)—$C_{1-12}$alkyl, —NHC(O)—$NH_2$, —NH—$SO_2$—$C_{1-12}$alkyl, —S(O)—$C_{1-12}$alkyl, —S(O)$_2$—$C_{1-12}$alkyl, —S(O)$_2$—$NH_2$, $C_{3-10}$cycloalkyl, or 3-15 membered heterocyclyl, wherein the $C_{1-12}$alkyl, $C_{1-12}$alkoxy, $C_{6-20}$aryloxy, the $C_{1-12}$alkyl of —C(O)NH($C_{1-12}$alkyl), the $C_{1-12}$alkyl of —C(O)N($C_{1-12}$alkyl)$_2$, —C(O)OH, —C(O)—$C_{1-12}$alkoxy, the 3-15 membered heterocyclyl of —C(O)-(3-15 membered heterocyclyl), $NH_2$, the $C_{1-12}$alkyl of —NH($C_{1-12}$alkyl), the $C_{1-12}$alkyl of —N($C_{1-12}$alkyl)$_2$, the $C_{1-12}$alkyl of —NHC(O)—$C_{1-12}$alkyl, —NHC(O)—$NH_2$, the $C_{1-12}$alkyl of —NH—$SO_2$—$C_{1-12}$alkyl, the $C_{1-12}$alkyl of —S(O)—$C_{1-12}$alkyl, the $C_{1-12}$alkyl of —S(O)$_2$—$C_{1-12}$alkyl, —S(O)$_2$—$NH_2$, $C_{3-10}$cycloalkyl, or 3-15 membered heterocyclyl of $R''$ is further optionally substituted by one or more OH, halo, cyano, oxo, $C_{1-12}$alkyl, $C_{1-12}$alkoxy, —C(O)$NH_2$, —C(O)NH($C_{1-12}$alkyl), —C(O)N($C_{1-12}$alkyl)$_2$, C(O)OH, $NH_2$, —NH($C_{1-12}$alkyl), —N($C_{1-12}$alkyl)$_2$, $C_{3-10}$cycloalkyl, $C_{6-20}$aryl, 3-15 membered heterocyclyl, or 5-20 membered heteroaryl, or c) optionally substituted $C_{3-10}$cycloalkenyl, or d) optionally substituted 5-20 membered heteroaryl, or e) optionally substituted 3-15 membered heterocyclyl, or f) optionally substituted amidinyl, or g) optionally substituted sulfonyl, or h) cyano; and $R^3$ is H, optionally substituted $C_{1-12}$alkyl, optionally substituted —C(O)$NH_2$, or optionally substituted —C(O)—$C_{1-12}$alkoxy; or $R^2$ and $R^3$ are taken together with the atoms to which they are attached to form a 5- or 6-membered heterocyclyl or 5- or 6-membered heteroaryl, wherein the 5- or 6-membered heterocyclyl or 5- or 6-membered heteroaryl independently comprises two or more annular heteroatoms and is independently optionally substituted; and $R^4$ is absent or is H, optionally substituted $C_{1-12}$alkyl, optionally substituted —C(O)$NH_2$, or optionally substituted —C(O)—$C_{1-12}$alkoxy, or any variation or embodiment thereof.

In another aspect, provided herein is a compound of formula (II):

(II)

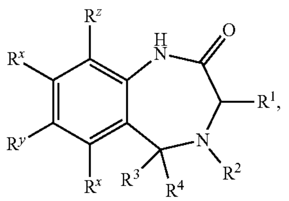

or a stereoisomer or tautomer thereof, or a pharmaceutically acceptable salt of any of the foregoing, wherein $R^x$, $R^y$, $R^z$, $R^1$, $R^2$, $R^3$, and $R^4$ are as defined for the compound of formula (I), or any variation or embodiment thereof.

In another aspect, provided herein is a compound of formula (III):

(III)

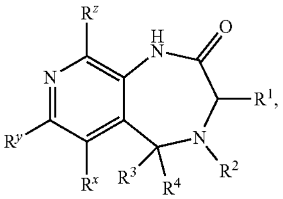

or a stereoisomer or tautomer thereof, or a pharmaceutically acceptable salt of any of the foregoing, wherein $R^x$, $R^y$, $R^z$, $R^1$, $R^2$, $R^3$, and $R^4$ are as defined for the compound of formula (I), or any variation or embodiment thereof.

In another aspect, provided herein is a compound of formula (IV):

(IV)

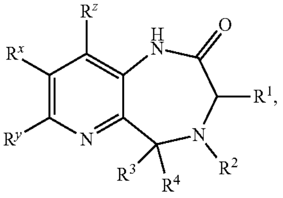

or a stereoisomer or tautomer thereof, or a pharmaceutically acceptable salt of any of the foregoing, wherein $R^x$, $R^y$, $R^z$, $R^1$, $R^2$, $R^3$, and $R^4$ are as defined for the compound of formula (I), or any variation or embodiment thereof.

In another aspect, provided herein is a compound of formula (V):

(V)

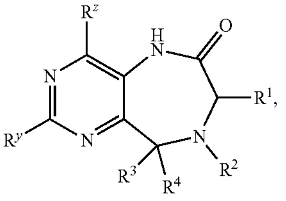

or a stereoisomer or tautomer thereof, or a pharmaceutically acceptable salt of any of the foregoing, wherein $R^y$, $R^z$, $R^1$, $R^2$, $R^3$, and $R^4$ are as defined for the compound of formula (I), or any variation or embodiment thereof.

In another aspect, provided herein is a compound of formula (I-A):

(I-A)

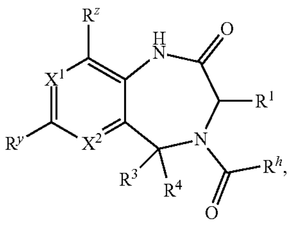

or a stereoisomer or tautomer thereof, or a pharmaceutically acceptable salt of any of the foregoing, wherein $X^1$, $X^2$, $R^y$, $R^z$, $R^1$, $R^3$, $R^4$, and $R^h$ are as defined for the compound of formula (I), or any variation or embodiment thereof.

In a further aspect, provided herein is a compound of (I-B):

(I-B)

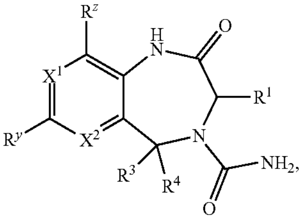

or a stereoisomer or tautomer thereof, or a pharmaceutically acceptable salt of any of the foregoing, wherein $X^1$, $X^2$, $R^y$, $R^z$, $R^1$, $R^3$, and $R^4$ are as defined for the compound of formula (I), or any variation or embodiment thereof.

In a further aspect, provided herein is a compound of (I-C):

(I-C)

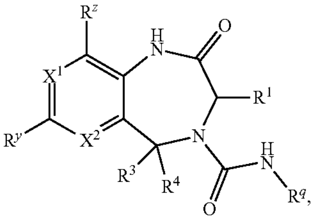

or a stereoisomer or tautomer thereof, or a pharmaceutically acceptable salt of any of the foregoing, wherein $X^1$, $X^2$, $R^y$, $R^z$, $R^1$, $R^3$, and $R^4$ are as defined for the compound of formula (I), and $R^q$ is optionally substituted $C_{1-12}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl, or any variation or embodiment thereof.

In another aspect, provided herein is a compound of formula (I-D):

(I-D)

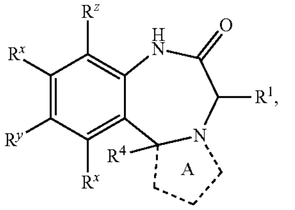

or a stereoisomer or tautomer thereof, or a pharmaceutically acceptable salt of any of the foregoing, wherein $R^x$, $R^y$, $R^z$, $R^1$, and $R^4$ are as defined for the compound of formula (I), and ring A is a 5-membered heterocyclyl or 5-membered heteroaryl, wherein the 5-membered heterocyclyl or 5-membered heteroaryl independently comprises two or more annular heteroatoms and is independently optionally substituted, or any variation or embodiment thereof.

Unless specifically described otherwise, when symbols in one formula in the specification are also used in other formulae, the same symbols denote the same meanings. When the same symbol is used more than once in a given formula, it is to be understood that each instance of that symbol in the formula represents an independently selected chemical moiety and that all instances of the symbol in the formula need not necessarily represent identical chemical moieties.

In a further aspect, the present invention relates to a pharmaceutical composition comprising one or more of the compounds described herein, or a stereoisomer or tautomer thereof, or a pharmaceutically acceptable salt of any of the foregoing, for preventing or treating various diseases, disorders, and conditions responsive to the modulation of the contractility of the skeletal sarcomere.

In some aspects, the present invention relates to methods of preventing or treating frailty associated with old age (termed sarcopenia); cachexia syndromes associated with diseases such as cancer, heart failure, chronic obstructive pulmonary disease (COPD), renal disease, and chronic kidney disease/dialysis; diseases and disorders of the central nervous system (CNS); neuromuscular diseases, such as amyotrophic lateral sclerosis (ALS), spinal muscular atrophy (SMA), and myasthenia gravis, peripheral neuropathies, Charcot-Marie-Tooth disease, Parkinson's disease, stroke, spinal cord injury, and motor units disorders; muscular myopathies, including body myositis myopathy, muscular dystrophies (limb girdle, facioscapulohumeral, oculopharyngeal), steroid myopathy, and mitochondrial myopathies; rehabilitation-related deficits: recovery from surgery (e.g., post-surgical muscle weakness), prolonged bed rest, immobilization/disuse atrophy, post-hip fracture recovery, ICU neuromyopathy, post trauma, stroke rehabilitation; Peripheral Vascular Disease (PVD) or Peripheral Arterial Disease (PAD) (e.g., claudication), metabolic syndrome, chronic fatigue syndrome, obesity, and frailty due to aging; post-anesthesia recovery or reversal of neuromuscular blockade; obstructive sleep apnea; chronic fatigue syndrome; metabolic syndrome, metabolic/ischemic disorders, or claudication; obesity; dysfunctions of pelvic floor and urethral/anal sphincter muscles (e.g., urinary incontinence such as stress urinary incontinence (SUI) and mixed urinary incontinence (MUI), and fecal incontinence); post-spinal cord injury (SCI) muscle dysfunction; ventilator-induced muscle weakness; or spinocerebral ataxias or demyelinating diseases, including multiple sclerosis, post-polio syndrome, or any combination of the foregoing, using one or more of the compounds described herein, or a stereoisomer or tautomer thereof, or a pharmaceutically acceptable salt of any of the foregoing, or a pharmaceutical composition thereof.

Additional embodiments, features, and advantages of the present disclosure will be apparent from the following detailed description and through practice of the present disclosure.

For the sake of brevity, the disclosures of publications cited in this specification, including patents, are herein incorporated by reference.

DETAILED DESCRIPTION

Definitions

Figure 1A:
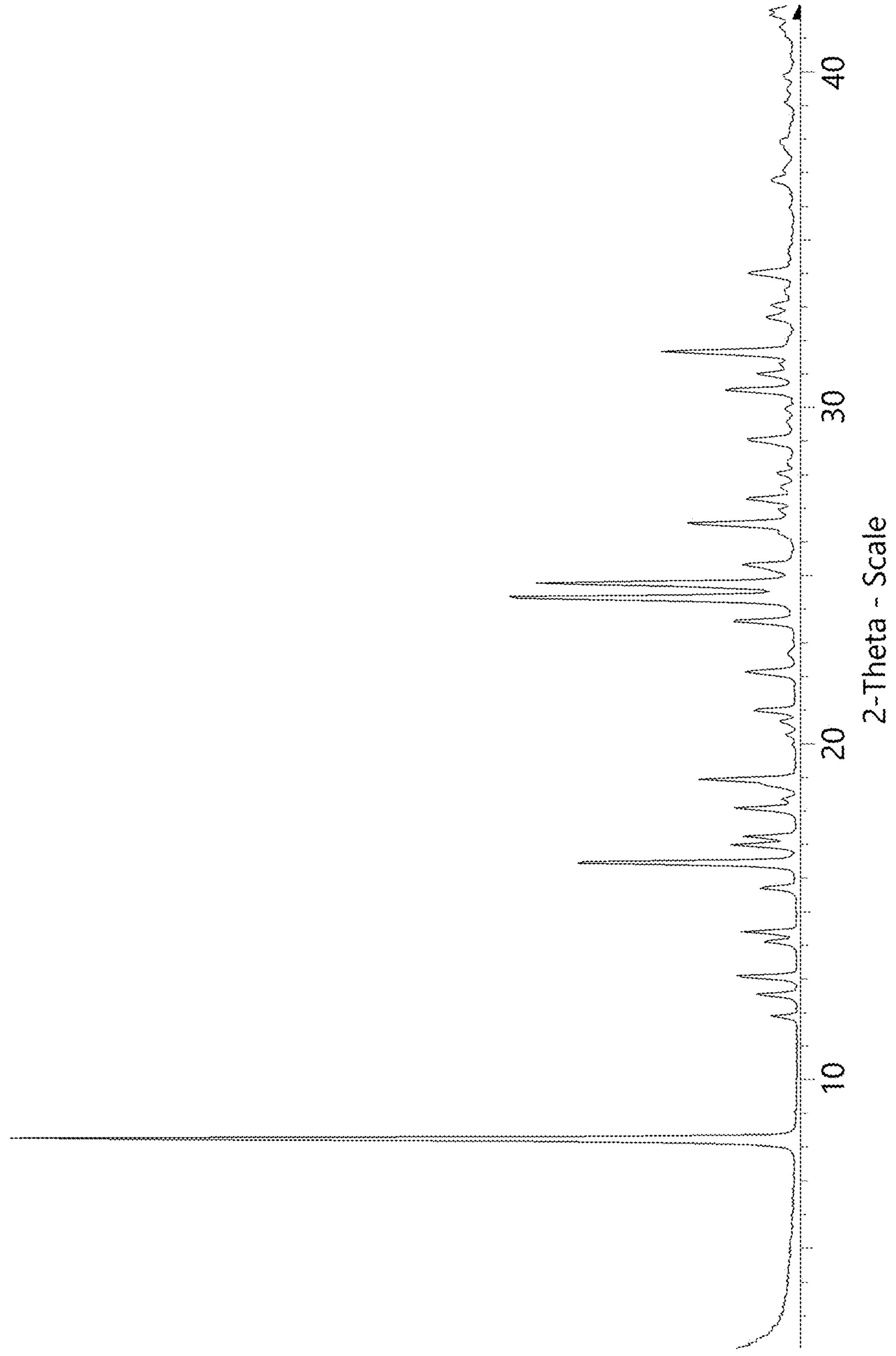
FIG. 1A shows an XRPD pattern of crystalline Form I of Compound 10.

As used in the present specification, the following words and phrases are generally intended to have the meanings as set forth below, except to the extent that the context in which they are used indicates otherwise.

Throughout this application, unless the context indicates otherwise, references to a compound of formula (I) includes all subgroups of formula (I) defined herein, such as formula (II), (III), (IV), (V), (I-A), (I-A1), (I-A2), (I-A3), (I-A4), (I-A5), (I-B), (I-B1), (I-B32), (I-B33), (I-B34), (I-B5), (I-B6), (I-B7), (I-B8), (I-C), or (I-D), including all substructures, subgenera, preferences, embodiments, examples, and particular compounds defined and/or described herein. References to a compound of formula (I) and subgroups thereof, such as formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of formula (I) and subgroups thereof, such as formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), include polymorphs, solvates, co-crystals, isomers, tautomers and/or oxides thereof. In some embodiments, references to a compound of formula (I) and subgroups thereof, such as (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), include polymorphs, solvates, and/or co-crystals thereof. In some embodiments, references to a compound of formula (I) and subgroups thereof, such as formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), include isomers, tautomers and/or oxides thereof. In some embodiments, references to a compound of formula (I) and subgroups thereof, such as formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), include solvates thereof. Similarly, the term "salts" includes solvates of salts of compounds.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl).

"Alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl).

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged, caged, and spirocyclic ring groups (e.g., norbornane, bicyclo[2.2.2]octane, spiro[3.3]heptane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group. Examples of polycyclic cycloalkyl groups consisting of a cycloalkyl group fused to an aromatic ring are described below.

"Cycloalkenyl" indicates a non-aromatic, partially unsaturated carbocyclic ring having the indicated number of carbon atoms, for example, 3 to 10, or 3 to 8, or 3 to 6 ring carbon atoms. Cycloalkenyl groups may be monocyclic or polycyclic (e.g., bicyclic, tricyclic). Examples of cycloalkyl groups include cyclopropenyl, cyclobutenyl, cyclopentenyl, and cyclohexenyl, as well as bridged, caged, and spirocyclic ring groups (e.g., norbornene, bicyclo[2.2.2]octene, spiro[3.3]heptene). In addition, one ring of a polycyclic cycloalkyl group may be aromatic, provided the polycyclic cycloalkyl group is bound to the parent structure via a non-aromatic carbon. For example, a 1,4-dihydronaphthalen-1-yl group (wherein the moiety is bound to the parent structure via a non-aromatic carbon atom) is a cycloalkyl group, while 1,4-dihydronaphthalen-5-yl (wherein the moiety is bound to the parent structure via an aromatic carbon atom) is not considered a cycloalkyl group.

"Aryl" indicates an aromatic carbocyclic ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl. Additional examples of aryl groups comprising an aromatic carbon ring fused to a non-aromatic ring are described below.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups.

In some instances, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group. Examples of polycyclic heteroaryl groups consisting of a heteroaryl ring fused to a non-aromatic ring are described below.

"Heterocyclyl" includes heterocycloalkyl moieties and heterocycloalkenyl moieties, as defined below.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic). Examples of heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl. Examples include thiomorpholine S-oxide and thiomorpholine S,S-dioxide. Examples of spirocyclic heterocycloalkyl groups include azaspiro[3.3]heptane, diazaspiro[3.3]heptane, diazaspiro[3.4]octane, and diazaspiro[3.5]nonane. In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group. Examples of polycyclic heterocycloalkyl groups consisting of a heterocycloalkyl group fused to an aromatic ring are described below.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group. Examples of polycyclic heterocycloalkenyl groups consisting of a heterocycloalkenyl group fused to an aromatic ring are described below.

Examples of polycyclic rings consisting of an aromatic ring (e.g., aryl or heteroaryl) fused to a non-aromatic ring (e.g., cycloalkyl, cycloalkenyl, heterocycloalkyl, heterocycloalkenyl) include indenyl, 2,3-dihydro-1H-indenyl, 1,2,3,4-tetrahydronaphthalenyl, benzo[1,3]dioxolyl, tetrahydroquinolinyl, 2,3-dihydrobenzo[1,4]dioxinyl, indolinyl, isoindolinyl, 2,3-dihydro-1H-indazolyl, 2,3-dihydro-1H-benzo[d]imidazolyl, 2,3-dihydrobenzofuranyl, 1,3-dihydroisobenzofuranyl, 1,3-dihydrobenzo[c]isoxazolyl, 2,3-dihydrobenzo[d]isoxazolyl, 2,3-dihydrobenzo[d]oxazolyl, 2,3-dihydrobenzo[b]thiophenyl, 1,3-dihydrobenzo[c]thiophenyl, 1,3-dihydrobenzo[c]isothiazolyl, 2,3-dihydrobenzo[d]isothiazolyl, 2,3-dihydrobenzo[d]thiazolyl, 5,6-dihydro-4H-cyclopenta[d]thiazolyl, 4,5,6,7-tetrahydrobenzo[d]thiazolyl, 5,6-dihydro-4H-pyrrolo[3,4-d]thiazolyl, 4,5,6,7-tetrahydrothiazolo[5,4-c]pyridinyl, indolin-2-one, indolin-3-one, isoindolin-1-one, 1,2-dihydroindazol-3-one, 1H-benzo[d]imidazol-2(3H)-one, benzofuran-2(3H)-one, benzofuran-3(2H)-one, isobenzofuran-1(3H)-one, benzo[c]isoxazol-3(1H)-one, benzo[d]isoxazol-3(2H)-one, benzo[d]oxazol-2(3H)-one, benzo[b]thiophen-2(3H)-one, benzo[b]thiophen-3(2H)-one, benzo[c]thiophen-1(3H)-one, benzo[c]isothiazol-3(1H)-one, benzo[d]isothiazol-3(2H)-one, benzo

[d]thiazol-2(3H)-one, 4,5-dihydropyrrolo[3,4-d]thiazol-6-one, 1,2-dihydropyrazolo[3,4-d]thiazol-3-one, quinolin-4(3H)-one, quinazolin-4(3H)-one, quinazoline-2,4(1H,3H)-dione, quinoxalin-2(1H)-one, quinoxaline-2,3(1H,4H)-dione, cinnolin-4(3H)-one, pyridin-2(1H)-one, pyrimidin-2(1H)-one, pyrimidin-4(3H)-one, pyridazin-3(2H)-one, 1H-pyrrolo[3,2-b]pyridin-2(3H)-one, 1H-pyrrolo[3,2-c]pyridin-2(3H)-one, 1H-pyrrolo[2,3-c]pyridin-2(3H)-one, 1H-pyrrolo[2,3-b]pyridin-2(3H)-one, 1,2-dihydropyrazolo[3,4-d]thiazol-3-one and 4,5-dihydropyrrolo[3,4-d]thiazol-6-one. As discussed herein, whether each ring is considered an aryl, heteroaryl, cycloalkyl, cycloalkenyl, heterocycloalkyl or heterocycloalkenyl group is determined by the atom through which the moiety is bound to the parent structure.

"Halogen" or "halo" refers to fluorine, chlorine, bromine or iodine.

"Annular" refers to a moiety that is a member of a ring, including, but not limited to, a cycloalkyl ring, a cycloalkenyl ring, an aryl ring, a heteroaryl ring, or a heterocyclyl ring. For example, if a heteroaryl ring is described as "comprising two or more annular heteroatoms", two or more of the ring members of the heteroaryl ring will be heteroatoms.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxy group protected with a hydroxy protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocycloalkyl, heterocycloalkenyl, aralkyl, aminosulfonyl, sulfonylamino, sulfonyl, oxo, carbonylalkylenealkoxy and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally", it is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^{2}H$, $^{3}H$, $^{11}C$, $^{13}C$ and/or $^{14}C$. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.,* 2000; 6(10); Kabalka, G. et al., The Synthesis of Radiolabeled Compounds via Organometallic Intermediates, *Tetrahedron,* 1989, 45(21), 6601-21; and Evans, E., Synthesis of radiolabeled compounds, *J. Radioanal. Chem.,* 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, the term "therapeutic" refers to the ability to treat a condition, disorder, or disease described herein, including, but not limited to, a condition, disorder, or disease responsive to the modulation of the contractility of the skeletal sarcomere. As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the chemical entity with the a target or due to the interaction of the chemical entity with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease, disorder, or condition described herein, including, but not limited to, a condition, disorder, or disease responsive to the modulation of the contractility of the skeletal sarcomere. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: preventing a disease or disorder (i.e., causing the clinical symptoms of the disease or disorder not to develop); inhibiting a disease or disorder; slowing or arresting the development of clinical symptoms of a disease or disorder; and/or relieving a disease or disorder (i.e., causing relief from or regression of clinical symptoms). The term encompasses situations where the disease or disorder is already being experienced by a patient, as well as situations where the disease or disorder is not currently being experienced but is expected to arise. The term covers both complete and partial reduction or prevention of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder. When used in a prophylactic manner, the compounds disclosed and/or described herein may prevent a disease or disorder from developing or lessen the extent of a disease or disorder that may develop.

As used herein and in the appended claims, the singular forms "a", "an" and "the" include plural forms, unless the context clearly dictates otherwise.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

As used herein, the term "polymorph" or "polymorphic form" refers to a crystalline form of a compound. Different polymorphs may have different physical properties such as, for example, melting temperatures, heats of fusion, solubilities, dissolution rates, and/or vibrational spectra as a result of the arrangement or conformation of the molecules or ions in the crystal lattice. The differences in physical properties exhibited by polymorphs may affect pharmaceutical parameters, such as storage stability, compressibility, density (important in formulation and product manufacturing), and dissolution rate (an important factor in bioavailability).

Differences in stability can result from changes in chemical reactivity (e.g., differential oxidation, such that a dosage form discolors more rapidly when comprised of one polymorph than when comprised of another polymorph), mechanical changes (e.g., tablets crumble on storage as a kinetically favored polymorph converts to thermodynamically more stable polymorph), or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of a crystalline form may be important in processing; for example, one polymorph might be more likely to form solvates or might be difficult to filter and wash free of impurities (e.g., particle shape and size distribution might be different between polymorphs).

As used herein, the term "substantially as shown in" when referring, for example, to an XRPD pattern, a DSC graph, a TGA graph, or a GVS graph, includes a pattern or graph that is not necessarily identical to those depicted herein, but that falls within the limits of experimental error or deviations when considered by one of ordinary skill in the art.

In some embodiments, the term "substantially pure" means that the crystalline form contains about less than 30%, about less than 20%, about less than 15%, about less than 10%, about less than 5%, or about less than 1% by weight of impurities. In other embodiments, "substantially pure" refers to a substance free of impurities. Impurities may, for example, include by-products or left over reagents from chemical reactions, contaminants, degradation products, other crystalline forms, water, and solvents.

As used herein, the term "substantially free of" means that the composition comprising the crystalline form contains less than 50%, less than 40%, less than 30%, less than 20%, less than 15%, less than 10%, less than 5%, less than 4%, less than 3%, less than 2%, or less than 1% by weight of the indicated substance or substances.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of formula (I):

(I)

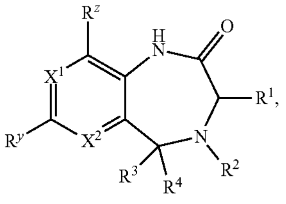

or a pharmaceutically acceptable salt, stereoisomer, or tautomer thereof, wherein:

$X^1$ and $X^2$ are each independently N or C—$R^x$;

each $R^x$, $R^y$, and $R^z$ is independently H, halo, $C_{3-10}$-cycloalkyl, $C_{3-10}$-cycloalkenyl, or $C_{6-20}$aryl;

$R^1$ is $C_{3-12}$alkyl, $C_{2-12}$alkenyl, $C_{2-12}$alkynyl, $C_{3-10}$-cycloalkyl, $C_{3-10}$-cycloalkenyl, or

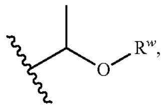

wherein $R^w$ is optionally substituted $C_{1-12}$alkyl;

$R^2$ is:

a) C(O)—$R^h$, wherein $R^h$ is (i) optionally substituted amino, optionally substituted $C_{1-3}$alkoxy, optionally substituted —$C(O)NH_2$, optionally substituted $C_{3-10}$cycloalkyl, optionally substituted $C_{3-10}$cycloalkenyl, optionally substituted $C_{6-20}$aryl, optionally substituted 3-15 membered heterocyclyl, or optionally substituted 5-20 membered heteroaryl, or (ii) $C_{1-12}$alkyl, wherein the $C_{1-12}$alkyl is unsubstituted or is substituted with one or more R″, wherein R″ is OH, oxo, halo, cyano, —$C(O)NH_2$, optionally substituted amino, optionally substituted sulfonyl, optionally substituted $C_{1-12}$alkoxy, optionally substituted $C_{6-20}$aryloxy, optionally substituted $C_{3-10}$cycloalkyl, optionally substituted $C_{3-10}$cycloalkenyl, optionally substituted 3-15 membered heterocyclyl, or optionally substituted 5-20 membered heteroaryl, or b) $C_{1-12}$alkyl, wherein the $C_{1-12}$alkyl is unsubstituted or is substituted with one or more R″, wherein R‴ is OH, halo, cyano, oxo, $C_{1-12}$alkyl, $C_{1-12}$alkoxy, $C_{6-20}$aryloxy, —$C(O)NH_2$, —C(O)NH($C_{1-12}$alkyl), —C(O)N($C_{1-12}$alkyl)$_2$, —C(O)OH, —C(O)—$C_{1-12}$alkoxy, —C(O)-(3-15 membered heterocyclyl), $NH_2$, —NH($C_{1-12}$alkyl), —N($C_{1-12}$alkyl)$_2$, —NHC(O)—$C_{1-12}$alkyl, —NHC(O)—$NH_2$, —NH—$SO_2$—$C_{1-12}$alkyl, —S(O)—$C_{1-12}$alkyl, —S(O)$_2$—$C_{1-12}$alkyl, —S(O)$_2$—$NH_2$, $C_{3-10}$cycloalkyl, or 3-15 membered heterocyclyl, wherein the $C_{1-12}$alkyl, $C_{1-12}$alkoxy, $C_{6-20}$aryloxy, the $C_{1-12}$alkyl of —C(O)NH($C_{1-12}$alkyl), the $C_{1-12}$alkyl of —C(O)N($C_{1-12}$alkyl)$_2$, —C(O)OH, —C(O)—$C_{1-12}$alkoxy, the 3-15 membered heterocyclyl of —C(O)-(3-15 membered heterocyclyl), $NH_2$, the $C_{1-12}$alkyl of —NH($C_{1-12}$alkyl), the $C_{1-12}$alkyl of —N($C_{1-12}$alkyl)$_2$, the $C_{1-12}$alkyl of —NHC(O)—$C_{1-12}$alkyl, —NHC(O)—$NH_2$, the $C_{1-12}$alkyl of —NH—$SO_2$—$C_{1-12}$alkyl, the $C_{1-12}$alkyl of —S(O)—$C_{1-12}$alkyl, the $C_{1-12}$alkyl of —S(O)$_2$—$C_{1-12}$alkyl, —S(O)$_2$—$NH_2$, $C_{3-10}$cycloalkyl, or 3-15 membered heterocyclyl of R″ is further optionally substituted by one or more OH, halo, cyano, oxo, $C_{1-12}$alkyl, $C_{1-12}$alkoxy, —$C(O)NH_2$, —C(O)NH($C_{1-12}$alkyl), —C(O)N($C_{1-12}$alkyl)$_2$, C(O)OH, $NH_2$, —NH($C_{1-12}$alkyl), —N($C_{1-12}$alkyl)$_2$, $C_{3-10}$cycloalkyl, $C_{6-20}$aryl, 3-15 membered heterocyclyl, or 5-20 membered heteroaryl, or c) optionally substituted $C_{3-10}$cycloalkenyl, or d) optionally substituted 5-20 membered heteroaryl, or e) optionally substituted 3-15 membered heterocyclyl, or f) optionally substituted amidinyl, or g) optionally substituted sulfonyl, or h) cyano, and $R^3$ is H, optionally substituted $C_{1-12}$alkyl, optionally substituted —C(O)$NH_2$, or optionally substituted —C(O)—$C_{1-12}$alkoxy; or $R^2$ and $R^3$ are taken together with the atoms to which they are attached to form a 5- or 6-membered heterocyclyl or 5- or 6-membered heteroaryl, wherein the 5- or 6-membered heterocyclyl or 5- or 6-membered heteroaryl independently comprises two or more annular heteroatoms and is independently optionally substituted; and $R^4$ is absent or is H, optionally substituted $C_{1-12}$alkyl, optionally substituted —C(O)$NH_2$, or optionally substituted —C(O)—$C_{1-12}$alkoxy.

In some embodiments, provided is a compound of formula (I), or a stereoisomer or tautomer thereof, or a pharmaceutically acceptable salt of any of the foregoing, wherein $X^1$ and $X^2$ are each independently C—$R^x$, such that the compound of formula (I) is a compound of formula (II):

(II)

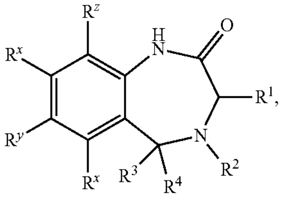

or a stereoisomer or tautomer thereof, or a pharmaceutically acceptable salt of any of the foregoing, wherein $R^x$, $R^y$, $R^z$, $R^1$, $R^2$, $R^3$, and $R^4$ are as defined above for formula (I).

In some embodiments, provided is a compound of formula (I), or a stereoisomer or tautomer thereof, or a pharmaceutically acceptable salt of any of the foregoing, wherein $X^1$ is N and $X^2$ is C—$R^x$, such that the compound of formula (I) is a compound of formula (III):

(III)

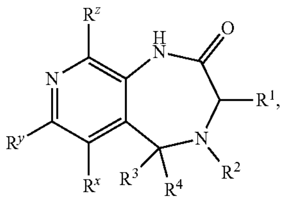

or a stereoisomer or tautomer thereof, or a pharmaceutically acceptable salt of any of the foregoing, wherein $R^x$, $R^y$, $R^z$, $R^1$, $R^2$, $R^3$, and $R^4$ are as defined above for formula (I).

In some embodiments, provided is a compound of formula (I), or a stereoisomer or tautomer thereof, or a pharmaceutically acceptable salt of any of the foregoing, wherein $X^1$ is C—$R^x$ and $X^2$ is N, such that the compound of formula (I) is a compound of formula (IV):

(IV)

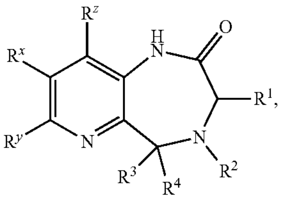

or a stereoisomer or tautomer thereof, or a pharmaceutically acceptable salt of any of the foregoing, wherein $R^x$, $R^y$, $R^z$, $R^1$, $R^2$, $R^3$, and $R^4$ are as defined above for formula (I).

In some embodiments, provided is a compound of formula (I), or a stereoisomer or tautomer thereof, or a pharmaceutically acceptable salt of any of the foregoing, wherein $X^1$ is N and $X^2$ is N, such that the compound of formula (I) is a compound of formula (V):

(V)

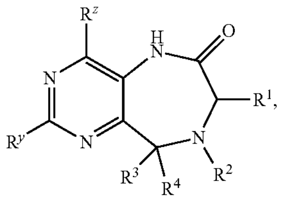

or a stereoisomer or tautomer thereof, or a pharmaceutically acceptable salt of any of the foregoing, wherein $R^y$, $R^z$, $R^1$, $R^2$, $R^3$, and $R^4$ are as defined above for formula (I).

In some embodiments, provided is a compound of formula (I), such as a compound of formula (II), (III), (IV), or (V), or a stereoisomer or tautomer thereof, or a pharmaceutically acceptable salt of any of the foregoing, wherein $R^2$ is C(O)—$R^h$, wherein $R^h$ is (i) optionally substituted amino, optionally substituted $C_{1-3}$alkoxy, optionally substituted —C(O)$NH_2$, optionally substituted $C_{3-10}$cycloalkyl, optionally substituted $C_{3-10}$cycloalkenyl, optionally substituted $C_{6-20}$aryl, optionally substituted 3-15 membered heterocyclyl, or optionally substituted 5-20 membered heteroaryl, or (ii) $C_{1-12}$alkyl, wherein the $C_{1-12}$alkyl is unsubstituted or is substituted with one or more $R''$, wherein $R''$ is OH, oxo, halo, cyano, —C(O)$NH_2$, optionally substituted amino, optionally substituted sulfonyl, optionally substituted $C_{1-12}$alkoxy, optionally substituted $C_{6-20}$aryloxy, optionally substituted $C_{3-10}$cycloalkyl, optionally substituted $C_{3-10}$cycloalkenyl, optionally substituted 3-15 membered heterocyclyl, or optionally substituted 5-20 membered heteroaryl.

In certain embodiments, provided is a compound of formula (I), or a stereoisomer or tautomer thereof, or a pharmaceutically acceptable salt of any of the foregoing, wherein the compound of formula (I) is a compound of formula (I-A):

(I-A)

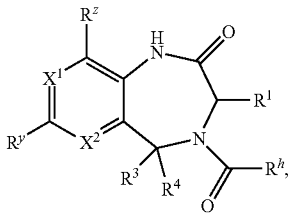

or a stereoisomer or tautomer thereof, or a pharmaceutically acceptable salt of any of the foregoing, wherein $X^1$, $X^2$, $R^y$, $R^z$, $R^1$, $R^3$, $R^4$, and $R^h$ are as defined above for formula (I).

In some embodiments, provided herein is a compound of formula (I) or (I-A), or a stereoisomer or tautomer thereof, or a pharmaceutically acceptable salt of any of the foregoing, wherein $X^1$ is N and $X^2$ is C—$R^x$, wherein $R^x$ is as defined above for formula (I). In other embodiments, provided herein is a compound of formula (I) or (I-A), or a stereoisomer or tautomer thereof, or a pharmaceutically acceptable salt of any of the foregoing, wherein $X^1$ is C—$R^x$ and $X^2$ is N. In still other embodiments, provided herein is a compound of formula (I) or (I-A), or a stereoisomer or tautomer thereof, or a pharmaceutically acceptable salt of any of the foregoing, wherein $X^1$ and $X^2$ are each independently C—$R^x$. In some embodiments, provided herein is a compound of formula (I) or (I-A), or a stereoisomer or tautomer thereof, or a pharmaceutically acceptable salt of any of the foregoing, wherein $X^1$ and $X^2$ are each independently N. In certain embodiments, provided herein is a compound of formula (I) or (I-A), or a stereoisomer or tautomer thereof, or a pharmaceutically acceptable salt of any of the foregoing, wherein the compound of formula (I) or (I-A) is a compound of formula (I-A1), (I-A2), (I-A3), (I-A4), or (I-A5):

(I-A1)

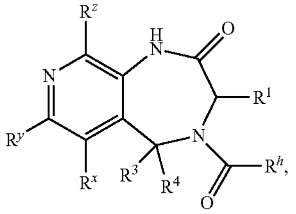

(I-A2)

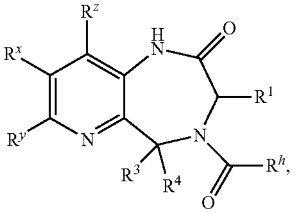

(I-A3)

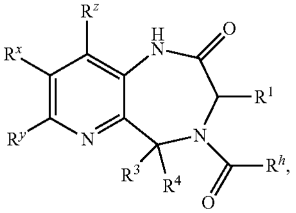

(I-A4)

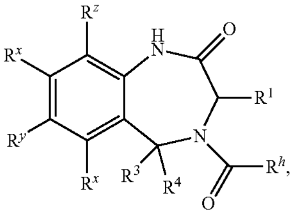

-continued (I-A5)

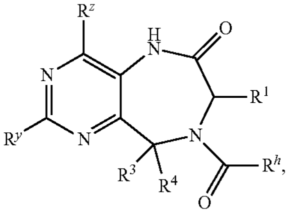

or a stereoisomer or tautomer thereof, or a pharmaceutically acceptable salt of any of the foregoing, In some embodiments of the compounds of formula (I-A), (I-A1), (I-A2), (I-A3), or (I-A4), each $R^x$ is independently H, halo, or $C_{3-10}$cycloalkyl. In other embodiments, each $R^x$ is independently H or halo. In some embodiments, the halo is fluoro, chloro, or bromo. In certain embodiments, the halo is fluoro. In some embodiments, each $R^x$ is independently H. In some embodiments, wherein $X^1$ and $X^2$ are each independently C—$R^x$, such as in a compound of formula (I-A) or (I-A4), each $R^x$ is independently H. In other embodiments, wherein $X^1$ and $X^2$ are each independently C—$R^x$, such as in a compound of formula (I-A) or (I-A4), each $R^x$ is independently halo. In certain embodiments, wherein $X^1$ and $X^2$ are each independently C—$R^x$, such as in a compound of formula (I-A) or (I-A4), each $R^x$ is independently fluoro. In some embodiments, one $R^x$ is H and the other $R^x$ is halo. In some embodiments, one $R^x$ is H and the other $R^x$ is fluoro. In some embodiments, each $R^x$ is independently H.

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is $NH_2$. In some embodiments, provided herein is a compound, or a stereoisomer or tautomer thereof, or a pharmaceutically acceptable salt of any of the foregoing, wherein the compound of formula (I), (I-A), (I-A1), (I-A2), (I-A3), (I-A4), or (I-A5), or a stereoisomer or tautomer thereof, or a pharmaceutically acceptable salt of any of the foregoing, is a compound of formula (I-B):

(I-B)

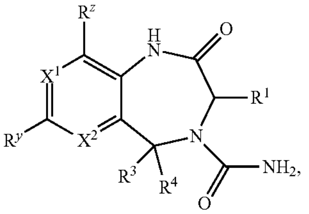

or a stereoisomer or tautomer thereof, or a pharmaceutically acceptable salt of any of the foregoing, wherein $X^1$, $X^2$, $R^y$, $R^z$, $R^1$, $R^3$, and $R^4$ are as defined above for formula (I).

In some embodiments, provided herein is a compound of formula (I) or (I-B), or a stereoisomer or tautomer thereof, or a pharmaceutically acceptable salt of any of the foregoing, wherein $X^1$ is N and $X^2$ is C—$R^x$, wherein $R^x$ is as defined above for formula (I). In other embodiments, provided herein is a compound of formula (I) or (I-B), or a stereoisomer or tautomer thereof, or a pharmaceutically acceptable salt of any of the foregoing, wherein $X^1$ is C—$R^x$ and $X^2$ is N. In still other embodiments, provided herein is a compound of formula (I) or (I-B), or a stereoisomer or tautomer thereof, or a pharmaceutically acceptable salt of any of the foregoing, wherein $X^1$ and $X^2$ are each independently C—$R^x$. In some embodiments, provided herein is a compound of formula (I) or (I-B), or a stereoisomer or tautomer thereof, or a pharmaceutically acceptable salt of any of the foregoing, wherein $X^1$ and $X^2$ are each independently N. In certain embodiments, provided herein is a compound of formula (I) or (I-B), or a stereoisomer or tautomer thereof, or a pharmaceutically acceptable salt of any of the foregoing, wherein the compound of formula (I) or (I-B) is a compound of formula (I-B1), (I-B2), (I-B3), (I-B4), or (I-B5):

(I-B1)

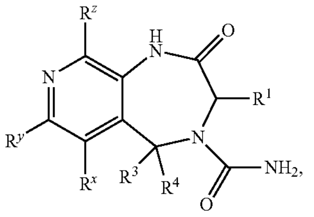

(I-B2)

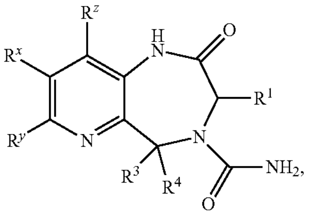

(I-B3)

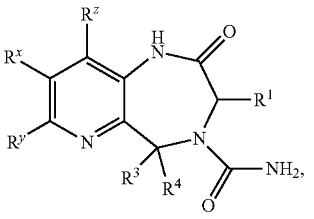

(I-B4)

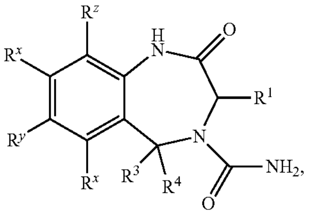

(I-B5)

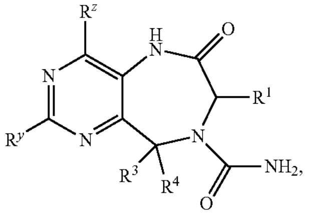

or a stereoisomer or tautomer thereof, or a pharmaceutically acceptable salt of any of the foregoing.

In some embodiments of the compounds of formula (I-B), (I-B1), (I-B2), (I-B3), or (I-B4), each $R^x$ is independently H, halo, or $C_{3-10}$cycloalkyl. In other embodiments, each $R^x$ is independently H or halo. In some embodiments, the halo is fluoro, chloro, or bromo. In certain embodiments, the halo is fluoro. In some embodiments, each $R^x$ is independently H. In some embodiments, wherein $X^1$ and $X^2$ are each independently C—$R^x$, such as in a compound of formula (I-B) or (I-B4), each $R^x$ is independently H. In other embodiments, wherein $X^1$ and $X^2$ are each independently C—$R^x$, such as in a compound of formula (I-B) or (I-B4), each $R^x$ is independently halo. In certain embodiments, wherein $X^1$ and $X^2$ are each independently C—$R^x$, such as in a compound of formula (I-B) or (I-B4), each $R^x$ is independently fluoro. In some embodiments, one $R^x$ is H and the other $R^x$ is halo. In some embodiments, one $R^x$ is H and the other $R^x$ is fluoro. In some embodiments, each $R^x$ is independently H.

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is substituted amino. In certain embodiments, the amino of $R^h$ is substituted with one or more $R^q$, wherein $R^q$ is optionally substituted $C_{1-12}$alkyl, optionally substituted $C_{3-10}$cycloalkyl, optionally substituted $C_{6-20}$aryl, optionally substituted 3-15 membered heterocyclyl, or optionally substituted 5-20 membered heteroaryl. In some embodiments, the amino of $R^h$ is substituted with two $R^q$. In certain embodiments, the amino of $R^h$ is substituted with one $R^q$.

In some embodiments, $R^q$ is unsubstituted $C_{1-12}$alkyl, unsubstituted $C_{3-10}$cycloalkyl, unsubstituted $C_{6-20}$aryl, unsubstituted 3-15 membered heterocyclyl, or unsubstituted 5-20 membered heteroaryl. In certain embodiments, $R^q$ is unsubstituted $C_{1-12}$alkyl. In some embodiments, $R^q$ is unsubstituted $C_{1-6}$alkyl. In some embodiments, $R^q$ is unsubstituted methyl.

In some embodiments, $R^q$ is $C_{1-12}$alkyl, $C_{3-10}$cycloalkyl, $C_{6-20}$aryl, 3-15 membered heterocyclyl, or 5-20 membered heteroaryl, wherein the $C_{1-12}$alkyl, $C_{3-10}$cycloalkyl, $C_{6-20}$aryl, 3-15 membered heterocyclyl, or 5-20 membered heteroaryl of $R^q$ is independently substituted with one or more $R^p$, wherein $R^p$ is OH, cyano, halo, oxo, optionally substituted —C(O)$NH_2$, optionally substituted —C(O)NH($C_{1-12}$alkyl), optionally substituted —C(O)-(3-15 membered heterocyclyl), optionally substituted —S(O)—$C_{1-12}$alkyl, optionally substituted —$S(O)_2$—$C_{1-12}$alkyl, optionally substituted —$S(O)_2$—$NH_2$, optionally substituted —N($C_{1-12}$alkyl)$_2$, optionally substituted —NHC(O)—$C_{1-12}$alkyl, optionally substituted —NHC(O)—$NH_2$, optionally substituted $C_{6-20}$aryl, optionally substituted 3-15 membered heterocyclyl, or optionally substituted 5-20 membered heteroaryl.

In some embodiments, $R^q$ is $C_{1-12}$alkyl, wherein the $C_{1-12}$alkyl of $R^q$ is independently substituted with one or more $R^p$, wherein $R^p$ is OH, —C(O)$NH_2$, —C(O)NH($C_{1-12}$alkyl), —C(O)-(3-15 membered heterocyclyl), —S(O)—$C_{1-12}$alkyl, —$S(O)_2$—$C_{1-12}$alkyl, —$S(O)_2$—$NH_2$, —N($C_{1-12}$alkyl)$_2$, —NHC(O)—$C_{1-12}$alkyl, —NHC(O)—$NH_2$, $C_{6-20}$aryl, 3-15 membered heterocyclyl, or 5-20 membered heteroaryl, wherein the $C_{6-20}$aryl, 3-15 membered heterocyclyl, 5-20 membered heteroaryl, or the 3-15 membered heterocyclyl of the C(O)-(3-15 membered heterocyclyl) of $R^p$ is independently optionally substituted with one or more $R^v$, wherein $R^v$ is OH, oxo, —C(O)$NH_2$, —C(O)OH, or $C_{1-12}$alkyl, wherein the $C_{1-12}$alkyl of $R^v$ is further optionally substituted with one or more OH.

In some embodiments, $R^q$ is $C_{3-10}$cycloalkyl, wherein the $C_{3-10}$cycloalkyl of $R^q$ is independently substituted with one or more $R^p$, wherein $R^p$ is OH or cyano.

In some embodiments, $R^q$ is $C_{6-20}$aryl, wherein the $C_{6-20}$aryl of $R^q$ is independently substituted with one or more $R^p$, wherein $R^p$ is halo.

In some embodiments, $R^q$ is 3-15 membered heterocyclyl, wherein the 3-15 membered heterocyclyl of $R^q$ is independently substituted with one or more $R^p$, wherein $R^p$ is oxo, $C_{1-12}$alkyl, 3-15 membered heterocyclyl, or 5-20 membered heteroaryl, wherein the $C_{1-12}$alkyl of $R^p$ is optionally substituted with one or more OH, halo, $C_{1-12}$alkoxy, or $C_{3-10}$cycloalkyl.

In some embodiments, $R^q$ is 5-20 membered heteroaryl, wherein the 5-20 membered heteroaryl of $R^q$ is independently substituted with one or more $R^p$, wherein $R^p$ is $C_{1-12}$alkyl, $C_{1-12}$alkoxy, —NHC(O)—$C_{1-12}$alkyl, —C(O)$NH_2$, or 5-20 membered heteroaryl, wherein the $C_{1-12}$alkyl of $R^p$ is optionally substituted with one or more OH, halo, or $C_{1-12}$alkoxy.

In some embodiments, the $C_{1-12}$alkyl, $C_{3-10}$cycloalkyl, $C_{6-20}$aryl, 3-15 membered heterocyclyl, or 5-20 membered heteroaryl of $R^q$ is independently substituted with one to six $R^p$. In some embodiments, the $C_{1-12}$alkyl, $C_{3-10}$cycloalkyl, $C_{6-20}$aryl, 3-15 membered heterocyclyl, or 5-20 membered heteroaryl of $R^q$ is independently substituted with one to five $R^p$. In some embodiments, the $C_{1-12}$alkyl, $C_{3-10}$cycloalkyl, $C_{6-20}$aryl, 3-15 membered heterocyclyl, or 5-20 membered heteroaryl of $R^q$ is independently substituted with one to four $R^p$. In some embodiments, the $C_{1-12}$alkyl, $C_{3-10}$ cycloalkyl, $C_{6-20}$aryl, 3-15 membered heterocyclyl, or 5-20 membered heteroaryl of $R^q$ is independently substituted with one to three $R^p$. In some embodiments, the $C_{1-12}$alkyl, $C_{3-10}$cycloalkyl, $C_{6-20}$aryl, 3-15 membered heterocyclyl, or 5-20 membered heteroaryl of $R^q$ is independently substituted with one to two $R^p$. In some embodiments, the $C_{1-12}$alkyl, $C_{3-10}$cycloalkyl, $C_{6-20}$aryl, 3-15 membered heterocyclyl, or 5-20 membered heteroaryl of $R^q$ is independently substituted with one $R^p$.

In some embodiments, the compound of formula (I) or (I-A), or a stereoisomer or tautomer thereof, or a pharmaceutically acceptable salt of any of the foregoing, is a compound of formula (I-C):

(I-C)

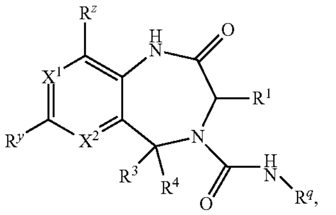

or a stereoisomer or tautomer thereof, or a pharmaceutically acceptable salt of any of the foregoing, wherein $X^1$, $X^2$, $R^y$, $R^z$, $R^1$, $R^3$, $R^4$, and $R^q$ are as defined above.

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is $C_{1-12}$alkyl, wherein the $C_{1-12}$alkyl is unsubstituted or is substituted with one or more $R''$, wherein $R''$ is OH, optionally substituted —$SO_2$—$C_{1-12}$alkyl, optionally substituted —$SO_2$—$NH_2$, optionally substituted $NH_2$, optionally substituted —NHC(O)—$C_{1-12}$alkyl, optionally substituted —C(O)$NH_2$, optionally substituted $C_{1-12}$alkoxy, optionally substituted $C_{6-20}$aryloxy, or optionally substituted 3-15 membered heterocyclyl.

In some embodiments, $R^h$ is unsubstituted $C_{1-12}$alkyl. In some embodiments, $R^h$ is $C_{1-12}$alkyl, wherein the $C_{1-12}$alkyl of $R^h$ is substituted with one or more $R''$, wherein $R''$ is OH, —$SO_2$—$C_{1-12}$alkyl, —$SO_2$—$NH_2$, $NH_2$, —NHC(O)—$C_{1-12}$alkyl, —C(O)$NH_2$, $C_{1-12}$alkoxy, $C_{6-20}$aryloxy, or 3-15 membered heterocyclyl, wherein the $C_{1-12}$alkoxy, $C_{6-20}$aryloxy, or 3-15 membered heterocyclyl of $R''$ is optionally substituted with one or more OH, —C(O)$NH_2$, or $C_{6-20}$aryl. In certain embodiments, $R^h$ is $C_{1-12}$alkyl, wherein the $C_{1-12}$alkyl of $R^h$ is substituted with one or more $R''$, wherein $R''$ is OH, $NH_2$, or —C(O)$NH_2$.

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is $C_{1-6}$alkyl, wherein the $C_{1-6}$alkyl is unsubstituted or is substituted with one or more $R''$, wherein $R''$ is OH, optionally substituted —$SO_2$—$C_{1-12}$alkyl, optionally substituted —$SO_2$—$NH_2$, optionally substituted $NH_2$, optionally substituted —NHC(O)—$C_{1-12}$alkyl, optionally substituted —C(O)$NH_2$, optionally substituted $C_{1-12}$alkoxy, optionally substituted $C_{6-20}$aryloxy, or optionally substituted 3-15 membered heterocyclyl.

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is $C_{1-12}$alkyl or $C_{1-6}$alkyl, the $C_{1-12}$alkyl or $C_{1-6}$alkyl of $R^h$ is substituted with one to six $R''$ substituents. In some embodiments of the foregoing, wherein $R^h$ is $C_{1-12}$alkyl or $C_{1-6}$alkyl, the $C_{1-12}$alkyl or $C_{1-6}$alkyl of $R^h$ is substituted with one to five $R''$ substituents. In some embodiments of the foregoing, wherein $R^h$ is $C_{1-12}$alkyl or $C_{1-6}$alkyl, the $C_{1-12}$alkyl or $C_{1-6}$alkyl of $R^h$ is substituted with one to four $R''$ substituents. In some embodiments of the foregoing, wherein $R^h$ is $C_{1-12}$alkyl or $C_{1-6}$alkyl, the $C_{1-12}$alkyl or $C_{1-6}$alkyl of $R^h$ is substituted with one to three $R''$ substituents. In some embodiments of the foregoing, wherein $R^h$ is $C_{1-12}$alkyl or $C_{1-6}$alkyl, the $C_{1-12}$alkyl or $C_{1-6}$alkyl of $R^h$ is substituted with one to two $R''$ substituents. In some embodiments of the foregoing, wherein $R^h$ is $C_{1-12}$alkyl or $C_{1-6}$alkyl, the $C_{1-12}$alkyl or $C_{1-6}$alkyl of $R^h$ is substituted with one $R''$ substituent.

In some embodiments, $R^h$ is methyl,

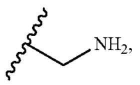 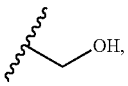 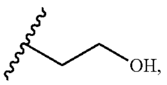 or

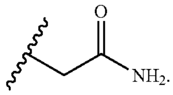

In certain embodiments, $R^h$ is

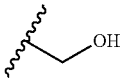 or 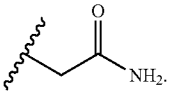

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is optionally substituted $C_{1-3}$alkoxy. In some embodiments, $R^h$ is unsubstituted $C_{1-3}$alkoxy. In certain embodiments, $R^h$ is unsubstituted methoxy.

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is optionally substituted 3-15 membered heterocyclyl. In some embodiments, the 3-15 membered heterocyclyl of $R^h$ is optionally substituted with one or more $R^j$, wherein $R^j$ is OH, oxo, halo, $NH_2$, —N($C_{1-12}$alkyl)$_2$, —N($C_{1-12}$alkyl)-C(O)$C_{1-12}$alkyl, —NH—$SO_2$—$C_{1-12}$alkyl, —$SO_2$—$C_{1-12}$alkyl, $C_{1-12}$alkyl, $C_{1-12}$alkoxy, —C(O)OH, —C(O)—$C_{1-12}$alkoxy, —C(O)$NH_2$, —C(O)NH($C_{1-12}$alkyl), —C(O)N($C_{1-12}$alkyl)$_2$, 3-15 membered heterocyclyl, or 5-20 membered heteroaryl, wherein the $C_{1-12}$alkyl, $C_{1-12}$alkoxy, 3-15 membered heterocyclyl, or 5-20 membered heteroaryl of $R^j$ is independently further optionally substituted with one or more $R^k$, wherein $R^k$ is OH, $C_{1-12}$alkyl, —C(O)$NH_2$, —C(O)NH($C_{1-12}$alkyl), —C(O)N($C_{1-12}$alkyl)$_2$, $C_{6-20}$aryl, or 5-20 membered heteroaryl, wherein the $C_{1-12}$alkyl of $R^k$ is independently further optionally substituted with one or more OH.

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is optionally substituted 5-20 membered heteroaryl. In some embodiments, $R^h$ is 5-20 membered heteroaryl, wherein the 5-20 membered heteroaryl is independently optionally substituted with one or more $R^t$, wherein $R^t$ is OH, $NH_2$, $C_{1-12}$alkyl, —C(O)OH, —C(O)—$C_{1-12}$alkoxy, —C(O)$NH_2$, —C(O)NH($C_{1-12}$alkyl), —C(O)N($C_{1-12}$alkyl)$_2$, or —C(O)-(3-15 membered heterocyclyl), wherein the $C_{1-12}$alkyl of $R^t$, the 3-15 membered heterocyclyl of the —C(O)-(3-15 membered heterocyclyl) of $R^t$, the $C_{1-12}$alkyl of the —C(O)NH($C_{1-12}$alkyl) of $R^t$, or the $C_{1-12}$alkyl of the —C(O)N($C_{1-12}$alkyl)$_2$ of $R^t$ is independently further optionally substituted with one or more OH, —$C_{1-12}$alkoxy, or —C(O)$NH_2$. In some embodiments, $R^h$ is 5-20 membered heteroaryl, wherein the 5-20 membered heteroaryl is independently optionally substituted with one or more $R^t$, wherein $R^t$ is OH, $NH_2$, or $C_{1-12}$alkyl, wherein the $C_{1-12}$alkyl of $R^t$ is further optionally substituted with one or more OH.

In some embodiments, the optionally substituted 5-20 membered heteroaryl of $R^h$ is an optionally substituted 5-16 membered heteroaryl. In other embodiments, the optionally substituted 5-20 membered heteroaryl of $R^h$ is an optionally substituted 5-11 membered heteroaryl. In still other embodiments, the optionally substituted 5-20 membered heteroaryl of $R^h$ is an optionally substituted 5-6 membered heteroaryl.

In some embodiments, $R^h$ is optionally substituted 5-6 membered heteroaryl, wherein the 5-6 membered heteroaryl is independently optionally substituted with one or more $R^t$, wherein $R^t$ is OH, $NH_2$, or $C_{1-12}$alkyl, wherein the $C_{1-12}$alkyl of $R^t$ is further optionally substituted with one or more OH. In some embodiments, $R^h$ is optionally substituted 5-6 membered heteroaryl, wherein the 5-6 membered heteroaryl is independently optionally substituted with one or more $R^t$, wherein $R^t$ is $C_{1-12}$alkyl, wherein the $C_{1-12}$alkyl of $R^t$ is further optionally substituted with one or more OH. In some embodiments, $R^h$ is optionally substituted pyrazolyl, wherein the pyrazolyl is independently optionally substituted with one or more $R^t$, wherein the $R^t$ is OH, $NH_2$, or $C_{1-12}$alkyl, wherein the $C_{1-12}$alkyl of $R^t$ is further optionally substituted with one or more OH. In some embodiments, $R^h$ is unsubstituted 5-6 membered heteroaryl. In some embodiments, $R^h$ is

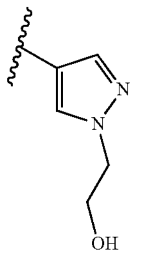

or

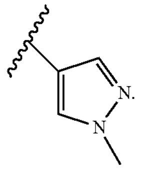

In some embodiments, provided herein is a compound of formula (I), (I-A), (I-A1), (I-A2), (I-A3), (I-A4), or (I-A5), or a stereoisomer or tautomer thereof, or a pharmaceutically acceptable salt of any of the foregoing, wherein $R^h$ is optionally substituted —C(O)$NH_2$. In certain embodiments, $R^h$ is unsubstituted —C(O)$NH_2$.

In some embodiments, provided herein is a compound of formula (I), or a stereoisomer or tautomer thereof, or a pharmaceutically acceptable salt of any of the foregoing, wherein $R^h$ is optionally substituted $C_{6-20}$aryl. In some embodiments, the $C_{6-20}$aryl of $R^h$ is optionally substituted with one or more OH, 5-20 membered heteroaryl, or —C(O)$NH_2$.

In some embodiments, provided herein is a compound of formula (I), or a stereoisomer or tautomer thereof, or a pharmaceutically acceptable salt of any of the foregoing, wherein $R^h$ is optionally substituted $C_{3-10}$cycloalkenyl. In some embodiments, the $C_{3-10}$cycloalkenyl of $R^h$ is optionally substituted with one or more oxo.

In some embodiments, provided herein is a compound of formula (I), such as a compound of formula (II), (III), (IV), or (V), or a stereoisomer or tautomer thereof, or a pharmaceutically acceptable salt of any of the foregoing, wherein $R^2$ is $C_{1-12}$alkyl, wherein the $C_{1-12}$alkyl is unsubstituted or is substituted with one or more $R^m$, wherein $R^m$ is OH, halo, cyano, oxo, $C_{1-12}$alkyl, $C_{1-12}$alkoxy, $C_{6-20}$aryloxy, —C(O)$NH_2$, —C(O)NH($C_{1-12}$alkyl), —C(O)N($C_{1-12}$alkyl)$_2$, —C(O)OH, —C(O)—$C_{1-12}$alkoxy, —C(O)-(3-15 membered heterocyclyl), $NH_2$, —NH($C_{1-12}$alkyl), —N($C_{1-12}$alkyl)$_2$, —NHC(O)—$C_{1-12}$alkyl, —NHC(O)—$NH_2$, —NH—$SO_2$—$C_{1-12}$alkyl, —S(O)—$C_{1-12}$alkyl, —S(O)$_2$—$C_{1-12}$alkyl, —S(O)$_2$—$NH_2$, $C_{3-10}$-cycloalkyl, or 3-15 membered heterocyclyl, wherein the $C_{1-12}$alkyl, $C_{1-12}$alkoxy, $C_{6-20}$aryloxy, the $C_{1-12}$alkyl of —C(O)NH($C_{1-12}$alkyl), the $C_{1-12}$alkyl of —C(O)N($C_{1-12}$alkyl)$_2$, —C(O)OH, —C(O)—$C_{1-12}$alkoxy, the 3-15 membered heterocyclyl of —C(O)-(3-15 membered heterocyclyl), $NH_2$, the $C_{1-12}$alkyl of —NH($C_{1-12}$alkyl), the $C_{1-12}$alkyl of —N($C_{1-12}$alkyl)$_2$, the $C_{1-12}$alkyl of —NHC(O)—$C_{1-12}$alkyl, —NHC(O)—$NH_2$, the $C_{1-12}$alkyl of —NH—$SO_2$—$C_{1-12}$alkyl, the $C_{1-12}$alkyl of —S(O)—$C_{1-12}$alkyl, the $C_{1-12}$alkyl of —S(O)$_2$—$C_{1-12}$alkyl, —S(O)$_2$—$NH_2$, $C_{3-10}$cycloalkyl, or 3-15 membered heterocyclyl of $R^m$ is further optionally substituted by one or more OH, halo, cyano, oxo, $C_{1-12}$alkyl, $C_{1-12}$alkoxy, —C(O)$NH_2$, —C(O)NH($C_{1-12}$alkyl), —C(O)N($C_{1-12}$alkyl)$_2$, C(O)OH, $NH_2$, —NH($C_{1-12}$alkyl), —N($C_{1-12}$alkyl)$_2$, $C_{3-10}$cycloalkyl, $C_{6-20}$aryl, 3-15 membered heterocyclyl, or 5-20 membered heteroaryl.

In certain embodiments, $R^2$ is $C_{1-12}$alkyl, wherein the $C_{1-12}$alkyl is unsubstituted or is substituted with one or more $R^m$, wherein $R^m$ is OH, cyano, —C(O)$NH_2$, —C(O)NH($C_{1-12}$alkyl), —C(O)N($C_{1-12}$alkyl)$_2$, $C_{3-10}$cycloalkyl, $C_{6-20}$aryl, or 5-20 membered heteroaryl, wherein the $C_{6-20}$aryl or 5-20 membered heteroaryl of $R^{m}$ is independently further optionally substituted with one or more halo or $C_{1-6}$alkyl.

In certain embodiments, $R^2$ is $C_{1-6}$alkyl, wherein the $C_{1-6}$alkyl is unsubstituted or is substituted with one or more $R^{m}$. In some embodiments, $R^2$ is unsubstituted $C_{1-6}$alkyl. In other embodiments, $R^2$ is $C_{1-6}$alkyl, wherein the $C_{1-6}$alkyl is substituted with one or more $R^{m}$. In some embodiments, $R^{m}$ is OH or —C(O)$NH_2$. In certain embodiments, $R^2$ is —$CH_2$—C(O)$NH_2$.

In some embodiments, provided herein is a compound of formula (I), such as a compound of formula (II), (III), (IV), or (V), or a stereoisomer or tautomer thereof, or a pharmaceutically acceptable salt of any of the foregoing, wherein $R^2$ is $C_{1-12}$alkyl or $C_{1-6}$alkyl, wherein the $C_{1-12}$alkyl or $C_{1-6}$alkyl is substituted with one to six $R^{m}$. In other embodiments, $R^2$ is $C_{1-12}$alkyl or $C_{1-6}$alkyl, wherein the $C_{1-12}$alkyl or $C_{1-6}$alkyl is substituted with one to five $R^{m}$. In some embodiments, $R^2$ is $C_{1-12}$alkyl or $C_{1-6}$alkyl, wherein the $C_{1-12}$alkyl or $C_{1-6}$alkyl is substituted with one to four $R^{m}$. In certain embodiments, $R^2$ is $C_{1-12}$alkyl or $C_{1-6}$alkyl, wherein the $C_{1-12}$alkyl or $C_{1-6}$alkyl is substituted with one to three $R^{m}$. In still other embodiments, $R^2$ is $C_{1-12}$alkyl or $C_{1-6}$alkyl, wherein the $C_{1-12}$alkyl or $C_{1-6}$alkyl is substituted with one to two $R^{m}$. In further embodiments, $R^2$ is $C_{1-12}$alkyl or $C_{1-6}$alkyl, wherein the $C_{1-12}$alkyl or $C_{1-6}$alkyl is substituted with one $R^{m}$.

In some embodiments, provided herein is a compound of formula (I), such as a compound of formula (II), (III), (IV), or (V), or a stereoisomer or tautomer thereof, or a pharmaceutically acceptable salt of any of the foregoing, wherein $R^2$ is optionally substituted $C_{3-10}$cycloalkenyl. In some embodiments, the $C_{3-10}$cycloalkenyl of $R^2$ is optionally substituted with one or more $R^{i}$, wherein $R^{i}$ is oxo, $NH_2$, —NH($C_{1-12}$alkyl), —N($C_{1-12}$alkyl)$_2$, or 3-15 membered heterocyclyl, wherein the 3-15 membered heterocyclyl of $R^{i}$, the $C_{1-12}$alkyl of the —NH($C_{1-12}$alkyl) of $R^{i}$, or the $C_{1-12}$alkyl of the —N($C_{1-12}$ alkyl)$_2$ of $R^{i}$ is independently optionally substituted with one or more OH or $C_{1-12}$alkoxy. In some embodiments, $R^2$ is $C_{3-10}$cycloalkenyl, wherein the $C_{3-10}$cycloalkenyl of $R^2$ is optionally substituted with one or more $R^{i}$, wherein $R^{i}$ is oxo or 3-15 membered heterocyclyl, wherein the 3-15 membered heterocyclyl of $R^{i}$ is optionally substituted with one or more OH. In certain embodiments, $R^2$ is $C_{3-10}$ cycloalkenyl optionally substituted with one or more $R^{i}$, wherein $R^{i}$ is oxo. In other embodiments, $R^2$ is $C_{3-10}$cycloalkenyl optionally substituted with one or more $R^{i}$, wherein $R^{i}$ is 3-15 membered heterocyclyl, wherein the 3-15 membered heterocyclyl of $R^{i}$ is optionally substituted with one or more OH.

In some embodiments, the optionally substituted $C_{3-10}$cycloalkenyl is an optionally substituted $C_{3-8}$cycloalkenyl. In other embodiments, the optionally substituted $C_{3-10}$cycloalkenyl is an optionally substituted $C_{3-6}$cycloalkenyl. In some embodiments, the optionally substituted $C_{3-10}$ cycloalkenyl is optionally substituted cyclobutenyl. In certain embodiments, the cyclobutenyl is substituted with one or more oxo or 3-15 membered heterocyclyl, wherein the 3-15 membered heterocyclyl is optionally substituted with one or more OH. In one embodiment, $R^2$ is

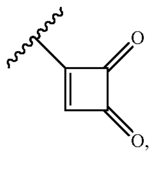 [SMILES: *c1cc(=O)c1=O]

, wherein the

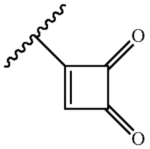 [SMILES: *c1cc(=O)c1=O]

is further optionally substituted with one or more 3-15 membered heterocyclyl, wherein the 3-15 membered heterocyclyl is optionally substituted with one or more OH. In some embodiments, $R^2$ is

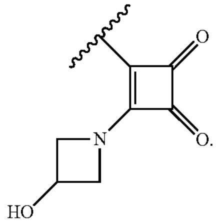 [SMILES: *c1c(N2CC(O)C2)c(=O)c1=O]

.

In some embodiments, provided herein is a compound of formula (I), such as a compound of formula (II), (III), (IV), or (V), or a stereoisomer or tautomer thereof, or a pharmaceutically acceptable salt of any of the foregoing, wherein $R^2$ is optionally substituted 5-20 membered heteroaryl. In some embodiments, $R^2$ is unsubstituted 5-20 membered heteroaryl. In other embodiments, $R^2$ is 5-20 membered heteroaryl, wherein the 5-20 membered heteroaryl is substituted with one or more OH, $NH_2$, $C_{1-12}$alkyl, or $C_{1-12}$alkoxy. In some embodiments, $R^2$ is 5-20 membered heteroaryl, wherein the 5-20 membered heteroaryl is substituted with one or more OH, $NH_2$, or $C_{1-12}$alkyl. In some embodiments, the optionally substituted 5-20 membered heteroaryl is optionally substituted 5-16 membered heteroaryl. In other embodiments, the optionally substituted 5-20 membered heteroaryl is optionally substituted 5-12 membered heteroaryl. In still other embodiments, the optionally substituted 5-20 membered heteroaryl is optionally substituted 5-10 membered heteroaryl. In other embodiments, the optionally substituted 5-20 membered heteroaryl is optionally substituted 5-8 membered heteroaryl. In some embodiments, the optionally substituted 5-20 membered heteroaryl is optionally substituted 5-6 membered heteroaryl. In other embodiments, the optionally substituted 5-20 membered heteroaryl is optionally substituted 5-membered heteroaryl. In some embodiments, the optionally substituted 5-20 membered heteroaryl is optionally substituted azolyl. In certain embodiments, the optionally substituted 5-20 membered heteroaryl is optionally substituted thiadiazolyl or optionally substituted thiazolyl. In some embodiments, the optionally substituted 5-20 membered heteroaryl is

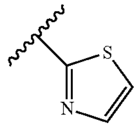

or

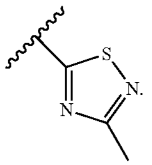

.

In some embodiments, the thiadiazolyl or thiazolyl is optionally substituted with one or more OH, $NH_2$, or $C_{1-12}$alkyl. In other embodiments, the optionally substituted 5-20 membered heteroaryl is optionally substituted tetrazolyl. In some embodiments, the optionally substituted 5-20 membered heteroaryl is

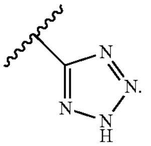 [SMILES: *c1nn[nH]n1]

In some embodiments, provided herein is a compound of formula (I), such as a compound of formula (II), (III), (IV), or (V), or a stereoisomer or tautomer thereof, or a pharmaceutically acceptable salt of any of the foregoing, wherein $R^2$ is optionally substituted 3-15 membered heterocyclyl. In certain embodiments, $R^2$ is unsubstituted 3-15 membered heterocyclyl. In other embodiments, $R^2$ is 3-15 membered heterocyclyl, wherein the 3-15 membered heterocyclyl is substituted with one or more OH, oxo, $NH_2$, or $C_{1-12}$alkyl. In certain embodiments, In other embodiments, $R^2$ is 3-15 membered heterocyclyl, wherein the 3-15 membered heterocyclyl is substituted with one or more OH, oxo, or $NH_2$. In some embodiments, the optionally substituted 3-15 membered heterocyclyl is optionally substituted 3-10 membered heterocyclyl. In still other embodiments, the optionally substituted 3-15 membered heterocyclyl is optionally substituted 3-8 membered heterocyclyl. In other embodiments, the optionally substituted 3-15 membered heterocyclyl is optionally substituted 3-6 membered heterocyclyl. In certain embodiments, the optionally substituted 3-15 membered heterocyclyl is optionally substituted 5-6 membered heterocyclyl. In some embodiments, the optionally substituted 3-15 membered heterocyclyl is optionally substituted 6-membered heterocyclyl. In some embodiments, the optionally substituted 3-15 membered heterocyclyl is optionally substituted dihydropyrimidinyl. In some embodiments, the dihydropyrimidinyl is optionally substituted with one or more oxo, OH, or $NH_2$. In some embodiments, the optionally substituted 3-15 membered heterocyclyl is

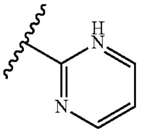,
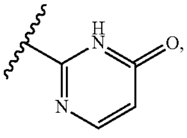,
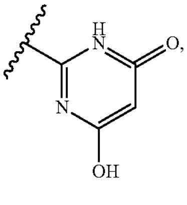,
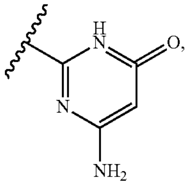,
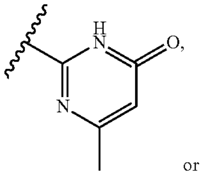,
or
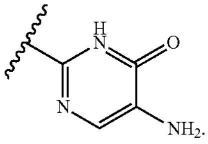.

In some embodiments, the the optionally substituted 3-15 membered heterocyclyl is

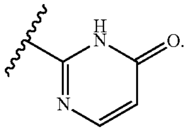 [SMILES: *c1nccc(=O)[nH]1].

In other embodiments, the optionally substituted 3-15 membered heterocyclyl is optionally substituted dihydrooxadiazolyl. In certain embodiments, the dihydrooxadiazolyl is substituted with one or more oxo. In some embodiments, the optionally substituted 3-15 membered heterocyclyl is

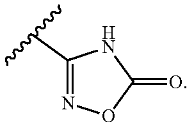 [SMILES: *c1noc(=O)[nH]1].

In some embodiments, provided herein is a compound of formula (I), such as a compound of formula (II), (III), (IV), or (V), or a stereoisomer or tautomer thereof, or a pharmaceutically acceptable salt of any of the foregoing, wherein $R^2$ is optionally substituted amidinyl. In some embodiments, $R^2$ is unsubstituted amidinyl. In other embodiments, $R^2$ is amidinyl, wherein the amidinyl is substituted with one or more $R^s$, wherein $R^s$ is OH, cyano, $C_{1-12}$alkyl, —C(O)—$C_{1-12}$alkyl, —C(O)—$C_{1-12}$alkoxy, $C_{6-20}$aryloxy, or —$SO_2$—$C_{1-12}$alkyl. In certain embodiments, $R^2$ is amidinyl, wherein the amidinyl is substituted with one or more $R^s$, wherein $R^s$ is cyano, $C_{1-12}$alkyl, or —C(O)—$C_{1-12}$alkoxy. In some embodiments, $R^2$ is

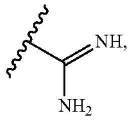,
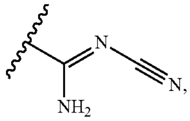,
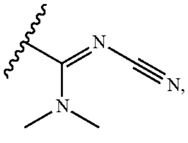, or
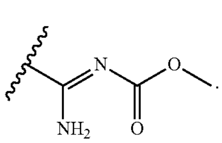.

In some embodiments, $R^2$ is

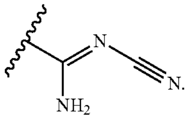.

In some embodiments, provided herein is a compound of formula (I), or a stereoisomer or tautomer thereof, or a pharmaceutically acceptable salt of any of the foregoing, wherein $R^2$ is optionally substituted sulfonyl. In some embodiments, $R^2$ is unsubstituted sulfonyl. In other embodiments, $R^2$ is sulfonyl, wherein the sulfonyl is substituted with one or more $R^u$, wherein $R^u$ is $C_{1-12}$alkyl, $NH_2$, —NH($C_{1-12}$alkyl), —N($C_{1-12}$alkyl)$_2$, or $C_{6-20}$aryl, wherein the $C_{1-12}$alkyl or $C_{6-20}$aryl of $R^u$ is independently further optionally substituted with one or more halo or $C_{1-12}$alkoxy. In certain embodiments, $R^2$ is sulfonyl, wherein the sulfonyl is substituted with one or more $R^u$, wherein $R^u$ is $C_{1-12}$alkyl or —N($C_{1-12}$alkyl)$_2$. In some embodiments, $R^2$ is optionally substituted sulfonyl, wherein the optionally substituted sulfonyl is

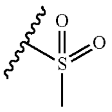
or
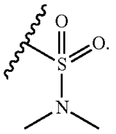

In some embodiments, provided herein is a compound of formula (I), such as a compound of formula (II), (III), (IV), or (V), or a stereoisomer or tautomer thereof, or a pharmaceutically acceptable salt of any of the foregoing, wherein $R^2$ is cyano.

In some embodiments, provided herein is a compound, such as a compound of formula (I), (II), (III), (IV), (V), (I-A), (I-A1), (I-A2), (I-A3), (I-A4), (I-A5), (I-B), (I-B1), (I-B32), (I-B33), (I-B34), (I-B5), or (I-C), or a stereoisomer or tautomer thereof, or a pharmaceutically acceptable salt of any of the foregoing, wherein $R^3$ and $R^4$ are each independently H, optionally substituted $C_{1-12}$alkyl, optionally substituted —C(O)$NH_2$, or optionally substituted —C(O)—$C_{1-12}$alkoxy. In certain embodiments, one of $R^3$ and $R^4$ is H, and the other of $R^3$ and $R^4$ is optionally substituted $C_{1-12}$alkyl, optionally substituted —C(O)$NH_2$, or optionally substituted —C(O)—$C_{1-12}$alkoxy. In certain embodiments, one of $R^3$ and $R^4$ is H, and the other of $R^3$ and $R^4$ is $C_{1-4}$alkyl optionally substituted with OH, optionally substituted —C(O)$NH_2$, or $CO_2$—$C_{1-6}$alkyl. In certain embodiments, one of $R^3$ and $R^4$ is H, and the other of $R^3$ and $R^4$ is methyl, —$CH_2$—OH, —C(O)NHMe, or —C(O)$_2$Me. In certain embodiments, $R^3$ and $R^4$ are both methyl. In certain embodiments, provided herein is a compound, such as a compound of formula (I), (I-A), (I-A1), (I-A2), (I-A3), (I-A4), (I-A5), (I-B), (I-B1), (I-B2), (I-B3), (I-B4), (I-B5), or (I-C), or a stereoisomer or tautomer thereof, or a pharmaceutically acceptable salt of any of the foregoing, wherein $R^3$ and $R^4$ are each independently H.

In certain embodiments, provided herein is a compound of formula (I) or (I-B), or a pharmaceutically acceptable salt of any of the foregoing, wherein $R^3$ and $R^4$ are each independently H, such that the compound of formula (I) or (I-B) is a compound of formula (I-B6):

(I-B6)

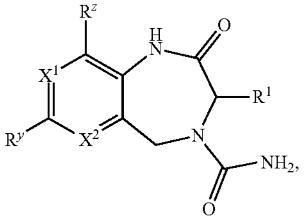

or a stereoisomer or tautomer thereof, or a pharmaceutically acceptable salt of any of the foregoing.

In certain embodiments, provided herein is a compound, such as a compound of formula (I), (II), (III), (IV), (V), (I-A), (I-A1), (I-A2), (I-A3), (I-A4), (I-A5), (I-B), (I-B1), (I-B32), (I-B33), (I-B4), (I-B5), (I-B6), or (I-C), or a stereoisomer or tautomer thereof, or a pharmaceutically acceptable salt of any of the foregoing, wherein $R^1$ is $C_{3-12}$alkyl, $C_{2-12}$alkenyl, $C_{2-12}$alkynyl, $C_{3-10}$-cycloalkyl, $C_{3-10}$cycloalkenyl, or

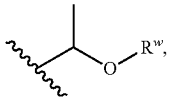

wherein $R^w$ is optionally substituted $C_{1-12}$alkyl. In some embodiments, $R^1$ is $C_{3-12}$alkyl or $C_{3-10}$-cycloalkyl. In certain embodiments, $R^1$ is $C_{3-6}$alkyl or $C_{3-8}$ cycloalkyl. In some embodiments, $C_{3-8}$cycloalkyl. In some embodiments, $R^1$ is $C_{3-6}$alkyl. In certain embodiments, $R^1$ is sec-butyl or i-propyl. In some embodiments, $R^1$ is sec-butyl. In other embodiments, $R^1$ is i-propyl. In some embodiments, $R^1$ is

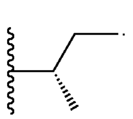 [SMILES: *[C@@H](C)CC]

In some embodiments, $R^1$ is

In certain embodiments, provided herein is a compound of formula (I), (I-B), or (I-B6), or a stereoisomer or tautomer thereof, or a pharmaceutically acceptable salt of any of the foregoing, wherein $R^1$ is sec-butyl, such that the compound of formula (I), (I-B), or (I-B6) is a compound of formula (I-B7):

(I-B7)

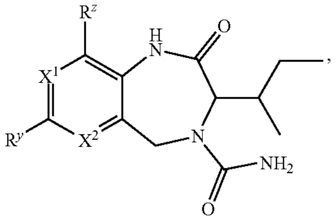

or a stereoisomer or tautomer thereof, or a pharmaceutically acceptable salt of any of the foregoing.

In certain embodiments, provided herein is a compound of formula (I), (I-B), (I-B6), or (I-B7), or a stereoisomer or tautomer thereof, or a pharmaceutically acceptable salt of any of the foregoing, wherein $R^1$ is (S)-sec-butyl, such that the compound of formula (I), (I-B), (I-B6), or (I-B7) is a compound of formula (I-B7):

(I-B8)

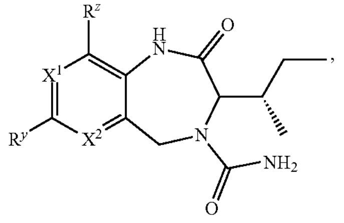

or a stereoisomer or tautomer thereof, or a pharmaceutically acceptable salt of any of the foregoing.

In some embodiments, provided herein is a compound of formula (I-B8), or a stereoisomer or tautomer thereof, or a pharmaceutically acceptable salt of any of the foregoing, wherein $X^1$ is N and $X^2$ is C—$R^x$, wherein $R^x$ is as defined above for formula (I). In other embodiments, provided herein is a compound of formula (I) or (I-B), or a stereoisomer or tautomer thereof, or a pharmaceutically acceptable salt of any of the foregoing, wherein $X^1$ is C—$R^x$ and $X^2$ is N. In still other embodiments, provided herein is a compound of formula (I) or (I-B), or a stereoisomer or tautomer thereof, or a pharmaceutically acceptable salt of any of the foregoing, wherein $X^1$ and $X^2$ are each independently C—$R^x$. In some embodiments, provided herein is a compound of formula (I) or (I-B), or a stereoisomer or tautomer thereof, or a pharmaceutically acceptable salt of any of the foregoing, wherein $X^1$ and $X^2$ are each independently N. In certain embodiments, provided herein is a compound of formula (I) or (I-B), or a stereoisomer or tautomer thereof, or a pharmaceutically acceptable salt of any of the foregoing, wherein the compound of formula (I-B8) is a compound of formula (I-B8-1), (I-B8-2), (I-B8-3), or (I-B8-4):

(I-B8-1)

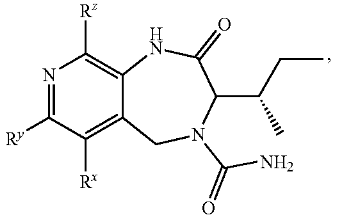

(I-B8-2)

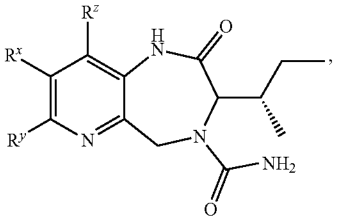

(I-B8-3)

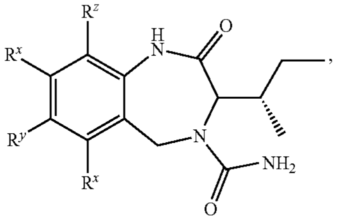

-continued (I-B8-4)

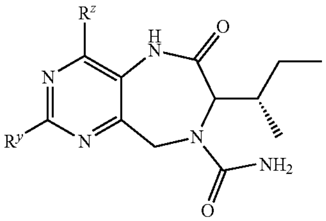

or a stereoisomer or tautomer thereof, or a pharmaceutically acceptable salt of any of the foregoing.

In some embodiments of the compounds of formula (I-B), (I-B8-1), (I-B8-2), (I-B8-3), or (I-B8-4), each $R^x$ is independently H, halo, or $C_{3-10}$cycloalkyl. In other embodiments, each $R^x$ is independently H or halo. In some embodiments, the halo is fluoro, chloro, or bromo. In certain embodiments, the halo is fluoro. In some embodiments, each $R^x$ is independently H. In some embodiments, wherein $X^1$ and $X^2$ are each independently C—$R^x$, such as in a compound of formula (I-B) or (I-B4), each $R^x$ is independently H. In other embodiments, wherein $X^1$ and $X^2$ are each independently C—$R^x$, such as in a compound of formula (I-B) or (I-B4), each $R^x$ is independently halo. In certain embodiments, wherein $X^1$ and $X^2$ are each independently C—$R^x$, such as in a compound of formula (I-B) or (I-B4), each $R^x$ is independently fluoro. In some embodiments, one $R^x$ is H and the other $R^x$ is halo. In some embodiments, one $R^x$ is H and the other $R^x$ is fluoro. In some embodiments, each $R^x$ is independently H.

In some embodiments, provided herein is a compound of formula (I), such as a compound of formula (II), (III), (IV), or (V), or a stereoisomer or tautomer thereof, or a pharmaceutically acceptable salt of any of the foregoing, wherein $R^2$ and $R^3$ are taken together with the atoms to which they are attached to form a 5- or 6-membered heterocyclyl or 5- or 6-membered heteroaryl, wherein the 5- or 6-membered heterocyclyl or 5- or 6-membered heteroaryl independently comprises two or more annular heteroatoms and is independently optionally substituted. In some embodiments, $R^2$ and $R^3$ are taken together with the atoms to which they are attached to form an unsubstituted 5- or 6-membered heterocyclyl or unsubstituted 5- or 6-membered heteroaryl, wherein the unsubstituted 5- or 6-membered heterocyclyl or unsubstituted 5- or 6-membered heteroaryl independently comprises two or more annular heteroatoms. In other embodiments, $R^2$ and $R^3$ are taken together with the atoms to which they are attached to form a 5- or 6-membered heterocyclyl or 5- or 6-membered heteroaryl, wherein the 5- or 6-membered heterocyclyl or 5- or 6-membered heteroaryl independently comprises two or more annular heteroatoms and is independently substituted with one or more oxo or OH.

In some embodiments, the 5- or 6-membered heterocyclyl is fully saturated. In other embodiments, the 5- or 6-membered heterocyclyl is partially unsaturated. It is to be understood that, in some embodiments, $R^4$ may be absent in order to satisfy the valence requirements of the ring-forming atoms. For example, in certain embodiments, $R^4$ may be absent if the 5- or 6-membered heterocyclyl or 5- or 6-membered heteroaryl formed by $R^2$ and $R^3$ is partially unsaturated or fully unsaturated.

In certain embodiments, $R^2$ and $R^3$ are taken together with the atoms to which they are attached to form a 5- or 6-membered heterocyclyl, wherein the 5- or 6-membered heterocyclyl independently comprises two or more annular heteroatoms and is independently optionally substituted. In other embodiments, $R^2$ and $R^3$ are taken together with the atoms to which they are attached to form a 5- or 6-membered heteroaryl, wherein the 5- or 6-membered heteroaryl independently comprises two or more annular heteroatoms and is independently optionally substituted. In some embodiments, $R^2$ and $R^3$ are taken together with the atoms to which they are attached to form a 5-membered heterocyclyl or 5-membered heteroaryl, wherein the 5-membered heterocyclyl or 5-membered heteroaryl independently comprises two or more annular heteroatoms and is independently optionally substituted.

In some embodiments, $R^2$ and $R^3$ are taken together with the atoms to which they are attached to form a 5-membered heterocyclyl, wherein the 5-membered heterocyclyl independently comprises two or more annular heteroatoms and is independently optionally substituted. In some embodiments, the 5-membered heterocyclyl is unsubstituted. In other embodiments, the 5-membered heterocyclyl is substituted with one or more oxo or OH. In other embodiments, $R^2$ and $R^3$ are taken together with the atoms to which they are attached to form a 5-membered heteroaryl, wherein the 5-membered heteroaryl independently comprises two or more annular heteroatoms and is independently optionally substituted. In some embodiments, the 5-membered heteroaryl is unsubstituted. In other embodiments, the 5-membered heteroaryl is substituted with one or more OH.

In some embodiments, $R^2$ and $R^3$ are taken together with the atoms to which they are attached to form a 5- or 6-membered heterocyclyl or 5- or 6-membered heteroaryl, wherein the 5- or 6-membered heterocyclyl or 5- or 6-membered heteroaryl independently comprises between two and four annular heteroatoms and is independently optionally substituted. In other embodiments, the 5- or 6-membered heterocyclyl or 5- or 6-membered heteroaryl independently comprises between two and three annular heteroatoms. In some embodiments, the 5- or 6-membered heterocyclyl or 5- or 6-membered heteroaryl independently comprises four annular heteroatoms. In other embodiments, the 5- or 6-membered heterocyclyl or 5- or 6-membered heteroaryl independently comprises between three annular heteroatoms. In still other embodiments, the 5- or 6-membered heterocyclyl or 5- or 6-membered heteroaryl independently comprises two annular heteroatoms. In some embodiments, the 5- or 6-membered heterocyclyl or 5- or 6-membered heteroaryl comprises two nitrogen atoms. In other embodiments, the 5- or 6-membered heterocyclyl or 5- or 6-membered heteroaryl comprises one nitrogen atom and one oxygen atom.

In some embodiments, provided herein is a compound of formula (I) or (II), or a stereoisomer or tautomer thereof, or a pharmaceutically acceptable salt of any of the foregoing, wherein $X^1$ and $X^2$ are each C—$R^x$, and $R^2$ and $R^3$ are taken together with the atoms to which they are attached to form a 5- or 6-membered heterocyclyl or 5- or 6-membered heteroaryl, wherein the 5- or 6-membered heterocyclyl or 5- or 6-membered heteroaryl independently comprises two or more annular heteroatoms and is independently optionally substituted.

In some embodiments, provided herein is a compound of formula (I) or (II), or a stereoisomer or tautomer thereof, or a pharmaceutically acceptable salt of any of the foregoing, wherein $X^1$ and $X^2$ are each C—$R^x$, and $R^2$ and $R^3$ are taken together with the atoms to which they are attached to form a 5-membered heterocyclyl or 5-membered heteroaryl, wherein the 5-membered heterocyclyl or 5-membered heteroaryl independently comprises two or more annular heteroatoms and is independently optionally substituted, such that the compound of formula (I) or (II) is a compound of formula (I-D):

(I-D)

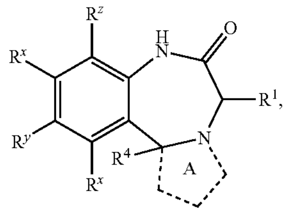

or a a stereoisomer or tautomer thereof, or a pharmaceutically acceptable salt of any of the foregoing, wherein: ring A is the 5-membered heterocyclyl or 5-membered heteroaryl, wherein the 5-membered heterocyclyl or 5-membered heteroaryl independently comprises two or more annular heteroatoms and is independently optionally substituted; and $R^x$, $R^y$, $R^z$, $R^1$, and $R^4$ are as defined above for the compound of formula (I).

In some embodiments of the compound of formula (I-D), ring A is

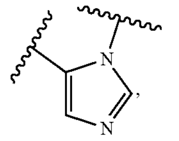 [SMILES: *c1cncn1*]

wherein the

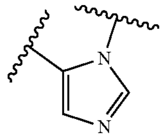 [SMILES: *c1cncn1*]

is optionally substituted with one or more OH, and $R^4$ is absent. In some embodiments, ring A is

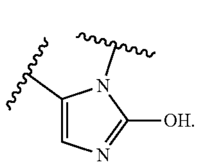 [SMILES: *c1cnc(O)n1*]

In other embodiments, ring A is

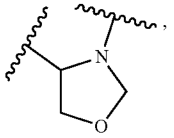 [SMILES: *C1COCN1*]

wherein the

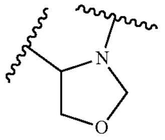 [SMILES: *C1COCN1*]

is optionally substituted with one or more oxo or OH, and $R^4$ is H. In some embodiments, ring A is

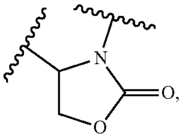 [SMILES: *C1COC(=O)N1*]

and $R^4$ is H.

In certain embodiments, provided herein is a compound, such as a compound of formula (I), (II), (III), (IV), (V), (I-A), (I-A1), (I-A2), (I-A3), (I-A4), (I-A5), (I-B), (I-B1), (I-B32), (I-B33), (I-B4), (I-B5), (I-B6), (I-B7), (I-B8), (I-C), or (I-D), or a stereoisomer or tautomer thereof, or a pharmaceutically acceptable salt of any of the foregoing, wherein $R^y$ and $R^z$ are independently H, halo, $C_{3-10}$cycloalkyl, $C_{3-10}$cycloalkenyl, or $C_{6-20}$aryl. In certain embodiments, $R^y$ and $R^z$ are independently H, halo, or $C_{3-10}$cycloalkyl. In other embodiments, $R^y$ and $R^z$ are independently H or halo. In some embodiments, one of $R^y$ and $R^z$ is H and the other of $R^y$ and $R^z$ is halo. In some embodiments, $R^y$ and $R^z$ are independently H or fluoro. In some embodiments, one of $R^y$ and $R^z$ is H and the other of $R^y$ and $R^z$ is fluoro. In certain embodiments, $R^y$ and $R^z$ are both H.

In some embodiments, provided herein is a compound, such as a compound of formula (I), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, wherein $X^1$ and $X^2$ are each C—$R^x$, wherein each $R^x$ is H, $R^y$ is H, and $R^z$ is H. In other embodiments, $X^1$ and $X^2$ are each C—$R^x$, wherein each $R^x$ is fluoro, $R^y$ is H, and $R^z$ is H. In other embodiments, $X^1$ and $X^2$ are each C—$R^x$, wherein each $R^x$ is H, $R^y$ is fluoro, and $R^z$ is H. In some embodiments, $X^1$ is N, $X^2$ is C—$R^x$, wherein $R^x$ is fluoro, $R^y$ is H, and $R^z$ is H. In certain embodiments, $X^1$ is N, $X^2$ is N, $R^y$ is H, and $R^z$ is H. In certain embodiments, $X^1$ is N, $X^2$ is C—$R^x$, wherein $R^x$ is H, $R^y$ is H, and $R^z$ is H. In some embodiments, $X^1$ is C—$R^x$, wherein $R^x$ is fluoro, $X^2$ is N, $R^y$ is H, and $R^z$ is H.

In some embodiments, provided herein is a compound, or a stereoisomer or tautomer thereof, or a pharmaceutically acceptable salt of any of the foregoing, wherein the compound is selected from Table 2.

TABLE 2

| Compound No. | Compound Structure | Compound Name |
|---|---|---|
| 1 | 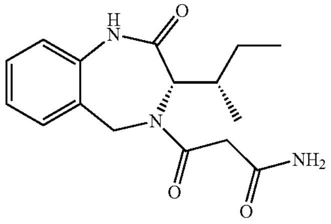 [SMILES: CC[C@H](C)[C@H]1C(=O)Nc2ccccc2CN1C(=O)CC(N)=O] | 3-((S)-3-((S)-sec-butyl)-2-oxo-1,2,3,5-tetrahydro-4H-benzo[e][1,4]diazepin-4-yl)-3-oxopropanamide |
| 2 | 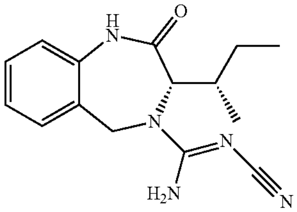 [SMILES: CC[C@H](C)[C@H]1C(=O)Nc2ccccc2CN1/C(N)=N/C#N] | (S,E)-3-((S)-sec-butyl)-N'-cyano-2-oxo-1,2,3,5-tetrahydro-4H-benzo[e][1,4]diazepine-4-carboximidamide |
| 3 | 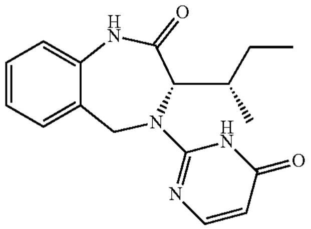 [SMILES: CC[C@H](C)[C@H]1C(=O)Nc2ccccc2CN1c1nccc(=O)[nH]1] | (S)-3-((S)-sec-butyl)-4-(6-oxo-1,6-dihydropyrimidin-2-yl)-1,3,4,5-tetrahydro-2H-benzo[e][1,4]diazepin-2-one |

TABLE 2-continued

| Compound No. | Compound Structure | Compound Name |
|---|---|---|
| 4 | 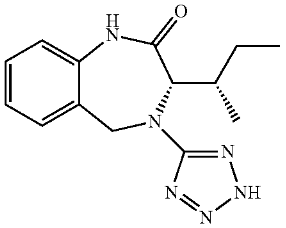 [SMILES: CC[C@H](C)[C@H]1C(=O)Nc2ccccc2CN1c1nn[nH]n1] | (S)-3-((S)-sec-butyl)-4-(2H-tetrazol-5-yl)-1,3,4,5-tetrahydro-2H-benzo[e][1,4]diazepine-2-one |
| 5 | 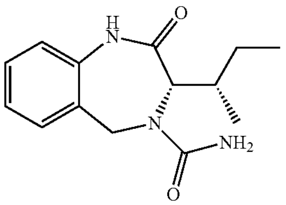 [SMILES: CC[C@H](C)[C@H]1C(=O)Nc2ccccc2CN1C(N)=O] | (S)-3-((S)-sec-butyl)-2-oxo-1,2,3,5-tetrahydro-4H-benzo[e][1,4]diazepine-4-carboxamide |
| 6 | 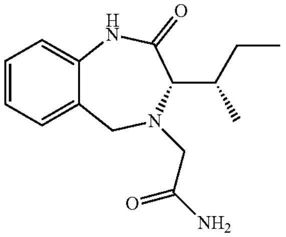 [SMILES: CC[C@H](C)[C@H]1C(=O)Nc2ccccc2CN1CC(N)=O] | 2-((S)-3-((S)-sec-butyl)-2-oxo-1,2,3,5-tetrahydro-4H-benzo[e][1,4]diazepin-4-yl)acetamide |
| 7 | 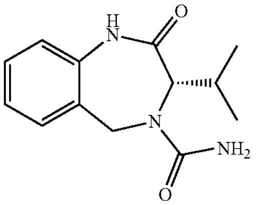 [SMILES: CC(C)[C@H]1C(=O)Nc2ccccc2CN1C(N)=O] | (S)-3-isopropyl-2-oxo-1,2,3,5-tetrahydro-4H-benzo[e][1,4]diazepine-4-carboxamide |
| 8 | 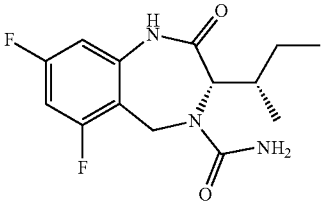 [SMILES: CC[C@H](C)[C@H]1C(=O)Nc2cc(F)cc(F)c2CN1C(N)=O] | (S)-3-((S)-sec-butyl)-6,8-difluoro-2-oxo-1,2,3,5-tetrahydro-4H-benzo[e][1,4]diazepine-4-carboxamide |
| 9 | 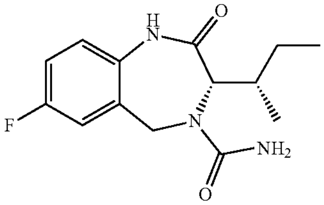 [SMILES: CC[C@H](C)[C@H]1C(=O)Nc2ccc(F)cc2CN1C(N)=O] | (S)-3-((S)-sec-butyl)-7-fluoro-2-oxo-1,2,3,5-tetrahydro-4H-benzo[e][1,4]diazepine-4-carboxamide |
| 10 | 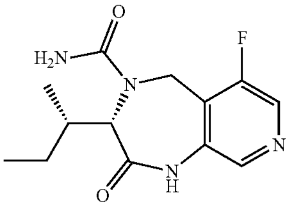 [SMILES: CC[C@H](C)[C@H]1C(=O)Nc2cncc(F)c2CN1C(N)=O] | (S)-3-((S)-sec-butyl)-6-fluoro-2-oxo-1,2,3,5-tetrahydro-4H-pyrido[3,4-e][1,4]diazepine-4-carboxamide |

TABLE 2-continued

| Compound No. | Compound Structure | Compound Name |
|---|---|---|
| 11 | 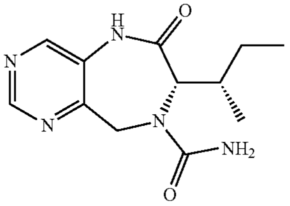 [SMILES: CC[C@H](C)[C@H]1C(=O)Nc2cncnc2CN1C(N)=O] | (S)-7-((S)-sec-butyl)-6-oxo-5,6,7,9-tetrahydro-8H-pyrimido[5,4-e][1,4]diazepine-8-carboxamide |
| 12 | 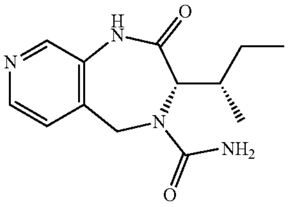 [SMILES: CC[C@H](C)[C@H]1C(=O)Nc2cnccc2CN1C(N)=O] | (S)-3-((S)-sec-butyl)-2-oxo-1,2,3,5-tetrahydro-4H-pyrido[3,4-e][1,4]diazepine-4-carboxamide |
| 13 | 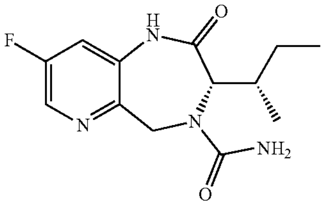 [SMILES: CC[C@H](C)[C@H]1C(=O)Nc2cc(F)cnc2CN1C(N)=O] | (S)-3-((S)-3-sec-butyl)-8-fluoro-2-oxo-1,2,3,5-tetrahydro-4H-pyrido[3,2-e][1,4]diazepine-4-carboxamide |
| 14 | 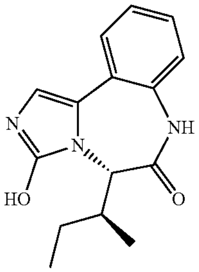 | (S)-5-((S)-sec-butyl)-3-hydroxy-5H-benzo[f]imidazo[1,5-d][1,4]diazepin-6(7H)-one |
| 15 | 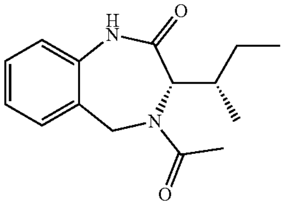 [SMILES: CC[C@H](C)[C@H]1C(=O)Nc2ccccc2CN1C(C)=O] | (S)-4-acetyl-3-((S)-sec-butyl)-1,3,4,5-tetrahydro-2H-benzo[e][1,4]diazepin-2-one |
| 16 | 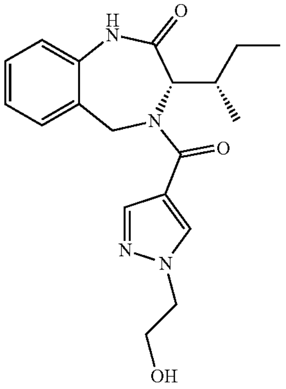 [SMILES: CC[C@H](C)[C@H]1C(=O)Nc2ccccc2CN1C(=O)c1cnn(CCO)c1] | (S)-3-((S)-sec-butyl)-4-(1-(2-hydroxyethyl)-1H-pyrazole-4-carbonyl)-1,3,4,5-tetrahydro-2H-benzo[e][1,4]diazepin-2-one |

TABLE 2-continued

| Compound No. | Compound Structure | Compound Name |
|---|---|---|
| 17 | 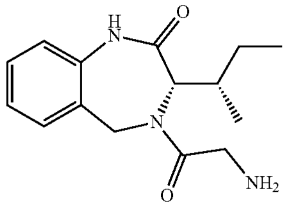 [SMILES: CC[C@H](C)[C@H]1C(=O)Nc2ccccc2CN1C(=O)CN] | (S)-3-((S)-sec-butyl)-4-glycyl-1,3,4,5-tetrahydro-2H-benzo[e][1,4]diazepin-2-one |
| 18 | 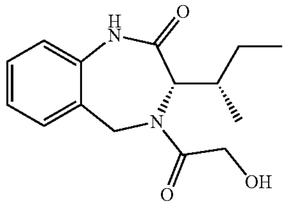 [SMILES: CC[C@H](C)[C@H]1C(=O)Nc2ccccc2CN1C(=O)CO] | (S)-3-((S)-sec-butyl)-4-(2-hydroxyacetyl)-1,3,4,5-tetrahydro-2H-benzo[e][1,4]diazepin-2-one |
| 19 | 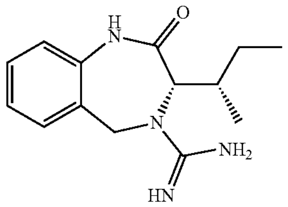 [SMILES: CC[C@H](C)[C@H]1C(=O)Nc2ccccc2CN1C(=N)N] | (S)-3-((S)-sec-butyl)-2-oxo-1,2,3,5-tetrahydro-4H-benzo[e][1,4]diazepine-4-carboximidamide |
| 20 | 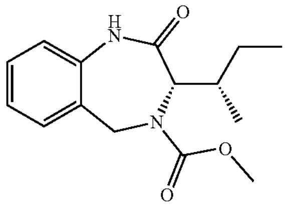 [SMILES: CC[C@H](C)[C@H]1C(=O)Nc2ccccc2CN1C(=O)OC] | methyl (S)-3-((S)-sec-butyl)-2-oxo-1,2,3,5-tetrahydro-4H-benzo[e][1,4]diazepine-4-carboxylate |
| 21 | 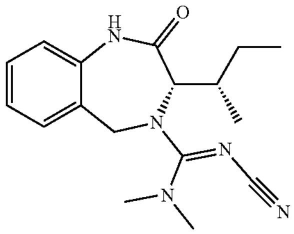 [SMILES: CC[C@H](C)[C@H]1C(=O)Nc2ccccc2CN1/C(=N/C#N)N(C)C] | (S,E)-3-((S)-sec-butyl)-N'-cyano-N,N-dimethyl-2-oxo-1,2,3,5-tetrahydro-4H-benzo[e][1,4]diazepine-4-carboximidamide |
| 22 | 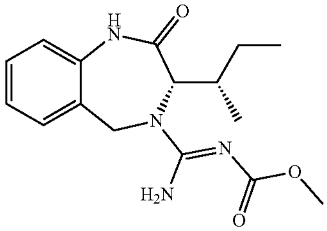 [SMILES: CC[C@H](C)[C@H]1C(=O)Nc2ccccc2CN1/C(N)=N/C(=O)OC] | methyl ((E)-amino((S)-3-((S)-sec-butyl)-2-oxo-1,2,3,5-tetrahydro-4H-benzo[e][1,4]diazepin-4-yl)methylene)carbamate |

TABLE 2-continued

| Compound No. | Compound Structure | Compound Name |
|---|---|---|
| 23 | 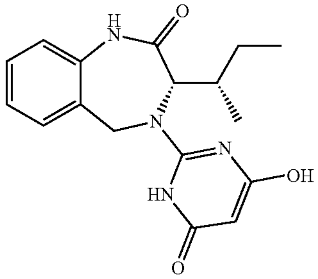 [SMILES: CC[C@H](C)[C@H]1C(=O)Nc2ccccc2CN1c1nc(O)cc(=O)[nH]1] | (S)-3-((S)-sec-butyl)-4-(4-hydroxy-6-oxo-1,6-dihydropyrimidin-2-yl)-1,3,4,5-tetrahydro-2H-benzo[e][1,4]diazepin-2-one |
| 24 | 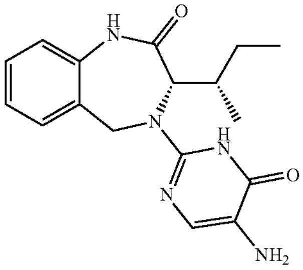 [SMILES: CC[C@H](C)[C@H]1C(=O)Nc2ccccc2CN1c1ncc(N)c(=O)[nH]1] | (S)-4-(5-amino-6-oxo-1,6-dihydropyrimidin-2-yl)-3-((S)-sec-butyl)-1,3,4,5-tetrahydro-2H-benzo[e][1,4]diazepin-2-one |
| 25 | 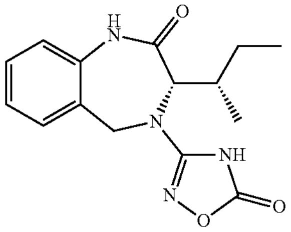 [SMILES: CC[C@H](C)[C@H]1C(=O)Nc2ccccc2CN1c1noc(=O)[nH]1] | 3-((S)-3-((S)-sec-butyl)-2-oxo-1,2,3,5-tetrahydro-4H-benzo[e][1,4]diazepin-4-yl)-1,2,4-oxadiazol-5(4H)-one |
| 26 | 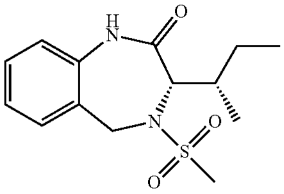 [SMILES: CC[C@H](C)[C@H]1C(=O)Nc2ccccc2CN1S(C)(=O)=O] | (S)-3-((S)-sec-butyl)-4-(methylsulfonyl)-1,3,4,5-tetrahydro-2H-benzo[e][1,4]diazepin-2-one |
| 27 | 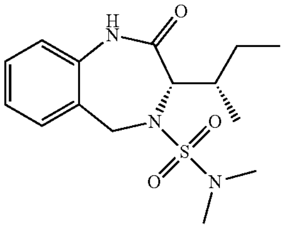 [SMILES: CC[C@H](C)[C@H]1C(=O)Nc2ccccc2CN1S(=O)(=O)N(C)C] | (S)-3-((S)-sec-butyl)-N,N-dimethyl-2-oxo-1,2,3,5-tetrahydro-4H-benzo[e][1,4]diazepine-4-sulfonamide |
| 28 | 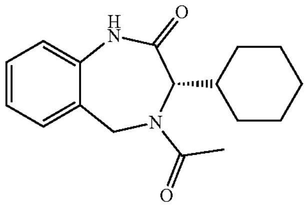 [SMILES: CC(=O)N1Cc2ccccc2NC(=O)[C@@H]1C1CCCCC1] | (S)-4-acetyl-3-cyclohexyl-1,3,4,5-tetrahydro-2H-benzo[e][1,4]diazepin-2-one |

TABLE 2-continued

| Compound No. | Compound Structure | Compound Name |
|---|---|---|
| 29 | 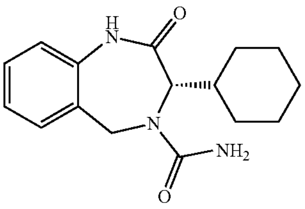 [SMILES: NC(=O)N1Cc2ccccc2NC(=O)[C@@H]1C1CCCCC1] | (S)-3-cyclohexyl-2-oxo-1,2,3,5-tetrahydro-4H-benzo[e][1,4]diazepine-4-carboxamide |
| 30 | 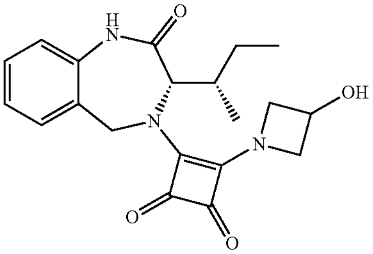 [SMILES: CC[C@H](C)[C@H]1C(=O)Nc2ccccc2CN1c1c(N2CC(O)C2)c(=O)c1=O] | 3-((S)-3-((S)-sec-butyl)-2-oxo-1,2,3,5-tetrahydro-4H-benzo[e][1,4]diazepin-4-yl)-4-(3-hydroxyazetidin-1-yl)cyclobut-3-ene-1,3-dione |
| 31 | 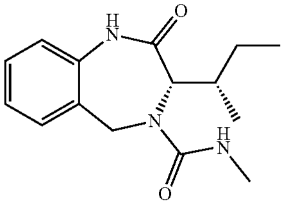 | (S)-3-((S)-sec-butyl)-N-methyl-2-oxo-1,2,3,5-tetrahydro-4H-benzo[e][1,4]diazepine-4-carboxamide |
| 32 | 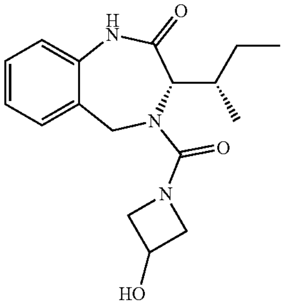 [SMILES: CC[C@H](C)[C@H]1C(=O)Nc2ccccc2CN1C(=O)N1CC(O)C1] | (S)-3-((S)-sec-butyl)-4-(3-hydroxyazetidine-1-carbonyl)-1,3,4,5-tetrahydro-2H-benzo[e][1,4]diazepin-2-one |
| 33 | 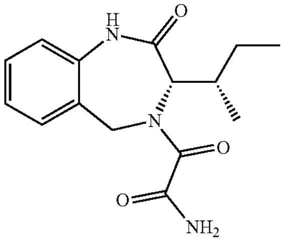 [SMILES: CC[C@H](C)[C@H]1C(=O)Nc2ccccc2CN1C(=O)C(N)=O] | 2-((S)-3-((S)-sec-butyl)-2-oxo-1,2,3,5-tetrahydro-4H-benzo[e][1,4]diazepin-4-yl)-2-oxoacetamide |
| 34 | 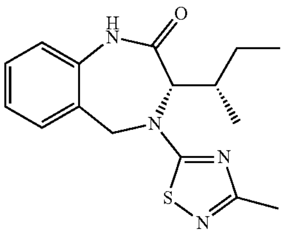 [SMILES: CC[C@H](C)[C@H]1C(=O)Nc2ccccc2CN1c1nc(C)ns1] | (S)-3-((S)-sec-butyl)-4-(3-methyl-1,2,4-thiadiazol-5-yl)-1,3,4,5-tetrahydro-2H-benzo[e][1,4]diazepin-2-one |

TABLE 2-continued

| Compound No. | Compound Structure | Compound Name |
|---|---|---|
| 35 | 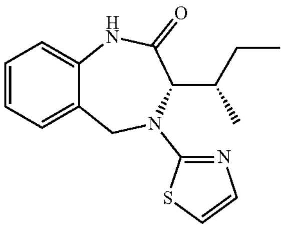 [SMILES: CC[C@H](C)[C@H]1C(=O)Nc2ccccc2CN1c1nccs1] | (S)-3-((S)-sec-butyl)-4-(thiazol-2-yl)-1,3,4,5-tetrahydro-2H-benzo[e][1,4]diazepin-2-one |
| 36 | 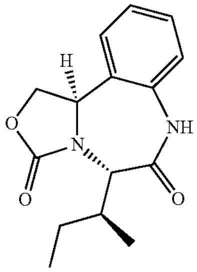 [SMILES: CC[C@H](C)[C@H]1C(=O)Nc2ccccc2[C@@H]2COC(=O)N12] | (5S,11bR)-5-((S)-sec-butyl)-7,11b-dihydro-1H,3H-benzo[f]oxazolo[3,4-d][1,4]diazepine-3,6(5H)-dione |
| 37 | 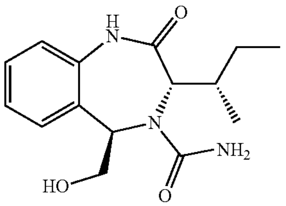 [SMILES: CC[C@H](C)[C@H]1C(=O)Nc2ccccc2[C@H](CO)N1C(N)=O] | (3S,5R)-3-((S)-sec-butyl)-5-(hydroxymethyl)-2-oxo-1,2,3,5-tetrahydro-4H-benzo[e][1,4]diazepine-4-carboxamide |
| 38 | 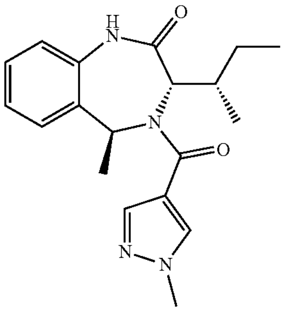 [SMILES: CC[C@H](C)[C@H]1C(=O)Nc2ccccc2[C@H](C)N1C(=O)c1cnn(C)c1] | (3S,5S)-3-((S)-sec-butyl)-5-methyl-4-(1-methyl-1H-pyrazole-4-carbonyl)-1,3,4,5-tetrahydro-2H-benzo[e][1,4]diazepin-2-one |
| 39 | 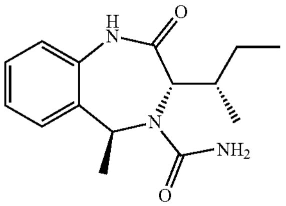 [SMILES: CC[C@H](C)[C@H]1C(=O)Nc2ccccc2[C@H](C)N1C(N)=O] | (3S,5S)-3-((S)-sec-butyl)-5-methyl-2-oxo-1,2,3,5-tetrahydro-4H-benzo[e][1,4]diazepine-4-carboxamide |
| 40 | 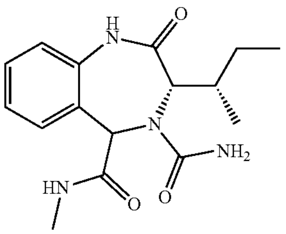 | (3S)-3-((S)-sec-butyl)-N5-methyl-2-oxo-1,2,3,5-tetrahydro-4H-benzo[e][1,4]diazepine-4,5-dicarboxamide |

TABLE 2-continued

| Compound No. | Compound Structure | Compound Name |
|---|---|---|
| 41 | 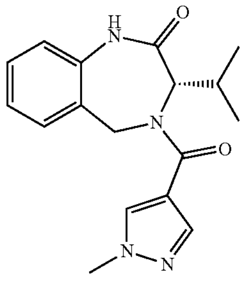 [SMILES: CC(C)[C@H]1C(=O)Nc2ccccc2CN1C(=O)c1cnn(C)c1] | (S)-3-isopropyl-4-(1-methyl-1H-pyrazole-4-carbonyl)-1,3,4,5-tetrahydro-2H-benzo[e][1,4]diazepin-2-one |
| 42 | 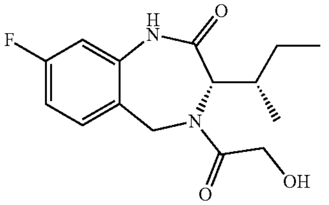 [SMILES: CC[C@H](C)[C@H]1C(=O)Nc2cc(F)ccc2CN1C(=O)CO] | (S)-3-((S)-sec-butyl)-8-fluoro-4-(2-hydroxyacetyl)-1,3,4,5-tetrahydro-2H-benzo[e][1,4]diazepin-2-one |
| 43 | 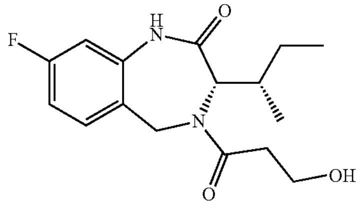 [SMILES: CC[C@H](C)[C@H]1C(=O)Nc2cc(F)ccc2CN1C(=O)CCO] | (S)-3-((S)-sec-butyl)-8-fluoro-4-(3-hydroxypropanoyl)-1,3,4,5-tetrahydro-2H-benzo[e][1,4]diazepin-2-one |
| 44 | 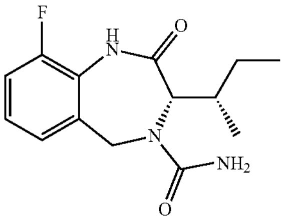 [SMILES: CC[C@H](C)[C@H]1C(=O)Nc2c(F)cccc2CN1C(N)=O] | (S)-3-((S)-sec-butyl)-9-fluoro-2-oxo-1,2,3,5-tetrahydro-4H-benzo[e][1,4]diazepine-4-carboxamide |
| 45 | 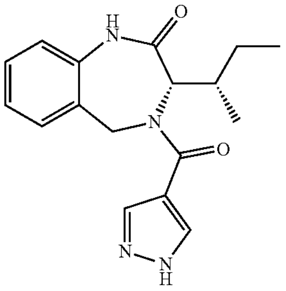 [SMILES: CC[C@H](C)[C@H]1C(=O)Nc2ccccc2CN1C(=O)c1cn[nH]c1] | (S)-3-((S)-sec-butyl)-4-(1H-pyrazole-4-carbonyl)-1,3,4,5-tetrahydro-2H-benzo[e][1,4]diazepin-2-one |
| 46 | 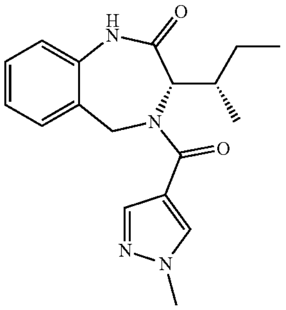 [SMILES: CC[C@H](C)[C@H]1C(=O)Nc2ccccc2CN1C(=O)c1cnn(C)c1] | (S)-3-((S)-sec-butyl)-4-(1-methyl-1H-pyrazole-4-carbonyl)-1,3,4,5-tetrahydro-2H-benzo[e][1,4]diazepin-2-one |

TABLE 2-continued

| Compound No. | Compound Structure | Compound Name |
|---|---|---|
| 47 | 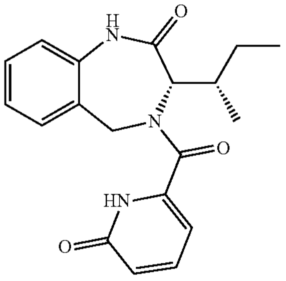 [SMILES: CC[C@H](C)[C@H]1C(=O)Nc2ccccc2CN1C(=O)c1cccc(=O)[nH]1] | (S)-3-((S)-sec-butyl)-4-(6-oxo-1,6-dihydropyridine-2-carbonyl)-1,3,4,5-tetrahydro-2H-benzo[e][1,4]diazepin-2-one |
| 48 | 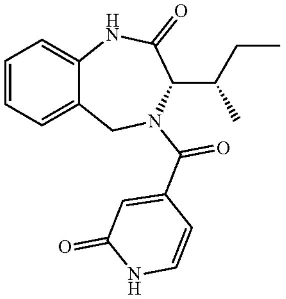 [SMILES: CC[C@H](C)[C@H]1C(=O)Nc2ccccc2CN1C(=O)c1cc[nH]c(=O)c1] | (S)-3-((S)-sec-butyl)-4-(2-oxo-1,2-dihydropyridine-4-carbonyl)-1,3,4,5-tetrahydro-2H-benzo[d][1,4]diazepin-2-one |
| 49 | 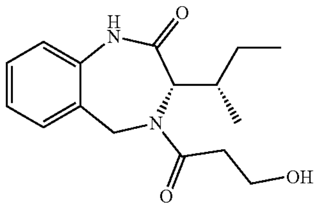 [SMILES: CC[C@H](C)[C@H]1C(=O)Nc2ccccc2CN1C(=O)CCO] | (S)-3-((S)-sec-butyl)-4-(3-hydroxypropanoyl)-1,3,4,5-tetrahydro-2H-benzo[e][1,4]diazepin-2-one |
| 50 | 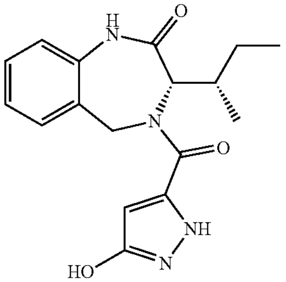 [SMILES: CC[C@H](C)[C@H]1C(=O)Nc2ccccc2CN1C(=O)c1cc(O)n[nH]1] | (S)-3-((S)-sec-butyl)-4-(3-hydroxy-1H-pyrazole-5-carbonyl)-1,3,4,5-tetrahydro-2H-benzo[e][1,4]diazepin-2-one |
| 51 | 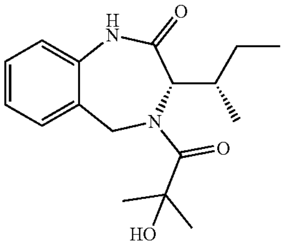 [SMILES: CC[C@H](C)[C@H]1C(=O)Nc2ccccc2CN1C(=O)C(C)(C)O] | (S)-3-((S)-sec-butyl)-4-(2-hydroxy-2-methylpropanoyl)-1,3,4,5-tetrahydro-2H-benzo[e][1,4]diazepin-2-one |

TABLE 2-continued

| Compound No. | Compound Structure | Compound Name |
|---|---|---|
| 52 | 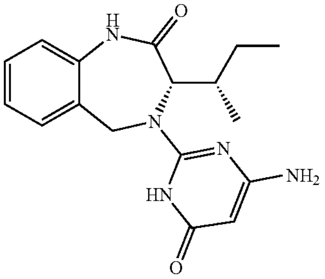 [SMILES: CC[C@H](C)[C@H]1C(=O)Nc2ccccc2CN1c1nc(N)cc(=O)[nH]1] | (S)-4-(4-amino-6-oxo-1,6-dihydropyrimidin-2-yl)-3-((S)-sec-butyl)-1,3,4,5-tetrahydro-2H-benzo[e][1,4]diazepin-2-one |
| 53 | 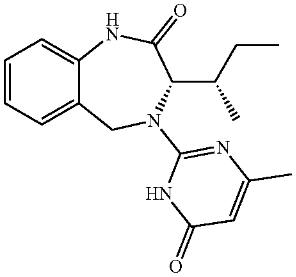 [SMILES: CC[C@H](C)[C@H]1C(=O)Nc2ccccc2CN1c1nc(C)cc(=O)[nH]1] | (S)-3-((S)-sec-butyl)-4-(4-methyl-6-oxo-1,6-dihydropyrimidin-2-yl)-1,3,4,5-tetrahydro-2H-benzo[e][1,4]diazepin-2-one |
| 54 | 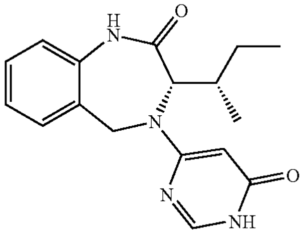 [SMILES: CC[C@H](C)[C@H]1C(=O)Nc2ccccc2CN1c1cc(=O)[nH]cn1] | (S)-3-((S)-sec-butyl)-4-(6-oxo-1,6-dihydropyrimidin-4-yl)-1,3,4,5-tetrahydro-2H-benzo[e][1,4]diazepin-2-one |
| 55 | 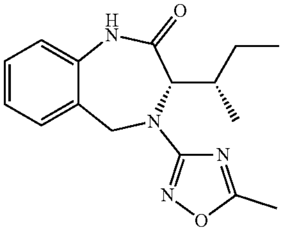 [SMILES: CC[C@H](C)[C@H]1C(=O)Nc2ccccc2CN1c1noc(C)n1] | (S)-3-((S)-sec-butyl)-4-(5-methyl-1,2,4-oxadiazol-3-yl)-1,3,4,5-tetrahydro-2H-benzo[e][1,4]diazepin-2-one |
| 56 | 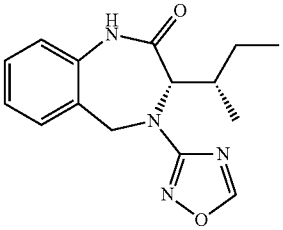 [SMILES: CC[C@H](C)[C@H]1C(=O)Nc2ccccc2CN1c1ncon1] | (S)-3-((S)-sec-butyl)-4-(1,2,4-oxadiazol-3-yl)-1,3,4,5-tetrahydro-2H-benzo[e][1,4]diazepin-2-one |
| 57 | 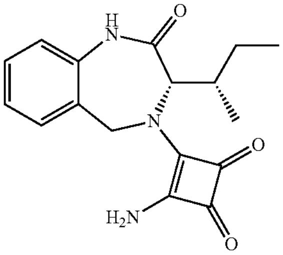 [SMILES: CC[C@H](C)[C@H]1C(=O)Nc2ccccc2CN1c1c(N)c(=O)c1=O] | 3-amino-4-((S)-3-((S)-sec-butyl)-2-oxo-1,2,3,5-tetrahydro-4H-benzo[e][1,4]diazepin-4-yl)cyclobut-3-ene-1,2-dione |

TABLE 2-continued

| Compound No. | Compound Structure | Compound Name |
| --- | --- | --- |
| 58 | 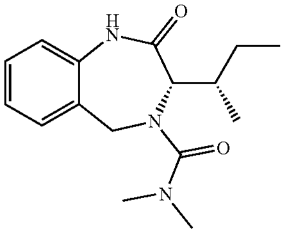 [SMILES: CC[C@H](C)[C@H]1C(=O)Nc2ccccc2CN1C(=O)N(C)C] | (S)-3-((S)-sec-butyl)-N,N-dimethyl-2-oxo-1,2,3,5-tetrahydro-4H-benzo[e][1,4]diazepine-4-carboxamide |
| 59 | 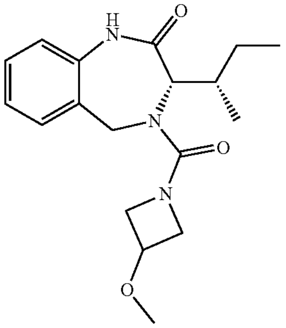 [SMILES: CC[C@H](C)[C@H]1C(=O)Nc2ccccc2CN1C(=O)N1CC(OC)C1] | (S)-3-((S)-sec-butyl)-4-(3-methoxyazetidine-1-carbonyl)-1,3,4,5-tetrahydro-2H-benzo[e][1,4]diazepin-2-one |
| 60 | 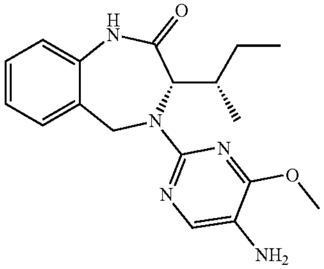 [SMILES: CC[C@H](C)[C@H]1C(=O)Nc2ccccc2CN1c1ncc(N)c(OC)n1] | (S)-4-(5-amino-4-methoxypyrimidin-2-yl)-3-((S)-sec-butyl)-1,3,4,5-tetrahydro-2H-benzo[e][1,4]diazepin-2-one |
| 61 | 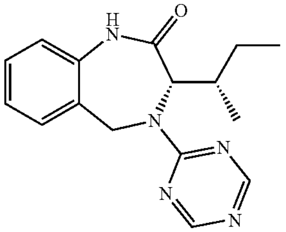 [SMILES: CC[C@H](C)[C@H]1C(=O)Nc2ccccc2CN1c1ncncn1] | (S)-3-((S)-sec-butyl)-4-(1,3,5-triazin-2-yl)-1,3,4,5-tetrahydro-2H-benzo[e][1,4]diazepin-2-one |
| 62 | 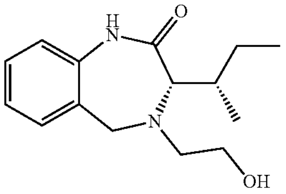 [SMILES: CC[C@H](C)[C@H]1C(=O)Nc2ccccc2CN1CCO] | (S)-3-((S)-sec-butyl)-4-(2-hydroxyethyl)-1,3,4,5-tetrahydro-2H-benzo[e][1,4]diazepin-2-one |
| 63 | 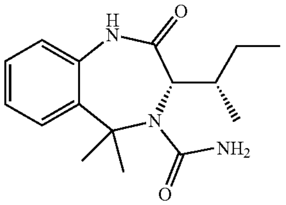 [SMILES: CC[C@H](C)[C@H]1C(=O)Nc2ccccc2C(C)(C)N1C(N)=O] | (S)-3-((S)-sec-butyl)-5,5-dimethyl-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 64 | 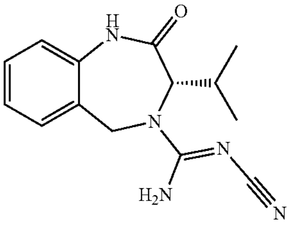 [SMILES: CC(C)[C@H]1C(=O)Nc2ccccc2CN1/C(N)=N/C#N] | (S,E)-N'-cyano-3-isopropyl-2-oxo-1,2,3,5-tetrahydro-4H-benzo[e][1,4]diazepine-4-carboximidamide |
| 65 | 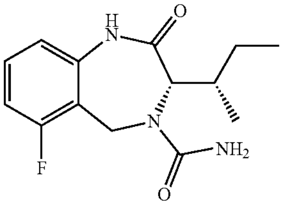 | (S)-3-((S)-sec-butyl)-6-fluoro-2-oxo-1,2,3,5-tetrahydro-4H-benzo[e][1,4]diazepine-4-carboxamide |
| 66 | 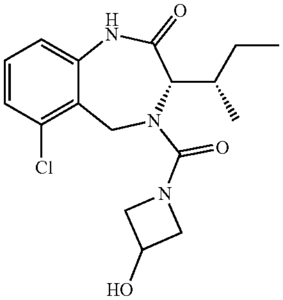 [SMILES: CC[C@H](C)[C@H]1C(=O)Nc2cccc(Cl)c2CN1C(=O)N1CC(O)C1] | (S)-3-((S)-sec-butyl)-6-chloro-4-(3-hydroxyazetidine-1-carbonyl)-1,3,4,5-tetrahydro-2H-benzo[e][1,4]diazepin-2-one |
| 67 | 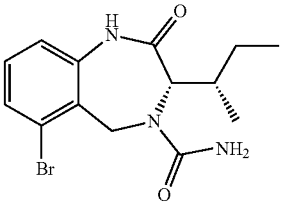 [SMILES: CC[C@H](C)[C@H]1C(=O)Nc2cccc(Br)c2CN1C(N)=O] | (S)-6-bromo-3-((S)-sec-butyl)-2-oxo-1,2,3,5-tetrahydro-4H-benzo[e][1,4]diazepine-4-carboxamide |
| 68 | 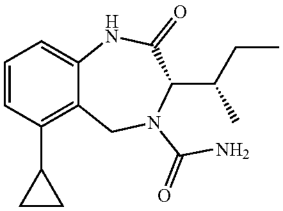 [SMILES: CC[C@H](C)[C@H]1C(=O)Nc2cccc(C3CC3)c2CN1C(N)=O] | (S)-3-((S)-sec-butyl)-6-cyclopropyl-2-oxo-1,2,3,5-tetrahydro-4H-benzo[e][1,4]diazepine-4-carboxamide |
| 69 | 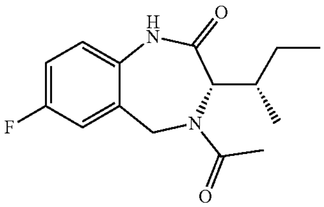 [SMILES: CC[C@H](C)[C@H]1C(=O)Nc2ccc(F)cc2CN1C(C)=O] | (S)-4-acetyl-3-((S)-sec-butyl)-7-fluoro-1,3,4,5-tetrahydro-2H-benzo[e][1,4]diazepin-2-one |

TABLE 2-continued

| Compound No. | Compound Structure | Compound Name |
|---|---|---|
| 70 | 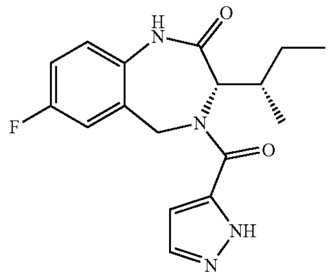 [SMILES: CC[C@H](C)[C@H]1C(=O)Nc2ccc(F)cc2CN1C(=O)c1ccn[nH]1] | (S)-3-((S)-sec-butyl)-7-fluoro-4-(1H-pyrazole-5-carbonyl)-1,3,4,5-tetrahydro-2H-benzo[e][1,4]diazepin-2-one |
| 71 | 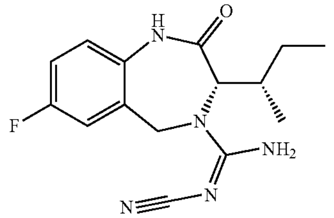 [SMILES: CC[C@H](C)[C@H]1C(=O)Nc2ccc(F)cc2CN1/C(N)=N\C#N] | (S,Z)-3-((S)-sec-butyl)-N'-cyano-7-fluoro-2-oxo-1,2,3,5-tetrahydro-4H-benzo[e][1,4]diazepine-4-carboximidamide |
| 72 | 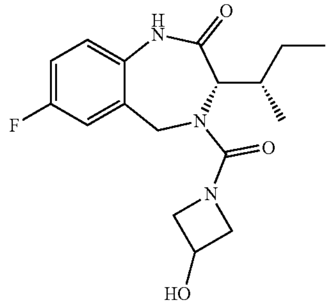 [SMILES: CC[C@H](C)[C@H]1C(=O)Nc2ccc(F)cc2CN1C(=O)N1CC(O)C1] | (S)-3-((S)-sec-butyl)-7-fluoro-4-(3-hydroxyazetidine-1-carbonyl)-1,3,4,5-tetrahydro-2H-benzo[e][1,4]diazepin-2-one |
| 73 | 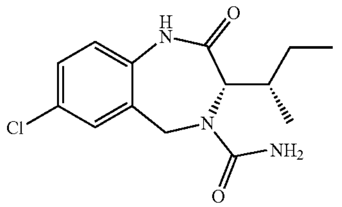 [SMILES: CC[C@H](C)[C@H]1C(=O)Nc2ccc(Cl)cc2CN1C(N)=O] | (S)-3-((S)-sec-butyl)-7-chloro-2-oxo-1,2,3,5-tetrahydro-4H-benzo[e][1,4]diazepine-4-carboxamide |
| 74 | 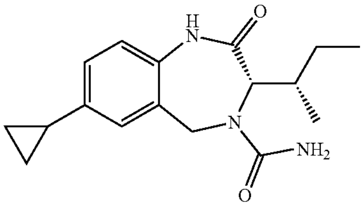 [SMILES: CC[C@H](C)[C@H]1C(=O)Nc2ccc(C3CC3)cc2CN1C(N)=O] | (S)-3-((S)-sec-butyl)-7-cyclopropyl-2-oxo-1,2,3,5-tetrahydro-4H-benzo[e][1,4]diazepine-4-carboxamide |
| 75 | 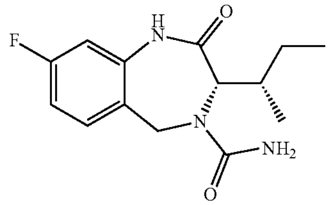 [SMILES: CC[C@H](C)[C@H]1C(=O)Nc2cc(F)ccc2CN1C(N)=O] | (S)-3-((S)-sec-butyl)-8-fluoro-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 76 | 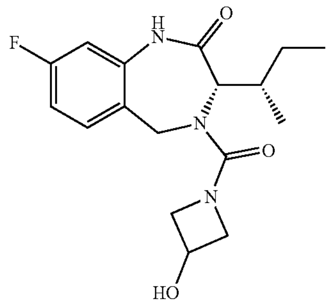 [SMILES: CC[C@H](C)[C@H]1C(=O)Nc2cc(F)ccc2CN1C(=O)N1CC(O)C1] | (S)-3-((S)-sec-butyl)-8-fluoro-4-(3-hydroxyazetidine-1-carbonyl)-1,3,4,5-tetrahydro-2H-benzo[e][1,4]diazepin-2-one |
| 77 | 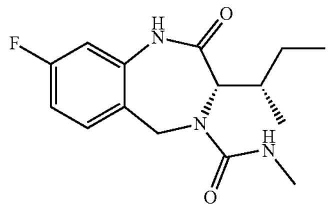 [SMILES: CC[C@H](C)[C@H]1C(=O)Nc2cc(F)ccc2CN1C(=O)NC] | (S)-3-((S)-sec-butyl)-8-fluoro-N-methyl-2-oxo-1,2,3,5-tetrahydro-4H-benzo[e][1,4]diazepine-4-carboxamide |
| 78 | 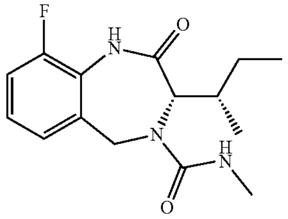 [SMILES: CC[C@H](C)[C@H]1C(=O)Nc2c(F)cccc2CN1C(=O)NC] | (S)-3-((S)-sec-butyl)-9-fluoro-N-methyl-2-oxo-1,2,3,5-tetrahydro-4H-benzo[e][1,4]diazepine-4-carboxamide |
| 79 | 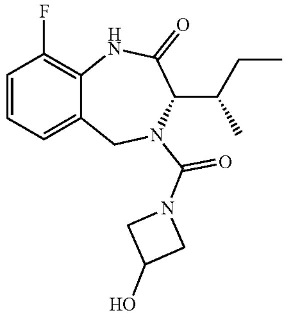 [SMILES: CC[C@H](C)[C@H]1C(=O)Nc2c(F)cccc2CN1C(=O)N1CC(O)C1] | (S)-3-((S)-sec-butyl)-9-fluoro-4-(3-hydroxyazetidine-1-carbonyl)-1,3,4,5-tetrahydro-2H-benzo[e][1,4]diazepin-2-one |
| 80 | 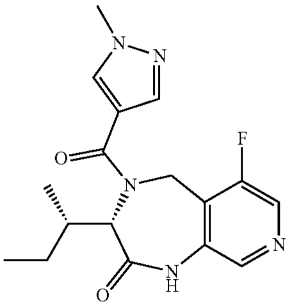 [SMILES: CC[C@H](C)[C@H]1C(=O)Nc2cncc(F)c2CN1C(=O)c1cnn(C)c1] | (S)-3-((S)-sec-butyl)-6-fluoro-4-(1-methyl-1H-pyrazole-4-carbonyl)-1,3,4,5-tetrahydro-2H-pyrido[3,4-e][1,4]diazepin-2-one |

TABLE 2-continued

| Compound No. | Compound Structure | Compound Name |
|---|---|---|
| 81 | 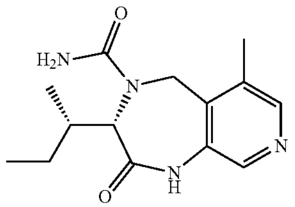 [SMILES: CC[C@H](C)[C@H]1C(=O)Nc2cncc(C)c2CN1C(N)=O] | (S)-3-((S)-sec-butyl)-6-methyl-2-oxo-1,2,3,5-tetrahydro-4H-pyrido[3,4-e][1,4]diazepine-4-carboxamide |
| 82 | 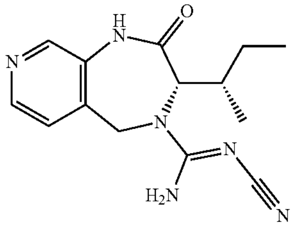 [SMILES: CC[C@H](C)[C@H]1C(=O)Nc2cnccc2CN1/C(N)=N/C#N] | (S,E)-3-((S)-sec-butyl)-N'-cyano-2-oxo-1,2,3,5-tetrahydro-4H-pyrido[3,4-e][1,4]diazepine-4-carboximidamide |
| 83 | 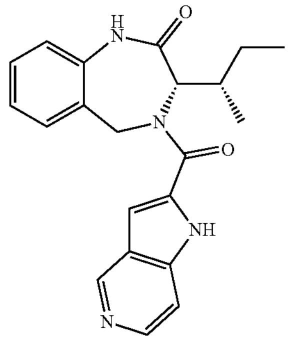 [SMILES: CC[C@H](C)[C@H]1C(=O)Nc2ccccc2CN1C(=O)c1cc2cnccc2[nH]1] | (S)-3-((S)-sec-butyl)-4-(1H-pyrrolo[3,2-c]pyridine-2-carbonyl)-1,3,4,5-tetrahydro-2H-benzo[e][1,4]diazepin-2-one |
| 84 | 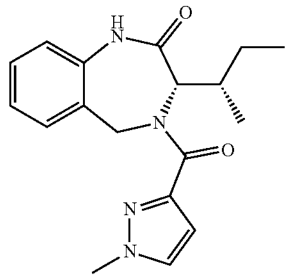 [SMILES: CC[C@H](C)[C@H]1C(=O)Nc2ccccc2CN1C(=O)c1ccn(C)n1] | (S)-3-((S)-sec-butyl)-4-(1-methyl-1H-pyrazole-3-carbonyl)-1,3,4,5-tetrahydro-2H-benzo[e][1,4]diazepin-2-one |
| 85 | 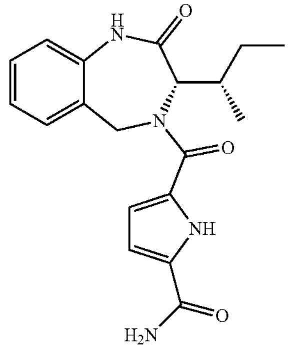 [SMILES: CC[C@H](C)[C@H]1C(=O)Nc2ccccc2CN1C(=O)c1ccc(C(N)=O)[nH]1] | 5-((S)-3-((S)-sec-butyl)-2-oxo-2,3,4,5-tetrahydro-1H-benzo[e][1,4]diazepine-4-carbonyl)-1H-pyrrole-2-carboxamide |

TABLE 2-continued

| Compound No. | Compound Structure | Compound Name |
|---|---|---|
| 86 | 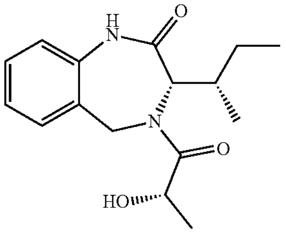 [SMILES: CC[C@H](C)[C@H]1C(=O)Nc2ccccc2CN1C(=O)[C@H](C)O] | (S)-3-((S)-sec-butyl)-4-((S)-2-hydroxypropanoyl)-1,3,4,5-tetrahydro-2H-benzo[e][1,4]diazepin-2-one |
| 87 | 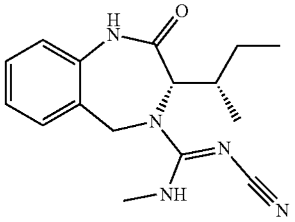 [SMILES: CC[C@H](C)[C@H]1C(=O)Nc2ccccc2CN1/C(=N/C#N)NC] | (S,E)-3-((S)-sec-butyl)-N'-cyano-N-methyl-2-oxo-1,2,3,5-tetrahydro-4H-benzo[e][1,4]diazepine-4-carboximidamide |
| 88 | 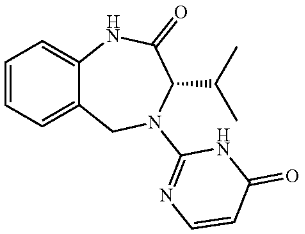 [SMILES: CC(C)[C@H]1C(=O)Nc2ccccc2CN1c1nccc(=O)[nH]1] | (S)-3-isopropyl-4-(6-oxo-1,6-dihydropyrimidin-2-yl)-1,3,4,5-tetrahydro-2H-benzo[e][1,4]diazepin-2-one |
| 89 | 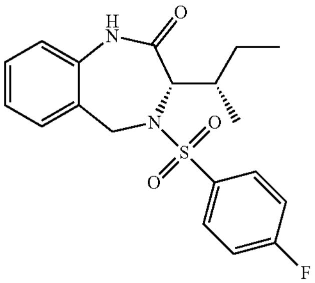 [SMILES: CC[C@H](C)[C@H]1C(=O)Nc2ccccc2CN1S(=O)(=O)c1ccc(F)cc1] | (S)-3-((S)-sec-butyl)-4-((4-fluorophenyl)sulfonyl)-1,3,4,5-tetrahydro-2H-benzo[e][1,4]diazepin-2-one |
| 90 | 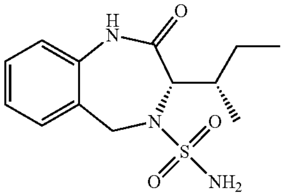 [SMILES: CC[C@H](C)[C@H]1C(=O)Nc2ccccc2CN1S(N)(=O)=O] | (S)-3-((S)-sec-butyl)-2-oxo-1,2,3,5-tetrahydro-4H-benzo[e][1,4]diazepine-4-sulfonamide |
| 91 | 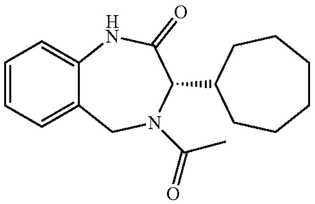 [SMILES: CC(=O)N1Cc2ccccc2NC(=O)[C@@H]1C1CCCCCC1] | (S)-4-acetyl-3-cycloheptyl-1,3,4,5-tetrahydro-2H-benzo[e][1,4]diazepin-2-one |

TABLE 2-continued

| Compound No. | Compound Structure | Compound Name |
|---|---|---|
| 92 | 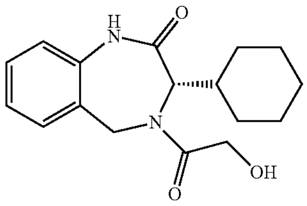 [SMILES: O=C1Nc2ccccc2CN(C(=O)CO)[C@H]1C1CCCCC1] | (S)-3-cyclohexyl-4-(2-hydroxyacetyl)-1,3,4,5-tetrahydro-2H-benzo[e][1,4]diazepin-2-one |
| 93 | 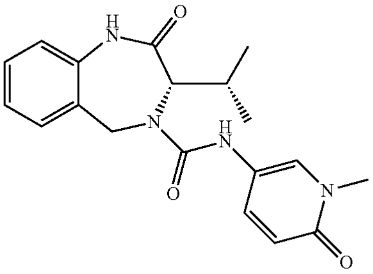 | (S)-3-((S)-sec-butyl)-N-(1-methyl-6-oxo-1,6-dihydropyridin-3-yl)-2-oxo-1,2,3,5-tetrahydro-4H-benzo[e][1,4]diazepine-4-carboxamide |
| 94 | 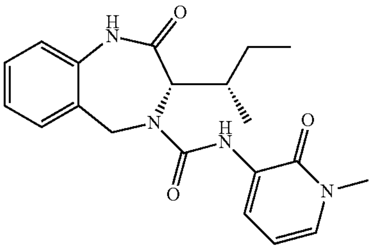 [SMILES: CC[C@H](C)[C@H]1C(=O)Nc2ccccc2CN1C(=O)Nc1cccn(C)c1=O] | (S)-3-((S)-sec-butyl)-N-(1-methyl-2-oxo-1,2-dihydropyridin-3-yl)-2-oxo-1,2,3,5-tetrahydro-4H-benzo[e][1,4]diazepine-4-carboxamide |
| 95 | 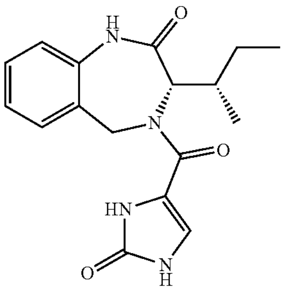 [SMILES: CC[C@H](C)[C@H]1C(=O)Nc2ccccc2CN1C(=O)c1c[nH]c(=O)[nH]1] | (S)-3-((S)-sec-butyl)-4-(2-oxo-2,3-dihydro-1H-imidazole-4-carbonyl)-1,3,4,5-tetrahydro-2H-benzo[e][1,4]diazepin-2-one |
| 96 | 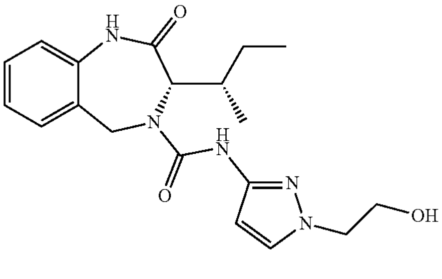 [SMILES: CC[C@H](C)[C@H]1C(=O)Nc2ccccc2CN1C(=O)Nc1ccn(CCO)n1] | (S)-3-((S)-sec-butyl)-N-(1-(2-hydroxyethyl)-1H-pyrazol-3-yl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 97 | 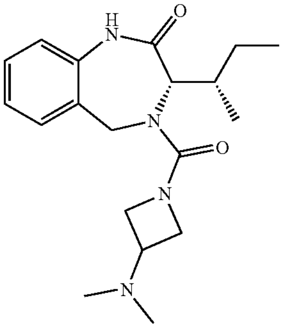 [SMILES: CC[C@H](C)[C@H]1C(=O)Nc2ccccc2CN1C(=O)N1CC(N(C)C)C1] | (S)-3-((S)-sec-butyl)-4-(3-(dimethylamino)azetidine-1-carbonyl)-1,3,4,5-tetrahydro-2H-benzo[e][1,4]diazepin-2-one |
| 98 | 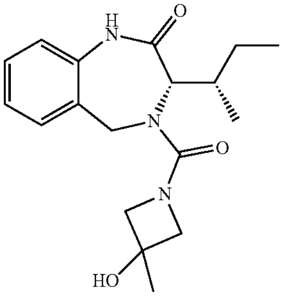 [SMILES: CC[C@H](C)[C@H]1C(=O)Nc2ccccc2CN1C(=O)N1CC(C)(O)C1] | (S)-3-((S)-sec-butyl)-4-(3-hydroxy-3-methylazetidine-1-carbonyl)-1,3,4,5-tetrahydro-2H-benzo[e][1,4]diazepin-2-one |
| 99 | 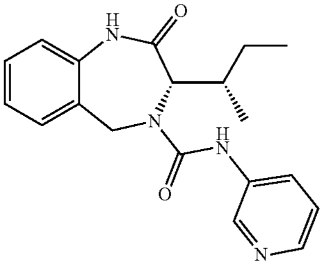 [SMILES: CC[C@H](C)[C@H]1C(=O)Nc2ccccc2CN1C(=O)Nc1cccnc1] | (S)-3-((S)-sec-butyl)-2-oxo-N-(pyridin-3-yl)-1,2,3,5-tetrahydro-4H-benzo[e][1,4]diazepine-4-carboxamide |
| 100 | 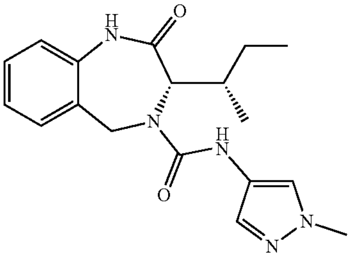 [SMILES: CC[C@H](C)[C@H]1C(=O)Nc2ccccc2CN1C(=O)Nc1cnn(C)c1] | (S)-3-((S)-sec-butyl)-N-(1-methyl-1H-pyrazol-4-yl)-2-oxo-1,2,3,5-tetrahydro-4H-benzo[e][1,4]diazepine-4-carboxamide |
| 101 | 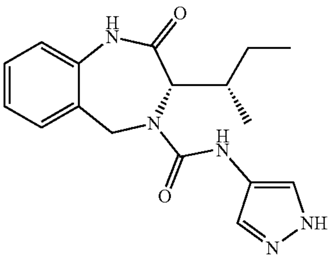 [SMILES: CC[C@H](C)[C@H]1C(=O)Nc2ccccc2CN1C(=O)Nc1cn[nH]c1] | (S)-3-((S)-sec-butyl)-2-oxo-N-(1H-pyrzol-4-yl)-1,2,3,5-tetrahydro-4H-benzo[e][1,4]diazepine-4-carboxamide |

TABLE 2-continued

| Compound No. | Compound Structure | Compound Name |
|---|---|---|
| 102 | 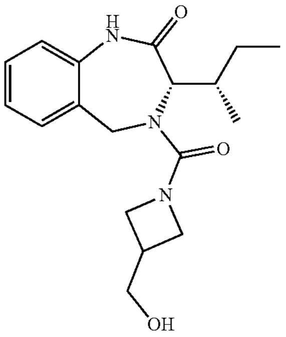 [SMILES: CC[C@H](C)[C@H]1C(=O)Nc2ccccc2CN1C(=O)N1CC(CO)C1] | (S)-3-((S)-sec-butyl)-4-(3-(hydroxymethyl)azetidine-1-carbonyl)-1,3,4,5-tetrahydro-2H-benzo[e][1,4]diazepin-2-one |
| 103 | 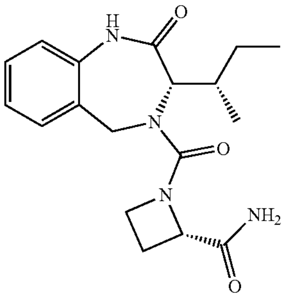 [SMILES: CC[C@H](C)[C@H]1C(=O)Nc2ccccc2CN1C(=O)N1CC[C@H]1C(N)=O] | (S)-1-((S)-3-((S)-sec-butyl)-2-oxo-2,3,4,5-tetrahydro-1H-benzo[e][1,4]diazepine-4-carbonyl)azetidine-2-carboxamide |
| 104 | 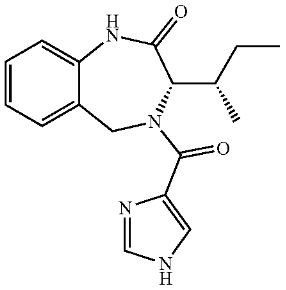 [SMILES: CC[C@H](C)[C@H]1C(=O)Nc2ccccc2CN1C(=O)c1c[nH]cn1] | (S)-3-((S)-sec-butyl)-4-(1H-imidazole-4-carbonyl)-1,3,4,5-tetrahydro-2H-benzo[e][1,4]diazepin-2-one |
| 105 | 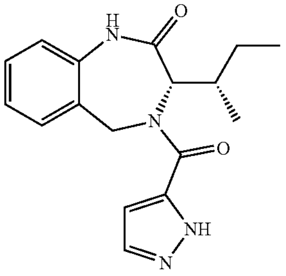 [SMILES: CC[C@H](C)[C@H]1C(=O)Nc2ccccc2CN1C(=O)c1ccn[nH]1] | (S)-3-((S)-sec-butyl)-4-(1H-pyrazole-5-carbonyl)-1,3,4,5-tetrahydro-2H-benzo[e][1,4]diazepin-2-one |
| 106 | 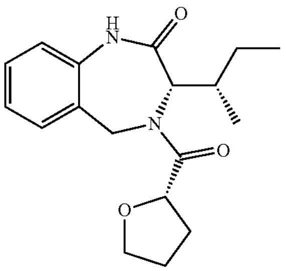 [SMILES: CC[C@H](C)[C@H]1C(=O)Nc2ccccc2CN1C(=O)[C@@H]1CCCO1] | (S)-3-((S)-sec-butyl)-4-((S)-tetrahydrofuran-2-carbonyl)-1,3,4,5-tetrahydro-2H-benzo[e][1,4]diazepin-2-one |

TABLE 2-continued

| Compound No. | Compound Structure | Compound Name |
|---|---|---|
| 107 | 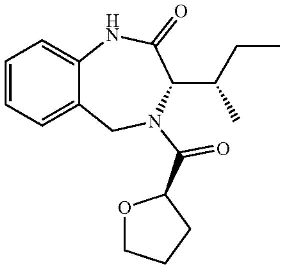 [SMILES: CC[C@H](C)[C@H]1C(=O)Nc2ccccc2CN1C(=O)[C@H]1CCCO1] | (S)-3-((S)-sec-butyl)-4-((R)-tetrahydrofuran-2-carbonyl)-1,3,4,5-tetrahydro-2H-benzo[e][1,4]diazepin-2-one |
| 108 | 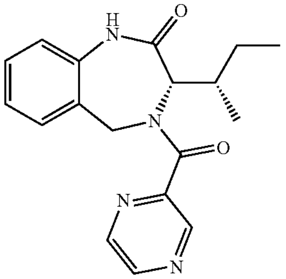 [SMILES: CC[C@H](C)[C@H]1C(=O)Nc2ccccc2CN1C(=O)c1cnccn1] | (S)-3-((S)-sec-butyl)-4-(pyrazine-2-carbonyl)-1,3,4,5-tetrahydro-2H-benzo[e][1,4]diazepin-2-one |
| 109 | 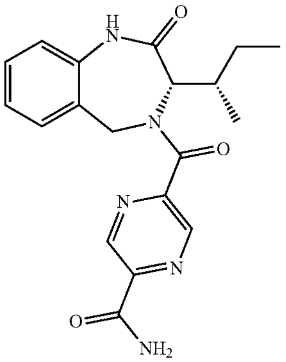 [SMILES: CC[C@H](C)[C@H]1C(=O)Nc2ccccc2CN1C(=O)c1cnc(C(N)=O)cn1] | 5-((S)-3-((S)-sec-butyl)-2-oxo-2,3,4,5-tetrahydro-1H-benzo[e][1,4]diazepine-4-carbonyl)pyrazine-2-carboxamide |
| 110 | 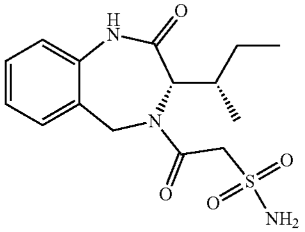 [SMILES: CC[C@H](C)[C@H]1C(=O)Nc2ccccc2CN1C(=O)CS(N)(=O)=O] | 2-((S)-3-((S)-sec-butyl)-2-oxo-1,2,3,5-tetrahydro-4H-benzo[e][1,4]diazepin-4-yl)-2-oxoethane-1-sulfonamide |
| 111 | 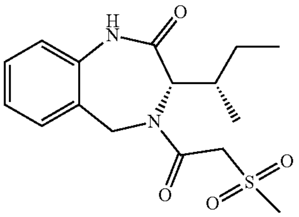 [SMILES: CC[C@H](C)[C@H]1C(=O)Nc2ccccc2CN1C(=O)CS(C)(=O)=O] | (S)-3-((S)-sec-butyl)-4-(2-(methylsulfonyl)acetyl)-1,3,4,5-tetrahydro-2H-benzo[e][1,4]diazepin-2-one |

TABLE 2-continued

| Compound No. | Compound Structure | Compound Name |
| --- | --- | --- |
| 112 | 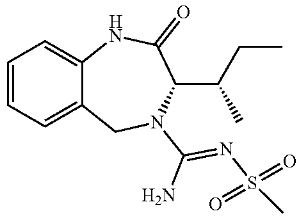 [SMILES: CC[C@H](C)[C@H]1C(=O)Nc2ccccc2CN1/C(N)=N/S(C)(=O)=O] | (S,E)-3-((S)-sec-butyl)-N'-(methylsulfonyl)-2-oxo-1,2,3,5-tetrahydro-4H-benzo[e][1,4]diazepine-4-carboximidamide |
| 113 | 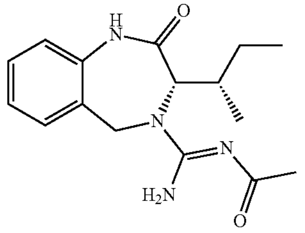 [SMILES: CC[C@H](C)[C@H]1C(=O)Nc2ccccc2CN1/C(N)=N/C(C)=O] | N-((E)-amino((S)-3-((S)-sec-butyl)-2-oxo-1,2,3,5-tetrahydro-2H-benzo[e][1,4]diazepin-4-yl)methylene)acetamide |
| 114 | 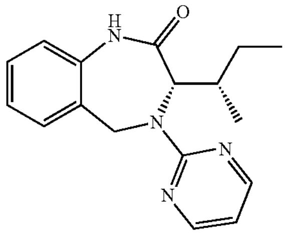 [SMILES: CC[C@H](C)[C@H]1C(=O)Nc2ccccc2CN1c1ncccn1] | (S)-3-((S)-sec-butyl)-4-(pyrimidin-2-yl)-1,3,4,5-tetrahydro-2H-benzo[e][1,4]diazepin-2-one |
| 115 | 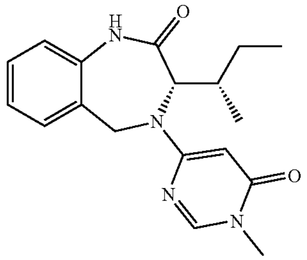 [SMILES: CC[C@H](C)[C@H]1C(=O)Nc2ccccc2CN1c1cc(=O)n(C)cn1] | (S)-3-((S)-sec-butyl)-4-(1-methyl-6-oxo-1,6-dihydropyrimidin-4-yl)-1,3,4,5-tetrahydro-2H-benzo[e][1,4]diazepin-2-one |
| 116 | 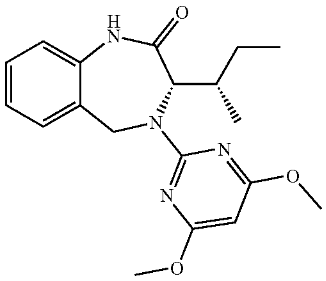 [SMILES: CC[C@H](C)[C@H]1C(=O)Nc2ccccc2CN1c1nc(OC)cc(OC)n1] | (S)-3-((S)-sec-butyl)-4-(4,6-dimethoxypyrimidin-2-yl)-1,3,4,5-tetrahydro-2H-benzo[e][1,4]diazepin-2-one |
| 117 | 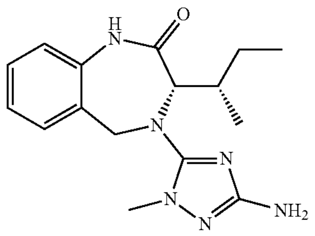 [SMILES: CC[C@H](C)[C@H]1C(=O)Nc2ccccc2CN1c1nc(N)nn1C] | (S)-4-(3-amino-1-methyl-1H-1,2,4-triazol-5-yl)-3-((S)-sec-butyl)-1,3,4,5-tetrahydro-2H-benzo[e][1,4]diazepin-2-one |

TABLE 2-continued

| Compound No. | Compound Structure | Compound Name |
|---|---|---|
| 118 | 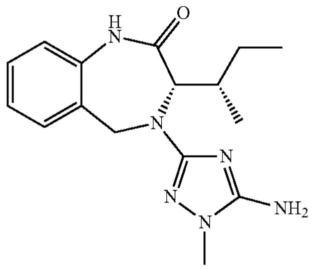 [SMILES: CC[C@H](C)[C@H]1C(=O)Nc2ccccc2CN1c1nc(N)n(C)n1] | (S)-4-(5-amino-1-methyl-1H-1,2,4-triazol-3-yl)-3-((S)-sec-butyl)-1,3,4,5-tetrahydro-2H-benzo[e][1,4]diazepin-2-one |
| 119 | 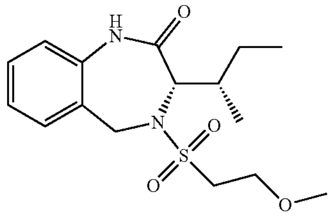 [SMILES: CC[C@H](C)[C@H]1C(=O)Nc2ccccc2CN1S(=O)(=O)CCOC] | (S)-3-((S)-sec-butyl)-4-((2-methoxyethyl)sulfonyl)-1,3,4,5-tetrahydro-2H-benzo[e][1,4]diazepin-2-one |
| 120 | 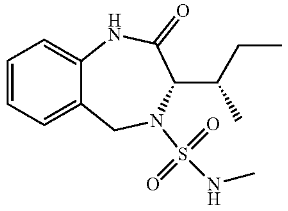 [SMILES: CC[C@H](C)[C@H]1C(=O)Nc2ccccc2CN1S(=O)(=O)NC] | (S)-3-((S)-sec-butyl)-N-methyl-2-oxo-1,2,3,5-tetrahydro-4H-benzo[e][1,4]diazepine-4-sulfonamide |
| 121 | 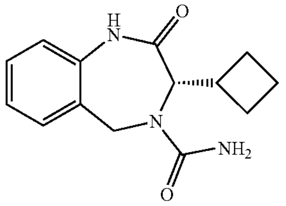 [SMILES: NC(=O)N1Cc2ccccc2NC(=O)[C@@H]1C1CCC1] | (S)-3-cyclobutyl-2-oxo-1,2,3,5-tetrahydro-4H-benzo[e][1,4]diazepine-4-carboxamide |
| 122 | 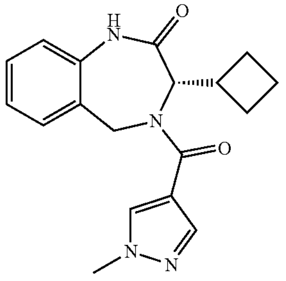 [SMILES: Cn1cc(C(=O)N2Cc3ccccc3NC(=O)[C@@H]2C2CCC2)cn1] | (S)-3-cyclobutyl-4-(1-methyl-1H-pyrazole-4-carbonyl)-1,3,4,5-tetrahydro-2H-benzo[e][1,4]diazepin-2-one |
| 123 | 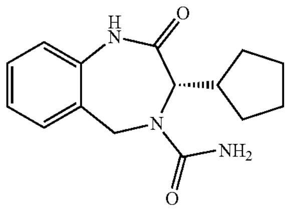 [SMILES: NC(=O)N1Cc2ccccc2NC(=O)[C@@H]1C1CCCC1] | (S)-3-cyclopentyl-2-oxo-1,2,3,5-tetrahydro-4H-benzo[e][1,4]diazepine-4-carboxamide |

TABLE 2-continued

| Compound No. | Compound Structure | Compound Name |
| --- | --- | --- |
| 124 | 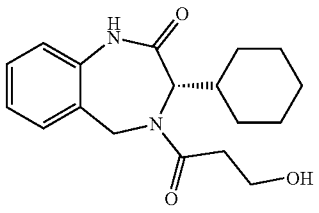 [SMILES: O=C1Nc2ccccc2CN(C(=O)CCO)[C@H]1C1CCCCC1] | (S)-3-cyclohexyl-4-(3-hydroxypropanoyl)-1,3,4,5-tetrahydro-2H-benzo[e][1,4]diazepin-2-one |
| 125 | 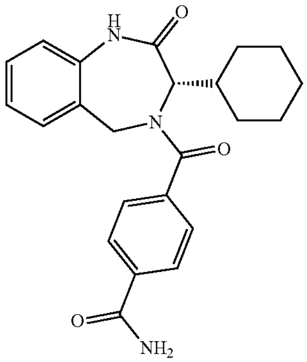 [SMILES: NC(=O)c1ccc(C(=O)N2Cc3ccccc3NC(=O)[C@@H]2C2CCCCC2)cc1] | (S)-4-(3-cyclohexyl-2-oxo-2,3,4,5-tetrahydro-1H-benzo[e][1,4]diazepine-4-carbonyl)benzamide |
| 126 | 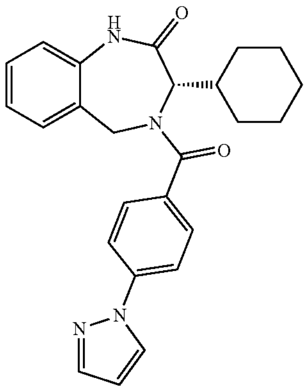 [SMILES: O=C1Nc2ccccc2CN(C(=O)c2ccc(-n3cccn3)cc2)[C@H]1C1CCCCC1] | (S)-4-(4-(1H-pyrazol-1-yl)benzoyl)-3-cyclohexyl-1,3,4,5-tetrahydro-2H-benzo[e][1,4]diazepin-2-one |
| 127 | 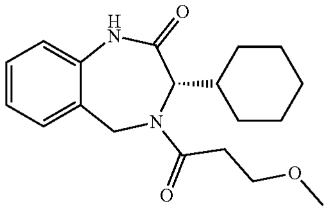 [SMILES: COCCC(=O)N1Cc2ccccc2NC(=O)[C@@H]1C1CCCCC1] | (S)-3-cylohexyl-4-(3-methoxypropanoyl)-1,3,4,5-tetrahydro-2H-benzo[e][1,4]diazepin-2-one |
| 128 | 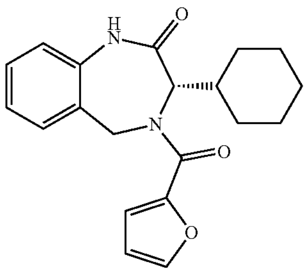 [SMILES: O=C1Nc2ccccc2CN(C(=O)c2ccco2)[C@H]1C1CCCCC1] | (S)-3-cyclohexyl-4-(furan-2-carbonyl)-1,3,4,5-tetrahydro-2H-benzo[e][1,4]diazepin-2-one |

TABLE 2-continued

| Compound No. | Compound Structure | Compound Name |
|---|---|---|
| 129 | 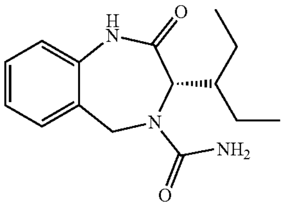 [SMILES: CCC(CC)[C@H]1C(=O)Nc2ccccc2CN1C(N)=O] | (S)-2-oxo-3-(pentan-3-yl)-1,2,3,5-tetrahydro-4H-benzo[e][1,4]diazepine-4-carboxamide |
| 130 | 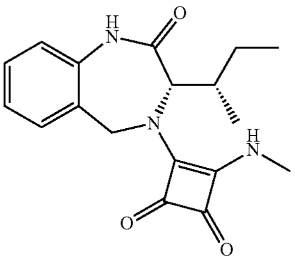 [SMILES: CC[C@H](C)[C@H]1C(=O)Nc2ccccc2CN1c1c(NC)c(=O)c1=O] | 3-((S)-3-((S)-sec-butyl)-2-oxo-1,2,3,5-tetrahydro-4H-benzo[e][1,4]diazepin-4-yl)-4-(methylamino)cyclobut-3-ene-1,2-dione |
| 131 | 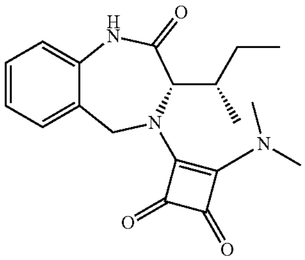 [SMILES: CC[C@H](C)[C@H]1C(=O)Nc2ccccc2CN1c1c(N(C)C)c(=O)c1=O] | 3-((S)-3-((S)-sec-butyl)-2-oxo-1,2,3,5-tetrahydro-4H-benzo[e][1,4]diazepin-4-yl)-4-(dimethylamino)cyclobut-3-ene-1,2-dione |
| 132 | 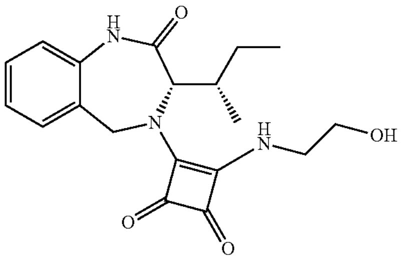 [SMILES: CC[C@H](C)[C@H]1C(=O)Nc2ccccc2CN1c1c(NCCO)c(=O)c1=O] | 3-((S)-3-((S)-sec-butyl)-2-oxo-1,2,3,5-tetrahydro-4H-benzo[e][1,4]diazepin-4-yl)-4-((2-hydroxyethyl)amino)cyclobut-3-ene-1,2-dione |
| 133 | 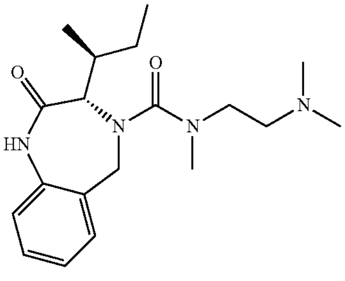 [SMILES: CC[C@H](C)[C@H]1C(=O)Nc2ccccc2CN1C(=O)N(C)CCN(C)C] | (S)-3-((S)-sec-butyl)-N-(2-(dimethylamino)ethyl)-N-methyl-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 134 | 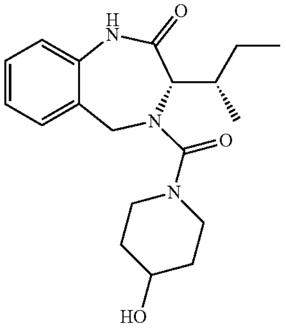 [SMILES: CC[C@H](C)[C@H]1C(=O)Nc2ccccc2CN1C(=O)N1CCC(O)CC1] | (S)-3-((S)-sec-butyl)-4-(4-hydroxypiperidine-1-carbonyl)-1,3,4,5-tetrahydro-2H-benzo[e][1,4]diazepin-2-one |
| 135 | 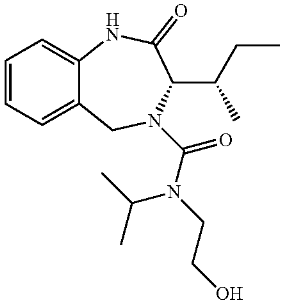 [SMILES: CC[C@H](C)[C@H]1C(=O)Nc2ccccc2CN1C(=O)N(CCO)C(C)C] | (S)-3-((S)-sec-butyl)-N-(2-hydroxyethyl)-N-isopropyl-2-oxo-1,2,3,5-tetrahydro-4H-benzo[e][1,4]diazepine-4-carboxamide |
| 136 | 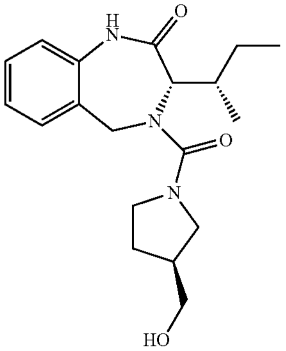 [SMILES: CC[C@H](C)[C@H]1C(=O)Nc2ccccc2CN1C(=O)N1CC[C@H](CO)C1] | (S)-3-((S)-sec-butyl)-4-((S)-3-(hydroxymethyl)pyrrolidine-1-carbonyl)-1,3,4,5-tetrahydro-2H-benzo[e][1,4]diazepin-2-one |
| 137 | 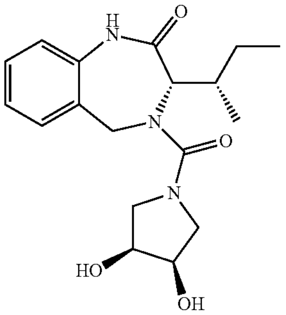 [SMILES: CC[C@H](C)[C@H]1C(=O)Nc2ccccc2CN1C(=O)N1C[C@@H](O)[C@@H](O)C1] | (S)-3-((S)-sec-butyl)-4-((3R,4S)-3,4-dihydroxypyrrolidine-1-carbonyl)-1,3,4,5-tetrahydro-2H-benzo[e][1,4]diazepin-2-one |
| 138 | 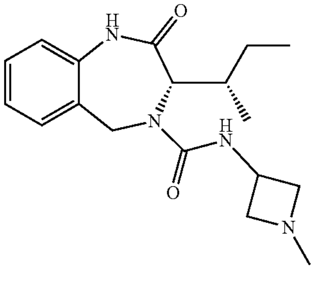 [SMILES: CC[C@H](C)[C@H]1C(=O)Nc2ccccc2CN1C(=O)NC1CN(C)C1] | (S)-3-((S)-sec-butyl)-N-(1-methylazetidin-3-yl)-2-oxo-1,2,3,5-tetrahydro-4H-benzo[e][1,4]diazepine-4-carboxamide |

TABLE 2-continued

| Compound No. | Compound Structure | Compound Name |
| --- | --- | --- |
| 139 | 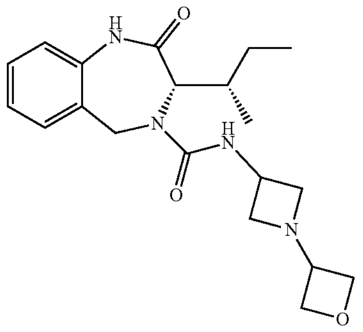 [SMILES: CC[C@H](C)[C@H]1C(=O)Nc2ccccc2CN1C(=O)NC1CN(C2COC2)C1] | (S)-3-((S)-sec-butyl)-N-(1-(oxetan-3-yl)azetidin-3-yl)-2-oxo-1,2,3,5-tetrahydro-4H-benzo[e][1,4]diazepine-4-carboxamide |
| 140 | 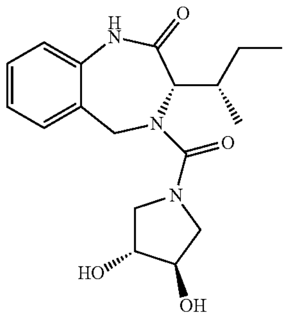 [SMILES: CC[C@H](C)[C@H]1C(=O)Nc2ccccc2CN1C(=O)N1C[C@@H](O)[C@H](O)C1] | (S)-3-((S)-sec-butyl)-4-((3R,4R)-3,4-dihydroxypyrrolidine-1-carbonyl)-1,3,4,5-tetrahydro-2H-benzo[e][1,4]diazepin-2-one |
| 141 | 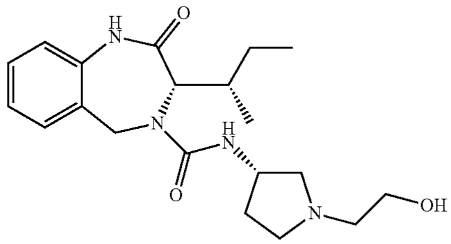 [SMILES: CC[C@H](C)[C@H]1C(=O)Nc2ccccc2CN1C(=O)N[C@H]1CCN(CCO)C1] | (S)-3-((S)-sec-butyl)-N-((S)-1-(2-hydroxyethyl)pyrrolidin-3-yl)-2-oxo-1,2,3,5-tetrahydro-4H-benzo[e][1,4]diazepine-4-carboxamide |
| 142 | 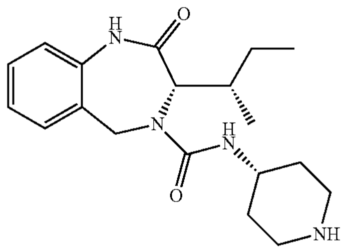 | (S)-3-((S)-sec-butyl)-2-oxo-N-(piperidin-4-yl)-1,2,3,5-tetrahydro-4H-benzo[e][1,4]diazepine-4-carboxamide |
| 143 | 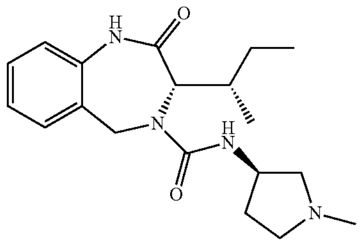 [SMILES: CC[C@H](C)[C@H]1C(=O)Nc2ccccc2CN1C(=O)N[C@@H]1CCN(C)C1] | (S)-3-((S)-sec-butyl)-N-((R)-1-methylpyrrolidin-3-yl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 144 | 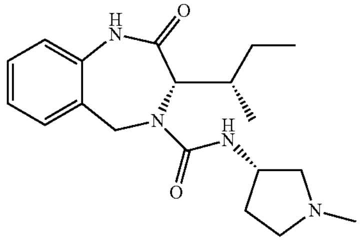 [SMILES: CC[C@H](C)[C@H]1C(=O)Nc2ccccc2CN1C(=O)N[C@H]1CCN(C)C1] | (S)-3-((S)-sec-butyl)-N-((S)-1-methylpyrrolidin-3-yl)-2-oxo-1,2,3,5-tetrahydro-4H-benzo[e][1,4]diazepine-4-carboxamide |
| 145 | 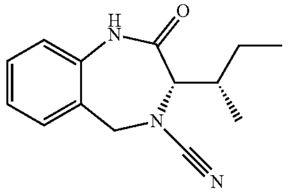 [SMILES: CC[C@H](C)[C@H]1C(=O)Nc2ccccc2CN1C#N] | (S)-3-((S)-sec-butyl)-2-oxo-1,2,3,5-tetrahydro-4H-benzo[e][1,4]diazepine-4-carbonitrile |
| 146 | 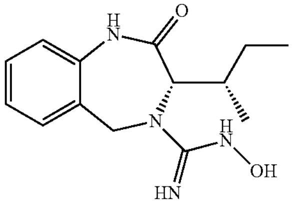 [SMILES: CC[C@H](C)[C@H]1C(=O)Nc2ccccc2CN1C(=N)NO] | (S)-3-((S)-sec-butyl)-N-hydroxy-2-oxo-1,2,3,5-tetrahydro-4H-benzo[e][1,4]diazepine-4-carboximidamide |
| 147 | 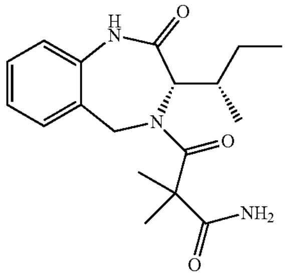 [SMILES: CC[C@H](C)[C@H]1C(=O)Nc2ccccc2CN1C(=O)C(C)(C)C(N)=O] | 3-((S)-3-((S)-sec-butyl)-2-oxo-1,2,3,5-tetrahydro-4H-benzo[e][1,4]diazepin-4-yl)-2,2-dimethyl-3-oxopropanamide |
| 148 | 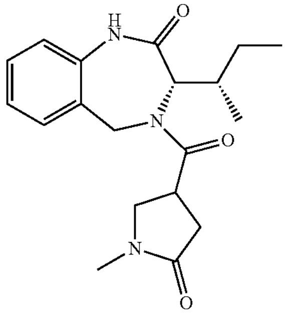 [SMILES: CC[C@H](C)[C@H]1C(=O)Nc2ccccc2CN1C(=O)C1CC(=O)N(C)C1] | (3S)-3-((S)-sec-butyl)-4-(1-methyl-5-oxopyrrolidine-3-carbonyl)-1,3,4,5-tetrahydro-2H-benzo[e][1,4]diazepin-2-one |
| 149 | 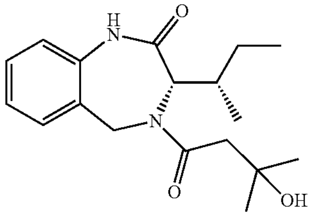 [SMILES: CC[C@H](C)[C@H]1C(=O)Nc2ccccc2CN1C(=O)CC(C)(C)O] | (S)-3-((S)-sec-butyl)-4-(3-hydroxy-3-methylbutanoyl)-1,3,4,5-tetrahydro-2H-benzo[e][1,4]diazepin-2-one |

TABLE 2-continued

| Compound No. | Compound Structure | Compound Name |
|---|---|---|
| 150 | 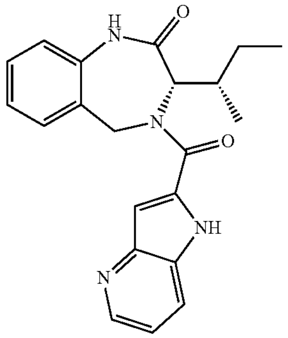 [SMILES: CC[C@H](C)[C@H]1C(=O)Nc2ccccc2CN1C(=O)c1cc2ncccc2[nH]1] | (S)-3-((S)-sec-butyl)-4-(1H-pyrrolo[3,2-b]pyridine-2-carbonyl)-1,3,4,5-tetrahydro-2H-benzo[e][1,4]diazepin-2-one |
| 151 | 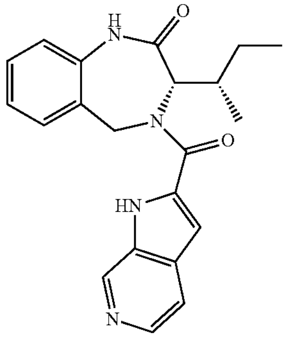 [SMILES: CC[C@H](C)[C@H]1C(=O)Nc2ccccc2CN1C(=O)c1cc2ccncc2[nH]1] | (S)-3-((S)-sec-butyl)-4-(1H-pyrrolo[2,3-c]pyridine-2-carbonyl)-1,3,4,5-tetrahydro-2H-benzo[e][1,4]diazepin-2-one |
| 152 | 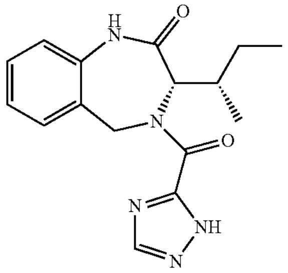 [SMILES: CC[C@H](C)[C@H]1C(=O)Nc2ccccc2CN1C(=O)c1ncn[nH]1] | (S)-3-((S)-sec-butyl)-4-(1H-1,2,4-triazole-5-carbonyl)-1,3,4,5-tetrahydro-2H-benzo[e][1,4]diazepin-2-one |
| 153 | 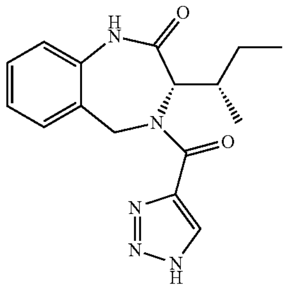 [SMILES: CC[C@H](C)[C@H]1C(=O)Nc2ccccc2CN1C(=O)c1c[nH]nn1] | (S)-3-((S)-sec-butyl)-4-(1H-1,2,3-triazole-4-carbonyl)-1,3,4,5-tetrahydro-2H-benzo[e][1,4]diazepin-2-one |
| 154 | 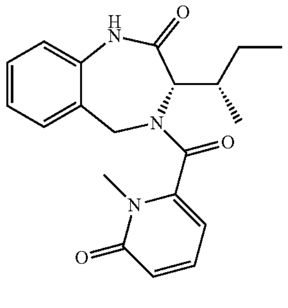 [SMILES: CC[C@H](C)[C@H]1C(=O)Nc2ccccc2CN1C(=O)c1cccc(=O)n1C] | (S)-3-((S)-sec-butyl)-4-(1-methyl-6-oxo-1,6-dihydropyridine-2-carbonyl)-1,3,4,5-tetrahydro-2H-benzo[e][1,4]diazepin-2-one |

TABLE 2-continued

| Compound No. | Compound Structure | Compound Name |
| --- | --- | --- |
| 155 | 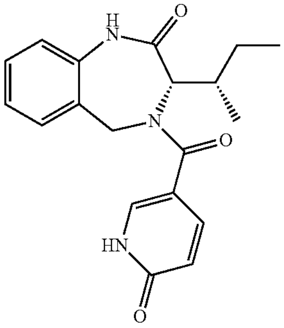 [SMILES: CC[C@H](C)[C@H]1C(=O)Nc2ccccc2CN1C(=O)c1ccc(=O)[nH]c1] | (S)-3-((S)-sec-butyl)-4-(6-oxo-1,6-dihydropyridine-3-carbonyl)-1,3,4,5-tetrahydro-2H-benzo[e][1,4]diazepin-2-one |
| 156 | 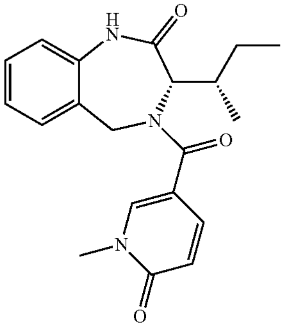 [SMILES: CC[C@H](C)[C@H]1C(=O)Nc2ccccc2CN1C(=O)c1ccc(=O)n(C)c1] | (S)-3-((S)-sec-butyl)-4-(1-methyl-6-oxo-1,6-dihydropyridine-3-carbonyl)-1,3,4,5-tetrahydro-2H-benzo[e][1,4]diazepin-2-one |
| 157 | 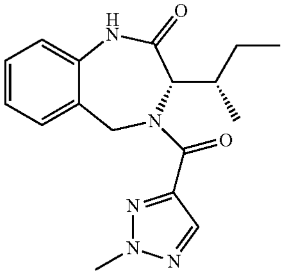 [SMILES: CC[C@H](C)[C@H]1C(=O)Nc2ccccc2CN1C(=O)c1cnn(C)n1] | (S)-3-((S)-sec-butyl)-4-(2-methyl-2H-1,2,3-triazole-4-carbonyl)-1,3,4,5-tetrahydro-2H-benzo[e][1,4]diazepin-2-one |
| 158 | 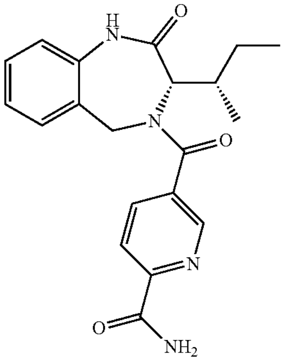 [SMILES: CC[C@H](C)[C@H]1C(=O)Nc2ccccc2CN1C(=O)c1ccc(C(N)=O)nc1] | 5-((S)-3-((S)-sec-butyl)-2-oxo-2,3,4,5-tetrahydro-1H-benzo[e][1,4]diazepine-4-carbonyl)picolinamide |
| 159 | 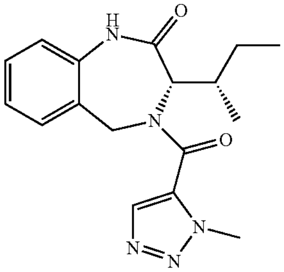 [SMILES: CC[C@H](C)[C@H]1C(=O)Nc2ccccc2CN1C(=O)c1cnnn1C] | (S)-3-((S)-sec-butyl)-4-(1-methyl-1H-1,2,3-triazole-5-carbonyl)-1,3,4,5-tetrahydro-2H-benzo[e][1,4]diazepin-2-one |

TABLE 2-continued
| Compound No. | Compound Structure | Compound Name |
|---|---|---|
| 160 | 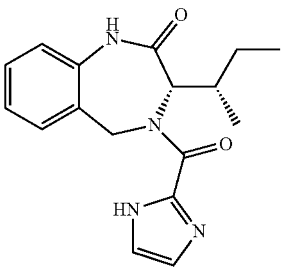 [SMILES: CC[C@H](C)[C@H]1C(=O)Nc2ccccc2CN1C(=O)c1ncc[nH]1] | (S)-3-((S)-sec-butyl)-4-(1H-imidazole-2-carbonyl)-1,3,4,5-tetrahydro-2H-benzo[e][1,4]diazepin-2-one |
| 161 | 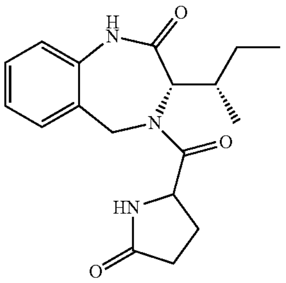 [SMILES: CC[C@H](C)[C@H]1C(=O)Nc2ccccc2CN1C(=O)C1CCC(=O)N1] | (3S)-3-((S)-sec-butyl)-4-(5-oxopyrrolidine-2-carbonyl)-1,3,4,5-tetrahydro-2H-benzo[e][1,4]diazepin-2-one |
| 162 | 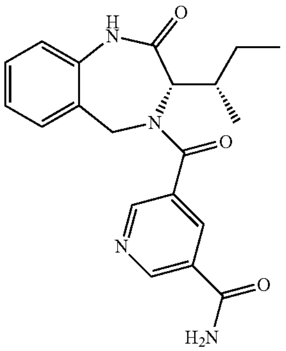 [SMILES: CC[C@H](C)[C@H]1C(=O)Nc2ccccc2CN1C(=O)c1cncc(C(N)=O)c1] | 5-((S)-3-((S)-sec-butyl)-2-oxo-2,3,4,5-tetrahydro-1H-benzo[e][1,4]diazepine-4-carbonyl)nicotinamide |
| 163 | 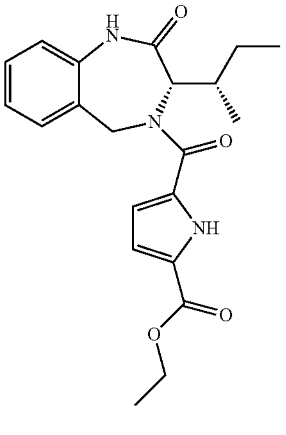 [SMILES: CCOC(=O)c1ccc(C(=O)N2Cc3ccccc3NC(=O)[C@@H]2[C@@H](C)CC)[nH]1] | ethyl 5-((S)-3-((S)-sec-butyl)-2-oxo-2,3,4,5-tetrahydro-1H-benzo[e][1,4]diazepine-4-carbonyl)-1H-pyrrole-2-carboxylate |

TABLE 2-continued

| Compound No. | Compound Structure | Compound Name |
|---|---|---|
| 164 | 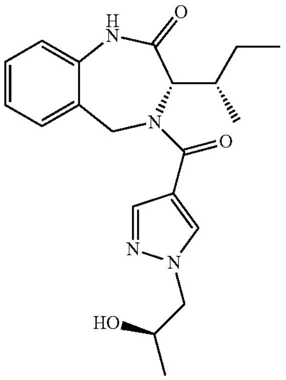 [SMILES: CC[C@H](C)[C@H]1C(=O)Nc2ccccc2CN1C(=O)c1cnn(C[C@@H](C)O)c1] | (S)-3-((S)-sec-butyl)-4-(1-((R)-2-hydroxypropyl)-1H-pyrazole-4-carbonyl)-1,3,4,5-tetrahydro-2H-benzo[e][1,4]diazepin-2-one |
| 165 | 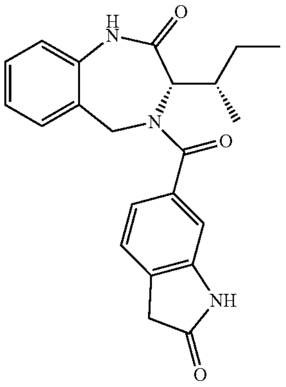 [SMILES: CC[C@H](C)[C@H]1C(=O)Nc2ccccc2CN1C(=O)c1ccc2c(c1)NC(=O)C2] | (S)-3-((S)-sec-butyl)-4-(2-oxoindoline-6-carbonyl)-1,3,4,5-tetrahydro-2H-benzo[e][1,4]diazepin-2-one |
| 166 | 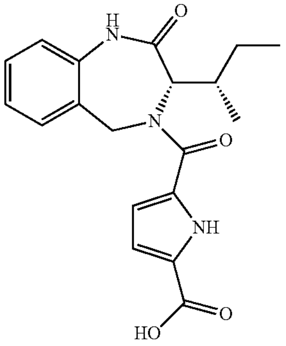 [SMILES: CC[C@H](C)[C@H]1C(=O)Nc2ccccc2CN1C(=O)c1ccc(C(=O)O)[nH]1] | 5-((S)-3-((S)-sec-butyl)-2-oxo-2,3,4,5-tetrahydro-1H-benzo[e][1,4]diazepine-4-carbonyl)-1H-pyrrole-2-carboxylic acid |
| 167 | 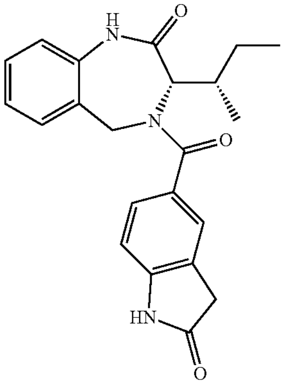 [SMILES: CC[C@H](C)[C@H]1C(=O)Nc2ccccc2CN1C(=O)c1ccc2c(c1)CC(=O)N2] | (S)-3-((S)-sec-butyl)-4-(2-oxoindoline-5-carbonyl)-1,3,4,5-tetrahydro-2H-benzo[e][1,4]diazepin-2-one |

TABLE 2-continued

| Compound No. | Compound Structure | Compound Name |
|---|---|---|
| 168 | 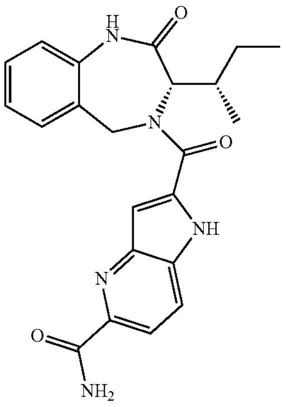 [SMILES: CC[C@H](C)[C@H]1C(=O)Nc2ccccc2CN1C(=O)c1cc2nc(C(N)=O)ccc2[nH]1] | 2-((S)-3-((S)-sec-butyl)-2-oxo-2,3,4,5-tetrahydro-1H-benzo[e][1,4]diazepine-4-carbonyl)-1H-pyrrolo[3,2-b]pyridine-5-carboxamide |
| 169 | 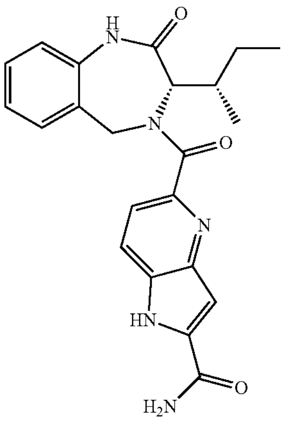 [SMILES: CC[C@H](C)[C@H]1C(=O)Nc2ccccc2CN1C(=O)c1ccc2[nH]c(C(N)=O)cc2n1] | 5-((S)-3-((S)-sec-butyl)-2-oxo-2,3,4,5-tetrahydro-1H-benzo[e][1,4]diazepine-4-carbonyl)-1H-pyrrolo[3,2-b]pyridine-2-carboxamide |
| 170 | 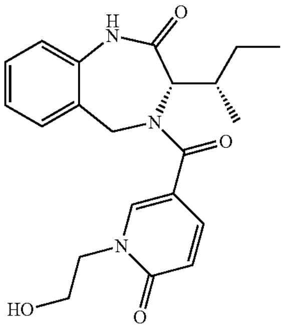 [SMILES: CC[C@H](C)[C@H]1C(=O)Nc2ccccc2CN1C(=O)c1ccc(=O)n(CCO)c1] | (S)-3-((S)-sec-butyl)-4-(1-(2-hydroxyethyl)-6-oxo-1,6-dihydropyridine-3-carbonyl)-1,3,4,5-tetrahydro-2H-benzo[e][1,4]diazepin-2-one |
| 171 | 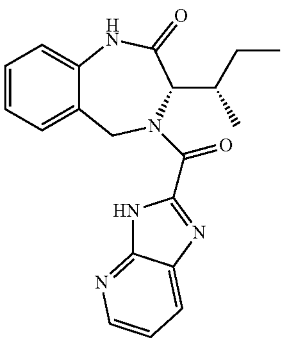 [SMILES: CC[C@H](C)[C@H]1C(=O)Nc2ccccc2CN1C(=O)c1nc2cccnc2[nH]1] | (S)-3-((S)-sec-butyl)-4-(3H-imidazo[4,5-b]pyridine-2-carbonyl)-1,3,4,5-tetrahydro-2H-benzo[e][1,4]diazepin-2-one |

TABLE 2-continued

| Compound No. | Compound Structure | Compound Name |
|---|---|---|
| 172 | 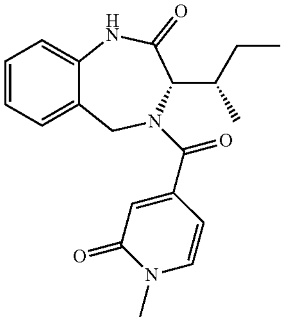 [SMILES: CC[C@H](C)[C@H]1C(=O)Nc2ccccc2CN1C(=O)c1ccn(C)c(=O)c1] | (S)-3-((S)-sec-butyl)-4-(1-methyl-2-oxo-1,2-dihydropyridine-4-carbonyl)-1,3,4,5-tetrahydro-2H-benzo[e][1,4]diazepin-2-one |
| 173 | 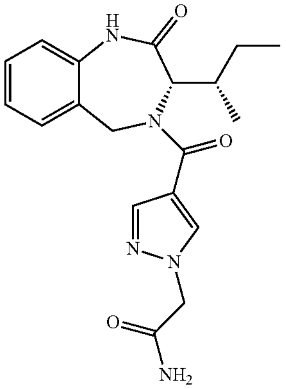 [SMILES: CC[C@H](C)[C@H]1C(=O)Nc2ccccc2CN1C(=O)c1cnn(CC(N)=O)c1] | 2-(4-((S)-3-((S)-sec-butyl)-2-oxo-2,3,4,5-tetrahydro-1H-benzo[e][1,4]diazepine-4-carbonyl)-1H-pyrazol-1-yl)acetamide |
| 174 | 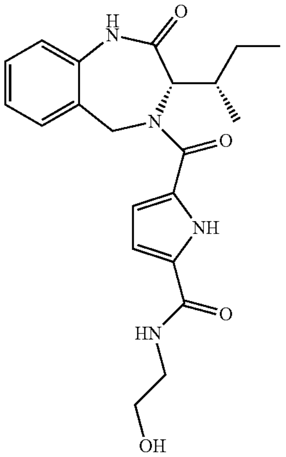 [SMILES: CC[C@H](C)[C@H]1C(=O)Nc2ccccc2CN1C(=O)c1ccc(C(=O)NCCO)[nH]1] | 5-((S)-3-((S)-sec-butyl)-2-oxo-2,3,4,5-tetrahydro-1H-benzo[e][1,4]diazepine-4-carbonyl)-N-(2-hydroxyethyl)-1H-pyrrole-2-carboxamide |
| 175 | 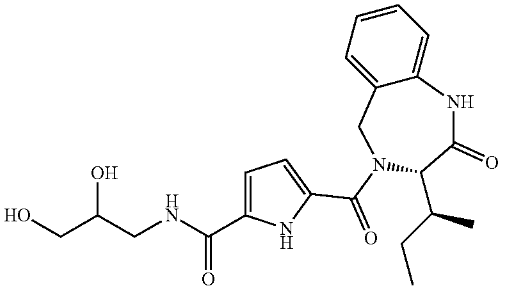 [SMILES: CC[C@H](C)[C@H]1C(=O)Nc2ccccc2CN1C(=O)c1ccc(C(=O)NCC(O)CO)[nH]1] | 5-((S)-3-((S)-sec-butyl)-2-oxo-2,3,4,5-tetrahydro-1H-benzo[e][1,4]diazepine-4-carbonyl)-N-(2,3-dihydroxypropyl)-1H-pyrrole-2-carboxamide |

TABLE 2-continued
| Compound No. | Compound Structure | Compound Name |
|---|---|---|
| 176 | 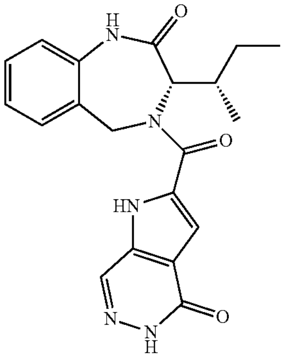 [SMILES: CC[C@H](C)[C@H]1C(=O)Nc2ccccc2CN1C(=O)c1cc2c(=O)[nH]ncc2[nH]1] | (S)-3-((S)-sec-butyl)-4-(4-oxo-4,5-dihydro-1H-pyrrolo[2,3-d]pyridazine-2-carbonyl)-1,3,4,5-tetrahydro-2H-benzo[e][1,4]diazepin-2-one |
| 177 | 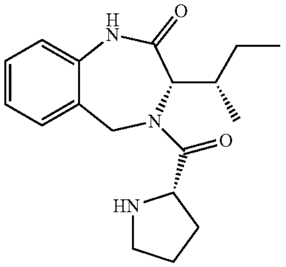 [SMILES: CC[C@H](C)[C@H]1C(=O)Nc2ccccc2CN1C(=O)[C@@H]1CCCN1] | (S)-4-(L-prolyl)-3-((S)-sec-butyl)-1,3,4,5-tetrahydro-2H-benzo[e][1,4]diazepin-2-one |
| 178 | 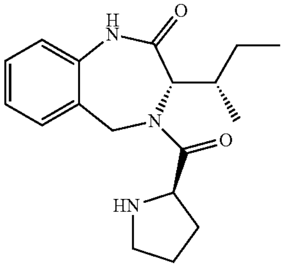 [SMILES: CC[C@H](C)[C@H]1C(=O)Nc2ccccc2CN1C(=O)[C@H]1CCCN1] | (S)-4-(D-prolyl)-3-((S)-sec-butyl)-1,3,4,5-tetrahydro-2H-benzo[e][1,4]diazepin-2-one |
| 179 | 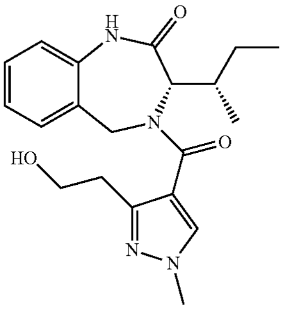 [SMILES: CC[C@H](C)[C@H]1C(=O)Nc2ccccc2CN1C(=O)c1cn(C)nc1CCO] | (S)-3-((S)-sec-butyl)-4-(3-(2-hydroxyethyl)-1-methyl-1H-pyrazole-4-carbonyl)-1,3,4,5-tetrahydro-2H-benzo[e][1,4]diazepin-2-one |

TABLE 2-continued

| Compound No. | Compound Structure | Compound Name |
|---|---|---|
| 180 | 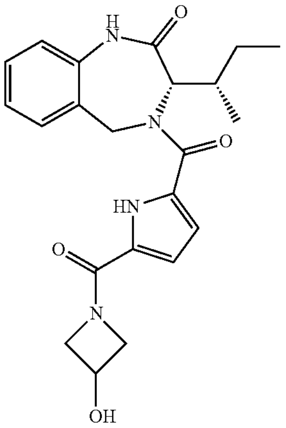 [SMILES: CC[C@H](C)[C@H]1C(=O)Nc2ccccc2CN1C(=O)c1ccc(C(=O)N2CC(O)C2)[nH]1] | (S)-3-((S)-sec-butyl)-4-(5-(3-hydroxyazetidine-1-carbonyl)-1H-pyrrole-2-carbonyl)-1,3,4,5-tetrahydro-2H-benzo[e][1,4]diazepin-2-one |
| 181 | 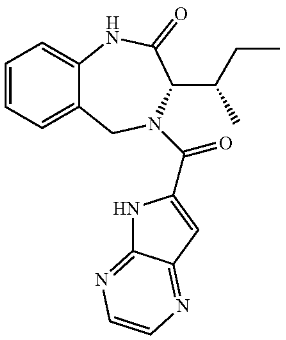 [SMILES: CC[C@H](C)[C@H]1C(=O)Nc2ccccc2CN1C(=O)c1cc2nccnc2[nH]1] | (S)-3-((S)-sec-butyl)-4-(5H-pyrrolo[2,3-b]pyrazine-6-carbonyl)-1,3,4,5-tetrahydro-2H-benzo[e][1,4]diazepin-2-one |
| 182 | 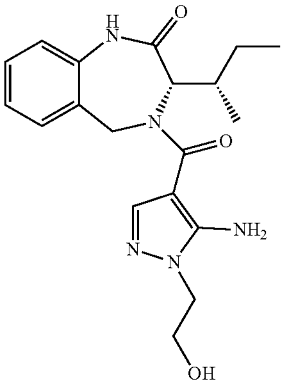 [SMILES: CC[C@H](C)[C@H]1C(=O)Nc2ccccc2CN1C(=O)c1cnn(CCO)c1N] | (S)-4-(5-amino-1-(2-hydroxyethyl)-1H-pyrazole-4-carbonyl)-3-((S)-sec-butyl)-1,3,4,5-tetrahydro-2H-benzo[e][1,4]diazepin-2-one |
| 183 | 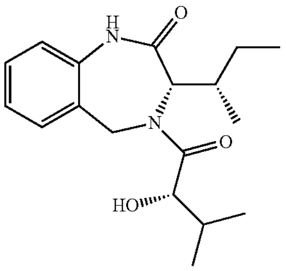 [SMILES: CC[C@H](C)[C@H]1C(=O)Nc2ccccc2CN1C(=O)[C@@H](O)C(C)C] | (S)-3-((S)-sec-butyl)-4-((S)-2-hydroxy-2-methylbutanoyl)-1,3,4,5-tetrahydro-2H-benzo[e][1,4]diazepin-2-one |

TABLE 2-continued

| Compound No. | Compound Structure | Compound Name |
|---|---|---|
| 184 | 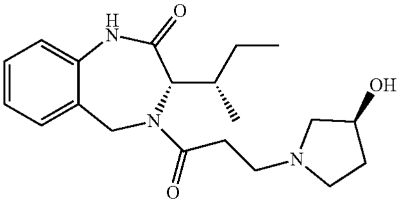 [SMILES: CC[C@H](C)[C@H]1C(=O)Nc2ccccc2CN1C(=O)CCN1CC[C@H](O)C1] | (S)-3-((S)-sec-butyl)-4-(3-((S)-3-hydroxypyrrolidin-1-yl)propanoyl)-1,3,4,5-tetrahydro-2H-benzo[e][1,4]diazepin-2-one |
| 185 | 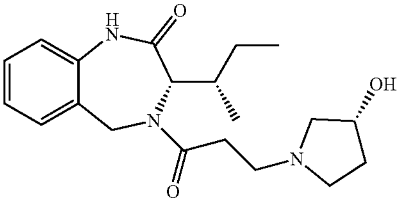 [SMILES: CC[C@H](C)[C@H]1C(=O)Nc2ccccc2CN1C(=O)CCN1CC[C@@H](O)C1] | (S)-3-((S)-sec-butyl)-4-(3-((R)-3-hydroxypyrrolidin-1-yl)propanoyl)-1,3,4,5-tetrahydro-2H-benzo[e][1,4]diazepin-2-one |
| 186 | 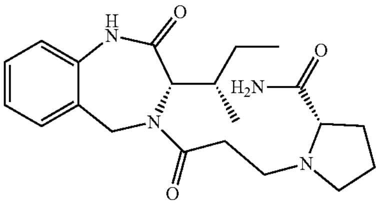 [SMILES: CC[C@H](C)[C@H]1C(=O)Nc2ccccc2CN1C(=O)CCN1CCC[C@H]1C(N)=O] | (S)-1-(3-((S)-3-((S)-sec-butyl)-2-oxo-1,2,3,5-tetrahydro-4H-benzo[e][1,4]diazepin-4-yl)-3-oxopropyl)pyrrolidine-2-carboxamide |
| 187 | 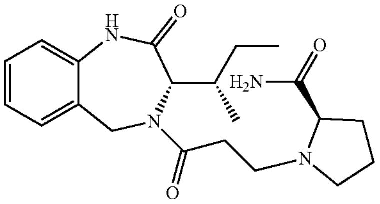 [SMILES: CC[C@H](C)[C@H]1C(=O)Nc2ccccc2CN1C(=O)CCN1CCC[C@@H]1C(N)=O] | (R)-1-(3-((S)-3-((S)-sec-butyl)-2-oxo-1,2,3,5-tetrahydro-4H-benzo[e][1,4]diazepin-4-yl)-3-oxopropyl)pyrrolidine-2-carboxamide |
| 188 | 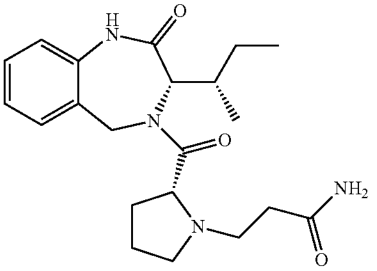 [SMILES: CC[C@H](C)[C@H]1C(=O)Nc2ccccc2CN1C(=O)[C@H]1CCCN1CCC(N)=O] | 3-((R)-2-((S)-3-((S)-sec-butyl)-2-oxo-2,3,4,5-tetrahydro-1H-benzo[e][1,4]diazepine-4-carbonyl)pyrrolidin-1-yl)propanamide |
| 189 | 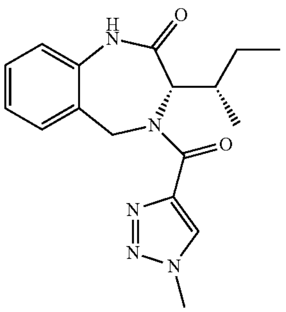 [SMILES: CC[C@H](C)[C@H]1C(=O)Nc2ccccc2CN1C(=O)c1cn(C)nn1] | (S)-3-((S)-sec-butyl)-4-(1-methyl-1H-1,2,3-triazole-4-carbonyl)-1,3,4,5-tetrahydro-2H-benzo[e][1,4]diazepin-2-one |

TABLE 2-continued

| Compound No. | Compound Structure | Compound Name |
|---|---|---|
| 190 | 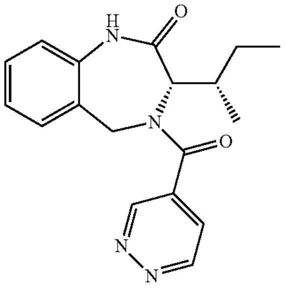 [SMILES: CC[C@H](C)[C@H]1C(=O)Nc2ccccc2CN1C(=O)c1ccnnc1] | (S)-3-((S)-sec-butyl)-4-(pyridazine-4-carbonyl)-1,3,4,5-tetrahydro-2H-benzo[e][1,4]diazepin-2-one |
| 191 | 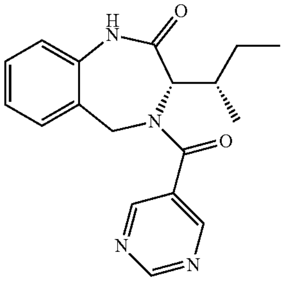 [SMILES: CC[C@H](C)[C@H]1C(=O)Nc2ccccc2CN1C(=O)c1cncnc1] | (S)-3-((S)-sec-butyl)-4-(pyrimidine-5-carbonyl)-1,3,4,5-tetrahydro-2H-benzo[e][1,4]diazepin-2-one |
| 192 | 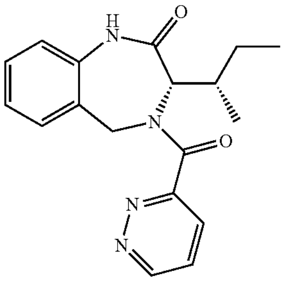 [SMILES: CC[C@H](C)[C@H]1C(=O)Nc2ccccc2CN1C(=O)c1cccnn1] | (S)-3-((S)-sec-butyl)-4-(pyridazine-3-carbonyl)-1,3,4,5-tetrahydro-2H-benzo[e][1,4]diazepin-2-one |
| 193 | 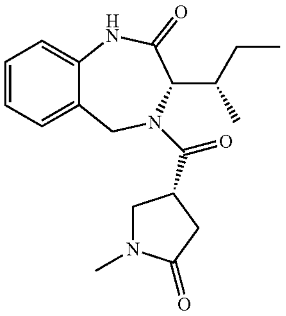 [SMILES: CC[C@H](C)[C@H]1C(=O)Nc2ccccc2CN1C(=O)[C@@H]1CC(=O)N(C)C1] | (S)-3-((S)-sec-butyl)-4-((R)-1-methyl-5-oxopyrrolidine-3-carbonyl)-1,3,4,5-tetrahydro-2H-benzo[e][1,4]diazepin-2-one |
| 194 | 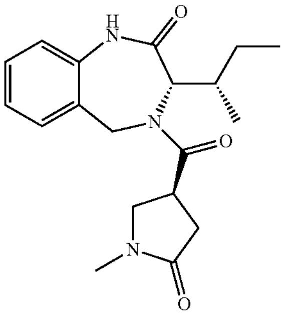 [SMILES: CC[C@H](C)[C@H]1C(=O)Nc2ccccc2CN1C(=O)[C@H]1CC(=O)N(C)C1] | (S)-3-((S)-sec-butyl)-4-((S)-1-methyl-5-oxopyrrolidine-3-carbonyl)-1,3,4,5-tetrahydro-2H-benzo[e][1,4]diazepin-2-one |

TABLE 2-continued

| Compound No. | Compound Structure | Compound Name |
|---|---|---|
| 195 | 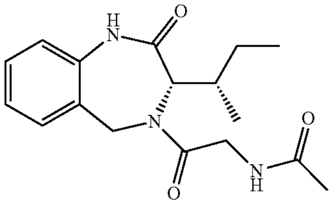 [SMILES: CC[C@H](C)[C@H]1C(=O)Nc2ccccc2CN1C(=O)CNC(C)=O] | N-(2-((S)-3-((S)-sec-butyl)-2-oxo-1,2,3,5-tetrahydro-4H-benzo[e][1,4]diazepin-4-yl)-2-oxoethyl)acetamide |
| 196 | 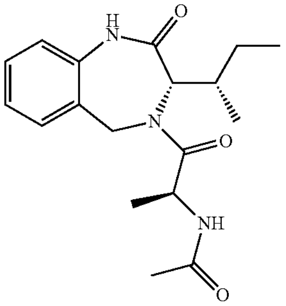 [SMILES: CC[C@H](C)[C@H]1C(=O)Nc2ccccc2CN1C(=O)[C@H](C)NC(C)=O] | N-((S)-1-((S)-3-((S)-sec-butyl)-2-oxo-1,2,3,5-tetrahydro-4H-benzo[e][1,4]diazepin-4-yl)-1-oxopropan-2-yl)acetamide |
| 197 | 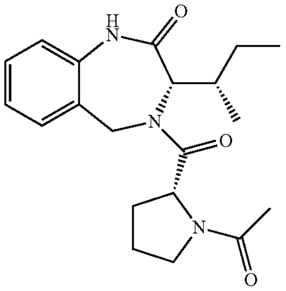 [SMILES: CC[C@H](C)[C@H]1C(=O)Nc2ccccc2CN1C(=O)[C@H]1CCCN1C(C)=O] | (S)-4-(acetyl-D-prolyl)-3-((S)-sec-butyl)-1,3,4,5-tetrahydro-2H-benzo[e][1,4]diazepin-2-one |
| 198 | 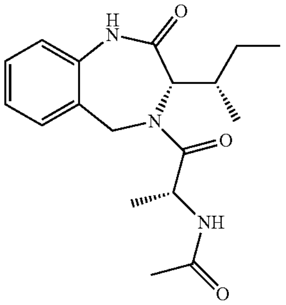 [SMILES: CC[C@H](C)[C@H]1C(=O)Nc2ccccc2CN1C(=O)[C@@H](C)NC(C)=O] | N-((R)-1-((S)-3-((S)-sec-butyl)-2-oxo-1,2,3,5-tetrahydro-4H-benzo[e][1,4]diazepin-4-yl)-1-oxopropan-2-yl)acetamide |
| 199 | 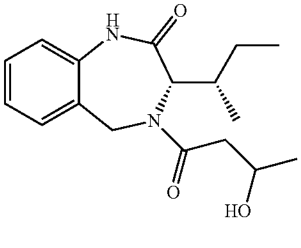 [SMILES: CC[C@H](C)[C@H]1C(=O)Nc2ccccc2CN1C(=O)CC(C)O] | (3S)-3-((S)-sec-butyl)-4-(3-hydroxybutanoyl)-1,3,4,5-tetrahydro-2H-benzo[e][1,4]diazepin-2-one |

TABLE 2-continued

| Compound No. | Compound Structure | Compound Name |
| --- | --- | --- |
| 200 | 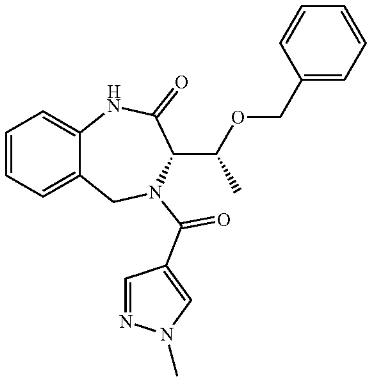 [SMILES: C[C@@H](OCc1ccccc1)[C@H]1C(=O)Nc2ccccc2CN1C(=O)c1cnn(C)c1] | (S)-3-((R)-1-(benzyloxy)ethyl)-4-(1-methyl-1H-pyrazole-4-carbonyl)-1,3,4,5-tetrahydro-2H-benzo[e][1,4]diazepin-2-one |
| 201 | 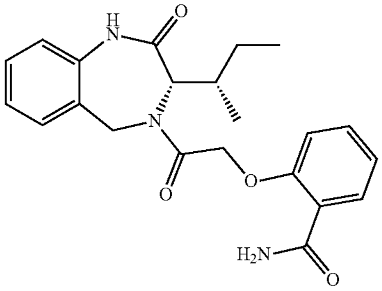 [SMILES: CC[C@H](C)[C@H]1C(=O)Nc2ccccc2CN1C(=O)COc1ccccc1C(N)=O] | 2-(2-((S)-3-((S)-sec-butyl)-2-oxo-1,2,3,5-tetrahydro-4H-benzo[e][1,4]diazepin-4-yl)-2-oxoethoxy)benzamide |
| 202 | 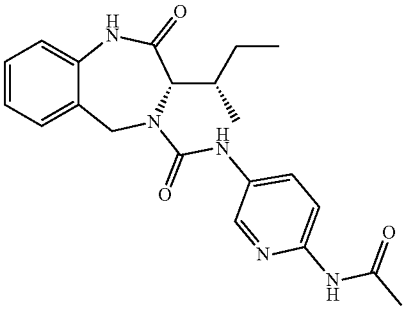 [SMILES: CC[C@H](C)[C@H]1C(=O)Nc2ccccc2CN1C(=O)Nc1ccc(NC(C)=O)nc1] | (S)-N-(6-acetamidopyridin-3-yl)-3-((S)-sec-butyl)-2-oxo-1,2,3,5-tetrahydro-4H-benzo[e][1,4]diazepine-4-carboxamide |
| 203 | 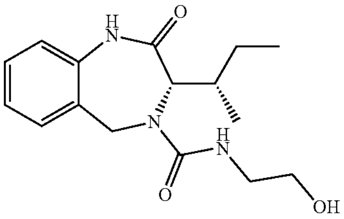 [SMILES: CC[C@H](C)[C@H]1C(=O)Nc2ccccc2CN1C(=O)NCCO] | (S)-3-((S)-sec-butyl)-N-(2-hydroxyethyl)-2-oxo-1,2,3,5-tetrahydro-4H-benzo[e][1,4]diazepine-4-carboxamide |
| 204 | 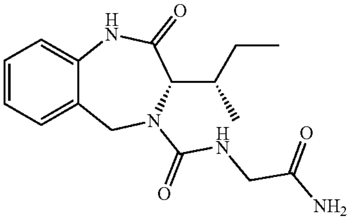 [SMILES: CC[C@H](C)[C@H]1C(=O)Nc2ccccc2CN1C(=O)NCC(N)=O] | (S)-N-(2-amino-2-oxoethyl)-3-((S)-sec-butyl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 205 | 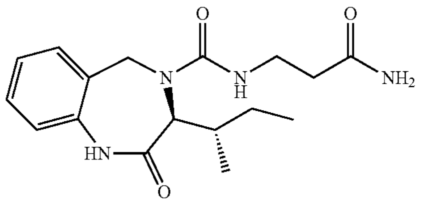 [SMILES: CC[C@H](C)[C@H]1C(=O)Nc2ccccc2CN1C(=O)NCCC(N)=O] | (S)-N-(3-amino-3-oxopropyl)-3-((S)-sec-butyl)-2-oxo-1,2,3,5-tetrahydro-4H-benzo[e][1,4]diazepine-4-carboxamide |
| 206 | 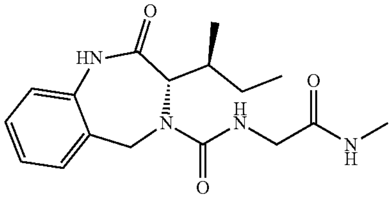 [SMILES: CC[C@H](C)[C@H]1C(=O)Nc2ccccc2CN1C(=O)NCC(=O)NC] | (S)-3-((S)-sec-butyl)-N-(2-(methylamino)-2-oxoethyl)-2-oxo-1,2,3,5-tetrahydro-4H-benzo[e][1,4]diazepine-4-carboxamide |
| 207 | 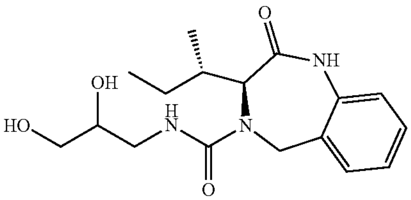 [SMILES: CC[C@H](C)[C@H]1C(=O)Nc2ccccc2CN1C(=O)NCC(O)CO] | (S)-3-((S)-sec-butyl)-N-((S)-2,3-dihydroxypropyl)-2-oxo-1,2,3,5-tetrahydro-4H-benzo[e][1,4]diazepine-4-carboxamide |
| 208 | 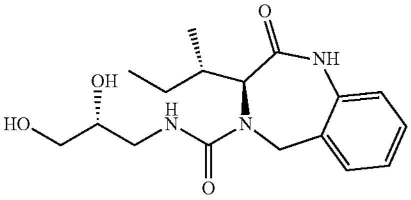 [SMILES: CC[C@H](C)[C@H]1C(=O)Nc2ccccc2CN1C(=O)NC[C@@H](O)CO] | (S)-3-((S)-sec-butyl)-N-((R)-2,3-dihydroxypropyl)-2-oxo-1,2,3,5-tetrahydro-4H-benzo[e][1,4]diazepine-4-carboxamide |
| 209 | 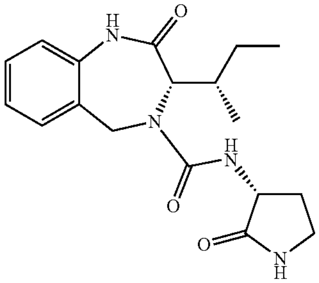 [SMILES: CC[C@H](C)[C@H]1C(=O)Nc2ccccc2CN1C(=O)N[C@@H]1CCNC1=O] | (S)-3-((S)-sec-butyl)-2-oxo-N-((R)-2-oxopyrrolidin-3-yl)-1,2,3,5-tetrahydro-4H-benzo[e][1,4]diazepine-4-carboxamide |
| 210 | 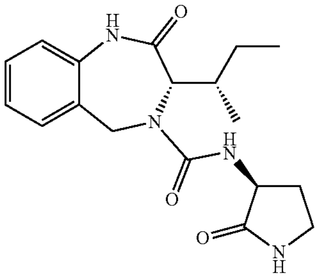 [SMILES: CC[C@H](C)[C@H]1C(=O)Nc2ccccc2CN1C(=O)N[C@H]1CCNC1=O] | (S)-3-((S)-sec-butyl)-2-oxo-N-((S)-2-oxopyrrolidin-3-yl)-1,2,3,5-tetrahydro-4H-benzo[e][1,4]diazepine-4-carboxamide |

TABLE 2-continued

| Compound No. | Compound Structure | Compound Name |
|---|---|---|
| 211 | 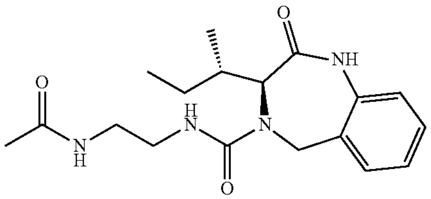 [SMILES: CC[C@H](C)[C@H]1C(=O)Nc2ccccc2CN1C(=O)NCCNC(C)=O] | (S)-N-(2-acetamidoethyl)-3-((S)-sec-butyl)-2-oxo-1,2,3,5-tetrahydro-4H-benzo[e][1,4]diazepine-4-carboxamide |
| 212 | 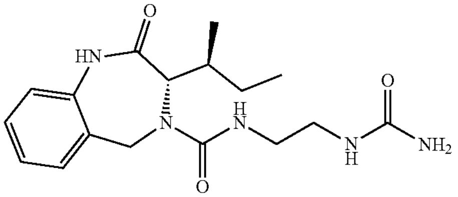 [SMILES: CC[C@H](C)[C@H]1C(=O)Nc2ccccc2CN1C(=O)NCCNC(N)=O] | (S)-3-((S)-sec-butyl)-2-oxo-N-(2-ureidoethyl)-1,2,3,5-tetrahydro-4H-benzo[e][1,4]diazepine-4-carboxamide |
| 213 | 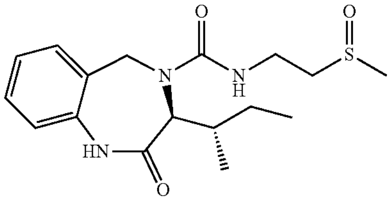 [SMILES: CC[C@H](C)[C@H]1C(=O)Nc2ccccc2CN1C(=O)NCCS(C)=O] | (3S)-3-((S)-sec-butyl)-N-(2-(methylsulfinyl)ethyl)-2-oxo-1,2,3,5-tetrahydro-4H-benzo[e][1,4]diazepine-4-carboxamide |
| 214 | 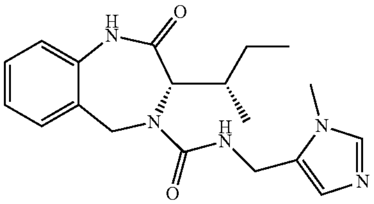 [SMILES: CC[C@H](C)[C@H]1C(=O)Nc2ccccc2CN1C(=O)NCc1cncn1C] | (S)-3-((S)-sec-butyl)-N-((1-methyl-1H-imidazol-5-yl)methyl)-2-oxo-1,2,3,5-tetrahydro-4H-benzo[e][1,4]diazepine-4-carboxamide |
| 215 | 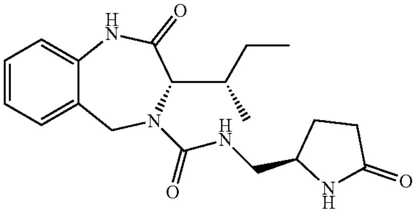 [SMILES: CC[C@H](C)[C@H]1C(=O)Nc2ccccc2CN1C(=O)NC[C@H]1CCC(=O)N1] | (S)-3-((S)-sec-butyl)-2-oxo-N-(((R)-5-oxopyrrolidin-2-yl)methyl)-1,2,3,5-tetrahydro-4H-benzo[e][1,4]diazepine-4-carboxamide |
| 216 | 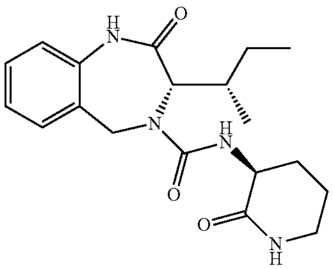 [SMILES: CC[C@H](C)[C@H]1C(=O)Nc2ccccc2CN1C(=O)N[C@H]1CCCNC1=O] | (S)-3-((S)-sec-butyl)-2-oxo-N-((S)-2-oxopiperidin-3-yl)-1,2,3,5-tetrahydro-4H-benzo[e][1,4]diazepine-4-carboxamide |

TABLE 2-continued

| Compound No. | Compound Structure | Compound Name |
|---|---|---|
| 217 | 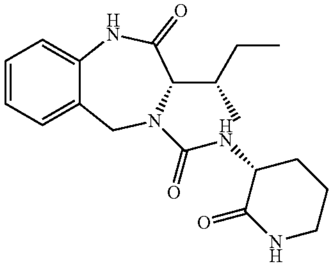 [SMILES: CC[C@H](C)[C@H]1C(=O)Nc2ccccc2CN1C(=O)N[C@@H]1CCCNC1=O] | (S)-3-((S)-sec-butyl)-2-oxo-N-((R)-2-oxopiperidin-3-yl)-1,2,3,5-tetrahydro-4H-benzo[e][1,4]diazepine-4-carboxamide |
| 218 | 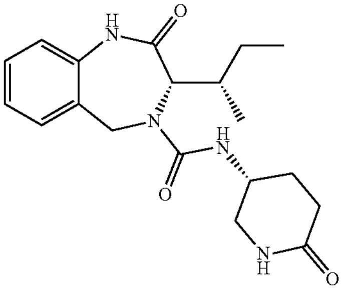 [SMILES: CC[C@H](C)[C@H]1C(=O)Nc2ccccc2CN1C(=O)N[C@@H]1CCC(=O)NC1] | (S)-3-((S)-sec-butyl)-2-oxo-N-((R)-6-oxopiperidin-3-yl)-1,2,3,5-tetrahydro-4H-benzo[e][1,4]diazepine-4-carboxamide |
| 219 | 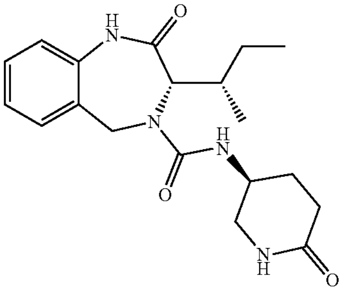 [SMILES: CC[C@H](C)[C@H]1C(=O)Nc2ccccc2CN1C(=O)N[C@H]1CCC(=O)NC1] | (S)-3-((S)-sec-butyl)-2-oxo-N-((S)-6-oxopiperidin-3-yl)-1,2,3,5-tetrahydro-4H-benzo[e][1,4]diazepine-4-carboxamide |
| 220 | 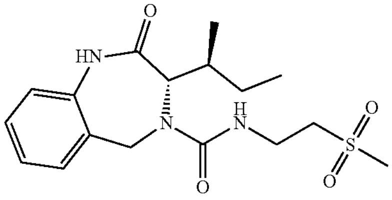 [SMILES: CC[C@H](C)[C@H]1C(=O)Nc2ccccc2CN1C(=O)NCCS(C)(=O)=O] | (S)-3-((S)-sec-butyl)-N-(2-(methylsulfonyl)ethyl)-2-oxo-1,2,3,5-tetrahydro-4H-benzo[e][1,4]diazepine-4-carboxamide |
| 221 | 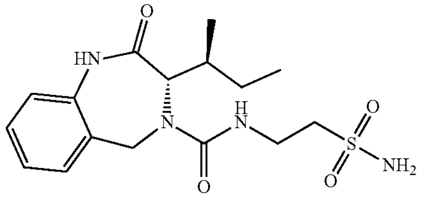 [SMILES: CC[C@H](C)[C@H]1C(=O)Nc2ccccc2CN1C(=O)NCCS(N)(=O)=O] | (S)-3-((S)-sec-butyl)-2-oxo-N-(2-sulfamoylethyl)-1,2,3,5-tetrahydro-4H-benzo[e][1,4]diazepine-4-carboxamide |
| 222 | 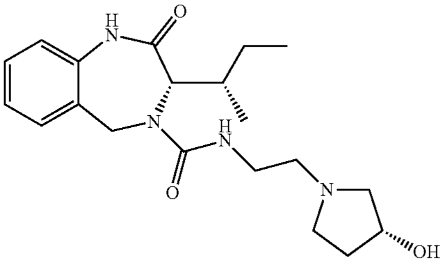 [SMILES: CC[C@H](C)[C@H]1C(=O)Nc2ccccc2CN1C(=O)NCCN1CC[C@@H](O)C1] | (S)-3-((S)-sec-butyl)-N-(2-((R)-3-hydroxypyrrolidin-1-yl)ethyl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 223 | 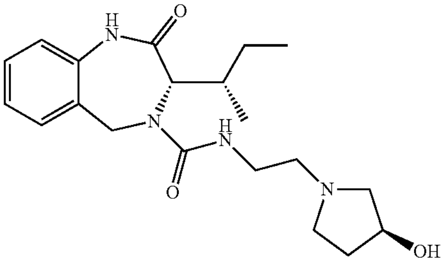 [SMILES: CC[C@H](C)[C@H]1C(=O)Nc2ccccc2CN1C(=O)NCCN1CC[C@H](O)C1] | (S)-3-((S)-sec-butyl)-N-(2-((S)-3-hydroxypyrrolidin-1-yl)ethyl)-2-oxo-1,2,3,5-tetrahydro-4H-benzo[e][1,4]diazepine-4-carboxamide |
| 224 | 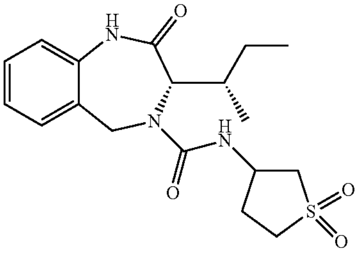 [SMILES: CC[C@H](C)[C@H]1C(=O)Nc2ccccc2CN1C(=O)NC1CCS(=O)(=O)C1] | (3S)-3-((S)-sec-butyl)-N-(1,1-dioxidotetrahydrothiophen-3-yl)-2-oxo-1,2,3,5-tetrahydro-4H-benzo[e][1,4]diazepine-4-carboxamide |
| 225 | 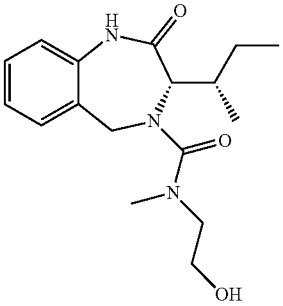 [SMILES: CC[C@H](C)[C@H]1C(=O)Nc2ccccc2CN1C(=O)N(C)CCO] | (S)-3-((S)-sec-butyl)-N-(2-hydroxyethyl)-N-methyl-2-oxo-1,2,3,5-tetrahydro-4H-benzo[e][1,4]diazepine-4-carboxamide |
| 226 | 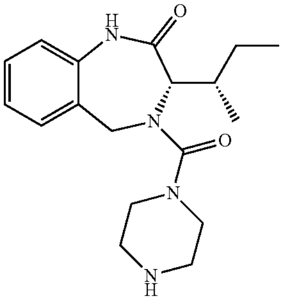 [SMILES: CC[C@H](C)[C@H]1C(=O)Nc2ccccc2CN1C(=O)N1CCNCC1] | (S)-3-((S)-sec-butyl)-4-(piperazine-1-carbonyl)-1,3,4,5-tetrahydro-2H-benzo[e][1,4]diazepin-2-one |
| 227 | 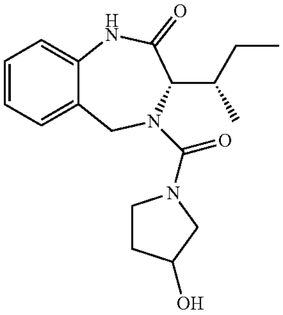 [SMILES: CC[C@H](C)[C@H]1C(=O)Nc2ccccc2CN1C(=O)N1CCC(O)C1] | (3S)-3-((S)-sec-butyl)-4-(3-hydroxypyrrolidine-1-carbonyl)-1,3,4,5-tetrahydro-2H-benzo[e][1,4]diazepin-2-one |

TABLE 2-continued

| Compound No. | Compound Structure | Compound Name |
|---|---|---|
| 228 | 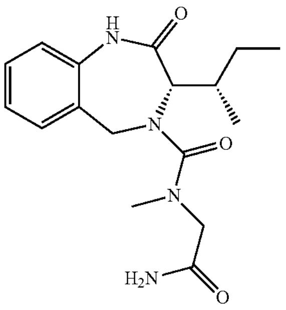 [SMILES: CC[C@H](C)[C@H]1C(=O)Nc2ccccc2CN1C(=O)N(C)CC(N)=O] | (S)-N-(2-amino-2-oxoethyl)-3-((S)-sec-butyl)-N-methyl-2-oxo-1,2,3,5-tetrahydro-4H-benzo[e][1,4]diazepine-4-carboxamide |
| 229 | 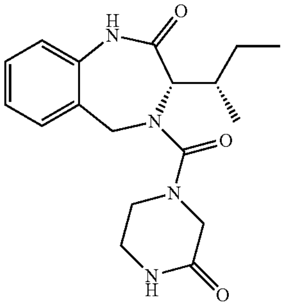 [SMILES: CC[C@H](C)[C@H]1C(=O)Nc2ccccc2CN1C(=O)N1CCNC(=O)C1] | (S)-3-((S)-sec-butyl)-4-(3-oxopiperazine-1-carbonyl)-1,3,4,5-tetrahydro-2H-benzo[e][1,4]diazepin-2-one |
| 230 | 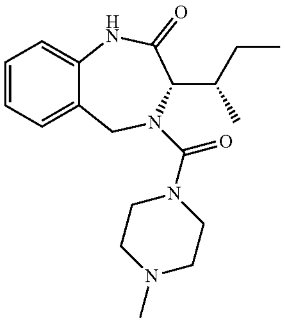 [SMILES: CC[C@H](C)[C@H]1C(=O)Nc2ccccc2CN1C(=O)N1CCN(C)CC1] | (S)-3-((S)-sec-butyl)-4-(4-methylpiperazine-1-carbonyl)-1,3,4,5-tetrahydro-2H-benzo[e][1,4]diazepin-2-one |
| 231 | 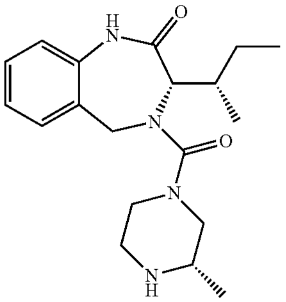 [SMILES: CC[C@H](C)[C@H]1C(=O)Nc2ccccc2CN1C(=O)N1CCN[C@@H](C)C1] | (S)-3-((S)-sec-butyl)-4-((S)-3-methylpiperazine-1-carbonyl)-1,3,4,5-tetrahydro-2H-benzo[e][1,4]diazepin-2-one |
| 232 | 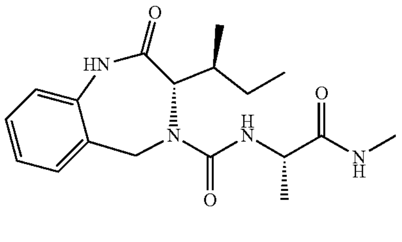 [SMILES: CC[C@H](C)[C@H]1C(=O)Nc2ccccc2CN1C(=O)N[C@@H](C)C(=O)NC] | (S)-3-((S)-sec-butyl)-N-((S)-1-(methylamino)-1-oxopropan-2-yl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 233 | 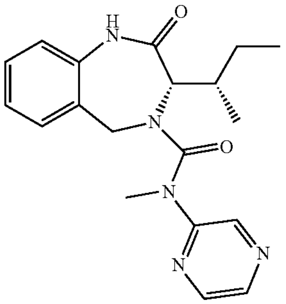 [SMILES: CC[C@H](C)[C@H]1C(=O)Nc2ccccc2CN1C(=O)N(C)c1cnccn1] | (S)-3-((S)-sec-butyl)-N-methyl-2-oxo-N-(pyrazin-2-yl)-1,2,3,5-tetrahydro-4H-benzo[e][1,4]diazepine-4-carboxamide |
| 234 | 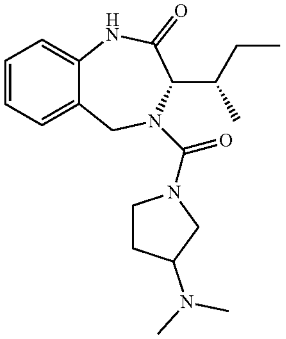 [SMILES: CC[C@H](C)[C@H]1C(=O)Nc2ccccc2CN1C(=O)N1CCC(N(C)C)C1] | (3S)-3-((S)-sec-butyl)-4-(3-(dimethylamino)pyrrolidine-1-carbonyl)-1,3,4,5-tetrahydro-2H-benzo[e][1,4]diazepin-2-one |
| 235 | 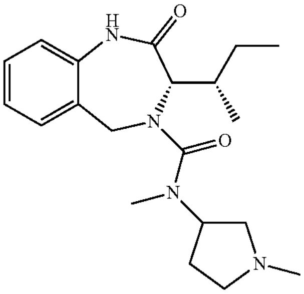 [SMILES: CC[C@H](C)[C@H]1C(=O)Nc2ccccc2CN1C(=O)N(C)C1CCN(C)C1] | (3S)-3-((S)-sec-butyl)-N-methyl-N-(1-methylpyrrolidin-3-yl)-2-oxo-1,2,3,5-tetrahydro-4H-benzo[e][1,4]diazepine-4-carboxamide |
| 236 | 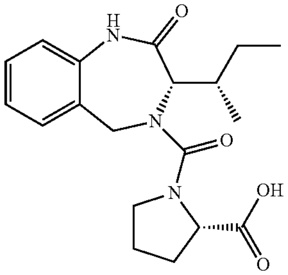 [SMILES: CC[C@H](C)[C@H]1C(=O)Nc2ccccc2CN1C(=O)N1CCC[C@H]1C(=O)O] | ((S)-3-((S)-sec-butyl)-2-oxo-2,3,4,5-tetrahydro-1H-benzo[e][1,4]diazepine-4-carbonyl)-L-proline |
| 237 | 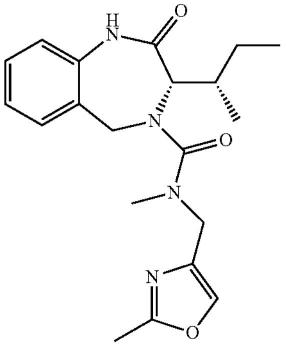 [SMILES: CC[C@H](C)[C@H]1C(=O)Nc2ccccc2CN1C(=O)N(C)Cc1coc(C)n1] | (S)-3-((S)-sec-butyl)-N-methyl-N-((2-methyloxazol-4-yl)methyl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 238 | 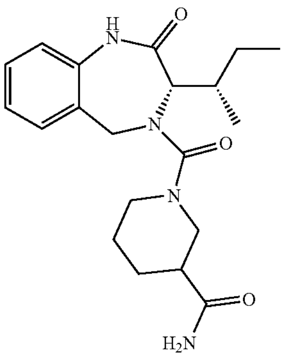 [SMILES: CC[C@H](C)[C@H]1C(=O)Nc2ccccc2CN1C(=O)N1CCCC(C(N)=O)C1] | 1-((S)-3-((S)-sec-butyl)-2-oxo-2,3,4,5-tetrahydro-1H-benzo[e][1,4]diazepine-4-carbonyl)piperidine-3-carboxamide |
| 239 | 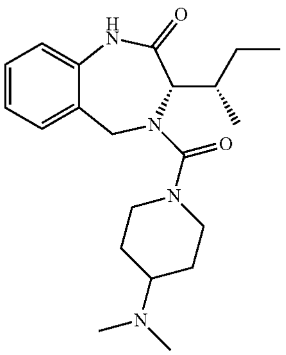 [SMILES: CC[C@H](C)[C@H]1C(=O)Nc2ccccc2CN1C(=O)N1CCC(N(C)C)CC1] | (S)-3-((S)-sec-butyl)-4-(4-(dimethylamino)piperidine-1-carbonyl)-1,3,4,5-tetrahydro-2H-benzo[e][1,4]diazepin-2-one |
| 240 | 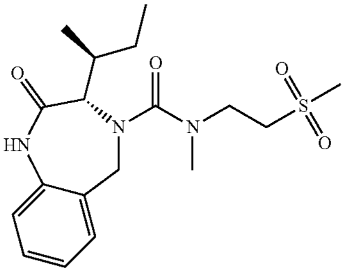 [SMILES: CC[C@H](C)[C@H]1C(=O)Nc2ccccc2CN1C(=O)N(C)CCS(C)(=O)=O] | (S)-3-((S)-sec-butyl)-N-methyl-N-(2-(methylsulfonyl)ethyl)-2-oxo-1,2,3,5-tetrahydro-4H-benzo[e][1,4]diazepine-4-carboxamide |
| 241 | 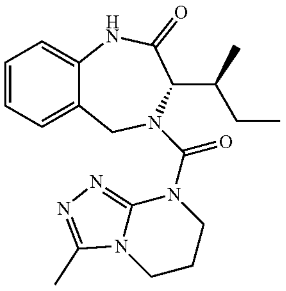 [SMILES: CC[C@H](C)[C@H]1C(=O)Nc2ccccc2CN1C(=O)N1CCCn2c(C)nnc21] | (S)-3-((S)-sec-butyl)-4-(3-methyl-5,6,7,8-tetrahydro-[1,2,4]triazolo[4,3-a]pyrimidine-8-carbonyl)-1,3,4,5-tetrahydro-2H-benzo[e][1,4]diazepin-2-one |

TABLE 2-continued

| Compound No. | Compound Structure | Compound Name |
|---|---|---|
| 242 | 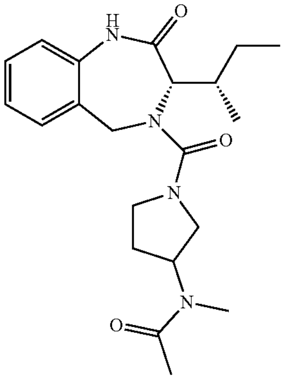 [SMILES: CC[C@H](C)[C@H]1C(=O)Nc2ccccc2CN1C(=O)N1CCC(N(C)C(C)=O)C1] | N-(1-((S)-3-((S)-sec-butyl)-2-oxo-2,3,4,5-tetrahydro-1H-benzo[e][1,4]diazepine-4-carbonyl)pyrrolidin-3-yl)-N-methylacetamide |
| 243 | 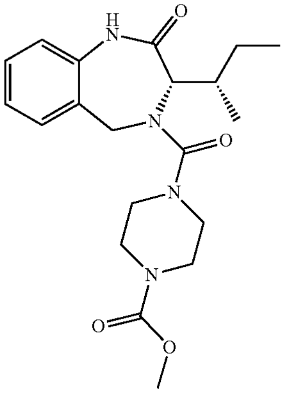 [SMILES: CC[C@H](C)[C@H]1C(=O)Nc2ccccc2CN1C(=O)N1CCN(C(=O)OC)CC1] | methyl 4-((S)-3-((S)-sec-butyl)-2-oxo-2,3,4,5-tetrahydro-1H-benzo[e][1,4]diazepine-4-carbonyl)piperazine-1-carboxylate |
| 244 | 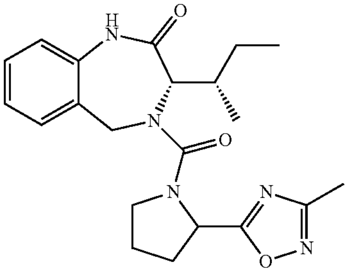 [SMILES: CC[C@H](C)[C@H]1C(=O)Nc2ccccc2CN1C(=O)N1CCCC1c1nc(C)no1] | (3S)-3-((S)-sec-butyl)-4-(2-(3-methyl-1,2,4-oxadiazol-5-yl)pyrrolidine-1-carbonyl)-1,3,4,5-tetrahydro-2H-benzo[e][1,4]diazepin-2-one |
| 245 | 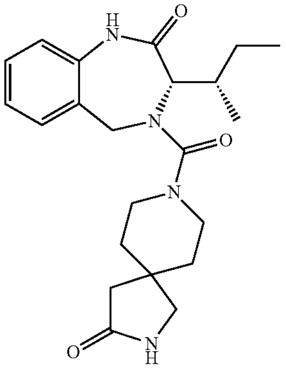 [SMILES: CC[C@H](C)[C@H]1C(=O)Nc2ccccc2CN1C(=O)N1CCC2(CC1)CNC(=O)C2] | (S)-3-((S)-sec-butyl)-4-(3-oxo-2,8-diazaspiro[4.5]decane-8-carbonyl)-1,3,4,5-tetrahydro-2H-benzo[e][1,4]diazepin-2-one |

TABLE 2-continued

| Compound No. | Compound Structure | Compound Name |
|---|---|---|
| 246 | 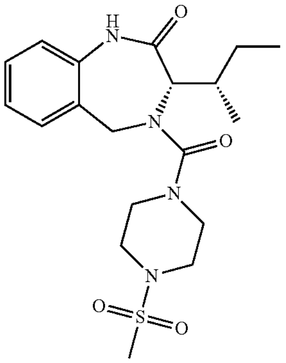 [SMILES: CC[C@H](C)[C@H]1C(=O)Nc2ccccc2CN1C(=O)N1CCN(S(C)(=O)=O)CC1] | (S)-3-((S)-sec-butyl)-4-(4-(methylsulfonyl)piperazine-1-carbonyl)-1,3,4,5-tetrahydro-2H-benzo[e][1,4]diazepin-2-one |
| 247 | 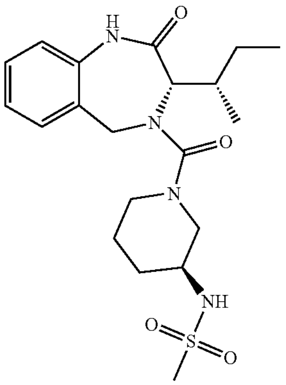 [SMILES: CC[C@H](C)[C@H]1C(=O)Nc2ccccc2CN1C(=O)N1CCC[C@H](NS(C)(=O)=O)C1] | N-((S)-1-((S)-3-((S)-sec-butyl)-2-oxo-2,3,4,5-tetrahydro-1H-benzo[e][1,4]diazepine-4-carbonyl)piperidin-3-yl)methanesulfonamide |
| 248 | 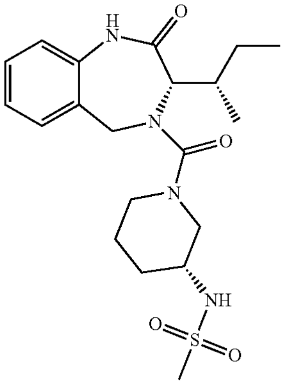 [SMILES: CC[C@H](C)[C@H]1C(=O)Nc2ccccc2CN1C(=O)N1CCC[C@@H](NS(C)(=O)=O)C1] | N-((R)-1-((S)-3-((S)-sec-butyl)-2-oxo-2,3,4,5-tetrahydro-1H-benzo[e][1,4]diazepine-4-carbonyl)piperidin-3-yl)methanesulfonamide |
| 249 | 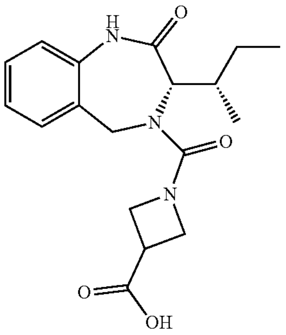 [SMILES: CC[C@H](C)[C@H]1C(=O)Nc2ccccc2CN1C(=O)N1CC(C(=O)O)C1] | 1-((S)-3-((S)-sec-butyl)-2-oxo-2,3,4,5-tetrahydro-1H-benzo[e][1,4]diazepine-4-carbonyl)azetidine-3-carboxylic acid |

TABLE 2-continued

| Compound No. | Compound Structure | Compound Name |
|---|---|---|
| 250 | 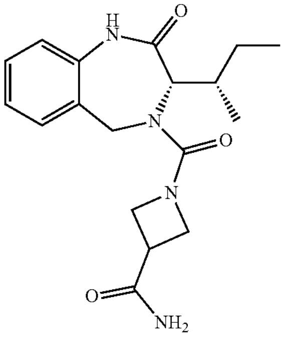 [SMILES: CC[C@H](C)[C@H]1C(=O)Nc2ccccc2CN1C(=O)N1CC(C(N)=O)C1] | 1-((S)-3-((S)-sec-butyl)-2-oxo-2,3,4,5-tetrahydro-1H-benzo[e][1,4]diazepine-4-carbonyl)azetidine-3-carboxamide |
| 251 | 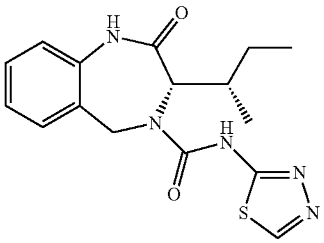 [SMILES: CC[C@H](C)[C@H]1C(=O)Nc2ccccc2CN1C(=O)Nc1nncs1] | (S)-3-((S)-sec-butyl)-2-oxo-N-(1,3,4-thiadiazol-2-yl)-1,2,3,5-tetrahydro-4H-benzo[e][1,4]diazepine-4-carboxamide |
| 252 | 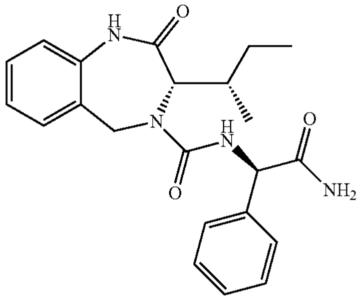 [SMILES: CC[C@H](C)[C@H]1C(=O)Nc2ccccc2CN1C(=O)N[C@@H](C(N)=O)c1ccccc1] | (S)-N-((R)-2-amino-2-oxo-1-phenylethyl)-3-((S)-sec-butyl)-2-oxo-1,2,3,5-tetrahydro-4H-benzo[e][1,4]diazepine-4-carboxamide |
| 253 | 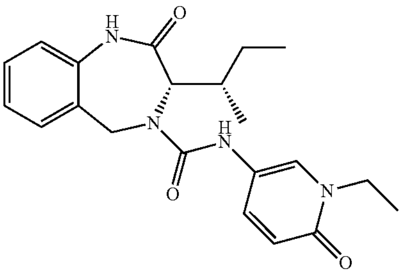 [SMILES: CC[C@H](C)[C@H]1C(=O)Nc2ccccc2CN1C(=O)Nc1ccc(=O)n(CC)c1] | (S)-3-((S)-sec-butyl)-N-(1-ethyl-6-oxo-1,6-dihydropyridin-3-yl)-2-oxo-1,2,3,5-tetrahydro-4H-benzo[e][1,4]diazepine-4-carboxamide |
| 254 | 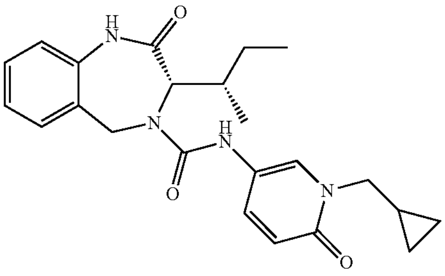 [SMILES: CC[C@H](C)[C@H]1C(=O)Nc2ccccc2CN1C(=O)Nc1ccc(=O)n(CC2CC2)c1] | (S)-3-((S)-sec-butyl)-N-(1-(cyclopropylmethyl)-6-oxo-1,6-dihydropyridin-3-yl)-2-oxo-1,2,3,5-tetrahydro-4H-benzo[e][1,4]diazepine-4-carboxamide |

TABLE 2-continued

| Compound No. | Compound Structure | Compound Name |
| --- | --- | --- |
| 255 | 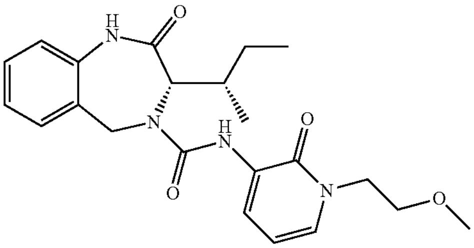 [SMILES: CC[C@H](C)[C@H]1C(=O)Nc2ccccc2CN1C(=O)Nc1cccn(CCOC)c1=O] | (S)-3-((S)-sec-butyl)-N-(1-(2-methoxyethyl)-2-oxo-1,2-dihydropyridin-3-yl)-2-oxo-1,2,3,5-tetrahydro-4H-benzo[e][1,4]diazepine-4-carboxamide |
| 256 | 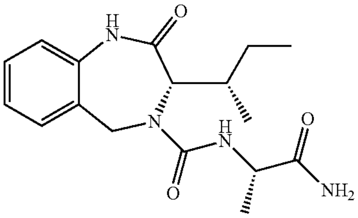 [SMILES: CC[C@H](C)[C@H]1C(=O)Nc2ccccc2CN1C(=O)N[C@@H](C)C(N)=O] | (S)-N-((S)-1-amino-1-oxopropan-2-yl)-3-((S)-sec-butyl)-2-oxo-1,2,3,5-tetrahydro-4H-benzo[e][1,4]diazepine-4-carboxamide |
| 257 | 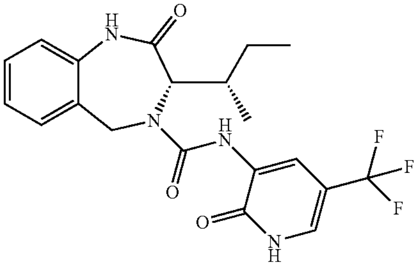 [SMILES: CC[C@H](C)[C@H]1C(=O)Nc2ccccc2CN1C(=O)Nc1cc(C(F)(F)F)c[nH]c1=O] | (S)-3-((S)-sec-butyl)-2-oxo-N-(2-oxo-5-(trifluoromethyl)-1,2-dihydropyridin-3-yl)-1,2,3,5-tetrahydro-4H-benzo[e][1,4]diazepine-4-carboxamide |
| 258 | 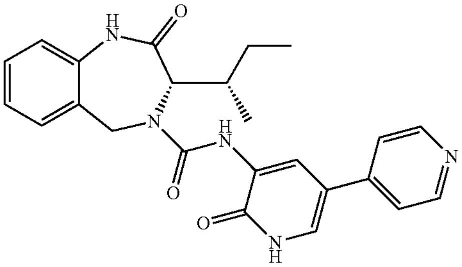 [SMILES: CC[C@H](C)[C@H]1C(=O)Nc2ccccc2CN1C(=O)Nc1cc(-c2ccncc2)c[nH]c1=O] | (S)-3-((S)-sec-butyl)-2-oxo-N-(6-oxo-1,6-dihydro-[3,4'-bipyridin]-5-yl)-1,2,3,5-tetrahydro-4H-benzo[e][1,4]diazepine-4-carboxamide |
| 259 | 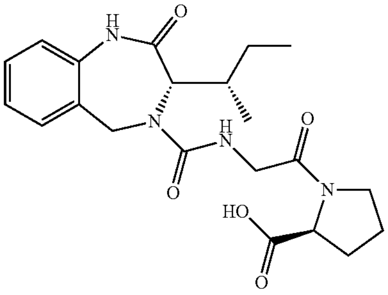 [SMILES: CC[C@H](C)[C@H]1C(=O)Nc2ccccc2CN1C(=O)NCC(=O)N1CCC[C@H]1C(=O)O] | ((S)-3-((S)-sec-butyl)-2-oxo-2,3,4,5-tetrahydro-1H-benzo[e][1,4]diazepine-4-carbonyl)glycyl-L-proline |

TABLE 2-continued

| Compound No. | Compound Structure | Compound Name |
|---|---|---|
| 260 | 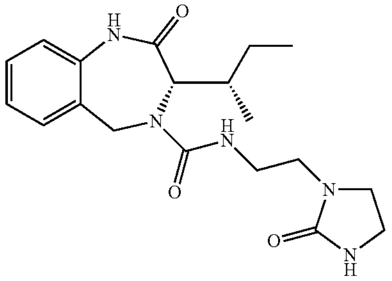 [SMILES: CC[C@H](C)[C@H]1C(=O)Nc2ccccc2CN1C(=O)NCCN1CCNC1=O] | (S)-3-((S)-sec-butyl)-2-oxo-N-(2-(2-oxoimidazolin-1-yl)ethyl)-1,2,3,5-tetrahydro-4H-benzo[e][1,4]diazepine-4-carboxamide |
| 261 | 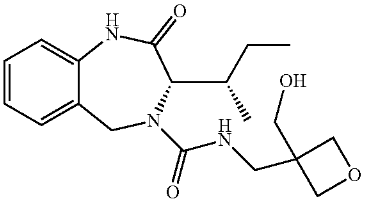 [SMILES: CC[C@H](C)[C@H]1C(=O)Nc2ccccc2CN1C(=O)NCC1(CO)COC1] | (S)-3-((S)-sec-butyl)-N-((3-(hydroxymethyl)oxetan-3-yl)methyl)-2-oxo-1,2,3,5-tetrahydro-4H-benzo[e][1,4]diazepine-4-carboxamide |
| 262 | 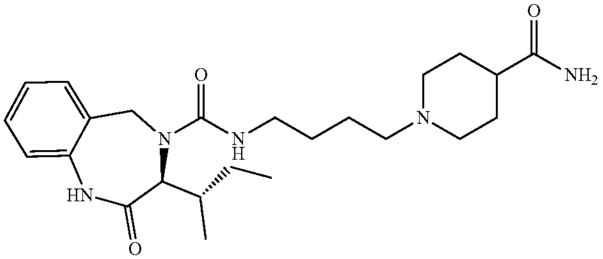 [SMILES: CC[C@H](C)[C@H]1C(=O)Nc2ccccc2CN1C(=O)NCCCCN1CCC(C(N)=O)CC1] | (S)-3-((S)-sec-butyl)-N-(4-(4-carbamoylpiperidin-1-yl)butyl)-2-oxo-1,2,3,5-tetrahydro-4H-benzo[e][1,4]diazepine-4-carboxamide |
| 263 | 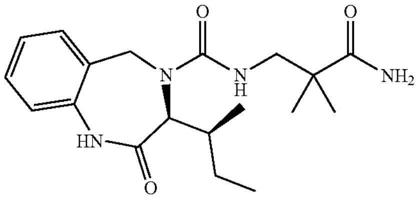 [SMILES: CC[C@H](C)[C@H]1C(=O)Nc2ccccc2CN1C(=O)NCC(C)(C)C(N)=O] | (S)-N-(3-amino-2,2-dimethyl-3-oxopropyl)-3-((S)-sec-butyl)-2-oxo-1,2,3,5-tetrahydro-4H-benzo[e][1,4]diazepine-4-carboxamide |
| 264 | 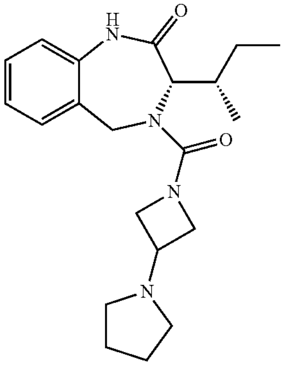 [SMILES: CC[C@H](C)[C@H]1C(=O)Nc2ccccc2CN1C(=O)N1CC(N2CCCC2)C1] | (S)-3-((S)-sec-butyl)-4-(3-(pyrrolidin-1-yl)azetidine-1-carbonyl)-1,3,4,5-tetrahydro-2H-benzo[e][1,4]diazepin-2-one |

TABLE 2-continued
| Compound No. | Compound Structure | Compound Name |
|---|---|---|
| 265 | 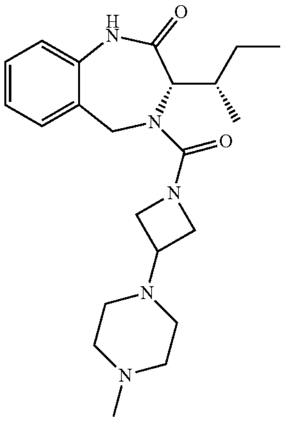 [SMILES: CC[C@H](C)[C@H]1C(=O)Nc2ccccc2CN1C(=O)N1CC(N2CCN(C)CC2)C1] | (S)-3-((S)-sec-butyl)-4-(3-(4-methylpiperazin-1-yl)azetidine-1-carbonyl)-1,3,4,5-tetrahydro-2H-benzo[e][1,4]diazepin-2-one |
| 266 | 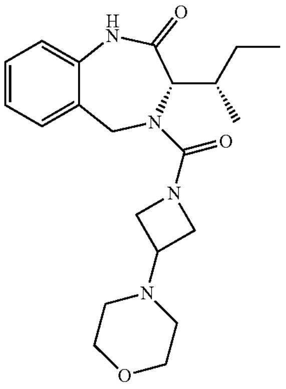 [SMILES: CC[C@H](C)[C@H]1C(=O)Nc2ccccc2CN1C(=O)N1CC(N2CCOCC2)C1] | (S)-3-((S)-sec-butyl)-4-(3-morpholinoazetidine-1-carbonyl)-1,3,4,5-tetrahydro-2H-benzo[e][1,4]diazepin-2-one |
| 267 | 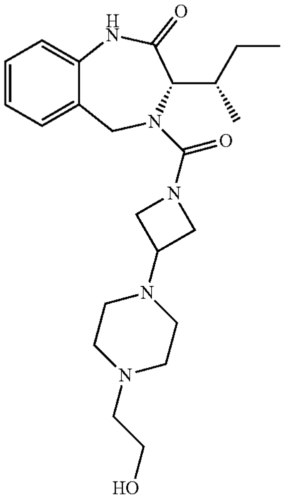 [SMILES: CC[C@H](C)[C@H]1C(=O)Nc2ccccc2CN1C(=O)N1CC(N2CCN(CCO)CC2)C1] | (S)-3-((S)-sec-butyl)-4-(3-(4-(2-hydroxyethyl)piperazin-1-yl)azetidine-1-carbonyl)-1,3,4,5-tetrahydro-2H-benzo[e][1,4]diazepin-2-one |

TABLE 2-continued
| Compound No. | Compound Structure | Compound Name |
|---|---|---|
| 268 | 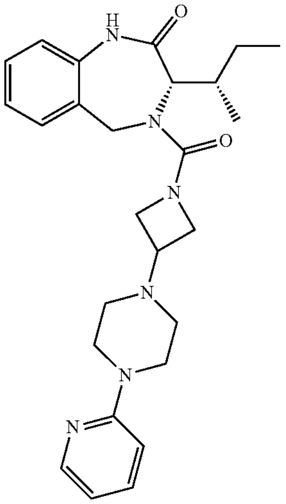 [SMILES: CC[C@H](C)[C@H]1C(=O)Nc2ccccc2CN1C(=O)N1CC(N2CCN(c3ccccn3)CC2)C1] | (S)-3-((S)-sec-butyl)-4-(3-(4-(pyridin-2-yl)piperazin-1-yl)azetidine-1-carbonyl)-1,3,4,5-tetrahydro-2H-benzo[e][1,4]diazepin-2-one |
| 269 | 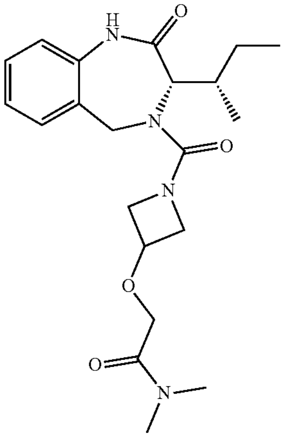 [SMILES: CC[C@H](C)[C@H]1C(=O)Nc2ccccc2CN1C(=O)N1CC(OCC(=O)N(C)C)C1] | 2-((1-((S)-3-((S)-sec-butyl)-2-oxo-2,3,4,5-tetrahydro-1H-benzo[e][1,4]diazepine-4-carbonyl)azetidin-3-yl)oxy)-N,N-dimethylacetamide |
| 270 | 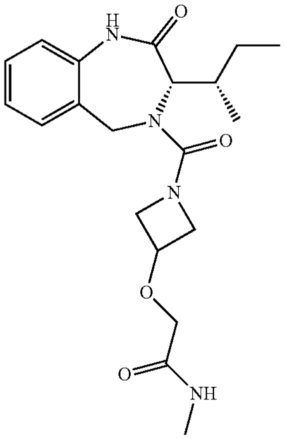 [SMILES: CC[C@H](C)[C@H]1C(=O)Nc2ccccc2CN1C(=O)N1CC(OCC(=O)NC)C1] | 2-((1-((S)-3-((S)-sec-butyl)-2-oxo-2,3,4,5-tetrahydro-1H-benzo[e][1,4]diazepine-4-carbonyl)azetidin-3-yl)oxy)-N-methylacetamide |

TABLE 2-continued

| Compound No. | Compound Structure | Compound Name |
|---|---|---|
| 271 | 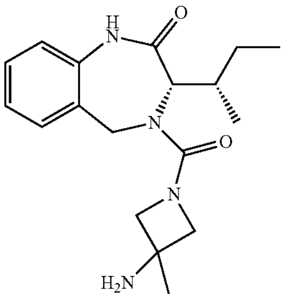 [SMILES: CC[C@H](C)[C@H]1C(=O)Nc2ccccc2CN1C(=O)N1CC(C)(N)C1] | (S)-4-(3-amino-3-methylazetidine-1-carbonyl)-3-((S)-sec-butyl)-1,3,4,5-tetrahydro-2H-benzo[e][1,4]diazepin-2-one |
| 272 | 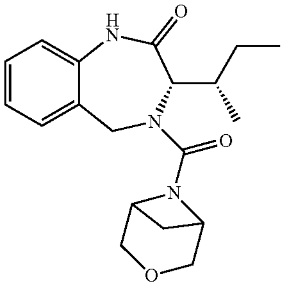 [SMILES: CC[C@H](C)[C@H]1C(=O)Nc2ccccc2CN1C(=O)N1C2COCC1C2] | (3S)-4-(3-oxa-6-azabicyclo[3.1.1]heptane-6-carbonyl)-3-((S)-sec-butyl)-1,3,4,5-tetrahydro-2H-benzo[e][1,4]diazepin-2-one |
| 273 | 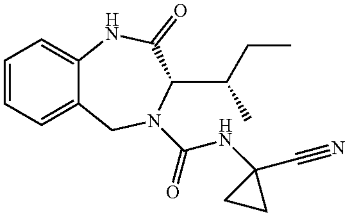 [SMILES: CC[C@H](C)[C@H]1C(=O)Nc2ccccc2CN1C(=O)NC1(C#N)CC1] | (S)-3-((S)-sec-butyl)-N-(1-cyanocyclopropyl)-2-oxo-1,2,3,5-tetrahydro-4H-benzo[e][1,4]diazepine-4-carboxamide |
| 274 | 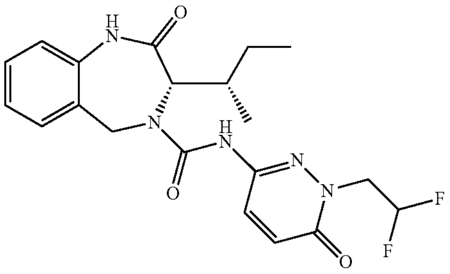 [SMILES: CC[C@H](C)[C@H]1C(=O)Nc2ccccc2CN1C(=O)Nc1ccc(=O)n(CC(F)F)n1] | (S)-3-((S)-sec-butyl)-N-(1-(2,2-difluoroethyl)-6-oxo-1,6-dihydropyridazin-3-yl)-2-oxo-1,2,3,5-tetrahydro-4H-benzo[e][1,4]diazepine-4-carboxamide |
| 275 | 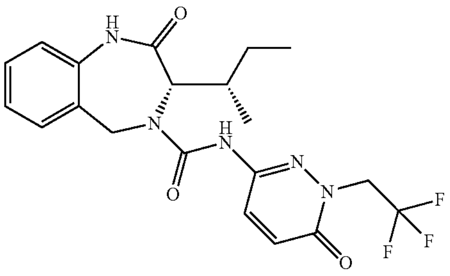 [SMILES: CC[C@H](C)[C@H]1C(=O)Nc2ccccc2CN1C(=O)Nc1ccc(=O)n(CC(F)(F)F)n1] | (S)-3-((S)-sec-butyl)-2-oxo-N-(6-oxo-1-(2,2,2-trifluoroethyl)-1,6-dihydropyridazin-3-yl)-1,2,3,5-tetrahydro-4H-benzo[e][1,4]diazepine-4-carboxamide |

TABLE 2-continued

| Compound No. | Compound Structure | Compound Name |
|---|---|---|
| 276 | 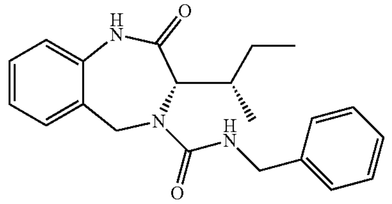 [SMILES: CC[C@H](C)[C@H]1C(=O)Nc2ccccc2CN1C(=O)NCc1ccccc1] | (S)-N-benzyl-3-((S)-sec-butyl)-2-oxo-1,2,3,5-tetrahydro-4H-benzo[e][1,4]diazepine-4-carboxamide |
| 277 | 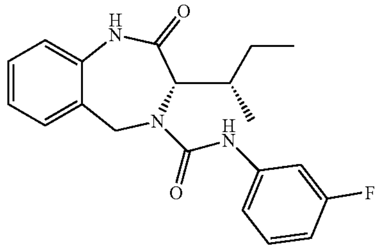 [SMILES: CC[C@H](C)[C@H]1C(=O)Nc2ccccc2CN1C(=O)Nc1cccc(F)c1] | (S)-3-((S)-sec-butyl)-N-(3-fluorophenyl)-2-oxo-1,2,3,5-tetrahydro-4H-benzo[e][1,4]diazepine-4-carboxamide |
| 278 | 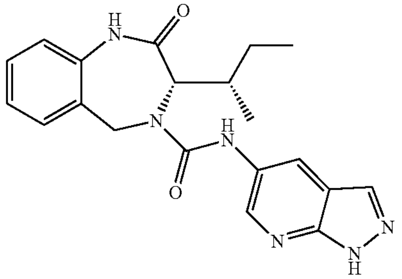 [SMILES: CC[C@H](C)[C@H]1C(=O)Nc2ccccc2CN1C(=O)Nc1cnc2[nH]ncc2c1] | (S)-3-((S)-sec-butyl)-2-oxo-N-(1H-pyrazolo[3,4-b]pyridin-5-yl)-1,2,3,5-tetrahydro-4H-benzo[e][1,4]diazepine-4-carboxamide |
| 279 | 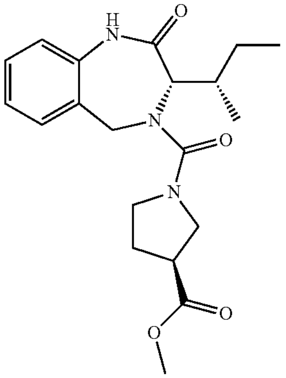 [SMILES: CC[C@H](C)[C@H]1C(=O)Nc2ccccc2CN1C(=O)N1CC[C@H](C(=O)OC)C1] | methyl (S)-1-((S)-3-((S)-sec-butyl)-2-oxo-2,3,4,5-tetrahydro-1H-benzo[e][1,4]diazepine-4-carbonyl)pyrrolidine-3-carboxylate |
| 280 | 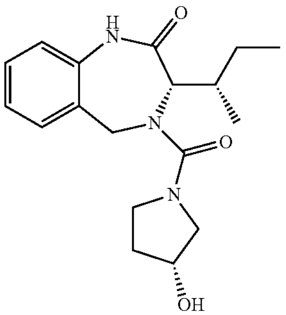 [SMILES: CC[C@H](C)[C@H]1C(=O)Nc2ccccc2CN1C(=O)N1CC[C@@H](O)C1] | (S)-3-((S)-sec-butyl)-4-((R)-3-hydroxypyrrolidine-1-carbonyl)-1,3,4,5-tetrahydro-2H-benzo[e][1,4]diazepin-2-one |

TABLE 2-continued

| Compound No. | Compound Structure | Compound Name |
|---|---|---|
| 281 | 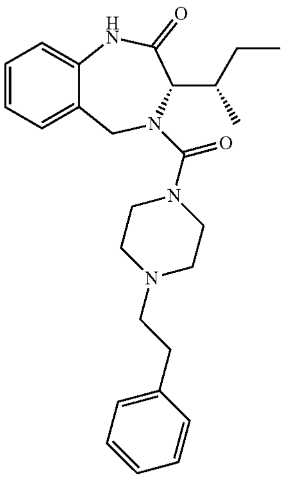 [SMILES: CC[C@H](C)[C@H]1C(=O)Nc2ccccc2CN1C(=O)N1CCN(CCc2ccccc2)CC1] | (S)-3-((S)-sec-butyl)-4-(4-phenethylpiperazine-1-carbonyl)-1,3,4,5-tetrahydro-2H-benzo[e][1,4]diazepin-2-one |
| 282 | 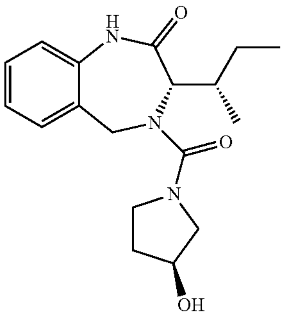 [SMILES: CC[C@H](C)[C@H]1C(=O)Nc2ccccc2CN1C(=O)N1CC[C@H](O)C1] | (S)-3-((S)-sec-butyl)-4-((S)-3-hydroxypyrrolidine-1-carbonyl)-1,3,4,5-tetrahydro-2H-benzo[e][1,4]diazepin-2-one |
| 283 | 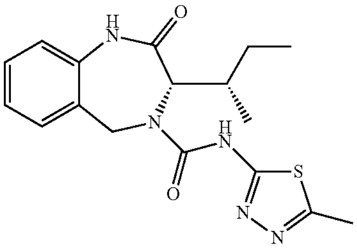 [SMILES: CC[C@H](C)[C@H]1C(=O)Nc2ccccc2CN1C(=O)Nc1nnc(C)s1] | (S)-3-((S)-sec-butyl)-N-(5-methyl-1,3,4-thiadiazol-2-yl)-2-oxo-1,2,3,5-tetrahydro-4H-benzo[e][1,4]diazepine-4-carboxamide |
| 284 | 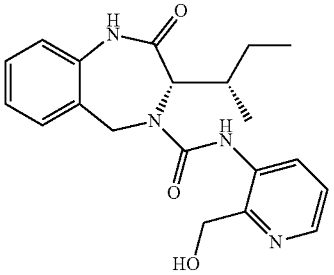 [SMILES: CC[C@H](C)[C@H]1C(=O)Nc2ccccc2CN1C(=O)Nc1cccnc1CO] | (S)-3-((S)-sec-butyl)-N-(2-(hydroxymethyl)pyridin-3-yl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 285 | 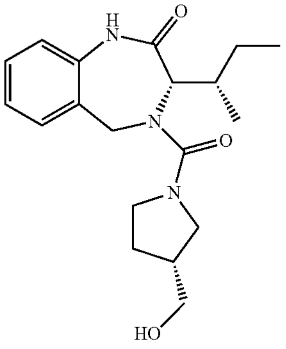 [SMILES: CC[C@H](C)[C@H]1C(=O)Nc2ccccc2CN1C(=O)N1CC[C@@H](CO)C1] | (S)-3-((S)-sec-butyl)-4-((R)-3-(hydroxymethyl)pyrrolidine-1-carbonyl)-1,3,4,5-tetrahydro-2H-benzo[e][1,4]diazepin-2-one |
| 286 | 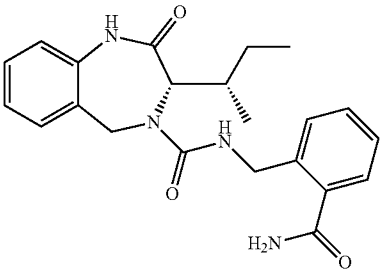 [SMILES: CC[C@H](C)[C@H]1C(=O)Nc2ccccc2CN1C(=O)NCc1ccccc1C(N)=O] | (S)-3-((S)-sec-butyl)-N-(2-carbamoyl)benzyl)-2-oxo-1,2,3,5-tetrahydro-4H-benzo[e][1,4]diazepine-4-carboxamide |
| 287 | 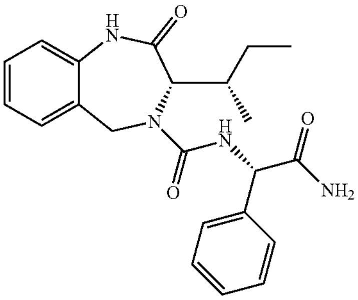 [SMILES: CC[C@H](C)[C@H]1C(=O)Nc2ccccc2CN1C(=O)N[C@H](C(N)=O)c1ccccc1] | (S)-N-((S)-2-amino-2-oxo-1-phenylethyl)-3-((S)-sec-butyl)-2-oxo-1,2,3,5-tetrahydro-4H-benzo[e][1,4]diazepine-4-carboxamide |
| 288 | 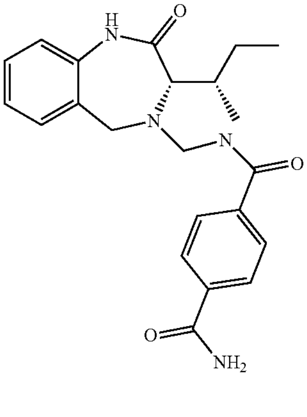 [SMILES: CC[C@H](C)[C@H]1C(=O)Nc2ccccc2CN1CNC(=O)c1ccc(C(N)=O)cc1] | 4-((S)-3-((S)-sec-butyl)-2-oxo-2,3,4,5-tetrahydro-1H-benzo[e][1,4]diazepine-4-carbonyl)benzamide |

TABLE 2-continued

| Compound No. | Compound Structure | Compound Name |
|---|---|---|
| 289 | 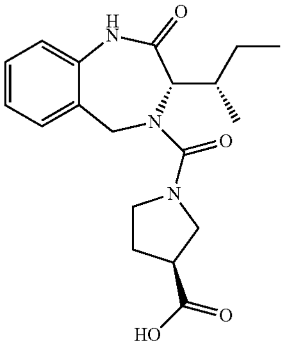 [SMILES: CC[C@H](C)[C@H]1C(=O)Nc2ccccc2CN1C(=O)N1CC[C@H](C(=O)O)C1] | (S)-1-((S)-3-((S)-sec-butyl)-2-oxo-2,3,4,5-tetrahydro-1H-benzo[e][1,4]diazepine-4-carbonyl)pyrrolidine-3-carboxylic acid |
| 290 | 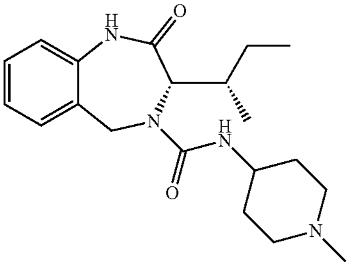 [SMILES: CC[C@H](C)[C@H]1C(=O)Nc2ccccc2CN1C(=O)NC1CCN(C)CC1] | (S)-3-((S)-sec-butyl)-N-(1-methylpiperidin-4-yl)-2-oxo-1,2,3,5-tetrahydro-4H-benzo[e][1,4]diazepine-4-carboxamide |
| 291 | 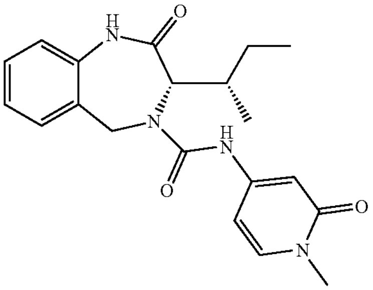 [SMILES: CC[C@H](C)[C@H]1C(=O)Nc2ccccc2CN1C(=O)Nc1ccn(C)c(=O)c1] | (S)-3-((S)-sec-butyl)-N-(1-methyl-2-oxo-1,2-dihydropyridin-4-yl)-2-oxo-1,2,3,5-tetrahydro-4H-benzo[e][1,4]diazepine-4-carboxamide |
| 292 | 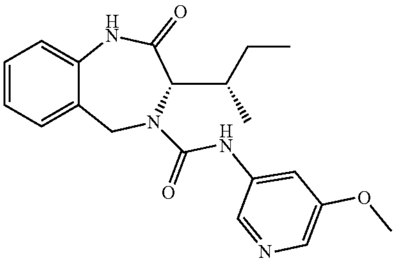 [SMILES: CC[C@H](C)[C@H]1C(=O)Nc2ccccc2CN1C(=O)Nc1cncc(OC)c1] | (S)-3-((S)-sec-butyl)-N-(5-methoxypyridin-3-yl)-2-oxo-1,2,3,5-tetrahydro-4H-benzo[e][1,4]diazepine-4-carboxamide |
| 293 | 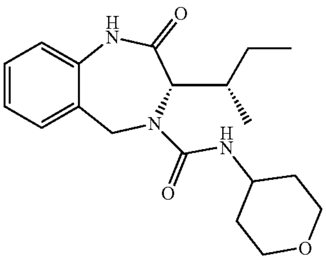 [SMILES: CC[C@H](C)[C@H]1C(=O)Nc2ccccc2CN1C(=O)NC1CCOCC1] | (S)-3-((S)-sec-butyl)-2-oxo-N-(tetrahydro-2H-pyran-4-yl)-1,2,3,5-tetrahydro-4H-benzo[e][1,4]diazepine-4-carboxamide |

TABLE 2-continued

| Compound No. | Compound Structure | Compound Name |
|---|---|---|
| 294 | 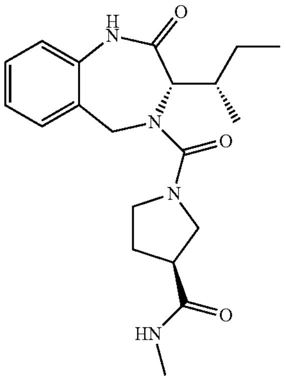 [SMILES: CC[C@H](C)[C@H]1C(=O)Nc2ccccc2CN1C(=O)N1CC[C@H](C(=O)NC)C1] | (S)-1-((S)-3-((S)-sec-butyl)-2-oxo-2,3,4,5-tetrahydro-1H-benzo[e][1,4]diazepine-4-carbonyl)-N-methylpyrrolidine-3-carboxamide |
| 295 | 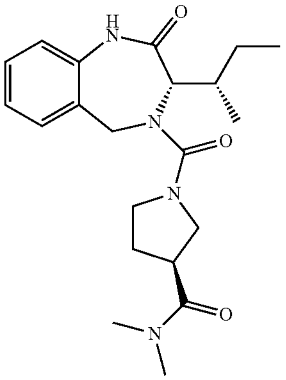 [SMILES: CC[C@H](C)[C@H]1C(=O)Nc2ccccc2CN1C(=O)N1CC[C@H](C(=O)N(C)C)C1] | (S)-1-((S)-sec-butyl)-2-oxo-2,3,4,5-tetrahydro-1H-benzo[e][1,4]diazepine-4-carbonyl)-N,N-dimethylpyrrolidine-3-carboxamide |
| 296 | 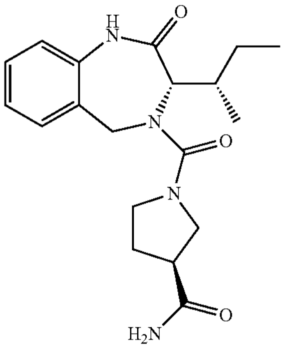 [SMILES: CC[C@H](C)[C@H]1C(=O)Nc2ccccc2CN1C(=O)N1CC[C@H](C(N)=O)C1] | (S)-1-((S)-3-((S)-sec-butyl)-2-oxo-2,3,4,5-tetrahydro-1H-benzo[e][1,4]diazepine-4-carbonyl)pyrrolidine-3-carboxamide |
| 297 | 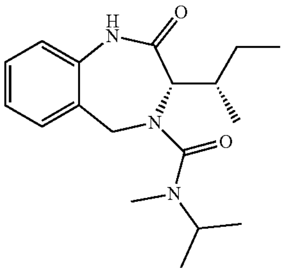 [SMILES: CC[C@H](C)[C@H]1C(=O)Nc2ccccc2CN1C(=O)N(C)C(C)C] | (S)-3-((S)-sec-butyl)-N-isopropyl-N-methyl-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 298 | 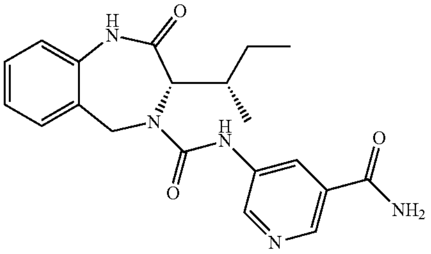 [SMILES: CC[C@H](C)[C@H]1C(=O)Nc2ccccc2CN1C(=O)Nc1cncc(C(N)=O)c1] | (S)-3-((S)-sec-butyl)-N-(5-carbamoylpyridin-3-yl)-2-oxo-1,2,3,5-tetrahydro-4H-benzo[e][1,4]diazepine-4-carboxamide |
| 299 | 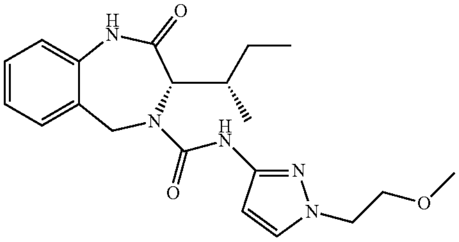 [SMILES: CC[C@H](C)[C@H]1C(=O)Nc2ccccc2CN1C(=O)Nc1ccn(CCOC)n1] | (S)-3-((S)-sec-butyl)-N-(1-(2-methoxyethyl)-1H-pyrazol-3-yl)-2-oxo-1,2,3,5-tetrahydro-4H-benzo[e][1,4]diazepine-4-carboxamide |
| 300 | 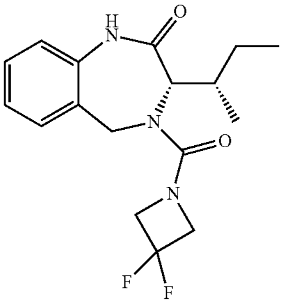 [SMILES: CC[C@H](C)[C@H]1C(=O)Nc2ccccc2CN1C(=O)N1CC(F)(F)C1] | (S)-3-((S)-sec-butyl)-4-(3,3-difluoroazetidine-1-carbonyl)-1,3,4,5-tetrahydro-2H-benzo[e][1,4]diazepin-2-one |
| 301 | 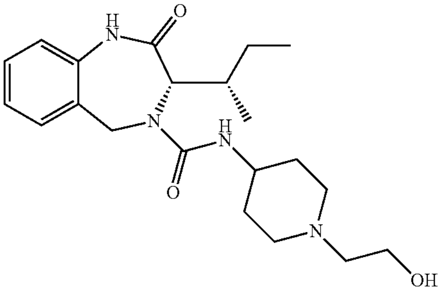 [SMILES: CC[C@H](C)[C@H]1C(=O)Nc2ccccc2CN1C(=O)NC1CCN(CCO)CC1] | (S)-3-((S)-sec-butyl)-N-(1-(2-hydroxyethyl)piperidin-4-yl)-2-oxo-1,2,3,5-tetrahydro-4H-benzo[e][1,4]diazepine-4-carboxamide |
| 302 | 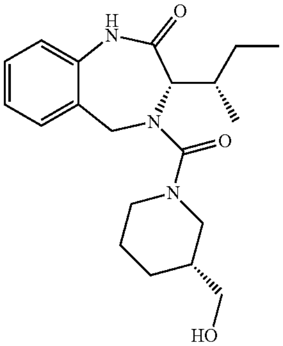 [SMILES: CC[C@H](C)[C@H]1C(=O)Nc2ccccc2CN1C(=O)N1CCC[C@@H](CO)C1] | (S)-3-((S)-sec-butyl)-4-((R)-3-(hydroxymethyl)piperidine-1-carbonyl)-1,3,4,5-tetrahydro-2H-benzo[e][1,4]diazepin-2-one |

TABLE 2-continued

| Compound No. | Compound Structure | Compound Name |
|---|---|---|
| 303 | 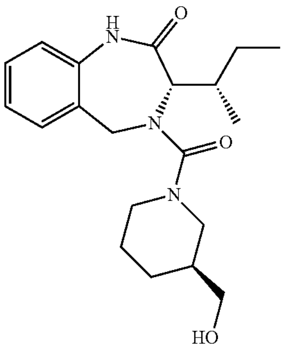 [SMILES: CC[C@H](C)[C@H]1C(=O)Nc2ccccc2CN1C(=O)N1CCC[C@H](CO)C1] | (S)-3-((S)-sec-butyl)--4-((S)-3-(hydroxymethyl)piperidine-1-carbonyl)-1,3,4,5-tetrahydro-2H-benzo[e][1,4]diazepin-2-one |
| 304 | 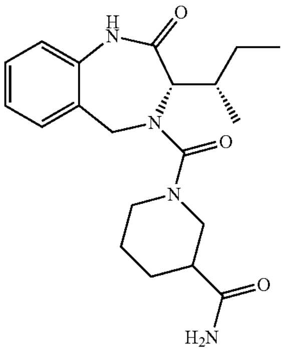 [SMILES: CC[C@H](C)[C@H]1C(=O)Nc2ccccc2CN1C(=O)N1CCCC(C(N)=O)C1] | 1-((S)-3-((S)-sec-butyl)-2-oxo-2,3,4,5-tetrahydro-1H-benzo[e][1,4]diazepine-4-carbonyl)piperidine-3-carboxamide |
| 305 | 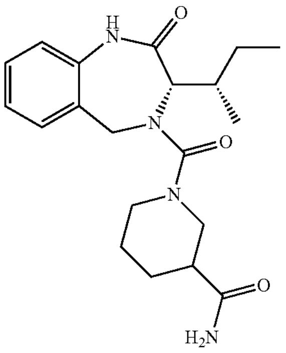 [SMILES: CC[C@H](C)[C@H]1C(=O)Nc2ccccc2CN1C(=O)N1CCCC(C(N)=O)C1] | 1-((S)-3-((S)-sec-butyl)-2-oxo-2,3,4,5-tetrahydro-1H-benzo[e][1,4]diazepine-4-carbonyl)piperidine-3-carboxamide |
| 306 | 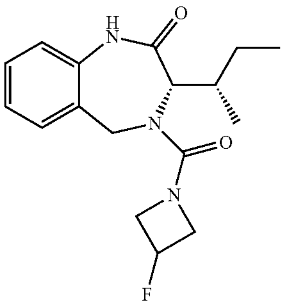 [SMILES: CC[C@H](C)[C@H]1C(=O)Nc2ccccc2CN1C(=O)N1CC(F)C1] | (S)-3-((S)-sec-butyl)-4-(3-fluoroazetidine-1-carbonyl)-1,3,4,5-tetrahydro-2H-benzo[e][1,4]diazepin-2-one |

TABLE 2-continued

| Compound No. | Compound Structure | Compound Name |
|---|---|---|
| 307 | 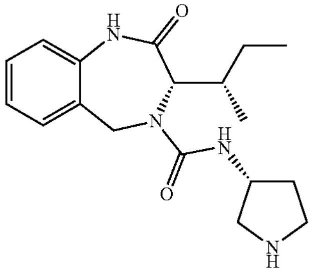 [SMILES: CC[C@H](C)[C@H]1C(=O)Nc2ccccc2CN1C(=O)N[C@@H]1CCNC1] | (S)-3-((S)-sec-butyl)-2-oxo-N-((R)-pyrrolidin-3-yl)-1,2,3,5-tetrahydro-4H-benzo[e][1,4]diazepine-4-carboxamide |
| 308 | 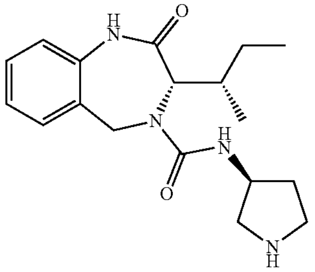 [SMILES: CC[C@H](C)[C@H]1C(=O)Nc2ccccc2CN1C(=O)N[C@H]1CCNC1] | (S)-3-((S)-sec-butyl)-2-oxo-N-((S)-pyrrolidin-3-yl)-1,2,3,5-tetrahydro-4H-benzo[e][1,4]diazepine-4-carboxamide |
| 309 | 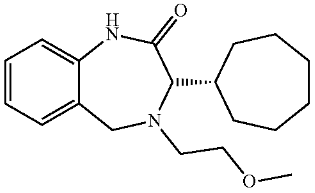 | (S)-3-cycloheptyl-4-(2-methoxyethyl)-1,3,4,5-tetrahydro-2H-benzo[e][1,4]diazepin-2-one |
| 310 | 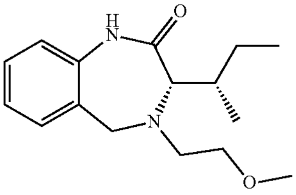 [SMILES: CC[C@H](C)[C@H]1C(=O)Nc2ccccc2CN1CCOC] | (S)-3-((S)-sec-butyl)-4-(2-methoxyethyl)-1,3,4,5-tetrahydro-2H-benzo[e][1,4]diazepin-2-one |
| 311 | 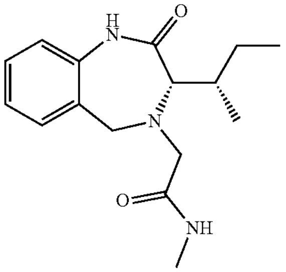 [SMILES: CC[C@H](C)[C@H]1C(=O)Nc2ccccc2CN1CC(=O)NC] | 2-((S)-3-((S)-sec-butyl)-2-oxo-1,2,3,4-tetrahydro-4H-benzo[e][1,4]diazepin-4-yl)-N-methylacetamide |
| 312 | 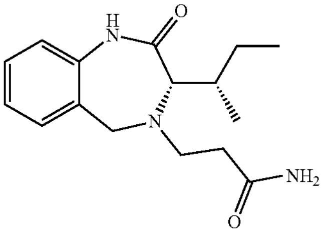 [SMILES: CC[C@H](C)[C@H]1C(=O)Nc2ccccc2CN1CCC(N)=O] | 3-((S)-3-((S)-sec-butyl)-2-oxo-1,2,3,5-tetrahydro-4H-benzo[e][1,4]diazepin-4-yl)propanamide |

TABLE 2-continued

| Compound No. | Compound Structure | Compound Name |
|---|---|---|
| 313 | 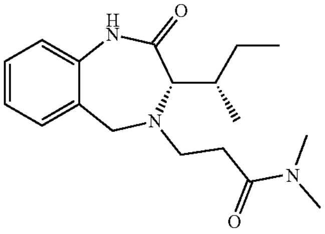 [SMILES: CC[C@H](C)[C@H]1C(=O)Nc2ccccc2CN1CCC(=O)N(C)C] | 3-((S)-3-((S)-sec-butyl)-2-oxo-1,2,3,5-tetrahydro-4H-benzo[e][1,4]diazepin-4-yl)-N,N-dimethylpropanamide |
| 314 | 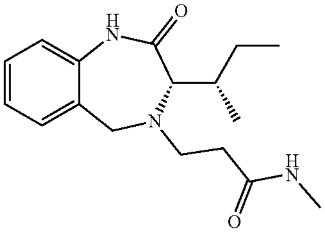 [SMILES: CC[C@H](C)[C@H]1C(=O)Nc2ccccc2CN1CCC(=O)NC] | 3-((S)-3-((S)-sec-butyl)-2-oxo-1,2,3,5-tetrahydro-4H-benzo[e][1,4]diazepin-4-yl)-N-methylpropanamide |
| 315 | 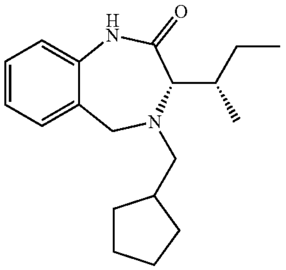 [SMILES: CC[C@H](C)[C@H]1C(=O)Nc2ccccc2CN1CC1CCCC1] | (S)-3-((S)-sec-butyl)-4-(cyclopentylmethyl)-1,3,4,5-tetrahydro-2H-benzo[e][1,4]diazepin-2-one |
| 316 | 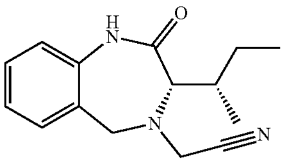 [SMILES: CC[C@H](C)[C@H]1C(=O)Nc2ccccc2CN1CC#N] | 2-((S)-3-((S)-sec-butyl)-2-oxo-1,2,3,5-tetrahydro-4H-benzo[e][1,4]diazepin-4-yl)acetonitrile |
| 317 | 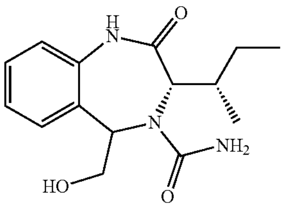 | (3S)-3-((S)-sec-butyl)-5-(hydroxymethyl)-2-oxo-1,2,3,5-tetrahydro-4H-benzo[e][1,4]diazepine-4-carboxamide |
| 318 | 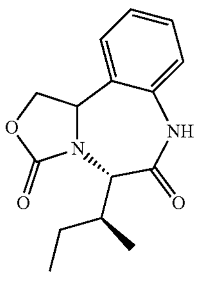 | (5S)-5-((S)-sec-butyl)-7,11b-dihydro-1H,3H-benzo[f]oxazolo[3,4-d][1,4]diazepine-3,6(5H)-dione |

TABLE 2-continued

| Compound No. | Compound Structure | Compound Name |
|---|---|---|
| 319 | 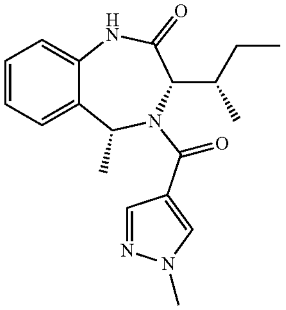 [SMILES: CC[C@H](C)[C@H]1C(=O)Nc2ccccc2[C@@H](C)N1C(=O)c1cnn(C)c1] | (3S,5R)-3-((S)-sec-butyl)-5-methyl-4-(1-methyl-1H-pyrazole-4-carbonyl)-1,3,4,5-tetrahydro-2H-benzo[e][1,4]diazepin-2-one |
| 320 | 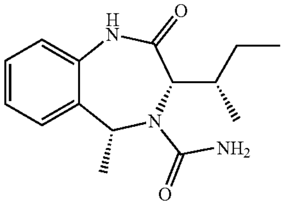 [SMILES: CC[C@H](C)[C@H]1C(=O)Nc2ccccc2[C@@H](C)N1C(N)=O] | (3S,5R)-3-((S)-sec-butyl)-5-methyl-2-oxo-1,2,3,5-tetrahydro-4H-benzo[e][1,4]diazepine-4-carboxamide |
| 321 | 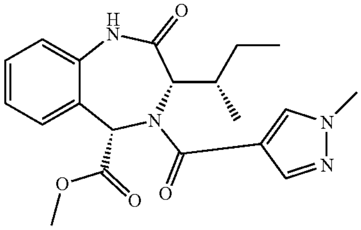 [SMILES: CC[C@H](C)[C@H]1C(=O)Nc2ccccc2[C@@H](C(=O)OC)N1C(=O)c1cnn(C)c1] | methyl (3S,5S)-3-((S)-sec-butyl)-4-(1-methyl-1H-pyrazole-4-carbonyl)-2-oxo-2,3,4,5-tetrahydro-1H-benzo[e][1,4]diazepine-5-carboxylate |
| 322 | 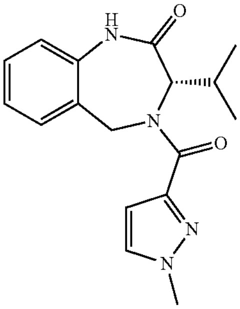 [SMILES: CC(C)[C@H]1C(=O)Nc2ccccc2CN1C(=O)c1ccn(C)n1] | (S)-3-isopropyl-4-(1-methyl-1H-pyrazole-3-carbonyl)-1,3,4,5-tetrahydro-2H-benzo[e][1,4]diazepin-2-one |
| 323 | 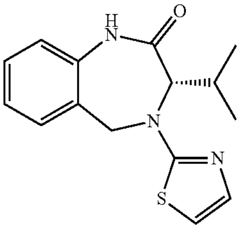 [SMILES: CC(C)[C@H]1C(=O)Nc2ccccc2CN1c1nccs1] | (S)-3-isopropyl-4-(thiazol-2-yl)-1,3,4,5-tetrahydro-2H-benzo[e][1,4]diazepin-2-one |
| 324 | 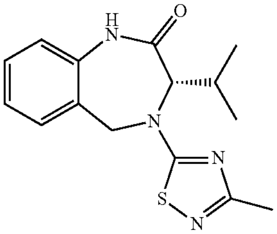 [SMILES: Cc1nsc(N2Cc3ccccc3NC(=O)[C@@H]2C(C)C)n1] | (S)-3-isopropyl-4-(3-methyl-1,2,4-thiadiazol-5-yl)-1,3,4,5-tetrahydro-2H-benzo[e][1,4]diazepin-2-one |

TABLE 2-continued

| Compound No. | Compound Structure | Compound Name |
|---|---|---|
| 325 | 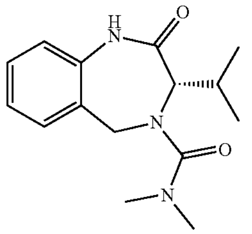 [SMILES: CC(C)[C@H]1C(=O)Nc2ccccc2CN1C(=O)N(C)C] | (S)-3-isopropyl-N,N-dimethyl-2-oxo-1,2,3,5-tetrahydro-4H-benzo[e][1,4]diazepine-4-carboxamide |
| 326 | 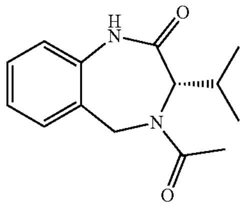 [SMILES: CC(=O)N1Cc2ccccc2NC(=O)[C@@H]1C(C)C] | (S)-4-acetyl-3-isopropyl-1,3,4,5-tetrahydro-2H-benzo[e][1,4]diazepin-2-one |
| 327 | 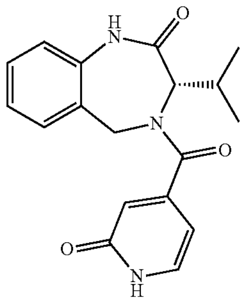 | (S)-3-isopropyl-4-(2-oxo-1,2-dihydropyridine-4-carbonyl)-1,3,4,5-tetrahydro-2H-benzo[e][1,4]diazepin-2-one |
| 328 | 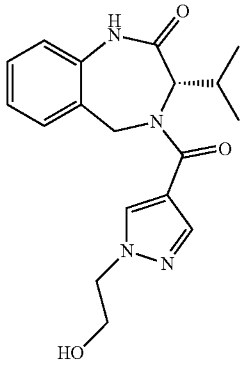 [SMILES: CC(C)[C@H]1C(=O)Nc2ccccc2CN1C(=O)c1cnn(CCO)c1] | (S)-4-(1-(2-hydroxyethyl)-1H-pyrazole-4-carbonyl)-3-isopropyl-1,3,4,5-tetrahydro-2H-benzo[e][1,4]diazepin-2-one |
| 329 | 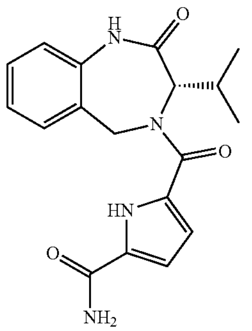 [SMILES: CC(C)[C@H]1C(=O)Nc2ccccc2CN1C(=O)c1ccc(C(N)=O)[nH]1] | (S)-5-(3-isopropyl-2-oxo-2,3,4,5-tetrahydro-1H-benzo[e][1,4]diazepine-4-carbonyl)-1H-pyrrole-2-carboxamide |

TABLE 2-continued

| Compound No. | Compound Structure | Compound Name |
| --- | --- | --- |
| 330 | 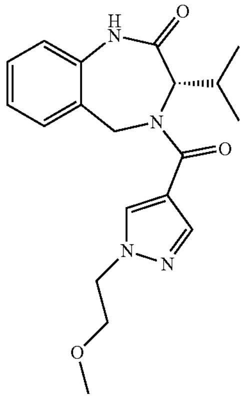 [SMILES: COCCn1cc(C(=O)N2Cc3ccccc3NC(=O)[C@@H]2C(C)C)cn1] | (S)-3-isopropyl-4-(1-(2-methoxyethyl)-1H-pyrazole-4-carbonyl)-1,3,4,5-tetrahydro-2H-benzo[e][1,4]diazepin-2-one |
| 331 | 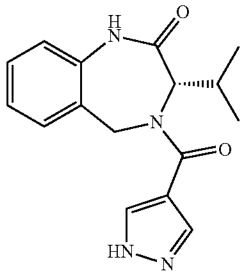 [SMILES: CC(C)[C@H]1C(=O)Nc2ccccc2CN1C(=O)c1cn[nH]c1] | (S)-3-isopropyl-4-(1H-pyrazole-4-carbonyl)-1,3,4,5-tetrahydro-2H-benzo[e][1,4]diazepin-2-one |
| 332 | 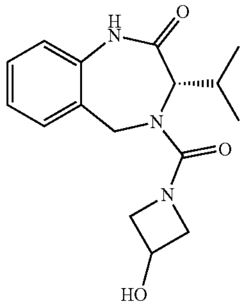 [SMILES: CC(C)[C@H]1C(=O)Nc2ccccc2CN1C(=O)N1CC(O)C1] | (S)-4-(3-hydroxyazetidine-1-carbonyl)-3-isopropyl-1,3,4,5-tetrahydro-2H-benzo[e][1,4]diazepin-2-one |
| 333 | 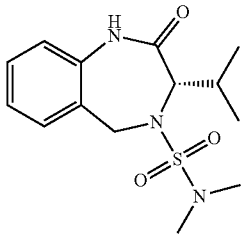 [SMILES: CC(C)[C@H]1C(=O)Nc2ccccc2CN1S(=O)(=O)N(C)C] | (S)-3-isopropyl-N,N-dimethyl-2-oxo-1,2,3,5-tetrahydro-4H-benzo[e][1,4]diazepine-4-sulfonamide |
| 334 | 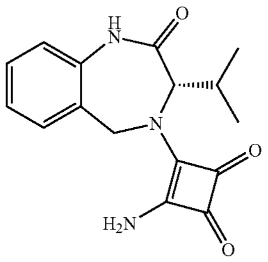 [SMILES: CC(C)[C@H]1C(=O)Nc2ccccc2CN1c1c(N)c(=O)c1=O] | (S)-3-amino-4-(3-isopropyl-2-oxo-1,2,3,5-tetrahydro-4H-benzo[e][1,4]diazepin-4-yl)cyclobut-3-ene-1,2-dione |

TABLE 2-continued

| Compound No. | Compound Structure | Compound Name |
|---|---|---|
| 335 | 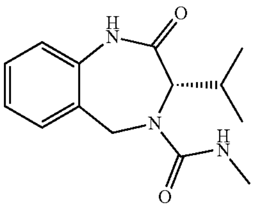 [SMILES: CNC(=O)N1Cc2ccccc2NC(=O)[C@@H]1C(C)C] | (S)-3-isopropyl-N-methyl-2-oxo-1,2,3,5-tetrahydro-4H-benzo[e][1,4]diazepine-4-carboxamide |
| 336 | 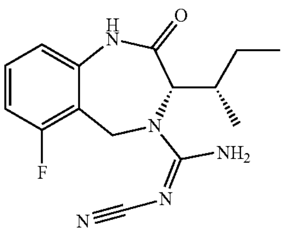 [SMILES: CC[C@H](C)[C@H]1C(=O)Nc2cccc(F)c2CN1/C(N)=N\C#N] | (S,Z)-3-((S)-sec-butyl)-N'-cyano-6-fluoro-2-oxo-1,2,3,5-tetrahydro-4H-benzo[e][1,4]diazepine-4-carboximidamide |
| 337 | 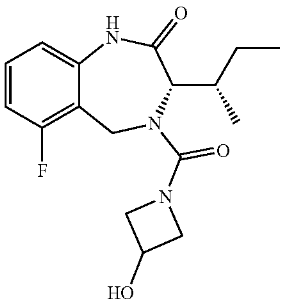 [SMILES: CC[C@H](C)[C@H]1C(=O)Nc2cccc(F)c2CN1C(=O)N1CC(O)C1] | (S)-3-((S)-sec-butyl)-6-fluoro-4-(3-hydroxyazetidine-1-carbonyl)-1,3,4,5-tetrahydro-2H-benzo[e][1,4]diazepin-2-one |
| 338 | 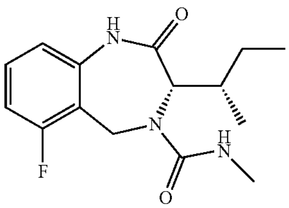 [SMILES: CC[C@H](C)[C@H]1C(=O)Nc2cccc(F)c2CN1C(=O)NC] | (S)-3-((S)-sec-butyl)-6-fluoro-N-methyl-2-oxo-1,2,3,5-tetrahydro-4H-benzo[e][1,4]diazepine-4-carboxamide |
| 339 | 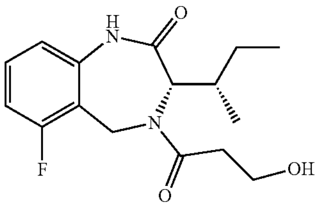 [SMILES: CC[C@H](C)[C@H]1C(=O)Nc2cccc(F)c2CN1C(=O)CCO] | (S)-3-((S)-sec-butyl)-6-fluoro-4-(3-hydroxypropanoyl)-1,3,4,5-tetrahydro-2H-benzo[e][1,4]diazepin-2-one |
| 340 | 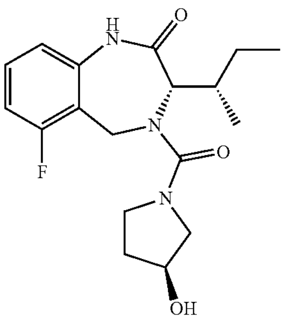 [SMILES: CC[C@H](C)[C@H]1C(=O)Nc2cccc(F)c2CN1C(=O)N1CC[C@H](O)C1] | (S)-3-((S)-sec-butyl)-6-fluoro-4-((S)-3-hydroxypyrrolidine-1-carbonyl)-1,3,4,5-tetrahydro-2H-benzo[e][1,4]diazepin-2-one |

TABLE 2-continued

| Compound No. | Compound Structure | Compound Name |
|---|---|---|
| 341 | 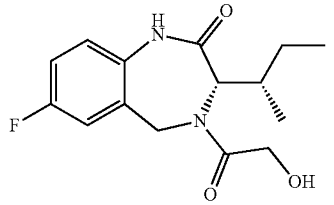 [SMILES: CC[C@H](C)[C@H]1C(=O)Nc2ccc(F)cc2CN1C(=O)CO] | (S)-3-((S)-sec-butyl)-7-fluoro-4-(2-hydroxyacetyl)-1,3,4,5-tetrahydro-2H-benzo[e][1,4]diazepin-2-one |
| 342 | 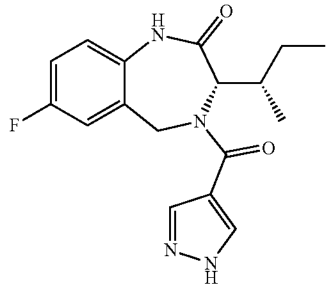 [SMILES: CC[C@H](C)[C@H]1C(=O)Nc2ccc(F)cc2CN1C(=O)c1cn[nH]c1] | (S)-3-((S)-sec-butyl)-7-fluoro-4-(1H-pyrazole-4-carbonyl)-1,3,4,5-tetrahydro-2H-benzo[e][1,4]diazepin-2-one |
| 343 | 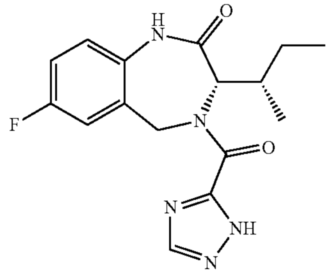 [SMILES: CC[C@H](C)[C@H]1C(=O)Nc2ccc(F)cc2CN1C(=O)c1ncn[nH]1] | (S)-3-((S)-sec-butyl)-7-fluoro-4-(1H-1,2,4-triazole-5-carbonyl)-1,3,4,5-tetrahydro-2H-benzo[e][1,4]diazepin-2-one |
| 344 | 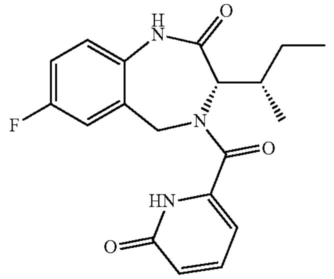 [SMILES: CC[C@H](C)[C@H]1C(=O)Nc2ccc(F)cc2CN1C(=O)c1cccc(=O)[nH]1] | (S)-3-((S)-sec-butyl)-7-fluoro-4-(6-oxo-1,6-dihydropyridine-2-carbonyl)-1,3,4,5-tetrahydro-2H-benzo[e][1,4]diazepin-2-one |
| 345 | 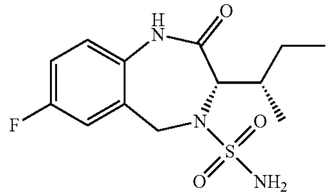 [SMILES: CC[C@H](C)[C@H]1C(=O)Nc2ccc(F)cc2CN1S(N)(=O)=O] | (S)-3-((S)-sec-butyl)-7-fluoro-2-oxo-1,2,3,5-tetrahydro-4H-benzo[e][1,4]diazepine-4-sulfonamide |
| 346 | 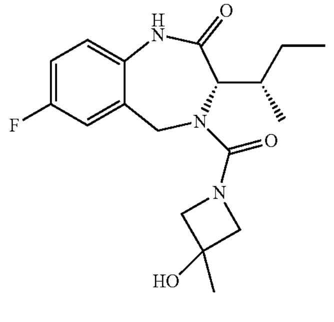 [SMILES: CC[C@H](C)[C@H]1C(=O)Nc2ccc(F)cc2CN1C(=O)N1CC(C)(O)C1] | (S)-3-((S)-sec-butyl)-7-fluoro-4-(3-hydroxy-3-methylazetidine-1-carbonyl)-1,3,4,5-tetrahydro-2H-benzo[e][1,4]diazepin-2-one |

TABLE 2-continued

| Compound No. | Compound Structure | Compound Name |
|---|---|---|
| 347 | 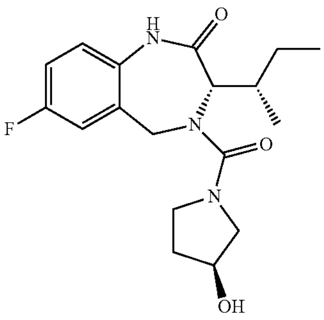 [SMILES: CC[C@H](C)[C@H]1C(=O)Nc2ccc(F)cc2CN1C(=O)N1CC[C@H](O)C1] | (S)-3-((S)-sec-butyl)-7-fluoro-4-((S)-3-hydroxypyrrolidine-1-carbonyl)-1,3,4,5-tetrahydro-2H-benzo[e][1,4]diazepin-2-one |
| 348 | 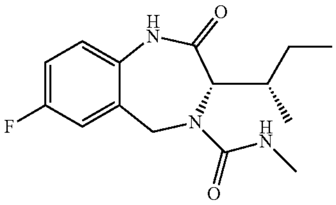 [SMILES: CC[C@H](C)[C@H]1C(=O)Nc2ccc(F)cc2CN1C(=O)NC] | (S)-3-((S)-sec-butyl)-7-fluoro-N-methyl-2-oxo-1,2,3,5-tetrahydro-4H-benzo[e][1,4]diazepine-4-carboxamide |
| 349 | 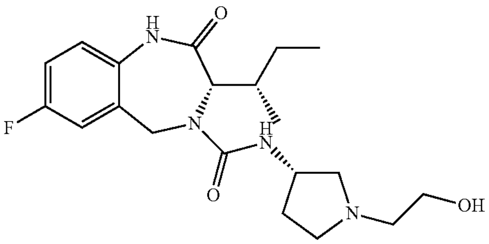 [SMILES: CC[C@H](C)[C@H]1C(=O)Nc2ccc(F)cc2CN1C(=O)N[C@H]1CCN(CCO)C1] | (S)-3-((S)-sec-butyl)-7-fluoro-N-((S)-1-(2-hydroxyethyl)pyrrolidin-3-yl)-2-oxo-1,2,3,5-tetrahydro-4H-benzo[e][1,4]diazepine-4-carboxamide |
| 350 | 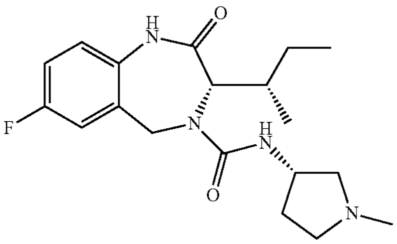 [SMILES: CC[C@H](C)[C@H]1C(=O)Nc2ccc(F)cc2CN1C(=O)N[C@H]1CCN(C)C1] | (S)-3-((S)-sec-butyl)-7-fluoro-N-((S)-1-methylpyrrolidin-3-yl)-2-oxo-1,2,3,5-tetrahydro-4H-benzo[e][1,4]diazepine-4-carboxamide |
| 351 | 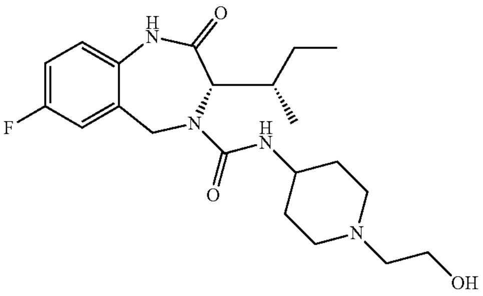 [SMILES: CC[C@H](C)[C@H]1C(=O)Nc2ccc(F)cc2CN1C(=O)NC1CCN(CCO)CC1] | (S)-3-((S)-sec-butyl)-7-fluoro-N-(1-(2-hydroxyethyl)piperidin-4-yl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 352 | 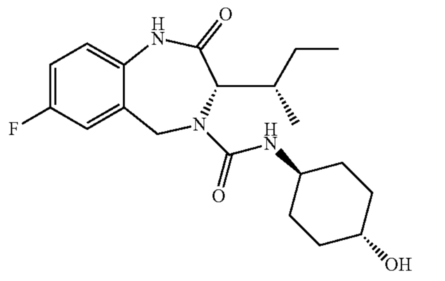 [SMILES: CC[C@H](C)[C@H]1C(=O)Nc2ccc(F)cc2CN1C(=O)N[C@H]1CC[C@H](O)CC1] | (S)-3-((S)-sec-butyl)-7-fluoro-N-((1r,4S)-4-hydroxycyclohexyl)-2-oxo-1,2,3,5-tetrahydro-4H-benzo[e][1,4]diazepine-4-carboxamide |
| 353 | 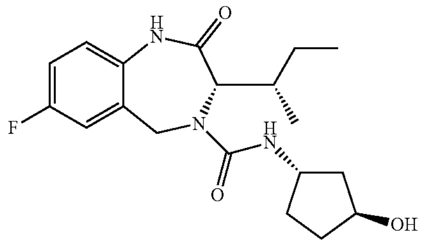 [SMILES: CC[C@H](C)[C@H]1C(=O)Nc2ccc(F)cc2CN1C(=O)N[C@H]1CC[C@H](O)C1] | (S)-3-((S)-sec-butyl)-7-fluoro-N-((1S,3S)-3-hydroxycyclopentyl)-2-oxo-1,2,3,5-tetrahydro-4H-benzo[e][1,4]diazepine-4-carboxamide |
| 354 | 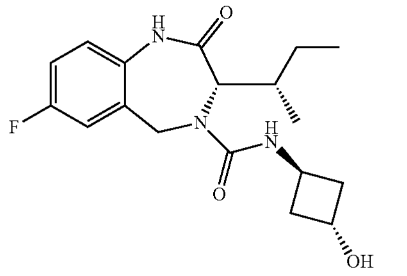 [SMILES: CC[C@H](C)[C@H]1C(=O)Nc2ccc(F)cc2CN1C(=O)N[C@H]1C[C@H](O)C1] | (S)-3-((S)-sec-butyl)-7-fluoro-N-((1r,3S)-3-hydroxycyclobutyl)-2-oxo-1,2,3,5-tetrahydro-4H-benzo[e][1,4]diazepine-4-carboxamide |
| 355 | 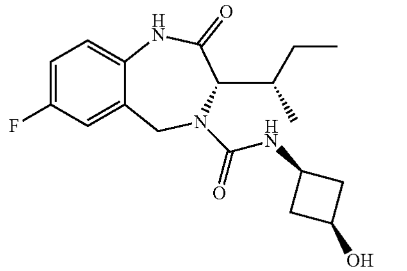 [SMILES: CC[C@H](C)[C@H]1C(=O)Nc2ccc(F)cc2CN1C(=O)N[C@H]1C[C@@H](O)C1] | (S)-3-((S)-sec-butyl)-7-fluoro-N-((1s,3R)-3-hydroxycyclobutyl)-2-oxo-1,2,3,5-tetrahydro-4H-benzo[e][1,4]diazepine-4-carboxamide |
| 356 | 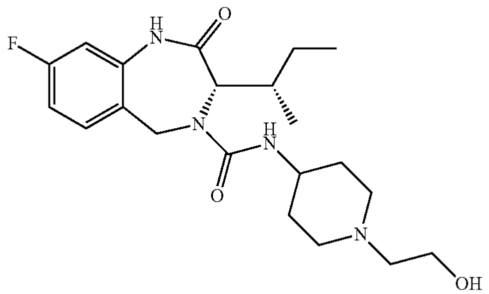 [SMILES: CC[C@H](C)[C@H]1C(=O)Nc2cc(F)ccc2CN1C(=O)NC1CCN(CCO)CC1] | (S)-3-((S)-sec-butyl)-8-fluoro-N-(1-(2-hydroxyethyl)piperidin-4-yl)-2-oxo-1,2,3,5-tetrahydro-4H-benzo[e][1,4]diazepine-4-carboxamide |

TABLE 2-continued

| Compound No. | Compound Structure | Compound Name |
|---|---|---|
| 357 | 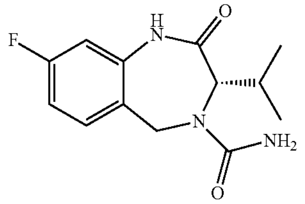 [SMILES: CC(C)[C@H]1C(=O)Nc2cc(F)ccc2CN1C(N)=O] | (S)-8-fluoro-3-isopropyl-2-oxo-1,2,3,5-tetrahydro-4H-benzo[e][1,4]diazepine-4-carboxamide |
| 358 | 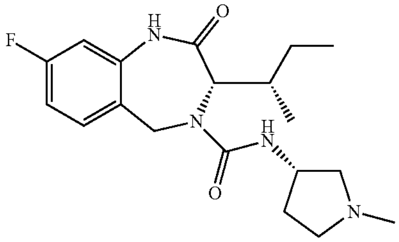 [SMILES: CC[C@H](C)[C@H]1C(=O)Nc2cc(F)ccc2CN1C(=O)N[C@H]1CCN(C)C1] | (S)-3-((S)-sec-butyl)-8-fluoro-N-((S)-1-methylpyrrolidin-3-yl)-2-oxo-1,2,3,5-tetrahydro-4H-benzo[e][1,4]diazepine-4-carboxamide |
| 359 | 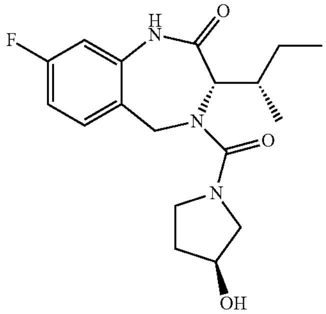 [SMILES: CC[C@H](C)[C@H]1C(=O)Nc2cc(F)ccc2CN1C(=O)N1CC[C@H](O)C1] | (S)-3-((S)-sec-butyl)-8-fluoro-4-((S)-3-hydroxypyrrolidine-1-carbonyl)-1,3,4,5-tetrahydro-2H-benzo[e][1,4]diazepin-2-one |
| 360 | 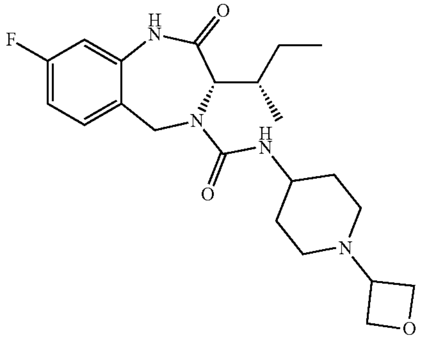 [SMILES: CC[C@H](C)[C@H]1C(=O)Nc2cc(F)ccc2CN1C(=O)NC1CCN(C2COC2)CC1] | (S)-3-((S)-sec-butyl)-8-fluoro-N-(1-(oxetan-3-yl)piperidin-4-yl)-2-oxo-1,2,3,5-tetrahydro-4H-benzo[e][1,4]diazepine-4-carboxamide |
| 361 | 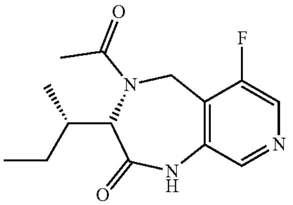 | (S)-4-acetyl-3-((S)-sec-butyl)-6-fluoro-1,3,4,5-tetrahydro-2H-pyrido[3,4-e][1,4]diazepin-2-one |
| 362 | 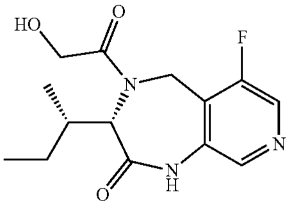 [SMILES: CC[C@H](C)[C@H]1C(=O)Nc2cncc(F)c2CN1C(=O)CO] | (S)-3-((S)-sec-butyl)-6-fluoro-4-(2-hydroxyacetyl)-1,3,4,5-tetrahydro-2H-pyrido[3,4-e][1,4]diazepin-2-one |

TABLE 2-continued

| Compound No. | Compound Structure | Compound Name |
|---|---|---|
| 363 | 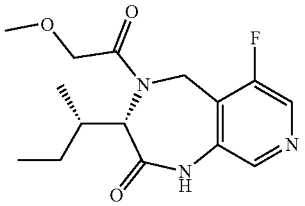 [SMILES: CC[C@H](C)[C@H]1C(=O)Nc2cncc(F)c2CN1C(=O)COC] | (S)-3-((S)-sec-butyl)-6-fluoro-4-(2-methoxyacetyl)-1,3,4,5-tetrahydro-2H-pyrido[3,4-e][1,4]diazepin-2-one |
| 364 | 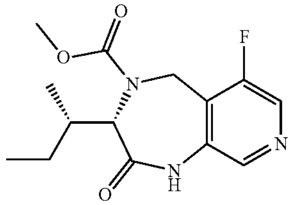 [SMILES: CC[C@H](C)[C@H]1C(=O)Nc2cncc(F)c2CN1C(=O)OC] | methyl (S)-3-((S)-sec-butyl)-6-fluoro-2-oxo-1,2,3,5-tetrahydro-4H-pyrido[3,4-e][1,4]diazepine-4-carboxylate |
| 365 | 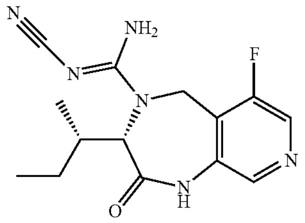 [SMILES: CC[C@H](C)[C@H]1C(=O)Nc2cncc(F)c2CN1/C(N)=N/C#N] | (S,E)-3-((S)-sec-butyl)-N'-cyano-6-fluoro-2-oxo-1,2,3,5-tetrahydro-4H-pyrido[3,4-e][1,4]diazepine-4-carboximidamide |
| 366 | 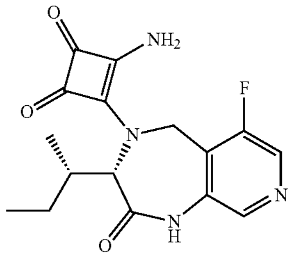 [SMILES: CC[C@H](C)[C@H]1C(=O)Nc2cncc(F)c2CN1c1c(N)c(=O)c1=O] | 3-amino-4-((S)-3-((S)-sec-butyl)-6-fluoro-2-oxo-1,2,3,5-tetrahydro-4H-pyrido[3,4-e][1,4]diazepin-4-yl)cyclobut-3-ene-1,2-dione |
| 367 | 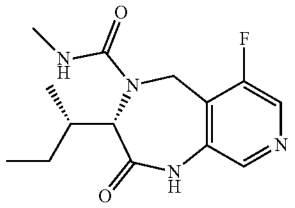 [SMILES: CC[C@H](C)[C@H]1C(=O)Nc2cncc(F)c2CN1C(=O)NC] | (S)-3-((S)-sec-butyl)-6-fluoro-N-methyl-2-oxo-1,2,3,5-tetrahydro-4H-pyrido[3,4-e][1,4]diazepine-4-carboxamide |
| 368 | 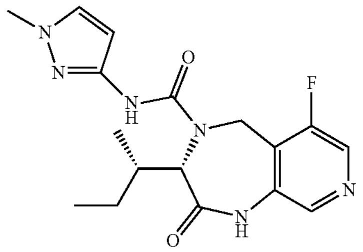 [SMILES: CC[C@H](C)[C@H]1C(=O)Nc2cncc(F)c2CN1C(=O)Nc1ccn(C)n1] | (S)-3-((S)-sec-butyl)-6-fluoro-N-(1-methyl-1H-pyrazol-3-yl)-2-oxo-1,2,3,5-tetrahydro-4H-pyrido[3,4-e][1,4]diazepine-4-carboxamide |

TABLE 2-continued

| Compound No. | Compound Structure | Compound Name |
|---|---|---|
| 369 | 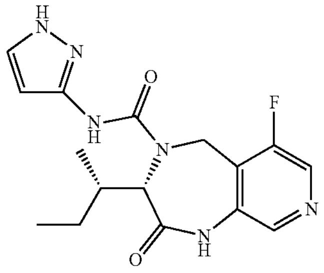 [SMILES: CC[C@H](C)[C@H]1C(=O)Nc2cncc(F)c2CN1C(=O)Nc1cc[nH]n1] | ((S)-3-((S)-sec-butyl)-6-fluoro-2-oxo-N-(1H-pyrazol-3-yl)-1,2,3,5-tetrahydro-4H-pyrido[3,4-e][1,4]diazepine-4-carboxamide |
| 370 | 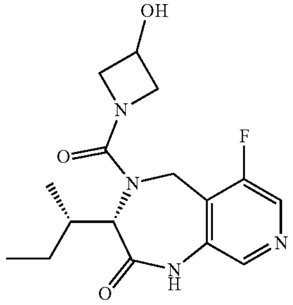 [SMILES: CC[C@H](C)[C@H]1C(=O)Nc2cncc(F)c2CN1C(=O)N1CC(O)C1] | (S)-3-((S)-sec-butyl)-6-fluoro-4-(3-hydroxyazetidine-1-carbonyl)-1,3,4,5-tetrahydro-2H-pyrido[3,4-e][1,4]diazepin-2-one |
| 371 | 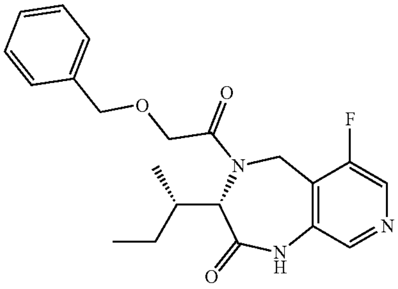 [SMILES: CC[C@H](C)[C@H]1C(=O)Nc2cncc(F)c2CN1C(=O)COCc1ccccc1] | (S)-4-(2-(benzyloxy)acetyl)-3-((S)-sec-butyl)-6-fluoro-1,3,4,5-tetrahydro-2H-pyrido[3,4-e][1,4]diazepin-2-one |
| 372 | 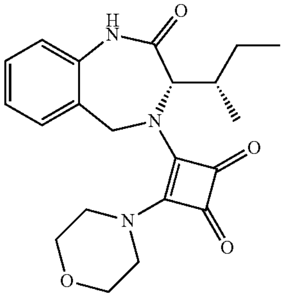 [SMILES: CC[C@H](C)[C@H]1C(=O)Nc2ccccc2CN1c1c(N2CCOCC2)c(=O)c1=O] | 3-((S)-3-((S)-sec-butyl)-2-oxo-1,2,3,5-tetrahydro-4H-benzo[e][1,4]diazepin-4-yl)-4-morpholinocyclobut-3-ene-1,2-dione |
| 373 | 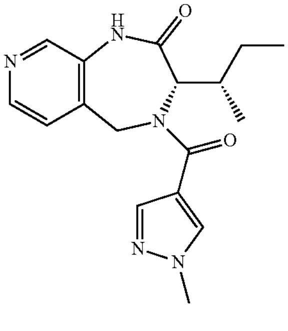 [SMILES: CC[C@H](C)[C@H]1C(=O)Nc2cnccc2CN1C(=O)c1cnn(C)c1] | (S)-3-((S)-sec-butyl)-4-(1-methyl-1H-pyrazole-4-carbonyl)-1,3,4,5-tetrahydro-2H-pyrido[3,4-e][1,4]diazepin-2-one |

TABLE 2-continued

| Compound No. | Compound Structure | Compound Name |
| --- | --- | --- |
| 374 | 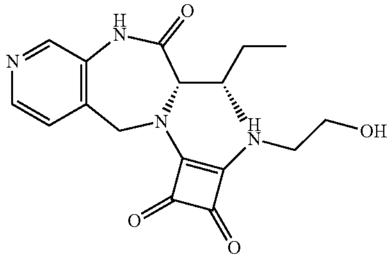 [SMILES: CC[C@H](C)[C@H]1C(=O)Nc2cnccc2CN1c1c(NCCO)c(=O)c1=O] | 3-((S)-3-((S)-sec-butyl)-2-oxo-1,2,3,5-tetrahydro-4H-pyrido[3,4-e][1,4]diazepin-4-yl)-4-((2-hydroxyethyl)amino)cyclobut-3-ene-1,2-dione |
| 375 | 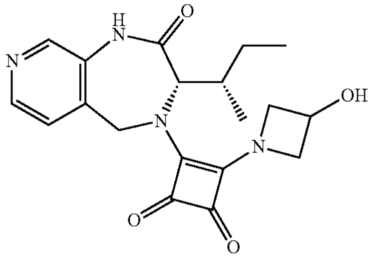 [SMILES: CC[C@H](C)[C@H]1C(=O)Nc2cnccc2CN1c1c(N2CC(O)C2)c(=O)c1=O] | 3-((S)-3-((S)-sec-butyl)-2-oxo-1,2,3,5-tetrahydro-4H-pyrido[3,4-e][1,4]diazepin-4-yl)-4-(3-hydroxyazetidin-1-yl)cyclobut-3-ene-1,2-dione |
| 376 | 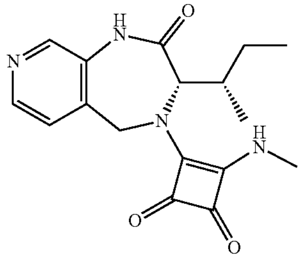 [SMILES: CC[C@H](C)[C@H]1C(=O)Nc2cnccc2CN1c1c(NC)c(=O)c1=O] | 3-((S)-3-((S)-sec-butyl)-2-oxo-1,2,3,5-tetrahydro-4H-pyrido[3,4-e][1,4]diazepin-4-yl)-4-(methylamino)cyclobut-3-ene-1,2-dione |
| 377 | 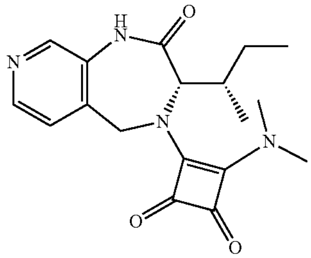 [SMILES: CC[C@H](C)[C@H]1C(=O)Nc2cnccc2CN1c1c(N(C)C)c(=O)c1=O] | 3-((S)-3-((S)-sec-butyl)-2-oxo-1,2,3,5-tetrahydro-4H-pyrido[3,4-e][1,4]diazepin-4-yl)-4-(dimethylamino)cyclobut-3-ene-1,2-dione |
| 378 | 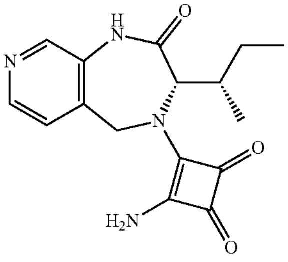 [SMILES: CC[C@H](C)[C@H]1C(=O)Nc2cnccc2CN1c1c(N)c(=O)c1=O] | 3-amino-4-((S)-3-((S)-sec-butyl)-2-oxo-1,2,3,5-tetrahydro-4H-pyrido[3,4-e][1,4]diazepin-4-yl)cyclobut-3-ene-1,2-dione |

TABLE 2-continued

| Compound No. | Compound Structure | Compound Name |
|---|---|---|
| 379 | 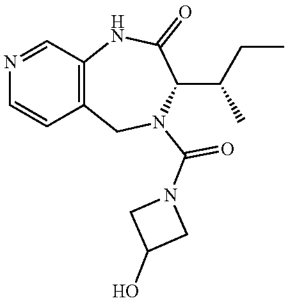 [SMILES: CC[C@H](C)[C@H]1C(=O)Nc2cnccc2CN1C(=O)N1CC(O)C1] | (S)-3-((S)-sec-butyl)-4-(3-hydroxyazetidine-1-carbonyl)-1,3,4,5-tetrahydro-2H-pyrido[3,4-e][1,4]diazepin-2-one |
| 380 | 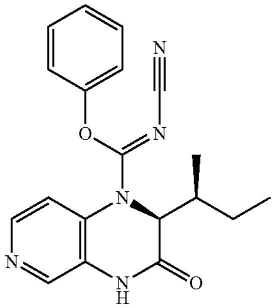 [SMILES: CC[C@H](C)[C@H]1C(=O)Nc2cnccc2N1/C(=N/C#N)Oc1ccccc1] | phenyl (S,Z)-2-((S)-sec-butyl)-N-cyano-3-oxo-3,4-dihydropyrido[3,4-b]pyrazine-1(2H)-carbimidate |
| 381 | 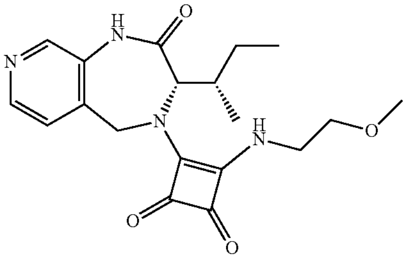 [SMILES: CC[C@H](C)[C@H]1C(=O)Nc2cnccc2CN1c1c(NCCOC)c(=O)c1=O] | 3-((S)-3-((S)-sec-butyl)-2-oxo-1,2,3,5-tetrahydro-4H-pyrido[3,4-e][1,4]diazepin-4-yl)-4-((2-methoxyethyl)amino)cyclobut-3-ene-1,2-dione |

In some variations, any of the compounds described herein, such as a compound of formula B37), (I-1B8), (I-C), or (I-D), or any variation thereof, or a compound of Table 2, may be deuterated (e.g., a hydrogen atom is replaced by a deuterium atom). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

In one aspect, provided herein is a compound of formula (I), such as a compound of formula (II), (III), (IV), (V), (I-A), (I-A1), (I-A2), (I-A3), (I-A4), (I-A5), (I-B), (I-B1), (I-1B2), (I-1B3), (I-B4), (I-B5), (I-B6), (I-B7), (I-B8), (I-C), or (I-D), or a stereoisomer or tautomer thereof, or a pharmaceutically acceptable salt of any of the foregoing, wherein the compound of formula (I) is selected from the group consisting of:

3-(3-(sec-butyl)-2-oxo-1,2,3,5-tetrahydro-4H-benzo[1,4]diazepin-4-yl)-3-oxopropanamide;

3-(sec-butyl)-N'-cyano-2-oxo-1,2,3,5-tetrahydro-4H-benzo[1,4]diazepine-4-carboximidamide;

3-(sec-butyl)-4-(6-oxo-1,6-dihydropyrimidin-2-yl)-1,3,4,5-tetrahydro-2H-benzo[1,4]diazepin-2-one;

3-(sec-butyl)-4-(2H-tetrazol-5-yl)-1,3,4,5-tetrahydro-2H-benzo[1,4]diazepin-2-one;

3-(sec-butyl)-2-oxo-1,2,3,5-tetrahydro-4H-benzo[1,4]diazepine-4-carboxamide;

2-(3-(sec-butyl)-2-oxo-1,2,3,5-tetrahydro-4H-benzo[1,4]diazepin-4-yl)acetamide;

3-isopropyl-2-oxo-1,2,3,5-tetrahydro-4H-benzo[1,4]diazepine-4-carboxamide;

3-(sec-butyl)-6,8-difluoro-2-oxo-1,2,3,5-tetrahydro-4H-benzo[1,4]diazepine-4-carboxamide;

3-(sec-butyl)-7-fluoro-2-oxo-1,2,3,5-tetrahydro-4H-benzo[1,4]diazepine-4-carboxamide;

3-(sec-butyl)-6-fluoro-2-oxo-1,2,3,5-tetrahydro-4H-pyrido[3,4-e][1,4]diazepine-4-carboxamide;

7-(sec-butyl)-6-oxo-5,6,7,9-tetrahydro-8H-pyrimido[5,4-e][1,4]diazepine-8-carboxamide;

3-(sec-butyl)-2-oxo-1,2,3,5-tetrahydro-4H-pyrido[3,4-e][1,4]diazepine-4-carboxamide;

3-(sec-butyl)-8-fluoro-2-oxo-1,2,3,5-tetrahydro-4H-pyrido[3,2-e][1,4]diazepine-4-carboxamide;

5-(sec-butyl)-3-hydroxy-5H-benzo[f]imidazo[1,5-d][1,4]diazepin-6(7H)-one;

4-acetyl-3-(sec-butyl)-1,3,4,5-tetrahydro-2H-benzo[1,4]diazepin-2-one;

3-(sec-butyl)-4-(1-(2-hydroxyethyl)-1H-pyrazole-4-carbonyl)-1,3,4,5-tetrahydro-2H-benzo[1,4]diazepin-2-one;

3-(sec-butyl)-4-glycyl-1,3,4,5-tetrahydro-2H-benzo[1,4]diazepin-2-one;
3-(sec-butyl)-4-(2-hydroxyacetyl)-1,3,4,5-tetrahydro-2H-benzo[1,4]diazepin-2-one;
3-(sec-butyl)-2-oxo-1,2,3,5-tetrahydro-4H-benzo[1,4]diazepine-4-carboximidamide;
methyl 3-(sec-butyl)-2-oxo-1,2,3,5-tetrahydro-4H-benzo[1,4]diazepine-4-carboxylate;
3-(sec-butyl)-N'-cyano-N,N-dimethyl-2-oxo-1,2,3,5-tetrahydro-4H-benzo[1,4]diazepine-4-carboximidamide;
methyl (amino(3-(sec-butyl)-2-oxo-1,2,3,5-tetrahydro-4H-benzo[1,4]diazepin-4-yl)methylene)carbamate;
3-(sec-butyl)-4-(4-hydroxy-6-oxo-1,6-dihydropyrimidin-2-yl)-1,3,4,5-tetrahydro-2H-benzo[e][1,4]diazepin-2-one;
4-(5-amino-6-oxo-1,6-dihydropyrimidin-2-yl)-3-(sec-butyl)-1,3,4,5-tetrahydro-2H-benzo[1,4]diazepin-2-one;
3-(3-(sec-butyl)-2-oxo-1,2,3,5-tetrahydro-4H-benzo[1,4]diazepin-4-yl)-1,2,4-oxadiazol-5(4H)-one;
3-(sec-butyl)-4-(methylsulfonyl)-1,3,4,5-tetrahydro-2H-benzo[1,4]diazepin-2-one;
3-(sec-butyl)-N,N-dimethyl-2-oxo-1,2,3,5-tetrahydro-4H-benzo[1,4]diazepine-4-sulfonamide;
4-acetyl-3-cyclohexyl-1,3,4,5-tetrahydro-2H-benzo[1,4]diazepin-2-one;
3-cyclohexyl-2-oxo-1,2,3,5-tetrahydro-4H-benzo[1,4]diazepine-4-carboxamide;
3-(3-(sec-butyl)-2-oxo-1,2,3,5-tetrahydro-4H-benzo[1,4]diazepin-4-yl)-4-(3-hydroxyazetidin-1-yl)cyclobut-3-ene-1,2-dione;
3-(sec-butyl)-N-methyl-2-oxo-1,2,3,5-tetrahydro-4H-benzo[1,4]diazepine-4-carboxamide;
3-(sec-butyl)-4-(3-hydroxyazetidine-1-carbonyl)-1,3,4,5-tetrahydro-2H-benzo[1,4]diazepin-2-one;
2-(3-(sec-butyl)-2-oxo-1,2,3,5-tetrahydro-4H-benzo[1,4]diazepin-4-yl)-2-oxoacetamide;
3-(sec-butyl)-4-(3-methyl-1,2,4-thiadiazol-5-yl)-1,3,4,5-tetrahydro-2H-benzo[1,4]diazepin-2-one;
3-(sec-butyl)-4-(thiazol-2-yl)-1,3,4,5-tetrahydro-2H-benzo[1,4]diazepin-2-one;
5-(sec-butyl)-7,11b-dihydro-1H,3H-benzo[f]oxazolo[3,4-d][1,4]diazepine-3,6(5H)-dione;
3-(sec-butyl)-5-(hydroxymethyl)-2-oxo-1,2,3,5-tetrahydro-4H-benzo[1,4]diazepine-4-carboxamide;
3-(sec-butyl)-5-methyl-4-(1-methyl-1H-pyrazole-4-carbonyl)-1,3,4,5-tetrahydro-2H-benzo[1,4]diazepin-2-one;
3-(sec-butyl)-5-methyl-2-oxo-1,2,3,5-tetrahydro-4H-benzo[1,4]diazepine-4-carboxamide;
3-(sec-butyl)-N5-methyl-2-oxo-1,2,3,5-tetrahydro-4H-benzo[1,4]diazepine-4,5-dicarboxamide;
3-isopropyl-4-(1-methyl-1H-pyrazole-4-carbonyl)-1,3,4,5-tetrahydro-2H-benzo[1,4]diazepin-2-one;
3-(sec-butyl)-8-fluoro-4-(2-hydroxyacetyl)-1,3,4,5-tetrahydro-2H-benzo[1,4]diazepin-2-one;
3-(sec-butyl)-8-fluoro-4-(3-hydroxypropanoyl)-1,3,4,5-tetrahydro-2H-benzo[1,4]diazepin-2-one;
3-(sec-butyl)-9-fluoro-2-oxo-1,2,3,5-tetrahydro-4H-benzo[1,4]diazepine-4-carboxamide;
3-(sec-butyl)-4-(1H-pyrazole-4-carbonyl)-1,3,4,5-tetrahydro-2H-benzo[1,4]diazepin-2-one;
3-(sec-butyl)-4-(1-methyl-1H-pyrazole-4-carbonyl)-1,3,4,5-tetrahydro-2H-benzo[1,4]diazepin-2-one;
3-(sec-butyl)-4-(6-oxo-1,6-dihydropyridine-2-carbonyl)-1,3,4,5-tetrahydro-2H-benzo[1,4]diazepin-2-one;
3-(sec-butyl)-4-(2-oxo-1,2-dihydropyridine-4-carbonyl)-1,3,4,5-tetrahydro-2H-benzo[1,4]diazepin-2-one;
3-(sec-butyl)-4-(3-hydroxypropanoyl)-1,3,4,5-tetrahydro-2H-benzo[1,4]diazepin-2-one;
3-(sec-butyl)-4-(3-hydroxy-1H-pyrazole-5-carbonyl)-1,3,4,5-tetrahydro-2H-benzo[1,4]diazepin-2-one;
3-(sec-butyl)-4-(2-hydroxy-2-methylpropanoyl)-1,3,4,5-tetrahydro-2H-benzo[1,4]diazepin-2-one;
4-(4-amino-6-oxo-1,6-dihydropyrimidin-2-yl)-3-(sec-butyl)-1,3,4,5-tetrahydro-2H-benzo[1,4]diazepin-2-one;
3-(sec-butyl)-4-(4-methyl-6-oxo-1,6-dihydropyrimidin-2-yl)-1,3,4,5-tetrahydro-2H-benzo[1,4]diazepin-2-one;
3-(sec-butyl)-4-(6-oxo-1,6-dihydropyrimidin-4-yl)-1,3,4,5-tetrahydro-2H-benzo[1,4]diazepin-2-one;
3-(sec-butyl)-4-(5-methyl-1,2,4-oxadiazol-3-yl)-1,3,4,5-tetrahydro-2H-benzo[1,4]diazepin-2-one;
3-(sec-butyl)-4-(1,2,4-oxadiazol-3-yl)-1,3,4,5-tetrahydro-2H-benzo[1,4]diazepin-2-one;
3-amino-4-(3-(sec-butyl)-2-oxo-1,2,3,5-tetrahydro-4H-benzo[1,4]diazepin-4-yl)cyclobut-3-ene-1,2-dione;
3-(sec-butyl)-N,N-dimethyl-2-oxo-1,2,3,5-tetrahydro-4H-benzo[1,4]diazepine-4-carboxamide;
3-(sec-butyl)-4-(3-methoxyazetidine-1-carbonyl)-1,3,4,5-tetrahydro-2H-benzo[1,4]diazepin-2-one;
4-(5-amino-4-methoxypyrimidin-2-yl)-3-(sec-butyl)-1,3,4,5-tetrahydro-2H-benzo[1,4]diazepin-2-one;
3-(sec-butyl)-4-(1,3,5-triazin-2-yl)-1,3,4,5-tetrahydro-2H-benzo[1,4]diazepin-2-one;
3-(sec-butyl)-4-(2-hydroxyethyl)-1,3,4,5-tetrahydro-2H-benzo[1,4]diazepin-2-one;
3-(sec-butyl)-5,5-dimethyl-2-oxo-1,2,3,5-tetrahydro-4H-benzo[1,4]diazepine-4-carboxamide;
N'-cyano-3-isopropyl-2-oxo-1,2,3,5-tetrahydro-4H-benzo[1,4]diazepine-4-carboximidamide;
3-(sec-butyl)-6-fluoro-2-oxo-1,2,3,5-tetrahydro-4H-benzo[1,4]diazepine-4-carboxamide;
3-(sec-butyl)-6-chloro-4-(3-hydroxyazetidine-1-carbonyl)-1,3,4,5-tetrahydro-2H-benzo[1,4]diazepin-2-one;
6-bromo-3-(sec-butyl)-2-oxo-1,2,3,5-tetrahydro-4H-benzo[1,4]diazepine-4-carboxamide;
3-(sec-butyl)-6-cyclopropyl-2-oxo-1,2,3,5-tetrahydro-4H-benzo[1,4]diazepine-4-carboxamide;
4-acetyl-3-(sec-butyl)-7-fluoro-1,3,4,5-tetrahydro-2H-benzo[1,4]diazepin-2-one;
3-(sec-butyl)-7-fluoro-4-(1H-pyrazole-5-carbonyl)-1,3,4,5-tetrahydro-2H-benzo[1,4]diazepin-2-one;
3-(sec-butyl)-N'-cyano-7-fluoro-2-oxo-1,2,3,5-tetrahydro-4H-benzo[1,4]diazepine-4-carboximidamide;
3-(sec-butyl)-7-fluoro-4-(3-hydroxyazetidine-1-carbonyl)-1,3,4,5-tetrahydro-2H-benzo[1,4]diazepin-2-one;
3-(sec-butyl)-7-chloro-2-oxo-1,2,3,5-tetrahydro-4H-benzo[1,4]diazepine-4-carboxamide;
3-(sec-butyl)-7-cyclopropyl-2-oxo-1,2,3,5-tetrahydro-4H-benzo[1,4]diazepine-4-carboxamide;
3-(sec-butyl)-8-fluoro-2-oxo-1,2,3,5-tetrahydro-4H-benzo[1,4]diazepine-4-carboxamide;
3-(sec-butyl)-8-fluoro-4-(3-hydroxyazetidine-1-carbonyl)-1,3,4,5-tetrahydro-2H-benzo[1,4]diazepin-2-one;
3-(sec-butyl)-8-fluoro-N-methyl-2-oxo-1,2,3,5-tetrahydro-4H-benzo[1,4]diazepine-4-carboxamide;
3-(sec-butyl)-9-fluoro-N-methyl-2-oxo-1,2,3,5-tetrahydro-4H-benzo[1,4]diazepine-4-carboxamide;
3-(sec-butyl)-9-fluoro-4-(3-hydroxyazetidine-1-carbonyl)-1,3,4,5-tetrahydro-2H-benzo[1,4]diazepin-2-one;
3-(sec-butyl)-6-fluoro-4-(1-methyl-1H-pyrazole-4-carbonyl)-1,3,4,5-tetrahydro-2H-pyrido[3,4-e][1,4]diazepin-2-one;
3-(sec-butyl)-6-methyl-2-oxo-1,2,3,5-tetrahydro-4H-pyrido[3,4-e][1,4]diazepine-4-carboxamide;
3-(sec-butyl)-N'-cyano-2-oxo-1,2,3,5-tetrahydro-4H-pyrido[3,4-e][1,4]diazepine-4-carboximidamide;

3-(sec-butyl)-4-(1H-pyrrolo[3,2-c]pyridine-2-carbonyl)-1,3,4,5-tetrahydro-2H-benzo[1,4]diazepin-2-one;
3-(sec-butyl)-4-(1-methyl-1H-pyrazole-3-carbonyl)-1,3,4,5-tetrahydro-2H-benzo[1,4]diazepin-2-one;
5-(3-(sec-butyl)-2-oxo-2,3,4,5-tetrahydro-1H-benzo[1,4]diazepine-4-carbonyl)-1H-pyrrole-2-carboxamide;
3-(sec-butyl)-4-(2-hydroxypropanoyl)-1,3,4,5-tetrahydro-2H-benzo[1,4]diazepin-2-one;
3-(sec-butyl)-N'-cyano-N-methyl-2-oxo-1,2,3,5-tetrahydro-4H-benzo[1,4]diazepine-4-carboximidamide;
3-isopropyl-4-(6-oxo-1,6-dihydropyrimidin-2-yl)-1,3,4,5-tetrahydro-2H-benzo[1,4]diazepin-2-one;
3-(sec-butyl)-4-((4-fluorophenyl)sulfonyl)-1,3,4,5-tetrahydro-2H-benzo[1,4]diazepin-2-one;
3-(sec-butyl)-2-oxo-1,2,3,5-tetrahydro-4H-benzo[1,4]diazepine-4-sulfonamide;
4-acetyl-3-cycloheptyl-1,3,4,5-tetrahydro-2H-benzo[1,4]diazepin-2-one;
3-cyclohexyl-4-(2-hydroxyacetyl)-1,3,4,5-tetrahydro-2H-benzo[1,4]diazepin-2-one;
3-(sec-butyl)-N-(1-methyl-6-oxo-1,6-dihydropyridin-3-yl)-2-oxo-1,2,3,5-tetrahydro-4H-benzo[1,4]diazepine-4-carboxamide;
3-(sec-butyl)-N-(1-methyl-2-oxo-1,2-dihydropyridin-3-yl)-2-oxo-1,2,3,5-tetrahydro-4H-benzo[1,4]diazepine-4-carboxamide;
3-(sec-butyl)-4-(2-oxo-2,3-dihydro-1H-imidazole-4-carbonyl)-1,3,4,5-tetrahydro-2H-benzo[1,4]diazepin-2-one;
3-(sec-butyl)-N-(1-(2-hydroxyethyl)-1H-pyrazol-3-yl)-2-oxo-1,2,3,5-tetrahydro-4H-benzo[1,4]diazepine-4-carboxamide;
3-(sec-butyl)-4-(3-(dimethylamino)azetidine-1-carbonyl)-1,3,4,5-tetrahydro-2H-benzo[1,4]diazepin-2-one;
3-(sec-butyl)-4-(3-hydroxy-3-methylazetidine-1-carbonyl)-1,3,4,5-tetrahydro-2H-benzo[1,4]diazepin-2-one;
3-(sec-butyl)-2-oxo-N-(pyridin-3-yl)-1,2,3,5-tetrahydro-4H-benzo[1,4]diazepine-4-carboxamide;
3-(sec-butyl)-N-(1-methyl-1H-pyrazol-4-yl)-2-oxo-1,2,3,5-tetrahydro-4H-benzo[1,4]diazepine-4-carboxamide;
3-(sec-butyl)-2-oxo-N-(1H-pyrazol-4-yl)-1,2,3,5-tetrahydro-4H-benzo[1,4]diazepine-4-carboxamide;
3-(sec-butyl)-4-(3-(hydroxymethyl)azetidine-1-carbonyl)-1,3,4,5-tetrahydro-2H-benzo[1,4]diazepin-2-one;
1-(3-(sec-butyl)-2-oxo-2,3,4,5-tetrahydro-1H-benzo[1,4]diazepine-4-carbonyl)azetidine-2-carboxamide;
3-(sec-butyl)-4-(1H-imidazole-4-carbonyl)-1,3,4,5-tetrahydro-2H-benzo[1,4]diazepin-2-one;
3-(sec-butyl)-4-(1H-pyrazole-5-carbonyl)-1,3,4,5-tetrahydro-2H-benzo[1,4]diazepin-2-one;
3-(sec-butyl)-4-(tetrahydrofuran-2-carbonyl)-1,3,4,5-tetrahydro-2H-benzo[1,4]diazepin-2-one;
3-(sec-butyl)-4-(tetrahydrofuran-2-carbonyl)-1,3,4,5-tetrahydro-2H-benzo[1,4]diazepin-2-one;
3-(sec-butyl)-4-(pyrazine-2-carbonyl)-1,3,4,5-tetrahydro-2H-benzo[1,4]diazepin-2-one;
5-(3-(sec-butyl)-2-oxo-2,3,4,5-tetrahydro-1H-benzo[1,4]diazepine-4-carbonyl)pyrazine-2-carboxamide;
2-(3-(sec-butyl)-2-oxo-1,2,3,5-tetrahydro-4H-benzo[1,4]diazepin-4-yl)-2-oxoethane-1-sulfonamide;
3-(sec-butyl)-4-(2-(methylsulfonyl)acetyl)-1,3,4,5-tetrahydro-2H-benzo[1,4]diazepin-2-one;
3-(sec-butyl)-N'-(methylsulfonyl)-2-oxo-1,2,3,5-tetrahydro-4H-benzo[1,4]diazepine-4-carboximidamide;
N-(amino(3-(sec-butyl)-2-oxo-1,2,3,5-tetrahydro-4H-benzo[1,4]diazepin-4-yl)methylene)acetamide;
3-(sec-butyl)-4-(pyrimidin-2-yl)-1,3,4,5-tetrahydro-2H-benzo[1,4]diazepin-2-one;
3-(sec-butyl)-4-(1-methyl-6-oxo-1,6-dihydropyrimidin-4-yl)-1,3,4,5-tetrahydro-2H-benzo[1,4]diazepin-2-one;
3-(sec-butyl)-4-(4,6-dimethoxypyrimidin-2-yl)-1,3,4,5-tetrahydro-2H-benzo[1,4]diazepin-2-one;
4-(3-amino-1-methyl-1H-1,2,4-triazol-5-yl)-3-(sec-butyl)-1,3,4,5-tetrahydro-2H-benzo[1,4]diazepin-2-one;
4-(5-amino-1-methyl-1H-1,2,4-triazol-3-yl)-3-(sec-butyl)-1,3,4,5-tetrahydro-2H-benzo[1,4]diazepin-2-one;
3-(sec-butyl)-4-((2-methoxyethyl)sulfonyl)-1,3,4,5-tetrahydro-2H-benzo[1,4]diazepin-2-one;
3-(sec-butyl)-N-methyl-2-oxo-1,2,3,5-tetrahydro-4H-benzo[1,4]diazepine-4-sulfonamide;
3-cyclobutyl-2-oxo-1,2,3,5-tetrahydro-4H-benzo[1,4]diazepine-4-carboxamide;
3-cyclobutyl-4-(1-methyl-H-pyrazole-4-carbonyl)-1,3,4,5-tetrahydro-2H-benzo[1,4]diazepin-2-one;
3-cyclopentyl-2-oxo-1,2,3,5-tetrahydro-4H-benzo[1,4]diazepine-4-carboxamide;
3-cyclohexyl-4-(3-hydroxypropanoyl)-1,3,4,5-tetrahydro-2H-benzo[1,4]diazepin-2-one;
4-(3-cyclohexyl-2-oxo-2,3,4,5-tetrahydro-1H-benzo[1,4]diazepine-4-carbonyl)benzamide;
4-(4-(1H-pyrazol-1-yl)benzoyl)-3-cyclohexyl-1,3,4,5-tetrahydro-2H-benzo[1,4]diazepin-2-one;
3-cyclohexyl-4-(3-methoxypropanoyl)-1,3,4,5-tetrahydro-2H-benzo[1,4]diazepin-2-one;
3-cyclohexyl-4-(furan-2-carbonyl)-1,3,4,5-tetrahydro-2H-benzo[1,4]diazepin-2-one;
2-oxo-3-(pentan-3-yl)-1,2,3,5-tetrahydro-4H-benzo[1,4]diazepine-4-carboxamide;
3-(3-(sec-butyl)-2-oxo-1,2,3,5-tetrahydro-4H-benzo[1,4]diazepin-4-yl)-4-(methylamino)cyclobut-3-ene-1,2-dione;
3-(3-(sec-butyl)-2-oxo-1,2,3,5-tetrahydro-4H-benzo[1,4]diazepin-4-yl)-4-(dimethylamino)cyclobut-3-ene-1,2-dione;
3-(3-(sec-butyl)-2-oxo-1,2,3,5-tetrahydro-4H-benzo[1,4]diazepin-4-yl)-4-((2-hydroxyethyl)amino)cyclobut-3-ene-1,2-dione;
3-(sec-butyl)-N-(2-(dimethylamino)ethyl)-N-methyl-2-oxo-1,2,3,5-tetrahydro-4H-benzo[1,4]diazepine-4-carboxamide;
3-(sec-butyl)-4-(4-hydroxypiperidine-1-carbonyl)-1,3,4,5-tetrahydro-2H-benzo[1,4]diazepin-2-one;
3-(sec-butyl)-N-(2-hydroxyethyl)-N-isopropyl-2-oxo-1,2,3,5-tetrahydro-4H-benzo[1,4]diazepine-4-carboxamide;
3-(sec-butyl)-4-(3-(hydroxymethyl)pyrrolidine-1-carbonyl)-1,3,4,5-tetrahydro-2H-benzo[1,4]diazepin-2-one;
3-(sec-butyl)-4-(3,4-dihydroxypyrrolidine-1-carbonyl)-1,3,4,5-tetrahydro-2H-benzo[1,4]diazepin-2-one;
3-(sec-butyl)-N-(1-methylazetidin-3-yl)-2-oxo-1,2,3,5-tetrahydro-4H-benzo[1,4]diazepine-4-carboxamide;
3-(sec-butyl)-N-(1-(oxetan-3-yl)azetidin-3-yl)-2-oxo-1,2,3,5-tetrahydro-4H-benzo[1,4]diazepine-4-carboxamide;
3-(sec-butyl)-4-(3,4-dihydroxypyrrolidine-1-carbonyl)-1,3,4,5-tetrahydro-2H-benzo[1,4]diazepin-2-one;
3-(sec-butyl)-N-(1-(2-hydroxyethyl)pyrrolidin-3-yl)-2-oxo-1,2,3,5-tetrahydro-4H-benzo[1,4]diazepine-4-carboxamide;
3-(sec-butyl)-2-oxo-N-(piperidin-4-yl)-1,2,3,5-tetrahydro-4H-benzo[1,4]diazepine-4-carboxamide;
3-(sec-butyl)-N-(1-methylpyrrolidin-3-yl)-2-oxo-1,2,3,5-tetrahydro-4H-benzo[1,4]diazepine-4-carboxamide;
3-(sec-butyl)-N-(1-methylpyrrolidin-3-yl)-2-oxo-1,2,3,5-tetrahydro-4H-benzo[1,4]diazepine-4-carboxamide;
3-(sec-butyl)-2-oxo-1,2,3,5-tetrahydro-4H-benzo[1,4]diazepine-4-carbonitrile;

3-(sec-butyl)-N-hydroxy-2-oxo-1,2,3,5-tetrahydro-4H-benzo[1,4]diazepine-4-carboximidamide;

3-(3-(sec-butyl)-2-oxo-1,2,3,5-tetrahydro-4H-benzo[1,4]diazepin-4-yl)-2,2-dimethyl-3-oxopropanamide;

3-(sec-butyl)-4-(1-methyl-5-oxopyrrolidine-3-carbonyl)-1,3,4,5-tetrahydro-2H-benzo[1,4]diazepin-2-one;

3-(sec-butyl)-4-(3-hydroxy-3-methylbutanoyl)-1,3,4,5-tetrahydro-2H-benzo[1,4]diazepin-2-one;

3-(sec-butyl)-4-(1H-pyrrolo[3,2-b]pyridine-2-carbonyl)-1,3,4,5-tetrahydro-2H-benzo[1,4]diazepin-2-one;

3-(sec-butyl)-4-(1H-pyrrolo[2,3-c]pyridine-2-carbonyl)-1,3,4,5-tetrahydro-2H-benzo[1,4]diazepin-2-one;

3-(sec-butyl)-4-(1H-1,2,4-triazole-5-carbonyl)-1,3,4,5-tetrahydro-2H-benzo[1,4]diazepin-2-one;

3-(sec-butyl)-4-(1H-1,2,3-triazole-4-carbonyl)-1,3,4,5-tetrahydro-2H-benzo[1,4]diazepin-2-one;

3-(sec-butyl)-4-(1-methyl-6-oxo-1,6-dihydropyridine-2-carbonyl)-1,3,4,5-tetrahydro-2H-benzo[1,4]diazepin-2-one;

3-(sec-butyl)-4-(6-oxo-1,6-dihydropyridine-3-carbonyl)-1,3,4,5-tetrahydro-2H-benzo[1,4]diazepin-2-one;

3-(sec-butyl)-4-(1-methyl-6-oxo-1,6-dihydropyridine-3-carbonyl)-1,3,4,5-tetrahydro-2H-benzo[1,4]diazepin-2-one;

3-(sec-butyl)-4-(2-methyl-2H-1,2,3-triazole-4-carbonyl)-1,3,4,5-tetrahydro-2H-benzo[1,4]diazepin-2-one;

5-(3-(sec-butyl)-2-oxo-2,3,4,5-tetrahydro-1H-benzo[1,4]diazepine-4-carbonyl)picolinamide;

3-(sec-butyl)-4-(1-methyl-1H-1,2,3-triazole-5-carbonyl)-1,3,4,5-tetrahydro-2H-benzo[1,4]diazepin-2-one;

3-(sec-butyl)-4-(1H-imidazole-2-carbonyl)-1,3,4,5-tetrahydro-2H-benzo[1,4]diazepin-2-one;

3-(sec-butyl)-4-(5-oxopyrrolidine-2-carbonyl)-1,3,4,5-tetrahydro-2H-benzo[1,4]diazepin-2-one;

5-(3-(sec-butyl)-2-oxo-2,3,4,5-tetrahydro-1H-benzo[1,4]diazepine-4-carbonyl)nicotinamide;

ethyl 5-(3-(sec-butyl)-2-oxo-2,3,4,5-tetrahydro-1H-benzo[1,4]diazepine-4-carbonyl)-1H-pyrrole-2-carboxylate;

3-(sec-butyl)-4-(1-(2-hydroxypropyl)-1H-pyrazole-4-carbonyl)-1,3,4,5-tetrahydro-2H-benzo[1,4]diazepin-2-one;

3-(sec-butyl)-4-(2-oxoindoline-6-carbonyl)-1,3,4,5-tetrahydro-2H-benzo[1,4]diazepin-2-one;

5-(3-(sec-butyl)-2-oxo-2,3,4,5-tetrahydro-1H-benzo[1,4]diazepine-4-carbonyl)-1H-pyrrole-2-carboxylic acid;

3-(sec-butyl)-4-(2-oxoindoline-5-carbonyl)-1,3,4,5-tetrahydro-2H-benzo[1,4]diazepin-2-one;

2-(3-(sec-butyl)-2-oxo-2,3,4,5-tetrahydro-1H-benzo[1,4]diazepine-4-carbonyl)-1H-pyrrolo[3,2-b]pyridine-5-carboxamide;

5-(3-(sec-butyl)-2-oxo-2,3,4,5-tetrahydro-1H-benzo[1,4]diazepine-4-carbonyl)-1H-pyrrolo[3,2-b]pyridine-2-carboxamide;

3-(sec-butyl)-4-(1-(2-hydroxyethyl)-6-oxo-1,6-dihydropyridine-3-carbonyl)-1,3,4,5-tetrahydro-2H-benzo[1,4]diazepin-2-one;

3-(sec-butyl)-4-(3H-imidazo[4,5-b]pyridine-2-carbonyl)-1,3,4,5-tetrahydro-2H-benzo[1,4]diazepin-2-one;

3-(sec-butyl)-4-(1-methyl-2-oxo-1,2-dihydropyridine-4-carbonyl)-1,3,4,5-tetrahydro-2H-benzo[1,4]diazepin-2-one;

2-(4-(3-(sec-butyl)-2-oxo-2,3,4,5-tetrahydro-1H-benzo[1,4]diazepine-4-carbonyl)-1H-pyrazol-1-yl)acetamide;

5-(3-(sec-butyl)-2-oxo-2,3,4,5-tetrahydro-1H-benzo[1,4]diazepine-4-carbonyl)-N-(2-hydroxyethyl)-1H-pyrrole-2-carboxamide;

5-(3-(sec-butyl)-2-oxo-2,3,4,5-tetrahydro-1H-benzo[1,4]diazepine-4-carbonyl)-N-(2,3-dihydroxypropyl)-1H-pyrrole-2-carboxamide;

3-(sec-butyl)-4-(4-oxo-4,5-dihydro-1H-pyrrolo[2,3-d]pyridazine-2-carbonyl)-1,3,4,5-tetrahydro-2H-benzo[1,4]diazepin-2-one;

4-(prolyl)-3-(sec-butyl)-1,3,4,5-tetrahydro-2H-benzo[1,4]diazepin-2-one;

4-(D-prolyl)-3-(sec-butyl)-1,3,4,5-tetrahydro-2H-benzo[1,4]diazepin-2-one;

3-(sec-butyl)-4-(3-(2-hydroxyethyl)-1-methyl-1H-pyrazole-4-carbonyl)-1,3,4,5-tetrahydro-2H-benzo[1,4]diazepin-2-one;

3-(sec-butyl)-4-(5-(3-hydroxyazetidine-1-carbonyl)-1H-pyrrole-2-carbonyl)-1,3,4,5-tetrahydro-2H-benzo[1,4]diazepin-2-one;

3-(sec-butyl)-4-(5H-pyrrolo[2,3-b]pyrazine-6-carbonyl)-1,3,4,5-tetrahydro-2H-benzo[1,4]diazepin-2-one;

4-(5-amino-1-(2-hydroxyethyl)-1H-pyrazole-4-carbonyl)-3-(sec-butyl)-1,3,4,5-tetrahydro-2H-benzo[1,4]diazepin-2-one;

3-(sec-butyl)-4-(2-hydroxy-3-methylbutanoyl)-1,3,4,5-tetrahydro-2H-benzo[1,4]diazepin-2-one;

3-(sec-butyl)-4-(3-(3-hydroxypyrrolidin-1-yl)propanoyl)-1,3,4,5-tetrahydro-2H-benzo[1,4]diazepin-2-one;

3-(sec-butyl)-4-(3-(3-hydroxypyrrolidin-1-yl)propanoyl)-1,3,4,5-tetrahydro-2H-benzo[1,4]diazepin-2-one;

1-(3-(3-(sec-butyl)-2-oxo-1,2,3,5-tetrahydro-4H-benzo[1,4]diazepin-4-yl)-3-oxopropyl)pyrrolidine-2-carboxamide;

1-(3-(3-(sec-butyl)-2-oxo-1,2,3,5-tetrahydro-4H-benzo[1,4]diazepin-4-yl)-3-oxopropyl)pyrrolidine-2-carboxamide;

3-(2-(3-(sec-butyl)-2-oxo-2,3,4,5-tetrahydro-1H-benzo[1,4]diazepine-4-carbonyl)pyrrolidin-1-yl)propanamide;

3-(sec-butyl)-4-(1-methyl-1H-1,2,3-triazole-4-carbonyl)-1,3,4,5-tetrahydro-2H-benzo[1,4]diazepin-2-one;

3-(sec-butyl)-4-(pyridazine-4-carbonyl)-1,3,4,5-tetrahydro-2H-benzo[1,4]diazepin-2-one;

3-(sec-butyl)-4-(pyrimidine-5-carbonyl)-1,3,4,5-tetrahydro-2H-benzo[1,4]diazepin-2-one;

3-(sec-butyl)-4-(pyridazine-3-carbonyl)-1,3,4,5-tetrahydro-2H-benzo[1,4]diazepin-2-one;

3-(sec-butyl)-4-(1-methyl-5-oxopyrrolidine-3-carbonyl)-1,3,4,5-tetrahydro-2H-benzo[1,4]diazepin-2-one;

3-(sec-butyl)-4-(1-methyl-5-oxopyrrolidine-3-carbonyl)-1,3,4,5-tetrahydro-2H-benzo[1,4]diazepin-2-one;

N-(2-(3-(sec-butyl)-2-oxo-1,2,3,5-tetrahydro-4H-benzo[1,4]diazepin-4-yl)-2-oxoethyl)acetamide;

N-(1-(3-(sec-butyl)-2-oxo-1,2,3,5-tetrahydro-4H-benzo[1,4]diazepin-4-yl)-1-oxopropan-2-yl)acetamide;

4-(acetyl-D-prolyl)-3-(sec-butyl)-1,3,4,5-tetrahydro-2H-benzo[1,4]diazepin-2-one;

N-(1-(3-(sec-butyl)-2-oxo-1,2,3,5-tetrahydro-4H-benzo[1,4]diazepin-4-yl)-1-oxopropan-2-yl)acetamide;

3-(sec-butyl)-4-(3-hydroxybutanoyl)-1,3,4,5-tetrahydro-2H-benzo[1,4]diazepin-2-one;

3-(1-(benzyloxy)ethyl)-4-(1-methyl-1H-pyrazole-4-carbonyl)-1,3,4,5-tetrahydro-2H-benzo[1,4]diazepin-2-one;

2-(2-(3-(sec-butyl)-2-oxo-1,2,3,5-tetrahydro-4H-benzo[1,4]diazepin-4-yl)-2-oxoethoxy)benzamide;

N-(6-acetamidopyridin-3-yl)-3-(sec-butyl)-2-oxo-1,2,3,5-tetrahydro-4H-benzo[1,4]diazepine-4-carboxamide;

3-(sec-butyl)-N-(2-hydroxyethyl)-2-oxo-1,2,3,5-tetrahydro-4H-benzo[1,4]diazepine-4-carboxamide;

N-(2-amino-2-oxoethyl)-3-(sec-butyl)-2-oxo-1,2,3,5-tetrahydro-4H-benzo[1,4]diazepine-4-carboxamide;

N-(3-amino-3-oxopropyl)-3-(sec-butyl)-2-oxo-1,2,3,5-tetrahydro-4H-benzo[1,4]diazepine-4-carboxamide;

3-(sec-butyl)-N-(2-(methylamino)-2-oxoethyl)-2-oxo-1,2,3,5-tetrahydro-4H-benzo[1,4]diazepine-4-carboxamide;

3-(sec-butyl)-N-(2,3-dihydroxypropyl)-2-oxo-1,2,3,5-tetrahydro-4H-benzo[1,4]diazepine-4-carboxamide;

3-(sec-butyl)-N-(2,3-dihydroxypropyl)-2-oxo-1,2,3,5-tetrahydro-4H-benzo[1,4]diazepine-4-carboxamide;

3-(sec-butyl)-2-oxo-N-(2-oxopyrrolidin-3-yl)-1,2,3,5-tetrahydro-4H-benzo[1,4]diazepine-4-carboxamide;

3-(sec-butyl)-2-oxo-N-(2-oxopyrrolidin-3-yl)-1,2,3,5-tetrahydro-4H-benzo[1,4]diazepine-4-carboxamide;

N-(2-acetamidoethyl)-3-(sec-butyl)-2-oxo-1,2,3,5-tetrahydro-4H-benzo[1,4]diazepine-4-carboxamide;

3-(sec-butyl)-2-oxo-N-(2-ureidoethyl)-1,2,3,5-tetrahydro-4H-benzo[1,4]diazepine-4-carboxamide;

3-(sec-butyl)-N-(2-(methylsulfinyl)ethyl)-2-oxo-1,2,3,5-tetrahydro-4H-benzo[1,4]diazepine-4-carboxamide;

3-(sec-butyl)-N-((1-methyl-1H-imidazol-5-yl)methyl)-2-oxo-1,2,3,5-tetrahydro-4H-benzo[1,4]diazepine-4-carboxamide;

3-(sec-butyl)-2-oxo-N-((5-oxopyrrolidin-2-yl)methyl)-1,2,3,5-tetrahydro-4H-benzo[1,4]diazepine-4-carboxamide;

3-(sec-butyl)-2-oxo-N-(2-oxopiperidin-3-yl)-1,2,3,5-tetrahydro-4H-benzo[1,4]diazepine-4-carboxamide;

3-(sec-butyl)-2-oxo-N-(2-oxopiperidin-3-yl)-1,2,3,5-tetrahydro-4H-benzo[1,4]diazepine-4-carboxamide;

3-(sec-butyl)-2-oxo-N-(6-oxopiperidin-3-yl)-1,2,3,5-tetrahydro-4H-benzo[1,4]diazepine-4-carboxamide;

3-(sec-butyl)-2-oxo-N-(6-oxopiperidin-3-yl)-1,2,3,5-tetrahydro-4H-benzo[1,4]diazepine-4-carboxamide;

3-(sec-butyl)-N-(2-(methylsulfonyl)ethyl)-2-oxo-1,2,3,5-tetrahydro-4H-benzo[1,4]diazepine-4-carboxamide;

3-(sec-butyl)-2-oxo-N-(2-sulfamoylethyl)-1,2,3,5-tetrahydro-4H-benzo[1,4]diazepine-4-carboxamide;

3-(sec-butyl)-N-(2-(3-hydroxypyrrolidin-1-yl)ethyl)-2-oxo-1,2,3,5-tetrahydro-4H-benzo[1,4]diazepine-4-carboxamide;

3-(sec-butyl)-N-(2-(3-hydroxypyrrolidin-1-yl)ethyl)-2-oxo-1,2,3,5-tetrahydro-4H-benzo[1,4]diazepine-4-carboxamide;

3-(sec-butyl)-N-(1,1-dioxidotetrahydrothiophen-3-yl)-2-oxo-1,2,3,5-tetrahydro-4H-benzo[1,4]diazepine-4-carboxamide;

3-(sec-butyl)-N-(2-hydroxyethyl)-N-methyl-2-oxo-1,2,3,5-tetrahydro-4H-benzo[1,4]diazepine-4-carboxamide;

3-(sec-butyl)-4-(piperazine-1-carbonyl)-1,3,4,5-tetrahydro-2H-benzo[1,4]diazepin-2-one;

3-(sec-butyl)-4-(3-hydroxypyrrolidine-1-carbonyl)-1,3,4,5-tetrahydro-2H-benzo[1,4]diazepin-2-one;

N-(2-amino-2-oxoethyl)-3-(sec-butyl)-N-methyl-2-oxo-1,2,3,5-tetrahydro-4H-benzo[1,4]diazepine-4-carboxamide;

3-(sec-butyl)-4-(3-oxopiperazine-1-carbonyl)-1,3,4,5-tetrahydro-2H-benzo[1,4]diazepin-2-one;

3-(sec-butyl)-4-(4-methylpiperazine-1-carbonyl)-1,3,4,5-tetrahydro-2H-benzo[1,4]diazepin-2-one;

3-(sec-butyl)-4-(3-methylpiperazine-1-carbonyl)-1,3,4,5-tetrahydro-2H-benzo[1,4]diazepin-2-one;

3-(sec-butyl)-N-(1-(methylamino)-1-oxopropan-2-yl)-2-oxo-1,2,3,5-tetrahydro-4H-benzo[1,4]diazepine-4-carboxamide;

3-(sec-butyl)-N-methyl-2-oxo-N-(pyrazin-2-yl)-1,2,3,5-tetrahydro-4H-benzo[1,4]diazepine-4-carboxamide;

3-(sec-butyl)-4-(3-(dimethylamino)pyrrolidine-1-carbonyl)-1,3,4,5-tetrahydro-2H-benzo[1,4]diazepin-2-one;

3-(sec-butyl)-N-methyl-N-(1-methylpyrrolidin-3-yl)-2-oxo-1,2,3,5-tetrahydro-4H-benzo[1,4]diazepine-4-carboxamide;

(3-(sec-butyl)-2-oxo-2,3,4,5-tetrahydro-1H-benzo[1,4]diazepine-4-carbonyl)-proline;

3-(sec-butyl)-N-methyl-N-((2-methyloxazol-4-yl)methyl)-2-oxo-1,2,3,5-tetrahydro-4H-benzo[1,4]diazepine-4-carboxamide;

1-(3-(sec-butyl)-2-oxo-2,3,4,5-tetrahydro-1H-benzo[1,4]diazepine-4-carbonyl)piperidine-3-carboxamide;

3-(sec-butyl)-4-(4-(dimethylamino)piperidine-1-carbonyl)-1,3,4,5-tetrahydro-2H-benzo[1,4]diazepin-2-one;

3-(sec-butyl)-N-methyl-N-(2-(methylsulfonyl)ethyl)-2-oxo-1,2,3,5-tetrahydro-4H-benzo[1,4]diazepine-4-carboxamide;

3-(sec-butyl)-4-(3-methyl-5,6,7,8-tetrahydro-[1,2,4]triazolo[4,3-a]pyrimidine-8-carbonyl)-1,3,4,5-tetrahydro-2H-benzo[1,4]diazepin-2-one;

N-(1-(3-(sec-butyl)-2-oxo-2,3,4,5-tetrahydro-1H-benzo[1,4]diazepine-4-carbonyl)pyrrolidin-3-yl)-N-methylacetamide;

methyl 4-(3-(sec-butyl)-2-oxo-2,3,4,5-tetrahydro-1H-benzo[1,4]diazepine-4-carbonyl)piperazine-1-carboxylate;

3-(sec-butyl)-4-(2-(3-methyl-1,2,4-oxadiazol-5-yl)pyrrolidine-1-carbonyl)-1,3,4,5-tetrahydro-2H-benzo[1,4]diazepin-2-one;

3-(sec-butyl)-4-(3-oxo-2,8-diazaspiro[4.5]decane-8-carbonyl)-1,3,4,5-tetrahydro-2H-benzo[1,4]diazepin-2-one;

3-(sec-butyl)-4-(4-(methylsulfonyl)piperazine-1-carbonyl)-1,3,4,5-tetrahydro-2H-benzo[1,4]diazepin-2-one;

N-(1-(3-(sec-butyl)-2-oxo-2,3,4,5-tetrahydro-1H-benzo[1,4]diazepine-4-carbonyl)piperidin-3-yl)methanesulfonamide;

N-(1-(3-(sec-butyl)-2-oxo-2,3,4,5-tetrahydro-1H-benzo[1,4]diazepine-4-carbonyl)piperidin-3-yl)methanesulfonamide;

1-(3-(sec-butyl)-2-oxo-2,3,4,5-tetrahydro-1H-benzo[1,4]diazepine-4-carbonyl)azetidine-3-carboxylic acid;

1-(3-(sec-butyl)-2-oxo-2,3,4,5-tetrahydro-1H-benzo[1,4]diazepine-4-carbonyl)azetidine-3-carboxamide;

3-(sec-butyl)-2-oxo-N-(1,3,4-thiadiazol-2-yl)-1,2,3,5-tetrahydro-4H-benzo[1,4]diazepine-4-carboxamide;

N-(2-amino-2-oxo-1-phenylethyl)-3-(sec-butyl)-2-oxo-1,2,3,5-tetrahydro-4H-benzo[1,4]diazepine-4-carboxamide;

3-(sec-butyl)-N-(1-ethyl-6-oxo-1,6-dihydropyridin-3-yl)-2-oxo-1,2,3,5-tetrahydro-4H-benzo[1,4]diazepine-4-carboxamide;

3-(sec-butyl)-N-(1-(cyclopropylmethyl)-6-oxo-1,6-dihydropyridin-3-yl)-2-oxo-1,2,3,5-tetrahydro-4H-benzo[1,4]diazepine-4-carboxamide;

3-(sec-butyl)-N-(1-(2-methoxyethyl)-2-oxo-1,2-dihydropyridin-3-yl)-2-oxo-1,2,3,5-tetrahydro-4H-benzo[1,4]diazepine-4-carboxamide;

N-(1-amino-1-oxopropan-2-yl)-3-(sec-butyl)-2-oxo-1,2,3,5-tetrahydro-4H-benzo[1,4]diazepine-4-carboxamide;

3-(sec-butyl)-2-oxo-N-(2-oxo-5-(trifluoromethyl)-1,2-dihydropyridin-3-yl)-1,2,3,5-tetrahydro-4H-benzo[1,4]diazepine-4-carboxamide;

3-(sec-butyl)-2-oxo-N-(6-oxo-1,6-dihydro-[3,4'-bipyridin]-5-yl)-1,2,3,5-tetrahydro-4H-benzo[1,4]diazepine-4-carboxamide;

(3-(sec-butyl)-2-oxo-2,3,4,5-tetrahydro-1H-benzo[1,4]diazepine-4-carbonyl)glycyl-proline;

3-(sec-butyl)-2-oxo-N-(2-(2-oxoimidazolidin-1-yl)ethyl)-1,2,3,5-tetrahydro-4H-benzo[1,4]diazepine-4-carboxamide;

3-(sec-butyl)-N-((3-(hydroxymethyl)oxetan-3-yl)methyl)-2-oxo-1,2,3,5-tetrahydro-4H-benzo[1,4]diazepine-4-carboxamide;

3-(sec-butyl)-N-(4-(4-carbamoylpiperidin-1-yl)butyl)-2-oxo-1,2,3,5-tetrahydro-4H-benzo[1,4]diazepine-4-carboxamide;

N-(3-amino-2,2-dimethyl-3-oxopropyl)-3-(sec-butyl)-2-oxo-1,2,3,5-tetrahydro-4H-benzo[1,4]diazepine-4-carboxamide;

3-(sec-butyl)-4-(3-(pyrrolidin-1-yl)azetidine-1-carbonyl)-1,3,4,5-tetrahydro-2H-benzo[1,4]diazepin-2-one;

3-(sec-butyl)-4-(3-(4-methylpiperazin-1-yl)azetidine-1-carbonyl)-1,3,4,5-tetrahydro-2H-benzo[1,4]diazepin-2-one;

3-(sec-butyl)-4-(3-morpholinoazetidine-1-carbonyl)-1,3,4,5-tetrahydro-2H-benzo[1,4]diazepin-2-one;

3-(sec-butyl)-4-(3-(4-(2-hydroxyethyl)piperazin-1-yl)azetidine-1-carbonyl)-1,3,4,5-tetrahydro-2H-benzo[1,4]diazepin-2-one;

3-(sec-butyl)-4-(3-(4-(pyridin-2-yl)piperazin-1-yl)azetidine-1-carbonyl)-1,3,4,5-tetrahydro-2H-benzo[1,4]diazepin-2-one;

2-((1-(3-(sec-butyl)-2-oxo-2,3,4,5-tetrahydro-1H-benzo[1,4]diazepine-4-carbonyl)azetidin-3-yl)oxy)-N,N-dimethylacetamide;

2-((1-(3-(sec-butyl)-2-oxo-2,3,4,5-tetrahydro-1H-benzo[1,4]diazepine-4-carbonyl)azetidin-3-yl)oxy)-N-methylacetamide;

4-(3-amino-3-methylazetidine-1-carbonyl)-3-(sec-butyl)-1,3,4,5-tetrahydro-2H-benzo[1,4]diazepin-2-one;

4-(3-oxa-6-azabicyclo[3.1.1]heptane-6-carbonyl)-3-(sec-butyl)-1,3,4,5-tetrahydro-2H-benzo[1,4]diazepin-2-one;

3-(sec-butyl)-N-(1-cyanocyclopropyl)-2-oxo-1,2,3,5-tetrahydro-4H-benzo[1,4]diazepine-4-carboxamide;

3-(sec-butyl)-N-(1-(2,2-difluoroethyl)-6-oxo-1,6-dihydropyridazin-3-yl)-2-oxo-1,2,3,5-tetrahydro-4H-benzo[1,4]diazepine-4-carboxamide;

3-(sec-butyl)-2-oxo-N-(6-oxo-1-(2,2,2-trifluoroethyl)-1,6-dihydropyridazin-3-yl)-1,2,3,5-tetrahydro-4H-benzo[1,4]diazepine-4-carboxamide;

N-benzyl-3-(sec-butyl)-2-oxo-1,2,3,5-tetrahydro-4H-benzo[1,4]diazepine-4-carboxamide;

3-(sec-butyl)-N-(3-fluorophenyl)-2-oxo-1,2,3,5-tetrahydro-4H-benzo[1,4]diazepine-4-carboxamide;

3-(sec-butyl)-2-oxo-N-(1H-pyrazolo[3,4-b]pyridin-5-yl)-1,2,3,5-tetrahydro-4H-benzo[1,4]diazepine-4-carboxamide;

methyl 1-(3-(sec-butyl)-2-oxo-2,3,4,5-tetrahydro-1H-benzo[1,4]diazepine-4-carbonyl)pyrrolidine-3-carboxylate;

3-(sec-butyl)-4-(3-hydroxypyrrolidine-1-carbonyl)-1,3,4,5-tetrahydro-2H-benzo[1,4]diazepin-2-one;

3-(sec-butyl)-4-(4-phenethylpiperazine-1-carbonyl)-1,3,4,5-tetrahydro-2H-benzo[1,4]diazepin-2-one;

3-(sec-butyl)-4-(3-hydroxypyrrolidine-1-carbonyl)-1,3,4,5-tetrahydro-2H-benzo[1,4]diazepin-2-one;

3-(sec-butyl)-N-(5-methyl-1,3,4-thiadiazol-2-yl)-2-oxo-1,2,3,5-tetrahydro-4H-benzo[1,4]diazepine-4-carboxamide;

3-(sec-butyl)-N-(2-(hydroxymethyl)pyridin-3-yl)-2-oxo-1,2,3,5-tetrahydro-4H-benzo[1,4]diazepine-4-carboxamide;

3-(sec-butyl)-4-(3-(hydroxymethyl)pyrrolidine-1-carbonyl)-1,3,4,5-tetrahydro-2H-benzo[1,4]diazepin-2-one;

3-(sec-butyl)-N-(2-carbamoylbenzyl)-2-oxo-1,2,3,5-tetrahydro-4H-benzo[1,4]diazepine-4-carboxamide;

N-(2-amino-2-oxo-1-phenylethyl)-3-(sec-butyl)-2-oxo-1,2,3,5-tetrahydro-4H-benzo[1,4]diazepine-4-carboxamide;

4-(3-(sec-butyl)-2-oxo-2,3,4,5-tetrahydro-1H-benzo[1,4]diazepine-4-carbonyl)benzamide;

1-(3-(sec-butyl)-2-oxo-2,3,4,5-tetrahydro-1H-benzo[1,4]diazepine-4-carbonyl)pyrrolidine-3-carboxylic acid;

3-(sec-butyl)-N-(1-methylpiperidin-4-yl)-2-oxo-1,2,3,5-tetrahydro-4H-benzo[1,4]diazepine-4-carboxamide;

3-(sec-butyl)-N-(1-methyl-2-oxo-1,2-dihydropyridin-4-yl)-2-oxo-1,2,3,5-tetrahydro-4H-benzo[1,4]diazepine-4-carboxamide;

3-(sec-butyl)-N-(5-methoxypyridin-3-yl)-2-oxo-1,2,3,5-tetrahydro-4H-benzo[1,4]diazepine-4-carboxamide;

3-(sec-butyl)-2-oxo-N-(tetrahydro-2H-pyran-4-yl)-1,2,3,5-tetrahydro-4H-benzo[1,4]diazepine-4-carboxamide;

1-(3-(sec-butyl)-2-oxo-2,3,4,5-tetrahydro-1H-benzo[1,4]diazepine-4-carbonyl)-N-methylpyrrolidine-3-carboxamide;

1-(3-(sec-butyl)-2-oxo-2,3,4,5-tetrahydro-1H-benzo[1,4]diazepine-4-carbonyl)-N,N-dimethylpyrrolidine-3-carboxamide;

1-(3-(sec-butyl)-2-oxo-2,3,4,5-tetrahydro-1H-benzo[1,4]diazepine-4-carbonyl)pyrrolidine-3-carboxamide;

3-(sec-butyl)-N-isopropyl-N-methyl-2-oxo-1,2,3,5-tetrahydro-4H-benzo[1,4]diazepine-4-carboxamide;

3-(sec-butyl)-N-(5-carbamoylpyridin-3-yl)-2-oxo-1,2,3,5-tetrahydro-4H-benzo[1,4]diazepine-4-carboxamide;

3-(sec-butyl)-N-(1-(2-methoxyethyl)-1H-pyrazol-3-yl)-2-oxo-1,2,3,5-tetrahydro-4H-benzo[1,4]diazepine-4-carboxamide;

3-(sec-butyl)-4-(3,3-difluoroazetidine-1-carbonyl)-1,3,4,5-tetrahydro-2H-benzo[1,4]diazepin-2-one;

3-(sec-butyl)-N-(1-(2-hydroxyethyl)piperidin-4-yl)-2-oxo-1,2,3,5-tetrahydro-4H-benzo[1,4]diazepine-4-carboxamide;

3-(sec-butyl)-4-(3-(hydroxymethyl)piperidine-1-carbonyl)-1,3,4,5-tetrahydro-2H-benzo[1,4]diazepin-2-one;

3-(sec-butyl)-4-(3-(hydroxymethyl)piperidine-1-carbonyl)-1,3,4,5-tetrahydro-2H-benzo[1,4]diazepin-2-one;

1-(3-(sec-butyl)-2-oxo-2,3,4,5-tetrahydro-1H-benzo[1,4]diazepine-4-carbonyl)piperidine-3-carboxamide;

1-(3-(sec-butyl)-2-oxo-2,3,4,5-tetrahydro-1H-benzo[1,4]diazepine-4-carbonyl)piperidine-3-carboxamide;

3-(sec-butyl)-4-(3-fluoroazetidine-1-carbonyl)-1,3,4,5-tetrahydro-2H-benzo[1,4]diazepin-2-one;

3-(sec-butyl)-2-oxo-N-(pyrrolidin-3-yl)-1,2,3,5-tetrahydro-4H-benzo[1,4]diazepine-4-carboxamide;

3-(sec-butyl)-2-oxo-N-(pyrrolidin-3-yl)-1,2,3,5-tetrahydro-4H-benzo[1,4]diazepine-4-carboxamide;

3-cycloheptyl-4-(2-methoxyethyl)-1,3,4,5-tetrahydro-2H-benzo[1,4]diazepin-2-one;

3-(sec-butyl)-4-(2-methoxyethyl)-1,3,4,5-tetrahydro-2H-benzo[1,4]diazepin-2-one;

2-(3-(sec-butyl)-2-oxo-1,2,3,5-tetrahydro-4H-benzo[1,4]diazepin-4-yl)-N-methylacetamide;

3-(3-(sec-butyl)-2-oxo-1,2,3,5-tetrahydro-4H-benzo[1,4]diazepin-4-yl)propanamide;

3-(3-(sec-butyl)-2-oxo-1,2,3,5-tetrahydro-4H-benzo[1,4]diazepin-4-yl)-N,N-dimethylpropanamide;

3-(3-(sec-butyl)-2-oxo-1,2,3,5-tetrahydro-4H-benzo[1,4]diazepin-4-yl)-N-methylpropanamide;

3-(sec-butyl)-4-(cyclopentylmethyl)-1,3,4,5-tetrahydro-2H-benzo[1,4]diazepin-2-one;

2-(3-(sec-butyl)-2-oxo-1,2,3,5-tetrahydro-4H-benzo[1,4]diazepin-4-yl)acetonitrile;

3-(sec-butyl)-5-(hydroxymethyl)-2-oxo-1,2,3,5-tetrahydro-4H-benzo[1,4]diazepine-4-carboxamide;

5-(sec-butyl)-7,11b-dihydro-1H,3H-benzo[f]oxazolo[3,4-d][1,4]diazepine-3,6(5H)-dione;

3-(sec-butyl)-5-methyl-4-(1-methyl-1H-pyrazole-4-carbonyl)-1,3,4,5-tetrahydro-2H-benzo[1,4]diazepin-2-one;

3-(sec-butyl)-5-methyl-2-oxo-1,2,3,5-tetrahydro-4H-benzo[1,4]diazepine-4-carboxamide;

methyl 3-(sec-butyl)-4-(1-methyl-1H-pyrazole-4-carbonyl)-2-oxo-2,3,4,5-tetrahydro-1H-benzo[1,4]diazepine-5-carboxylate;

3-isopropyl-4-(1-methyl-1H-pyrazole-3-carbonyl)-1,3,4,5-tetrahydro-2H-benzo[1,4]diazepin-2-one;

3-isopropyl-4-(thiazol-2-yl)-1,3,4,5-tetrahydro-2H-benzo[1,4]diazepin-2-one;

3-isopropyl-4-(3-methyl-1,2,4-thiadiazol-5-yl)-1,3,4,5-tetrahydro-2H-benzo[1,4]diazepin-2-one;

3-isopropyl-N,N-dimethyl-2-oxo-1,2,3,5-tetrahydro-4H-benzo[1,4]diazepine-4-carboxamide;

4-acetyl-3-isopropyl-1,3,4,5-tetrahydro-2H-benzo[1,4]diazepin-2-one;

3-isopropyl-4-(2-oxo-1,2-dihydropyridine-4-carbonyl)-1,3,4,5-tetrahydro-2H-benzo[1,4]diazepin-2-one;

4-(1-(2-hydroxyethyl)-1H-pyrazole-4-carbonyl)-3-isopropyl-1,3,4,5-tetrahydro-2H-benzo[1,4]diazepin-2-one;

5-(3-isopropyl-2-oxo-2,3,4,5-tetrahydro-1H-benzo[1,4]diazepine-4-carbonyl)-1H-pyrrole-2-carboxamide;

3-isopropyl-4-(1-(2-methoxyethyl)-1H-pyrazole-4-carbonyl)-1,3,4,5-tetrahydro-2H-benzo[1,4]diazepin-2-one;

3-isopropyl-4-(1H-pyrazole-4-carbonyl)-1,3,4,5-tetrahydro-2H-benzo[1,4]diazepin-2-one;

4-(3-hydroxyazetidine-1-carbonyl)-3-isopropyl-1,3,4,5-tetrahydro-2H-benzo[1,4]diazepin-2-one;

3-isopropyl-N,N-dimethyl-2-oxo-1,2,3,5-tetrahydro-4H-benzo[1,4]diazepine-4-sulfonamide;

3-amino-4-(3-isopropyl-2-oxo-1,2,3,5-tetrahydro-4H-benzo[1,4]diazepin-4-yl)cyclobut-3-ene-1,2-dione;

3-isopropyl-N-methyl-2-oxo-1,2,3,5-tetrahydro-4H-benzo[1,4]diazepine-4-carboxamide;

3-(sec-butyl)-N'-cyano-6-fluoro-2-oxo-1,2,3,5-tetrahydro-4H-benzo[1,4]diazepine-4-carboximidamide;

3-(sec-butyl)-6-fluoro-4-(3-hydroxyazetidine-1-carbonyl)-1,3,4,5-tetrahydro-2H-benzo[1,4]diazepin-2-one;

3-(sec-butyl)-6-fluoro-N-methyl-2-oxo-1,2,3,5-tetrahydro-4H-benzo[1,4]diazepine-4-carboxamide;

3-(sec-butyl)-6-fluoro-4-(3-hydroxypropanoyl)-1,3,4,5-tetrahydro-2H-benzo[1,4]diazepin-2-one;

3-(sec-butyl)-6-fluoro-4-(3-hydroxypyrrolidine-1-carbonyl)-1,3,4,5-tetrahydro-2H-benzo[1,4]diazepin-2-one;

3-(sec-butyl)-7-fluoro-4-(2-hydroxyacetyl)-1,3,4,5-tetrahydro-2H-benzo[1,4]diazepin-2-one;

3-(sec-butyl)-7-fluoro-4-(1H-pyrazole-4-carbonyl)-1,3,4,5-tetrahydro-2H-benzo[1,4]diazepin-2-one;

3-(sec-butyl)-7-fluoro-4-(1H-1,2,4-triazole-5-carbonyl)-1,3,4,5-tetrahydro-2H-benzo[1,4]diazepin-2-one;

3-(sec-butyl)-7-fluoro-4-(6-oxo-1,6-dihydropyridine-2-carbonyl)-1,3,4,5-tetrahydro-2H-benzo[1,4]diazepin-2-one;

3-(sec-butyl)-7-fluoro-2-oxo-1,2,3,5-tetrahydro-4H-benzo[1,4]diazepine-4-sulfonamide;

3-(sec-butyl)-7-fluoro-4-(3-hydroxy-3-methylazetidine-1-carbonyl)-1,3,4,5-tetrahydro-2H-benzo[1,4]diazepin-2-one;

3-(sec-butyl)-7-fluoro-4-(3-hydroxypyrrolidine-1-carbonyl)-1,3,4,5-tetrahydro-2H-benzo[1,4]diazepin-2-one;

3-(sec-butyl)-7-fluoro-N-methyl-2-oxo-1,2,3,5-tetrahydro-4H-benzo[1,4]diazepine-4-carboxamide;

3-(sec-butyl)-7-fluoro-N-(1-(2-hydroxyethyl)pyrrolidin-3-yl)-2-oxo-1,2,3,5-tetrahydro-4H-benzo[1,4]diazepine-4-carboxamide;

3-(sec-butyl)-7-fluoro-N-(1-methylpyrrolidin-3-yl)-2-oxo-1,2,3,5-tetrahydro-4H-benzo[1,4]diazepine-4-carboxamide;

3-(sec-butyl)-7-fluoro-N-(1-(2-hydroxyethyl)piperidin-4-yl)-2-oxo-1,2,3,5-tetrahydro-4H-benzo[1,4]diazepine-4-carboxamide;

3-(sec-butyl)-7-fluoro-N-(4-hydroxycyclohexyl)-2-oxo-1,2,3,5-tetrahydro-4H-benzo[1,4]diazepine-4-carboxamide;

3-(sec-butyl)-7-fluoro-N-(3-hydroxycyclopentyl)-2-oxo-1,2,3,5-tetrahydro-4H-benzo[1,4]diazepine-4-carboxamide;

3-(sec-butyl)-7-fluoro-N-(3-hydroxycyclobutyl)-2-oxo-1,2,3,5-tetrahydro-4H-benzo[1,4]diazepine-4-carboxamide;

3-(sec-butyl)-7-fluoro-N-(3-hydroxycyclobutyl)-2-oxo-1,2,3,5-tetrahydro-4H-benzo[1,4]diazepine-4-carboxamide;

3-(sec-butyl)-8-fluoro-N-(1-(2-hydroxyethyl)piperidin-4-yl)-2-oxo-1,2,3,5-tetrahydro-4H-benzo[1,4]diazepine-4-carboxamide;

8-fluoro-3-isopropyl-2-oxo-1,2,3,5-tetrahydro-4H-benzo[1,4]diazepine-4-carboxamide;

3-(sec-butyl)-8-fluoro-N-(1-methylpyrrolidin-3-yl)-2-oxo-1,2,3,5-tetrahydro-4H-benzo[1,4]diazepine-4-carboxamide;

3-(sec-butyl)-8-fluoro-4-(3-hydroxypyrrolidine-1-carbonyl)-1,3,4,5-tetrahydro-2H-benzo[1,4]diazepin-2-one;

3-(sec-butyl)-8-fluoro-N-(1-(oxetan-3-yl)piperidin-4-yl)-2-oxo-1,2,3,5-tetrahydro-4H-benzo[1,4]diazepine-4-carboxamide;

4-acetyl-3-(sec-butyl)-6-fluoro-1,3,4,5-tetrahydro-2H-pyrido[3,4-e][1,4]diazepin-2-one;

3-(sec-butyl)-6-fluoro-4-(2-hydroxyacetyl)-1,3,4,5-tetrahydro-2H-pyrido[3,4-e][1,4]diazepin-2-one;

3-(sec-butyl)-6-fluoro-4-(2-methoxyacetyl)-1,3,4,5-tetrahydro-2H-pyrido[3,4-e][1,4]diazepin-2-one;

methyl 3-(sec-butyl)-6-fluoro-2-oxo-1,2,3,5-tetrahydro-4H-pyrido[3,4-e][1,4]diazepine-4-carboxylate;

3-(sec-butyl)-N'-cyano-6-fluoro-2-oxo-1,2,3,5-tetrahydro-4H-pyrido[3,4-e][1,4]diazepine-4-carboximidamide;

3-amino-4-(3-(sec-butyl)-6-fluoro-2-oxo-1,2,3,5-tetrahydro-4H-pyrido[3,4-e][1,4]diazepin-4-yl)cyclobut-3-ene-1,2-dione;

3-(sec-butyl)-6-fluoro-N-methyl-2-oxo-1,2,3,5-tetrahydro-4H-pyrido[3,4-e][1,4]diazepine-4-carboxamide;

3-(sec-butyl)-6-fluoro-N-(1-methyl-1H-pyrazol-3-yl)-2-oxo-1,2,3,5-tetrahydro-4H-pyrido[3,4-e][1,4]diazepine-4-carboxamide;

3-(sec-butyl)-6-fluoro-2-oxo-N-(1H-pyrazol-3-yl)-1,2,3,5-tetrahydro-4H-pyrido[3,4-e][1,4]diazepine-4-carboxamide;

3-(sec-butyl)-6-fluoro-4-(3-hydroxyazetidine-1-carbonyl)-1,3,4,5-tetrahydro-2H-pyrido[3,4-e][1,4]diazepin-2-one;

4-(2-(benzyloxy)acetyl)-3-(sec-butyl)-6-fluoro-1,3,4,5-tetrahydro-2H-pyrido[3,4-e][1,4]diazepin-2-one;

3-(3-(sec-butyl)-2-oxo-1,2,3,5-tetrahydro-4H-benzo[1,4]diazepin-4-yl)-4-morpholinocyclobut-3-ene-1,2-dione;

3-(sec-butyl)-4-(1-methyl-1H-pyrazole-4-carbonyl)-1,3,4,5-tetrahydro-2H-pyrido[3,4-e][1,4]diazepin-2-one;

3-(3-(sec-butyl)-2-oxo-1,2,3,5-tetrahydro-4H-pyrido[3,4-e][1,4]diazepin-4-yl)-4-((2-hydroxyethyl)amino)cyclobut-3-ene-1,2-dione;

3-(3-(sec-butyl)-2-oxo-1,2,3,5-tetrahydro-4H-pyrido[3,4-e][1,4]diazepin-4-yl)-4-(3-hydroxyazetidin-1-yl)cyclobut-3-ene-1,2-dione;

3-(3-(sec-butyl)-2-oxo-1,2,3,5-tetrahydro-4H-pyrido[3,4-e][1,4]diazepin-4-yl)-4-(methylamino)cyclobut-3-ene-1,2-dione;

3-(3-(sec-butyl)-2-oxo-1,2,3,5-tetrahydro-4H-pyrido[3,4-e][1,4]diazepin-4-yl)-4-(dimethylamino)cyclobut-3-ene-1,2-dione;

3-amino-4-(3-(sec-butyl)-2-oxo-1,2,3,5-tetrahydro-4H-pyrido[3,4-e][1,4]diazepin-4-yl)cyclobut-3-ene-1,2-dione;

3-(sec-butyl)-4-(3-hydroxyazetidine-1-carbonyl)-1,3,4,5-tetrahydro-2H-pyrido[3,4-e][1,4]diazepin-2-one;

phenyl 2-(sec-butyl)-N-cyano-3-oxo-3,4-dihydropyrido[3,4-b]pyrazine-1(2H)-carbimidate; and 3-(3-(sec-butyl)-2-oxo-1,2,3,5-tetrahydro-4H-pyrido[3,4-e][1,4]diazepin-4-yl)-4-((2-methoxyethyl)amino)cyclobut-3-ene-1,2-dione, or a stereoisomer or tautomer thereof, or a pharmaceutically acceptable salt of any of the foregoing. Also provided herein are, where applicable, any and all stereoisomers of the compounds depicted herein, including geometric isomers (e.g., cis/trans isomers or E/Z isomers), enantiomers, diastereomers, or mixtures thereof in any ratio, including racemic mixtures.

Any formula given herein, such as formula (I), (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 2 is depicted with a particular stereochemical configuration, also provided herein is any alternative stereochemical configuration of the compound, as well as a mixture of stereoisomers of the compound in any ratio. For example, where a compound of Table 2 has a stereocenter that is in an "S" stereochemical configuration, also provided herein is enantiomer of the compound wherein that stereocenter is in an "R" stereochemical configuration. Likewise, when a compound of Table 2 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 2 has two or more stereocenters, also provided are any enantiomer or diastereomer of the compound. For example, if a compound of Table 2 contains a first stereocenter and a second stereocenter with "R" and "R" stereochemical configurations, respectively, also provided are stereoisomers of the compound having first and second stereocenters with "S" and "S" stereochemical configurations, respectively, "S" and "R" stereochemical configurations, respectively, and "R" and "S" stereochemical configurations, respectively. If a compound of Table 2 contains a first stereocenter and a second stereocenter with "S" and "S" stereochemical configurations, respectively, also provided are stereoisomers of the compound having first and second stereocenters with "R" and "R" stereochemical configurations, respectively, "S" and "R" stereochemical configurations, respectively, and "R" and "S" stereochemical configurations, respectively. If a compound of Table 2 contains a first stereocenter and a second stereocenter with "S" and "R" stereochemical configurations, respectively, also provided are stereoisomers of the compound having first and second stereocenters with "R" and "S" stereochemical configurations, respectively, "R" and "R" stereochemical configurations, respectively, and "S" and "S" stereochemical configurations, respectively. Similarly, if a compound of Table 2 contains a first stereocenter and a second stereocenter with "R" and "S" stereochemical configurations, respectively, also provided are stereoisomers of the compound having first and second stereocenters with "S" and "R" stereochemical configurations, respectively, "R" and "R" stereochemical configurations, respectively, and "S" and "S" stereochemical configurations, respectively. Furthermore, certain structures may exist as geometric isomers (i.e., cis and trans isomers), as tautomers, or as atropisomers. Additionally, any formula given herein is intended to refer also to any one of hydrates, solvates, and amorphous and crystalline forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual or subject.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual or subject. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $X^1$, $X^2$, $R^x$, $R^y$, $R^z$, $R^1$, $R^2$, $R^3$, $R^4$, $R^h$, $R^i$, $R^j$, $R^k$, $R^m$, $R^n$, $R^p$, $R^q$, $R^s$, $R^t$, $R^u$, $R^v$, and $R^w$ provided herein can be combined with every other variation or embodiment of $X^1$, $X^2$, $R^x$, $R^y$, $R^z$, $R^1$, $R^2$, $R^3$, $R^4$, $R^h$, $R^i$, $R^j$, $R^k$, $R^m$, $R^n$, $R^p$, $R^q$, $R^s$, $R^t$, $R^u$, $R^v$, and $R^w$, the same as if each and every combination had been individually and specifically described.

Other embodiments will be apparent to those skilled in the art from the following detailed description.

As used herein, when any variable occurs more than one time in a chemical formula, its definition on each occurrence is independent of its definition at every other occurrence.

Formula (I) includes all subformulae thereof. For example, formula (I) includes compounds of (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing.

The names for compounds 1-381 provided herein, as shown in Table 2 and Examples 1-57, are provided by ChemInnovation's Chem 4d software version 7.5.0.0. The names for the intermediates 1.1-10.0 as shown in Examples A-J are provided by ChemBioDraw Professional 15.0. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

Also provided herein is an amorphous form of compound 10.

Crystalline Forms

In one aspect, provided herein are crystalline forms of Compound 10, a compound having the structure shown below, Compound 10

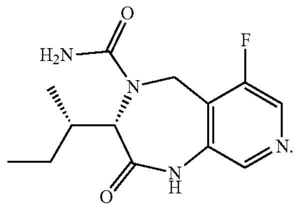

The crystalline forms may have properties such as bioavailability and stability under certain conditions that are suitable for medical or pharmaceutical uses.

A crystalline form of Compound 10 may provide the advantages of bioavailability and stability and may be suitable for use as an active agent in a pharmaceutical composition. Variations in the crystal structure of a pharmaceutical drug substance may affect the dissolution rate (which may affect bioavailability, etc.), manufacturability (e.g., ease of handling, ease of purification, ability to consistently prepare doses of known strength, etc.) and stability (e.g., thermal stability, shelf life (including resistance to degradation), etc.) of a pharmaceutical drug product. Such variations may affect the methods of preparation or formulation of pharmaceutical compositions in different dosage or delivery forms, such as solid oral dosage forms including tablets and capsules. Compared to other forms such as non-crystalline or amorphous forms, crystalline forms may provide desired or suitable hygroscopicity, particle size control, dissolution rate, solubility, purity, physical and chemical stability, manufacturability, yield, reproducibility, and/or process control. Thus, crystalline forms of Compound 10 may provide advantages of improving the manufacturing process of an active agent or the stability or storability of a drug product form of the active agent, or having suitable bioavailability and/or stability as an active agent.

The use of certain conditions, such as the use of different solvents and/or temperatures, has been found to produce different crystalline forms of Compound 10, including crystalline Forms I and II described herein, which may exhibit one or more favorable characteristics described herein. The processes for the preparation of the crystalline forms described herein and characterization of these crystalline forms are described in greater detail below.

Form I

In some embodiments, provided herein is crystalline Form I of Compound 10.

In some embodiments, Form I has an XRPD pattern substantially as shown in FIG. 1A. Angles 2-theta and relative peak intensities that may be observed for Form I using XRPD are shown in Table 3.

TABLE 3

| XRPD Peaks of Form I | |
|---|---|
| Angle (°2θ) | Intensity (%) |
| 8.256 | 100 |
| 11.836 | 3.6 |
| 12.486 | 5.4 |
| 13.075 | 7.8 |
| 14.105 | 4.4 |
| 14.377 | 7.2 |
| 15.712 | 4.9 |
| 16.47 | 28 |
| 16.958 | 8.6 |
| 17.199 | 7 |
| 18.045 | 8.2 |
| 18.389 | 2.1 |
| 18.921 | 12.7 |
| 20.286 | 1.6 |
| 20.675 | 2.4 |
| 20.992 | 5.7 |
| 22.126 | 6.8 |
| 22.672 | 1.4 |
| 23.653 | 8.2 |
| 24.356 | 36.7 |
| 24.754 | 33.2 |
| 25.3 | 7.2 |
| 26.234 | 2.7 |
| 26.571 | 14.1 |
| 26.966 | 2.6 |
| 27.295 | 6.7 |
| 27.663 | 2.3 |
| 28.068 | 2.8 |
| 28.359 | 1.5 |
| 29.063 | 6.5 |
| 29.583 | 1.6 |
| 29.975 | 1.8 |
| 30.535 | 9.3 |
| 31.036 | 5.4 |
| 31.331 | 2.4 |
| 31.669 | 17.5 |
| 32.703 | 4.2 |

In some embodiments, crystalline Form I has an XRPD pattern displaying at least two, at least three, at least four, at least five, at least six, at least seven, at least eight, at least nine, or at least ten of the peaks at angles 2-theta with the greatest intensity in the XRPD pattern substantially as shown in FIG. 1A or as provided in Table 3. It should be understood that relative intensities can vary depending on a number of factors, including sample preparation, mounting, and the instrument and analytical procedure and settings used to obtain the spectrum. Relative peak intensities and peak assignments can vary within experimental error. In some embodiments, peak assignments listed herein, including for crystalline Form I, can vary by about ±0.6 degrees, ±0.4 degrees, ±0.2 degrees, or ±0.1 degrees 2-theta.

In some embodiments, crystalline Form I has an XRPD pattern comprising peaks at angles 2-theta of 8.26±0.2, 11.84±0.2, 12.49±0.2, 13.08±0.2, 14.11±0.2, 14.38±0.2, 15.71±0.2, 16.47±0.2, 16.96±0.2, 17.20±0.2, 18.05±0.2, 18.39±0.2, 18.92±0.2, 20.29±0.2, 20.68±0.2, 20.99±0.2, 22.13±0.2, 22.67±0.2, 23.65±0.2, 24.36±0.2, 24.75±0.2, 25.30±0.2, 26.23±0.2, 26.57±0.2, 26.97±0.2, 27.30±0.2, 27.66±0.2, 28.07±0.2, 28.36±0.2, 29.06±0.2, 29.58±0.2, 29.98±0.2, 30.54±0.2, 31.04±0.2, 31.33±0.2, 31.67±0.2, and 32.70±0.2 degrees.

In some embodiments, provided is a crystalline form of Compound 10:

Compound 10

Figure 1B:
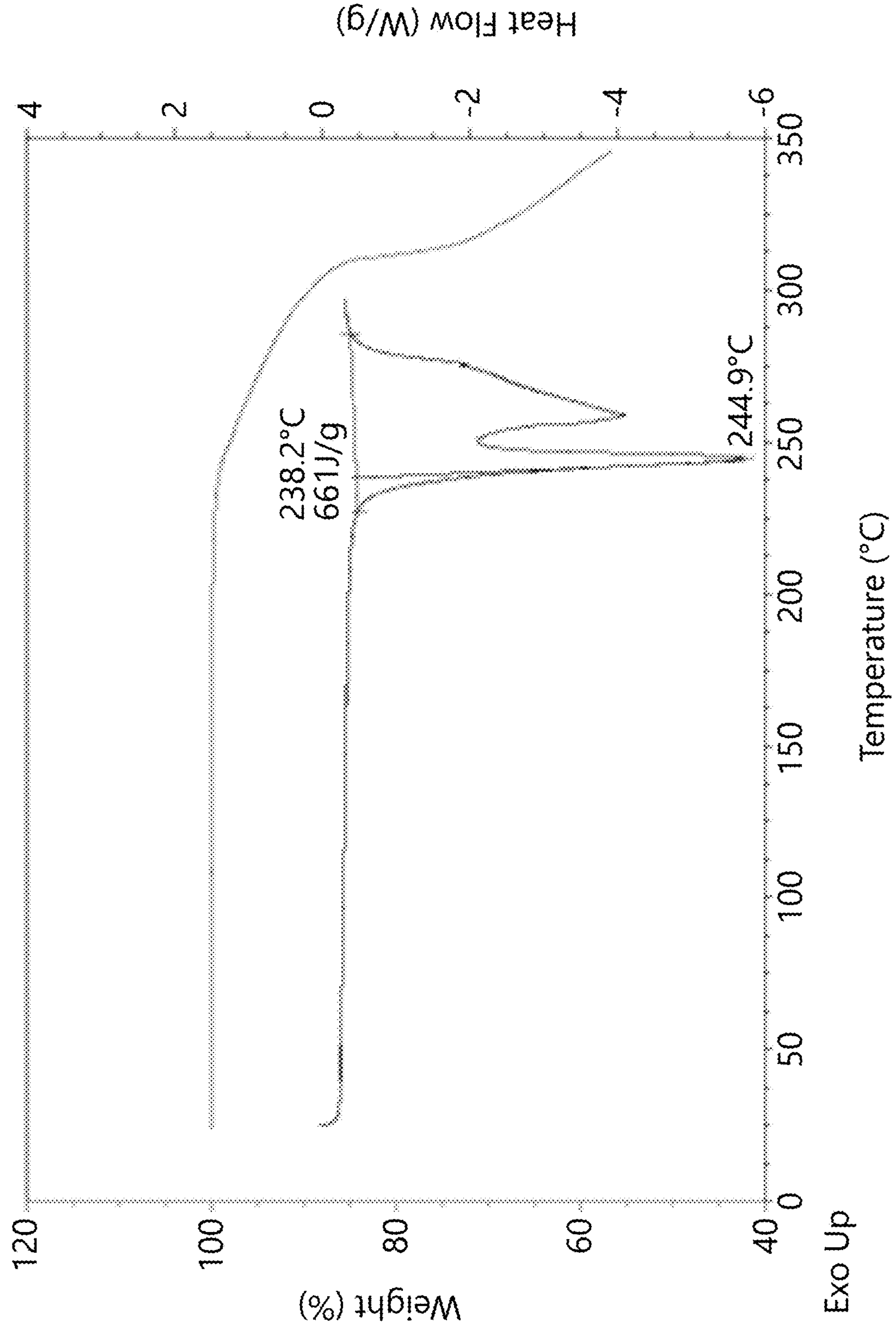
FIG. 1B shows differential scanning calorimetry (DSC) and thermal gravimetric analysis (TGA) graphs of crystalline Form I of Compound 10.

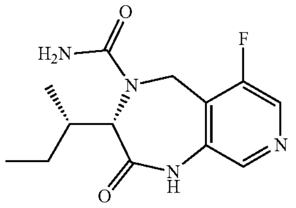

characterized by having an XRPD pattern comprising peaks at angles 2-theta of 8.26±0.2, 16.47±0.2, 24.36±0.2, and 24.75±0.2 degrees. In some embodiments, the XRPD pattern is further characterized by having additional peaks at angles 2-theta of 18.92±0.2, 26.57±0.2, and 31.67±0.2 degrees. In some embodiments, the XRPD pattern is further characterized by having two or more additional peaks at angles 2-theta selected from the group consisting of 11.84±0.2, 12.49±0.2, 13.08±0.2, 14.11±0.2, 14.38±0.2, 15.71±0.2, 16.96±0.2, 17.20±0.2, 18.05±0.2, 18.39±0.2, 20.29±0.2, 20.68±0.2, 20.99±0.2, 22.13±0.2, 22.67±0.2, 23.65±0.2, 25.30±0.2, 26.23±0.2, 26.97±0.2, 27.30±0.2, 27.66±0.2, 28.07±0.2, 28.36±0.2, 29.06±0.2, 29.58±0.2, 29.98±0.2, 30.54±0.2, 31.04±0.2, 31.33±0.2, and 32.70±0.2 degrees. In some embodiments, the crystalline form is characterized by a differential scanning calorimetry trace recorded at a heating rate of 10° C. per minute which shows a maximum in endothermic heat flow at a temperature between 238° C. and 250° C. In some embodiments, the crystalline form is characterized by a powder X-ray diffraction pattern in which the peak positions are substantially in accordance with the peak positions of the pattern shown in FIG. 1A. In some embodiments, the crystalline form is characterized by a differential scanning calorimetry trace substantially in accordance with that shown in FIG. 1B. In some embodiments, the crystalline form is characterized by a TGA graph substantially as shown in FIG. 1B. In some embodiments, the crystalline form is characterized as showing substantially no weight loss attributable to solvent loss prior to degradation at 245° C., as determined by TGA.

Form II

In some embodiments, provided herein is crystalline Form II of Compound 10.

Figure 2A:
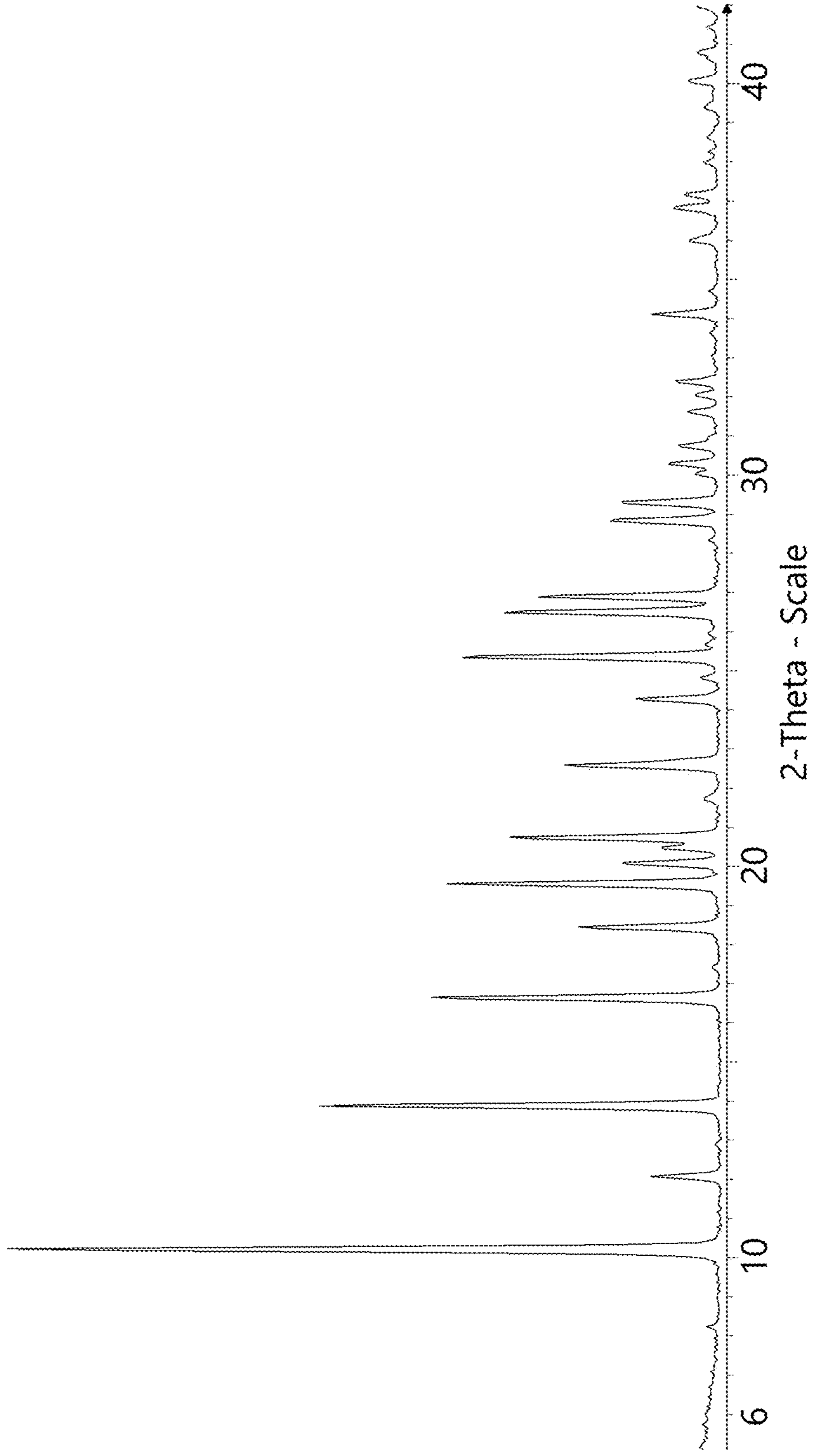
FIG. 2A shows an XRPD pattern of crystalline Form II of Compound 10.

In some embodiments, Form II has an XRPD pattern substantially as shown in FIG. 2A. Angles 2-theta and relative peak intensities that may be observed for Form II using XRPD are shown in Table 4.

TABLE 4

| XRPD Peaks of Form II | |
|---|---|
| Angle (°2θ) | Intensity (%) |
| 8.178 | 2.7 |
| 10.16 | 100 |
| 12.04 | 10.4 |
| 13.864 | 56.5 |
| 16.596 | 40.9 |
| 17.418 | 1.8 |
| 18.413 | 20.4 |
| 19.542 | 38.8 |
| 20.032 | 14.2 |
| 20.437 | 8.8 |
| 20.702 | 30.2 |
| 21.717 | 3 |
| 22.56 | 22.5 |
| 24.246 | 12.4 |
| 24.793 | 3.4 |
| 25.379 | 36.5 |
| 25.733 | 2.7 |
| 25.921 | 2.3 |
| 26.513 | 30.7 |
| 26.915 | 26.1 |
| 28.378 | 2.3 |
| 28.85 | 15.9 |
| 29.333 | 14.4 |
| 30.08 | 4.2 |
| 30.327 | 7.9 |
| 30.733 | 6.5 |
| 31.632 | 5.2 |
| 32.036 | 4.1 |
| 32.432 | 6.9 |

In some embodiments, crystalline Form II has an XRPD pattern displaying at least two, at least three, at least four, at least five, at least six, at least seven, at least eight, at least nine, or at least ten of the peaks at angles 2-theta with the greatest intensity in the XRPD pattern substantially as shown in FIG. 2A or as provided in Table 4. It should be understood that relative intensities can vary depending on a number of factors, including sample preparation, mounting, and the instrument and analytical procedure and settings used to obtain the spectrum. Relative peak intensities and peak assignments can vary within experimental error. In some embodiments, peak assignments listed herein, including for crystalline Form I, can vary by about ±0.6 degrees, ±0.4 degrees, ±0.2 degrees, or ±0.1 degrees 2-theta.

In some embodiments, crystalline Form II has an XRPD pattern comprising peaks at angles 2-theta of 8.18±0.2, 10.16±0.2, 12.04±0.2, 13.86±0.2, 16.60±0.2, 17.42±0.2, 18.41±0.2, 19.54±0.2, 20.03±0.2, 20.44±0.2, 20.70±0.2, 21.72±0.2, 22.56±0.2, 24.25±0.2, 24.79±0.2, 25.38±0.2, 25.73±0.2, 25.92±0.2, 26.51±0.2, 26.92±0.2, 28.38±0.2, 28.85±0.2, 29.33±0.2, 30.08±0.2, 30.33±0.2, 30.73±0.2, 31.63±0.2, 32.04±0.2, and 32.43±0.2 degrees.

In some embodiments, provided is a crystalline form of Compound 10:

Compound 10

Figure 2B:
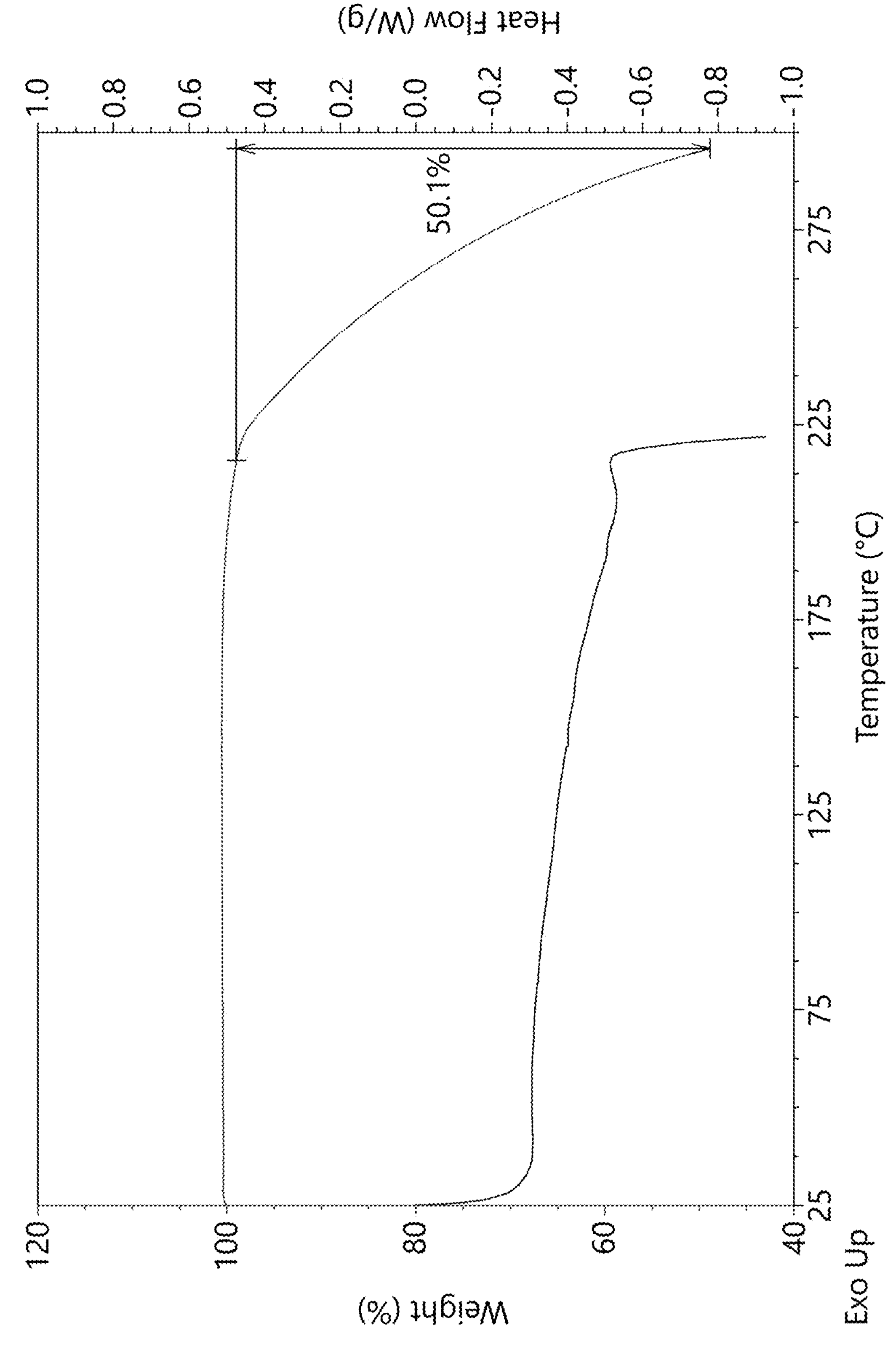
FIG. 2B shows DSC and TGA graphs of crystalline Form II of Compound 10.

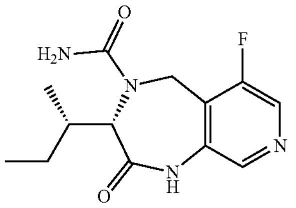

characterized by having an XRPD pattern comprising peaks at angles 2-theta of 10.16±0.2, 13.86±0.2, 16.60±0.2, and 19.54±0.2 degrees. In some embodiments, the XRPD pattern is further characterized by having additional peaks at angles 2-theta of 20.70±0.2, 25.38±0.2, 26.51±0.2, and 26.92±0.2 degrees. In some embodiments, the XRPD pattern is further characterized by having two or more additional peaks at angles 2-theta selected from the group consisting of 8.18±0.2, 12.04±0.2, 17.42±0.2, 18.41±0.2, 20.03±0.2, 20.44±0.2, 21.72±0.2, 22.56±0.2, 24.25±0.2, 24.79±0.2, 25.73±0.2, 25.92±0.2, 28.38±0.2, 28.85±0.2, 29.33±0.2, 30.08±0.2, 30.33±0.2, 30.73±0.2, 31.63±0.2, 32.04±0.2, and 32.43±0.2 degrees. In some embodiments, the crystalline form is characterized by a differential scanning calorimetry trace recorded at a heating rate of 10° C. per minute which shows no thermal events before thermal decomposition at 180° C. In some embodiments, the crystalline form is characterized by a differential scanning calorimetry trace recorded at a heating rate of 10° C. per minute which shows no thermal events before thermal decomposition at 220° C. In some embodiments, the crystalline form is characterized by a powder X-ray diffraction pattern in which the peak positions are substantially in accordance with the peak positions of the pattern shown in FIG. 2A. In some embodiments, the crystalline form is characterized by a differential scanning calorimetry trace substantially in accordance with that shown in FIG. 2B. In some embodiments, the crystalline form is characterized by a TGA graph substantially as shown in FIG. 2B. In some embodiments, the crystalline form is characterized as showing substantially no weight loss attributable to solvent loss between 25° C. and 150° C., prior to degradation at 245° C., as determined by TGA.

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or a pharmaceutically acceptable salt thereof.

In some embodiments, provided is a pharmaceutically acceptable composition comprising a compound of formula (I), (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a compound of Table 2, or a stereoisomer or tautomer thereof, or a pharmaceutically acceptable salt of any of the foregoing. In some aspects, a composition may contain a synthetic intermediate that may be used in the preparation of a compound described herein. The compositions described herein may contain any other suitable active or inactive agents.

Also provided herein are compositions containing crystalline forms of Compound 10 described herein, such as Form I of Compound 10, Form II of Compound 10, or a mixture thereof. In some embodiments, the composition contains Form I. In some embodiments, the composition contains Form II. In some embodiment, the composition further comprises a pharmaceutically acceptable carrier.

In some embodiments, provided is a composition containing Form I of Compound 10. In some embodiments, the composition is substantially free of crystalline Form II of Compound 10. In some embodiments, the composition is substantially free of amorphous or non-crystalline form of Compound 10. In some embodiments, the composition is substantially free of salts of Compound 10.

In some embodiments of the composition containing Form I of Compound 10, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of the total composition is Form I. In some embodiments of the composition containing Form I of Compound 10, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of Compound 10 exists in Form I.

In some embodiments, provided is a composition containing Form II of Compound 10. In some embodiments, the composition is substantially free of crystalline Form I of Compound 10. In some embodiments, the composition is substantially free of amorphous or non-crystalline form of Compound 10. In some embodiments, the composition is substantially free of salts of Compound 10.

In some embodiments of the composition containing Form II of Compound 10, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of the total composition is Form II. In some embodiments of the composition containing Form II of Compound 10, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of Compound 10 exists in Form II.

In some embodiments, provided is a composition containing Form I and Form II of Compound 10. In some embodiments, Form I and Form II are present in a weight ratio of 99 to 1, 90 to 10, 80 to 20, 70 to 30, 60 to 40, 50 to 50, 40 to 60, 30 to 70, 20 to 80, 10 to 90, or 1 to 99. In some embodiments, the weight ratio of Form I to Form II is between 90 to 10 and 99 to 1. In some embodiments of a composition containing Form I and Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of the total composition is Form I. In some embodiments of a composition containing Form I and Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of Compound 10 exists in Form I. In some embodiments of a composition containing Form I and Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of the total composition is Form II. In some embodiments of a composition containing Form I and Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of Compound 10 exists in Form II.

In some embodiments, provided is a tablet or capsule containing one or more of the crystalline forms described herein (e.g., Form I, II, or a mixture thereof), and one or more pharmaceutically acceptable carriers. In some embodiments, provided is a tablet or capsule containing substantially pure crystalline Form I of Compound 10, and one or more pharmaceutically acceptable carriers. In some embodiments, provided is a tablet or capsule containing substantially pure crystalline Form II of Compound 10, and one or more pharmaceutically acceptable carriers.

Any of the compositions described herein may be sterile or contain components that are sterile. Sterilization can be achieved by methods known in the art. Any of the compositions described herein may contain one or more compounds or conjugates that are substantially pure.

Also provided are packaged pharmaceutical compositions, comprising a pharmaceutical composition as described herein and instructions for using the composition to treat a patient suffering from a disease or condition described herein.

Methods of Preparation

Form I

In some embodiments, provided is a method of preparing crystalline Form I of Compound 10:

Compound 10

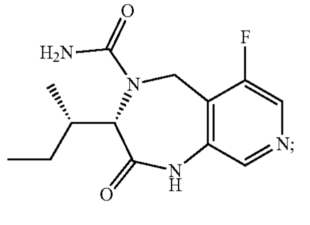

wherein the method comprises:

(a) reacting (S)-3-((S)-sec-butyl)-6-fluoro-1,3,4,5-tetrahydro-2H-pyrido[3,4-e][1,4]diazepin-2-one with potassium cyanate in the presence of a first acid to form Compound 10; and (b) isolating the crystalline form of Compound 10.

In some embodiments, the step of isolating the crystalline form of Compound 10 comprises:

(b-1) dissolving Compound 10 in acetic acid to form a homogeneous solution;

(b-2) adding the homogeneous solution to water to form a heterogeneous solution; (b-3) filtering the heterogeneous solution to obtain a solid; and (b-4) drying the solid under reduced pressure to obtain crystalline Form I of Compound 10.

In some embodiments, step (a) is conducted in the presence of methyl tert-butyl ether. In some embodiments, the first acid is acetic acid. In some embodiments, the method further comprises reacting methyl ((3-amino-5-fluoropyridin-4-yl)methyl)-L-isoleucinate with a first base to form the (S)-3-((S)-sec-butyl)-6-fluoro-1,3,4,5-tetrahydro-2H-pyrido[3,4-e][1,4]diazepin-2-one. In some embodiments, the first base is sodium bis(trimethylsilyl)amide. In some embodiments, the method further comprises reacting 3-amino-5-fluoroisonicotinaldehyde, or a salt thereof, with methyl L-isoleucine in the presence of a reducing agent to form the methyl ((3-amino-5-fluoropyridin-4-yl)methyl)-L-isoleucinate. In some embodiments, the reducing agent is sodium triacetoxyborohydride. In some embodiments, the 3-amino-5-fluoroisonicotinaldehyde or salt thereof is 3-amino-5-fluoroisonicotinaldehyde hydrochloride. In some embodiments, the method further comprises reacting tert-butyl (5-fluoro-4-formylpyridin-3-yl)carbamate with a second acid to form the 3-amino-5-fluoroisonicotinaldehyde hydrochloride or salt thereof. In some embodiments, the second acid is hydrochloric acid. In some embodiments, the method further comprises reacting tert-butyl (5-fluoropyridin-3-yl) carbamate with dimethylformamide in the presence of a second base to form the tert-butyl (5-fluoro-4-formylpyridin-3-yl)carbamate. In some embodiments, the second base is n-butyl lithium. In some embodiments, the method further comprises reacting 5-fluoropyridin-3-amine with di-tert-butyl carbonate in the presence of a catalyst to form the tert-butyl (5-fluoropyridin-3-yl)carbamate. In some embodiments, the catalyst is dimethylaminopyridine. It is understood that Form I may also be prepared using a suitable method as described in Example 59 below.

Form II

In some embodiments, provided is a method of preparing crystalline Form II of Compound 10, comprising: (1) forming a mixture of crystalline Form I of Compound 10 and a solvent; (2) removing the solvent to form an amorphous form of Compound 10, and (3) heating the amorphous form of Compound 10 to a first elevated temperature to form the crystalline Form II of Compound 10. In some embodiments, the solvent comprises a mixture of tetrahydrofuran and water. In some embodiments, the mixture of tetrahydrofuran and water has a 10:3 to 5:3 volume:volume ratio. In some embodiments, the mixture of tetrahydrofuran and water has a 7:3 volume:volume ratio. In some embodiments, step (1) comprises heating the mixture to a second elevated temperature such as about 80° C., about 75° C., about 70° C., about 65° C., about 60° C., about 55° C., about 50° C., about 45° C., about 40° C., or about 35° C. In some embodiments, step (1) comprises heating the mixture to between 4° and 60° C. In some embodiments, step (1) comprises heating the mixture to about 50° C. In some embodiments, the mixture of step (1) is stirred before step (2) is performed. In some embodiments, the mixture of step (1) is stirred for between 10 minutes and 6 hours. In some embodiments, the mixture of step (1) is stirred for about 10 minutes, about 20 minutes, about 30 minutes, about 40 minutes, about 50 minutes, about 1 hour, about 2 hours, about 3 hours, about 4 hours, about 5 hours, or about 6 hours. In some embodiments, the mixture of step (1) is stirred for about 10 minutes. In some embodiments, step (1) comprises heating the amorphous form of Compound 10 to about 120° C. In some embodiments, step (1) comprises heating the amorphous form of Compound 10 to between 10° and 140° C.

Methods of Use

Compounds, crystalline forms, and compositions detailed herein, such as a pharmaceutical composition comprising a compound of any formula provided herein, or a pharmaceutically acceptable salt thereof, and a pharmaceutically acceptable carrier or excipient, may be used in methods of administration and treatment as provided herein.

Further, the invention relates to a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing or a stereoisomer or tautomer thereof, or a pharmaceutically acceptable salt of any of the foregoing, and a pharmaceutically acceptable excipient. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II. Furthermore, the invention relates to a pharmaceutical composition for preventing or treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof, in a subject, comprising a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II. Furthermore, the invention relates to an agent for preventing or treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof, comprising a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

Furthermore, the invention relates to a pharmaceutical composition for treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof, in a subject, comprising a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II. Furthermore, the invention relates to an agent for treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof, comprising a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

Moreover, the invention relates to use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for preventing or treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

Moreover, the invention relates to use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In one aspect, provided herein is the use of the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for preventing or treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In one aspect, provided herein is the use of the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In one aspect, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in preventing or treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In one aspect, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In one aspect, provided herein is a method for preventing or treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof, comprising administering to the subject an effective amount of the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II. Further, the "subject" is a human or a non-human animal in need of the prevention or treatment, and in one embodiment, a human in need of the prevention or treatment.

In one aspect, provided herein is a method for treating a disease or condition responsive to modulation of the contractility of the skeletal sarcomere in a subject, for example, modulation of the troponin complex of the fast skeletal muscle sarcomere through one or more of fast skeletal myosin, actin, tropomyosin, troponin C, troponin I, and troponin T, and fragments and isoforms thereof, comprising administering to the subject an effective amount of the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II. Further, the "subject" is a human or a non-human animal in need of the prevention or treatment, and in one embodiment, a human in need of the prevention or treatment.

In one aspect, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in medical therapy. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II. Such medical therapy may be relating to a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof.

In one aspect, a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, modulates the contractility of the skeletal sarcomere. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II. Specifically, the compounds modulate the troponin complex of the fast skeletal muscle sarcomere through one or more of fast skeletal myosin, actin, tropomyosin, troponin C, troponin I, and troponin T, and fragments and isoforms thereof. As used in this context, "modulate" means either increasing or decreasing activity. In some instances, a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, potentiates (i.e., increases activity) of one or more of fast skeletal myosin, actin, tropomyosin, troponin C, troponin I, and troponin T, and fragments and isoforms thereof. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In another aspect, provided herein is a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, inhibits (i.e., decreases activity) of one or more of fast skeletal myosin, actin, tropomyosin, troponin C, troponin I, and troponin T, and fragments and isoforms thereof. As used in this context, "activation of the fast skeletal muscle fiber such as myofibril" means to amplify the response of fast skeletal muscle fiber (such as myofibril) to stimulation/$Ca^{2+}$. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is a method of preventing or treating: frailty associated with old age (termed sarcopenia); cachexia syndromes associated with diseases such as cancer, heart failure, chronic obstructive pulmonary disease (COPD), renal disease, and chronic kidney disease/dialysis; diseases and disorders of the central nervous system (CNS); neuromuscular diseases, such as amyotrophic lateral sclerosis (ALS), spinal muscular atrophy (SMA), and myasthenia gravis, peripheral neuropathies, Charcot-Marie-Tooth disease, Parkinson's disease, stroke, spinal cord injury, and motor units disorders; muscular myopathies, including body myositis myopathy, muscular dystrophies (limb girdle, facioscapulohumeral, oculopharyngeal), steroid myopathy, and mitochondrial myopathies; rehabilitation-related deficits: recovery from surgery (e.g., post-surgical muscle weakness), prolonged bed rest, immobilization/disuse atrophy, post-hip fracture recovery, ICU neuromyopathy, post trauma, stroke rehabilitation; Peripheral Vascular Disease (PVD) or Peripheral Arterial Disease (PAD) (e.g., claudication), metabolic syndrome, chronic fatigue syndrome, obesity, and frailty due to aging; post-anesthesia recovery or reversal of neuromuscular blockade; obstructive sleep apnea; chronic fatigue syndrome; metabolic syndrome, metabolic/ischemic disorders, or claudication; obesity; dysfunctions of pelvic floor and urethral/anal sphincter muscles (e.g., urinary incontinence such as stress urinary incontinence (SUI) and mixed urinary incontinence (MUI), and fecal incontinence); post-spinal cord injury (SCI) muscle dysfunction; ventilator-induced muscle weakness; or spinocerebral ataxias or demyelinating diseases, including multiple sclerosis, post-polio syndrome, or any combination of the foregoing, in a subject, comprising administering to the subject an effective amount of a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, or an effective amount of a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is a method of treating: frailty associated with old age (termed sarcopenia); cachexia syndromes associated with diseases such as cancer, heart failure, chronic obstructive pulmonary disease (COPD), renal disease, and chronic kidney disease/dialysis; diseases and disorders of the central nervous system (CNS); neuromuscular diseases, such as amyotrophic lateral sclerosis (ALS), spinal muscular atrophy (SMA), and myasthenia gravis, peripheral neuropathies, Charcot-Marie-Tooth disease, Parkinson's disease, stroke, spinal cord injury, and motor units disorders; muscular myopathies, including body myositis myopathy, muscular dystrophies (limb girdle, facioscapulohumeral, oculopharyngeal), steroid myopathy, and mitochondrial myopathies; rehabilitation-related deficits: recovery from surgery (e.g., post-surgical muscle weakness), prolonged bed rest, immobilization/disuse atrophy, post-hip fracture recovery, ICU neuromyopathy, post trauma, stroke rehabilitation; Peripheral Vascular Disease (PVD) or Peripheral Arterial Disease (PAD) (e.g., claudication), metabolic syndrome, chronic fatigue syndrome, obesity, and frailty due to aging; post-anesthesia recovery or reversal of neuromuscular blockade; obstructive sleep apnea; chronic fatigue syndrome; metabolic syndrome, metabolic/ischemic disorders, or claudication; obesity; dysfunctions of pelvic floor and urethral/anal sphincter muscles (e.g., urinary incontinence such as stress urinary incontinence (SUI) and mixed urinary incontinence (MUI), and fecal incontinence); post-spinal cord injury (SCI) muscle dysfunction; ventilator-induced muscle weakness; or spinocerebral ataxias or demyelinating diseases, including multiple sclerosis, post-polio syndrome, or any combination of the foregoing, in a subject, comprising administering to the subject an effective amount of a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, or an effective amount of a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is a method for preventing or treating a disease or condition selected from the group consisting of peripheral vascular disease, peripheral arterial disease, rehabilitation-related deficits, metabolic syndrome, obesity, ventilator-induced muscle weakness, chronic fatigue syndrome, neuromuscular disorders, conditions of muscle wasting, muscular myopathies, muscle atrophy and fatigue, and frailty, in a subject, comprising administering to the subject an effective amount of a compound of formula (I), such as a compound of formula (II), (III), (IV), (V), (I-A), (I-A1), (I-A2), (I-A3), (I-A4), (I-A5), (I-B), (I-B1), (I-B32), (I-B33), (I-B34), (I-B35), (I-B6), (I-B7), (I-B8), (I-C), or (I-D), or a stereoisomer or tautomer thereof, or a pharmaceutically acceptable salt of any of the foregoing, or a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is a method for treating a disease or condition selected from the group consisting of peripheral vascular disease, peripheral arterial disease, rehabilitation-related deficits, metabolic syndrome, obesity, ventilator-induced muscle weakness, chronic fatigue syndrome, neuromuscular disorders, conditions of muscle wasting, muscular myopathies, muscle atrophy and fatigue, and frailty, in a subject, comprising administering to the subject an effective amount of a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, or a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is a method for preventing or treating a disease or condition selected from the group consisting of amyotrophic lateral sclerosis (ALS), spinal muscular atrophy (SMA), myasthenia gravis, and muscular myopathies, in a subject, comprising administering to the subject an effective amount of a compound of formula (I), such as a compound of formula (II), (III), (IV), (V), (I-A), (I-A1), (I-A2), (I-A3), (I-A4), (I-A5), (I-B), (I-B1), (I-B32), (I-B33), (I-B34), (I-B5), (I-B6), (I-B7), (I-B8), (I-C), or (I-D), or a stereoisomer or tautomer thereof, or a pharmaceutically acceptable salt of any of the foregoing, or a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is a method for treating a disease or condition selected from the group consisting of amyotrophic lateral sclerosis (ALS), spinal muscular atrophy (SMA), myasthenia gravis, and muscular myopathies, in a subject, comprising administering to the subject an effective amount of a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, or a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is a method for preventing or treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome, muscle wasting caused by heart failure, cancer, or chronic kidney disease/dialysis, post-spinal cord injury (SCI) muscle dysfunction, and post-stroke muscle dysfunction, in a subject, comprising administering to the subject an effective amount of a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, or a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is a method for treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome, muscle wasting caused by heart failure, cancer, or chronic kidney disease/dialysis, post-spinal cord injury (SCI) muscle dysfunction, and post-stroke muscle dysfunction, in a subject, comprising administering to the subject an effective amount of a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, or a pharmaceutical composition comprising a compound of formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for preventing or treating: frailty associated with old age (termed sarcopenia); cachexia syndromes associated with diseases such as cancer, heart failure, chronic obstructive pulmonary disease (COPD), renal disease, and chronic kidney disease/dialysis; diseases and disorders of the central nervous system (CNS); neuromuscular diseases, such as amyotrophic lateral sclerosis (ALS), spinal muscular atrophy (SMA), and myasthenia gravis, peripheral neuropathies, Charcot-Marie-Tooth disease, Parkinson's disease, stroke, spinal cord injury, and motor units disorders; muscular myopathies, including body myositis myopathy, muscular dystrophies (limb girdle, facioscapulohumeral, oculopharyngeal), steroid myopathy, and mitochondrial myopathies; rehabilitation-related deficits: recovery from surgery (e.g., post-surgical muscle weakness), prolonged bed rest, immobilization/disuse atrophy, post-hip fracture recovery, ICU neuromyopathy, post trauma, stroke rehabilitation; Peripheral Vascular Disease (PVD) or Peripheral Arterial Disease (PAD) (e.g., claudication), metabolic syndrome, chronic fatigue syndrome, obesity, and frailty due to aging; post-anesthesia recovery or reversal of neuromuscular blockade; obstructive sleep apnea; chronic fatigue syndrome; metabolic syndrome, metabolic/ischemic disorders, or claudication; obesity; dysfunctions of pelvic floor and urethral/anal sphincter muscles (e.g., urinary incontinence such as stress urinary incontinence (SUI) and mixed urinary incontinence (MUI), and fecal incontinence); post-spinal cord injury (SCI) muscle dysfunction; ventilator-induced muscle weakness; or spinocerebral ataxias or demyelinating diseases, including multiple sclerosis, post-polio syndrome, or any combination of the foregoing, in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for treating: frailty associated with old age (termed sarcopenia); cachexia syndromes associated with diseases such as cancer, heart failure, chronic obstructive pulmonary disease (COPD), renal disease, and chronic kidney disease/dialysis; diseases and disorders of the central nervous system (CNS); neuromuscular diseases, such as amyotrophic lateral sclerosis (ALS), spinal muscular atrophy (SMA), and myasthenia gravis, peripheral neuropathies, Charcot-Marie-Tooth disease, Parkinson's disease, stroke, spinal cord injury, and motor units disorders; muscular myopathies, including body myositis myopathy, muscular dystrophies (limb girdle, facioscapulohumeral, oculopharyngeal), steroid myopathy, and mitochondrial myopathies; rehabilitation-related deficits: recovery from surgery (e.g., post-surgical muscle weakness), prolonged bed rest, immobilization/disuse atrophy, post-hip fracture recovery, ICU neuromyopathy, post trauma, stroke rehabilitation; Peripheral Vascular Disease (PVD) or Peripheral Arterial Disease (PAD) (e.g., claudication), metabolic syndrome, chronic fatigue syndrome, obesity, and frailty due to aging; post-anesthesia recovery or reversal of neuromuscular blockade; obstructive sleep apnea; chronic fatigue syndrome; metabolic syndrome, metabolic/ischemic disorders, or claudication; obesity; dysfunctions of pelvic floor and urethral/anal sphincter muscles (e.g., urinary incontinence such as stress urinary incontinence (SUI) and mixed urinary incontinence (MUI), and fecal incontinence); post-spinal cord injury (SCI) muscle dysfunction; ventilator-induced muscle weakness; or spinocerebral ataxias or demyelinating diseases, including multiple sclerosis, post-polio syndrome, or any combination of the foregoing, in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for preventing or treating a disease or condition selected from the group consisting of peripheral vascular disease, peripheral arterial disease, rehabilitation-related deficits, metabolic syndrome, obesity, ventilator-induced muscle weakness, chronic fatigue syndrome, neuromuscular disorders, conditions of muscle wasting, muscular myopathies, muscle atrophy and fatigue, and frailty in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for treating a disease or condition selected from the group consisting of peripheral vascular disease, peripheral arterial disease, rehabilitation-related deficits, metabolic syndrome, obesity, ventilator-induced muscle weakness, chronic fatigue syndrome, neuromuscular disorders, conditions of muscle wasting, muscular myopathies, muscle atrophy and fatigue, and frailty in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for preventing or treating a disease or condition selected from the group consisting of amyotrophic lateral sclerosis (ALS), spinal muscular atrophy (SMA), myasthenia gravis, and muscular myopathies in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for treating a disease or condition selected from the group consisting of amyotrophic lateral sclerosis (ALS), spinal muscular atrophy (SMA), myasthenia gravis, and muscular myopathies in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for preventing or treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome, muscle wasting caused by heart failure, cancer, or chronic kidney disease/dialysis, post-spinal cord injury (SCI) muscle dysfunction, and post-stroke muscle dysfunction in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the use of a compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, or a pharmaceutically acceptable salt of any of the foregoing, for the manufacture of a pharmaceutical composition for treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome, muscle wasting caused by heart failure, cancer, or chronic kidney disease/dialysis, post-spinal cord injury (SCI) muscle dysfunction, and post-stroke muscle dysfunction in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in preventing or treating: frailty associated with old age (termed sarcopenia); cachexia syndromes associated with diseases such as cancer, heart failure, chronic obstructive pulmonary disease (COPD), renal disease, and chronic kidney disease/dialysis; diseases and disorders of the central nervous system (CNS); neuromuscular diseases, such as amyotrophic lateral sclerosis (ALS), spinal muscular atrophy (SMA), and myasthenia gravis, peripheral neuropathies, Charcot-Marie-Tooth disease, Parkinson's disease, stroke, spinal cord injury, and motor units disorders; muscular myopathies, including body myositis myopathy, muscular dystrophies (limb girdle, facioscapulohumeral, oculopharyngeal), steroid myopathy, and mitochondrial myopathies; rehabilitation-related deficits: recovery from surgery (e.g., post-surgical muscle weakness), prolonged bed rest, immobilization/disuse atrophy, post-hip fracture recovery, ICU neuromyopathy, post trauma, stroke rehabilitation; Peripheral Vascular Disease (PVD) or Peripheral Arterial Disease (PAD) (e.g., claudication), metabolic syndrome, chronic fatigue syndrome, obesity, and frailty due to aging; post-anesthesia recovery or reversal of neuromuscular blockade; obstructive sleep apnea; chronic fatigue syndrome; metabolic syndrome, metabolic/ischemic disorders, or claudication; obesity; dysfunctions of pelvic floor and urethral/anal sphincter muscles (e.g., urinary incontinence such as stress urinary incontinence (SUI) and mixed urinary incontinence (MUI), and fecal incontinence); post-spinal cord injury (SCI) muscle dysfunction; ventilator-induced muscle weakness; or spinocerebral ataxias or demyelinating diseases, including multiple sclerosis, post-polio syndrome, or any combination of the foregoing, in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in treating: frailty associated with old age (termed sarcopenia); cachexia syndromes associated with diseases such as cancer, heart failure, chronic obstructive pulmonary disease (COPD), renal disease, and chronic kidney disease/dialysis; diseases and disorders of the central nervous system (CNS); neuromuscular diseases, such as amyotrophic lateral sclerosis (ALS), spinal muscular atrophy (SMA), and myasthenia gravis, peripheral neuropathies, Charcot-Marie-Tooth disease, Parkinson's disease, stroke, spinal cord injury, and motor units disorders; muscular myopathies, including body myositis myopathy, muscular dystrophies (limb girdle, facioscapulohumeral, oculopharyngeal), steroid myopathy, and mitochondrial myopathies; rehabilitation-related deficits: recovery from surgery (e.g., post-surgical muscle weakness), prolonged bed rest, immobilization/disuse atrophy, post-hip fracture recovery, ICU neuromyopathy, post trauma, stroke rehabilitation; Peripheral Vascular Disease (PVD) or Peripheral Arterial Disease (PAD) (e.g., claudication), metabolic syndrome, chronic fatigue syndrome, obesity, and frailty due to aging; post-anesthesia recovery or reversal of neuromuscular blockade; obstructive sleep apnea; chronic fatigue syndrome; metabolic syndrome, metabolic/ischemic disorders, or claudication; obesity; dysfunctions of pelvic floor and urethral/anal sphincter muscles (e.g., urinary incontinence such as stress urinary incontinence (SUI) and mixed urinary incontinence (MUI), and fecal incontinence); post-spinal cord injury (SCI) muscle dysfunction; ventilator-induced muscle weakness; or spinocerebral ataxias or demyelinating diseases, including multiple sclerosis, post-polio syndrome, or any combination of the foregoing, in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in preventing or treating a disease or condition selected from the group consisting of peripheral vascular disease, peripheral arterial disease, rehabilitation-related deficits, metabolic syndrome, obesity, ventilator-induced muscle weakness, chronic fatigue syndrome, neuromuscular disorders, conditions of muscle wasting, muscular myopathies, muscle atrophy and fatigue, and frailty in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in treating a disease or condition selected from the group consisting of peripheral vascular disease, peripheral arterial disease, rehabilitation-related deficits, metabolic syndrome, obesity, ventilator-induced muscle weakness, chronic fatigue syndrome, neuromuscular disorders, conditions of muscle wasting, muscular myopathies, muscle atrophy and fatigue, and frailty in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in preventing or treating a disease or condition selected from the group consisting of amyotrophic lateral sclerosis (ALS), spinal muscular atrophy (SMA), myasthenia gravis, and muscular myopathies in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in treating a disease or condition selected from the group consisting of amyotrophic lateral sclerosis (ALS), spinal muscular atrophy (SMA), myasthenia gravis, and muscular myopathies in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in preventing or treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome, muscle wasting caused by heart failure, cancer, or chronic kidney disease/dialysis, post-spinal cord injury (SCI) muscle dysfunction, and post-stroke muscle dysfunction in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

In some aspects, provided herein is the compound of the formula (I), such as a compound of formula (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D), or a stereoisomer or tautomer thereof, a pharmaceutically acceptable salt of any of the foregoing, or a pharmaceutical composition thereof, for use in treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome, muscle wasting caused by heart failure, cancer, or chronic kidney disease/dialysis, post-spinal cord injury (SCI) muscle dysfunction, and post-stroke muscle dysfunction in a subject. In some embodiments, the compound is a crystalline form. In some embodiments, the compound is compound 10 in the form of crystalline Form I and/or crystalline Form II. In some embodiments, the compound is compound 10 in the form of crystalline Form I. In some embodiments, the compound is compound 10 in the form of crystalline Form II.

Dosages

The compounds, crystalline forms, and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the compounds, crystalline forms, and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound, crystalline form, or composition is administered orally or intravenously. In some embodiments, the compound, crystalline form, or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds, crystalline forms, or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

Combinations

The compounds, crystalline forms, and compositions described and/or disclosed herein may be administered alone or in combination with other therapies and/or therapeutic agents useful in the treatment of the aforementioned disorders, diseases, or conditions.

General Synthetic Methods

Compounds of formula (I), (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme, with or without protection, as appropriate, to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (for example: amino, carboxy, or side chain groups) from reaction conditions, and that such groups are removed under standard conditions when appropriate. It is also to be understood that any of the steps shown in any of the following general schemes may be used in any combination and in any order that is chemically feasible to achieve a desired intermediate or disclosed compound. Unless otherwise specified, the variables are as defined above in reference to formula (I), (II), (III), (IV), (V), (I-A), (I-A1), (I-A2), (I-A3), (I-A4), (I-A5), (I-B), (I-B1), (I-B2), (I-B3), (I-B4), (I-B5), (I-B6), (I-B7), (I-B8), (I-C), or (I-D).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization, and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for formula (I), (II), (III), (IV), (V), (I-A), (I-A1), (I-A2), (I-A3), (I-A4), (I-A5), (I-B), (I-B1), (I-B32), (I-B33), (I-B34), (I-B5), (I-B6), (I-B7), (I-B8), (I-C), or (I-D), or any variation thereof. Other compounds described herein may be prepared by similar methods.

In some embodiments, compounds provided herein may be synthesized according to Scheme 1:

Scheme 1

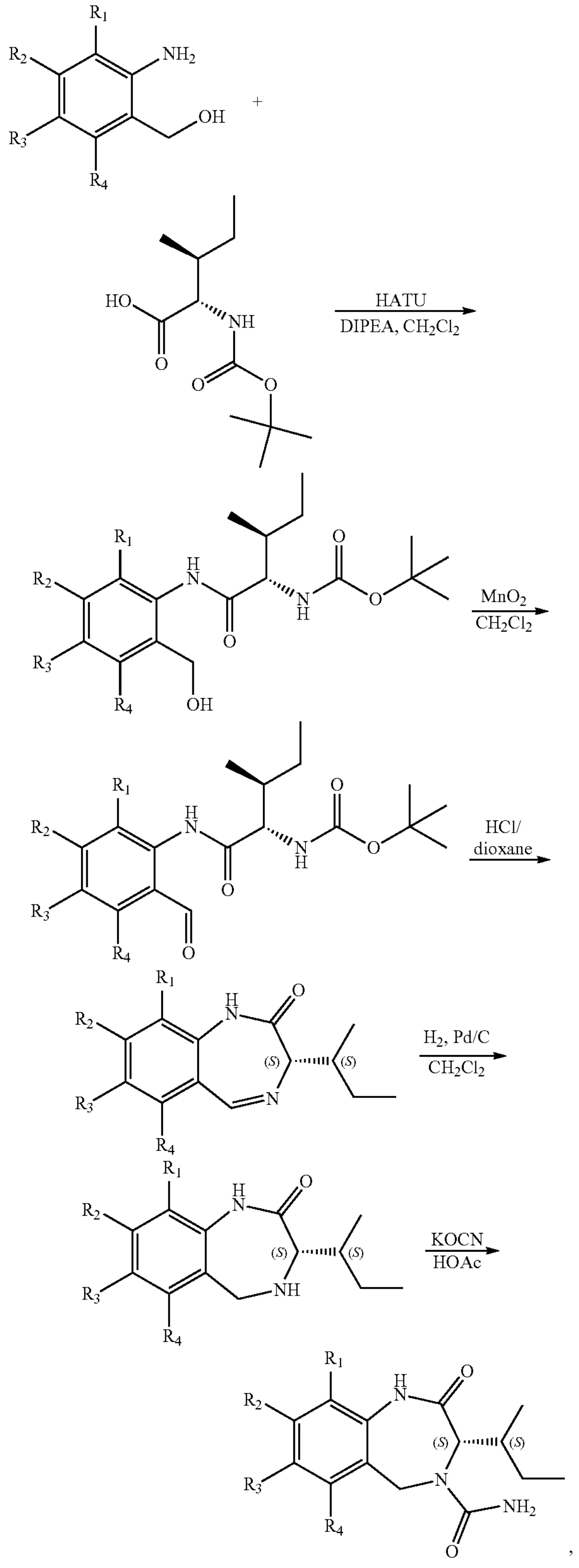

wherein $R^1$, $R^2$, $R^3$, and $R^4$ are as described herein for a compound of formula (I), or any variation thereof.

In some embodiments, compounds provided herein may be synthesized according to Scheme 2:

Scheme 2

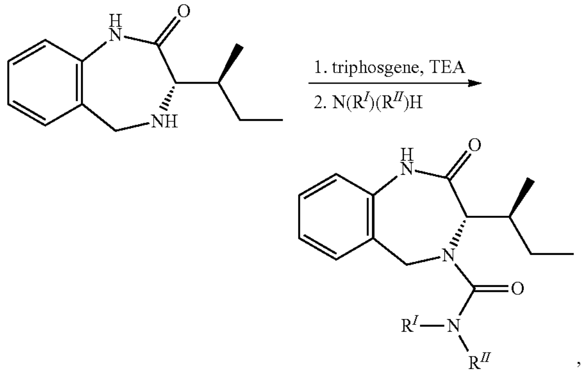

wherein $R^I$ and $R^{II}$ are each independently H or $R^q$, wherein $R^q$ is as defined herein for a compound of formula (I), or any variation thereof.

In some embodiments, compounds provided herein may be synthesized according to Scheme 3:

Scheme 3

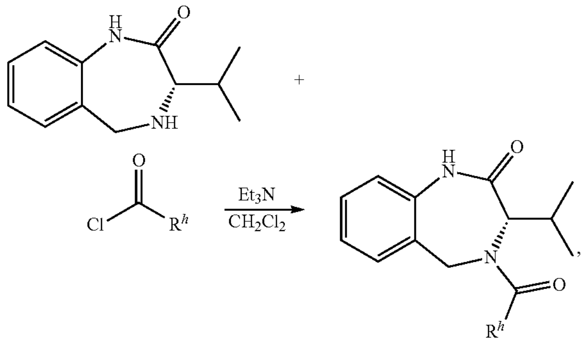

wherein $R^h$ is as defined herein for a compound of formula (I), or any variation thereof.

In some embodiments, compounds provided herein may be synthesized according to Scheme 4:

Scheme 4

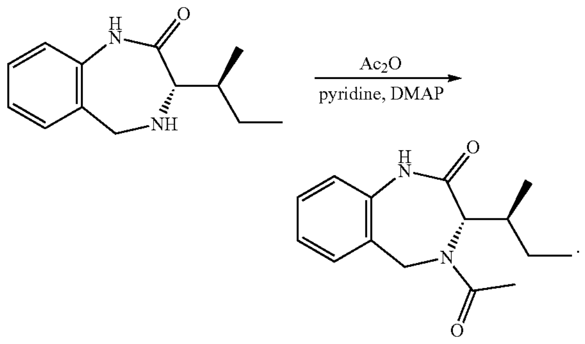

In some embodiments, compounds provided herein may be synthesized according to Scheme 5:

Scheme 5

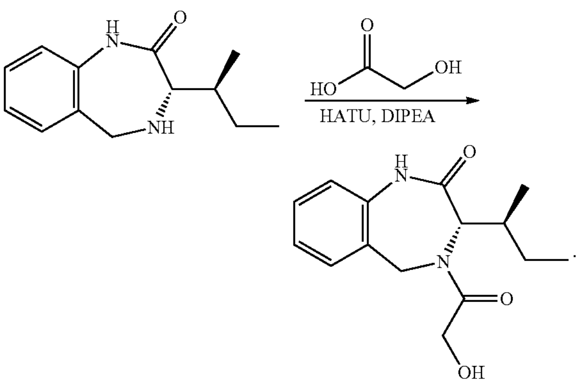

In some embodiments, compounds provided herein may be synthesized according to Scheme 6:

Scheme 6

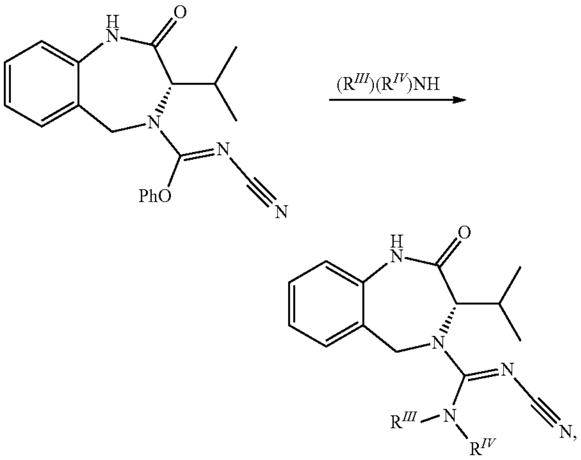

wherein $R^{III}$ and $R^{IV}$ are each independently H or $R^s$, wherein $R^s$ is as defined herein for a compound of formula (I), or any variation thereof.

In some embodiments, compounds provided herein may be synthesized according to Scheme 7:

Scheme 7

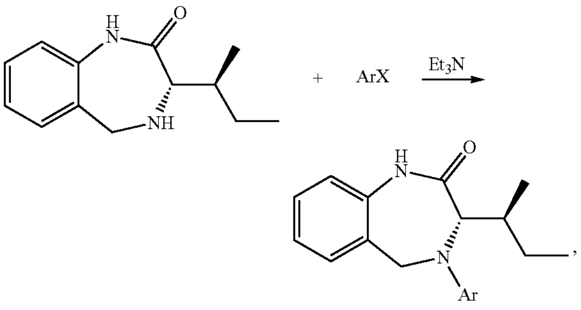

wherein X is a leaving group and Ar is $C_{6-20}$aryl.

In some embodiments, compounds provided herein may be synthesized according to Scheme 8:

Scheme 8

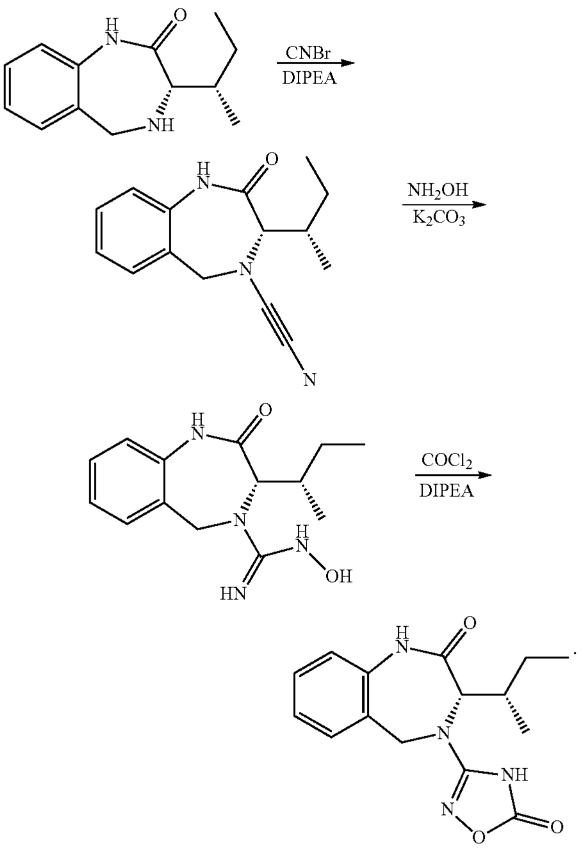

In some embodiments, compounds provided herein may be synthesized according to Scheme 9:

Scheme 9

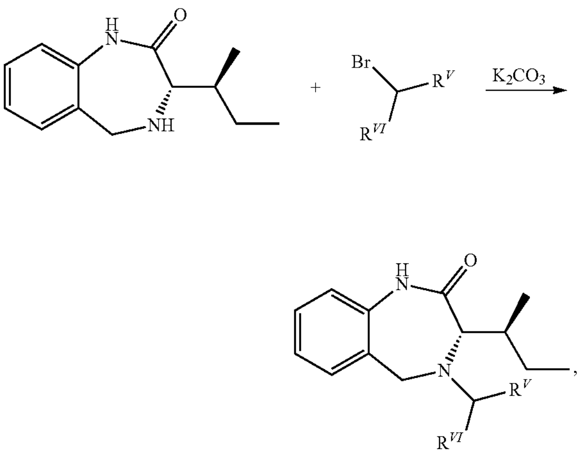

wherein $R^V$ and $R^{VI}$ are each independently H, $C_{1-12}$alkyl, or $R^m$, wherein $R^m$ is as defined herein for a compound of formula (I), or any variation thereof.

In some embodiments, compounds provided herein may be synthesized according to Scheme 10:
Scheme 10
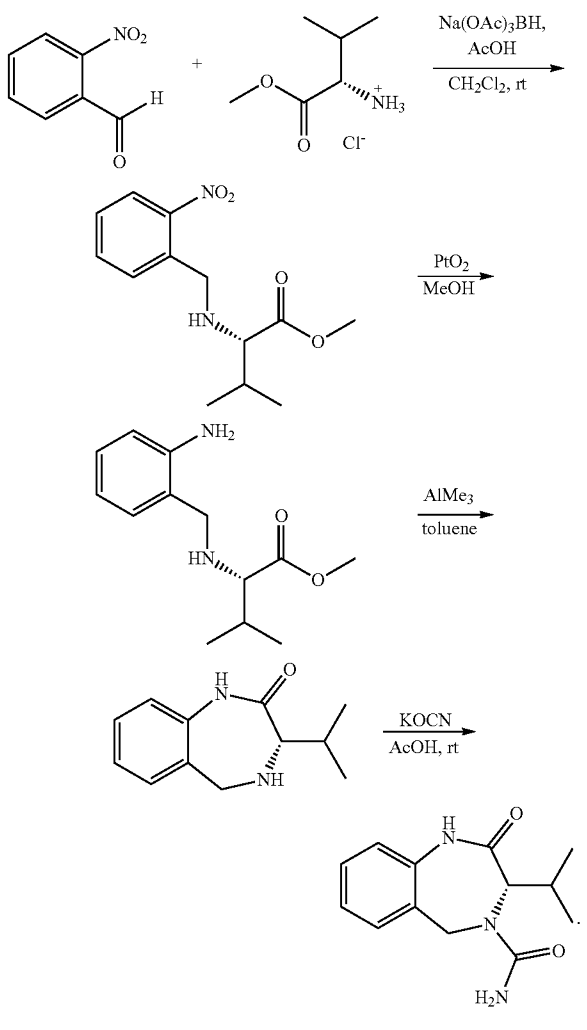
In some embodiments, compounds provided herein may be synthesized according to Scheme 11:
Scheme 11
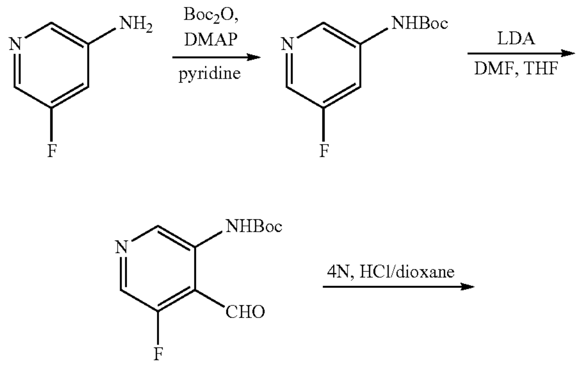
-continued
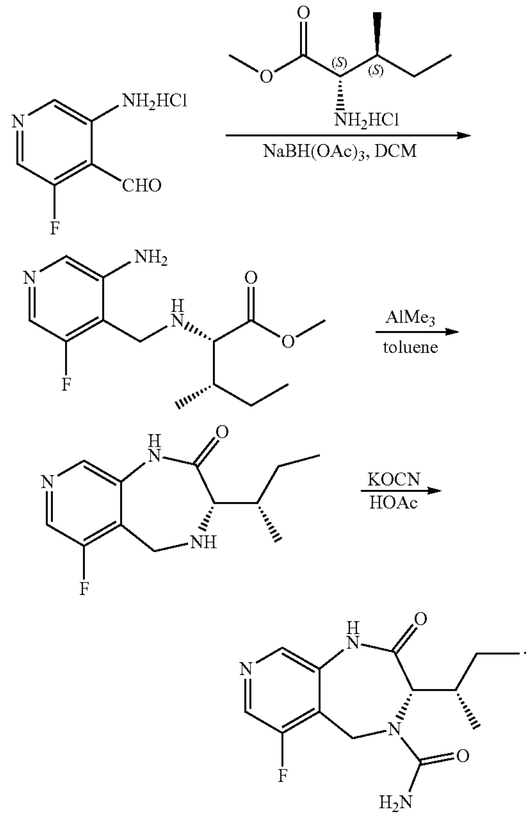
In some embodiments, compounds provided herein may be synthesized according to Scheme 12:
Scheme 12
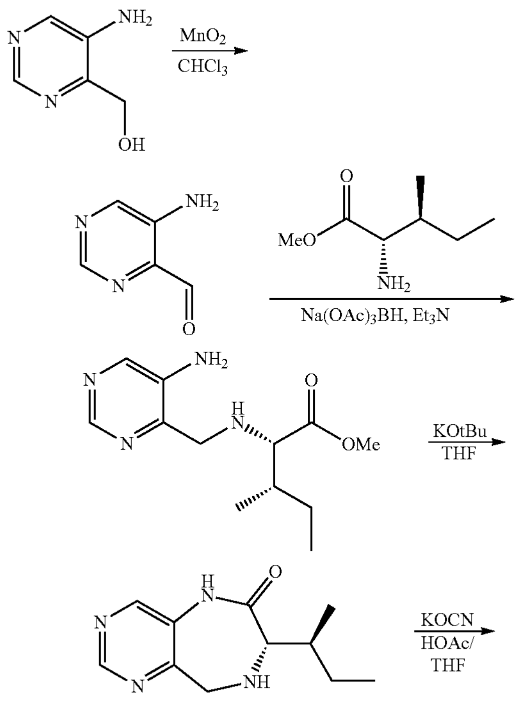

-continued
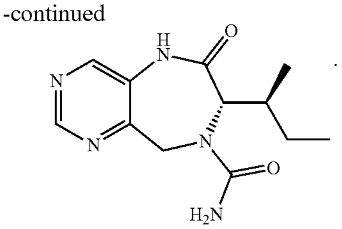
In some embodiments, compounds provided herein may be synthesized according to Scheme 13:
Scheme 13
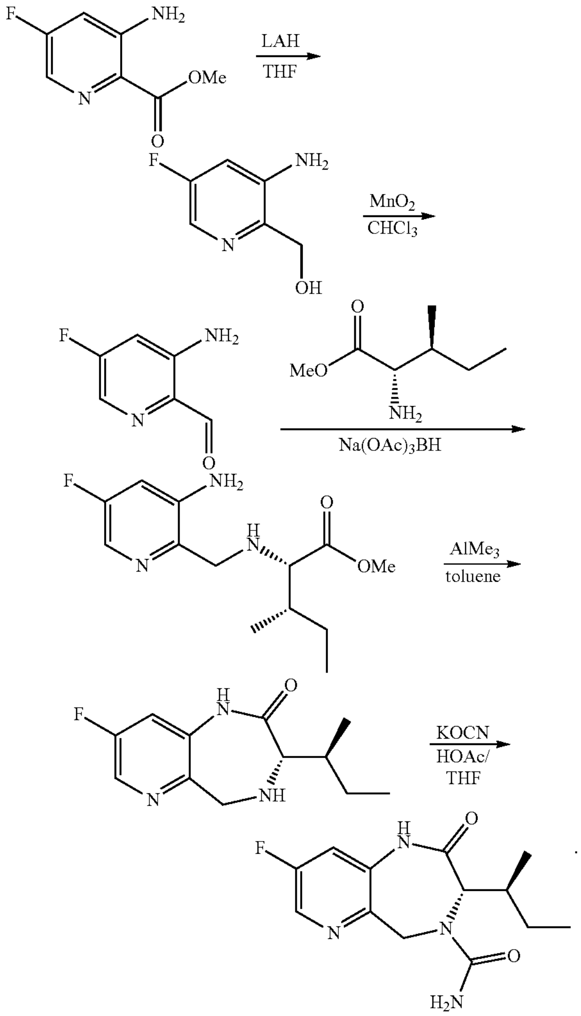
In some embodiments, compounds provided herein may be synthesized according to Scheme 14:
Scheme 14
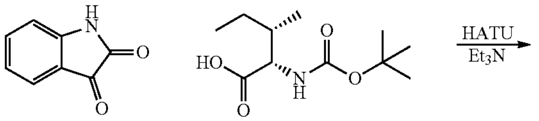
-continued
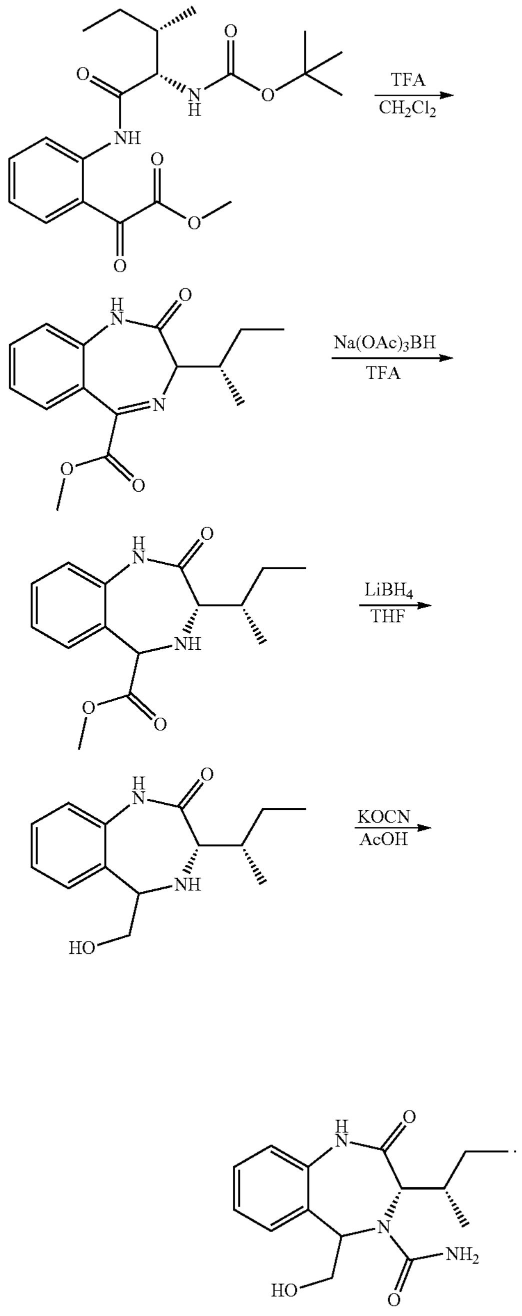
In some embodiments, compounds provided herein may be synthesized according to Scheme 15:
Scheme 15
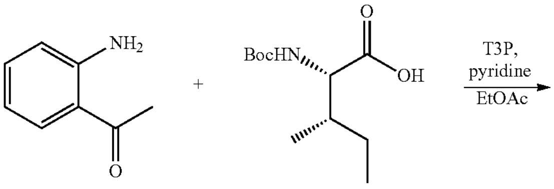

-continued

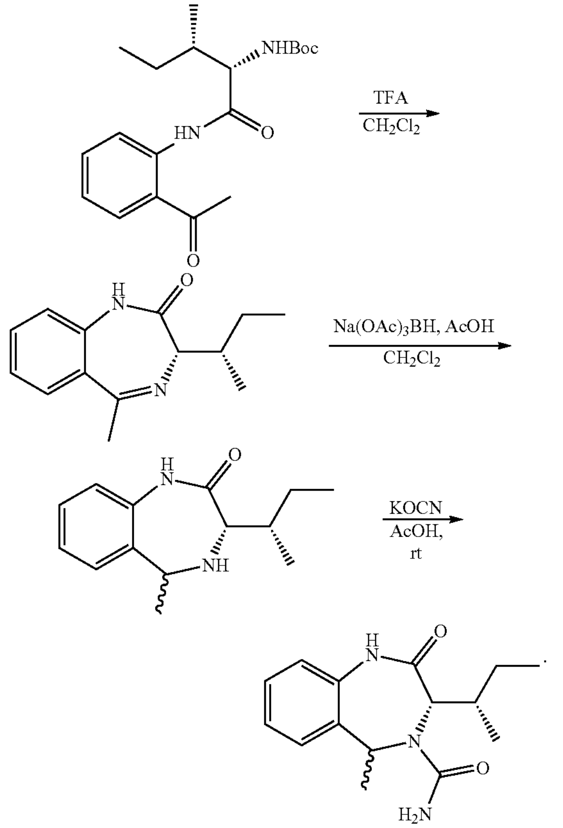

In some embodiments, compounds provided herein may be synthesized according to Scheme 16:

Scheme 16

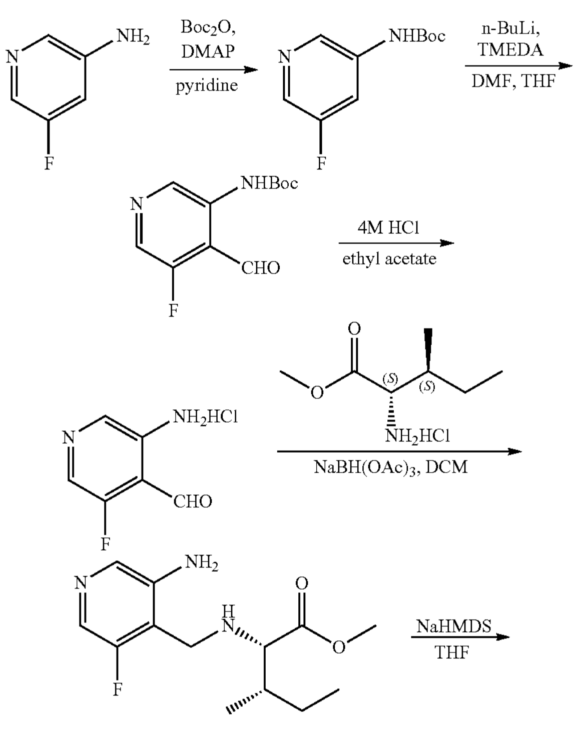

-continued

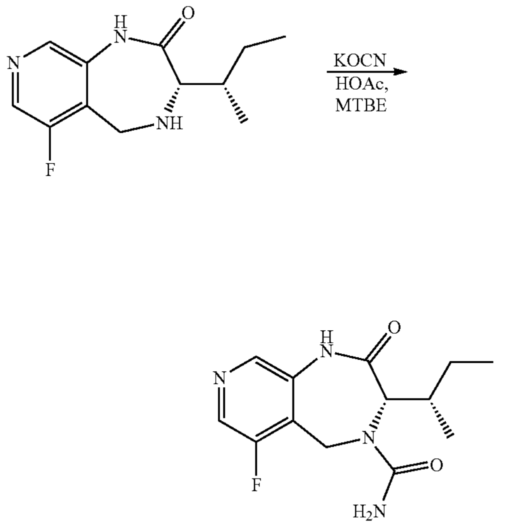

Also provided herein are intermediate compounds, or a salt thereof, to make the compounds of Formula (I). In some embodiments, the intermediate compounds are the intermediate compounds shown in Schemes 1-16. In some embodiments, the intermediate compounds are the intermediate compounds shown in the Example section below.

EXAMPLES

The following examples are offered to illustrate, but not to limit, the compounds, compositions, uses, and methods provided herein. In some examples, the compounds and intermediates are prepared using the general methods described above.

The following abbreviations are used throughout the Examples: HATU (1-[bis(dimethylamino)methylene]-1H-1,2,3-triazolo[4,5-b]pyridinium 3-oxid hexafluorophosphate), DIPEA (N,N-diisopropylethylamine), LRMS (low-resolution mass spectrometry), Ac (acetyl), Et (ethyl), Me (methyl), tBu (tert-butyl), APCI (atmospheric pressure chemical ionization), THF (tetrahydrofuran), MTBE (methyl tert-butyl ether), DMAP (4-dimethylaminopyridine), TMEDA (N,N,N',N'-tetramethylethylenediamine), DMF (dimethylformamide), DMSO (dimethylsulfoxide), TFA (trifluoroacetic acid), HPLC (high-performance liquid chromatography), DCM (dichloromethane), DBU (1,8-diazabicyclo[5.4.0]undec-7-ene), DavePhos (2-dicyclohexylphosphino-2'-(N,N-dimethylamino)biphenyl), Boc (tert-butoxycarbonyl), LDA (lithium diisopropylamide), n-BuLi (n-butyl lithium), NaHMDS (sodium bis(trimethylsilyl)amide), TEA (triethylamine), ES (electrospray), TBSCl (tert-butyldimethylsilyl chloride), TBAF (tetra-n-butylammonium fluoride), T3P (propanephosphonic acid anhydride), LAH (lithium aluminum hydride), Dess-Martin periodinane (3-oxo-1,3-dihydro-1$\lambda^5$,2-benziodoxole-1,1,1-triyl triacetate), XRPD, (X-Ray Powder Diffraction), DSC (Differential Scanning Calorimetry), TGA (Thermal Gravimetric Analysis), DVS (Dynamic Vapor Sorption), GVS (Gravimetric Vapour Sorption), FaSSIF (Fasted State Simulated Intestinal Fluid), and KF (Karl Fischer Titration).

Example 1: Synthesis of Compound 5

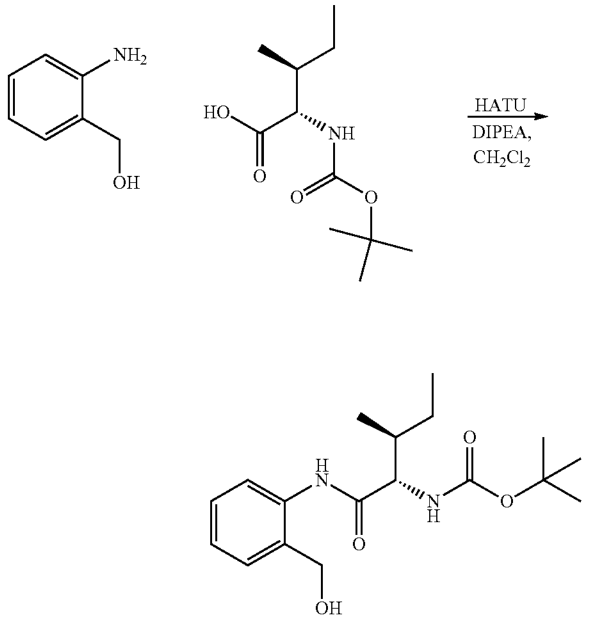

Step 1: tert-Butyl ((2S,3S)-1-((2-(hydroxymethyl)phenyl) amino)-3-methyl-1-oxopentan-2-yl)carbamate. To an ice-cooled mixture of (tert-butoxycarbonyl)-L-isoleucine (50 g, 216 mmol) and (2-aminophenyl)methanol (40 g, 325 mmol) in $CH_2Cl_2$ (500 mL) was added HATU (86 g, 226 mmol) and DIPEA (56 mL, 327 mmol). The reaction mixture was stirred at rt under an argon atmosphere for 23 h and then quenched with water (275 mL). The organic layer was separated and added to 20 wt % citric acid (275 mL), followed by stirring at rt for 10 min. The precipitate was collected, washed with $CH_2Cl_2$ (110 mL), and the layers were shaken and separated. To the organic phase was added 20 wt % citric acid (275 mL), and the mixture was stirred at rt for 10 min. The precipitate was collected, washed with $CH_2Cl_2$ (55 mL), and the layers were shaken and separated. The organic layer was washed by brine (280 mL), dried over $MgSO_4$, filtered, and concentrated under reduced pressure. The residue was purified using silica gel chromatography (15-30% EtOAc/toluene) to afford the product as an off-white solid that was then recrystallized from ethyl acetate/hexane give tert-butyl ((2S,3S)-1-((2-(hydroxymethyl)phenyl)amino)-3-methyl-1-oxopentan-2-yl)carbamate (62.7 g, 186 mmol, 86%) as a colorless solid.

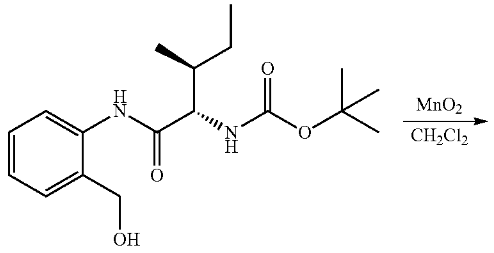

-continued

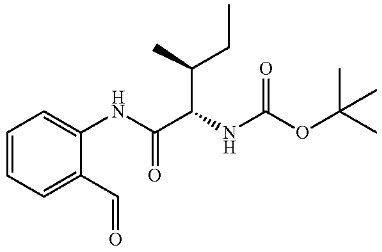

Step 2: tert-Butyl ((2S,3S)-1-((2-formylphenyl)amino)-3-methyl-1-oxopentan-2-yl)carbamate. To a 1-L round-bottom flask was added tert-butyl ((2S,3S)-1-((2-(hydroxymethyl) phenyl)amino)-3-methyl-1-oxopentan-2-yl)carbamate (62.7 g, 186 mmol) and $CH_2Cl_2$ (500 mL). The flask was placed in a water bath followed by the addition of $MnO_2$ (286 g, 2.8 mol), and the reaction mixture was stirred at rt for 4 d. The mixture was then filtered through Celite, and the filter cake was washed twice with $CH_2Cl_2$ (800 mL). The filtrate was concentrated to give tert-butyl ((2S,3S)-1-((2-formylphenyl) amino)-3-methyl-1-oxopentan-2-yl)carbamate (54.7 g, 164 mmol, 88%) as a pale yellow solid.

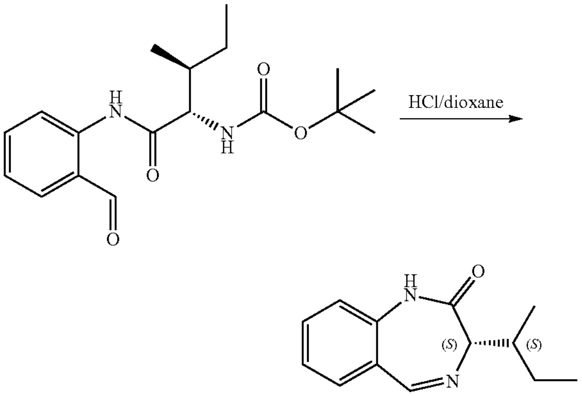

Step 3: (S)-3-((S)-sec-Butyl)-1,3-dihydro-2H-benzo[e][1,4]diazepin-2-one. To a 1-L round-bottom flask was added tert-butyl ((2S,3S)-1-((2-formylphenyl)amino)-3-methyl-1-oxopentan-2-yl)carbamate (54.6 g, 163 mmol) and EtOAc (270 mL). The flask was placed in a water bath followed by the addition of 4 M HCl in EtOAc (200 mL, 800 mmol). The reaction mixture was stirred at rt for 16 h, and the subsequent precipitate was collected and washed with EtOAc. The solid was mixed with $CH_2Cl_2$ and saturated sodium bicarbonate and then stirred for 30 min. The mixture was extracted three times with $CHCl_3$, and the combined organic layer was dried over $MgSO_4$, filtered, and concentrated in vacuo to give (S)-3-((S)-sec-butyl)-1,3-dihydro-2H-benzo[e][1,4]diazepin-2-one (27.6 g, 127 mmol, 78%) as a colorless solid.

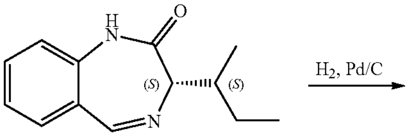

-continued

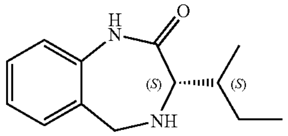

Step 4: (S)-3-((S)-sec-Butyl)-1,3,4,5-tetrahydro-2H-benzo[e][1,4]diazepin-2-one. To a solution of (S)-3-((S)-sec-butyl)-1,3-dihydro-2H-benzo[e][1,4]diazepin-2-one (27.5 g, 127 mmol) in EtOH (150 mL) was added Pd/C-ethylenediamine complex (ca 5 wt % Pd, 4 g, 1.5 mmol), and the mixture was stirred under a hydrogen atmosphere at rt for 30 h. The mixture was filtered through a Celite pad, and the cake washed with EtOH and evaporated in vacuo. The residue was then mixed with EtOH (150 mL), Pd/C-ethylenediamine complex (Pd ca.5%, 4 g, 1.5 mmol), and the mixture was stirred in a hydrogen atmosphere at rt for 7.5 h. The mixture was filtered through a Celite pad, and the cake washed with EtOH and evaporated in vacuo. The residue was triturated with hexane and the precipitation was collected to give (S)-3-((S)-sec-butyl)-1,3,4,5-tetrahydro-2H-benzo[e][1,4]diazepin-2-one (27 g, 124 mmol, 97%) as a colorless solid.

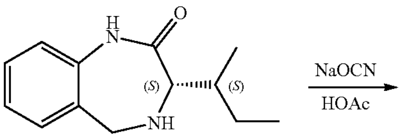

-continued

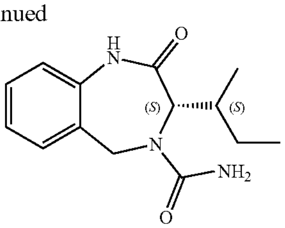

Step 5: (S)-3-((S)-sec-Butyl)-2-oxo-1,2,3,5-tetrahydro-4H-benzo[e][1,4]diazepine-4-carboxamide (Compound 5). To a 250-mL round-bottom flask was added (S)-3-((S)-sec-butyl)-1,3,4,5-tetrahydro-2H-benzo[e][1,4]diazepin-2-one (2.0 g, 9.2 mmol), AcOH (4.72 mL, 82.5 mmol) and EtOH (36 mL). The mixture was heated to 40° C. followed by the addition of sodium cyanate (20 mL of an 0.46 M aqueous solution, 9.3 mmol). After stirring at 40° C. for 1.5 h, additional sodium cyanate (6 mL and 4 mL of an 0.46 M aqueous solution, 4.7 mmol) was added. The reaction mixture was stirred at 40° C. for 1 h, concentrated under reduced pressure, and recrystallized with 30 mL of water to give (S)-3-((S)-sec-butyl)-2-oxo-1,2,3,5-tetrahydro-4H-benzo[e][1,4]diazepine-4-carboxamide (compound 5, 2.28 g, 8.72 mmol, 95%) as a colorless solid. LRMS (ES, m/z) 262.4 (M+H). $^1$H NMR (400 MHz, DMSO-$d_6$) δ 9.92 (s, 1H), 7.29 (d, J=7.7 Hz, 1H), 7.21-7.27 (m, 1H), 7.01-7.08 (m, 2H), 6.13 (s, 2H), 4.60 (d, J=9.7 Hz, 1H), 4.38-4.50 (m, 2H), 1.27-1.46 (m, 2H), 0.90-1.03 (m, 1H), 0.78 (d, J=6.8 Hz, 3H), 0.69 (t, J=7.3 Hz, 3H).

The following compounds were prepared by methods analogous to the method described for Compound 5:

| Compound # | LRMS m/z [M + H] | $^1$H NMR |
|---|---|---|
| 8 | 298.1 | $^1$H NMR (400 MHz, Methanol-$d_4$) δ 6.80 (ddd, J = 10.4, 8.9, 2.5 Hz, 1H), 6.71 (dt, J = 10.1, 2.2 Hz, 1H), 4.72-4.55 (m, 3H), 1.57 (ddp, J = 15.0,7.4, 3.7, 3.1 Hz, 2H), 1.13 (ddq, J = 13.7, 9.0, 7.1 Hz, 1H), 0.94 (d, J = 6.6 Hz, 3H), 0.86 (t, J = 7.4 Hz, 3H). |
| 44 | 280.4 | $^1$H NMR (500 MHz, DMSO-$d_6$) δ 9.80 (s, 1 H), 7.27-7.14 (m, 3H), 6.21 (s, 2H), 4.59 (d, J = 13.2 Hz, 2H), 4.35 (d, J = 13.9 Hz, 1H), 1.38-1.29 (m, 1H), 1.00-0.83 (m, 2H), 0.71 (d, J = 6.4 Hz, 3H), 0.64-0.59 (m, 3H) |
| 65 | 280.2 | $^1$H NMR (399 MHz, DMSO-$d_6$) δ 10.0 (brs, 1 H), 7.28-7.22 (m, 1H), 6.93-6.88 (m, 2H), 6.20 (s, 2H), 4.60 (d, J = 15.7 Hz, 1H), 4.50-4.40 (m, 2H), 1.52-1.38 (m, 2H), 1.07-0.95 (m, 1H), 0.82 (d, J = 6.7 Hz, 3H), 0.75 (t, J = 7.4 Hz, 3H) |
| 67 | 340.0 | $^1$H NMR (500 MHz, DMSO-$d_6$) δ 10.08 (s, 1H), 7.38 (dd, J = 1.1, 8.0 Hz, 1H), 7.19 (dd, J = 8.0 Hz, 1H), 7.08 (dd, J = 1.0, 8.0 Hz, 1H), 6.19 (s, 2H), 4.68 (d, J = 15.1 Hz, 1H), 4.50 (d, J = 15.0 Hz, 1H), 4.43-4.31 (m, 1H), 1.47-1.39 (m, 1H), 1.27-1.09 (m, 1H), 1.06-0.88 (m, 1H), 0.76 (d, J = 6.6 Hz, 3H), 0.70 (t, J = 7.4 Hz, 3H) |
| 68 | 302.4 | $^1$H NMR (500 MHz, DMSO-$d_6$) δ 9.91 (s, 1H), 7.17 (dd, J = 7.8 Hz, 1H), 6.88 (d, J = 8.0 Hz, 1H), 6.85 (d, J = 7.6 Hz, 1H), 6.17 (s, 2H), 5.01 (d, J = 14.2 Hz, 1H), 4.49-4.36 (m, 1H), 4.28 (d, J = 14.2 Hz, 1H), 2.07-2.01 (m, 1H), 1.42-1.33 (m, 1H), 0.97-0.83 (m, 4H), 0.70-0.64 (m, 4 H), 0.60 (t, J = 7.2 Hz, 3H), 0.44-0.51 (1H, m) |
| 73 | 296.3 | $^1$H NMR (500 MHz, DMSO-$d_6$) δ 9.89 (brs, 1H), 7.39 (d, J = 2.5 Hz, 1H), 7.28 (dd, J = 2.5, 8.6 Hz, 1H), 7.08 (d, J = 8.6Hz, 1H), 6.16 (s, 2H), 4.63 (d, J = 9.2 Hz, 1H), 4.52 (d, J = 16.0 Hz, 1H), 4.35 (d, J = 15.9 Hz, 1H), 1.66-1.58 (m, 1H), 1.47-1.39 (m, 1H), 1.08-0.99 (m, 1H), 0.86 (d, J = 6.7 Hz, 3H), 0.77 (t, J = 7.4 Hz, 3H) |

-continued

| Compound # | LRMS m/z [M + H] | $^1$H NMR |
|---|---|---|
| 74 | 302.4 | $^1$H NMR (500 MHz, DMSO-$d_6$) δ 9.79 (s, 1H), 7.02 (d, J = 1.7 Hz, 1H), 6.95-6.91 (m, 2H), 6.10 (s, 2H), 4.56 (d, J = 9.7 Hz, 1H), 4.43 (d, J = 15.1 Hz, 1H), 4.36 (d, J = 15.1 Hz, 1H), 1.88-1.83 (m 1H), 1.43-1.32 (m, 2H), 1.01-0.93 (m, 1H), 0.93-0.89 (m, 2H), 0.78 (d, J = 6.7 Hz, 3H), 0.70 (t, J = 7.3 Hz, 3H), 0.66-0.61 (m, 1 H), 0.60-0.56 (m, 1H) |
| 75 | 280.3 | $^1$H NMR (500 MHz, DMSO-$d_6$) δ 10.00 (s, 1H), 7.35-7.32 (m, 1H), 6.90-6.85 (m, 2H), 6.15 (s, 2H), 4.63 (d, J = 9.4 Hz, 1H), 4.47 (d, J = 15.4 Hz, 1H), 4.37 (d, J = 15.4 Hz, 1H), 1.52-1.44 (m, 1H), 1.44-1.37 (m, 1H) 1.04-0.95 (m, 1H), 0.83 (d, J = 6.7 Hz, 3H), 0.73 (t, J = 7.4 Hz, 3H) |
| 81 | 277.1 | $^1$H NMR (400 MHz, Methanol-$d_4$) δ 8.14 (d, J = 13.9 Hz, 2H), 8.07 (s, 1H), 4.42 (s, 2H), 2.39 (s, 3H), 1.85 (s, 1H), 1.63 (dtd, J = 15.1, 7.6, 3.0 Hz, 1H), 1.20 (ddt, J = 14.2, 8.8, 7.2 Hz, 1H), 1.01 (d, J = 6.6 Hz, 3H), 0.93 (t, J = 7.4 Hz, 3H). |
| 121 | 260.1 | N/A |
| 123 | 274.4 | N/A |
| 129 | 276.4 | N/A |

Example 2: Synthesis of Compound 29

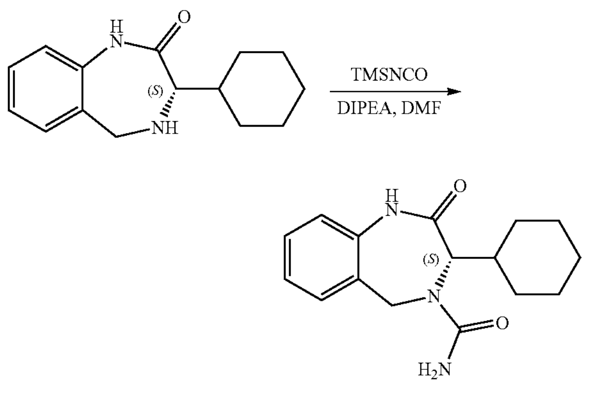

(S)-3-Cyclohexyl-2-oxo-1,2,3,5-tetrahydro-4H-benzo[e][1,4]diazepine-4-carboxamide (Compound 29). To a mixture of (S)-3-cyclohexyl-1,3,4,5-tetrahydro-2H-benzo[e][1,4]diazepin-2-one (50 mg) and DIPEA (0.1 mL) in DMF (1 mL) was added isocyanato(trimethyl)silane (0.033 mL). After stirring at rt overnight, the resulting mixture was cooled with an ice-bath, followed by the addition of isocyanato(trimethyl)silane (0.050 mL) and DIPEA (0.1 mL). The reaction was stirred at 0° C. for 1 h and then at rt overnight. The reaction mixture was diluted with water and saturated aqueous $NaHCO_3$, and then extracted with EtOAc. The organic layer was washed with $H_2O$, dried over $MgSO_4$, concentrated. The residue was purified by column chromatography on silica gel ($CHCl_3$/MeOH) to give a solid that was stirred in ethyl acetate (1 mL) for 1 h, followed by filtration and dried in vacuo to give (S)-3-cyclohexyl-2-oxo-1,2,3,5-tetrahydro-4H-benzo[e][1,4]diazepine-4-carboxamide (compound 29, 21 mg) as a colorless solid. LRMS (APCI) m/z 288.2 (M+H). $^1$H NMR (500 MHz, DMSO-$d_6$) δ 9.91 (s, 1H), 7.30 (d, J=7.5 Hz, 1H), 7.24 (td, J=1.5 Hz, 7.7 Hz, 1H), 7.07-7.01 (m, 2H), 6.10 (s, 2H), 4.62 (d, J=9.0 Hz, 1H), 4.50-4.34 (m, 2H), 1.68-1.48 (m, 5H), 1.39-1.26 (m, 1H), 1.11-0.86 (m, 5H).

Example 3: Synthesis of Compound 32

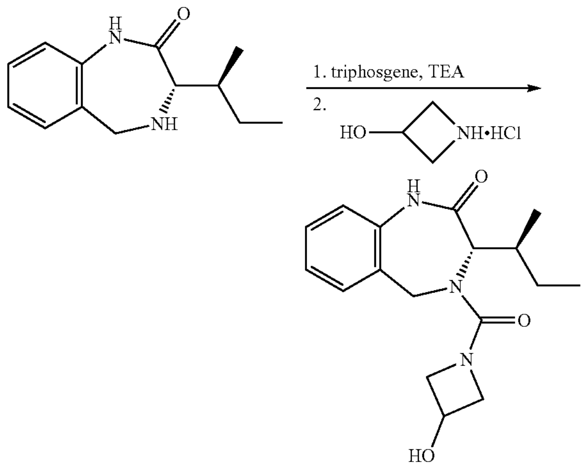

(S)-3-((S)-sec-Butyl)-4-(3-hydroxyazetidine-1-carbonyl)-1,3,4,5-tetrahydro-2H-benzo[e][1,4]diazepin-2-one (Compound 32). To a mixture of (S)-3-((S)-sec-butyl)-1,3,4,5-tetrahydro-2H-benzo[e][1,4]diazepin-2-one (300 mg), and DIPEA (1.2 mL) in THF (6 mL) was added triphosgene (140 mg). The mixture was stirred for 30 min, followed by the addition of azetidin-3-ol hydrogen chloride (300 mg). The reaction was stirred for 3 h, concentrated, and partitioned in 10% citric acid aq. and $CHCl_3$. The organic layer was separated, concentrated, and purified using silica gel column chromatography ($CHCl_3$/MeOH) to give (S)-3-((S)-sec-butyl)-4-(3-hydroxyazetidine-1-carbonyl)-1,3,4,5-tetrahydro-2H-benzo[e][1,4]diazepin-2-one (Compound 32, 379 mg) as a colorless solid. LRMS (ES) m/z 318.2 (M+H). $^1$H NMR (399 MHz, DMSO-$d_6$) δ 9.89 (s, 1H), 7.20-7.32 (m, 2H), 7.01-7.09 (m, 2H), 5.58 (d, J=6.2 Hz, 1H), 4.46-4.52 (m, 1H), 4.31-4.44 (m, 3H), 4.13-4.19 (m, 1H), 4.03-4.10 (m, 1H), 3.63-3.75 (m, 2H), 1.33-1.49 (m, 2H), 0.91-1.06 (m, 1H), 0.80 (d, J=6.6 Hz, 3H), 0.72 (t, J=7.3 Hz, 3H).

The following compounds were prepared by methods analogous to the methods described for Compound 32 and related compounds:

| Compound # | LRMS m/z [M + H] | $^1$H NMR |
|---|---|---|
| 58 | 290.2 | $^1$H NMR (400 MHz, DMSO-$d_6$) δ 9.83 (s, 1 H), 7.26-7.18 (m, 2H), 7.08-6.97 (m, 2H), 4.44-4.34 (m, 2H), 4.14 (d, J = 9.5 Hz, 1H), 2.78 (s, 6H), 1.66-1.55 (m, 1H), 1.47-1.35 (m, 1H), 1.08-0.96 (m, 1H), 0.81 (d, J = 6.8 Hz, 3H), 0.76 (t, J = 7.4 Hz, 3H). |
| 59 | 332.2 | $^1$H NMR (500 MHz, DMSO-$d_6$) δ 9.91 (brs, 1H), 7.30 (d, J = 7.6 Hz, 1H), 7.25-7.22 (m, 1H), 7.06-7.02 (m, 2H), 4.48 (d, J = 15.7 Hz, 1H), 4.37 (d, J = 15.8 Hz, 1H), 4.35-4.33 (m, 1H), 4.20-4.12 (m, 2H), 4.07 (dd, J = 6.4, 8.9 Hz, 1H), 3.81 (dd, J = 3.7, 9.1, Hz, 1H), 3.72 (dd, J = 3.7, 9.1, Hz, 1H), 3.19 (s, 3H), 1.47-1.34 (m, 2H), 1.01-0.92 (m, 1 H), 0.79 (d, J = 6.7 Hz, 3H), 0.71 (t, J = 7.4 Hz, 3H) |
| 66 | 352.1 | $^1$H NMR (400 MHz, DMSO-$d_6$) δ 10.06 (s, 1H), 7.26 (t, J = 8.0 Hz, 1H), 7.20 (dd, J = 8.0, 1.4 Hz, 1H), 7.09 (dd, J = 8.0, 1.4 Hz, 1H), 5.61 (d, 7 = 6.3 Hz, 1H), 4.66 (d, J = 16.4 Hz, 1H), 4.45 (d, J = 16.4 Hz, 1H), 4.44-4.33 (m, 1H), 4.25 (s, 1H), 4.17-3.99 (m, 2H), 3.74-3.65 (m, 2H), 1.55-1.37 (m, 2H), 1.01 (dt, J = 15.1, 7.9 Hz, 1H), 0.83 (d, J = 6.6 Hz, 3H), 0.76 (t, J = 7.4 Hz, 3H). |
| 72 | 336.2 | $^1$H NMR (399 MHz, DMSO-$d_6$) δ 9.89 (brs, 1H), 7.21 (d, J = 8.8 Hz, 1H), 7.10-7.07 (m, 2H), 5.58 (d, J = 6.2 Hz, 1H), 4.50 (d, J = 6.2 Hz, 1H), 4.42-4.29 (m, 3H), 4.16 (t, J = 7.7 Hz, 1H), 4.05 (t, J = 7.7 Hz, 1H), 3.72 (dd, J = 8.7, 4.8 Hz, 1H), 3.65 (dd, J = 8.7, 4.8 Hz, 1H), 1.54-1.34 (m, 2H), 1.04-0.92 (m, 1H), 0.81 (d, J = 6.7 Hz, 3H), 0.74 (t, J = 7.4 Hz, 3H) |
| 76 | 336.4 | $^1$H NMR (500 MHz, DMSO-$d_6$) δ 10.00 (s, 1H), 7.36-7.30 (m, 1H), 6.91-6.85 (m, 2H), 5.58 (d, J = 6.3 Hz, 1H), 4.50-4.43 (m, 1H), 4.41-4.29 (m, 3H), 4.16 (t, J = 7.7 Hz, 1H), 4.08-4.00 (m, 1 H) 3.72 (dd, J = 8.6, 4.8 Hz, 1H), 3.66-3.58 (m, 1H), 1.61-1.48 (m, 1H), 1.46-1.33 (m, 1H), 1.07-0.95 (m, 1H), 0.83 (d, J = 6.6 Hz, 3H), 0.75 (t, J = 7.4 Hz, 3H) |
| 77 | 294.2 | $^1$H NMR (500 MHz, DMSO-$d_6$) δ 10.02 (s, 1 H) 7.37-7.30 (m, 1 H), 6.90-6.86 (m, 2 H), 6.61-6.53 (1 H, m), 4.62 (br d, J = 9.8 Hz, 1 H), 4.47-4.36 (m, 2 H), 2.56 (d, J = 4.3 Hz, 3 H), 1.45-1.35 (m, 2 H), 1.01-0.93 (m, 1 H), 0.81 (d, J = 6.7 Hz, 3 H), 0.76-0.67 (m, 3 H) |
| 78 | 294.2 | $^1$H NMR (500 MHz, DMSO-$d_6$) δ 9.89-9.78 (m, 1 H), 7.30-7.12 (m, 3 H), 6.68-6.57 (m, 1 H), 4.65-4.51 (m, 2 H), 4.40-4.27 (m, 1 H), 2.67-2.56 (m, 3 H), 1.32 (m, 1 H), 1.22-1.12 (m, 1 H), 0.92-0.81 (m, 1 H), 0.75-0.66 (m, 3 H), 0.63-0.58 (m, 3 H) |
| 79 | 336.4 | $^1$H NMR (500 MHz, DMSO-$d_6$) δ 9.75 (br s, 1H), 7.27-7.13 (3H, m), 5.60 (d, J = 6.3 Hz, 1H), 4.50-4.34 (m, 4H), 4.23-4.15 (m, 1H), 4.14-4.08 (m, 1H), 3.77 (dd, J = 4.9, 8.7 Hz, 1H), 3.70 (dd, J = 5.2, 8.7 Hz, 1H), 1.36-1.22 (m, 1H), 1.11-1.00 (m, 1H), 0.95-0.83 (m, 1H), 0.72 (d, J = 6.6 Hz, 3H), 0.63 (t, J = 7.3 Hz, 3H) |

| Compound # | LRMS m/z [M + H] |
|---|---|
| 93 | 369.0 |
| 94 | 369.0 |
| 96 | 371.4 |
| 97 | 344.5 |
| 98 | 331.4 |
| 99 | 339.3 |
| 100 | 341.4 |
| 101 | 328.3 |
| 102 | 332.4 |
| 103 | 345.1 |
| 133 | 347.3 |
| 134 | 346.4 |
| 135 | 348.4 |
| 136 | 348.4 |
| 137 | 348.4 |
| 138 | 331.4 |
| 139 | 373.4 |
| 140 | 348.4 |
| 141 | 375.5 |

-continued

| Compound # | LRMS m/z [M + H] |
|---|---|
| 142 | 345.3 |
| 143 | 345.2 |
| 144 | 345.4 |
| 220 | 368.2 |
| 221 | 369.2 |
| 222 | 375.3 |
| 223 | 375.3 |
| 224 | 380.3 |
| 225 | 320.0 |
| 226 | 331.0 |
| 227 | 332.0 |
| 228 | 333.0 |
| 229 | 345.0 |
| 230 | 345.3 |
| 231 | 345.3 |
| 232 | 347.0 |
| 233 | 354.0 |
| 234 | 359.3 |

-continued

| Compound # | LRMS m/z [M + H] |
|---|---|
| 235 | 359.3 |
| 236 | 360.0 |
| 237 | 371.0 |
| 238 | 373.0 |
| 239 | 373.4 |
| 240 | 382.3 |
| 241 | 383.3 |
| 242 | 387.3 |
| 243 | 389.3 |
| 244 | 398.3 |
| 245 | 399.3 |
| 246 | 409.3 |
| 247 | 423.3 |
| 248 | 423.3 |
| 249 | 346.2 |
| 250 | 345.2 |
| 251 | 346.0 |
| 252 | 395.3 |
| 253 | 383.3 |
| 254 | 409.4 |
| 255 | 413.3 |
| 256 | 333.0 |
| 257 | 423.0 |
| 258 | 432.3 |
| 259 | 417.3 |
| 260 | 374.3 |
| 261 | 362.0 |
| 262 | 444.4 |
| 263 | 361.3 |
| 264 | 371.4 |
| 265 | 400.4 |
| 266 | 387.3 |
| 267 | 430.4 |
| 268 | 463.4 |
| 269 | 403.4 |
| 270 | 389.3 |
| 271 | 331.0 |
| 272 | 344.0 |
| 273 | 327.0 |
| 274 | 420.0 |
| 275 | 438.4 |
| 276 | 352.1 |
| 277 | 356.4 |
| 278 | 379.4 |
| 279 | 374.4 |
| 279 | 435.4 |
| 280 | 332.4 |
| 281 | 435.4 |
| 282 | 332.3 |
| 283 | 360.3 |
| 284 | 369.4 |
| 285 | 346.4 |
| 286 | 395.3 |
| 287 | 395.3 |
| 288 | 366.2 |
| 289 | 360.2 |
| 290 | 359.3 |
| 291 | 369.2 |
| 292 | 369.2 |
| 293 | 346.4 |
| 294 | 373.4 |
| 295 | 387.4 |
| 296 | 359.4 |
| 297 | 318.4 |
| 298 | 382.4 |
| 299 | 386.3 |
| 300 | 338.3 |
| 301 | 389.3 |
| 302 | 360.2 |
| 303 | 360.3 |
| 304 | 373.4 |
| 305 | 373.4 |
| 306 | 320.4 |
| 307 | 331.4 |
| 308 | 331.4 |
| 325 | 276.1 |
| 332 | 304.1 |

-continued

| Compound # | LRMS m/z [M + H] |
|---|---|
| 335 | 262.1 |
| 337 | 336.2 |
| 338 | 294.2 |
| 340 | 350.4 |
| 346 | 350.5 |
| 347 | 350.4 |
| 348 | 294.4 |
| 349 | 393.4 |
| 350 | 363.5 |
| 351 | 407.3 |
| 352 | 378.3 |
| 354 | 350.4 |
| 355 | 350.2 |
| 356 | 407.5 |
| 357 | 266.4 |
| 358 | 363.3 |
| 359 | 350.4 |
| 363 | 364.4 |
| 369 | 347.2 |
| 370 | 337.1 |
| 379 | 319.1 |

Example 4: Synthesis of Compound 31

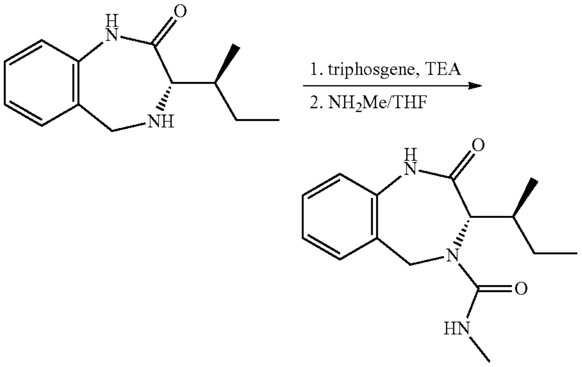

(S)-3-((S)-sec-Butyl)-N-methyl-2-oxo-1,2,3,5-tetrahydro-4H-benzo[e][1,4]diazepine-4-carboxamide (Compound 31). To an ice-cooled mixture of (S)-3-((S)-sec-butyl)-1,3,4,5-tetrahydro-2H-benzo[e][1,4]diazepin-2-one (200 mg, 916 μmol) and DIPEA (470 μL, 2.75 mmol) in $CH_2Cl_2$ (4 mL) was added triphosgene (110 mg, 370 μmol). The reaction was stirred for 30 min and then cooled with an ice bath. Methylamine (2 M in THF, 1.3 mL, 2.6 mmol) was added, and the reaction was warmed to rt and stirred for 1 h. The reaction mixture was quenched with water, the layers were separated, and the organic layer was concentrated. The residue was purified using silica gel chromatography (20-80% EtOAc/hexane) to give a solid that was triturated with diisopropylether and the precipitate was collected to give (S)-3-((S)-sec-butyl)-N-methyl-2-oxo-1,2,3,5-tetrahydro-4H-benzo[e][1,4]diazepine-4-carboxamide (Compound 31, 161 mg, 584 μmol, 64%) as a colorless solid. LRMS (ES) m/z 276.2 (M+H). $^1$H NMR (400 MHz, DMSO-$d_6$) δ 9.92 (s, 1H), 7.22-7.31 (m, 2H), 7.02-7.07 (m, 2H), 6.52-6.58 (m, 1H), 4.59 (d, J=10.1 Hz, 1H), 4.38-4.48 (m, 2H), 2.58 (d, J=4.4 Hz, 3H), 1.32-1.43 (m, 1H), 1.17-1.32 (m, 1H), 0.86-1.00 (m, 1H), 0.76 (d, J=6.6 Hz, 3H), 0.67 (t, J=7.4 Hz, 3H).

Example 5: Synthesis of Compound 41

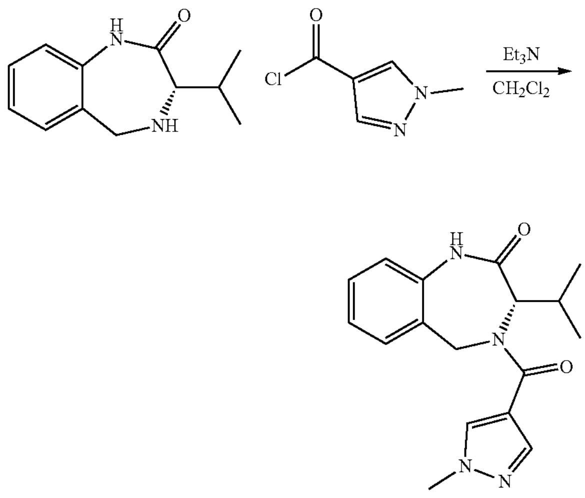

(S)-3-Isopropyl-4-(1-methyl-1H-pyrazole-4-carbonyl)-1,3,4,5-tetrahydro-2H-benzo[e][1,4]diazepin-2-one (Compound 41). 1-Methyl-1H-pyrazole-4-carbonyl chloride (62 mg, 0.431 mmol) was added to a stirring solution of (S)-3-isopropyl-1,3,4,5-tetrahydro-2H-benzo[e][1,4]diazepin-2-one (80 mg, 0.392 mmol) and triethylamine (106 mL, 0.783 mmol) in $CH_2Cl_2$ (2 mL) at rt. After 4 h, the reaction was concentrated, the resultant residue suspended in MeOH (total volume 1.8 mL) and filtered through a 0.4 μm syringe filter, followed by purification using reverse phase HPLC (0->30% MeCN/$H_2O$ w/0.1% formic acid) to give (S)-3-isopropyl-4-(1-methyl-1H-pyrazole-4-carbonyl)-1,3,4,5-tetrahydro-2H-benzo[e][1,4]diazepin-2-one as a white solid (Compound 41, 55 mg, 45%). LRMS (APCI) m/z 313.1 (M+H). $^1$H NMR (400 MHz, methanol-$d_4$) δ 7.95 (s, 1H), 7.72 (s, 1H), 7.22 (dt, J=7.3, 13.2 Hz, 2H), 7.05 (t, J=7.5 Hz, 1H), 6.98 (d, J=8.0 Hz, 1H), 4.85 (s, 2H), 3.85 (s, 3H), 1.51 (s, 1H), 0.81 (d, J=6.1 Hz, 3H), 0.73 (d, J=6.5 Hz, 3H).

The following compounds were prepared by methods analogous to the method described for Compound 41:

| Compound # | LRMS m/z [M + H] |
|---|---|
| 373 | 328.1 |
| 371 | 386.1 |
| 363 | 310.1 |

Example 6: Synthesis of Compound 15

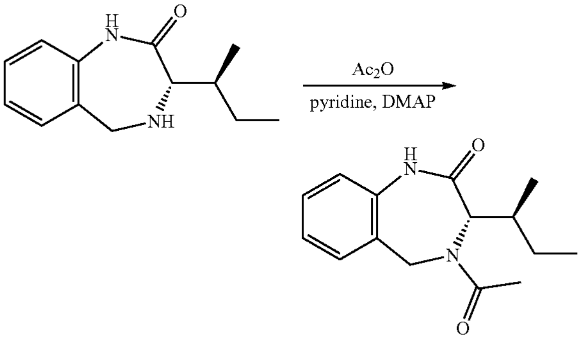

(S)-4-Acetyl-3-((S)-sec-butyl)-1,3,4,5-tetrahydro-2H-benzo[e][1,4]diazepin-2-one (Compound 15). To a mixture of (S)-3-((S)-sec-butyl)-1,3,4,5-tetrahydro-2H-benzo[e][1,4]diazepin-2-one (200 mg, 916 μmol), DMAP (12 mg, 98 μmol), and pyridine (2 mL) was added $Ac_2O$ (170 μL, 1.8 mmol). After stirring at rt for 3 h, the reaction mixture was concentrated under reduced pressure. The residue was purified with silica gel chromatography (10-60% EtOAc/hexane) to give (S)-4-acetyl-3-((S)-sec-butyl)-1,3,4,5-tetrahydro-2H-benzo[e][1,4]diazepin-2-one (Compound 15, 93 mg, 357 μmol, 39%) as a colorless solid. LRMS (ES) m/z 261.3 (M+H). $^1$H NMR (400 MHz, DMSO-$d_6$) δ 10.06 (s, 1H), 7.39 (d, J=7.5 Hz, 0.75H), 7.32-7.26 (m, 1H), 7.23 (d, J=7.5 Hz, 0.25H), 7.12-7.03 (m, 2H), 4.88 (d, J=10.1 Hz, 0.75H), 4.81 (d, J=15.9 Hz, 0.25H), 4.66-4.55 (m, 1.5H), 4.49-4.37 (m, 0.25H), 4.15 (d, J=10.1 Hz, 0.25H), 2.14 (s, 2.25H), 2.07 (s, 0.75H), 1.49-1.37 (m, 0.5H), 1.37-1.24 (m, 1.5H), 1.09-0.97 (m, 0.25H), 0.96-0.86 (m, 0.75H), 0.84 (d, J=6.6 Hz, 0.75H), 0.78 (d, J=6.6 Hz, 2.25H), 0.73 (t, J=7.3 Hz, 0.75H), 0.65 (t, J=7.3 Hz, 2.25H)

The following compounds were prepared by methods analogous to the method described for Compound 15:

| Compound # | LRMS m/z [M + H] | $^1$H NMR |
|---|---|---|
| 28 | 287.2 | $^1$H NMR (500 MHz, DMSO-$d_6$) δ 10.05 (s, 1H), 7.38 (d, J = 7.5 Hz, 1H), 7.31-7.22 (m, 1H), 7.10-7.03 (m, 2 H), 4.89 (br d, J = 9.8 Hz, 0.8 H), 4.75 (br d, J = 15.2 Hz, 0.2H), 4.63-4.54 (m, 1.6H), 4.42 (br d, J = 15.6 Hz, 0.2 H), 4.19 (br d J = 10.1 Hz, 0.2 H), 2.13 (s, 2.3 H), 2.06 (s, 0.7 H), 1.68-1.37 (5 H, m), 1.31-1.19 (m, 1 H, m) 0.77-1.12 (5 H, m) |
| 69 | 279.2 | $^1$H NMR (500 MHz, DMSO-$d_6$) δ 10.06 (s, 1H), 7.33 (dd, J = 9.2, 2.9 Hz, 0.75H), 7.22-7.06 (m, 2.25H), 4.89-4.80 (m, 1H), 4.66-4.56 (m, 1.5H), 4.17-4.15 (m, 0.25H), 4.05-4.01 (m, 0.25H), 2.14 (s, 2.25H), 2.07 (s, 0.75H), 1.55-1.23 (m, 2H), 0.84-0.93 (m, 1H), 0.78-0.75 (m, 3H), 0.68-0.65 (m, 3H) |
| 91 | 301.3 | N/A |
| 326 | 247.2 | N/A |
| 361 | 280.1 | N/A |

Example 7: Synthesis of Compound 18

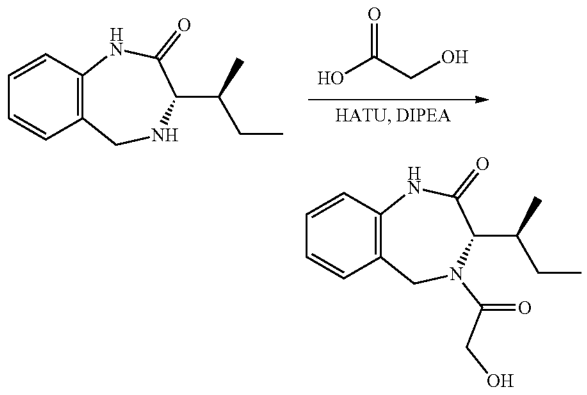

(S)-3-((S)-sec-Butyl)-4-(2-hydroxyacetyl)-1,3,4,5-tetrahydro-2H-benzo[e][1,4]diazepin-2-one. To a mixture of (S)-3-((S)-sec-butyl)-1,3,4,5-tetrahydro-2H-benzo[e][1,4]diazepin-2-one (300 mg) and hydroxyacetic acid (157 mg) in DMF (6 mL) was added HATU (784 mg) and DIPEA (710 L). The mixture was stirred for 3 d. The mixture was diluted with water and extracted with EtOAc. The combined organic layer was washed with saturated ammonium chloride, brine, and then concentrated in vacuo. The residue was purified by silica gel column chromatography (hexane/EtOAc) to give (S)-3-((S)-sec-butyl)-4-(2-hydroxyacetyl)-1,3,4,5-tetrahydro-2H-benzo[e][1,4]diazepin-2-one (Compound 18, 152 mg) as a colorless solid. LRMS (ES), m/z 277.2 z(M+H). $^1$H NMR (500 MHz, DMSO-$d_6$) δ 10.11 (s, 1H), 7.38 (d, J=7.3 Hz, 1H), 7.29-7.34 (m, 1H), 7.04-7.13 (m, 2H), 4.83 (br d, J=10.3 Hz, 1H), 4.68 (t, J=5.7 Hz, 1H), 4.40-4.57 (m, 3H), 4.04-4.20 (m, 1H), 1.22-1.32 (m, 1H), 1.15-1.22 (m, 1H), 0.81-0.93 (m, 1H), 0.77 (d, J=6.6 Hz, 3H), 0.63 (t, J=7.3 Hz, 3H).

The following compounds were prepared by methods analogous to the method described for Compound 18:

| Compound # | LRMS m/z [M + H] | $^1$H NMR |
|---|---|---|
| 42 | 295.3 | $^1$H NMR (500 MHz, DMSO-$d_6$) δ 10.21-10.16 (m, 1H), 7.45-7.32 (m, 1H), 6.97-6.89 (m, 2H), 4.92-4.82 (m, 1H), 4.70 (t, J = 5.7 Hz, 1H), 4.56-4.34 (m, 2H), 4.18-4.05 (m, 2H), 1.68-1.25 (m, 2H), 0.97-0.66 (m, 7H). |
| 43 | 309.4 | $^1$H NMR (500 MHz, DMSO-$d_6$) δ 10.19-10.15 (m, 1H), 7.47-7.31 (m, 1H), 6.96-6.87 (m, 2H), 4.92-4.83 (m, 1H), 4.67-4.18 (m, 3H), 3.65-3.58 (m, 2H), 2.83-2.36 (m, 2H), 1.58-1.28 (m, 2H), 0.97-0.66 (m, 7H) |
| 45 | 313.2 | $^1$H NMR (500 MHz, DMSO-$d_6$) δ 13.26 (br s, 1H), 10.11 (br s, 1H), 8.38-7.71 (m, 2H), 7.34-7.22 (m, 2H), 7.12-7.04 (m, 2H), 5.26-4.38 (m, 3H), 1.42-1.22 (m, 2H), 0.95 (br d, J = 6.7 Hz, 1H), 0.79 (d, J = 6.6 Hz, 3H), 0.65 (t, J = 7.3 Hz, 3H). |
| 46 | 327.4 | $^1$H NMR (500 MHz, DMSO-$d_6$) δ 10.11 (br s, 1H), 8.17 (br s, 1H), 7.77 (s, 1H), 7.33-7.20 (m, 2H), 7.14-7.02 (m, 2H), 5.05-4.68 (m, 3H), 3.89-3.85 (m, 3H), 1.42-1.25 (m, 2H), 0.99-0.89 (m, 1H), 0.79 (d, J = 6.6 Hz, 3H), 0.65 (t, J = 7.4 Hz, 3H). |
| 47 | 340.3 | $^1$H NMR (399 MHz, DMSO-$d_6$) δ 10.22-10.11 (m, 1H), 7.67-7.53 (m, 1H), 7.38-7.24 (m, 1H), 7.15-7.01 (m, 3H), 6.69-6.43 (m, 2H), 4.95-4.74 (m, 1H), 4.68-4.50 (m, 2H), 4.41-4.01 (m, 1H), 1.56-1.21 (m, 2H), 1.08-0.88 (m, 1H), 0.81 (d, J = 6.4 Hz, 3H), 0.67 (t, J = 7.2 Hz, 3H). |
| 48 | 340.2 | $^1$H NMR (399 MHz, DMSO-$d_6$) δ 11.81 (br s, 1H), 10.22-10.11 (m, 1H), 7.48 (d, J = 6.6 Hz, 1H), 7.40-7.26 (m, 1H), 7.14-7.03 (m, 3H), 6.23-6.13 (m, 1H), 6.10-6.01 (m, 1H), 4.96-4.77 (m, 1H), 4.70-4.48 (m, 2H), 1.48-1.29 (m, 2H), 1.12-0.93 (m, 1H), 0.88-0.77 (m, 3H), 0.75-0.62 (m, 3H) |
| 49 | 291.2 | $^1$H NMR (500 MHz, DMSO-$d_6$) δ 10.05 (s, 1H), 7.41-7.22 (m, 2H), 7.11-7.04 (m, 2H), 4.94-4.18 (m, 4H), 3.68-3.59 (m, 2H), 2.86-2.78 (m, 1H), 2.50-2.43 (m, 1H), 1.50-1.22 (m, 2H), 1.06-0.86 (m, 1H), 0.86-0.76 (m, 3H), 0.76-0.61 (m, 3H) |
| 50 | 329.2 | N/A |
| 70 | 331.4 | $^1$H NMR (500 MHz, DMSO-$d_6$) δ 13.31-13.25 (m, 1H), 10.05 (br s, 1H), 7.85-7.80 (m, 1H), 7.25-7.02 (m, 3H), 6.60 (br s, 1H), 5.71 (br d, J = 8.7 Hz, 0.35H), 5.22-4.83 (m, 2.2H), 4.55 (br d, J = 15.9 Hz, 0.45H), 1.63-1.42 (m, 2H), 1.09-0.98 (m, 1H), 0.87-0.65 (m, 6H) |

-continued
| Compound # | LRMS m/z [M + H] |
|---|---|
| 83 | 363.3 |
| 84 | 327.3 |
| 85 | 355.2 |
| 86 | 291.2 |
| 92 | 303.4 |
| 95 | 329.2 |
| 104 | 313.2 |
| 105 | 313.3 |
| 106 | 317.2 |
| 107 | 317.2 |
| 108 | 325.2 |
| 109 | 368.2 |
| 110 | 340.1 |
| 111 | 339.1 |
| 122 | 325.1 |
| 124 | 317.3 |
| 125 | 392.3 |
| 126 | 414.5 |
| 127 | 330.4 |
| 128 | 339.0 |
| 147 | 332.1 |
| 148 | 344.0 |
| 149 | 319.1 |
| 150 | 363.3 |
| 151 | 363.3 |
| 152 | 314.3 |
| 153 | 314.4 |
| 154 | 354.4 |
| 155 | 340.3 |
| 156 | 354.3 |
| 157 | 328.2 |
| 158 | 367.3 |
| 159 | 328.4 |
| 160 | 313.1 |
| 161 | 330.2 |
| 162 | 367.2 |
| 163 | 384.2 |
| 164 | 371.2 |
| 165 | 378.2 |
| 166 | 356.2 |
| 167 | 378.2 |
| 168 | 406.2 |
| 169 | 406.2 |
| 170 | 384.2 |
| 171 | 364.2 |
| 172 | 354.2 |
| 173 | 370.2 |
| 174 | 399.2 |
| 175 | 429.2 |
| 176 | 380.2 |
| 177 | 316.2 |
| 178 | 316.2 |
| 179 | 371.2 |
| 180 | 411.2 |
| 181 | 364.2 |
| 182 | 372.2 |
| 183 | 319.3 |
| 184 | 360.3 |
| 185 | 360.3 |
| 186 | 387.2 |
| 190 | 325.1 |
| 191 | 325.0 |
| 192 | 325.0 |
| 193 | 344.1 |
| 194 | 344.1 |
| 195 | 318.1 |
| 196 | 332.2 |
| 197 | 358.1 |
| 198 | 332.2 |
| 199 | 305.1 |
| 200 | 405.1 |
| 322 | 313.1 |
| 327 | 326.0 |
| 328 | 343.1 |
| 329 | 341.1 |
| 330 | 357.1 |
| 331 | 299.1 |
| 339 | 309.4 |
| 341 | 295.3 |
| 342 | 331.3 |
| 343 | 332.4 |
| 344 | 358.4 |
| 360 | 419.4 |
| 362 | 296.1 |
| 367 | 295.1 |
| 368 | 361.1 |
Example 8: Synthesis of Compound 16
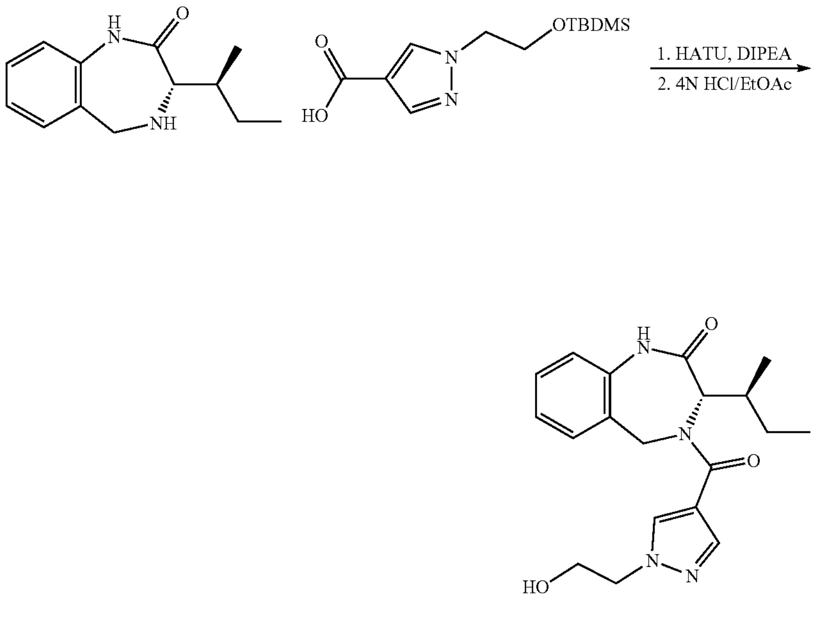

(S)-3-((S)-sec-Butyl)-4-(1-(2-hydroxyethyl)-1H-pyrazole-4-carbonyl)-1,3,4,5-tetrahydro-2H-benzo[e][1,4]diazepin-2-one (Compound 16). To a mixture of (S)-3-((S)-sec-butyl)-1,3,4,5-tetrahydro-2H-benzo[e][1,4]diazepin-2-one (160 mg) and 1-(2-{[tert-butyl(dimethyl)silyl]oxy}ethyl)-1H-pyrazole-4-carboxylic acid (210 mg) in DMF (3 mL) was added HATU (310 mg) and DIPEA (320 L). The reaction mixture was stirred for 3.5 h. The mixture was diluted with water and extracted with EtOAc twice. The combined organic layer was washed with a 50% brine solution, brine, and then dried over $MgSO_4$ and concentrated in vacuo. The residue was purified by silica gel column chromatography ($CHCl_3$/EtOAc) to give 265 mg of (S)-3-((S)-sec-butyl)-4-(1-(2-((tert-butyldimethylsilyl)oxy)ethyl)-1H-pyrazole-4-carbonyl)-1,3,4,5-tetrahydro-2H-benzo[e][1,4]diazepin-2-one. Methanol (1.5 mL) was then added to (S)-3-((S)-sec-butyl)-4-(1-(2-((tert-butdhydihylsilyl)oxy)ethyl)-1H-pyrazole-4-carbonyl)-1,3,4,5-tetrahydro-2H-benzo[e][1,4]diazepin-2-one, followed by the addition of HCl/EtOAc (4 M, 1.5 mL). The reaction mixture was stirred for 2 h and then concentrated in vacuo. The residue was purified by column chromatography on amino functionalized silica gel ($CHCl_3$/MeOH) to give (S)-3-((S)-sec-butyl)-4-(1-(2-hydroxyethyl)-1H-pyrazole-4-carbonyl)-1,3,4,5-tetrahydro-2H-benzo[e][1,4]diazepin-2-one (Compound 16,107 mg) as a colorless solid. LRMS (ES), m/z 357.3 (M+H). $^1$H NMR (400 MHz, DMSO-$d_6$) δ 10.10 (1H, br s), 8.16 (1H, br s), 7.79 (1H, s), 7.23-7.35 (H, m), 7.04-7.12 (2H, m), 4.69-4.99 (4H, m), 4.17 (2H, t, J=5.5 Hz), 3.71-3.79 (2H, m), 1.21-1.48 (2H, m), 0.88-1.04 (1H, m), 0.79 (3H, d, J=6.8 Hz), 0.65 (3H, t, J=7.4 Hz).

Example 9: Synthesis of Compound 1

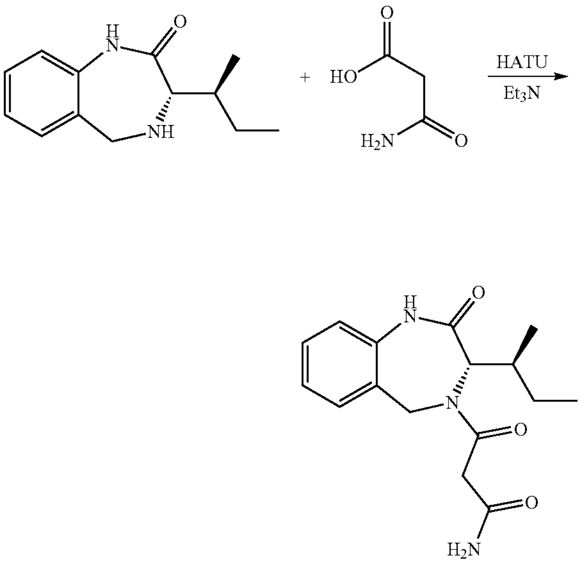

3-((S)-3-((S)-sec-Butyl)-2-oxo-1,2,3,5-tetrahydro-4H-benzo[e][1,4]diazepin-4-yl)-3-oxopropanamide (Compound 1). To a suspension of (S)-3-((S)-sec-butyl)-1,3,4,5-tetrahydro-2H-benzo[e][1,4]diazepin-2-one (1.02 g, 4.67 mmol), malonamic acid (578 mg, 5.61 mmol), HATU (2.13 g, 5.61 mmol) in DMF (10 mL) was added triethylamine (1.95 mL, 14.0 mmol), and then stirred at rt overnight. The reaction was diluted with EtOAc (30 mL), washed with $H_2O$ (10 mL) and brine (10 mL), dried with $Na_2SO_4$, filtered, purified by reverse phase HPLC (5-70% MeCN/$H_2O$, 0.1% formic acid buffer), and re-purified by silica gel (0-10% MeOH/DCM) to provide 3-((S)-3-((S)-sec-butyl)-2-oxo-1,2,3,5-tetrahydro-4H-benzo[e][1,4]diazepin-4-yl)-3-oxopropanamide (717 mg, 51%) as a white solid. LRMS (APCI) m/z 304.1 (M+H). $^1$H NMR (400 MHz, 343 K, DMSO-$d_6$) δ 9.87 (s, 1H), 7.40-7.25 (m, 3H), 7.12-7.07 (m, 2H), 6.84 (s, 1H), 4.89 (d, J=9.8 Hz, 1H), 4.73 (d, J=14.6 Hz, 1H), 4.62 (d, J=14.7 Hz, 1H), 3.52 (d, J=15.2 Hz, 1H), 3.32 (d, J=14.6 Hz, 1H), 1.45-1.26 (m, 2H), 1.00-0.90 (m, 1H), 0.88-0.76 (m, 3H), 0.73-0.63 (m, 3H).

Example 10: Synthesis of Compound 17

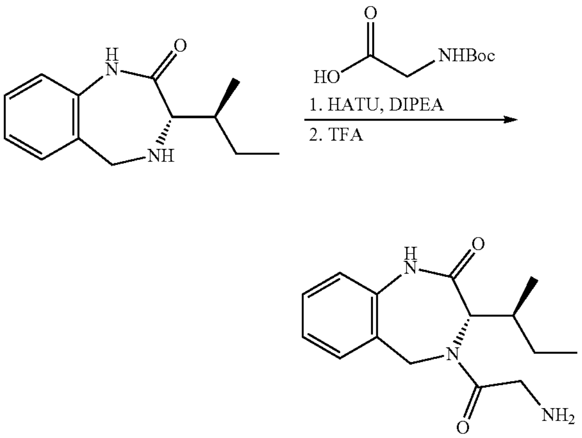

(S)-3-((S)-sec-Butyl)-4-glycyl-1,3,4,5-tetrahydro-2H-benzo[e][1,4]diazepin-2-one (Compound 17). To a solution of (S)-3-((S)-sec-butyl)-1,3,4,5-tetrahydro-2H-benzo[e][1,4]diazepin-2-one (200 mg, 0.916 mmol) in DMF (2 mL) was added DIPEA (314 uL, 1.83 mmol), N-Boc-glycine (193 mg, 1.10 mmol) and HATU (453 mg, 1.19 mmol). The reaction mixture was stirred overnight, and then quenched by water and extracted with EtOAc. The organic layer was dried over $Na_2SO_4$ and concentrated to a crude residue which was purified using silica gel chromatography (0 to 5% MeOH/$CHCl_3$) to give tert-butyl (2-((S)-3-((S)-sec-butyl)-2-oxo-1,2,3,5-tetrahydro-4H-benzo[e][1,4]diazepin-4-yl)-2-oxoethyl)carbamate as an oil.

To a solution of tert-butyl (2-((S)-3-((S)-sec-butyl)-2-oxo-1,2,3,5-tetrahydro-4H-benzo[e][1,4]diazepin-4-yl)-2-oxoethyl)carbamate in $CH_2Cl_2$ (1 mL) was added TFA (1 mL). After stirring overnight, the resulting mixture was concentrated under reduced pressure. The residue was purified with amino functionalized silica gel (0 to 10% MeOH/$CHCl_3$) and silica gel chromatography (0 to 20% MeOH/$CHCl_3$) to give (S)-3-((S)-sec-butyl)-4-glycyl-1,3,4,5-tetrahydro-2H-benzo[e][1,4]diazepin-2-one (Compound 17, 253 mg, 0.920 mmol, 100% yield) as a pale yellow foam. LRMS (ES), m/z 276.2 (M+H). $^1$H NMR (500 MHz, DMSO-$d_6$) δ 10.1 (br s, 1H,), 7.41-7.21 (m, 2H), 7.12-7.04 (m, 2H), 4.88 (d, J=10.2 Hz, 1H), 4.59 (d, J=14.7 Hz, 1H), 4.52 (d, J=14.8 Hz, 1H), 3.73 (d, J=17.2 Hz, 1H), 3.51-3.20 (m, 2H), 3.37 (d, J=17.1 Hz, 1H), 1.58-1.20 (m, 2H), 1.08-0.60 (m, 7H).

Example 11: Synthesis of Compound 33

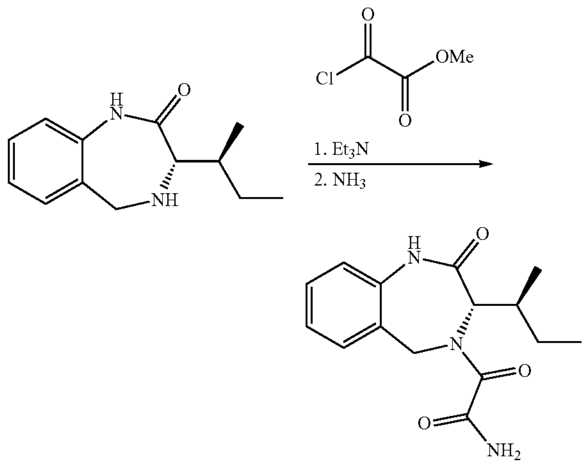

2-((S)-3-((S)-sec-Butyl)-2-oxo-1,2,3,5-tetrahydro-4H-benzo[e][1,4]diazepin-4-yl)-2-oxoacetamide (Compound 33). To a solution of (S)-3-((S)-sec-butyl)-1,3,4,5-tetrahydro-2H-benzo[e][1,4]diazepin-2-one (60 mg, 0.28 mmol) and DIPEA (0.14 mL, 0.83 mmol) in DCM (1 mL) at 0° C. was added methyl 2-chloro-2-oxoacetate (25 μL, 0.28 mmol), and the mixture was stirred at 0° C. for 15 min. MeOH (2 mL) was added to quench the reaction mixture. The reaction was concentrated, and DCM (1 mL) and ammonia (7 M in MeOH, 0.39 mL, 2.75 mmol) were added. The reaction mixture was then stirred at 50° C. overnight, concentrated, and purified using reverse phase HPLC (5-70% $MeCN/H_2O$, 0.1% formic acid buffer) to afford 2-((S)-3-((S)-sec-butyl)-2-oxo-1,2,3,5-tetrahydro-4H-benzo[e][1,4]diazepin-4-yl)-2-oxoacetamide (Compound 33, 37 mg, 47%) as a white solid. LRMS (APCI) m/z 290.1 (M+H). $^1$H NMR (400 MHz, methanol-$d_4$) δ 7.47-7.29 (m, 2H), 7.24-7.15 (m, 1H), 7.13-7.06 (m, 1H), 4.90-4.85 (m, 1H), 4.79-4.64 (m, 2H), 1.60-1.37 (m, 1H), 1.28-1.06 (m, 1H), 1.03-0.93 (m, 1H), 0.89-0.81 (m, 3H), 0.78-0.65 (m, 3H).

Example 12: Synthesis of Compound 51

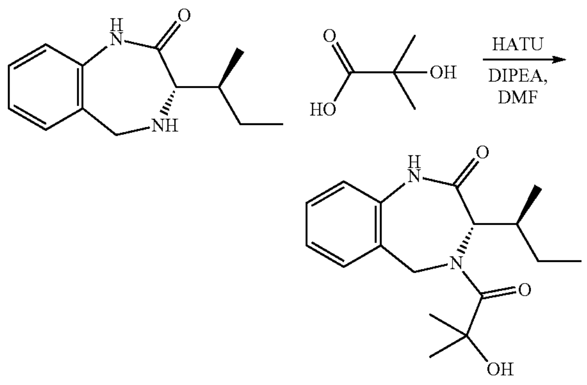

(S)-3-((S)-sec-Butyl)-4-(2-hydroxy-2-methylpropanoyl)-1,3,4,5-tetrahydro-2H-benzo[e][1,4]diazepin-2-one (Compound 51). To a mixture of (S)-3-((S)-sec-butyl)-1,3,4,5-tetrahydro-2H-benzo[e][1,4]diazepin-2-one (300 mg) and 2-hydroxy-2-methylpropanoic acid (310 mg) in DMF (6 mL) was added HATU (1.15 g) and DIPEA (710 μL). The mixture was stirred for 1 d, followed by dilution with water and extraction with EtOAc. The organic layer was washed with $H_2O$, brine, and then concentrated. The residue was purified by column chromatography on amino silica gel (hexane/EtOAc) to give (S)-3-((S)-sec-butyl)-4-(2-hydroxy-2-methylpropanoyl)-1,3,4,5-tetrahydro-2H-benzo[e][1,4]diazepin-2-one (Compound 51, 78 mg) as a colorless solid. LRMS (ES) m/z 305.2 (M+H). $^1$H NMR (400 MHz, DMSO-$d_6$) δ 9.95 (br s, 1H), 7.26 (br d, J=7.06 Hz, 2H), 7.06 (br d, J=7.94 Hz, 2H), 5.70-5.20 (m, 2H), 5.02-4.66 (m, 2H), 1.48-1.09 (m, 8H), 0.98-0.56 (br s, 7H).

Example 13: Synthesis of Compound 64

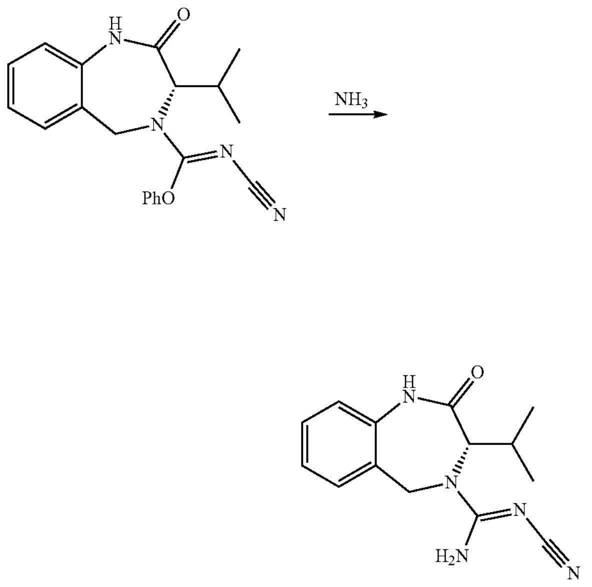

(S,E)-N'-Cyano-3-isopropyl-2-oxo-1,2,3,5-tetrahydro-4H-benzo[e][1,4]diazepine-4-carboximidamide (Compound 66). A mixture of phenyl (S,Z)—N-cyano-3-isopropyl-2-oxo-1,2,3,5-tetrahydro-4H-benzo[e][1,4]diazepine-4-carbimidate (77 mg, 0.22 mmol), ammonia (7 M in MeOH, 0.32 mL, 2.2 mmol) and THF (1 mL) was stirred at 100° C. in microwave reactor for 30 min. The mixture was filtered and purified by reverse phase HPLC (5-70% $MeCN/H_2O$, 0.1% formic acid buffer) to provide (S,E)-N'-cyano-3-isopropyl-2-oxo-1,2,3,5-tetrahydro-4H-benzo[e][1,4]diazepine-4-carboximidamide as a white solid (Compound 66, 19 mg, 32%). LRMS (APCI) m/z 272.1 (M+H). $^1$H zNMR (400 MHz, methanol-$d_4$) δ 7.41-7.35 (m, 2H), 7.19 (dd, J=7.4, 7.4 Hz, 1H), 7.09 (d, J=8.0 Hz, 1H), 4.81 (d, J=9.5 Hz, 1H), 4.71 (d, J=14.6 Hz, 1H), 4.62 (d, J=14.5 Hz, 1H), 1.68-1.54 (m, 1H), 0.91 (d, J=6.5 Hz, 3H), 0.87 (d, J=6.5 Hz, 3H).

The following compounds were prepared by methods analogous to the method described for Compound 66:

| Compound # | LRMS m/z [M + H] | $^1H$ NMR |
|---|---|---|
| 71 | 304.4 | $^1H$ NMR (500 MHz, DMSO-$d_6$) δ 10.10 (brs, 1H), 7.38 (brs, 2H), 7.24 (dd, J = 2.7, 9.0 Hz, 1H), 7.15 (dt, J = 2.9, 8.5 Hz, 1H), 7.10 (dd, J = 5.2, 8.9 Hz, 1H), 4.77-4.70 (m, 1H), 4.60-4.51 (m, 2H), 1.56-1.45 (m, 1H), 1.41-1.34 (m, 1H), 1.07-0.98 (m, 1H), 0.84 (d, J = 6.7 Hz, 3H), 0.73 (t, J = 7.4 Hz, 3H) |
| 82 | 287.1 | $^1H$ NMR (400 MHz, Acetone-$d_6$) δ 9.34 (s, 1H), 8.48 (s, 1H), 8.24 (d, J = 4.9 Hz, 1H), 7.34 (d, J = 4.9 Hz, 1H), 6.88 (s, 2H), 5.13 (d, J = 17.8 Hz, 1H),4.90-4.70 (m, 2H), 2.08-1.92 (m, 1H), 1.61 (dtd, J = 15.0, 7.5, 3.1 Hz, 1H), 1.22 (ddt, J = 14.0, 8.5, 7.1 Hz, 1H), 1.03 (d, J = 6.6 Hz, 3H), 0.91 (t, 7 = 7.4 Hz, 3H). |
| 336 | 304.4 | N/A |
| 365 | 305.1 | N/A |
| 380 | 350.1 | N/A |

Example 14: Synthesis of Compound 2

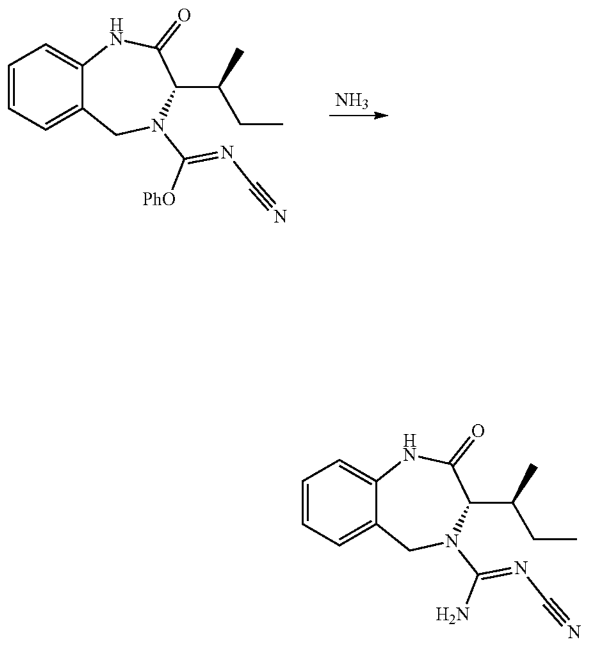

(S,E)-3-((S)-sec-Butyl)-N'-cyano-2-oxo-1,2,3,5-tetrahydro-4H-benzo[e][1,4]diazepine-4-carboximidamide (Compound 2). A mixture of phenyl (S,Z)-3-((S)-sec-butyl)-N-cyano-2-oxo-1,2,3,5-tetrahydro-4H-benzo[e][1,4]diazepine-4-carbimidate (62 mg, 0.17 mmol), ammonia (7 M in MeOH, 0.24 mL, 1.7 mmol) and THF (1 mL) was stirred at 50° C. for 2 h. The mixture was filtered and purified by reverse phase HPLC (5-70% MeCN/$H_2O$, 0.1% formic acid buffer) to provide (S,E)-3-((S)-sec-butyl)-N'-cyano-2-oxo-1,2,3,5-tetrahydro-4H-benzol[e][1,4]diazepine-4-carboximidamide (Compound 2, 19 mg, 39%) as a white solid. LRMS (APCI) m/z 286.1 (M+H). $^1H$ NMR (400 MHz, methanol-$d_4$) δ 7.42-7.35 (m, 2H), 7.20 (dd, J=7.6, 7.6 Hz, 1H), 7.09 (d, J=8.0 Hz, 1H), 4.87 (d, J=10.4 Hz 1H), 4.73-4.60 (m, 2H), 1.51-1.41 (m, 1H), 1.37-1.24 (m, 1H), 1.14-1.01 (m, 1H), 0.86 (d, J=6.5 Hz, 3H), 0.74 (t, J=7.3 Hz, 3H).

Example 15: Synthesis of Compound 19

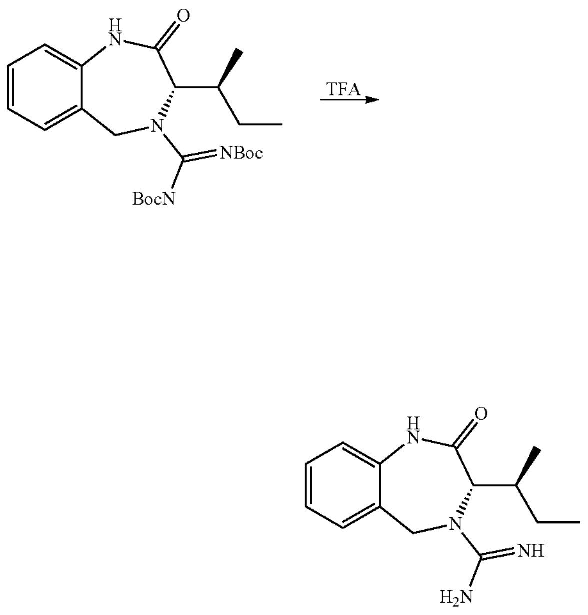

(S)-3-((S)-sec-Butyl)-2-oxo-1,2,3,5-tetrahydro-4H-benzo[e][1,4]diazepine-4-carboximidamide (Compound 19). A solution of tert-butyl ((Z)-((tert-butoxycarbonyl)imino)((S)-3-((S)-sec-butyl)-2-oxo-1,2,3,5-tetrahydro-4H-benzo[e][1,4]diazepin-4-yl)methyl)-12-azanecarboxylate (35 mg, 0.076 mmol) and TFA (0.12 mL, 1.52 mmol) in DCM (1 mL) was stirred at rt for 2 h. The crude was filtered and purified by reverse phase HPLC (0-50% MeCN/$H_2O$, 0.1% formic acid buffer) to provide (S)-3-((S)-sec-butyl)-2-oxo-1,2,3,5-tetrahydro-4H-benzo[e][1,4]diazepine-4-carboximidamide as a white solid (Compound 19, 14 mg, 71%). LRMS (APCI) m/z 261.1 (M+H). $^1H$ NMR (400 MHz, DMSO-$d_6$) δ 10.39 (s, 1H), 8.41 (s, 1H), 8.16 (s, 2H), 7.41 (d, J=7.6 Hz, 1H), 7.36 (dd, J=7.7, 7.7 Hz, 1H), 7.16-7.10 (m, 2H), 4.64-4.52 (m, 2H), 4.40 (d, J=9.4 Hz, 1H), 1.52-1.33 (m, 2H), 1.14-0.98 (m, 1H), 0.86 (d, J=6.5 Hz, 3H), 0.70 (t, J=7.3 Hz, 3H).

Example 16: Synthesis of Compound 21

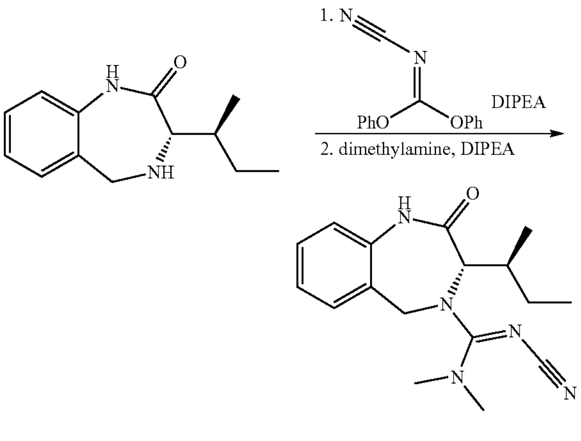

(S,E)-3-((S)-sec-Butyl)-N'-cyano-N,N-dimethyl-2-oxo-1,2,3,5-tetrahydro-4H-benzo[e][1,4]diazepine-4-carboximidamide (Compound 21). To a suspension of diphenyl cyanocarbonimidate (40 mg, 0.17 mmol) in THF (1 mL) was added (S)-3-((S)-sec-butyl)-1,3,4,5-tetrahydro-2H-benzo[e][1,4]diazepin-2-one (37 mg, 0.17 mmol) and DIPEA (88 μL, 0.50 mmol), which was stirred at rt overnight. The reaction was filtered and purified by reverse phase HPLC (2-60% $MeCN/H_2O$, 0.1% formic acid buffer) to give phenyl (S,Z)-3-((S)-sec-butyl)-N-cyano-2-oxo-1,2,3,5-tetrahydro-4H-benzo[e][1,4]diazepine-4-carbimidate.

Phenyl (S,Z)-3-((S)-sec-butyl)-N-cyano-2-oxo-1,2,3,5-tetrahydro-4H-benzo[e][1,4]diazepine-4-carbimidate (from above) and dimethylamine (2 M in THF, 0.42 mL, 0.84 mmol) in THF (1 mL) was stirred at rt for 2 d. The reaction was filtered and purified using reverse phase HPLC (5-35% $MeCN/H_2O$, 0.1% formic acid buffer) to give (S,E)-3-((S)-sec-butyl)-N'-cyano-N,N-dimethyl-2-oxo-1,2,3,5-tetrahydro-4H-benzo[e][1,4]diazepine-4-carboximidamide as a white solid (Compound 21, 1 mg, 2%). LRMS (APCI) m/z 314.1 (M+H). $^1H$ NMR (400 MHz, methanol-$d_4$) δ 7.40 (d, J=7.7 Hz, 1H), 7.34 (dd, J=7.6, 7.6 Hz, 1H), 7.17 (dd, J=7.5, 7.5 Hz, 1H), 7.09 (d, J=7.9 Hz, 1H), 4.73-4.56 (m, 2H), 4.35 (d, J=9.5 Hz, 1H), 3.11 (s, 6H), 1.72-1.59 (m, 1H), 1.58-1.46 (m, 1H), 1.19-1.07 (m, 1H), 0.91 (d, J=6.6 Hz, 3H), 0.84 (t, J=7.2 Hz, 3H).

The following compounds were prepared by methods analogous to the method described for Compound 21:

| Compound # | LRMS m/z [M + H] |
|---|---|
| 87 | 300.1 |

Example 17: Synthesis of Compound 22

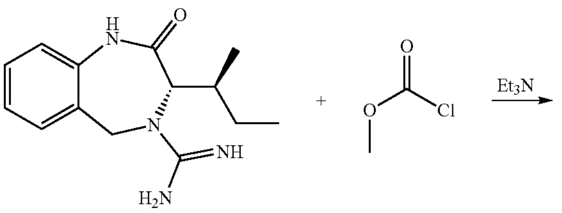

-continued

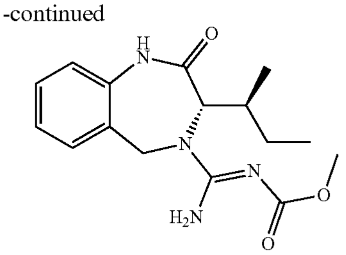

Methyl ((E)-amino((S)-3-((S)-sec-butyl)-2-oxo-1,2,3,5-tetrahydro-4H-benzo[e][1,4]diazepin-4-yl)methylene)carbamate (Compound 22). To a solution of (S)-3-((S)-sec-butyl)-2-oxo-1,2,3,5-tetrahydro-4H-benzo[e][1,4]diazepine-4-carboximidamide (75 mg, 0.79 mmol) and triethylamine (0.12 mL, 0.86 mmol) in DCM (0.5 mL) at 0° C. was added methyl chloroformate (8.9 μL, 0.12 mmol), followed by stirring at 0° C. for 10 min. The reaction was concentrated and then purified using reverse phase HPLC (5-70% $MeCN/H_2O$, 0.1% formic acid buffer) to provide methyl ((E)-amino((S)-3-((S)-sec-butyl)-2-oxo-1,2,3,5-tetrahydro-4H-benzo[e][1,4]diazepin-4-yl)methylene)carbamate as a white solid (Compound 22, 25 mg, 27%). LRMS (APCI) m/z 319.1 (M+H). $^1H$ NMR (400 MHz, methanol-$d_4$) δ 7.46-7.30 (m, 2H), 7.18 (dd, J=7.5, 7.5 Hz, 1H), 7.09 (d, J=7.9 Hz, 1H), 5.25-5.05 (m, 1H), 4.78-4.58 (m, 2H), 3.68 (s, 3H), 1.56-1.32 (m, 2H), 1.15-1.04 (m, 1H), 0.89 (d, J=6.6 Hz, 3H), 0.75 (t, J=7.4 Hz, 3H).

The following compounds were prepared by methods analogous to the method described for Compound 22:

| Compound # | LRMS m/z [M + H] |
|---|---|
| 112 | 339.0 |
| 113 | 303.1 |

Example 18: Synthesis of Compound 3

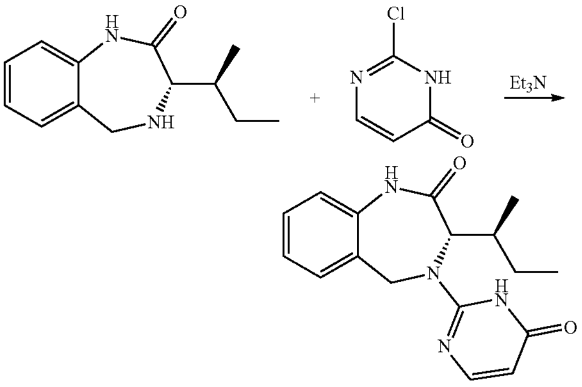

(S)-3-((S)-sec-Butyl)-4-(6-oxo-1,6-dihydropyrimidin-2-yl)-1,3,4,5-tetrahydro-2H-benzo[e][1,4]diazepin-2-one (Compound 3). A mixture of (S)-3-((S)-sec-butyl)-1,3,4,5-tetrahydro-2H-benzo[e][1,4]diazepin-2-one (80 mg, 0.37 mmol), 2-chloropyrimidin-4(3H)-one (72 mg, 0.55 mmol), and triethylamine (0.26 mL, 1.83 mmol) in EtOH (1 mL) was stirred at 150° C. in microwave reactor for 6 h. The reaction was concentrated and purified using reverse phase HPLC (5-70% $MeCN/H_2O$, 0.1% formic acid buffer) and silica gel column chromatography purification (0-8% MeOH/DCM) to provide (S)-3-((S)-sec-butyl)-4-(6-oxo-1,6-dihydropyrimidin-2-yl)-1,3,4,5-tetrahydro-2H-benzo[e][1,4]diazepin-2-one (Compound 3, 5 mg, 4%) as a white solid. LRMS (APCI) m/z 313.1 (M+H). $^1H$ NMR (400 MHz, methanol-$d_4$) δ 7.91-7.72 (m, 1H), 7.41 (d, J=7.3 Hz, 1H), 7.36 (dd, J=7.7, 7.7 Hz, 1H), 7.18 (dd, J=7.5 Hz, 1H), 7.08 (d, J=7.9 Hz, 1H), 5.91 (d, J=6.2 Hz, 1H), 5.27 (d, J=10.3 Hz, 1H), 4.85-4.73 (m, 2H), 1.55-1.40 (m, 2H), 1.17-1.05 (m, 1H), 0.91 (d, J=6.6 Hz, 3H), 0.74 (t, J=7.4 Hz, 3H).

The following compounds were prepared by methods analogous to the method described for Compound 3:

| Compound # | LRMS m/z [M + H] |
|---|---|
| 88 | 299.1 |
| 114 | 297.1 |
| 115 | 327.1 |
| 116 | 357.1 |

Example 19: Synthesis of Compound 54

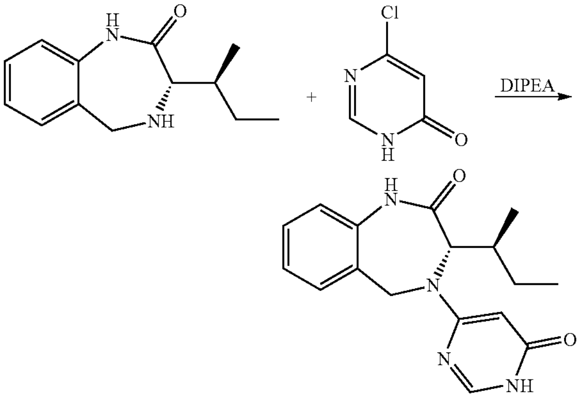

(S)-3-((S)-sec-butyl)-4-(6-oxo-1,6-dihydropyrimidin-4-yl)-1,3,4,5-tetrahydro-2H-benzo[e][1,4]diazepin-2-one (Compound 54). A mixture of (S)-3-((S)-sec-butyl)-1,3,4,5-tetrahydro-2H-benzo[e][1,4]diazepin-2-one (70 mg, 0.32 mmol), 6-chloropyrimidin-4(5H)-one (84 mg, 0.64 mmol), and DIPEA (0.17 mL, 0.96 mmol) in EtOH (2 mL) was stirred at 180° C. in a microwave reactor for 9 h. The mixture was filtered and purified by reverse phase HPLC (5-70% $MeCN/H_2O$, 0.1% formic acid buffer) and silica gel (0-10% MeOH/DCM) to provide (S)-3-((S)-sec-butyl)-4-(6-oxo-1,6-dihydropyrimidin-4-yl)-1,3,4,5-tetrahydro-2H-benzo[e][1,4]diazepin-2-one as a white solid (Compound 54, 21 mg, 21%). LRMS (APCI) m/z 313.1 (M+H). $^1H$ NMR (400 MHz, chloroform-d and methanol-$d_4$) δ 7.82 (s, 1H), 7.34-7.25 (m, 2H), 7.12 (dd, J=7.5, 7.5 Hz, 1H), 6.99 (d, J=7.9 Hz, 1H), 5.52 (s, 1H), 5.35 (d, J=31.3 Hz, 1H), 4.63-4.48 (m, 2H), 1.63-1.40 (m, 2H), 1.26-1.00 (m, 1H), 0.94-0.66 (m, 6H).

Example 20: Synthesis of Compound 23

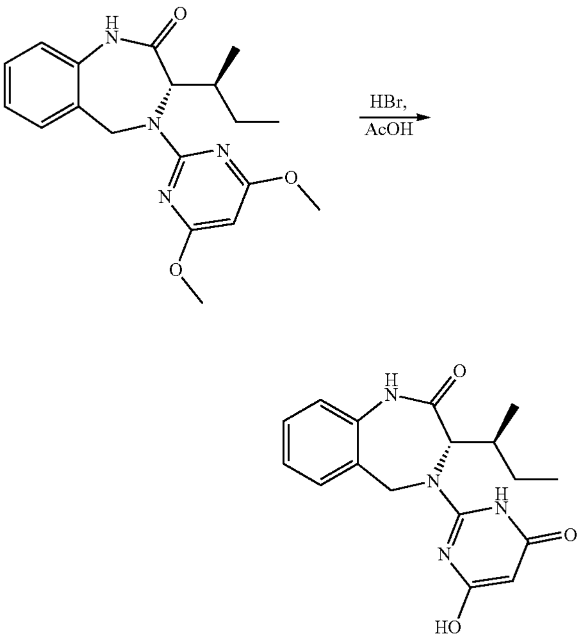

(S)-3-((S)-sec-Butyl)-4-(4-hydroxy-6-oxo-1,6-dihydropyrimidin-2-yl)-1,3,4,5-tetrahydro-2H-benzo[e][1,4]diazepin-2-one (Compound 23). A mixture of (S)-3-((S)-sec-butyl)-4-(4,6-dimethoxypyrimidin-2-yl)-1,3,4,5-tetrahydro-2H-benzo[e][1,4]diazepin-2-one (65 mg, 0.18 mmol) and HBr (33% in AcOH, 2 mL) was stirred at 100° C. for 6 h. The reaction was concentrated, azeotroped with toluene (2 mL×2), diluted with EtOAc (15 mL), washed with brine (5 mL), and purified with reverse phase HPLC (5-70% MeCN/$H_2O$, 0.1% formic acid buffer) to provide (S)-3-((S)-sec-butyl)-4-(4-hydroxy-6-oxo-1,6-dihydropyrimidin-2-yl)-1,3,4,5-tetrahydro-2H-benzo[e][1,4]diazepin-2-one (Compound 23, 8 mg, 13%) as a white solid. LRMS (APCI) m/z 329.1 (M+H). $^1H$ NMR (400 MHz, acetone-$d_6$) δ 10.03 (s, 1H), 9.10 (d, J=21.0 Hz, 1H), 7.47-7.40 (m, 1H), 7.32-7.25 (m, 1H), 7.18-7.13 (m, 1H), 7.12-7.05 (m, 1H), 5.45-5.20 (m, 1H), 5.12 (d, J=4.6 Hz, 1H), 5.00-4.90 (m, 1H), 4.87-4.75 (m, 1H), 1.80-1.50 (m, 2H), 1.19-1.07 (m, 1H), 0.95-0.72 (m, 6H).

Example 21: Synthesis of Compound 60

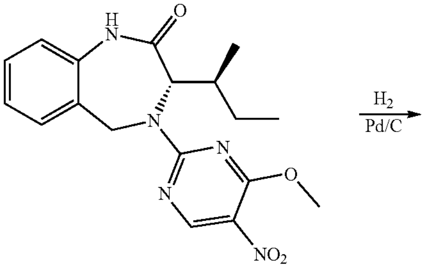

-continued

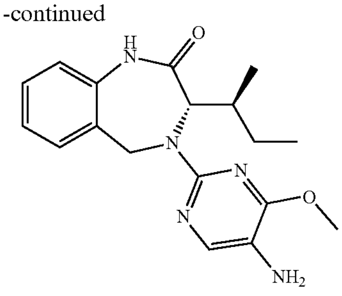

(S)-4-(5-Amino-4-methoxypyrimidin-2-yl)-3-((S)-sec-butyl)-1,3,4,5-tetrahydro-2H-benzo[e][1,4]diazepin-2-one (Compound 61). A mixture of (S)-3-((S)-sec-butyl)-4-(4-methoxy-5-nitropyrimidin-2-yl)-1,3,4,5-tetrahydro-2H-benzo[e][1,4]diazepin-2-one (85 mg, 0.23 mmol) and Pd/C (10%, 20 mg, 0.19 mmol) in MeOH (3 mL) was stirred under hydrogen atmosphere (60 psi) at rt for 2 h. The crude mixture was filtered with Celite, concentrated, and purified with reverse phase HPLC (5-70% $MeCN/H_2O$, 0.1% formic acid buffer). The purified eluent was basified with saturated $NaHCO_3$ (10 mL), diluted with EtOAc (20 mL), and the organic layer was dried with $Na_2SO_4$, filtered, and concentrated to give (S)-4-(5-amino-4-methoxypyrimidin-2-yl)-3-((S)-sec-butyl)-1,3,4,5-tetrahydro-2H-benzo[e][1,4]diazepin-2-one (Compound 61, 52 mg, 67%) as a clear oil. LRMS (APCI) m/z 342.1 (M+H). $^1$H NMR (400 MHz, methanol-$d_4$) δ 7.72 (s, 1H), 7.42-7.34 (m, 1H), 7.33-7.26 (m, 1H), 7.20-7.10 (m, 1H), 7.07-6.99 (m, 1H), 5.25-5.13 (m, 1H), 4.85-4.72 (m, 2H), 4.01 (s, 3H), 1.65-1.53 (m, 1H), 1.5.2-1.38 (m, 1H), 1.18-1.05 (m, 1H), 0.97-0.90 (m, 3H), 0.80-0.67 (m, 3H).

Example 22: Synthesis of Compound 24

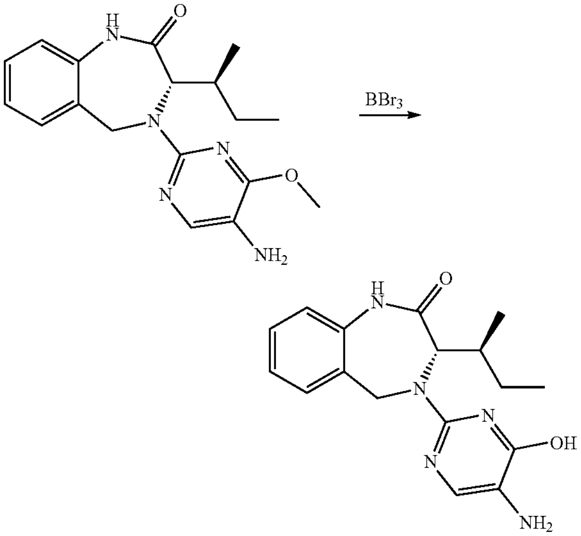

(S)-4-(5-Amino-4-hydroxypyrimidin-2-yl)-3-((S)-sec-butyl)-1,3,4,5-tetrahydro-2H-benzo[e][1,4]diazepin-2-one (Compound 24). To a mixture of (S)-4-(5-amino-4-methoxypyrimidin-2-yl)-3-((S)-sec-butyl)-1,3,4,5-tetrahydro-2H-benzo[e][1,4]diazepin-2-one (45 mg, 0.13 mmol) in DCM (1 mL) at 0° C. was added $BBr_3$ (1 M in DCM, 0.40 mL, 0.40 mmol). The mixture was stirred at 0° C. for 30 min, then at rt overnight. The crude mixture was filtered and purified with reverse phase HPLC (5-70% $MeCN/H_2O$, 0.1% formic acid buffer). The purified eluent was basified with saturated $NaHCO_3$ (10 mL), diluted with EtOAc (20 mL), the organic layer was dried with $Na_2SO_4$, filtered, and concentrated in vacuo to give (S)-4-(5-amino-4-hydroxypyrimidin-2-yl)-3-((S)-sec-butyl)-1,3,4,5-tetrahydro-2H-benzo[e][1,4]diazepin-2-one (Compound 24, 8 mg, 19%) as a clear oil. LRMS (APCI) m/z 328.1 (M+H). $^1$H NMR (400 MHz, methanol-$d_4$) δ 7.33-7.17 (m, 2H), 7.09-7.02 (m, 1H), 7.00 (m, 2H), 4.97 (d, J=9.9 Hz, 1H), 4.64-4.49 (m, 2H), 1.54-1.35 (m, 1H), 1.32-1.20 (m, 1H), 1.05-0.93 (m, 1H), 0.84-0.72 (m, 3H), 0.66-0.58 (m, 3H).

Example 23: Synthesis of Compound 52

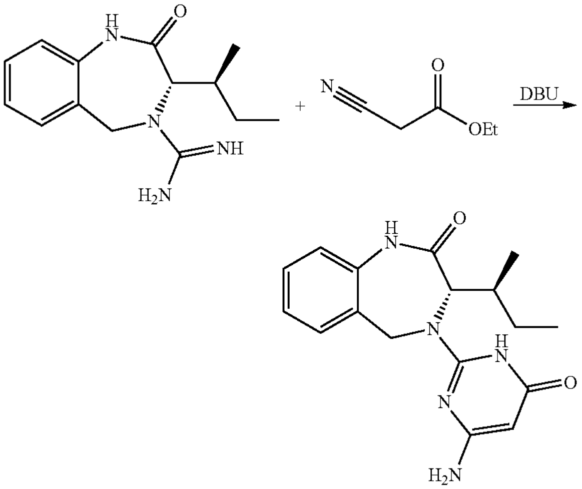

(S)-4-(4-Amino-6-oxo-1,6-dihydropyrimidin-2-yl)-3-((S)-sec-butyl)-1,3,4,5-tetrahydro-2H-benzo[e][1,4]diazepin-2-one (Compound 52). A mixture of (S)-3-((S)-sec-butyl)-2-oxo-1,2,3,5-tetrahydro-4H-benzo[e][1,4]diazepine-4-carboximidamide formic acid salt (40 mg, 0.13 mmol), ethyl 2-cyanoacetate (21 μL, 0.20 mmol), and DBU (78 μL, 0.52 mmol) in EtOH (2 mL) was refluxed overnight. The mixture was filtered and purified with reverse phase HPLC (5-70% $MeCN/H_2O$, 0.1% formic acid buffer) to afford (S)-4-(4-amino-6-oxo-1,6-dihydropyrimidin-2-yl)-3-((S)-sec-butyl)-1,3,4,5-tetrahydro-2H-benzo[e][1,4]diazepin-2-one as a white solid (Compound 52, 2 mg, 5%). LRMS (APCI) m/z 328.1 (M+H). $^1$H NMR (400 MHz, methanol-$d_4$) δ 7.48 (s, 1H), 7.35-7.26 (m, 2H), 7.12 (dd, J=7.5, 7.5 Hz, 1H), 7.00 (d, J=7.9 Hz, 1H), 5.32-4.97 (m, 1H), 4.84-4.62 (m, 2H), 1.76-1.40 (m, 2H), 1.27-1.04 (m, 1H), 0.96-0.65 (m, 6H).

Example 24: Synthesis of Compound 53

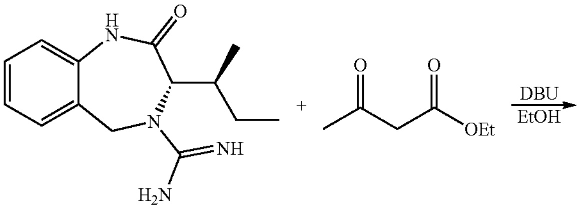

-continued

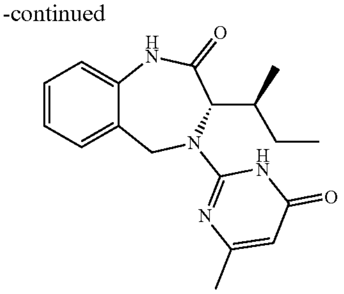

(S)-3-((S)-sec-Butyl)-4-(4-methyl-6-oxo-1,6-dihydropyrimidin-2-yl)-1,3,4,5-tetrahydro-2H-benzo[e][1,4]diazepin-2-one (Compound 53). A mixture of (S)-3-((S)-sec-butyl)-2-oxo-1,2,3,5-tetrahydro-4H-benzo[e][1,4]diazepine-4-carboximidamide formic acid salt (40 mg, 0.13 mmol), ethyl 3-oxobutanoate (25 μL, 0.20 mmol), and DBU (78 μL, 0.52 mmol) in EtOH (2 mL) was stirred at reflux for 5 h, then at 100° C. for 90 min. The reaction mixture was filtered and purified with reverse phase HPLC (5-70% MeCN/$H_2O$, 0.1% formic acid buffer) to afford (S)-3-((S)-sec-butyl)-4-(4-methyl-6-oxo-1,6-dihydropyrimidin-2-yl)-1,3,4,5-tetrahydro-2H-benzo[e][1,4]diazepin-2-one (Compound 53, 4 mg, 9%) as a white solid. LRMS (APCI) m/z 327.1 (M+H). $^1$H NMR (400 MHz, methanol-$d_4$) δ 7.38-7.27 (m, 2H), 7.14 (dd, J=7.5, 7.5 Hz, 1H), 7.03 (d, J=8.0 Hz, 1H), 5.72 (m, 1H), 5.40-5.20 (m, 1H), 4.90-4.75 (m, 1H), 4.35-4.25 (m, 1H), 2.18 (s, 3H), 1.55-1.43 (m, 2H), 1.15-1.05 (m, 1H), 0.91 (d, J=6.5 Hz, 3H), 0.76 (t, J=7.3 Hz, 3H).

Example 25: Synthesis of Compound 61

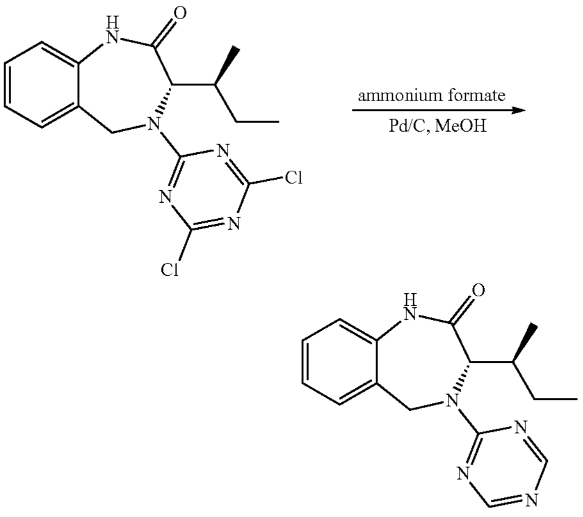

(S)-3-((S)-sec-Butyl)-4-(1,3,5-triazin-2-yl)-1,3,4,5-tetrahydro-2H-benzo[e][1,4]diazepin-2-one (Compound 62). To a mixture of (S)-3-((S)-sec-butyl)-4-(4,6-dichloro-1,3,5-triazin-2-yl)-1,3,4,5-tetrahydro-2H-benzo[e][1,4]diazepin-2-one (79 mg, 0.22 mmol) and ammonium formate (136 mg, 2.16 mmol) in MeOH (1 mL) was added Pd/C (10%, 10 mg). The reaction mixture was heated to reflux and stirred for 1 h. The mixture was then filtered through Celite and purified with reverse phase HPLC (5-70% MeCN/$H_2O$, 0.1% formic acid buffer) to provide (S)-3-((S)-sec-butyl)-4-(1,3,5-triazin-2-yl)-1,3,4,5-tetrahydro-2H-benzo[e][1,4]diazepin-2-one (Compound 62, 10 mg, 16%) as a white solid. LRMS (APCI) m/z 298.1 (M+H). $^1$H NMR (400 MHz, methanol-$d_4$) δ 8.69-8.57 (m, 2H), 7.42 (d, J=7.5 Hz, 1H), 7.37 (dd, J=7.7, 7.7 Hz, 1H), 7.19 (dd, J=7.5, 7.5 Hz, 1H), 7.09 (d, J=7.9 Hz, 1H), 5.43 (d, J=10.2 Hz, 1H), 5.11 (d, J=15.1 Hz, 1H), 4.82 (d, J=15.1 Hz, 1H), 1.55-1.37 (m, 2H), 1.15-1.02 (m, 1H), 0.93 (d, J=6.6 Hz, 3H), 0.73 (t, J=7.4 Hz, 3H).

Example 26: Synthesis of Compound 25

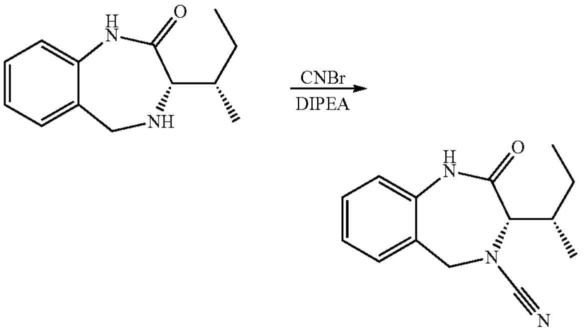

Step 1: (S)-3-((S)-sec-Butyl)-2-oxo-1,2,3,5-tetrahydro-4H-benzo[e][1,4]diazepine-4-carbonitrile (Compound 148). To a mixture of (S)-3-((S)-sec-butyl)-1,3,4,5-tetrahydro-2H-benzo[e][1,4]diazepin-2-one (284 mg, 1.3 mmol), DIPEA (0.68 mL, 3.9 mmol), and DCM (5 mL) was added 5M cyanogen bromide (0.39 mL, 2.0 mmol) dropwise. The reaction mixture was stirred at rt for 30 min, diluted with dichloromethane, washed with saturated $NaHCO_3$, brine, dried over sodium sulfate, and concentrated. The residue was triturated with diethyl ether, followed by filtration to give (S)-3-((S)-sec-butyl)-2-oxo-1,2,3,5-tetrahydro-4H-benzo[e][1,4]diazepine-4-carbonitrile (Compound 148, 0.32 g, 92%) as an off-white solid. LRMS (APCI) m/z 244.1 (M+H).

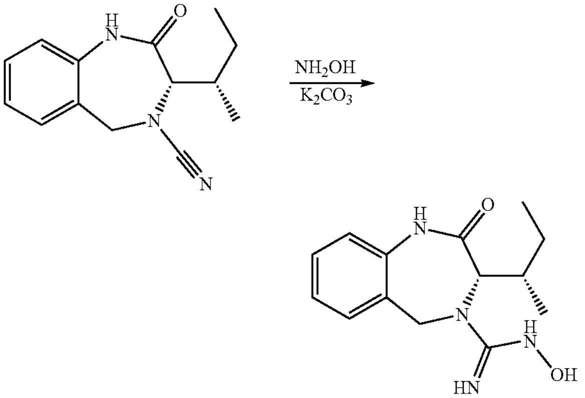

Step 2: (S)-3-((S)-sec-Butyl)-N-hydroxy-2-oxo-1,2,3,5-tetrahydro-4H-benzo[e][1,4]diazepine-4-carboximidamide (Compound 149). A mixture of (S)-3-((S)-sec-butyl)-2-oxo-1,2,3,5-tetrahydro-4H-benzo[e][1,4]diazepine-4-carbonitrile (96 mg, 0.40 mmol), hydroxylamine hydrochloride (26 mg, 0.79 mmol), $K_2CO_3$ (110 mg, 0.789 mmol), and ethanol (3 mL) was stirred at 50° C. for 14 h, filtered, and solvent was removed by rotary evaporation. The residue was purified with reverse phase HPLC (10-100% $MeCN/H_2O$, 0.1% formic acid buffer over 40 min) to give (S)-3-((S)-sec-butyl)-N-hydroxy-2-oxo-1,2,3,5-tetrahydro-4H-benzo[e][1,4]diazepine-4-carboximidamide as an off-white solid (Compound 149, 109 mg, 73%). LRMS (APCI) m/z 277.1 (M+H).

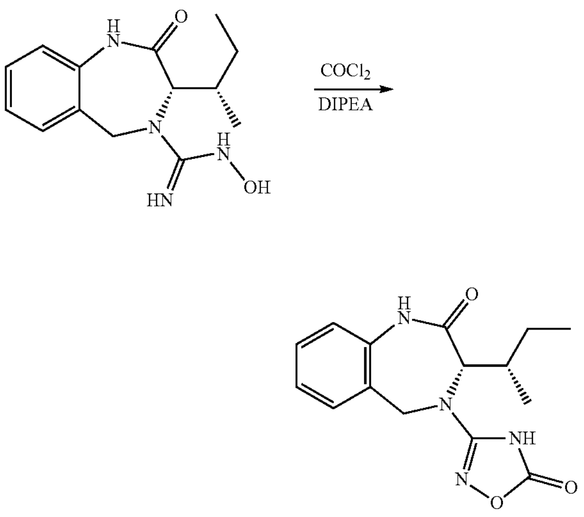

Step 3: 3-((S)-3-((S)-sec-Butyl)-2-oxo-1,2,3,5-tetrahydro-4H-benzo[e][1,4]diazepin-4-yl)-1,2,4-oxadiazol-5(4H)-one (Compound 25). To a mixture of (S)-3-((S)-sec-butyl)-N-hydroxy-2-oxo-1,2,3,5-tetrahydro-4H-benzo[e][1,4]diazepine-4-carboximidamide (30 mg, 0.11 mmol), DIPEA (42 mg, 0.33 mmol) and THF (1 mL) was added phosgene (15% in toluene, 86 mg, 0.13 mmol) dropwise. The reaction mixture was stirred at rt for 1 h, and solvent was removed by rotary evaporation. The residue was purified using reverse phase HPLC (10-100% $MeCN/H_2O$, 0.1% formic acid buffer) over 40 min to give 3-((S)-3-((S)-sec-butyl)-2-oxo-1,2,3,5-tetrahydro-4H-benzo[e][1,4]diazepin-4-yl)-1,2,4-oxadiazol-5(4H)-one as an off-white solid (Compound 25, 16 mg, 49%). LRMS (APCI) m/z 303.1 (M+H). $^1H$ NMR (400 MHz, acetone-$d_6$) δ 9.26 (s, 1H), 7.53-7.30 (m, 2H), 7.23-7.15 (m, 2H), 4.75-4.48 (m, 2H), 4.15 (d, J=10.3 Hz, 1H), 1.63 (m, 1H), 1.45 (m, 1H), 1.14 (m, 1H), 0.87 (d, J=6.6 Hz, 3H), 0.77 (t, J=7.4 Hz, 3H). LRMS (APCI) m/z 303.1 (M+H).

Example 27: Synthesis of Compound 55

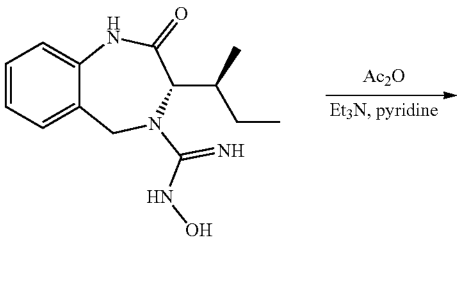

-continued

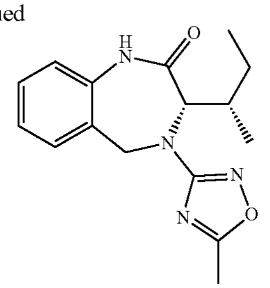

(S)-3-((S)-sec-Butyl)-4-(5-methyl-1,2,4-oxadiazol-3-yl)-1,3,4,5-tetrahydro-2H-benzo[e][1,4]diazepin-2-one (Compound 55). A mixture of (S)-3-((S)-sec-butyl)-N-hydroxy-2-oxo-1,2,3,5-tetrahydro-4H-benzo[e][1,4]diazepine-4-carboximidamide (20 mg, 0.072 mmol), acetic anhydride (8 μL, 0.087 mmol), triethylamine (30 μL, 0.22 mmol) and pyridine (0.2 mL) was stirred at 80° C. for 63 h. The reaction mixture was filtered and purified with reverse phase HPLC (5-70% $MeCN/H_2O$, 0.1% formic acid buffer) to provide (S)-3-((S)-sec-butyl)-4-(5-methyl-1,2,4-oxadiazol-3-yl)-1,3,4,5-tetrahydro-2H-benzo[e][1,4]diazepin-2-one (Compound 55, 3 mg, 14%) as a white solid. LRMS (APCI) m/z 301.1 (M+H). $^1H$ NMR (400 MHz, methanol-$d_4$) δ 7.41-7.34 (m, 2H), 7.20 (dd, J=7.6, 7.6 Hz, 1H), 7.08 (d, J=8.0 Hz, 1H), 4.64 (d, J=14.4 Hz, 1H), 4.58-4.45 (m, 2H), 2.48 (s, 3H), 1.60-1.49 (m, 1H), 1.34-1.20 (m, 1H), 1.12-1.00 (m, 1H), 0.85 (d, J=6.4 Hz, 3H), 0.73 (t, J=7.4 Hz, 3H).

Example 28: Synthesis of Compound 56

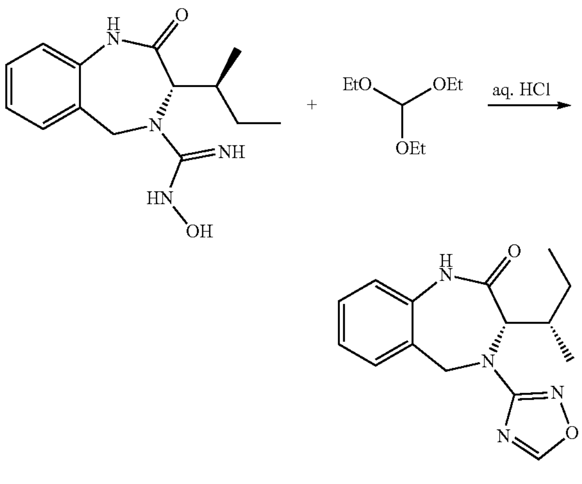

(S)-3-((S)-sec-Butyl)-4-(1,2,4-oxadiazol-3-yl)-1,3,4,5-tetrahydro-2H-benzo[e][1,4]diazepin-2-one (Compound 56). A mixture of (S)-3-((S)-sec-butyl)-N-hydroxy-2-oxo-1,2,3,5-tetrahydro-4H-benzo[e][1,4]diazepine-4-carboximidamide (50 mg, 0.18 mmol), HCl (36% in $H_2O$, 2.5 μL), and triethoxymethane (0.5 mL, 3.0 mmol) was stirred at 110° C. for 30 min. The reaction mixture was concentrated in vacuo, followed by purification with reverse phase HPLC (5-70% $MeCN/H_2O$, 0.1% formic acid buffer) to provide (S)-3-((S)-sec-butyl)-4-(1,2,4-oxadiazol-3-yl)-1,3,4,5-tetrahydro-2H-benzo[e][1,4]diazepin-2-one (Compound 56, 32 mg, 62%) as a white solid. LRMS (APCI) m/z 287.1 (M+H). $^1H$ NMR (400 MHz, methanol-$d_4$) δ 8.80 (s, 1H), 7.42-7.34 (m, 2H), 7.24-7.17 (m, 1H), 7.09 (dd, J=8.0, 2.5 Hz, 1H), 4.70 (d, J=14.2 Hz, 1H), 4.62-4.51 (m, 2H), 1.60-1.47 (m, 1H), 1.35-1.23 (m, 1H), 1.13-1.02 (m, 1H), 0.86 (d, J=6.1 Hz, 3H), 0.73 (t, J=7.1 Hz, 3H).

Example 29: Synthesis of Compound 34

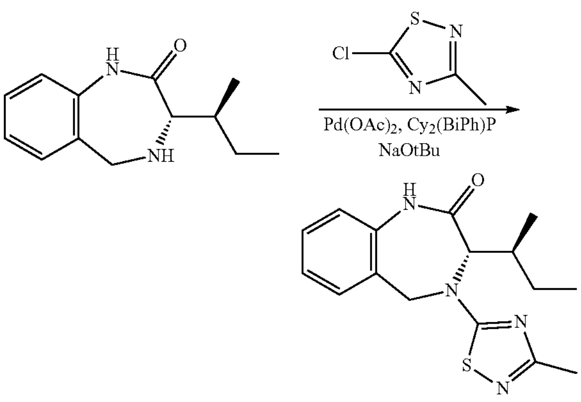

(S)-3-((S)-sec-Butyl)-4-(3-methyl-1,2,4-thiadiazol-5-yl)-1,3,4,5-tetrahydro-2H-benzo[e][1,4]diazepin-2-one (Compound 34). To a mixture of (S)-3-((S)-sec-butyl)-1,3,4,5-tetrahydro-2H-benzo[e][1,4]diazepin-2-one (100 mg), $Pd(OAc)_2$ (10 mg), (2-biphenyl)dicyclohexylphosphine (32 mg), and NaOt-Bu (88 mg) in dioxane (3 mL) was added 5-chloro-3-methyl-1,2,4-thiadiazole (123 mg). The reaction was heated to 80° C. and stirred overnight under an argon atmosphere. The reaction mixture was then diluted with water and extracted with $CHCl_3$. The organic layer was washed with brine, dried over $MgSO_4$, concentrated in vacuo, and purified using silica gel column chromatography (hexanes/EtOAc) to give (S)-3-((S)-sec-butyl)-4-(3-methyl-1,2,4-thiadiazol-5-yl)-1,3,4,5-tetrahydro-2H-benzo[e][1,4]diazepin-2-one (Compound 34, 22 mg) as a pale yellow solid. LRMS (ES) m/z 317.3 (M+H). $^1$H NMR (500 MHz, DMSO-$d_6$) δ 10.02 (s, 1H), 7.37-7.30 (m, 1H), 6.90-6.86 (m, 2H), 6.61-6.53 (m, 1H), 4.62 (br d, J=9.8 Hz, 1H), 4.47-4.36 (m, 2H), 2.56 (d, J=4.3 Hz, 3H), 1.35-1.45 (m, 2H), 0.93-1.01 (m, 1H), 0.81 (d, J=6.7 Hz, 3H), 0.67-0.76 (3H, m).

The following compounds were prepared by methods analogous to the method for the last step described for Compound 34:

| Compound # | LRMS m/z [M + H] |
|---|---|
| 324 | 303.3 |

Example 30: Synthesis of Compound 35

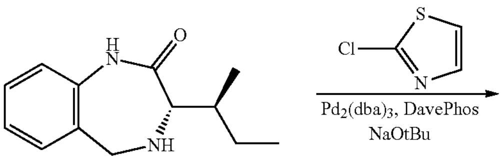

-continued

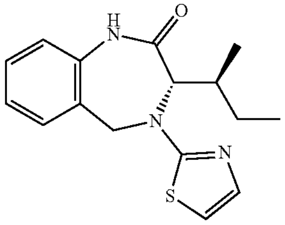

(3S)-3-[(2S)-Butan-2-yl]-4-(1,3-thiazol-2-yl)-1,3,4,5-tetrahydro-2H-1,4-benzodiazepin-2-one (Compound 35). To a mixture of (3S)-3-[(2S)-butan-2-yl]-1,3,4,5-tetrahydro-2H-1,4-benzodiazepin-2-one (100 mg), $Pd_2(dba)_3$ (42 mg), DavePhos (36 mg), and NaOt-Bu (88 mg) in toluene (1.5 mL) was added 2-chloro-1,3-thiazole (110 mg). The reaction was heated to 130° C. under an argon atmosphere in a microwave reactor for 30 min. The reaction mixture was diluted with water and extracted with $CHCl_3$. The organic layer was washed with brine, dried over $MgSO_4$, concentrated, and purified using silica gel column chromatography (hexanes/EtOAc) to give (3S)-3-[(2S)-butan-2-yl]-4-(1,3-thiazol-2-yl)-1,3,4,5-tetrahydro-2H-1,4-benzodiazepin-2-one (Compound 35, 124 mg) as a pale yellow solid. LRMS (ES) m/z 302.3 (M+H). $^1$H NMR (500 MHz, DMSO-$d_6$) δ 10.16-10.06 (m, 1H), 7.45-7.39 (m, 1H), 7.34-7.27 (m, 1H), 7.18 (dd, J=3.5, 2.4 Hz, 1H), 7.14-7.04 (m, 2H), 6.86 (dd, J=3.7, 3.7 Hz, 1H), 4.68-4.48 (m, 3H), 1.51-1.34 (m, 2H), 1.19-0.99 (m, 1H), 0.84-0.66 (m, 6H).

The following compounds were prepared by methods analogous to the method for the last step described for Compound 35:

| Compound # | LRMS m/z [M + H] |
|---|---|
| 323 | 288.3 |

Example 31: Synthesis of Compound 4

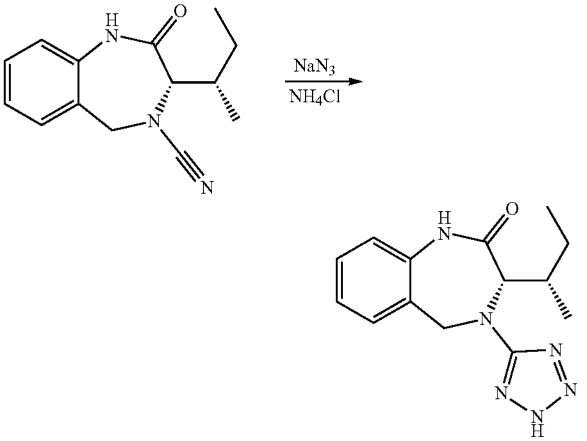

(S)-3-((S)-sec-Butyl)-4-(2H-tetrazol-5-yl)-1,3,4,5-tetrahydro-2H-benzo[e][1,4]diazepin-2-one (Compound 4). A mixture of (S)-3-((S)-sec-butyl)-2-oxo-1,2,3,5-tetrahydro-4H-benzo[e][1,4]diazepine-4-carbonitrile (442 mg, 1.8 mmol), $NaN_3$ (709 mg, 10.9 mmol), $NH_4Cl$ (486 mg, 9.1 mmol), and DMF (4 mL) was stirred at 90° C. for 1 h. The reaction mixture was cooled to rt, diluted with 1M HCl (4 mL), and extracted with EtOAc. The organic layer was washed with brine, dried over sodium sulfate, and concentrated. The residue was purified with reverse phase HPLC (5-70% acetonitrile in water with 0.1% formic acid) to give (S)-3-((S)-sec-butyl)-4-(2H-tetrazol-5-yl)-1,3,4,5-tetrahydro-2H-benzo[e][1,4]diazepin-2-one as an off-white solid (Compound 4, 385 mg, 72%). LRMS (APCI) m/z 287.1 (M+H). $^1$H NMR (400 MHz, DMSO-$d_6$) δ 15.33 (s, 1H), 10.16 (s, 1H), 7.41 (d, J=7.5 Hz, 1H), 7.33 (t, J=7.7 Hz, 1H), 7.13 (t, J=7.4 Hz, 1H), 7.08 (d, J=7.9 Hz, 1H), 4.66 (d, J=14.1 Hz, 1H), 4.54 (d, J=14.1 Hz, 1H), 4.37 (d, J=10.4 Hz, 1H), 1.43 (ddd, J=13.6, 7.5, 3.3 Hz, 1H), 1.30 (s, 1H), 1.03 (dp, J=20.7, 7.5 Hz, 1H), 0.80 (d, J=6.6 Hz, 3H), 0.68 (t, J=7.4 Hz, 3H).

Example 32: Synthesis of Compound 6

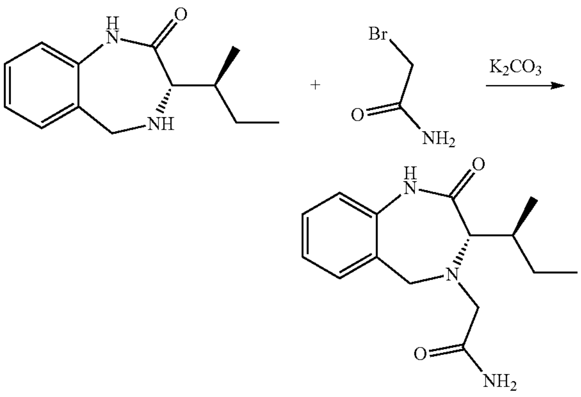

2-((S)-3-((S)-sec-Butyl)-2-oxo-1,2,3,5-tetrahydro-4H-benzo[e][1,4]diazepin-4-yl)acetamide (Compound 6). A mixture of (S)-3-((S)-sec-butyl)-1,3,4,5-tetrahydro-2H-benzo[e][1,4]diazepin-2-one (30 mg, 0.14 mmol), 2-bromoacetamide (19 mg, 0.14 mmol) and $K_2CO_3$ (38 mg, 0.28 mmol) in acetonitrile (1 mL) was stirred at rt overnight. The reaction was then concentrated and purified with reverse phase HPLC (5-70% MeCN/$H_2O$, 0.1% formic acid buffer) to provide 2-((S)-3-((S)-sec-butyl)-2-oxo-1,2,3,5-tetrahydro-4H-benzo[e][1,4]diazepin-4-yl)acetamide as a white solid (Compound 6, 7 mg, 18%). LRMS (APCI) m/z 276.1 (M+H). $^1$H NMR (400 MHz, methanol-$d_4$) δ 7.37-7.31 (m, 2H), 7.18 (dd, J=7.5, 7.5 Hz, 1H), 7.05 (d, J=7.8 Hz, 1H), 3.96 (d, J=12.5 Hz, 1H), 3.70 (d, J=12.7 Hz, 1H), 3.48 (d, J=16.2 Hz, 1H), 3.23-3.05 (m, 2H), 1.82-1.71 (m, 1H), 1.51-1.41 (m, 1H), 1.14-1.02 (m, 1H), 0.85-0.80 (m, 6H).

The following compounds were prepared by methods analogous to the method for the last step using an appropriate electrophile as described for Compound 6 or using a reductive amination:

| Compound # | LRMS m/z [M + H] |
|---|---|
| 309 | 317.3 |
| 310 | 277.2 |
| 311 | 290.1 |
| 312 | 290.1 |
| 313 | 318.2 |
| 314 | 304.1 |

-continued

| Compound # | LRMS m/z [M + H] |
|---|---|
| 315 | 301.2 |
| 316 | 258.1 |

Example 33: Synthesis of Compound 62

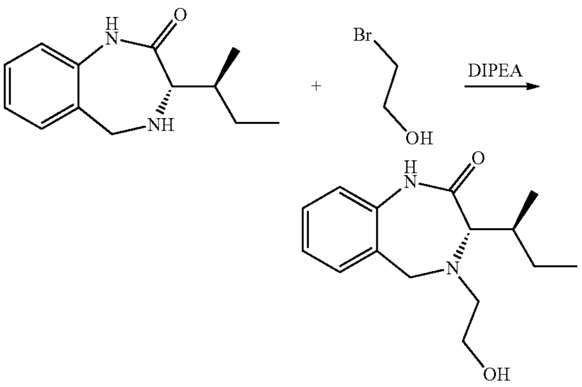

(S)-3-((S)-sec-Butyl)-4-(2-hydroxyethyl)-1,3,4,5-tetrahydro-2H-benzo[e][1,4]diazepin-2-one (Compound 63). A mixture of (S)-3-((S)-sec-butyl)-1,3,4,5-tetrahydro-2H-benzo[e][1,4]diazepin-2-one (30 mg, 0.14 mmol), 2-bromoethanol (52 mg, 0.41 mmol) and DIPEA (76 μL, 0.41 mmol) in ACN (1 mL) was heated to reflux and stirred overnight. The reaction was filtered and purified with reverse phase HPLC (5-70% MeCN/$H_2O$, 0.1% formic acid buffer) to give (S)-3-((S)-sec-butyl)-4-(2-hydroxyethyl)-1,3,4,5-tetrahydro-2H-benzo[e][1,4]diazepin-2-one (Compound 63, 3 mg, 8%) as a formic acid salt and white solid. LRMS (APCI) m/z 263.1 (M+H). $^1$H NMR (400 MHz, chloroform-d) δ 8.48 (s, 1H), 8.13 (s, 1H), 7.38-7.25 (m, 2H), 7.17 (dd, J=7.5, 7.5 Hz, 1H), 6.99 (d, J=8.0 Hz, 1H), 4.44 (s, 1H), 4.02 (d, J=13.6 Hz, 1H), 3.88 (d, J=13.7 Hz, 1H), 3.82-3.70 (m, 2H), 3.24 (d, J=10.5 Hz, 1H), 3.08-3.00 (m, 1H), 2.90-2.72 (m, 1H), 1.79-1.67 (m, 1H), 1.56-1.45 (m, 1H), 1.15-1.03 (m, 1H), 0.91-0.76 (m, 6H).

Example 34: Synthesis of Compound 7

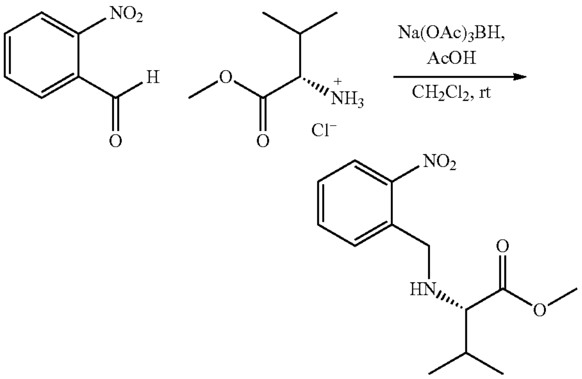

Step 1: Methyl (2-nitrobenzyl)-L-valinate. AcOH (9.1 mL, 158.8 mmol) was added to a stirring solution of 2-nitrobenzaldehyde (20 g, 132.3 mmol) and valine methyl ester hyrochloride (26.6 g, 158.8 mmol) in $CH_2Cl_2$ (150 mL) at rt. After 1 h, the reaction was placed in a water bath before $Na(OAc)_3BH$ (56.1 g, 264.7 mmol) was added portion wise over 20 min. After 2 h, the reaction was cooled to 0° C., quenched with saturated sodium bicarbonate (400 mL), and stirred vigorously for 30 min. The reaction mixture was extracted with $CH_2Cl_2$ (3×300 mL), and the combined organic layers were dried over sodium sulfate, filtered, concentrated, and purified using silica chromatography (0->20% EtOAc/hexanes with 1% $NEt_3$) to give methyl (2-nitrobenzyl)-L-valinate as a yellow oil (22.34 g, 64%). LRMS (APCI) m/z 267.1 (M+H). $^1H$ NMR (400 MHz, chloroform-d) δ 7.92 (dd, J=8.1, 1.0 Hz, 1H), 7.68-7.62 (m, 1H), 7.58 (td, J=7.5, 1.3 Hz, 1H), 7.51-7.37 (m, 1H), 4.18-3.88 (m, 2H), 3.72 (s, 3H), 3.01 (d, J=6.1 Hz, 1H), 1.97-1.89 (m, 1H), 1.59 (s, 1H), 0.95 (d, J=6.8 Hz, 6H).

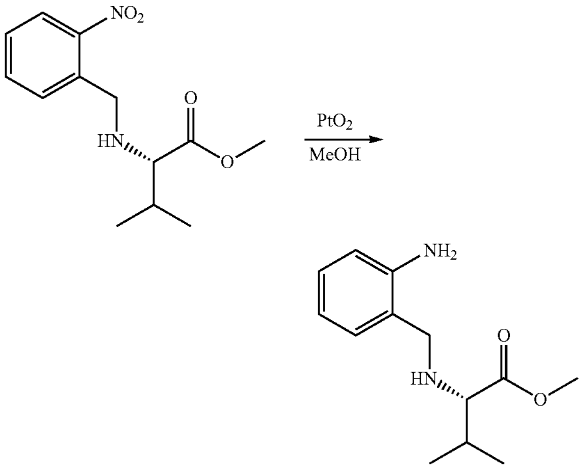

Step 2: Methyl (2-aminobenzyl)-L-valinate. Methyl (2-nitrobenzyl)-L-valinate (21.4 g, 80.4 mmol) and $PtO_2$ (730 mg, 3.2 mmol) were suspended in MeOH (100 mL) before being stirred under $H_2$ (80 psi) at rt. After 3 h, the reaction was filtered through a pad of Celite and solvent was removed by rotary evaporation to give methyl (2-aminobenzyl)-L-valinate (18.5 g, 97%) as a tan oil which was used in the next step without further purification. LRMS (APCI) m/z 237.1 (M+H). $^1H$ NMR (400 MHz, methanol-d$_4$) δ 7.06 (t, J=7.6 Hz, 1H), 6.97 (d, J=7.2 Hz, 1H), 6.76 (d, J=7.9 Hz, 1H), 6.66 (t, J=7.4 Hz, 1H), 3.81 (d, J=12.5 Hz, 1H), 3.75 (s, 3H), 3.55 (d, J=12.5 Hz, 1H), 3.00 (d, J=6.1 Hz, 1H), 1.92 (dq, J=13.4, 6.7 Hz, 1H), 0.93 (t, J=7.2 Hz, 6H).

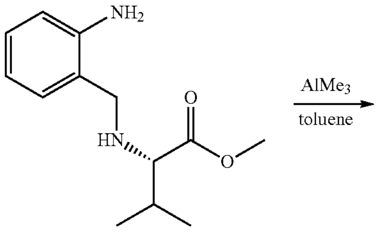

-continued

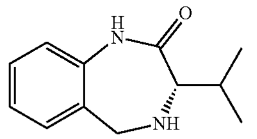

Step 3: (S)-3-Isopropyl-1,3,4,5-tetrahydro-2H-benzo[e][1,4]diazepin-2-one. Trimethylaluminium (43.6 mL, 87.1 mmol, 2M in heptane) was added slowly over 10 min to a stirring solution of methyl (2-aminobenzyl)-L-valinate (10.3 g, 43.6 mmol) in toluene (85 mL) at 0° C. After 10 min, the reaction mixture was warmed to rt and stirred for 2 h. The reaction was then cooled to 0° C., quenched with slow addition of isopropanol (8 mL) followed by MeOH (8 mL) and stirred vigorously for 10 min. Saturated sodium bicarbonate (250 mL) and EtOAc (250 mL) were then added, the reaction mixture filtered, and the aqueous layer separated. The organic layer was washed with brine (2×150 mL), dried over sodium sulfate, filtered, and the solvent was removed by rotary evaporation to give (S)-3-isopropyl-1,3,4,5-tetrahydro-2H-benzo[e][1,4]diazepin-2-one as a white solid (6.9 g, 77%). LRMS (APCI) m/z 205.1 (M+H). $^1H$ NMR (400 MHz, methanol-d$_4$) δ 7.38-7.29 (m, 2H), 7.20 (t, J=7.5 Hz, 1H), 7.06 (d, J=7.8 Hz, 1H), 3.89 (q, J=13.3 Hz, 2H), 2.98 (d, J=8.8 Hz, 1H), 2.12 (ddt, J=13.4, 8.6, 6.8 Hz, 1H), 0.92 (dd, J=16.2, 6.7 Hz, 6H).

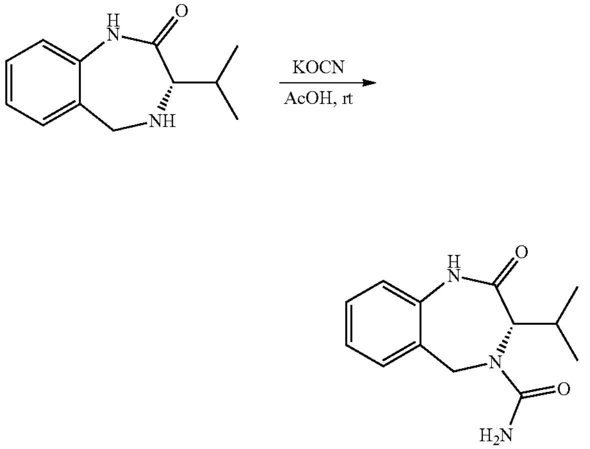

Step 4: (S)-3-Isopropyl-2-oxo-1,2,3,5-tetrahydro-4H-benzo[e][1,4]diazepine-4-carboxamide (Compound 7). KOCN (160 mg, 1.96 mmol) was added to a stirring solution of (S)-3-isopropyl-1,3,4,5-tetrahydro-2H-benzo[e][1,4]diazepin-2-one (80 mg, 0.392 mmol) in AcOH (2 mL) at rt. After 4 h, the reaction was concentrated, suspended in MeOH (total volume 1.8 mL), filtered through a 0.4 μm syringe filter, and then purified using reverse phase HPLC (0->30% MeCN/$H_2O$ w/0.1% formic acid) to give (S)-3-isopropyl-2-oxo-1,2,3,5-tetrahydro-4H-benzo[e][1,4]diazepine-4-carboxamide as a white solid (Compound 7, 67 mg, 69%). LRMS (APCI) m/z 248.1 (M+H). $^1H$ NMR (400 MHz, methanol-d$_4$) δ 7.43-7.27 (m, 2H), 7.16 (t, J=7.5 Hz, 1H), 7.07 (d, J=7.9 Hz, 1H), 4.64 (d, J=6.3 Hz, 1H), 4.59 (q, J=14.4, 12.4 Hz, 2H), 1.58 (tt, J=13.2, 6.7 Hz, 1H), 0.89 (dd, J=16.2, 6.6 Hz, 6H).

Example 35: Synthesis of Compound 9

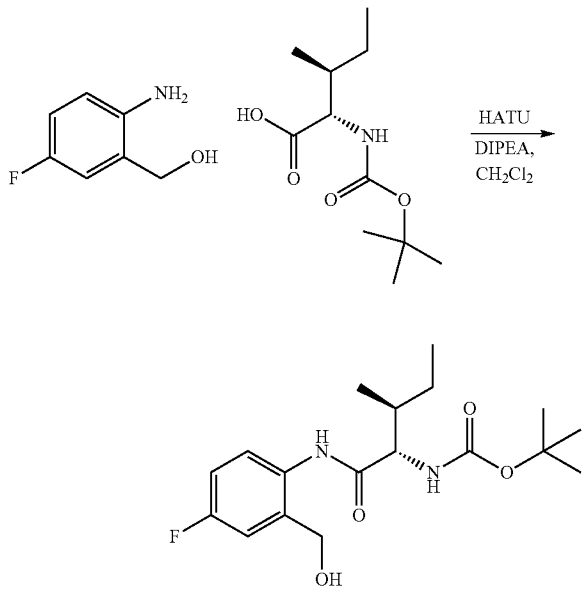

Step 1: tert-Butyl ((2S,3S)-1-((4-fluoro-2-(hydroxymethyl)phenyl)amino)-3-methyl-1-oxopentan-2-yl)carbamate. To an ice-cooled mixture of (tert-butoxycarbonyl)-L-isoleucine (48.0 g, 208 mmol) and 4-fluoro-2-hydroxymethylaniline (57.1 g, 405 mmol) in $CH_2Cl_2$ (500 mL) was added HATU (83.0 g, 218 mmol) and DIPEA (54.0 mL, 315 mmol). The reaction mixture was stirred at rt overnight and then concentrated. Water was added to the residue, and the mixture was extracted twice with ethyl acetate. The organic layer was separated and then combined with 20% citric acid (500 mL). The mixture was vigorously stirred for 30 min and organic layer was separated. This washing step was repeated once with 20% citric acid and then with saturated sodium bicarbonate. The organic layer was then washed with brine, dried over $MgSO_4$, filtered, and mixed with silica gel (200 g). This mixture was stirred for 30 min, filtered, and concentrated under reduced pressure. To the resulting residue was added MeOH (50 mL) and saturated ammonium chloride (500 mL), and the mixture was stirred for 2 h. The precipitate was collected by filtration, washed with water, and dried under reduced pressure. This solid was then recrystallized using ethyl acetate and hexanes to give tert-butyl ((2S,3S)-1-((4-fluoro-2-(hydroxymethyl)phenyl)amino)-3-methyl-1-oxopentan-2-yl)carbamate (62.2 g, 175 mmol, 84% yield) as a colorless solid.

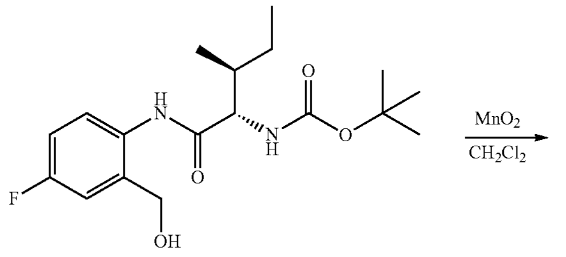

-continued

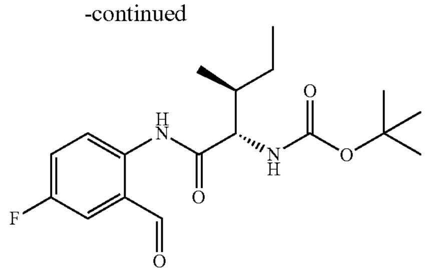

Step 2: tert-Butyl ((2S,3S)-1-((4-fluoro-2-formylphenyl)amino)-3-methyl-1-oxopentan-2-yl)carbamate. To a 1-L round-bottom flask was added tert-butyl ((2S,3S)-1-((4-fluoro-2-(hydroxymethyl)phenyl)amino)-3-methyl-1-oxopentan-2-yl)carbamate (62.2 g, 175 mmol) and $CH_2Cl_2$ (900 mL), followed by $MnO_2$ (198 g, 2.28 mol). The reaction mixture was stirred at rt for 2 d, and the resulting mixture was filtered through Celite. The filtrate was then concentrated to give tert-butyl ((2S,3S)-1-((4-fluoro-2-formylphenyl)amino)-3-methyl-1-oxopentan-2-yl)carbamate (53.5 g, 152 mmol, 87% yield) as a yellow solid.

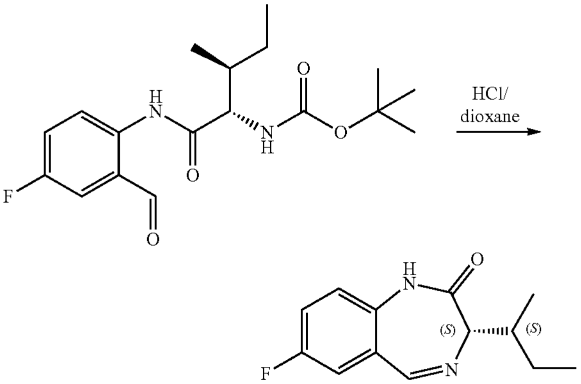

Step 3: (S)-3-((S)-sec-Butyl)-7-fluoro-1,3-dihydro-2H-benzo[e][1,4]diazepin-2-one. To a 1-L round-bottom flask was added tert-butyl ((2S,3S)-1-((2-formylphenyl)amino)-3-methyl-1-oxopentan-2-yl)carbamate (53.5 g, 152 mmol), EtOAc (220 mL), and 4 M HCl in EtOAc (190 mL, 760 mmol). After stirring at rt overnight, the resultant precipitate was collected by filtration and washed with EtOAc The solid was then suspended in EtOAc, neutralized with saturated sodium bicarbonate, and stirred at rt for 1 h. The resulting mixture was diluted with water and extracted with EtOAc. The organic layer was dried over sodium sulfate, filtered, and concentrated under reduced pressure. The residue was suspended in hexane, filtered, washed with hexane, and dried under reduced pressure to give (S)-3-((S)-sec-butyl)-7-fluoro-1,3-dihydro-2H-benzo[e][1,4]diazepin-2-one (20.2 g, 86.2 mmol, 57% yield) as a colorless solid. The filtrate stored in the previous step was neutralized with 1M NaOH, extracted with EtOAc, dried over $MgSO_4$, filtered, and concentrated under reduced pressure. The residue was purified using silica gel column chromatography (0 to 10% MeOH/$CHCl_3$) to give additional (S)-3-((S)-sec-butyl)-7-fluoro-1,3-dihydro-2H-benzo[e][1,4]diazepin-2-one (5.89 g, 25.1 mmol, 17% yield) as a pale yellow solid. The combined yield for this reaction was 26.1 g (74% yield).

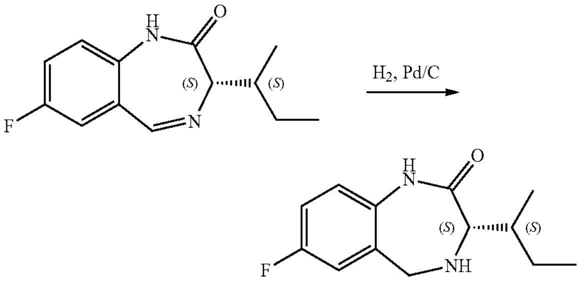

Step 4: (S)-3-((S)-sec-Butyl)-7-fluoro-1,3,4,5-tetrahydro-2H-benzo[e][1,4]diazepin-2-one. To a solution of (3S)-3-[(2S)-butan-2-yl]-7-fluoro-1,3-dihydro-2H-1,4-benzodiazepin-2-one (26.1 g, 111 mmol) in MeOH (320 mL) was added Pd/C-ethylenediamine complex (ca 4 wt % Pd, 1.93 g, 725 μmol) under an argon atmosphere that was then replaced with a hydrogen atmosphere. After stirring at rt overnight, the resulting mixture was filtered through Celite, and the filtrate was concentrated under reduced pressure. The residue was purified with using silica gel chromatography (0 to 100% EtOAc/hexane), and the resulting solid was suspended in hexane, filtered, washed with hexane, and dried under reduced pressure to give (S)-3-((S)-sec-butyl)-7-fluoro-1,3,4,5-tetrahydro-2H-benzo[e][1,4]diazepin-2-one (18.3 g, 77.4 mmol, 70% yield) as a colorless solid.

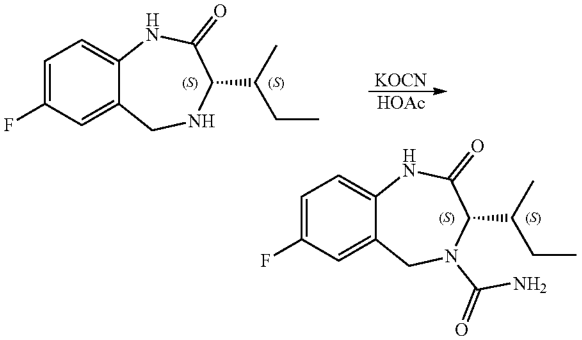

Step 5: (S)-3-((S)-sec-Butyl)-7-fluoro-2-oxo-1,2,3,5-tetrahydro-4H-benzo[e][1,4]diazepine-4-carboxamide (Compound 9). To a 250-mL round-bottom flask was added (S)-3-((S)-sec-butyl)-7-fluoro-1,3,4,5-tetrahydro-2H-benzo[e][1,4]diazepin-2-one (17.3 g, 73.2 mmol), AcOH (8.4 mL, 150 mmol), and MeOH (175 mL). The mixture was cooled with an ice bath and potassium cyanate (7.15 g, 110 mmol) was added. After stirring at rt for 5 d, the resulting mixture was cooled with ice-bath, neutralized with saturated sodium bicarbonate, and concentrated under reduced pressure. The residue was suspended in water, collected by filtration, washed with water, and dried under reduced pressure to give (S)-3-((S)-sec-butyl)-7-fluoro-2-oxo-1,2,3,5-tetrahydro-4H-benzo[e][1,4]diazepine-4-carboxamide (Compound 9, 19.9 g, 71.2 mmol, 97% yield) as a colorless solid. LRMS (ES) m/z 280.4 (M+H). $^1$H NMR (400 MHz, DMSO-$d_6$) δ 9.93 (1H, s), 7.19 (1H, dd, J=9.1, 2.6 Hz), 7.12-7.06 (2H, m), 6.15 (2H, s), 4.60 (1H, d, J=9.5 Hz), 4.48 (1H, d, J=15.4 Hz), 4.40 (1H, d, J=15.5 Hz), 1.48-1.38 (2H, m), 1.04-0.93 (1H, m), 0.81 (3H, d, J=6.7 Hz), 0.73 (3H, t, J=7.3 Hz).

Example 36

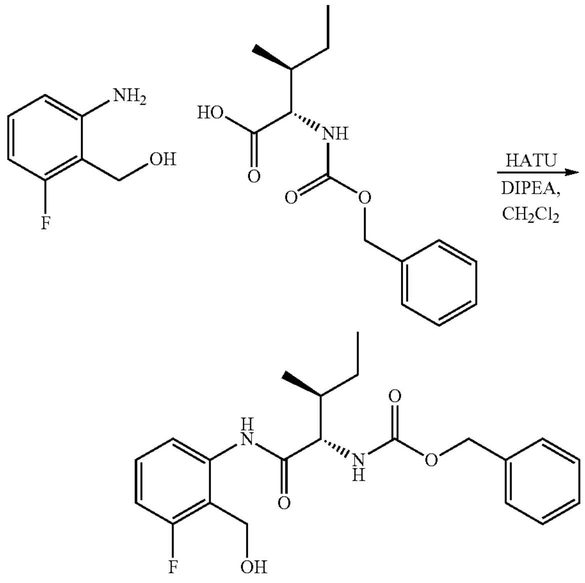

Benzyl ((2S,3S)-1-((3-fluoro-2-(hydroxymethyl)phenyl)amino)-3-methyl-1-oxopentan-2-yl)carbamate. To a mixture of ((benzyloxy)carbonyl)-L-isoleucine (500 mg) and (2-amino-6-fluorophenyl)methanol (500 mg) in $CH_2Cl_2$ (10 mL) was added HATU (800 mg) and DIPEA (0.8 mL). The reaction was stirred for 2 h. The reaction mixture was then diluted with water and extracted with EtOAc twice. The combined organic layers were washed with 1M aqueous HCl and concentrated. The residue was purified using silica gel column chromatography ($CHCl_3$/MeOH) to give benzyl ((2S,3S)-1-((3-fluoro-2-(hydroxymethyl)phenyl)amino)-3-methyl-1-oxopentan-2-yl)carbamate (355 mg) as an orange solid.

Example 37: Synthesis of Compound 10

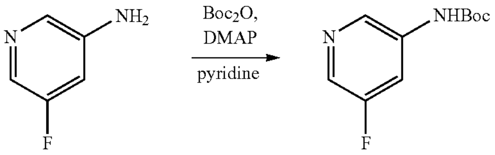 [SMILES: Nc1cncc(F)c1 ; CC(C)(C)OC(=O)Nc1cncc(F)c1]

Step 1: tert-Butyl (5-fluoropyridin-3-yl)carbamate. To a 3-L round-bottom flask purged and maintained with an inert atmosphere of argon was added a solution of 5-fluoropyridin-3-amine (300.0 g, 1.0 equiv) and DMAP (32.6 g, 0.1 equiv) in pyridine (1200 mL). The reaction mixture was cooled with an ice bath followed by the addition of $Boc_2O$ (700.0 g, 1.2 equiv) in portions to maintain the reaction temperature between 0 and 15° C. After the addition was completed, the reaction was stirred overnight at 30° C. The reaction mixture was then concentrated and the residue was dissolved in 1500 mL of MeOH. Water was added to the mixture, and the resultant solid was collected by filtration. The crude solid was dissolved in a minimum amount of dichloromethane and then chromatographed through silica gel (20% ethyl acetate/petroleum ether to give 500 g (88%) of tert-butyl N-(5-fluoropyridin-3-yl)-carbamate as an off-white solid. LRMS (ES) m/z 212.9 (M+H). $^1$H NMR (400 MHz, chloroform-d) δ 8.18 (dd, J=16.4, 2.1 Hz, 2H), 7.98 (d, J=10.7 Hz, 1H), 7.07-7.02 (m, 1H), 1.55 (s, 9H).

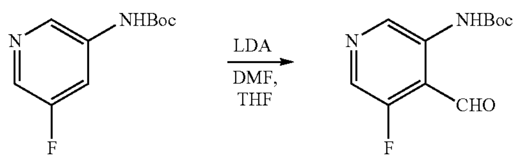 [SMILES: CC(C)(C)OC(=O)Nc1cncc(F)c1 ; CC(C)(C)OC(=O)Nc1cncc(F)c1C=O]

Step 2: tert-Butyl (5-fluoro-4-formylpyridin-3-yl)carbamate. To a 1-L round-bottom flask purged and maintained with an inert atmosphere of argon was added a solution of tert-butyl N-(5-fluoropyridin-3-yl)-carbamate (500.0 g, 1.0 equiv) in THF (5 L). The reaction mixture was cooled with a dry ice/acetone bath, followed by the dropwise addition of 2 M LDA in THF (3.5 L, 3.0 equiv) while maintaining the reaction temperature below −70° C. The reaction mixture was warmed to −30° C. for 45 min and then cooled to −70° C. DMF (860.0 g, 5.0 equiv) was added to the solution over 10 min to maintain the temperature of the reaction below −50° C., and the reaction mixture was then warmed to rt and stirred for 2 h. The reaction was then quenched by the addition of 4 L of saturated ammonium chloride, and the resulting solution was extracted three times with ethyl acetate (1.5 L). The organic layers were combined, concentrated, dried over sodium sulfate, and chromatographed through silica gel (20% ethyl acetate/petroleum ether) to give 300 g (53%) of tert-butyl N-(5-fluoro-4-formylpyridin-3-yl)carbamate as a yellow solid. LRMS (ES) m/z 241.0 (M+H). $^1$H NMR (300 MHz, DMSO-$d_6$) δ 10.17 (s, 1H), 10.07 (s, 1H), 9.11 (s, 1H), 8.47 (d, J=1.3 Hz, 1H), 1.49 (s, 9H).

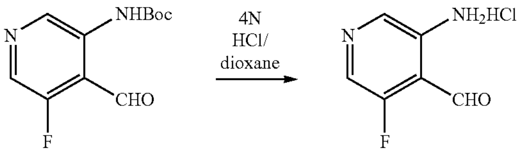

Step 3: 3-Amino-5-fluoroisonicotinaldehyde hydrochloride. To a 3-L round-bottom flask purged and maintained with an inert atmosphere of argon was added a solution of tert-butyl N-(5-fluoro-4-formylpyridin-3-yl)carbamate (300.0 g, 1.0 equiv) in HCl (2M in dioxane, 2 L). The resulting reaction mixture was stirred at rt overnight. The solid formed in the reaction was filtered, washed twice with 500 mL of ether, and then dried under vacuum to give 280 g of 3-amino-5-fluoroisonicotinaldehyde hydrochloride as a yellow solid. LRMS (ES) m/z 141.2 (M+H).

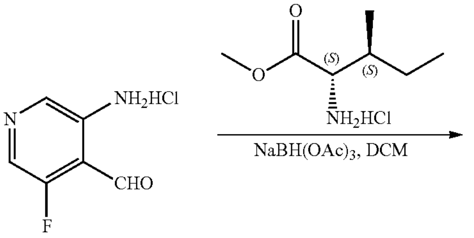

-continued

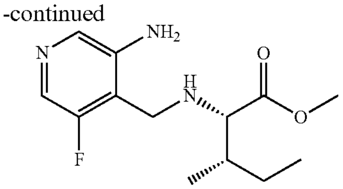

Step 4: Methyl ((3-amino-5-fluoropyridin-4-yl)methyl)-L-isoleucinate. To a 3-L round-bottom flask purged and maintained with an inert atmosphere of argon was added 3-amino-5-fluoroisonicotinaldehyde hydrochloride (280.0 g, 1.0 equiv), methyl L-isoleucinate hydrochloride (260.0 g, 1.1 equiv), and dichloromethane (3 L). The mixture was cooled with an ice bath, followed by the addition of TEA (396.0 g, 3.0 equiv) and AcOH (785.0 g, 10.0 equiv). The mixture was stirred for 30 min, followed by the addition of sodium triacetoxyborohydride (970.0 g, 3.5 equiv) at 0° C. The reaction mixture was stirred overnight at rt. The reaction was then quenched slowly by cooling the reaction with an ice bath to less than 5° C. and then slowly adding 2 L of saturated sodium bicarbonate. The resulting mixture was extracted three times with dichloromethane (2 L), and the organic layers were combined, concentrated, and chromatographed through silica gel (25% ethyl acetate/petroleum ether) to give 240 g (70% over two steps) of methyl ((3-amino-5-fluoropyridin-4-yl)methyl)-L-isoleucinate as a yellow oil. LRMS (ES) m/z 270.2 (M+H). $^1$H NMR (300 MHz, chloroform-d) δ 7.72 (s, 1H), 7.64 (s, 1H), 4.97 (s, 2H), 3.76-3.53 (m, 5H), 2.94 (d, J=5.8 Hz, 1H), 1.65-1.48 (m, 1H), 1.33 (m, 1H), 1.13-0.89 (m, 1H), 0.83-0.62 (m, 6H).

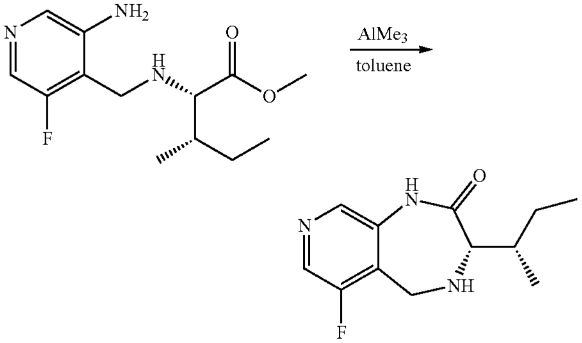

Step 5: (S)-3-((S)-sec-Butyl)-6-fluoro-1,3,4,5-tetrahydro-2H-pyrido[3,4-e][1,4]diazepin-2-one. To a 3-L round-bottom flask purged and maintained with an inert atmosphere of argon was added a solution of methyl ((3-amino-5-fluoropyridin-4-yl)methyl)-L-isoleucinate (240.0 g, 1.0 equiv) in toluene (1 L), followed by the addition of 2 M trimethylaluminum in toluene (1.0 L, 2.0 equiv) dropwise at 0° C. The resulting solution was warmed to rt and stirred for 3 h. The reaction was then quenched by the addition of methanol (3 L) at 0° C. The resultant solid was filtered and washed with methanol three times. The filtrate was concentrated, and the residue was purified by recrystallization from ether to give 140 g (66%) of (S)-3-((S)-sec-butyl)-6-fluoro-1,3,4,5-tetrahydro-2H-pyrido[3,4-e][1,4]diazepin-2-one as a white solid. LRMS (ES) m/z 238.0 (M+H). $^1$H NMR (400 MHz, DMSO-$d_6$) δ 10.03 (s, 1H), 8.20 (s, 1H), 8.11 (s, 1H), 4.14 (d, J=16.9 Hz, 1H), 3.92 (d, J=17.1 Hz, 1H), 3.25 (d, J=5.4

Hz, 1H), 2.93 (s, 1H), 1.87 (m, 1H), 1.51 (m, 1H), 1.20-1.04 (m, 1H), 0.92 (d, J=6.8 Hz, 3H), 0.84 (t, J=7.4 Hz, 3H).

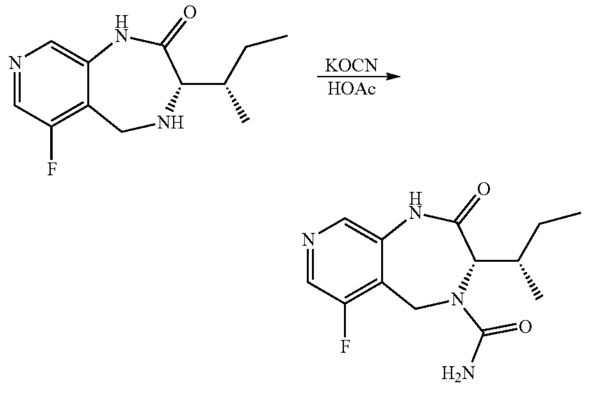

Step 6: (S)-3-((S)-sec-Butyl)-6-fluoro-2-oxo-1,2,3,5-tetrahydro-4H-pyrido[3,4-e][1,4]diazepine-4-carboxamide (Compound 10). To a 1-L round-bottom flask was added (S)-3-((S)-sec-butyl)-6-fluoro-1,3,4,5-tetrahydro-2H-pyrido[3,4-e][1,4]diazepin-2-one (140.0 g, 1.0 equiv) in AcOH (400 mL). The mixture was cooled to 0° C. and potassium cyanate (95.0 g, 2.0 equiv) was added. The reaction mixture was stirred for 1 h at rt and then concentrated. The reaction mixture was diluted with water (200 mL), cooled with an ice bath, and the pH of the solution was adjusted slowly to 7-8 with 2M sodium bicarbonate at 0° C. The solids were collected by filtration, washed with water three times, and dried in vacuo to give 120 g (72%) of (S)-3-((S)-sec-butyl)-6-fluoro-2-oxo-1,2,3,5-tetrahydro-4H-pyrido[3,4-e][1,4]diazepine-4-carboxamide (Compound 10) as a white solid. LRMS (ES) m/z 281.1 (M+H). $^1$H NMR (400 MHz, DMSO-$d_6$) δ 10.14 (s, 1H), 8.11 (s, 1H), 8.07 (s, 1H), 6.29 (s, 2H), 5.03 (s, 1H), 4.33 (s, 2H), 2.0 (s, 1H), 1.50 (m, 1H), 1.22-1.01 (m, 1H), 1.01-0.78 (m, 6H).

Example 38: Synthesis of Compound 11

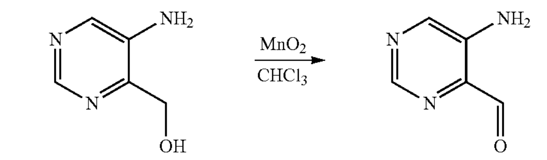 [SMILES: Nc1cncnc1CO ; "MnO2" ; "CHCl3" ; Nc1cncnc1C=O]

Step 1: 5-Aminopyrimidine-4-carbaldehyde. To a solution of (5-aminopyrimidin-4-yl)methanol (0.35 g, 2.8 mmol) in $CHCl_3$ (10 mL) was added manganese dioxide (0.97 g, 11 mmol). The reaction mixture was heated at 65° C. for 2 h. The mixture was cooled down to rt, filtered through Celite, and washed with $CH_2Cl_2$ (20 mL). The filtrate was concentrated to give 5-aminopyrimidine-4-carbaldehyde as an off-white solid which was used directly in the next step (0.32 g, 93% yield). LRMS (APCI) m/z 124.1 (M+H).

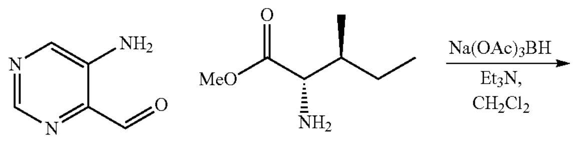

-continued

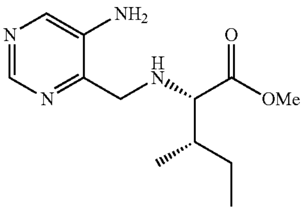

Step 2: Methyl ((5-aminopyrimidin-4-yl)methyl)-L-isoleucinate. To a solution of L-isoleucine methyl ester (0.51 g, 2.8 mmol) in $CH_2Cl_2$(10 mL) was added diisopropylethylamine (0.49 mL, 2.8 mmol), followed by 5-aminopyrimidine-4-carbaldehyde (0.23 g, 1.9 mmol), and the mixture was stirred for 30 min. $Na(OAc)_3BH$ (0.80 g, 3.8 mmol) was added, and the reaction mixture was stirred for 1 h. The reaction mixture was then cooled down to 0° C., diluted with saturated $NaHCO_3$ (10 mL), and then stirred at rt for 1 h. The layers were separated, and the aqueous phase was extracted with additional DCM (10 mL). The organic phases were combined, dried over $Na_2SO_4$, concentrated, and purified using silica gel chromatography (0-25% EtOAc/hexane) to give methyl ((5-aminopyrimidin-4-yl)methyl)-L-isoleucinate as a yellowish oil (0.36 g, 76% yield). LRMS (APCI) m/z 253.2 (M+H).

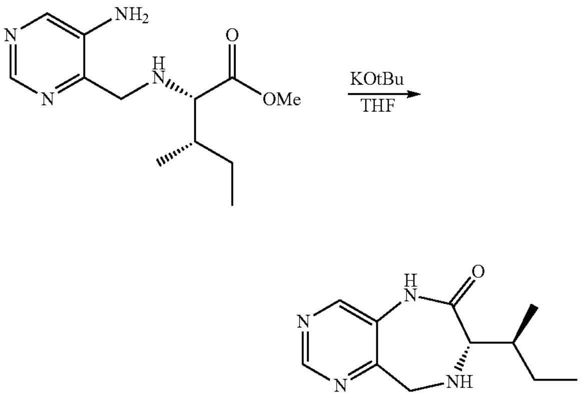

Step 3: (S)-7-((S)-sec-Butyl)-5,7,8,9-tetrahydro-6H-pyrimido[5,4-e][1,4]diazepin-6-one. To a solution of methyl ((5-aminopyrimidin-4-yl)methyl)-L-isoleucinate (202 mg, 0.8 mmol) in THF (5 mL) was added potassium tert-butoxide (90 mg, 0.8 mmol). The reaction mixture was stirred at rt for 1 h. The solvent was removed, and the residue was purified using reverse phase HPLC (5-100% MeCN/$H_2O$, 0.1% formic acid buffer) over 40 min to give (S)-7-((S)-sec-butyl)-5,7,8,9-tetrahydro-6H-pyrimido[5,4-e][1,4]diazepin-6-one as an off-white solid (80 mg, 45% yield). LRMS (APCI) m/z 221.2 (M+H).

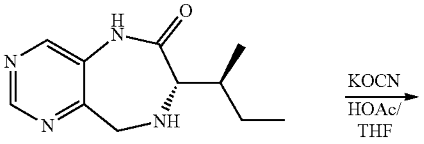

-continued

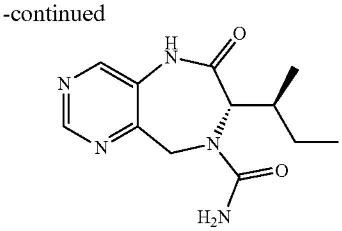

Step 4: (S)-7-((S)-sec-Butyl)-6-oxo-5,6,7,9-tetrahydro-8H-pyrimido[5,4-e][1,4]diazepine-8-carboxamide (Compound 11). To a 100-mL round bottom flask under a nitrogen atmosphere was added (S)-7-((S)-sec-butyl)-5,7,8,9-tetrahydro-6H-pyrimido[5,4-e][1,4]diazepin-6-one (26 mg, 0.12 mmol) and HOAc (1 mL), followed by potassium cyanate (29 mg, 0.36 mmol). The reaction mixture was stirred for 1 h. The mixture was purified using reverse phase HPLC (5-100% $MeCN/H_2O$, 0.1% formic acid buffer) over 40 min to give (S)-7-((S)-sec-butyl)-6-oxo-5,6,7,9-tetrahydro-8H-pyrimido[5,4-e][1,4]diazepine-8-carboxamide as an off-white solid (Compound 11, 25 mg, 79% yield). LRMS (APCI) m/z 264.1 (M+H). $^1H$ NMR (400 MHz, methanol-$d_4$) δ 8.77 (s, 1H), 8.50 (s, 1H), 5.27-5.10 (m, 1H), 4.67-4.35 (m, 2H), 2.06-1.91 (m, 1H), 1.71-1.61 (m, 1H), 1.29-1.18 (m, 1H), 1.05 (d, J=4.0 Hz, 3H), 0.97 (t, J=8.0 Hz, 3H).

Example 39: Synthesis of Compound 13

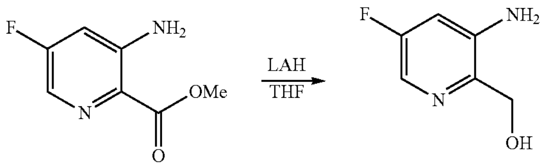 [SMILES: COC(=O)c1ncc(F)cc1N ; Nc1cc(F)cnc1CO ; "THF"]

Step 1: (3-Amino-5-fluoropyridin-2-yl)methanol. To a solution of methyl 3-amino-5-fluoropicolinate (0.51 g, 3.0 mmol) in THF (10 mL) at 0° C. was added lithium aluminum hydride (2.3 M in hexane, 1.56 mL) dropwise. The reaction mixture was stirred at 0° C. for 30 min, followed by the addition of $H_2O$ (0.11 mL), NaOH (3N, 0.11 mL), and $H_2O$ (0.33 mL) in sequence. The mixture was then dried over $Na_2SO_4$, filtered through Celite, and washed with THF (20 mL). The filtrate was concentrated to afford (3-amino-5-fluoropyridin-2-yl)methanol as a yellow solid (0.4 g, 94% yield). LRMS (APCI) m/z 143.1 (M+H).

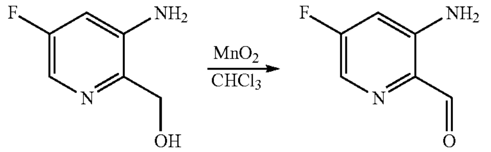

Step 2: 3-Amino-5-fluoropicolinaldehyde. To a solution of (3-amino-5-fluoropyridin-2-yl)methanol (0.40 g, 2.8 mmol) in $CHCl_3$ (10 mL) was added manganese dioxide (1.22 g, 14.0 mmol). The reaction mixture was heated at 65° C. for 2 h. The mixture was cooled down to rt and then was filtered through a Celite and washed with dichloromethane (20 mL). The filtrate was concentrated to give 3-amino-5-fluoropicolinaldehyde as an off-white solid which was used directly in the next step (0.33 g, 84% yield). LRMS (APCI) m/z 141.1 (M+H).

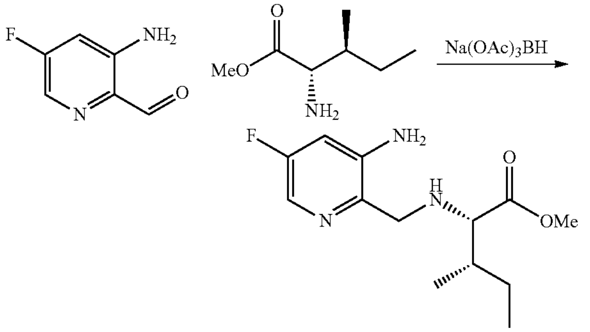

Step 3: Methyl ((3-amino-5-fluoropyridin-2-yl)methyl)-L-isoleucinate. To a solution of 3-amino-5-fluoropicolinaldehyde (0.32 g, 2.3 mmol) in $CH_2Cl_2$(10 mL) at rt was added methyl L-isoleucinate (0.54 g, 2.90 mmol). The reaction mixture was stirred at rt for 1 h and then cooled down to 0° C. followed by the addition of $Na(OAc)_3BH$ (0.98 g, 4.6 mmol) in portions. The reaction mixture was warmed up to rt and stirred for 1 h. The reaction mixture was cooled down to 0° C. and quenched with saturated $NaHCO_3$ (10 mL). The resulting mixture was stirred at rt for 1 h. The layers were separated, and the aqueous phase was extracted with additional dichloromethane (10 mL). The organic phases were combined, dried over $Na_2SO_4$, concentrated, and purified with silica gel chromatography (50% EtOAc/hexane) to give methyl ((3-amino-5-fluoropyridin-2-yl)methyl)-L-isoleucinate as a yellowish oil (0.12 g, 19% yield). LRMS (APCI) m/z 270.2 (M+H).

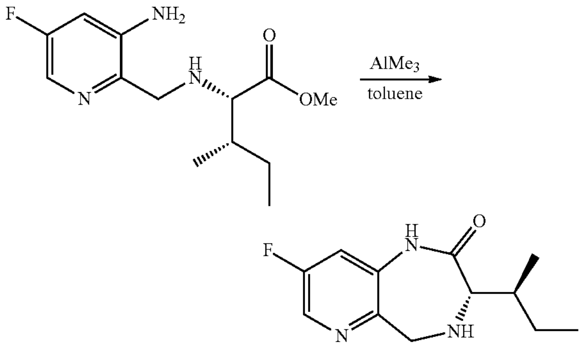

Step 4: (S)-3-((S)-sec-Butyl)-8-fluoro-1,3,4,5-tetrahydro-2H-pyrido[3,2-e][1,4]diazepin-2-one. To a solution of methyl ((3-amino-5-fluoropyridin-2-yl)methyl)-L-isoleucinate (0.12 g, 0.45 mmol) in toluene (10 mL) at rt was added trimethylaluminum (2.0 M in hexane, 0.68 mL, 1.4 mmol) dropwise. The resulting mixture was stirred for 16 h, cooled down to 0° C., and treated sequentially with MeOH (0.5 mL), saturated $NaHCO_3$ (5 mL), and EtOAc (10 mL). The resulting mixture was warmed up to rt and stirred for 1 h. The layers were separated, and the organic layer was dried over $Na_2SO_4$ and concentrated to provide (S)-3-((S)-sec-butyl)-8-fluoro-1,3,4,5-tetrahydro-2H-pyrido[3,2-e][1,4]diazepin-2-one as a white solid (85 mg, 80% yield). LRMS (APCI) m/z 238.1 (M+H).

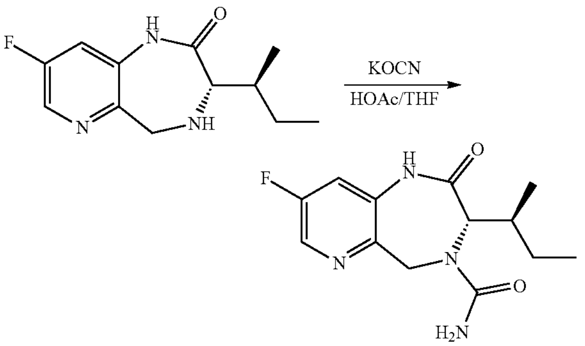

Step 5: (S)-3-((S)-sec-Butyl)-8-fluoro-2-oxo-1,2,3,5-tetrahydro-4H-pyrido[3,2-e][1,4]diazepine-4-carboxamide (Compound 13). To a 100-mL round bottom flask under a nitrogen atmosphere was added (S)-3-((S)-sec-butyl)-8-fluoro-1,3,4,5-tetrahydro-2H-pyrido[3,2-e][1,4]diazepin-2-one (36 mg, 0.15 mmol) and HOAc (1 mL), followed by potassium cyanate (61 mg, 0.75 mmol). The reaction mixture was stirred for 1 h. The mixture was purified using reverse phase HPLC (20-100% MeCN/$H_2O$, 0.1% formic acid buffer) over 40 min to give (S)-3-((S)-sec-butyl)-8-fluoro-2-oxo-1,2,3,5-tetrahydro-4H-pyrido[3,2-e][1,4]diazepine-4-carboxamide as an off-white solid (Compound 13, 16 mg, 38% yield). LRMS (APCI) m/z 281.1 (M+H). $^1$H NMR (400 MHz, methanol-$d_4$) δ 8.19 (d, J=4.0 Hz, 1H), 7.29 (dd, J=4 Hz, 1H), 4.95 (d, J=16 Hz, 1H), 4.70-4.55 (m, 2H), 1.90-1.75 (m, 1H), 1.69-1.57 (m, 1H), 1.26-1.15 (m, 1H), 1.01 (d, J=8.0 Hz, 3H), 0.92 (t, J=8.0 Hz, 3H).

Example 40: Synthesis of Compound 20

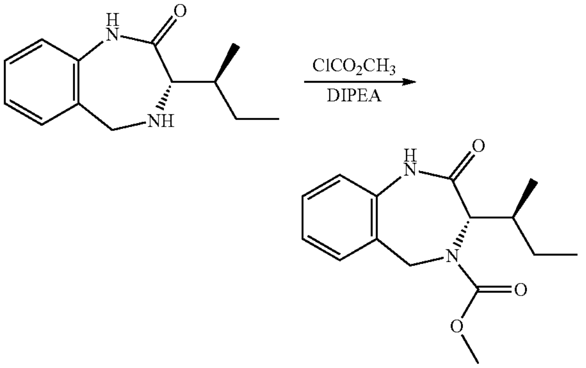

Methyl (S)-3-((S)-sec-butyl)-2-oxo-1,2,3,5-tetrahydro-4H-benzo[e][1,4]diazepine-4-carboxylate (Compound 20). To an ice-cooled solution of (S)-3-((S)-sec-butyl)-1,3,4,5-tetrahydro-2H-benzo[e][1,4]diazepin-2-one (200 mg, 0.916 mmol) in THF (4 mL) was added DIPEA (320 uL, 1.87 mmol) and methyl chloroformate (78 uL, 1.11 mmol). After stirring at 0° C. for 2 h, the reaction mixture was concentrated and then purified using silica gel chromatography (0 to 3% MeOH/$CHCl_3$) to give methyl (S)-3-((S)-sec-butyl)-2-oxo-1,2,3,5-tetrahydro-4H-benzo[e][1,4]diazepine-4-carboxylate (Compound 20, 250 mg, 0.90 mmol, 99% yield) as a colorless solid. LRMS (ES) m/z 277.1 (M+H). $^1$H NMR (399 MHz, DMSO-$d_6$) δ 10.10 (br s, 1H), 7.32-7.26 (m, 2H), 7.09-7.05 (m, 2H), 4.60-4.29 (m, 2H), 3.76 (s, 3H), 3.63 (s, 1H), 1.41-1.20 (m, 2H), 1.02-0.89 (m, 1H), 0.77 (d, J=6.7 Hz, 3H), 0.68 (t, J=7.3 Hz, 3H).

The following compounds were prepared by methods analogous to the method described for Compound 20:

| Compound # | LRMS m/z [M + H] |
|---|---|
| 364 | 296.1 |

Example 41: Synthesis of Compound 26

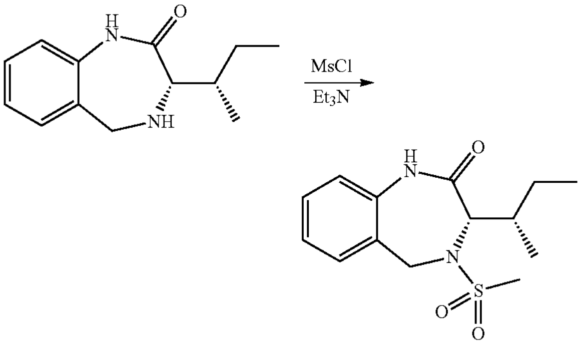

(S)-3-((S)-sec-Butyl)-4-(methylsulfonyl)-1,3,4,5-tetrahydro-2H-benzo[e][1,4]diazepin-2-one (Compound 26). MsCl (30 μL, 0.4 mmol) was added to a stirring solution of (S)-3-((S)-sec-butyl)-1,3,4,5-tetrahydro-2H-benzo[e][1,4]diazepin-2-one (77 mg, 0.4 mmol) and triethylamine (0.12 mL, 0.7 mmol) in $CH_2Cl_2$ (1.5 mL) at rt. After 2 h, the reaction was quenched with MeOH (0.5 mL), concentrated, the residue suspended in MeOH (1.8 mL) and filtered through a syringe filter (0.4 μm), and then purified using reverse phase HPLC (0-70% MeCN/$H_2O$ w/0.1% formic acid) to give (S)-3-((S)-sec-butyl)-4-(methylsulfonyl)-1,3,4,5-tetrahydro-2H-benzo[e][1,4]diazepin-2-one as a white fluffy solid (Compound 26, 47 mg, 45%). LRMS (APCI) m/z 297.0 (M+H). $^1$H NMR (400 MHz, methanol-$d_4$) δ 7.43 (d, J=7.5 Hz, 2H), 7.27 (t, J=7.5 Hz, 1H), 7.10 (d, J=7.9 Hz, 1H), 4.61 (d, J=12.3 Hz, 1H), 4.40 (d, J=12.3 Hz, 1H), 3.96 (d, J=10.4 Hz, 1H), 3.04 (s, 3H), 1.68 (dq, J=14.0, 7.7 Hz, 1H), 0.89 (ddt, J=30.1, 16.3, 8.0 Hz, 2H), 0.77 (d, J=6.3 Hz, 3H), 0.69 (d, J=7.2 Hz, 3H).

The following compounds were prepared by methods analogous to the method described for Compound 26:

| Compound # | LRMS m/z [M + H] |
|---|---|
| 89 | 377.0 |
| 119 | 341.1 |

Example 42: Synthesis of Compound 27

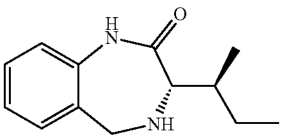

+

-continued

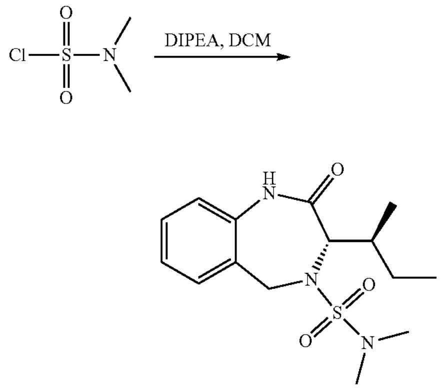

(S)-3-((S)-sec-Butyl)-N,N-dimethyl-2-oxo-1,2,3,5-tetrahydro-4H-benzo[e][1,4]diazepine-4-sulfonamide (Compound 27). To a stirring mixture of (S)-3-((S)-sec-butyl)-1,3,4,5-tetrahydro-2H-benzo[e][1,4]diazepin-2-one (35 mg, 0.16 mmol) and DIPEA (84 μL, 0.48 mmol) in DCM (1 mL) was added dimethylsulfamoyl chloride (25 mg, 0.18 mmol), and the mixture was stirred at rt for 30 min. The reaction was concentrated, followed by purification using reverse phase HPLC (10-100% $MeCN/H_2O$, 0.1% formic acid buffer) to provide (S)-3-((S)-sec-butyl)-N,N-dimethyl-2-oxo-1,2,3,5-tetrahydro-4H-benzo[e][1,4]diazepine-4-sulfonamide as a white solid (Compound 27, 6 mg, 11%). LRMS (APCI) m/z 326.0 (M+H). $^1H$ NMR (400 MHz, methanol-$d_4$) δ 7.41-7.35 (m, 2H), 7.22 (dd, J=7.5, 7.5 Hz, 1H), 7 (d, J=7.7 Hz, 1H), 4.56-4.42 (m, 2H), 4.11 (d, J=9.6 Hz, 1H), 2.90 (s, 6H), 1.73-1.59 (m, 1H), 1.09-0.93 (m, 2H), 0.79 (d, J=5.3 Hz, 3H), 0.72 (t, J=6.7 Hz, 3H).

The following compounds were prepared by methods analogous to the method described for Compound 27:

| Compound # | LRMS m/z [M + H] |
|---|---|
| 90 | 299.1 |
| 120 | 312.1 |
| 333 | 312.0 |
| 345 | 316.3 |

Example 43: Synthesis of Compound 30

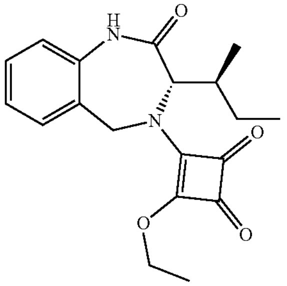

+

-continued

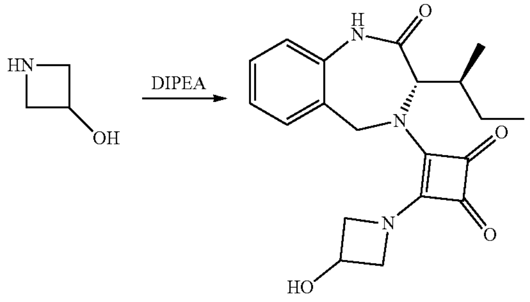

3-((S)-3-((S)-sec-Butyl)-2-oxo-1,2,3,5-tetrahydro-4H-benzo[e][1,4]diazepin-4-yl)-4-(3-hydroxyazetidin-1-yl)cyclobut-3-ene-1,2-dione (Compound 30). A mixture of 3-((S)-3-((S)-sec-butyl)-2-oxo-1,2,3,5-tetrahydro-4H-benzo[e][1,4]diazepin-4-yl)-4-ethoxycyclobut-3-ene-1,2-dione (70 mg, 0.20 mmol), DIPEA (0.12 mL, 0.69 mmol), and 3-hydroxyazetidine HCl salt (67 mg, 0.61 mmol) in EtOH (1 mL) was stirred at rt overnight. The reaction mixture was filtered and purified by reverse phase HPLC (5-70% MeCN/$H_2O$, 0.1% formic acid buffer) to afford 3-((S)-3-((S)-sec-butyl)-2-oxo-1,2,3,5-tetrahydro-4H-benzol[e][1,4]diazepin-4-yl)-4-(3-hydroxyazetidin-1-yl)cyclobut-3-ene-1,2-dione (Compound 30, 35 mg, 46%) as a white solid. LRMS (APCI) m/z 370.1 (M+H). $^1H$ NMR (400 MHz, methanol-$d_4$) δ 7.47-7.41 (m, 2H), 7.25 (dd, J=7.5, 7.5 Hz, 1H), 7.13 (d, J=7.8 Hz, 1H), 4.86-4.73 (m, 5H), 4.60 (d, J=13.4 Hz, 1H), 4.46-4.38 (m, 1H), 4.33 (dd, J=9.4, 3.1 Hz, 1H), 1.55-1.44 (m, 1H), 1.25-0.94 (m, 2H), 0.82 (d, J=6.4 Hz, 3H), 0.69 (t, J=7.3 Hz, 3H).

The following compounds were prepared by methods analogous to the method described for Compound 30:

| Compound # | LRMS m/z [M + H] |
|---|---|
| 130 | 328.1 |
| 131 | 342.1 |
| 132 | 358.1 |
| 372 | 384.1 |
| 374 | 359.1 |
| 375 | 371.1 |
| 376 | 329.1 |
| 377 | 343.1 |
| 381 | 373.0 |

Example 44: Synthesis of Compound 57

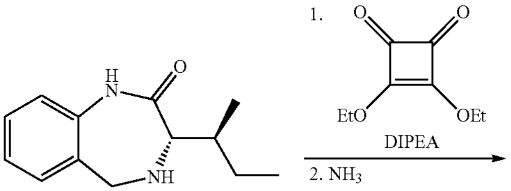

-continued

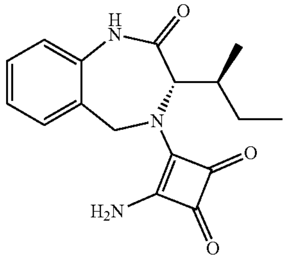

3-Amino-4-((S)-3-((S)-sec-butyl)-2-oxo-1,2,3,5-tetrahydro-4H-benzo[e][1,4]diazepin-4-yl)cyclobut-3-ene-1,2-dione (Compound 57). To a solution of 3,4-diethoxycyclobut-3-ene-1,2-dione (47 mg, 0.28 mmol) in EtOH (1 mL) at rt was added a solution of (S)-3-((S)-sec-butyl)-1,3,4,5-tetrahydro-2H-benzo[e][1,4]diazepin-2-one (60 mg, 0.28 mmol) and DIPEA (0.14 mL, 0.83 mmol) in EtOH (1 mL) dropwise, followed stirred at rt overnight. A solution of ammonia (7 M in MeOH, 0.39 mL, 2.75 mmol) was then added to the reaction mixture at rt, then stirred overnight. The resulting suspension was concentrated and then purified using reverse phase HPLC (5-70% MeCN/$H_2O$, 0.1% formic acid buffer) to afford 3-amino-4-((S)-3-((S)-sec-butyl)-2-oxo-1,2,3,5-tetrahydro-4H-benzo[e][1,4]diazepin-4-yl) cyclobut-3-ene-1,2-dione (Compound 58, 68 mg, 78%) as a white solid. LRMS (APCI) m/z 314.1 (M+H). $^1H$ NMR (400 MHz, DMSO-$d_6$) δ 10.29 (s, 1H), 7.94 (s, 2H), 7.49-7.40 (m, 1H), 7.35 (dd, J=7.6, 7.6 Hz, 1H), 7.15 (t, J=7.5 Hz, 1H), 7.10 (d, J=7.9 Hz, 1H), 5.15-4.70 (m, 3H), 1.47-1.35 (m, 1H), 1.34-1.15 (m, 1H), 1.05-0.90 (m, 1H), 0.76 (d, J=6.5 Hz, 3H), 0.67 (t, J=7.4 Hz, 3H).

The following compounds were prepared by methods analogous to the method described for Compound 57:

| Compound # | LRMS m/z [M + H] |
|---|---|
| 334 | 300.1 |
| 366 | 333.1 |
| 378 | 315.1 |

Example 45

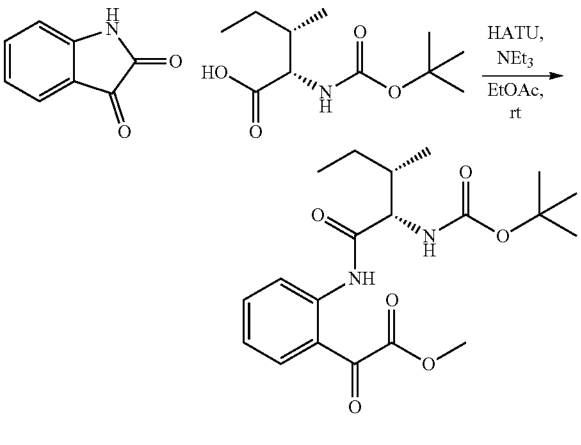

Step 1: Methyl 2-(2-((2S,3S)-2-((tert-butoxycarbonyl)amino)-3-methylpentanamido)phenyl)-2-oxoacetate. HATU (25.8 g, 67.97 mmol) was added to a stirring solution of isatin (5 g, 33.98 mmol), isoleucine (15.72 g, 67.97 mmol), and $NEt_3$ (13.8 mL, 102 mmol) in EtOAc (50 mL) at rt. After 14 h, MeOH (5 mL) was added and the reaction stirred for 1 h. The reaction was then poured into EtOAc (500 mL), washed with saturated sodium bicarbonate (2×250 mL) and ammonium chloride (2×250 mL), dried over sodium sulfate, filtered, and solvent removed by rotary evaporation. The crude material was suspended in EtOAc/hexanes (1:1), filtered through a pad of silica, and the solvent was removed by rotary evaporation to give methyl 2-(2-((2S,3S)-2-((tert-butoxycarbonyl)amino)-3-methylpentanamido)phenyl)-2-oxoacetate as a tan solid (13 g). LRMS (APCI) m/z 293.1 (M+H-Boc).

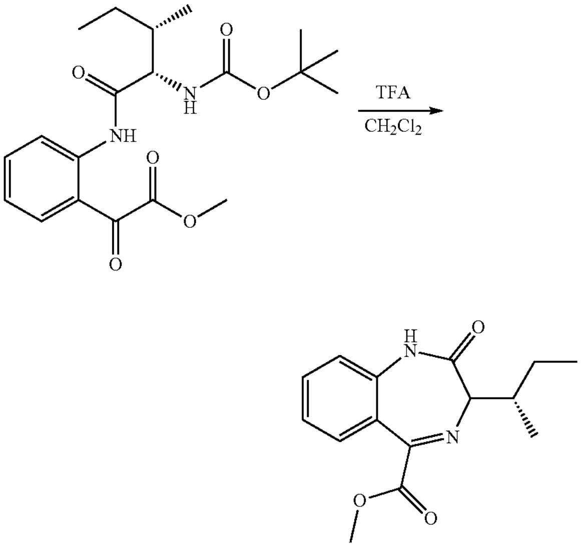

Step 2: Methyl 3-((S)-sec-butyl)-2-oxo-2,3-dihydro-1H-benzo[e][1,4]diazepine-5-carboxylate. TFA (100 mL) was added to a stirring solution of methyl 2-(2-((2S,3S)-2-((tert-butoxycarbonyl)amino)-3-methylpentanamido)phenyl)-2-oxoacetate (13 g, 33.13 mmol, 1 equiv.) in $CH_2Cl_2$ (250 mL) at rt. After 1 h, the solvent was removed by rotary evaporation. The crude oil was suspended in saturated sodium bicarbonate (500 mL) and extracted with $CH_2Cl_2$ (3×500 mL). The organic layers were combined, dried over sodium sulfate, filtered, and the solvent was removed by rotary evaporation to give methyl 3-((S)-sec-butyl)-2-oxo-2,3-dihydro-1H-benzo[e][1,4]diazepine-5-carboxylate as a pale red oil (10 g). LRMS (APCI) m/z 275.0 (M+H).

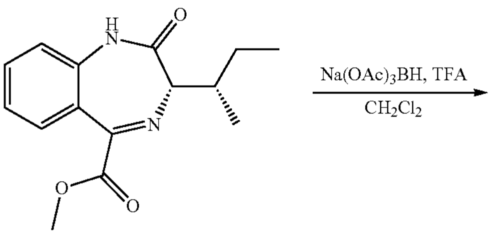

-continued

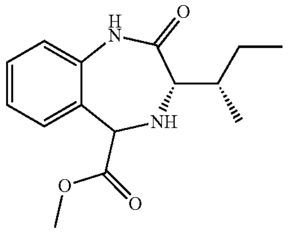

Step 3: Methyl (3S)-3-((S)-sec-butyl)-2-oxo-2,3,4,5-tetrahydro-1H-benzo[e][1,4]diazepine-5-carboxylate. $Na(OAc)_3BH$ (13.91 g, 65.62 mmol) was added to a stirring solution of methyl 3-((S)-sec-butyl)-2-oxo-2,3-dihydro-1H-benzo[e][1,4]diazepine-5-carboxylate (9.0 g, 32.8 mmol) in $CH_2Cl_2$ (300 mL) at rt. TFA (3.8 mL, 49.2 mmol) was added dropwise and the reaction stirred for 6 h. The reaction was slowly poured into a stirring solution of sat sodium bicarbonate (600 mL) and stirred vigorously for 10 min. The organic layer was removed and the aqueous layer extracted with $CH_2Cl_2$ (3×300 mL). The organic layers were combined, dried over sodium sulfate, filtered, and the solvent was removed by rotary evaporation to give methyl (3S)-3-((S)-sec-butyl)-2-oxo-2,3,4,5-tetrahydro-1H-benzo[e][1,4]diazepine-5-carboxylate (5.5 g) as a red tinged oil. LRMS (APCI) m/z 277.1 (M+H).

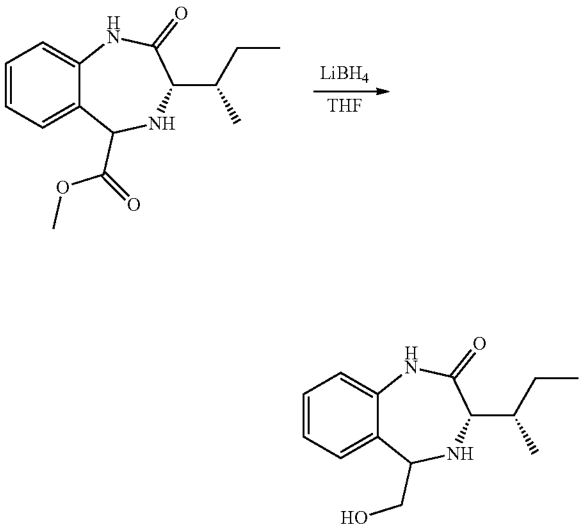

Step 4: (3S)-3-((S)-sec-Butyl)-5-(hydroxymethyl)-1,3,4,5-tetrahydro-2H-benzo[e][1,4]diazepin-2-one. $LiBH_4$ (5.4 mL, 10.86 mmol) was added to a stirring solution of methyl (3S)-3-((S)-sec-butyl)-2-oxo-2,3,4,5-tetrahydro-1H-benzo[e][1,4]diazepine-5-carboxylate (1 g, 3.62 mmol) in THF (20 mL) at rt. After 2 h, the reaction was quenched with 1M HCl (20 mL) and stirred vigorously for 5 min. The reaction was then poured into saturated sodium bicarbonate (100 mL) and extracted with $CH_2Cl_2$ (3×100 mL). The organic layers were combined, dried over sodium sulfate, filtered, and the solvent was removed by rotary evaporation to give (3S)-3-((S)-sec-butyl)-5-(hydroxymethyl)-1,3,4,5-tetrahydro-2H-benzo[e][1,4]diazepin-2-one (0.9 g) as an off-white solid. LRMS (APCI) m/z 249.1 (M+H).

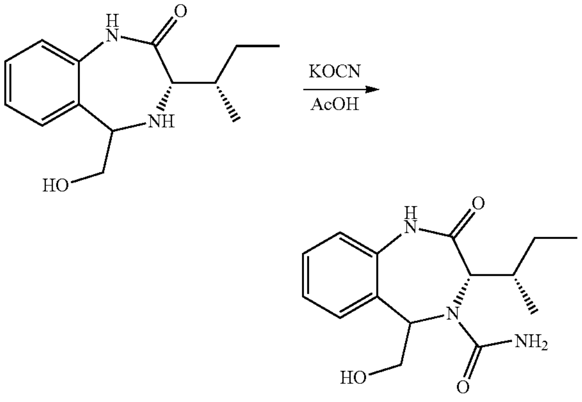

Step 5: (3S)-3-((S)-sec-Butyl)-5-(hydroxymethyl)-2-oxo-1,2,3,5-tetrahydro-4H-benzo[e][1,4]diazepine-4-carboxamide. Potassium cyanate (245 mg, 3.02 mmol) was added to a stirring solution of (3S)-3-((S)-sec-butyl)-5-(hydroxymethyl)-1,3,4,5-tetrahydro-2H-benzo[e][1,4]diazepin-2-one (150 mg, 0.604 mmol) in AcOH (5 mL) at rt. After 2 h, the reaction was concentrated, diluted to 3 mL total volume with MeOH, filtered through a 0.4 μm syringe filter, and purified using reverse phase HPLC (0-40% $MeCN/H_2O$ w/0.1% formic acid) to give (3S)-3-((S)-sec-butyl)-5-(hydroxymethyl)-2-oxo-1,2,3,5-tetrahydro-4H-benzo[e][1,4]diazepine-4-carboxamide isolated as a white solid (10 mg, 6% yield). LRMS (APCI) m/z 292.1 (M+H). $^1H$ NMR (400 MHz, methanol-$d_4$) δ 7.35-7.22 (m, 2H), 7.11 (t, J=7.6 Hz, 1H), 6.95 (d, J=7.8 Hz, 1H), 3.89 (s, 1H), 3.70 (dd, J=10.8, 7.7 Hz, 1H), 1.32-0.74 (m, 5H), 0.66 (d, J=5.9 Hz, 3H), 0.47 (t, J=7.1 Hz, 3H).

Example 46: Synthesis of Compound 318

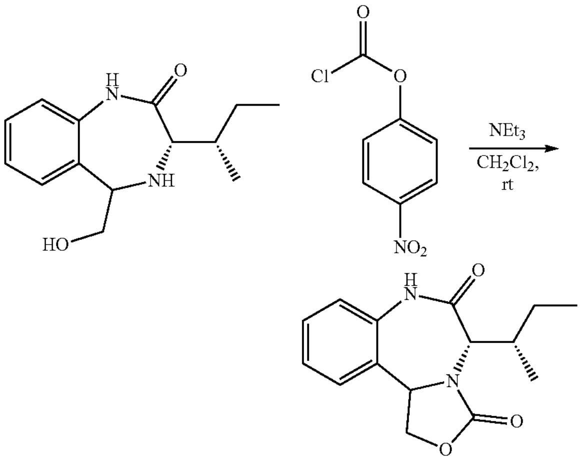

(5S)-5-((S)-sec-Butyl)-7,11b-dihydro-1H,3H-benzo[f]oxazolo[3,4-d][1,4]diazepine-3,6(5H)-dione (Compound 318). Nitrophenyl chloroformate (81 mg, 0.403 mg) was added to a stirring solution of (3S)-3-((S)-sec-butyl)-5-(hydroxymethyl)-1,3,4,5-tetrahydro-2H-benzo[e][1,4]diazepin-2-one (100 mg, 0.403 mmol) and triethylamine (81 mg, 0.805 mmol) in $CH_2Cl_2$ (2 mL) at rt. After 2 h, the reaction was concentrated, diluted to 1.8 mL with MeOH, filtered through a 0.4 μm syringe filter, and purified using reverse phase HPLC (0-40% $MeCN/H_2O$ w/0.1% formic acid) to give (5S)-5-((S)-sec-butyl)-7,11b-dihydro-1H,3H-benzo[f]oxazolo[3,4-d][1,4]diazepine-3,6(5H)-dione by as a white solid and a mixture of diastereomers (Compound 318, 42 mg, 38%, 2.3:1 d.r.). LRMS (APCI) m/z 275.1 (M+H). $^1H$ NMR (400 MHz, methanol-$d_4$) δ 7.34 (ddd, J=8.4, 6.5, 2.5 Hz, 0.7H), 7.25-7.15 (m, 2H), 7.08 (td, J=8.0, 1.4 Hz, 0.4H), 7.06-7.02 (m, 0.7H), 6.96 (dd, J=8.2, 1.2 Hz, 0.3H), 5.27-5.20 (m, 0.3H), 5.14 (dd, J=10.3, 8.2 Hz, 0.7H), 4.61 (d, J=3.0 Hz, 2H), 4.16 (d, J=11.4 Hz, 0.3H), 3.94 (d, J=11.1 Hz, 0.7H), 1.88-1.73 (m, 0.4H), 1.56 (dqd, J=15.0, 7.4, 2.7 Hz, 0.4H), 1.32 (ddh, J=15.2, 7.7, 3.4 Hz, 0.7H), 1.24-0.99 (m, 2H), 0.88 (tt, J=15.6, 7.4 Hz, 2H), 0.73 (d, J=6.7 Hz, 2H), 0.60 (t, J=7.4 Hz, 2H).

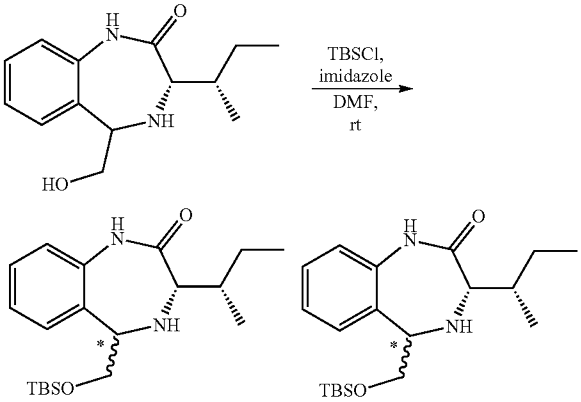

A B (3S)-3-((S)-sec-Butyl)-5-(((tert-butyldimethylsilyl)oxy)methyl)-1,3,4,5-tetrahydro-2H-benzo[e][1,4]diazepin-2-one (Diastereomers A and B). TBSCl (0.71 g, 4.71 mmol) was added to a stirring solution of (5S)-5-((S)-sec-butyl)-7,11b-dihydro-1H,3H-benzo[f]oxazolo[3,4-d][1,4]diazepine-3,6(5H)-dione (0.9 g, 3.62 mmol) and imidazole (0.642 g, 9.42 mmol) in DMF (25 mL) at rt. After 12 h, the reaction was poured into EtOAc (500 mL) and then washed with saturated ammonium chloride (250 mL) and brine (2×250 mL). The organic layer was dried over sodium sulfate, filtered, concentrated, and purified by silica gel chromatography (0-40% EtOAc/hexanes w/1% $NEt_3$) to give two diastereomers of (3S)-3-((S)-sec-butyl)-5-(((tert-butyldimethylsilyl)oxy)methyl)-1,3,4,5-tetrahydro-2H-benzo[e][1,4]diazepin-2-one, diastereomer A (0.4 g, 30% yield) and diastereomer B (0.5 g, 38% yield) as white solids. Diastereomer A elutes first from normal phase chromatography using stated conditions, followed by diastereomer B.

Diastereomer A: LRMS (APCI) m/z 363.1 (M+H). $^1H$ NMR (400 MHz, chloroform-d) δ 8.08 (s, 1H), 7.31-7.13 (m, 2H), 7.09 (t, J=7.5 Hz, 1H), 6.93 (d, J=7.9 Hz, 1H), 4.20 (dd, J=7.2, 5.0 Hz, 1H), 3.92-3.80 (m, 2H), 3.35 (d, J=6.8 Hz, 1H), 2.29 (s, 1H), 1.73 (m, 2H), 1.24-1.09 (m, 1H), 0.96 (d, J=6.8 Hz, 3H), 0.86 (s, 12H), 0.00 (d, J=3.4 Hz, 6H).

Diastereomer B: LRMS (APCI) m/z 363.1 (M+H). $^1H$ NMR (400 MHz, chloroform-d) δ z7.65 (s, 1H), 7.25-7.17 (m, 2H), 7.09 (t, J=7.1 Hz, 1H), 6.89 (d, J=7.6 Hz, 1H), 4.03-3.89 (m, 3H), 3.00 (d, J=8.2 Hz, 1H), 2.30 (s, 1H), 1.96-1.78 (m, 1H), 1.56 (m, 1H), 1.15-0.97 (m, 1H), 0.84-0.78 (m, 15H), 0.00 (d, J=3.3 Hz, 6H).

Example 47: Synthesis of Compound 37

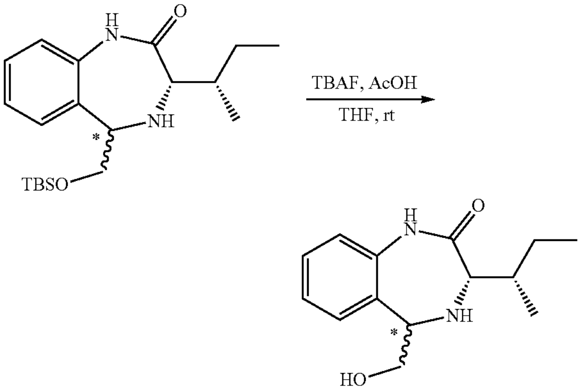

(3S)-3-((S)-sec-Butyl)-5-(hydroxymethyl)-1,3,4,5-tetrahydro-2H-benzo[e][1,4]diazepin-2-one (Diastereomer A). TBAF (1M in THF, 0.61 mL, 0.61 mmol) was added to a stirring solution of (3S)-3-((S)-sec-butyl)-5-(((tert-butyldimethylsilyl)oxy)methyl)-1,3,4,5-tetrahydro-2H-benzo[e][1,4]diazepin-2-one (Diastereomer A, 177 mg, 0.488 mmol) and AcOH (58 μL, 0.97 mmol) in THF (5 mL) at rt. After 1 h, $CaCO_3$ (244 mg, 2.4 mmol) and MeOH (3 mL) were added and the reaction stirred vigorously for 5 min. Dowex 50WX8 (1 g) was then added and the reaction stirred vigorously for 30 min. The reaction was then filtered through a pad of Celite and concentrated to give (3S)-3-((S)-sec-butyl)-5-(hydroxymethyl)-1,3,4,5-tetrahydro-2H-benzo[e][1,4]diazepin-2-one as an off-white solid (121 mg). LRMS (APCI) m/z 249.1 (M+H).

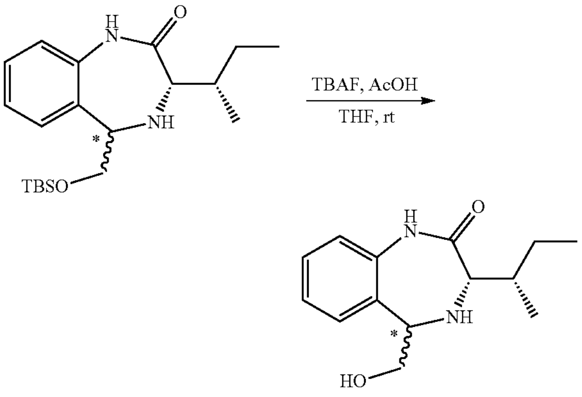

(3S)-3-((S)-sec-Butyl)-5-(hydroxymethyl)-1,3,4,5-tetrahydro-2H-benzo[e][1,4]diazepin-2-one (Diastereomer B). TBAF (1 M in THF, 0.60 mL, 0.61 mmol) was added to a stirring solution of (3S)-3-((S)-sec-butyl)-5-(((tert-butyldimethylsilyl)oxy)methyl)-1,3,4,5-tetrahydro-2H-benzo[e][1,4]diazepin-2-one (Diastereomer B, 174 mg, 0.480 mmol) and AcOH (58 μL, 0.97 mmol) in THF (5 mL) at rt. After 1 h, $CaCO_3$ (244 mg, 2.4 mmol) and MeOH (3 mL) were added and the reaction stirred vigorously for 5 min. Dowex 50WX8 (1 g) was then added and the reaction stirred vigorously for 30 min. The reaction was then filtered through a pad of Celite and concentrated to give (3S)-3-((S)-sec-butyl)-5-(hydroxymethyl)-1,3,4,5-tetrahydro-2H-benzo[e][1,4]diazepin-2-one as an off-white solid (119 mg). LRMS (APCI) m/z 249.1 (M+H).

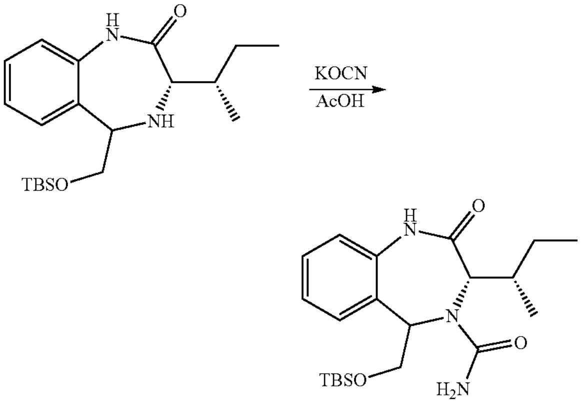

(3S)-3-((S)-sec-Butyl)-5-(((tert-butyldimethylsilyl)oxy)methyl)-2-oxo-1,2,3,5-tetrahydro-4H-benzo[e][1,4]diazepine-4-carboxamide. KOCN (3.24 g, 40.0 mmol) was added to a stirring solution of (3S)-3-((S)-sec-butyl)-5-(((tert-butyldimethylsilyl)oxy)methyl)-1,3,4,5-tetrahydro-2H-benzo[e][1,4]diazepin-2-one (2.9 g, 8.00 mmol) in AcOH (50 mL) at rt. After 2 h, the reaction was concentrated, and the subsequent oil suspended in $CH_2Cl_2$ (100 mL) and stirred vigorously for 5 min. The suspension was filtered and concentrated to give (3S)-3-((S)-sec-butyl)-5-(((tert-butyldimethylsilyl)oxy)methyl)-2-oxo-1,2,3,5-tetrahydro-4H-benzo[e][1,4]diazepine-4-carboxamide as a yellow tinged waxy solid (3.7 g). LRMS (APCI) m/z 406.1 (M+H).

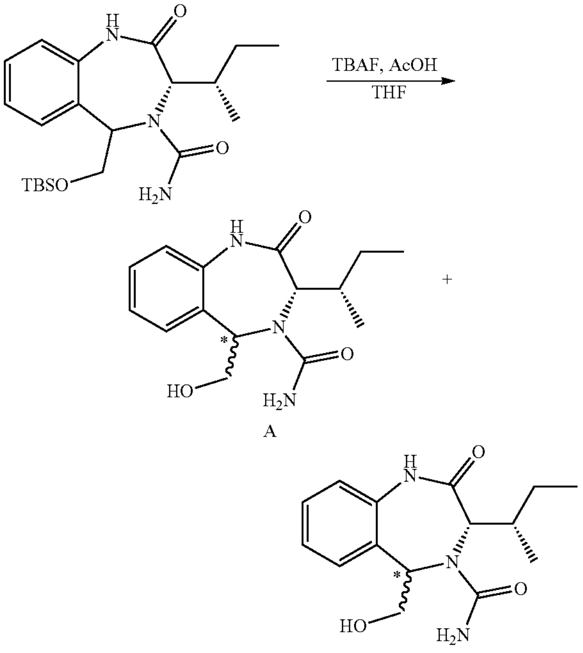

A

B (3S)-3-((S)-sec-Butyl)-5-(hydroxymethyl)-2-oxo-1,2,3,5-tetrahydro-4H-benzo[e][1,4]diazepine-4-carboxamide (Diastereomer A, Compound 37). TBAF (5.2 mL, 5.24 mmol, 1 M in THF) was added to a stirring solution of (3S)-3-((S)-sec-butyl)-5-(((tert-butyldimethylsilyl)oxy)methyl)-2-oxo-1,2,3,5-tetrahydro-4H-benzo[e][1,4]diazepine-4-carboxamide (1.7 g, 4.191 mmol) and AcOH (380 mL, 6.29 mmol) in THF (50 mL) at rt. After 1 h, the reaction was diluted with MeOH (20 mL), and $CaCO_3$ (2.10 g, 20.96 mmol) was added. The reaction was stirred vigorously for 10 min. Dowex 50WX8 (10 g) was then added, and the reaction stirred vigorously for 30 min. The reaction was then filtered through a pad of Celite and concentrated to give the crude product as a mixture of diastereomers. (3S)-3-((S)-sec-butyl)-5-(hydroxymethyl)-2-oxo-1,2,3,5-tetrahydro-4H-benzo[e][1,4]diazepine-4-carboxamide (150 mg) was resolved by reverse phase HPLC (0-50% MeCN/$H_2O$ with 0.1% formic acid) to give diastereomer A (Compound 37, 15 mg, 80% purity) and diastereomer B (75 mg, 80% purity, 2:1 d.r.) as white solids.

Diastereomer A eluted first from normal phase chromatography using stated conditions. Diastereomer A: LRMS (APCI) m/z 292.1 (M+H). $^1H$ NMR (400 MHz, methanol-$d_4$) δ 7.54 (d, J=7.9 Hz, 1H), 7.16 (t, J=7.6 Hz, 1H), 7.04 (td, J=7.6, 1.3 Hz, 1H), 6.90 (dd, J=7.9, 1.2 Hz, 1H), 5.09 (d, J=4.1 Hz, 1H), 4.32 (d, J=10.1 Hz, 1H), 4.08 (dd, J=11.0, 7.0 Hz, 1H), 1.97-1.83 (m, 1H), 1.67-1.53 (m, 2H), 1.30-1.14 (m, 1H), 0.98 (d, J=6.8 Hz, 3H), 0.92 (t, J=7.4 Hz, 3H).

Example 48: Synthesis of Compound 36

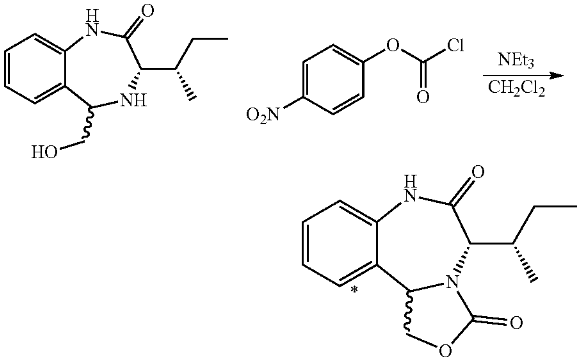

(5S)-5-((S)-sec-Butyl)-7,11b-dihydro-1H,3H-benzo[f]oxazolo[3,4-d][1,4]diazepine-3,6(5H)-dione (Diastereomer A, Compound 36). p-Nitrophenyl chloroformate (108 mg, 0.536 mmol) was added to a stirring solution of (3S)-3-((S)-sec-butyl)-5-(hydroxymethyl)-1,3,4,5-tetrahydro-2H-benzo[e][1,4]diazepin-2-one (Diastereomer A, 121 mg, 0.487 mmol) and $NEt_3$ (132 mL, 0.975 mmol) in $CH_2Cl_2$ (5 mL) at rt. After 4 h, the reaction was concentrated, the resultant solid was suspended in 3 mL MeOH, filtered through a 0.4 μm syringe filter, and purified using reverse phase HPLC (0-50% MeCN/$H_2O$ with 0.1% formic acid) to give (5S)-5-((S)-sec-butyl)-7,11b-dihydro-1H,3H-benzo[f]oxazolo[3,4-d][1,4]diazepine-3,6(5H)-dione (Compound 36, 32 mg) as a white solid. LRMS (APCI) m/z 275.0 (M+H). $^1H$ NMR (400 MHz, methanol-$d_4$) δ 7.34 (td, J=8.2, 7.3, 2.4 Hz, 1H), 7.25-7.16 (m, 2H), 7.04 (d, J=7.8 Hz, 1H), 5.14 (dd, J=10.1, 8.3 Hz, 1H), 4.67-4.56 (m, 2H), 3.94 (d, J=11.1 Hz, 1H), 1.36-1.21 (m, 1H), 1.15-0.98 (m, 1H), 0.88 (tt, J=16.0, 8.2 Hz, 1H), 0.73 (d, J=6.7 Hz, 3H), 0.60 (t, J=7.4 Hz, 3H).

Example 49: Synthesis of Compound 40

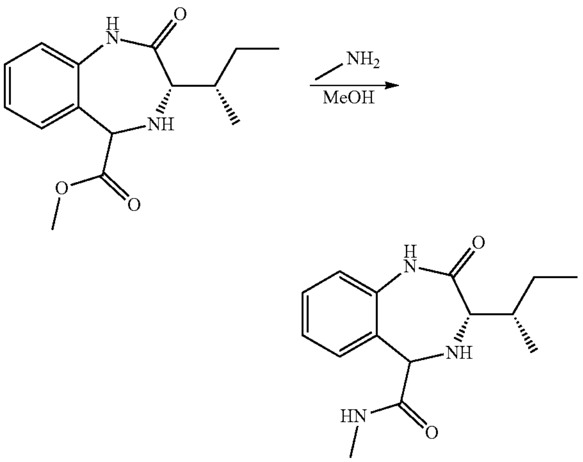

Step 1: (3S)-3-((S)-sec-Butyl)-N-methyl-2-oxo-2,3,4,5-tetrahydro-1H-benzo[e][1,4]diazepine-5-carboxamide. Methyl (3S)-3-((S)-sec-butyl)-2-oxo-2,3,4,5-tetrahydro-1H-benzo[e][1,4]diazepine-5-carboxylate (200 mg, 0.724 mmol) was suspended in methylamine (2 mL, 70% in MeOH) and heated to 80° C. in microwave reactor for 20 min. The solvent was removed by rotary evaporation to give (3S)-3-((S)-sec-butyl)-N-methyl-2-oxo-2,3,4,5-tetrahydro-1H-benzo[e][1,4]diazepine-5-carboxamide as an off-white oil (210 mg). LRMS (APCI) m/z 276.0 (M+H).

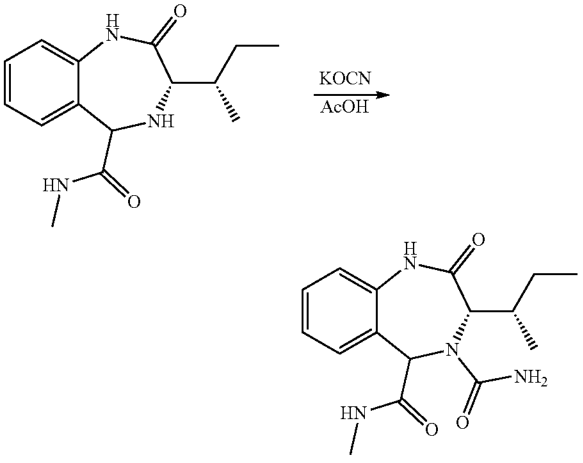

Step 2: (3S)-3-((S)-sec-Butyl)-$N^5$-methyl-2-oxo-1,2,3,5-tetrahydro-4H-benzo[e][1,4]diazepine-4,5-dicarboxamide (Compound 40). KOCN (221 mg, 2.72 mmol) was added to a stirring solution of (3S)-3-((S)-sec-butyl)-N-methyl-2-oxo-2,3,4,5-tetrahydro-1H-benzo[e][1,4]diazepine-5-carboxamide (150 mg, 0.545 mmol) in AcOH (5 mL) at rt. After 2 h, the solvent was concentrated, diluted to 3 mL with MeOH, and filtered through a 0.4 μm syringe filter. The crude material was then purified by reverse phase HPLC (0-40% $MeCN/H_2O$ with 0.1% formic acid) and lyophilization to give (3S)-3-((S)-sec-butyl)-N5-methyl-2-oxo-1,2,3,5-tetrahydro-4H-benzo[e][1,4]diazepine-4,5-dicarboxamide (Compound 40, 24 mg, 14%) as a white solid. LRMS (APCI) m/z 319.0 (M+H). $^1H$ NMR (400 MHz, methanol-$d_4$) δ 7.48-7.23 (m, 2H), 7.16 (t, J=7.5 Hz, 1H), 6.95 (dd, J=13.4, 7.9 Hz, 1H), 5.53 (s, 1H), 3.94 (d, J=10.3 Hz, 1H), 2.54 (s, 3H), 1.31 (dd, J=11.4, 2.9 Hz, 1H), 0.90-0.81 (m, 1H), 0.65 (d, J=5.6 Hz, 3H), 0.59 (d, J=6.3 Hz, 1H), 0.50 (t, J=7.1 Hz, 3H).

Example 50: Synthesis of Compound 321

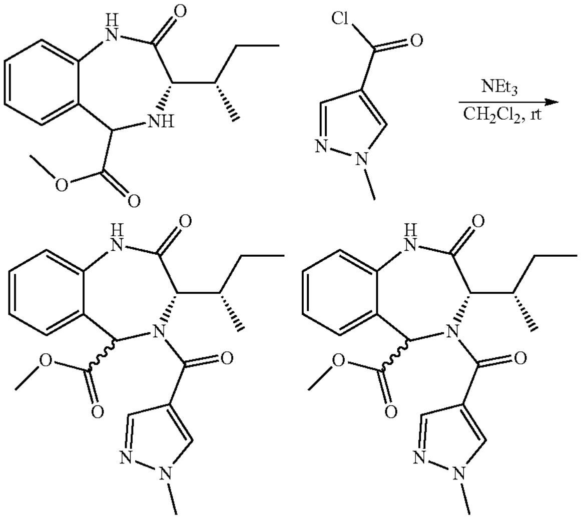

Methyl (3S)-3-((S)-sec-butyl)-4-(1-methyl-1H-pyrazole-4-carbonyl)-2-oxo-2,3,4,5-tetrahydro-1H-benzo[e][1,4]diazepine-5-carboxylate (Diastereomers B, Compound 321). 1-Methyl-1H-pyrazole-4-carbonyl chloride (131 mg, 0.905 mmol) was added to a stirring solution of methyl (3S)-3-((S)-sec-butyl)-2-oxo-2,3,4,5-tetrahydro-1H-benzo[e][1,4]diazepine-5-carboxylate (100 mg, 0.362 mmol) and $NEt_3$ (110 mg, 1.09 mmol) in $CH_2Cl_2$ (2 mL) at rt. After 2 h, the reaction was quenched with isopropylamine, (0.5 mL), concentrated, diluted to 1.8 mL with MeOH, and filtered through a 0.4 μm syringe filter. Resolution of methyl (3S)-3-((S)-sec-butyl)-4-(1-methyl-1H-pyrazole-4-carbonyl)-2-oxo-2,3,4,5-tetrahydro-1H-benzo[e][1,4]diazepine-5-carboxylate by reverse phase HPLC (0-40% $MeCN/H_2O$ with 0.1% formic acid) yielded diastereomer A (10 mg, 7% yield) and diastereomer B (27 mg, 19% yield) as white solids. Diastereomer A elutes first from normal phase chromatography using stated conditions, followed by diastereomer B. Diastereomer A: LRMS (APCI) m/z 385.1 (M+H). $^1H$ NMR (400 MHz, methanol-$d_4$) δ 7.97 (s, 1H), 7.77 (s, 1H), 7.48-7.40 (m, 1H), 7.35 (td, J=7.7, 1.5 Hz, 1H), 7.19 (t, J=7.5 Hz, 1H), 6.98 (d, J=8.0 Hz, 1H), 5.92 (s, 1H), 4.64 (d, J=11.1 Hz, 1H), 3.86 (d, J=4.4 Hz, 3H), 3.52 (d, J=12.0 Hz, 3H), 1.30-1.15 (m, 1H), 0.97 (dd, J=13.7, 6.7 Hz, 1H), 0.68 (d, J=6.0 Hz, 1H), 0.57 (d, J=6.7 Hz, 3H), 0.47 (dt, J=24.2, 7.3 Hz, 3H).

Diastereomer B (Compound 321): LRMS (APCI) m/z 385.1 (M+H). $^1H$ NMR (400 MHz, methanol-$d_4$) δ 7.95 (s, 1H), 7.73 (s, 1H), 7.34 (t, J=7.7 Hz, 1H), 7.16 (t, J=8.2 Hz, 1H), 7.05 (d, J=8.7 Hz, 1H), 6.98 (d, J=7.9 Hz, 1H), 5.49 (s, 1H), 4.52 (d, J=10.9 Hz, 1H), 3.85 (s, 3H), 3.79 (s, 3H), 1.79 (t, J=10.5 Hz, 1H), 1.15-0.95 (m, 1H), 0.78 (0.81-0.73, 1H), 0.60-0.43 (m, 6H).

Example 51: Synthesis of Compound 39

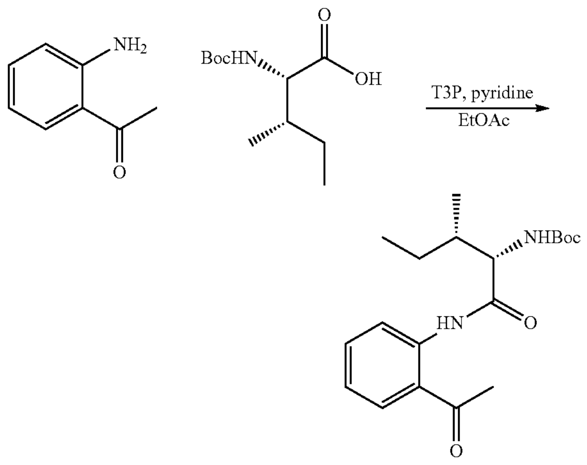

Step 1: tert-Butyl ((2S,3S)-1-((2-acetylphenyl)amino)-3-methyl-1-oxopentan-2-yl)carbamate. Propanephosphonic acid anhydride (T3P) (50% solution in EtOAc 75 g, 117.92 mmol) was added dropwise over 30 min to a stirring solution of 1-(2-aminophenyl)ethan-1-one (7.97 g, 59.0 mmol), iso-leucine (15 g, 64.9 mmol), and pyridine (19 mL, 235.8 mmol) in EtOAc (150 mL) at 0° C. The reaction was warmed to rt and stirred for 2 h. The reaction was then diluted to ca 500 mL with EtOAc, washed with saturated ammonium chloride (3×250 mL) and saturated sodium bicarbonate (250 mL). The organic layer was then dried over sodium sulfate, filtered, and concentrated to give tert-butyl ((2S,3S)-1-((2-acetylphenyl)amino)-3-methyl-1-oxopentan-2-yl)carbamate (3 g) as an off-white oil. LRMS (APCI) m/z 249.1 (M+H-Boc).

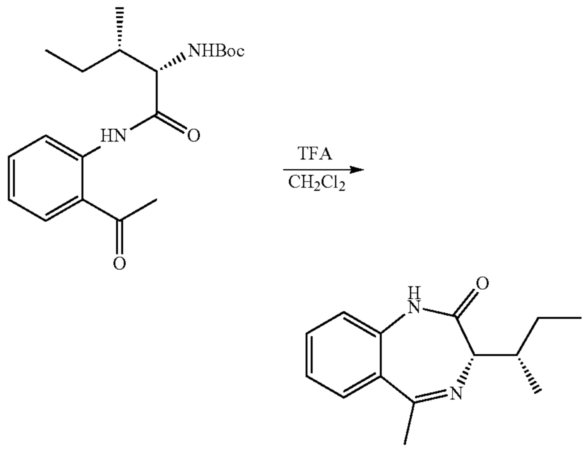

Step 2: (S)-3-((S)-sec-Butyl)-5-methyl-1,3-dihydro-2H-benzo[e][1,4]diazepin-2-one. TFA (50 mL) was added to a stirring solution of tert-butyl ((2S,3S)-1-((2-acetylphenyl)amino)-3-methyl-1-oxopentan-2-yl)carbamate in $CH_2Cl_2$ (50 mL) at rt. After 1 h, the solvent was concentrated, the residue suspended in saturated sodium bicarbonate (250 mL) and extracted with $CH_2Cl_2$ (4×100 mL). The combined organic layers were dried over sodium sulfate, filtered, and concentrated. The crude material was then suspended in toluene (50 mL) and heated to reflux under a nitrogen atmosphere for 1.5 h, with additional aliquots of toluene added to keep the total volume between 30-50 mL. The reaction was then cooled to rt and the solvent removed by rotary evaporation to give (S)-3-((S)-sec-butyl)-5-methyl-1,3-dihydro-2H-benzo[e][1,4]diazepin-2-one (1.6 g) as a tan hydroscopic solid. LRMS (APCI) m/z 231.1 (M+H). $^1$H NMR (400 MHz, methanol-$d_4$) δ 7.63 (d, J=7.9 Hz, 1H), 7.43 (t, J=7.8 Hz, 1H), 7.18 (t, J=7.7 Hz, 1H), 7.06 (d, J=8.1 Hz, 1H), 2.91 (d, J=10.4 Hz, 1H), 2.36 (s, 3H), 2.23 (d, J=8.7 Hz, 1H), 1.72 (dq, J=14.6, 7.3 Hz, 1H), 0.98 (dp, J=14.9, 7.3 Hz, 1H), 0.87 (d, J=6.4 Hz, 3H), 0.79 (t, J=7.4 Hz, 3H).

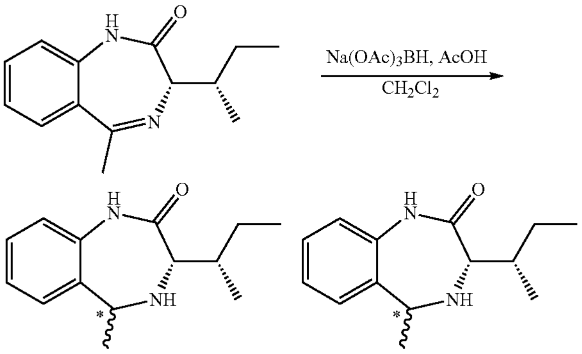

Step 3: (3S)-3-((S)-sec-Butyl)-5-methyl-1,3,4,5-tetra-hydro-2H-benzo[e][1,4]diazepin-2-one (Diastereomer A and Diastereomer B). $Na(OAc)_3BH$ (768 mg, 3.62 mmol, 2 equiv.) was added to a stirring solution of (S)-3-((S)-sec-butyl)-5-methyl-1,3-dihydro-2H-benzo[e][1,4]diazepin-2-one (417 mg, 1.81 mmol) and AcOH (0.11 mL, 1.81 mmol) in $CH_2Cl_2$ (20 mL) at rt. After stirring for 16 h, the reaction was quenched with saturated sodium bicarbonate (50 mL) and extracted with $CH_2Cl_2$ (3×50 mL). The organic layers were combined, dried over sodium sulfate, filtered, concentrated, and purified by silica chromatography (0-100% EtOAc/hexanes with 1% $NEt_3$) to give two diastereomers of (3S)-3-((S)-sec-butyl)-5-methyl-1,3,4,5-tetrahydro-2H-benzo[e][1,4]diazepin-2-one (diastereomer A (118 mg, 28% yield) and diastereomer B (200 mg, 48% yield)) as white solids. Diastereomer A elutes first from normal phase chromatography using stated conditions, followed by diastereomer B. Diastereomer A: LRMS (APCI) m/z 233.1 (M+H). $^1$H NMR (400 MHz, methanol-$d_4$) δ 7.28 (td, J=8.1, 2.7 Hz, 2H), 7.15 (q, J=7.3 Hz, 1H), 7.02 (d, J=7.8 Hz, 1H), 4.23 (dq, J=13.0, 6.8 Hz, 1H), 3.35-3.25 (m, 1H), 1.76-1.55 (m, 1H), 1.47 (d, J=6.8 Hz, 4H), 1.20-0.96 (m, 1H), 0.95-0.75 (m, 6H). Diastereomer B: LRMS (APCI) m/z 233.1 (M+H). $^1$H NMR (400 MHz, methanol-$d_4$) δ 7.41 (d, J=7.6 Hz, 1H), 7.34 (t, J=7.6 Hz, 1H), 7.27 (t, J=7.5 Hz, 1H), 7.06 (d, J=7.7 Hz, 1H), 4.12 (q, J=6.7 Hz, 1H), 2.96 (d, J=8.9 Hz, 1H), 2.03-1.85 (m, 1H), 1.70-1.42 (m, 4H), 1.04 (ddt, J=27.1, 13.6, 7.0 Hz, 1H), 0.97-0.84 (m, 6H).

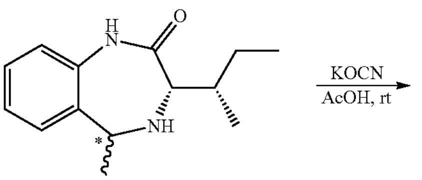

-continued

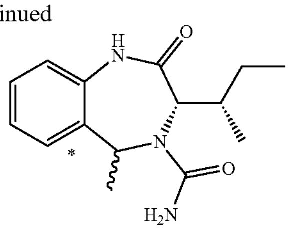

Step 4: (3S)-3-((S)-sec-Butyl)-5-methyl-2-oxo-1,2,3,5-tetrahydro-4H-benzo[e][1,4]diazepine-4-carboxamide (Compound 39). KOCN (87 mg, 1.076 mmol) was added to a stirring solution of (3S)-3-((S)-sec-butyl)-5-methyl-1,3,4,5-tetrahydro-2H-benzo[e][1,4]diazepin-2-one (Diastereomer A, 50 mg, 0.215 mmol, 1 equiv.) in AcOH (2 mL) at rt. After 12 h, the reaction was concentrated. The resultant solid was suspended in MeOH (1.8 mL), filtered through a 0.4 μm syringe filter, and purified using reverse phase HPLC (0-70% $MeCN/H_2O$ with 0.1% formic acid) to give (3S)-3-((S)-sec-butyl)-5-methyl-2-oxo-1,2,3,5-tetrahydro-4H-benzo[e][1,4]diazepine-4-carboxamide (Compound 39, 27 mg, 46% yield) as a white solid. LRMS (APCI) m/z 276.1 (M+H). $^1$H NMR (400 MHz, methanol-$d_4$) δ 7.28 (t, J=7.4 Hz, 1H), 7.14 (d, J=7.9 Hz, 1H), 7.03 (q, J=8.3 Hz, 1H), 6.94-6.84 (m, 1H), 5.20-5.10 (m, 1H), 4.53 (dd, J=10.1 Hz, 34.1 Hz, 1H), 1.82-1.37 (m, 5H), 1.06-0.95 (m, 1H), 0.86 (d, J=6.5 Hz, 1H), 0.75 (t, J=6.1 Hz, 4H), 0.69 (t, J=7.4 Hz, 1H).

The following compounds were prepared by methods analogous to the method described for Compound 39:

| Compound # | LRMS m/z [M + H] |
|---|---|
| 319 | 341.1 |
| 320 | 276.1 |

Example 52: Synthesis of Compound 38

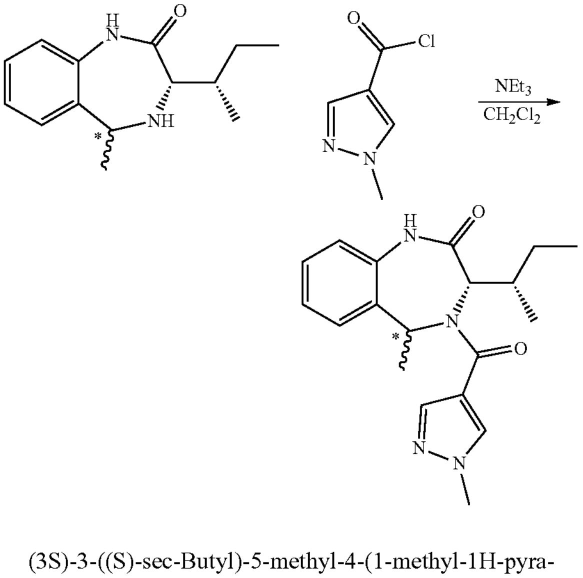

(3S)-3-((S)-sec-Butyl)-5-methyl-4-(1-methyl-1H-pyrazole-4-carbonyl)-1,3,4,5-tetrahydro-2H-benzo[e][1,4]diazepin-2-one (Diastereomer A, Compound 38). 1-Methyl-1H-pyrazole-4-carbonyl chloride (47 mg, 0.323 mmol) was added to a stirring solution of (3S)-3-((S)-sec-butyl)-5-methyl-1,3,4,5-tetrahydro-2H-benzo[e][1,4]diazepin-2-one (Diastereomer A, 50 mg, 0.215 mmol) and $NEt_3$ (89 μL, 0.646 mmol) in $CH_2Cl_2$ (2 mL) at rt. After 2 h, the reaction was quenched with methyl amine (0.5 mL, 40% in MeOH) and concentrated. The crude residue was suspended in MeOH (1.8 mL), filtered through a 0.4 μm syringe filter, and purified using reverse phase HPLC (0-70% $MeCN/H_2O$ w/0.1% formic acid) to give (3S)-3-((S)-sec-butyl)-5-methyl-4-(1-methyl-1H-pyrazole-4-carbonyl)-1,3,4,5-tetrahydro-2H-benzo[e][1,4]diazepin-2-one (Compound 38, 38 mg, 52% yield) as a white solid. LRMS (APCI) m/z 341.1 (M+H). $^1$H NMR (400 MHz, methanol-$d_4$) δ 7.95 (d, J=13.4 Hz, 1H), 7.72 (d, J=15.1 Hz, 1H), 7.31 (dd, J=19.0, 8.0 Hz, 1H), 7.19 (t, J=7.7 Hz, 1H), 7.08 (q, J=7.6 Hz, 1H), 6.94 (t, J=7.0 Hz, 1H), 5.62 (dq, J=19.8, 6.5 Hz, 1H), 4.59 (dd, J=24.3, 10.2 Hz, 1H), 3.85 (s, 3H), 1.72 (d, J=4.8 Hz, 4H), 1.65-1.51 (m, 1H), 1.33-1.18 (m, 1H), 1.03-0.90 (m, 1H), 0.85 (d, J=6.5 Hz, 1H), 0.68 (t, J=6.3 Hz, 3H), 0.61 (t, J=7.5 Hz, 1H).

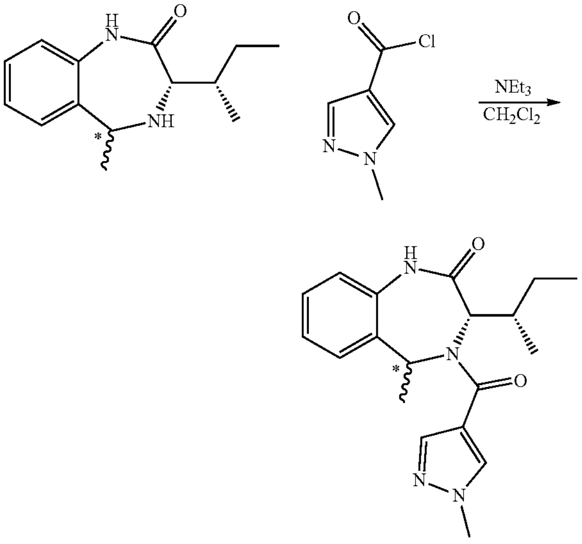

(3S)-3-((S)-sec-Butyl)-5-methyl-4-(1-methyl-1H-pyrazole-4-carbonyl)-1,3,4,5-tetrahydro-2H-benzo[e][1,4]diazepin-2-one (Diastereomer B). 1-Methyl-1H-pyrazole-4-carbonyl chloride (47 mg, 0.323 mmol) was added to a stirring solution of (3S)-3-((S)-sec-butyl)-5-methyl-1,3,4,5-tetrahydro-2H-benzo[e][1,4]diazepin-2-one (Diastereomer A, 50 mg, 0.215 mmol) and $NEt_3$ (89 μL, 0.646 mmol) in $CH_2Cl_2$ (2 mL) at rt. After 2 h, the reaction was quenched with methyl amine (0.5 mL, 40% in MeOH) and concentrated. The crude residue was suspended in MeOH (1.8 mL), filtered through a 0.4 μm syringe filter, and purified using reverse phase HPLC (0-70% $MeCN/H_2O$ with 0.1% formic acid) to give (3S)-3-((S)-sec-butyl)-5-methyl-4-(1-methyl-1H-pyrazole-4-carbonyl)-1,3,4,5-tetrahydro-2H-benzo[e][1,4]diazepin-2-one (21 mg, 29% yield) as a white solid. LRMS (APCI) m/z 341.1 (M+H). $^1$H NMR (400 MHz, methanol-$d_4$) δ 7.90 (s, 1H), 7.70 (s, 1H), 7.28 (dt, J=13.7, 7.4 Hz, 2H), 7.13 (t, J=7.8 Hz, 1H), 7.04-6.91 (m, 1H), 5.52 (t, J=7.3 Hz, 1H), 4.67-4.51 (m, 1H), 3.85 (s, 3H), 1.58-1.43 (m, 1H), 1.38 (d, J=6.6 Hz, 3H), 1.07 (dt, J=21.2, 13.4 Hz, 2H), 0.82-0.70 (m, 1H), 0.59-0.32 (m, 6H).

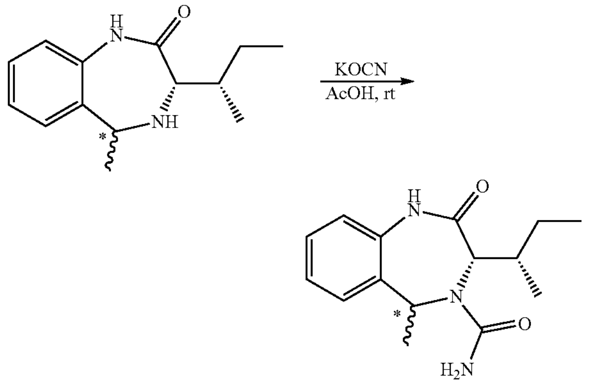

(3S)-3-((S)-sec-Butyl)-5-methyl-2-oxo-1,2,3,5-tetrahydro-4H-benzo[e][1,4]diazepine-4-carboxamide (Diastereomer B). KOCN (87 mg, 1.076 mmol) was added to a stirring solution of (3S)-3-((S)-sec-butyl)-5-methyl-1,3,4,5-tetrahydro-2H-benzo[e][1,4]diazepin-2-one (Diastereomer A, 50 mg, 0.215 mmol, 1 equiv.) in AcOH (2 mL) at rt. After 12 h, the reaction was concentrated. The resultant solid was suspended in MeOH (1.8 mL), filtered through a 0.4 μm syringe filter, and purified using reverse phase HPLC (0-70% MeCN/$H_2O$ with 0.1% formic acid) to give (3S)-3-((S)-sec-butyl)-5-methyl-2-oxo-1,2,3,5-tetrahydro-4H-benzo[e][1,4]diazepine-4-carboxamide (30 mg, 51% yield) as a white solid. LRMS (APCI) m/z 276.1 (M+H). $^1$H NMR (400 MHz, methanol-$d_4$) δ 7.27 (t, J=7.7 Hz, 1H), 7.22 (t, J=6.6 Hz, 1H), 7.10 (t, J=7.6 Hz, 1H), 6.95 (t, J=6.3 Hz, 1H), 5.18-4.86 (m, 2H), 1.41 (d, J=6.6 Hz, 3H), 1.23 (d, J=9.9 Hz, 1H), 1.06-0.72 (m, 2H), 0.72-0.54 (m, 4H), 0.50 (t, J=7.1 Hz, 2H).

Example 53: Synthesis of Compound 63

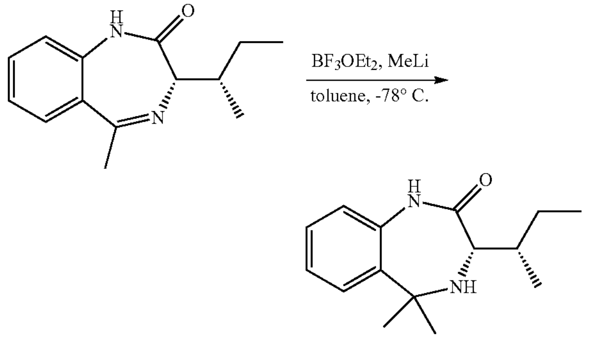

Step 1: (S)-3-((S)-sec-Butyl)-5,5-dimethyl-1,3,4,5-tetrahydro-2H-benzo[e][1,4]diazepin-2-one. $BF_3$ (2.2 mL, 18.1 mmol) was added dropwise to a stirring solution of (S)-3-((S)-sec-butyl)-5-methyl-1,3-dihydro-2H-benzo[e][1,4]diazepin-2-one (1.39 g, 6.04 mmol) in THF (12 mL) at −78° C. After 1 h, MeLi (1.6 M in hexanes, 11.3 mL, 18.1 mmol) was added dropwise over ca 10 min and the reaction stirred for 2 h. The reaction was quenched with saturated sodium bicarbonate (50 mL) and extracted with EtOAc (3×50 mL). The organic layers were combined, dried over sodium sulfate, filtered, concentrated, and purified using silica gel chromatography (0-70% EtOAc/hexanes with 1% $NEt_3$) to give (S)-3-((S)-sec-butyl)-5,5-dimethyl-1,3,4,5-tetrahydro-2H-benzo[e][1,4]diazepin-2-one (530 mg, 36% yield) as a white solid. LRMS (APCI) m/z 247.1 (M+H). $^1$H NMR (400 MHz, chloroform-d) δ 7.62 (s, 1H), 7.35 (d, J=7.9 Hz, 1H), 7.18 (t, J=7.5 Hz, 1H), 7.07 (t, J=7.5 Hz, 1H), 6.84 (d, J=7.9 Hz, 1H), 3.37 (s, 1H), 2.08-1.88 (m, 1H), 1.82-1.61 (m, 2H), 1.57 (s, 3H), 1.53 (s, 3H), 1.21-1.09 (m, 1H), 1.03 (d, J=6.7 Hz, 3H), 0.95 (t, J=7.4 Hz, 3H).

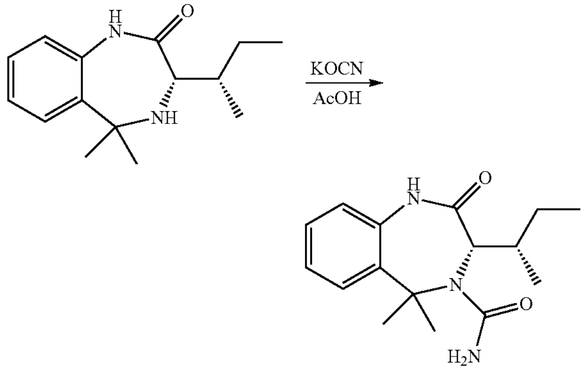

(S)-3-((S)-sec-Butyl)-5,5-dimethyl-2-oxo-1,2,3,5-tetrahydro-4H-benzo[e][1,4]diazepine-4-carboxamide (Compound 63). Potassium cyanate (203 mg) was added to a stirring solution of (S)-3-((S)-sec-butyl)-5,5-dimethyl-1,3,4,5-tetrahydro-2H-benzo[e][1,4]diazepin-2-one (123 mg) in AcOH (2 mL) at rt. After 14 h, the reaction was concentrated. The resultant residue was suspended in MeOH (1.8 mL) followed by filtration through a 0.4 μm syringe filter, and purification using reverse phase HPLC (0-70% MeCN/$H_2O$) to give (S)-3-((S)-sec-butyl)-5,5-dimethyl-2-oxo-1,2,3,5-tetrahydro-4H-benzo[e][1,4]diazepine-4-carboxamide (Compound 63, 49 mg, 34% yield) as a white solid. LRMS (APCI) m/z 290.1 (M+H). $^1$H NMR (400 MHz, methanol-$d_4$) δ 7.56 (d, J=8.0 Hz, 1H), 7.31 (t, J=7.3 Hz, 1H), 7.24 (t, J=7.6 Hz, 1H), 7.06 (d, J=7.8 Hz, 1H), 3.93 (d, J=10.8 Hz, 1H), 2.25-1.90 (m, 1H), 1.93 (s, 3H), 1.79 (s, 3H), 1.76-1.55 (m, 1H), 1.10-0.93 (m, 1H), 0.88 (t, J=7.1 Hz, 3H), 0.76 (d, J=6.2 Hz, 3H).

Example 54: Synthesis of Compound 80

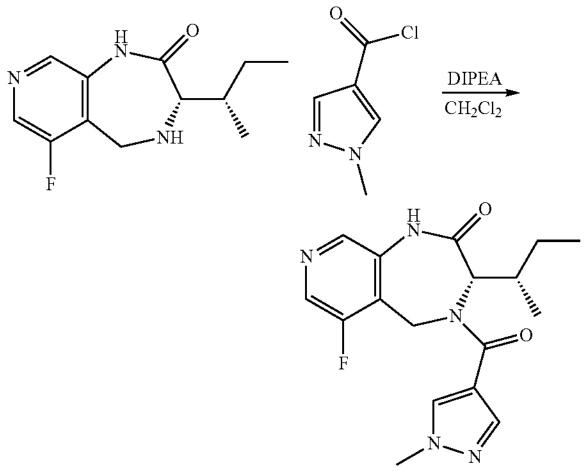

(S)-3-((S)-sec-Butyl)-6-fluoro-4-(1-methyl-1H-pyrazole-4-carbonyl)-1,3,4,5-tetrahydro-2H-pyrido[3,4-e][1,4]diazepin-2-one (Compound 80). To a solution of (S)-3-((S)-sec-butyl)-6-fluoro-1,3,4,5-tetrahydro-2H-pyrido[3,4-e][1,4]diazepine-2-one (24 mg, 0.1 mmol) in DCM (2 mL) was added DIEA (0.30 mmol, 41 μL). The mixture was cooled down to 0° C., and a solution of 1-methyl-1H-pyrazole-4-carbonyl chloride (17 mg, 0.12 mmol) in DCM (1 mL) was added slowly. The resulting mixture was warmed up to rt and stirred for 1 h. The mixture was concentrated and purified using reverse phase HPLC (20-100% MeCN/$H_2O$, 0.1% formic acid buffer) over 40 min to give (S)-3-((S)-sec-butyl)-6-fluoro-4-(1-methyl-1H-pyrazole-4-carbonyl)-1,3,4,5-tetrahydro-2H-pyrido[3,4-e][1,4]diazepin-2-one as an off-white solid (Compound 80, 7.0 mg, 20% yield). LRMS (APCI) m/z 346.1 (M+H). $^1$H NMR (400 MHz, methanol-$d_4$) δ 8.20 (s, 1H), 8.16 (s, 1H), 8.07 (s, 1H), 7.81 (s, 1H), 5.75-5.25 (m, 1H), 4.75-4.40 (m, 2H), 3.95 (s, 3H), 2.18-2.00 (m, 1H), 1.69-1.50 (m, 1H), 1.26-1.10 (m, 1H), 1.03 (d, J=4.0 Hz, 3H), 0.91 (t, J=8.0 Hz, 3H).

Example 55

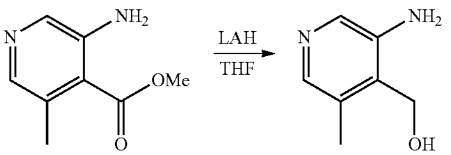

(3-Amino-5-methylpyridin-4-yl)methanol. To a solution of methyl 3-amino-5-methylisonicotinate (1.0 g, 6.0 mmol) in THF (30 mL) at 0° C. was added lithium aluminum hydride (2.3 M in hexane, 3.1 mL) dropwise. The reaction mixture was stirred at 0° C. for 30 min, followed by the addition of $H_2O$ (0.22 mL), NaOH (3 N, 0.22 mL), and $H_2O$ (0.66 mL) in sequence. The mixture was then dried over $Na_2SO_4$, filtered through Celite, and washed with THF (40 mL). The filtrate was concentrated to afford (3-amino-5-methylpyridin-4-yl)methanol as a yellow solid (0.80 g, 96% yield). LRMS (APCI) m/z 139.1 (M+H).

Example 56

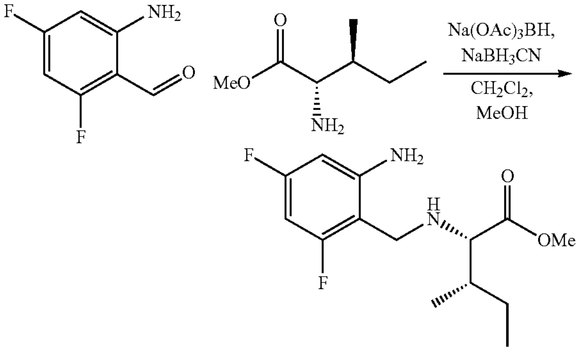

Methyl (2-amino-4,6-difluorobenzyl)-L-isoleucinate. To a solution of 2-amino-4,6-difluorobenzaldehyde (0.55 g, 3.5 mmol) in $CH_2Cl_2$(10 mL) at rt was added L-isoleucine methyl ester (0.95 g, 5.3 mmol). The mixture was stirred for 1 h, followed by the addition of $Na(OAc)_3BH$ (1.48 g, 7.0 mmol). The reaction mixture was stirred for 1 h. Methanol and $Na(CN)BH_3$ (0.44 g, 7.0 mmol) were then added, and the reaction was stirred at rt for 1 h. The reaction mixture was cooled down to 0° C., quenched with saturated $NaHCO_3$ (10 mL), warm to rt, and stirred for 1 h. The layers were separated, and the aqueous phase was extracted with additional $CH_2Cl_2$ (10 mL). The organic phases were combined, dried over $Na_2SO_4$, concentrated, and purified with silica gel chromatography (0-25% EtOAc/hexane) to give methyl (2-amino-4,6-difluorobenzyl)-L-isoleucinate as a yellowish oil (0.50 g, 50% yield). LRMS (APCI) m/*z* 287.2 (M+H).

Example 57: Synthesis of Compound 14

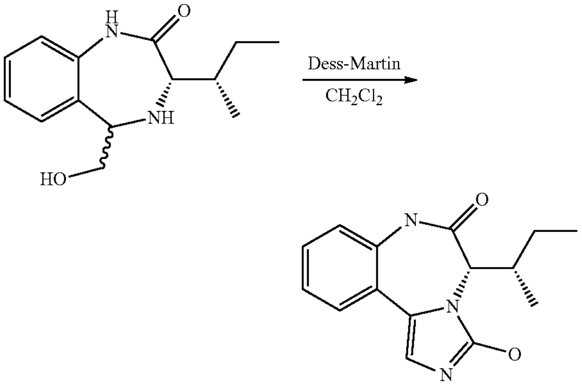

(S)-5-((S)-sec-Butyl)-3-hydroxy-5H-benzo[f]imidazo[1,5-d][1,4]diazepin-6(7H)-one. Dess-Martin periodinane (146 mg, 0.343 mmol) was added to a stirring solution of (3S)-3-((S)-sec-butyl)-5-(hydroxymethyl)-1,3,4,5-tetrahydro-2H-benzo[e][1,4]diazepin-2-one (80 mg, 0.275 mmol) in $CH_2Cl_2$ (2 mL) at rt. After 6 h, the solvent was removed by rotary evaporation, diluted with MeOH (1.5 mL), filtered through a 0.4 μm syringe filter, and (S)-5-((S)-sec-butyl)-3-hydroxy-5H-benzo[f]imidazo[1,5-d][1,4]diazepin-6(7H)-one was isolated using reverse phase HPLC (0-30% MeCN/$H_2O$ w/0.1% formic acid) as a white solid (Compound 14, 15 mg, 21% yield). LRMS (APCI) m/z 272.1 (M+H). $^1$H NMR (400 MHz, Methanol-$d_4$) δ 7.41 (dd, J=7.8, 1.3 Hz, 1H), 7.23 (td, J=7.9, 1.4 Hz, 1H), 7.12-7.08 (m, 1H), 7.01-6.96 (m, 1H), 6.67 (s, 1H), 4.53 (d, J=11.7 Hz, 1H), 1.68-1.49 (m, 1H), 1.18-1.02 (m, 1H), 0.91 (dd, J=14.6, 7.1 Hz, 1H), 0.85 (d, J=6.7 Hz, 3H), 0.62 (t, J=7.5 Hz, 3H).

Example 58: Synthesis of Compound 12

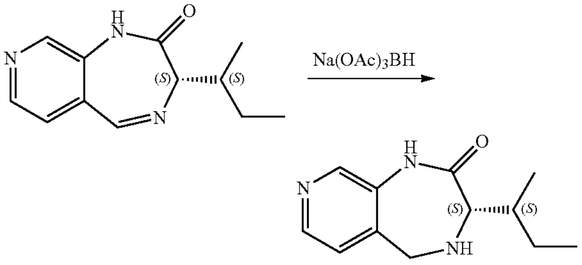

(S)-3-((S)-sec-butyl)-1,3,4,5-tetrahydro-2H-pyrido[3,4-e][1,4]diazepin-2-one. To a 1-L round-bottom flask was added tert-butyl ((2S,3S)-1-((4-formylpyridin-3-yl)amino)-3-methyl-1-oxopentan-2-yl)carbamate (2.0 g, 8.5 mmol), acetic acid (50 mL), and dichloromethane (500 mL). After stirring at rt for 1 h, sodium triacetoxyborohydride (5.4 g, 25.5 mmol) was added and the reaction mixture was stirred for 12 h. The reaction was then quenched by adding saturated aqueous sodium bicarbonate (400 mL) and stirring vigorously for 10 min. The organic layer was separated, and the aqueous layer was extracted twice with dichloromethane (500 mL). The organic layers were combined, dried over sodium sulfate, and concentrated to give (S)-3-((S)-sec-butyl)-1,3,4,5-tetrahydro-2H-pyrido[3,4-e][1,4]diazepin-2-one which was used directly in the next step without purification.

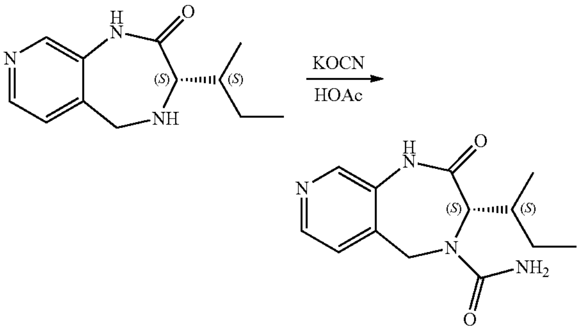

(S)-3-((S)-sec-butyl)-2-oxo-1,2,3,5-tetrahydro-4H-pyrido[3,4-e][1,4]diazepine-4-carboxamide (Compound 12). To a 100-mL round-bottom flask was added (S)-3-((S)-sec-butyl)-1,3,4,5-tetrahydro-2H-pyrido[3,4-e][1,4]diazepin-2-one (1.0 g, 4.6 mmol) and AcOH (50 mL). Potassium cyanate (1.1 g, 13.7 mmol) was then added, and the reaction mixture was stirred for 2 h. The reaction was then concentrated, diluted with methanol (14 mL), filtered, and purified using reverse phase HPLC (0-20% MeCN/$H_2O$, 0.1% formic acid buffer) to give (S)-3-((S)-sec-butyl)-2-oxo-1,2,3,5-tetrahydro-4H-pyrido[3,4-e][1,4]diazepine-4-carboxamide (compound 12, 0.74 g, 2.8 mmol, 62%) as a colorless solid. LRMS (ES, m/z) 263.0 (M+H). 1H NMR (400 MHz, Methanol-$d_4$) δ 8.18 (s, 1H), 8.07 (d, J=5.1 Hz, 1H), 7.22 (d, J=5.0 Hz, 1H), 4.86 (d, J=17.5 Hz, 1H), 4.47 (s, 2H), 1.76 (d, J=8.0 Hz, 1H), 1.56-1.46 (m, 1H), 1.10 (dp, J=15.0, 7.5 Hz, 1H), 0.94-0.86 (m, 3H), 0.82 (t, J=7.4 Hz, 3H).

Example 59: Synthesis of Compound 10 and Form I

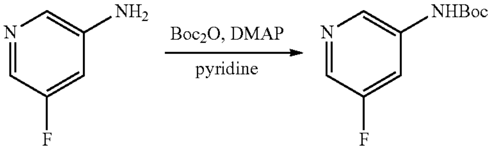 [SMILES: Nc1cncc(F)c1 ; CC(C)(C)OC(=O)Nc1cncc(F)c1]

Step 1: tert-Butyl (5-fluoropyridin-3-yl)carbamate. Pyridine (22.0 kg, 22.4 L), 5-fluoropyridin-3-amine (8.0 kg, 1.0 equiv), and DMAP (872.0 g, 0.1 equiv) were charged into a reactor at 20±5° C. and stirred for 30 min. Di-tert-butyl carbonate (17.1 kg, 1.1 equiv) was charged into the reactor and the mixture was stirred for 13 h. The reaction mixture was transferred to a reactor containing water (128.0 kg, 128.0 L) at 0-5° C. and agitated for 30 min. The heterogeneous mixture was filtered and the cake was washed with $H_2O$ (8.0 kg, 8.0 L). The crude solid was transferred back into the reactor, heptane (16.4 kg, 24.0 L) was added, and the mixture was agitated for 1 h at 25° C. The reaction mixture was then filtered, and the cake was washed with heptane (5.5 kg, 8.0 L). This whole procedure was repeated twice to give tert-butyl (5-fluoropyridin-3-yl)carbamate (25.8 kg, 85%).

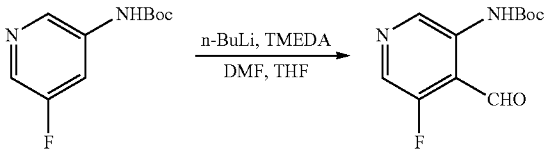 [SMILES: CC(C)(C)OC(=O)Nc1cncc(F)c1 ; CC(C)(C)OC(=O)Nc1cncc(F)c1C=O]

Step 2: tert-Butyl (5-fluoro-4-formylpyridin-3-yl)carbamate. Tetrahydrofuran (229.0 kg, 257.6 L), tert-butyl (5-fluoropyridin-3-yl)carbamate (25.8 kg, 1.0 equiv) and N,N,N',N'-tetramethylethylenediamine (35.3 kg, 2.5 equiv) were added to the reactor and the temperature was adjusted to −55±5° C. n-Butyllithium (2.5 M, 83.0 kg, 2.5 equiv) was added slowly at −55±10° C. The reaction was stirred for 2 h. DMF (44.5 kg, 5.0 equiv) was slowly added at −55±10° C., and the reaction was stirred for 2 h. The reaction mixture was warmed to 0-10° C. and stirred for 1 h. This solution was added to phosphoric acid solution (4 M, 387 kg) in a separate reactor, and agitated while the temperature was maintained between 0-10° C. The reaction mixture was heated to 20±5° C., stirred for 30 min, and then the agitation was stopped and the mixture was let standing for 30 min. The phases were separated and the organic phase was washed with 20% aqueous sodium chloride solution (309.0 kg). The organic phase was filtered through an activated carbon filter and then concentrated under reduced pressure to about ⅓ of the original volume at temperatures less than 45° C. The solution was azeotropically dried with three solvent swaps to ethyl acetate (3×348 kg, 3×394 L). The combined ethyl acetate phases were partially concentrated under reduced pressure to give 232.7 kg of tert-butyl (5-fluoro-4-formylpyridin-3-yl)carbamate in ethyl acetate (11.5 wt %, 26.77 kg, 92% yield).

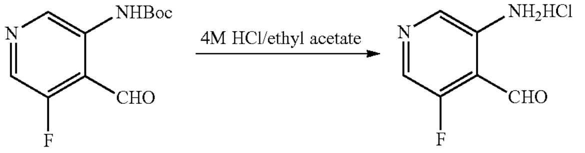

Step 3: Amino-5-fluoroisonicotinaldehyde hydrochloride. tert-Butyl (5-fluoro-4-formylpyridin-3-yl)carbamate ethyl acetate solution (168.0 kg, 11.5 wt %, 19.0 kg, 1.0 equiv) and 4 M hydrogen chloride in ethyl acetate (56.0 kg) were stirred at 20±5° C. for at least 3 h. When the reaction was deemed to be complete, the reactor contents were concentrated under vacuum with the jacket temperature less than 35° C. to give 18.58 kg (99%) of 3-amino-5-fluoroisonicotinaldehyde hydrochloride.

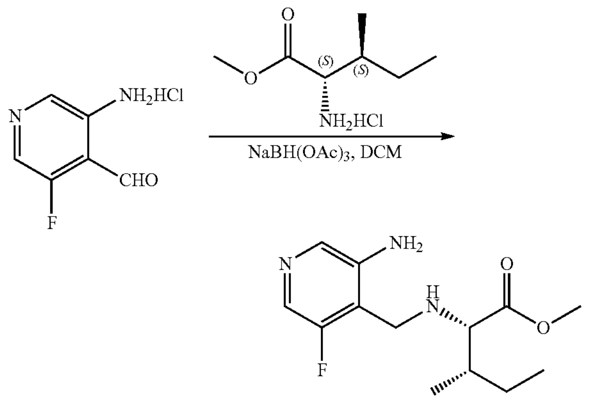

Step 4: Methyl ((3-amino-5-fluoropyridin-4-yl)methyl)-L-isoleucinate. Dichloromethane (241.37 kg, 321.02 L), methyl L-isoleucine (17.17 kg, 1.2 equiv.) and sodium acetate (19.40 kg, 3.0 equiv) were stirred at 25±5° C. for 30 min. 3-Amino-5-fluoroisonicotinaldehyde hydrochloride (18.38 kg, 1.0 equiv) was added at 25±5° C., and the reaction mixture was stirred for 2 h. Dichloromethane (50.00 kg, 37.59 L) was then added, followed by acetic acid (1.40 kg, 0.30 equiv) and sodium triacetoxyborohydride (41.88 kg, 2.5 equiv). The reaction mixture was stirred at 25±5° C. for 12 h. The reaction was cooled to 20±5° C. and 85% phosphoric acid (69.88 kg, 38.10 L) and water (69.80 kg, 69.80 L) were added. The mixture was stirred for 30 min at 25±5° C. The phases were separated and the aqueous phase was extracted with dichloromethane (185.67 kg, 246.90 L). The combined organic phases were washed with water (139.69 kg, 139.60 L), 10% aqueous sodium bicarbonate solution (153.15 kg), and 10% aqueous sodium chloride solution (154.15 kg). The organic phase was concentrated to about 50% of the original volume under reduced pressure at 40° C. The solution was azeotropically dried using tetrahydrofuran and partially concentrated to give 186.80 kg of methyl ((3-amino-5-fluoropyridin-4-yl)methyl)-L-isoleucinate as a tetrahydrofuran solution (8.8 wt %, 16.44 kg, 77% yield).

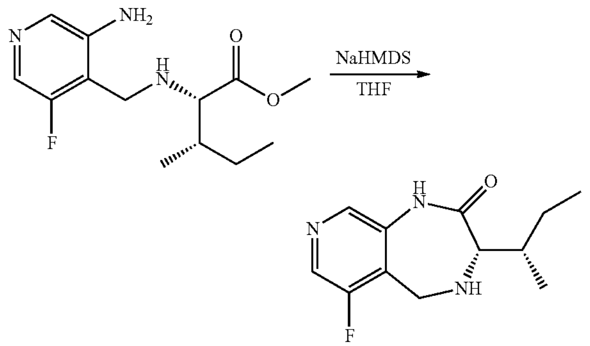

Step 5: (S)-3-((S)-sec-Butyl)-6-fluoro-1,3,4,5-tetrahydro-2H-pyrido[3,4-e][1,4]diazepin-2-one. Tetrahydrofuran (40.0 kg, 45.0 L) and methyl ((3-amino-5-fluoropyridin-4-yl)methyl)-L-isoleucinate tetrahydrofuran solution (170.95 kg, 1.00 equiv) were added to a reactor and the temperature was adjusted to 15±5° C. Sodium bis(trimethylsilyl)amide (37.65 kg, 1.5 equiv) was added slowly to the reactor and the reaction mixture was warmed to 25±5° C. and stirred for 12 h. Phosphoric acid solution (4 M, 36.0 kg) was added at 15±5° C. The temperature was adjusted to 20±5° C. and the reaction mixture was stirred for 30 min. The reaction solution was filtered, and the solid residue was washed with tetrahydrofuran (26.70 kg, 30.0 L). The filtrate was then washed with 20 wt % aqueous sodium chloride solution (56.09 kg) and then extracted with methyl tert-butyl ether (55.55 kg, 75.1 L). The organic phases were combined, washed with 20 wt % aqueous sodium chloride solution (56.30 kg), and the layers were separated. The organic phase was concentrated to 1.0 volume under reduced pressure at 40° C. Isopropyl ether (32.63 kg, 45.0 L) was added to the reactor at 25±5° C. and the mixture was stirred for 12 h. The product was isolated by centrifugation and washed with isopropyl ether (21.7 kg, 29.4 L) to give (S)-3-((S)-sec-butyl)-6-fluoro-1,3,4,5-tetrahydro-2H-pyrido[3,4-e][1,4]diazepin-2-one (9.5 kg, 72% yield).

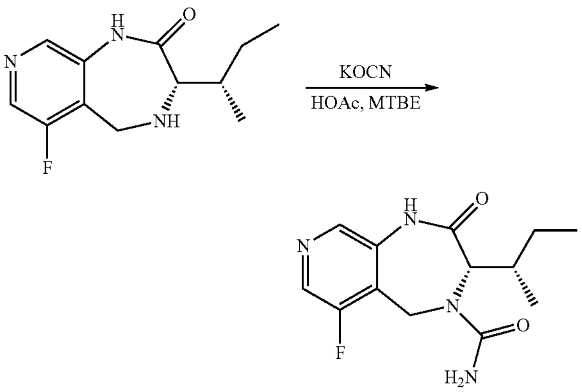

Step 6: (S)-3-((S)-sec-Butyl)-6-fluoro-2-oxo-1,2,3,5-tetrahydro-4H-pyrido[3,4-e][1,4]diazepine-4-carboxamide (Compound 10). To a 100 L reactor was added acetic acid (14.7 kg, 14.0 L) and methyl tert-butyl ether (15.54 kg, 21.0 L). The mixture was cooled to 10±5° C., and (S)-3-((S)-sec-butyl)-6-fluoro-1,3,4,5-tetrahydro-2H-pyrido[3,4-e][1,4]diazepin-2-one (7.00 kg, 1.0 equiv) was added at 10±5° C. Potassium cyanate (4.79 kg, 2.0 equiv) was added in several batches at 10±5° C., and the mixture was stirred for 12 h at 20±5° C. Once the reaction was deemed complete by HPLC, the mixture was diluted with methyl tert-butyl ether (46.52 kg, 63.0 L) and stirred for 1 h at 20±5° C. The product from the heterogeneous mixture was isolated by centrifugation and the product cake was washed with methyl tert-butyl ether (10.36 kg, 14.0 L). The product cake was then stirred with water (175.00 kg, 175.00 L) for 1 h. The product was isolated by centrifugation and then washed with water (7.00 kg, 7.00 L), followed by transfer of the solid out of the centrifuge. Acetic acid (23.52 kg, 22.4 L) and the product cake were added to the reactor, and the mixture was stirred for 1 h at 20±5° C. resulting in a homogeneous solution. To the cleaned reactor, water (175.00 kg, 175.00 L) was added followed by the acetic acid solution of the product. The mixture was agitated for 2 h to provide a heterogeneous mixture. The product was then isolated by centrifugation and washed with water (7.00 kg, 7.00 L), followed by drying in vacuo to give form I of (S)-3-((S)-sec-Butyl)-6-fluoro-2-oxo-1,2,3,5-tetrahydro-4H-pyrido[3,4-e][1,4]diazepine-4-carboxamide (Compound 10, 5.7 kg, 69%).

Characterization and Preparation of Crystalline Forms

The crystalline forms of Compound 10 were characterized by various analytical techniques, including XRPD, DSC, and TGA using the procedures described below.

XRPD

XRPD diffractograms were collected using one of the three methods below:

Method 1: XRPD diffractograms were collected on a Bruker AXS C2 GADDS diffractometer using Cu Kα radiation (40 kV, 40 mA), an automated XYZ stage, a laser video microscope for auto-sample positioning and a Våntec-500 2-dimensional area detector. X-ray optics consists of a single Gabel multilayer mirror coupled with a pinhole collimator of 0.3 mm.

The beam divergence, i.e., the effective size of the X-ray beam on the sample, was approximately 4 mm. A θ-θ continuous scan mode was employed with a sample—detector distance of 20 cm which gives an effective 2θ range of 1.5°-32.5°. Typically, the sample was exposed to the X-ray beam for 120 seconds. The software used for data collection and analysis was GADDS for Win7/XP and Diffrac Plus EVA respectively.

For variable temperature (VT-XRPD) experiments samples were mounted on an Anton Paar DHS 900 hot stage at ambient conditions. The sample was then heated to the appropriate temperature at 10° C./min and subsequently held isothermally for 2 minutes before data collection. Samples were prepared and analysed on a silicon wafer mounted to the hot stage using a heat-conducting paste.

Method 2: XRPD diffractograms were collected on a Bruker D8 diffractometer using Cu Kα radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the standard Pharmorphix data collection method are:

Angular range: 2 to 42° 2θ

Step size: 0.05° 2θ

Collection time: 0.5 s/step (total collection time: 6.40 min)

Method 3: XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel$^{3D}$ detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus.

Samples were prepared and analysed in either a metal or Millipore 96 well-plate in transmission mode. X-ray transparent film was used between the metal sheets on the metal well-plate and powders (approximately 1-2 mg) were used as received. The Millipore plate was used to isolate and analyse solids from suspensions by adding a small amount of suspension directly to the plate before filtration under a light vacuum.

The scan mode for the metal plate used the gonio scan axis, whereas a 2θ scan was utilised for the Millipore plate.

The details of the standard screening data collection method are:

Angular range: 2.5 to 32.0° 2θ

Step size: 0.0130° 2θ

Collection time: 12.75 s/step (total collection time of 2.07 min) DSC

DSC data were collected using one of the two methods below:

Method 1: DSC data were collected on a TA Instruments Q2000 equipped with a 50 position auto-sampler. Typically, 0.5-3 mg of each sample, in a pin-holed aluminium pan, was heated at 10° C./min from 25° C. to 225° C. A purge of dry nitrogen at 50 mL/min was maintained over the sample. Modulated temperature DSC was carried out using an underlying heating rate of 2° C./min and temperature modulation parameters of ±0.636° C. (amplitude) every 60 seconds (period). The instrument control software was Advantage for Q Series and Thermal Advantage and the data were analysed using Universal Analysis or TRIOS.

Method 2: DSC data were collected on a TA Instruments Discovery DSC equipped with a 50 position auto-sampler. Typically, 0.5-3 mg of each sample, in a pin-holed aluminium pan, was heated at 10° C./min from 25° C. to 225° C. A purge of dry nitrogen at 50 ml/min was maintained over the sample. The instrument control software was TRIOS and the data were analysed using TRIOS or Universal Analysis.

TGA

TGA data were collected using one of the two methods below:

Method 1: TGA data were collected on a TA Instruments Q500 TGA, equipped with a 16 position auto-sampler. Typically, 2-5 mg of each sample was loaded onto a pre-tared aluminium DSC pan and heated at 10° C./min from ambient temperature to 300° C. A nitrogen purge at 60 ml/min was maintained over the sample. The instrument control software was Advantage for Q Series and Thermal Advantage and the data were analysed using Universal Analysis or TRIOS.

Method 2: TGA data were collected on a TA Instruments Discovery TGA, equipped with a 25 position auto-sampler. Typically, 2-5 mg of each sample was loaded onto a pre-tared aluminium DSC pan and heated at 10° C./min from ambient temperature to 300° C. A nitrogen purge at 25 ml/min was maintained over the sample. The instrument control software was TRIOS and the data were analysed using TRIOS or Universal Analysis.

GVS

Sorption isotherms were obtained using a SMS DVS Intrinsic moisture sorption analyser, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

Method Parameters for SMS DVS Intrinsic Experiments

| Parameter | Value |
|---|---|
| Adsorption - Scan 1 | 40-90 |
| Desorption, Adsorption - Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

The sample was recovered after completion of the isotherm and re-analysed by XRPD.

Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

Thermodynamic Aqueous Solubility

Aqueous solubility was determined by suspending sufficient compound in relevant media to give a maximum final concentration of >10 mg/ml of the parent free-form of the compound. The suspension was equilibrated at 37° C., on a Heidolph plate shaker set to 750 rpm for 24 hours. The pH of the saturated solution was then measured, and the suspension filtered through a glass fibre C filter (particle retention 1.2 μm) and diluted appropriately. Quantitation was by HPLC with reference to a standard solution of approximately 0.15 mg/ml in DMSO. Different volumes of the standard, diluted and undiluted sample solutions were injected. The solubility was calculated using the peak areas determined by integration of the peak found at the same retention time as the principal peak in the standard injection.

Example 60: Characterization of Crystalline Form I

Crystalline Form I of Compound 10 was prepared according to the synthetic procedure of Example 59 and analyzed by XRPD, DSC, TGA, and GVS. FIG. 1A shows an XRPD pattern of Form I of Compound 10. Table 5 recites the peaks of the XRPD pattern of Form I. FIG. 1B shows DSC and TGA graphs of Form I. As shown in the DSC graph (FIG. 1B), no thermal features were observed until thermal decomposition of the sample. As shown in the TGA graph (FIG. 1B), no weight loss was observed prior to degradation. GVS showed that Form I is slightly hygroscopic with a mass gain of 0.29% between 0 and 90% RH (0.04 mol equivalents of water). The material was unchanged after GVS analysis as demonstrated by XRPD. Static storage at conditions of both 25° C./97% RH and 40° C./75% RH for one week showed Form I remain unchanged by XPRD. KF analysis of the material showed a water content of 0.1% consistent with the hygroscopicity at ambient conditions demonstrated by GVS. Form I was found to be anhydrous. The characterization results of Form I are presented in Table 6.

TABLE 5

XRPD Peaks of Form I

| Angle (° 2θ) | Intensity (%) |
|---|---|
| 8.256 | 100 |
| 11.836 | 3.6 |
| 12.486 | 5.4 |
| 13.075 | 7.8 |
| 14.105 | 4.4 |
| 14.377 | 7.2 |
| 15.712 | 4.9 |
| 16.47 | 28 |
| 16.958 | 8.6 |
| 17.199 | 7 |
| 18.045 | 8.2 |
| 18.389 | 2.1 |
| 18.921 | 12.7 |
| 20.286 | 1.6 |
| 20.675 | 2.4 |
| 20.992 | 5.7 |
| 22.126 | 6.8 |
| 22.672 | 1.4 |
| 23.653 | 8.2 |
| 24.356 | 36.7 |
| 24.754 | 33.2 |
| 25.3 | 7.2 |
| 26.234 | 2.7 |
| 26.571 | 14.1 |
| 26.966 | 2.6 |
| 27.295 | 6.7 |
| 27.663 | 2.3 |
| 28.068 | 2.8 |
| 28.359 | 1.5 |
| 29.063 | 6.5 |
| 29.583 | 1.6 |
| 29.975 | 1.8 |
| 30.535 | 9.3 |
| 31.036 | 5.4 |
| 31.331 | 2.4 |
| 31.669 | 17.5 |
| 32.703 | 4.2 |

TABLE 6

Characterisation data for Crystalline Form I

| | |
|---|---|
| TGA | No mass loss prior to ca. 245° C. where degradation commences |
| DSC | Onset of melt degradation at 238.2° C. |
| GVS | 0.29% Mass change between 0 and 90% RH. 0.04 mol. equivalents water. Unchanged by XRPD post analysis |
| KF | 0.1% water |
| Thermodynamic solubility in FaSSIF (37° C.) | 0.46 mg/mL. XRPD of solid residues: Form I |

Example 61: Preparation of Amorphous Compound 10 and Crystalline Form II and Characterization of Crystalline Form II Crystalline Form I of Compound 10 (1 g) was weighed into a round-bottom flask, THF/$H_2O$ 7:3 (v/v, 60 mL) was added and the mixture was heated with stirring (500 rpm) to 55° C. on a Polar Bear. After approximately 10 minutes of stirring a clear yellow solution formed. This clear solution was filtered using a syringe filter (0.45 μm, PTFE) directly into an a round-bottom flask held in an acetone/dry ice bath to rapidly freeze the mixture. After the sample had completely frozen it was transferred to a freeze-dryer for lyophilisation overnight. After 18 hours on the freeze-dryer the sample was removed, then analysed by XRPD to confirm amorphous formation. The amorphous sample was then placed in a fan oven set to 120° C. for 1 hour to yield Crystalline Form II of Compound 10.

XRPD, DSC, TGA, and GVS were performed on Crystalline Form II. Table 7 recites the peaks of the XRPD pattern of Form II. FIG. 2B shows DSC and TGA graphs of Form II. As shown in the DSC graph (FIG. 2B), no thermal events associated with the melting of the structure were observed prior to the start of thermal decomposition. As shown in the TGA graph (FIG. 2B), no weight loss was observed between RT and 150° C.; TGA and $^1$H-NMR together suggested that Form II is anhydrous. GVS analysis of the material shows it to be slightly hygroscopic with a 0.23% mass change between 0 and 90% RH, with the material shown to be unchanged by XRPD analysis after the GVS measurement. HPLC of Form II showed a chemical purity of 99.4%. Static storage of Form II for 7 days at 40° C./75% RH showed no changes by XRPD. The characterization results of Form II are presented in Table 8.

TABLE 7

XRPD Peaks of Form II

| Angle (° 2θ) | Intensity (%) |
|---|---|
| 8.178 | 2.7 |
| 10.16 | 100 |
| 12.04 | 10.4 |
| 13.864 | 56.5 |
| 16.596 | 40.9 |
| 17.418 | 1.8 |
| 18.413 | 20.4 |
| 19.542 | 38.8 |
| 20.032 | 14.2 |
| 20.437 | 8.8 |
| 20.702 | 30.2 |
| 21.717 | 3 |
| 22.56 | 22.5 |
| 24.246 | 12.4 |
| 24.793 | 3.4 |
| 25.379 | 36.5 |
| 25.733 | 2.7 |
| 25.921 | 2.3 |
| 26.513 | 30.7 |
| 26.915 | 26.1 |
| 28.378 | 2.3 |
| 28.85 | 15.9 |
| 29.333 | 14.4 |
| 30.08 | 4.2 |
| 30.327 | 7.9 |
| 30.733 | 6.5 |
| 31.632 | 5.2 |
| 32.036 | 4.1 |
| 32.432 | 6.9 |

TABLE 8

Characterisation data for Crystalline Form II

| | | |
|---|---|---|
| DSC | | No thermal events before 220° C. Large endotherm observed after due to thermal decomposition. |
| TGA | | No weight loss between RT-150° C. Thermal decomposition begins 220° C. |
| GVS | | Slightly hygroscopic showing a weight change of 0.23% between 0-90% RH., XRPD after GVS: Pattern for Form 2 |
| XRPD | 40° C./75% RH | 7 days: Remains as Form II |
| XRPD | 25° C./97% RH | Form II + very small pattern for Form I |
| XRPD | 40° C./75% RH | 7 days: Remains as Form II |
| Thermodynamic solubility in FaSSIF (37° C.) | | 0.56 mg/mL. XRPD of solid residues: converted to Form I |

Biological Example 1

Assay Example 1: Preparation and Assay of Fast Skeletal Myofibrils

Preparation of fast skeletal myofibrils: Rabbit skeletal myofibrils were prepared based upon the method of Herrmann et al. (Biochem. 32(28):7255-7263(1993). Myofibrils were prepared from rabbit psoas muscle purchased from Pel-Freez Biologicals (Arkansas) within 2 days of ordering, stored on ice. Minced muscle was homogenized in 10 volumes of ice-cold “standard” buffer (50 mM Tris, pH 7.4, 0.1 M KOAc, 5 mM KCl, 2 mM dithiothreitol (DTT), 0.2 mM phenylmethylsulfonyl fluoride (PMSF), 10 μM leupeptin, 5 μM pepstatin, and 0.5 mM sodium azide) containing 5 mM ethylenediaminetetraacetic acid (EDTA) and 0.5% Triton X-100 using an Omni-Macro homogenizer. Myofibrils were recovered by low speed centrifugation (3000 rpm for 10 minutes) and washed 2 times in the Triton X-100 containing buffer to ensure removal of cellular membrane. Following the Triton washes, myofibrils were washed 3 times in “standard” buffer containing 2 mM magnesium acetate. A final wash in assay buffer (12 mM piperazine-1,4-bis(2-ethanesulfonic acid) (PIPES), pH 6.8, 60 mM KCl, 1 mM DTT) was performed and brought to 10% sucrose for flash freezing in liquid nitrogen and storage at −80° C.

Activation of Fast Skeletal Myofibrils: Fast fiber activators were identified by measuring the enzymatic activity of muscle myofibril preparations using the proprietary PUMA (trademark) (see, e.g., U.S. Pat. Nos. 6,410,254, 6,743,599, 7,202,051, and 7,378,254) assay system. Myofibril preparations consisted of rabbit skeletal muscle (approximately 90% fast fibers) that had been mechanically homogenized and washed with a detergent (Triton X-100) to remove cellular membranes. This preparation retained all of the sarcomeric components in a native conformation and the enzymatic activity was still regulated by calcium. Compounds were tested using a myofibril suspension and a level of calcium sufficient to increase enzymatic activity of the myofibrils to 25% of their maximal rate (termed pCa25). Enzymatic activity was tracked via a pyruvate kinase and lactate dehydrogenase-coupled enzyme system. This assay regenerates myosin-produced ADP into ATP by oxidizing NADH, producing an absorbance change at 340 nm. The buffering system was 12 mM PIPES, 2 mM $MgCl_2$, 1 mM DTT at pH 6.8 (PM12 buffer). Data were reported as AC1.4, which is the concentration at which the compound increased the enzymatic activity by 40%. In Table 9, “Example Compound” refers to the compound labeled with the same number in Table 2.

TABLE 9

| Example Compound | AC1.4 (μM) |
|---|---|
| 1 | 0.91 |
| 2 | 0.08 |

TABLE 9-continued

| Example Compound | AC1.4 (μM) |
|---|---|
| 3 | 0.09 |
| 4 | 0.21 |
| 5 | 0.08 |
| 6 | 0.89 |
| 7 | 1.80 |
| 8 | 0.37 |
| 9 | 0.28 |
| 10 | 0.71 |
| 11 | 1.30 |
| 12 | 0.84 |
| 13 | 1.03 |
| 14 | 0.15 |
| 15 | 0.27 |
| 16 | 0.14 |
| 17 | 2.83 |
| 18 | 0.31 |
| 19 | 0.13 |
| 20 | 0.25 |
| 21 | 0.18 |
| 22 | 0.07 |
| 23 | 0.16 |
| 24 | 0.08 |
| 25 | 0.12 |
| 26 | 0.78 |
| 27 | 0.23 |
| 28 | 0.28 |
| 29 | 0.22 |
| 30 | 0.08 |
| 31 | 0.21 |
| 32 | 0.13 |
| 33 | 1.14 |
| 34 | 0.09 |
| 35 | 0.07 |
| 36 | 0.09 |
| 37 | 0.26 |
| 38 | 0.10 |
| 39 | 0.17 |
| 40 | 2.57 |
| 41 | 0.96 |
| 42 | 0.33 |
| 43 | 0.81 |
| 44 | 0.26 |
| 45 | 0.08 |
| 46 | 0.13 |
| 47 | 0.14 |
| 48 | 0.06 |
| 49 | 0.55 |
| 50 | 0.17 |
| 51 | 1.23 |
| 52 | 0.03 |
| 53 | 0.10 |
| 54 | 0.09 |
| 55 | 0.21 |
| 56 | 0.08 |
| 57 | 0.03 |
| 58 | 0.13 |
| 59 | 0.17 |
| 60 | 0.07 |
| 61 | 0.07 |
| 62 | 2.25 |
| 63 | 0.10 |
| 64 | 0.53 |
| 65 | 0.37 |
| 66 | 3.00 |
| 67 | 2.15 |
| 68 | 4.30 |
| 69 | 0.72 |
| 70 | 0.23 |
| 71 | 0.15 |
| 72 | 0.41 |
| 73 | 0.93 |
| 74 | 2.39 |
| 75 | 0.13 |
| 76 | 0.14 |
| 77 | 0.19 |
| 78 | 0.50 |
| 79 | 0.32 |
| 80 | 0.47 |

TABLE 9-continued

| Example Compound | AC1.4 (μM) |
|---|---|
| 81 | 3.80 |
| 82 | 0.24 |
| 83 | 0.03 |
| 84 | 0.09 |
| 85 | 0.01 |
| 86 | 1.81 |
| 87 | 0.07 |
| 88 | 1.22 |
| 89 | 0.18 |
| 90 | 0.45 |
| 91 | 0.08 |
| 92 | 0.40 |
| 93 | 0.13 |
| 94 | 0.15 |
| 95 | 0.04 |
| 96 | 0.08 |
| 97 | 0.92 |
| 98 | 0.31 |
| 99 | 0.05 |
| 100 | 0.08 |
| 101 | 0.05 |
| 102 | 0.37 |
| 103 | 1.22 |
| 104 | 0.08 |
| 105 | 0.10 |
| 106 | 0.89 |
| 107 | 0.29 |
| 108 | 0.19 |
| 109 | 0.17 |
| 110 | 1.36 |
| 111 | 4.90 |
| 112 | 0.81 |
| 113 | 0.15 |
| 114 | 0.05 |
| 115 | 0.08 |
| 116 | 0.05 |
| 117 | 0.07 |
| 118 | 0.08 |
| 119 | 2.44 |
| 120 | 0.12 |
| 121 | 4.80 |
| 122 | 3.16 |
| 123 | 0.35 |
| 124 | 0.38 |
| 125 | 0.29 |
| 126 | 0.15 |
| 127 | 0.66 |
| 128 | 0.06 |
| 129 | 0.10 |
| 130 | 0.06 |
| 131 | 0.02 |
| 132 | 0.07 |
| 133 | 0.48 |
| 134 | 0.71 |
| 135 | 3.72 |
| 136 | 1.03 |
| 137 | 3.35 |
| 138 | 0.52 |
| 139 | 0.93 |
| 140 | 4.74 |
| 141 | 0.54 |
| 142 | 0.36 |
| 143 | 0.35 |
| 144 | 0.28 |
| 145 | 0.50 |
| 146 | 0.30 |
| 147 | 2.57 |
| 148 | 0.98 |
| 149 | 2.08 |
| 150 | 0.03 |
| 151 | 0.06 |
| 152 | 0.07 |
| 153 | 0.09 |
| 154 | 0.65 |
| 155 | 0.54 |
| 156 | 0.90 |
| 157 | 0.11 |
| 158 | 0.44 |

TABLE 9-continued

| Example Compound | AC1.4 (μM) |
|---|---|
| 159 | 0.59 |
| 160 | 0.16 |
| 161 | 2.25 |
| 162 | 0.11 |
| 163 | 0.05 |
| 164 | 0.10 |
| 165 | 0.14 |
| 166 | 0.45 |
| 167 | 0.05 |
| 168 | 0.04 |
| 169 | 0.06 |
| 170 | 0.79 |
| 171 | 0.03 |
| 172 | 0.63 |
| 173 | 0.22 |
| 174 | 0.03 |
| 175 | 0.04 |
| 176 | 0.05 |
| 177 | 2.64 |
| 178 | 3.37 |
| 179 | 2.27 |
| 180 | 0.10 |
| 181 | 0.04 |
| 182 | 0.07 |
| 183 | 1.34 |
| 184 | 0.55 |
| 185 | 0.92 |
| 186 | 2.18 |
| 187 | 1.39 |
| 188 | 3.46 |
| 189 | 0.10 |
| 190 | 0.54 |
| 191 | 0.19 |
| 192 | 0.19 |
| 193 | 0.72 |
| 194 | 1.52 |
| 195 | 1.84 |
| 196 | 2.09 |
| 197 | 1.76 |
| 198 | 1.66 |
| 199 | 0.94 |
| 200 | 4.22 |
| 201 | 0.05 |
| 202 | 0.17 |
| 203 | 1.75 |
| 204 | 3.66 |
| 205 | 1.58 |
| 206 | 4.98 |
| 207 | 3.62 |
| 208 | 2.70 |
| 209 | 4.17 |
| 210 | 4.25 |
| 211 | 2.92 |
| 212 | 1.27 |
| 213 | 4.04 |
| 214 | 1.72 |
| 215 | 4.65 |
| 216 | 2.64 |
| 217 | 2.45 |
| 218 | 0.88 |
| 219 | 2.10 |
| 220 | 3.01 |
| 221 | 1.80 |
| 222 | 2.02 |
| 223 | 1.43 |
| 224 | 2.85 |
| 225 | 1.67 |
| 226 | 3.91 |
| 227 | 2.29 |
| 228 | 3.76 |
| 229 | 3.74 |
| 230 | 1.31 |
| 231 | 4.86 |
| 232 | 3.47 |
| 233 | 2.16 |
| 234 | 4.64 |
| 235 | 1.45 |
| 236 | 3.43 |

TABLE 9-continued

| Example Compound | AC1.4 (μM) |
|---|---|
| 237 | 1.86 |
| 238 | 4.49 |
| 239 | 1.65 |
| 240 | 2.87 |
| 241 | 1.35 |
| 242 | 4.30 |
| 243 | 1.93 |
| 244 | 2.43 |
| 245 | 3.88 |
| 246 | 1.64 |
| 247 | 2.49 |
| 248 | 3.71 |
| 249 | 4.51 |
| 250 | 0.60 |
| 251 | 0.08 |
| 252 | 0.44 |
| 253 | 0.08 |
| 254 | 0.07 |
| 255 | 0.13 |
| 256 | 1.89 |
| 257 | 0.02 |
| 258 | 0.29 |
| 259 | 2.44 |
| 260 | 1.91 |
| 261 | 3.34 |
| 262 | 0.46 |
| 263 | 2.70 |
| 264 | 0.84 |
| 265 | 0.70 |
| 266 | 2.47 |
| 267 | 0.95 |
| 268 | 1.03 |
| 269 | 0.92 |
| 270 | 0.94 |
| 271 | 0.95 |
| 272 | 2.62 |
| 273 | 3.02 |
| 274 | 0.06 |
| 275 | 0.06 |
| 276 | 0.24 |
| 277 | 0.08 |
| 278 | 0.05 |
| 279 | 1.46 |
| 280 | 1.06 |
| 281 | 0.30 |
| 282 | 0.38 |
| 283 | 0.09 |
| 284 | 0.11 |
| 285 | 0.54 |
| 286 | 0.30 |
| 287 | 0.35 |
| 288 | 0.16 |
| 289 | 3.59 |
| 290 | 0.15 |
| 291 | 0.05 |
| 292 | 0.05 |
| 293 | 0.55 |
| 294 | 2.32 |
| 295 | 3.41 |
| 296 | 1.75 |
| 297 | 1.13 |
| 298 | 0.07 |
| 299 | 0.18 |
| 300 | 0.42 |
| 301 | 0.36 |
| 302 | 0.82 |
| 303 | 0.89 |
| 304 | 2.27 |
| 305 | 1.42 |
| 306 | 0.11 |
| 307 | 0.52 |
| 308 | 0.32 |
| 309 | 0.59 |
| 310 | 4.17 |
| 311 | 2.60 |
| 312 | 1.22 |
| 313 | 1.22 |
| 314 | 0.72 |

TABLE 9-continued

| Example Compound | AC1.4 (μM) |
|---|---|
| 315 | 0.65 |
| 316 | 1.07 |
| 317 | 1.30 |
| 318 | 0.19 |
| 319 | 0.80 |
| 320 | 1.25 |
| 321 | 0.12 |
| 322 | 1.15 |
| 323 | 0.66 |
| 324 | 1.16 |
| 325 | 1.81 |
| 326 | 4.38 |
| 327 | 1.50 |
| 328 | 2.56 |
| 329 | 0.20 |
| 330 | 1.71 |
| 331 | 1.03 |
| 332 | 2.37 |
| 333 | 2.44 |
| 334 | 0.65 |
| 335 | 3.75 |
| 336 | 0.12 |
| 337 | 0.72 |
| 338 | 0.69 |
| 339 | 2.79 |
| 340 | 3.00 |
| 341 | 2.37 |
| 342 | 0.27 |
| 343 | 0.25 |
| 344 | 1.91 |
| 345 | 2.43 |
| 346 | 1.57 |
| 347 | 3.59 |
| 348 | 0.72 |
| 349 | 1.57 |
| 350 | 1.11 |
| 351 | 1.17 |
| 352 | 0.73 |
| 353 | 1.76 |
| 354 | 1.59 |
| 355 | 1.49 |
| 356 | 0.24 |
| 357 | 1.69 |
| 358 | 0.40 |
| 359 | 0.77 |
| 360 | 0.37 |
| 361 | 1.62 |
| 362 | 1.68 |
| 363 | 2.60 |
| 364 | 3.31 |
| 365 | 0.19 |
| 366 | 0.21 |
| 367 | 1.05 |
| 368 | 0.41 |
| 369 | 0.24 |
| 370 | 0.88 |
| 371 | 0.50 |
| 372 | 0.18 |
| 373 | 0.66 |
| 374 | 0.42 |
| 375 | 0.26 |
| 376 | 0.18 |
| 377 | 0.29 |
| 378 | 0.15 |
| 379 | 0.92 |
| 380 | 1.25 |
| 381 | 0.48 |

Assay Example 2: Preparation and Assay of Rat Isometric Ankle Plantarflexor Muscle Force Female Sprague Dawley rats were placed under a stable anesthetic plane with inhaled isoflurane (1-5%). One incision was made on the mid-thigh region of the right leg to expose the sciatic nerve. To prevent co-contraction of the ankle dorsiflexors, an additional incision was made lateral to the patella to isolate and sever the peroneal nerve. Rats were then placed on a temperature-maintained in situ muscle analysis rig (Aurora Scientific, Model 806C). The knee was immobilized in a clamp between two sharpened screws and the foot was taped to a footplate attached to a force transducer (Aurora Scientific, Ontario, Canada). Stainless steel needle electrodes (0.10 mm) were hooked around the exposed sciatic nerve. Isometric ankle plantarflexor muscle contractile force was assessed with the ankle joint at 90° flexion. A 30 Hz electrical stimulation (under supramaximal voltage conditions) was applied to the nerve and the resulting muscle force was recorded via a servomotor. A pre-dose 30 Hz force response was established as the baseline force. A pre-dose 150 Hz force response was established as the maximum isometric force. Compounds were formulated in 50% polyethylene glycol (PEG): 16% Cavitron: 10% dimethylacetamide (DMA) and administered by continuous intravenous infusion over a sixty minute period. The muscle force response to compound was measured every two minutes over the dosing period. Data were reported as an estimated $EC_{50}$ value, which is the concentration at which muscle force is 50% of the pre-dose maximum tension. The $EC_{50}$ results are summarized in Table 10 below. In Table 10, "Example Compound" refers to the compound labeled with the same number in Table 2.

TABLE 10

| Example Compound | PLANTARFLEXOR $EC_{50}$ (μM) |
|---|---|
| 1 | 26.2 |
| 2 | 19.1 |
| 6 | 20.3 |
| 7 | 41.1 |
| 8 | 15.2 |
| 9 | 19.1 |
| 10 | 18.8 |
| 12 | 38.7 |
| 32 | 12.6 |
| 49 | 28.0 |
| 64 | 20.1 |
| 65 | 11.3 |
| 82 | 21.4 |
| 144 | 10.5 |
| 357 | 58.3 |

The invention claimed is:

1. A method for treating a disease or condition selected from the group consisting of peripheral vascular disease, peripheral arterial disease, rehabilitation-related deficits, metabolic syndrome, obesity, ventilator-induced muscle weakness, chronic fatigue syndrome, neuromuscular disorders, conditions of muscle wasting, muscular myopathies, muscle atrophy and fatigue, frailty, amyotrophic lateral sclerosis (ALS), spinal muscular atrophy (SMA), myasthenia gravis, muscular myopathies, stress urinary incontinence (SUI), mixed urinary incontinence (MUI), fecal incontinence, frailty, sarcopenia, chronic obstructive pulmonary disease (COPD), cachexia syndrome, muscle wasting caused by heart failure, cancer, or chronic kidney disease/dialysis, post-spinal cord injury (SCI) muscle dysfunction, post-stroke muscle dysfunction, facioscapulohumeral dystrophy, and Charcot-Marie-Tooth disease, in a subject, comprising administering to the subject an effective amount of a compound of Formula (I):

(I)

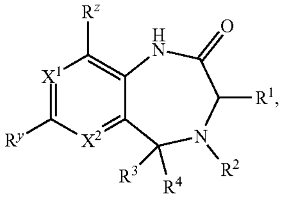

or a pharmaceutically acceptable salt, stereoisomer, or tautomer thereof, or a pharmaceutical composition comprising any of the foregoing and a pharmaceutical carrier, wherein:

$X^1$ and $X^2$ are each independently N or C—$R^x$;

each $R^x$, $R^y$, and $R^z$ is independently H, halo, $C_{3-10}$cycloalkyl, $C_{3-10}$cycloalkenyl, or $C_{6-20}$aryl;

$R^1$ is $C_{3-12}$alkyl, $C_{2-12}$alkenyl, $C_{2-12}$alkynyl, $C_{3-10}$cycloalkyl, $C_{3-10}$cycloalkenyl, or

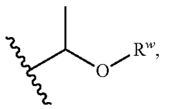

wherein $R^w$ is $C_{1-12}$alkyl;

$R^2$ is:

a) C(O)—$R^h$, wherein $R^h$ is (i) amino optionally substituted with one or more $R^q$, wherein $R^q$ is $C_{1-12}$alkyl, $C_{3-10}$cycloalkyl, $C_{6-20}$aryl, 3-15 membered heterocyclyl, or 5-20 membered heteroaryl, wherein the $C_{1-12}$alkyl, $C_{3-10}$cycloalkyl, $C_{6-20}$aryl, 3-15 membered heterocyclyl, or 5-20 membered heteroaryl of $R^q$ is optionally substituted with one or more $R^p$, wherein $R^p$ is OH, cyano, halo, oxo, —C(O)$NH_2$, —C(O)NH($C_{1-12}$alkyl), —C(O)-(3-15 membered heterocyclyl), —S(O)—$C_{1-12}$alkyl, —$S(O)_2$—$C_{1-12}$alkyl, —$S(O)_2$—$NH_2$, —N($C_{1-12}$alkyl)$_2$, —NHC(O)—$C_{1-12}$alkyl, —NHC(O)—$NH_2$, $C_{6-20}$aryl, 3-15 membered heterocyclyl, or 5-20 membered heteroaryl, wherein the $C_{6-20}$aryl, 3-15 membered heterocyclyl, 5-20 membered heteroaryl, or the 3-15 membered heterocyclyl of the C(O)-(3-15 membered heterocyclyl) of $R^p$ is independently optionally substituted with one or more $R^v$, wherein $R^v$ is OH, oxo, —C(O)$NH_2$, —C(O)OH, or $C_{1-12}$alkyl, wherein the $C_{1-12}$alkyl of $R^v$ is further optionally substituted with one or more OH, $C_{1-3}$alkoxy,

C(O)$NH_2$, $C_{3-10}$cycloalkyl, $C_{3-10}$cycloalkenyl, wherein the $C_{3-10}$cycloalkenyl is unsubstituted or substituted with one or more oxo, $C_{6-20}$aryl, wherein the $C_{6-20}$aryl is unsubstituted or substituted with one or more OH, 5-20 membered heteroaryl, or —C(O)$NH_2$, 3-15 membered heterocyclyl, wherein the 3-15 membered heterocyclyl is unsubstituted or substituted with one or more $R^j$, wherein $R^j$ is OH, oxo, halo, $NH_2$, —N($C_{1-12}$alkyl)$_2$, —N($C_{1-12}$alkyl)-C(O)$C_{1-12}$alkyl, —NH—$SO_2$—$C_{1-12}$alkyl, —$SO_2$—$C_{1-12}$alkyl, $C_{1-12}$alkyl, $C_{1-12}$alkoxy, —C(O)OH, —C(O)—$C_{1-12}$alkoxy, —C(O)$NH_2$, —C(O)NH($C_{1-12}$alkyl), —C(O)N($C_{1-12}$alkyl)$_2$, 3-15 membered heterocyclyl, or 5-20 membered heteroaryl, wherein the $C_{1-12}$alkyl, $C_{1-12}$alkoxy, 3-15 membered heterocyclyl, or 5-20 membered heteroaryl of $R^j$ is independently further optionally substituted with one or more $R^k$, wherein $R^k$ is OH, $C_{1-12}$alkyl, —C(O)$NH_2$, —C(O)NH($C_{1-12}$alkyl), —C(O)N($C_{1-12}$alkyl)$_2$, $C_{6-20}$aryl, or 5-20 membered heteroaryl, wherein the $C_{1-12}$alkyl of $R^k$ is independently further optionally substituted with one or more OH, or 5-20 membered heteroaryl, wherein the 5-20 membered heteroaryl is unsubstituted or substituted with one or more $R^t$, wherein $R^t$ is OH, $NH_2$, $C_{1-12}$alkyl, —C(O)OH, —C(O)—$C_{1-12}$alkoxy, —C(O)$NH_2$, —C(O)NH($C_{1-12}$alkyl), —C(O)N($C_{1-12}$alkyl)$_2$, or —C(O)-(3-15 membered heterocyclyl), wherein the $C_{1-12}$alkyl of $R^t$, the 3-15 membered heterocyclyl of the —C(O)-(3-15 membered heterocyclyl) of $R^t$, the $C_{1-12}$alkyl of the —C(O)NH($C_{1-12}$alkyl) of $R^t$, or the $C_{1-12}$alkyl of the —C(O)N($C_{1-12}$alkyl)$_2$ of R' is independently further optionally substituted with one or more OH, —$C_{1-12}$alkoxy, or —C(O)$NH_2$, or (ii) $C_{1-12}$alkyl, wherein the $C_{1-12}$alkyl is unsubstituted or is substituted with one or more $R^n$, wherein $R^n$ is OH, oxo, halo, cyano, —C(O)$NH_2$, amino, sulfonyl, $C_{1-12}$alkoxy, $C_{6-20}$aryloxy, $C_{3-10}$cycloalkyl, $C_{3-10}$cycloalkenyl, 3-15 membered heterocyclyl, or 5-20 membered heteroaryl, or b) $C_{1-12}$alkyl, wherein the $C_{1-12}$alkyl is unsubstituted or is substituted with one or more $R^m$, wherein $R^m$ is OH, halo, cyano, oxo, $C_{1-12}$alkyl, $C_{1-3}$alkoxy, $C_{6-20}$aryloxy, —C(O)$NH_2$, —C(O)NH($C_{1-12}$alkyl), —C(O)N($C_{1-12}$alkyl)$_2$, —C(O)OH, —C(O)—$C_{1-12}$alkoxy, —C(O)-(3-15 membered heterocyclyl), $NH_2$, —NH($C_{1-12}$alkyl), —N($C_{1-12}$alkyl)$_2$, —NHC(O)—$C_{1-12}$alkyl, —NHC(O)—$NH_2$, —NH—$SO_2$—$C_{1-12}$alkyl, —S(O)—$C_{1-12}$alkyl, —$S(O)_2$—$C_{1-12}$alkyl, —$S(O)_2$—$NH_2$, $C_{3-10}$cycloalkyl, or 3-15 membered heterocyclyl, wherein the $C_{1-12}$alkyl, $C_{6-20}$aryloxy, the $C_{1-12}$alkyl of —C(O)NH($C_{1-12}$alkyl), the $C_{1-12}$alkyl of —C(O)N($C_{1-12}$alkyl)$_2$, —C(O)OH, —C(O)—$C_{1-12}$alkoxy, the 3-15 membered heterocyclyl of —C(O)-(3-15 membered heterocyclyl), $NH_2$, the $C_{1-12}$alkyl of —NH($C_{1-12}$alkyl), the $C_{1-12}$alkyl of —N($C_{1-12}$alkyl)$_2$, the $C_{1-12}$alkyl of —NHC(O)—$C_{1-12}$alkyl, —NHC(O)—$NH_2$, the $C_{1-12}$alkyl of —NH—$SO_2$—$C_{1-12}$alkyl, the $C_{1-12}$alkyl of —S(O)—$C_{1-12}$alkyl, the $C_{1-12}$alkyl of —$S(O)_2$—$C_{1-12}$alkyl, —$S(O)_2$—$NH_2$, $C_{3-10}$cycloalkyl, or 3-15 membered heterocyclyl of $R^m$ is further optionally substituted by one or more OH, halo, cyano, oxo, $C_{1-12}$alkyl, $C_{1-12}$alkoxy, —C(O)$NH_2$, —C(O)NH($C_{1-12}$alkyl), —C(O)N($C_{1-12}$alkyl)$_2$, C(O)OH, $NH_2$, —NH($C_{1-12}$alkyl), —N($C_{1-12}$alkyl)$_2$, $C_{3-10}$cycloalkyl, $C_{6-20}$aryl, 3-15 membered heterocyclyl, or 5-20 membered heteroaryl, or c) $C_{3-10}$cycloalkenyl, wherein the $C_{3-10}$cycloalkenyl is unsubstituted or is substituted with one or more $R^i$, wherein $R^i$ is oxo, $NH_2$, —NH($C_{1-12}$alkyl), —N($C_{1-12}$alkyl)$_2$, or 3-15 membered heterocyclyl, wherein the 3-15 membered heterocyclyl of $R^i$, the $C_{1-12}$alkyl of the —NH($C_{1-12}$alkyl) of $R^i$, or the $C_{1-12}$alkyl of the —N($C_{1-12}$alkyl)$_2$ of $R^i$ is independently optionally substituted with one or more OH or $C_{1-12}$alkoxy, or d) 5-20 membered heteroaryl, wherein the 5-20 membered heteroaryl is unsubstituted or substituted with one or more OH, oxo, $NH_2$, or $C_{1-12}$alkyl, or e) 3-15 membered heterocyclyl, wherein the 3-15 membered heterocyclyl is unsubstituted or substituted with one or more OH, oxo, $NH_2$, or $C_{1-12}$alkyl, or f) amidinyl, wherein the amidinyl is unsubstituted or substituted with one or more $R^s$, wherein $R^s$ is OH, cyano, $C_{1-12}$alkyl, —C(O)—$C_{1-12}$alkyl, —C(O)—$C_{1-12}$alkoxy, $C_{6-20}$aryloxy, or —$SO_2$—$C_{1-12}$alkyl, or g) optionally substituted sulfonyl, wherein the sulfonyl is unsubstituted or substituted with one or more $R^u$, wherein $R^u$ is $C_{1-12}$alkyl, $NH_2$, —NH($C_{1-12}$alkyl), —N($C_{1-12}$alkyl)$_2$, or $C_{6-20}$aryl, wherein the $C_{1-12}$alkyl or $C_{6-20}$aryl of $R^u$ is independently further optionally substituted with one or more halo or $C_{1-12}$alkoxy, or h) cyano, and $R^3$ is H, $C_{1-12}$alkyl, C(O)$NH_2$, or C(O)—$C_{1-12}$alkoxy; or $R^2$ and $R^3$ are taken together with the atoms to which they are attached to form a 5- or 6-membered heterocyclyl or 5- or 6-membered heteroaryl, wherein the 5- or 6-membered heterocyclyl or 5- or 6-membered heteroaryl independently comprises two or more annular heteroatoms and is independently optionally substituted with one or more oxo or OH; and $R^4$ is absent or is H, $C_{1-12}$alkyl, C(O)$NH_2$, or C(O)—$C_{1-12}$alkoxy.

2. The method of claim 1, wherein the disease or condition is facioscapulohumeral dystrophy.

3. The method of claim 1, wherein at least one of $X^1$ and $X^2$ is N.

4. The method of claim 1, wherein $X^1$ is N and $X^2$ is C—$R^x$.

5. The method of claim 1, wherein $X^1$ is C—$R^x$ and $X^2$ is N.

6. The method of claim 1, wherein $X^1$ and $X^2$ are each independently C—$R^x$.

7. The method of claim 1, wherein each $R^x$ is independently H or fluoro.

8. The method of claim 1, wherein $X^1$ and $X^2$ are each N.

9. The method of claim 1, wherein $R^2$ is C(O)—$R^h$, wherein $R^h$ is (i) amino optionally substituted with one or more $R^q$, wherein $R^q$ is $C_{1-12}$alkyl, $C_{3-10}$cycloalkyl, $C_{6-20}$aryl, 3-15 membered heterocyclyl, or 5-20 membered heteroaryl, wherein the $C_{1-12}$alkyl, $C_{3-10}$cycloalkyl, $C_{6-20}$aryl, 3-15 membered heterocyclyl, or 5-20 membered heteroaryl of $R^q$ is optionally substituted with one or more $R^p$, wherein $R^p$ is OH, cyano, halo, oxo, —C(O)$NH_2$, —C(O)NH($C_{1-12}$alkyl), —C(O)-(3-15 membered heterocyclyl), —S(O)—$C_{1-12}$alkyl, —S(O)$_2$—$C_{1-12}$alkyl, —S(O)$_2$—$NH_2$, —N($C_{1-12}$alkyl)$_2$, —NHC(O)—$C_{1-12}$alkyl, —NHC(O)—$NH_2$, $C_{6-20}$aryl, 3-15 membered heterocyclyl, or 5-20 membered heteroaryl, wherein the $C_{6-20}$aryl, 3-15 membered heterocyclyl, 5-20 membered heteroaryl, or the 3-15 membered heterocyclyl of the C(O)-(3-15 membered heterocyclyl) of $R^p$ is independently optionally substituted with one or more $R^v$, wherein $R^v$ is OH, oxo, —C(O)$NH_2$, —C(O)OH, or $C_{1-12}$alkyl, wherein the $C_{1-12}$alkyl of $R^v$ is further optionally substituted with one or more OH, $C_{1-3}$alkoxy,

C(O)$NH_2$, $C_{3-10}$cycloalkyl, $C_{3-10}$cycloalkenyl, wherein the $C_{3-10}$cycloalkenyl is unsubstituted or substituted with one or more oxo, $C_{6-20}$aryl, wherein the $C_{6-20}$aryl is unsubstituted or substituted with one or more OH, 5-20 membered heteroaryl, or —C(O)$NH_2$, 3-15 membered heterocyclyl, wherein the 3-15 membered heterocyclyl is unsubstituted or substituted with one or more $R^j$, wherein $R^j$ is OH, oxo, halo, $NH_2$, —N($C_{1-12}$alkyl)$_2$, —N($C_{1-12}$alkyl)-C(O)$C_{1-12}$alkyl, —NH—$SO_2$—$C_{1-12}$alkyl, —$SO_2$—$C_{1-12}$alkyl, $C_{1-12}$alkyl, $C_{1-12}$alkoxy, —C(O)OH, —C(O)—$C_{1-12}$alkoxy, —C(O)$NH_2$, —C(O)NH($C_{1-12}$alkyl), —C(O)N($C_{1-12}$alkyl) 2,3-15 membered heterocyclyl, or 5-20 membered heteroaryl, wherein the $C_{1-12}$alkyl, $C_{1-12}$alkoxy, 3-15 membered heterocyclyl, or 5-20 membered heteroaryl of $R^j$ is independently further optionally substituted with one or more $R^k$ wherein $R^k$ is OH, $C_{1-12}$alkyl, —C(O)$NH_2$, —C(O)NH($C_{1-12}$alkyl), —C(O)N($C_{1-12}$alkyl)$_2$, $C_{6-20}$aryl, or 5-20 membered heteroaryl, wherein the $C_{1-12}$alkyl of $R^k$ is independently further optionally substituted with one or more OH, or 5-20 membered heteroaryl, wherein the 5-20 membered heteroaryl is unsubstituted or substituted with one or more $R^t$, wherein $R^t$ is OH, $NH_2$, $C_{1-12}$alkyl, —C(O)OH, —C(O)—$C_{1-12}$alkoxy, —C(O)$NH_2$, —C(O)NH($C_{1-12}$alkyl), —C(O)N($C_{1-12}$alkyl)$_2$, or —C(O)-(3-15 membered heterocyclyl), wherein the $C_{1-12}$alkyl of $R^t$, the 3-15 membered heterocyclyl of the —C(O)-(3-15 membered heterocyclyl) of $R^t$, the $C_{1-12}$alkyl of the —C(O)NH($C_{1-12}$alkyl) of $R^t$, or the $C_{1-12}$alkyl of the —C(O)N($C_{1-12}$alkyl)$_2$ of $R^t$ is independently further optionally substituted with one or more OH, —$C_{1-12}$alkoxy, or —C(O)$NH_2$, or (ii) $C_{1-12}$alkyl, wherein the $C_{1-12}$alkyl is unsubstituted or is substituted with one or more $R^n$, wherein $R^n$ is OH, oxo, halo, cyano, —C(O)$NH_2$, amino, sulfonyl, $C_{1-12}$alkoxy, $C_{6-20}$aryloxy, $C_{3-10}$cycloalkyl, $C_{3-10}$cycloalkenyl, 3-15 membered heterocyclyl, or 5-20 membered heteroaryl.

10. The method of claim 1, wherein $R^h$ is $NH_2$.

11. The method of claim 1, wherein $R^h$ is amino substituted with one or more $R^q$, wherein $R^q$ is $C_{1-12}$alkyl, $C_{3-10}$cycloalkyl, $C_{6-20}$aryl, 3-15 membered heterocyclyl, or 5-20 membered heteroaryl, wherein the $C_{1-12}$alkyl, $C_{3-10}$cycloalkyl, $C_{6-20}$aryl, 3-15 membered heterocyclyl, or 5-20 membered heteroaryl of $R^q$ is optionally substituted with one or more $R^p$, wherein $R^p$ is OH, cyano, halo, oxo, —C(O)$NH_2$, —C(O)NH($C_{1-12}$alkyl), —C(O)-(3-15 membered heterocyclyl), —S(O)—$C_{1-12}$alkyl, —S(O)$_2$—$C_{1-12}$alkyl, —S(O)$_2$—$NH_2$, —N($C_{1-12}$alkyl)$_2$, —NHC(O)—$C_{1-12}$alkyl, —NHC(O)—$NH_2$, $C_{6-20}$aryl, 3-15 membered heterocyclyl, or 5-20 membered heteroaryl, wherein the $C_{6-20}$aryl, 3-15 membered heterocyclyl, 5-20 membered heteroaryl, or the 3-15 membered heterocyclyl of the C(O)-(3-15 membered heterocyclyl) of $R^p$ is independently optionally substituted with one or more $R^v$, wherein $R^v$ is OH, oxo, —C(O)$NH_2$, —C(O)OH, or $C_{1-12}$alkyl, wherein the $C_{1-12}$alkyl of $R^v$ is further optionally substituted with one or more OH.

12. The method of claim 1, wherein $R^q$ is unsubstituted methyl.

13. The method of claim 1, wherein $R^h$ is $C_{1-12}$alkyl, wherein the $C_{1-12}$alkyl is unsubstituted or is substituted with one or more $R^n$, wherein $R^n$ is OH, $NH_2$, —C(O)$NH_2$, $C_{1-12}$alkoxy, $C_{6-20}$aryloxy, or 3-15 membered heterocyclyl.

14. The method of claim 1, wherein $R^n$ is OH, $NH_2$, or —C(O)$NH_2$.

15. The method of claim 1, wherein $R^h$ is $C_{1-3}$alkoxy, —C(O)$NH_2$, 3-15 membered heterocyclyl, or 5-20 membered heteroaryl, wherein the 3-15 membered heterocyclyl or 5-20 membered heteroaryl is independently optionally substituted with one or more OH, $NH_2$, or $C_{1-12}$alkyl, wherein the $C_{1-12}$alkyl is further optionally substituted with one or more OH.

16. The method of claim 1, wherein $R^2$ is:

(a) 5-20 membered heteroaryl, wherein the 5-20 membered heteroaryl is unsubstituted or substituted with one or more OH, oxo, $NH_2$, or $C_{1-12}$alkyl, or (b) $C_{1-12}$alkyl, wherein the $C_{1-12}$alkyl is unsubstituted or is substituted with one or more $R^m$, wherein $R^m$ is OH, halo, cyano, oxo, $C_{1-12}$alkyl, $C_{1-3}$alkoxy, $C_{6-20}$aryloxy, —C(O)$NH_2$, —C(O)NH($C_{1-12}$alkyl), —C(O)N($C_{1-12}$alkyl)$_2$, —C(O)OH, —C(O)—$C_{1-12}$alkoxy, —C(O)-(3-15 membered heterocyclyl), $NH_2$, —NH($C_{1-12}$alkyl), —N($C_{1-12}$alkyl)$_2$, —NHC(O)—$C_{1-12}$alkyl, —NHC(O)—$NH_2$, —NH—$SO_2$—$C_{1-12}$alkyl, —S(O)—$C_{1-12}$alkyl, —S(O)$_2$—$C_{1-12}$alkyl, —S(O)$_2$—$NH_2$, $C_{3-10}$cycloalkyl, or 3-15 membered heterocyclyl, wherein the $C_{1-12}$alkyl, $C_{6-20}$aryloxy, the $C_{1-12}$alkyl of —C(O)NH($C_{1-12}$alkyl), the $C_{1-12}$alkyl of —C(O)N($C_{1-12}$alkyl)$_2$, —C(O)OH, —C(O)—$C_{1-12}$alkoxy, the 3-15 membered heterocyclyl of —C(O)-(3-15 membered heterocyclyl), $NH_2$, the $C_{1-12}$alkyl of —NH($C_{1-12}$alkyl), the $C_{1-12}$alkyl of -N($C_{1-12}$alkyl)$_2$, the $C_{1-12}$alkyl of —NHC(O)—$C_{1-12}$alkyl, —NHC(O)—$NH_2$, the $C_{1-12}$alkyl of —NH—$SO_2$—$C_{1-12}$alkyl, the $C_{1-12}$alkyl of —S(O)—$C_{1-12}$alkyl, the $C_{1-12}$alkyl of —S(O)$_2$—$C_{1-12}$alkyl, —S(O)$_2$—$NH_2$, $C_{3-10}$cycloalkyl, or 3-15 membered heterocyclyl of $R^m$ is further optionally substituted by one or more OH, halo, cyano, oxo, $C_{1-12}$alkyl, $C_{1-12}$alkoxy, —C(O)$NH_2$, —C(O)NH($C_{1-12}$alkyl), —C(O)N($C_{1-12}$alkyl)$_2$, C(O)OH, $NH_2$, —NH($C_{1-12}$alkyl), —N($C_{1-12}$alkyl)$_2$, $C_{3-10}$cycloalkyl, $C_{6-20}$aryl, 3-15 membered heterocyclyl, or 5-20 membered heteroaryl, or (c) $C_{3-10}$cycloalkenyl, wherein the $C_{3-10}$cycloalkenyl is unsubstituted or is substituted with one or more $R^i$, wherein $R^i$ is oxo, $NH_2$, —NH($C_{1-12}$alkyl), —N($C_{1-12}$alkyl)$_2$, or 3-15 membered heterocyclyl, wherein the 3-15 membered heterocyclyl of $R^i$, the $C_{1-12}$alkyl of the —NH($C_{1-12}$alkyl) of $R^i$, or the $C_{1-12}$alkyl of the —N($C_{1-12}$alkyl)$_2$ of $R^i$ is independently optionally substituted with one or more OH or $C_{1-12}$alkoxy, or (d) 3-15 membered heterocyclyl, wherein the 3-15 membered heterocyclyl is unsubstituted or substituted with one or more OH, oxo, $NH_2$, or $C_{1-12}$alkyl, or (e) amidinyl, wherein the amidinyl is unsubstituted or substituted with with one or more $R^s$, wherein $R^s$ is OH, cyano, $C_{1-12}$alkyl, —C(O)—$C_{1-12}$alkyl, —C(O)—$C_{1-12}$alkoxy, $C_{6-20}$aryloxy, or -$SO_2$—$C_{1-12}$alkyl, or (f) sulfonyl, wherein the sulfonyl is unsubstituted or substituted with one or more $R^u$, wherein $R^u$ is $C_{1-12}$alkyl, $NH_2$, —NH($C_{1-12}$alkyl), —N($C_{1-12}$alkyl)$_2$, or $C_{6-20}$aryl, wherein the $C_{1-12}$alkyl or $C_{6-20}$aryl of $R^u$ is independently further optionally substituted with one or more halo or $C_{1-12}$alkoxy.

17. The method of claim 1, wherein $R^1$ is $C_{3-12}$alkyl or $C_{3-10}$cycloalkyl.

18. The method of claim 1, wherein $R^1$ is sec-butyl, i-propyl, or cyclohexyl.

19. The method of claim 1, wherein $R^1$ is sec-butyl.

20. The method of claim 1, wherein $R^3$ and $R^4$ are each independently H.

21. The method of claim 1, wherein one of $R^3$ and $R^4$ is H, and the other of $R^3$ and $R^4$ is $C_{1-12}$alkyl, C(O)$NH_2$, or C(O)—$C_{1-12}$alkoxy.

22. The method of claim 1, wherein $R^y$ and $R^z$ are each independently H or fluoro.

23. The method of claim 1, wherein the compound is a compound selected from the group consisting of

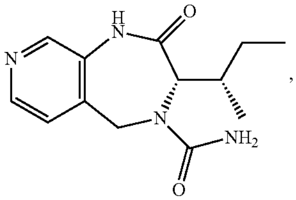
,
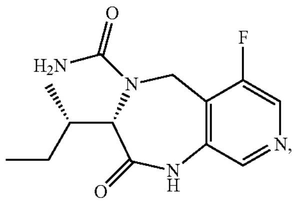
,
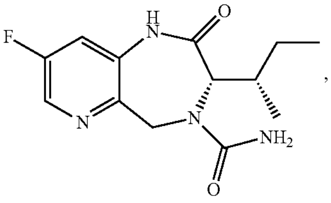
,
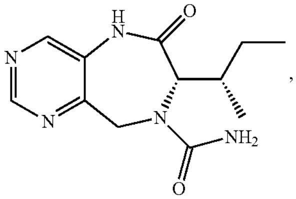
,
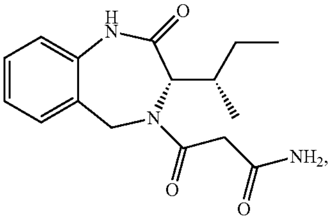
,
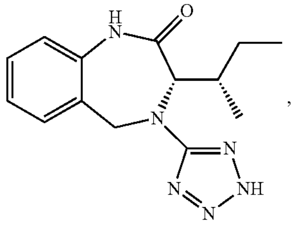
, -continued

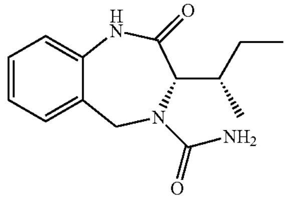

,

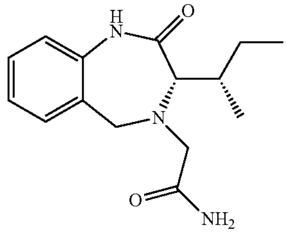

,

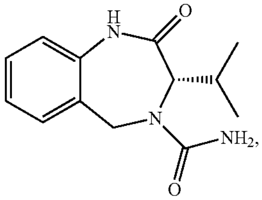

and

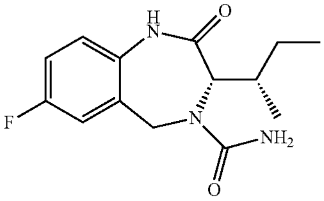

, or a pharmaceutically acceptable salt thereof.

24. The method of claim 1, wherein the compound is Compound 9

Compound 9

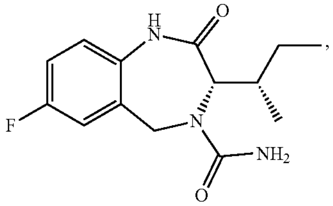

or a pharmaceutically acceptable salt thereof.

25. The method of claim 1, wherein the compound is Compound 10

Compound 10

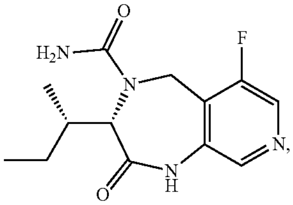

or a pharmaceutically acceptable salt thereof.

26. The method of claim 1, wherein the compound is Compound 12

Compound 12

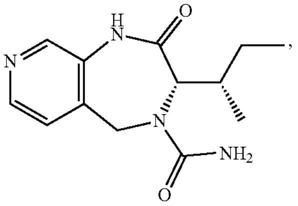

or a pharmaceutically acceptable salt thereof.

27. The method of claim 1, wherein the compound is a compound selected from the group consisting of

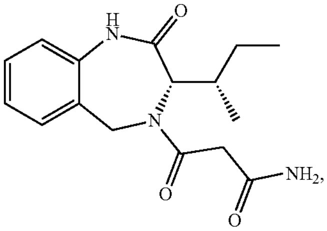

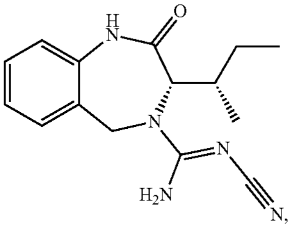

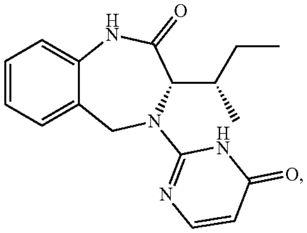

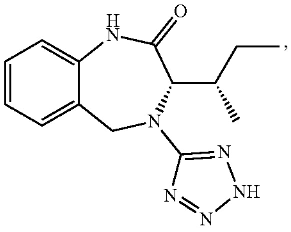

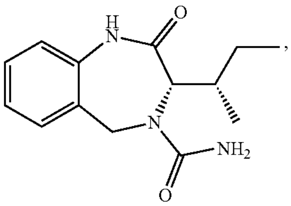

-continued
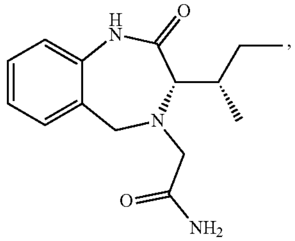
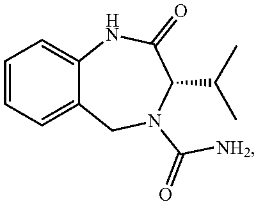
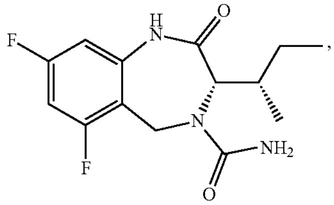
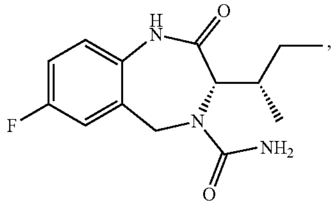
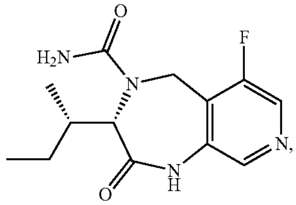
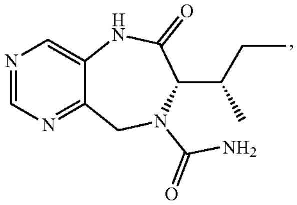
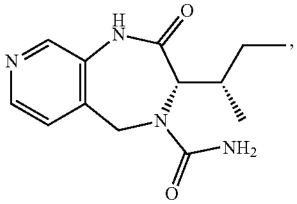
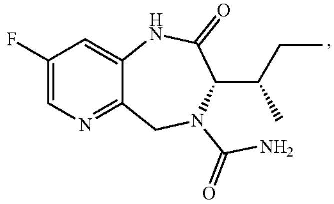
-continued
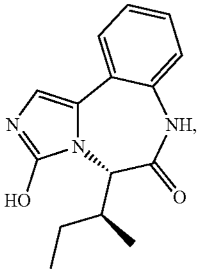
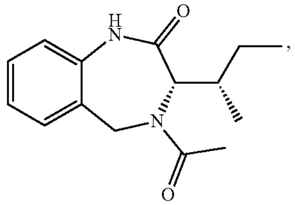
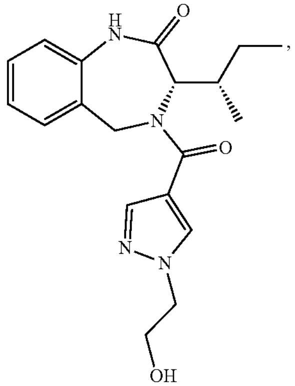
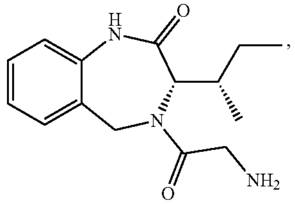
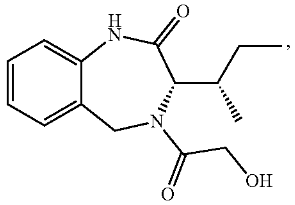
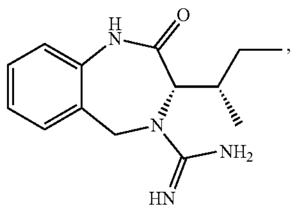
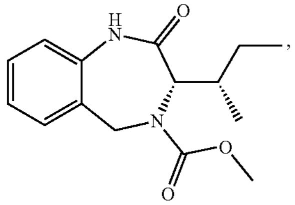

-continued
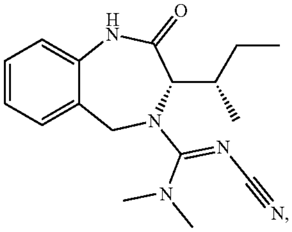 [SMILES: CC[C@H](C)[C@H]1C(=O)Nc2ccccc2CN1/C(=N/C#N)N(C)C]
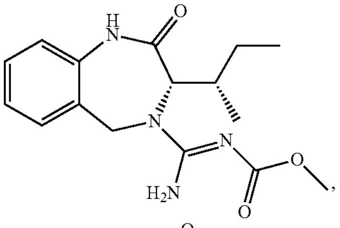
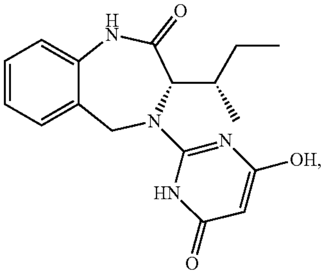
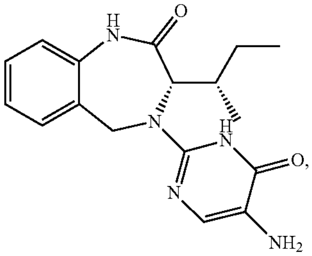
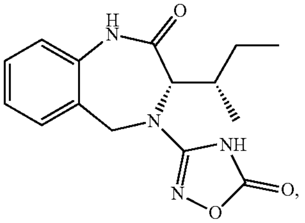
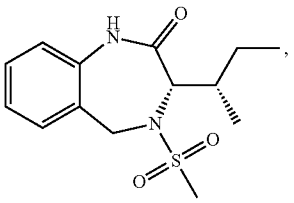
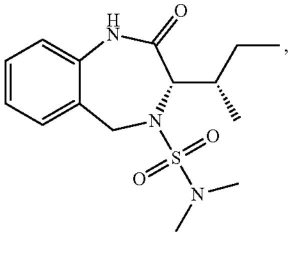
-continued
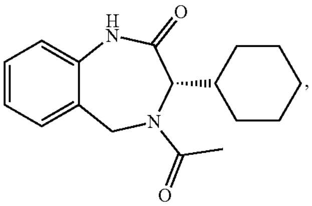
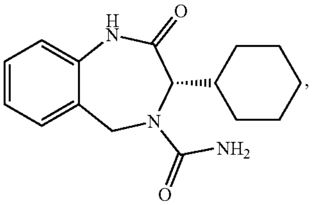
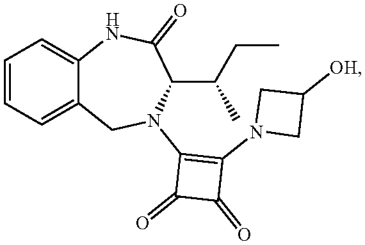
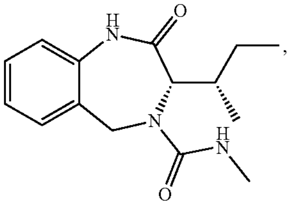
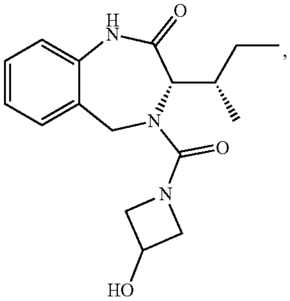
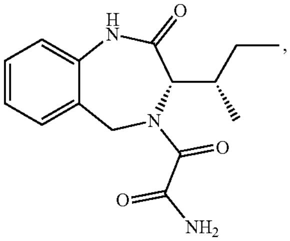
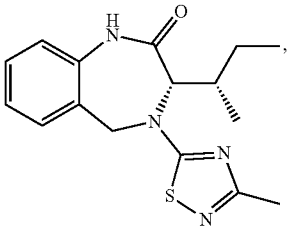

-continued
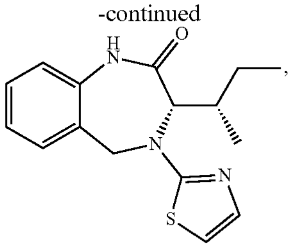
,
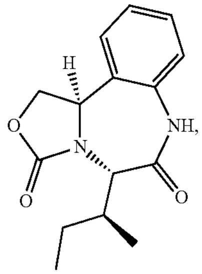
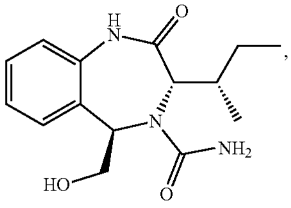
,
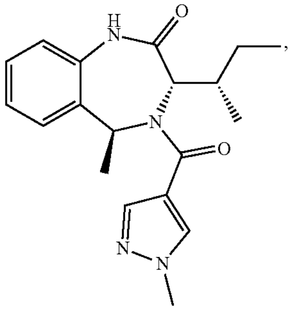
,
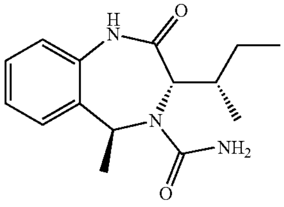
,
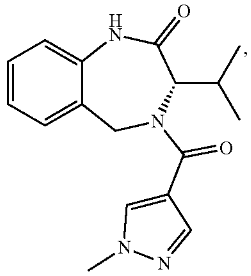
,
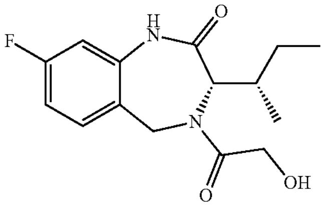
,
-continued
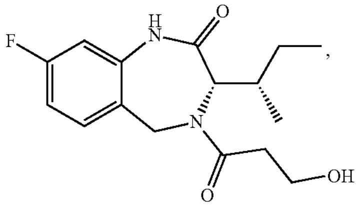
,
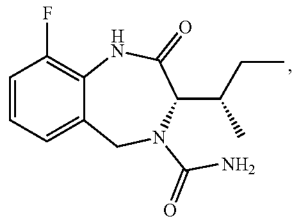
,
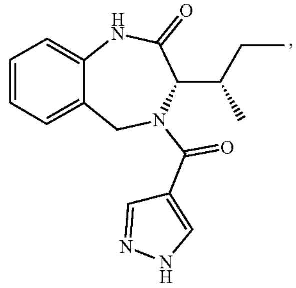
,
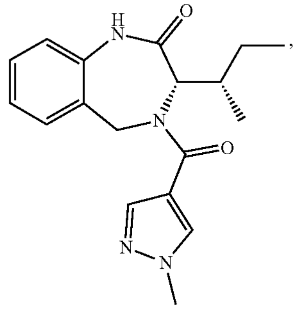
,
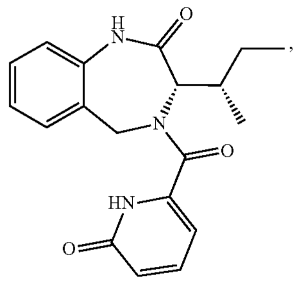
,
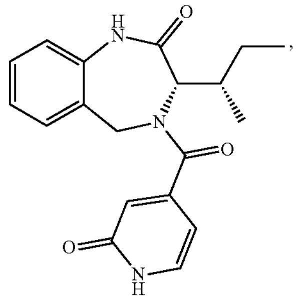
, -continued
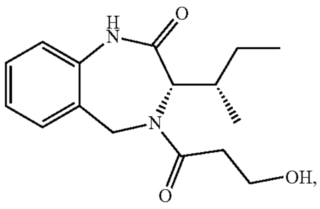
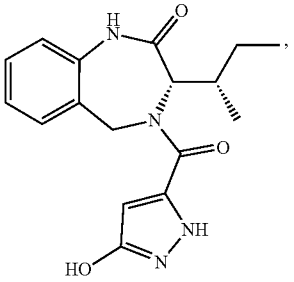
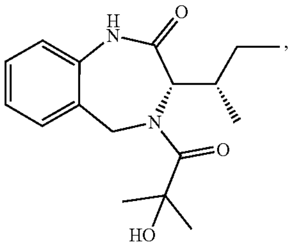
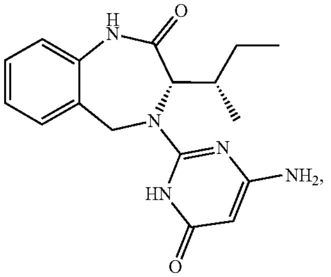
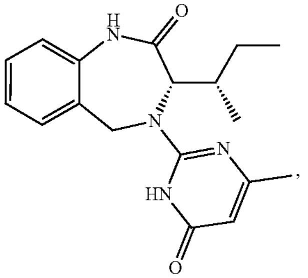
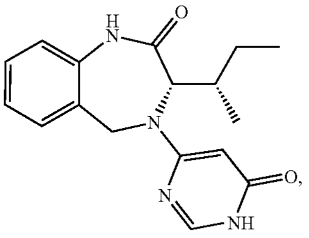
-continued
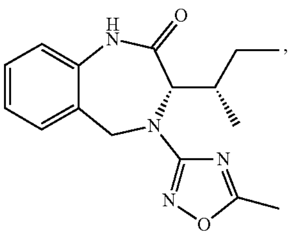
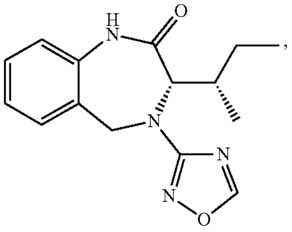
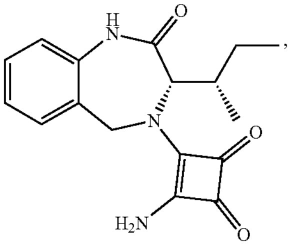
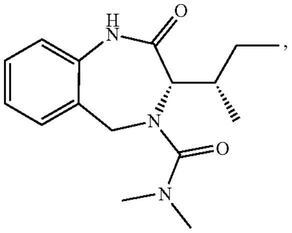
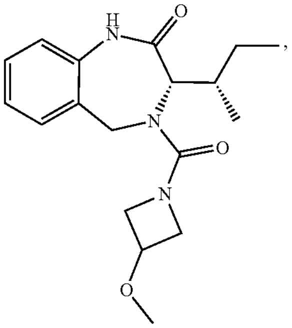
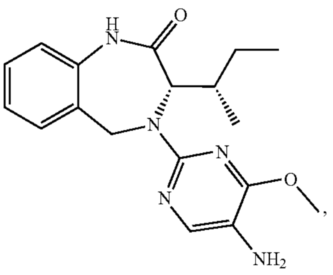

-continued
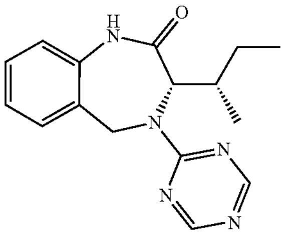,
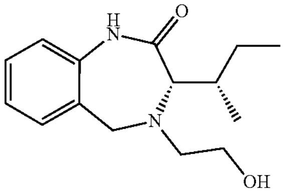,
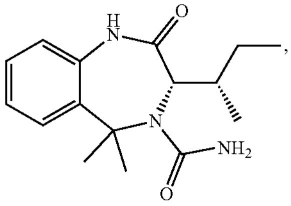,
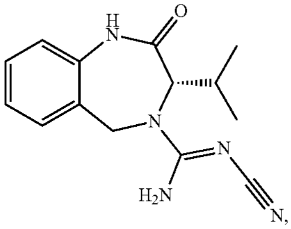,
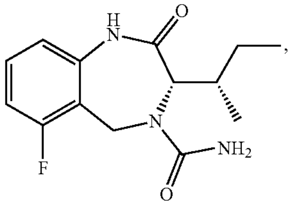,
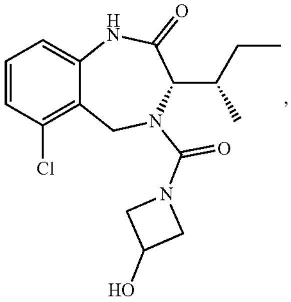,
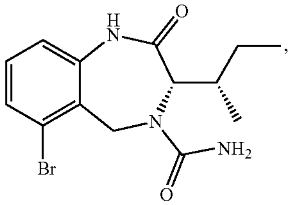,
-continued
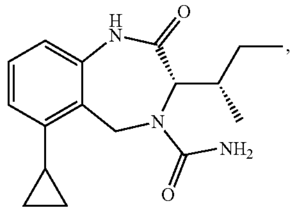,
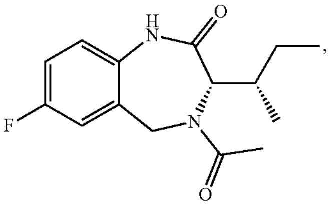,
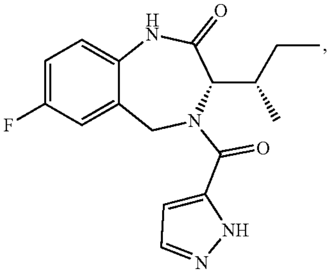,
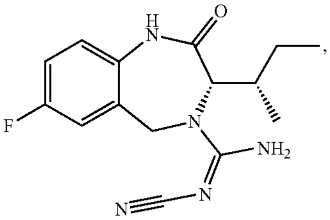,
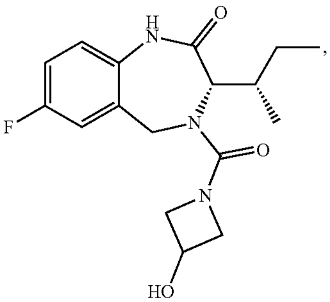,
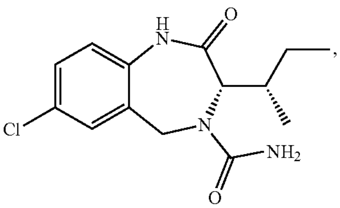,
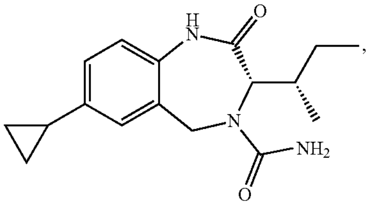, -continued
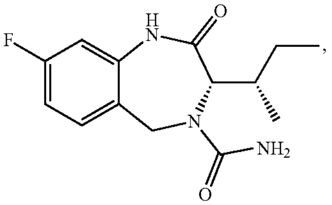
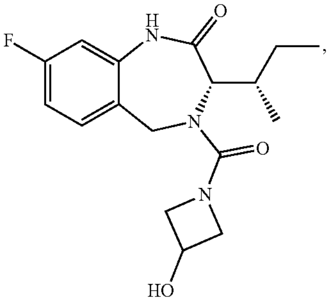
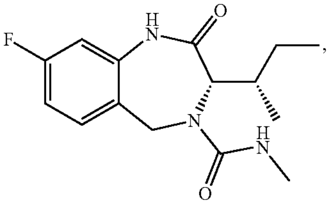
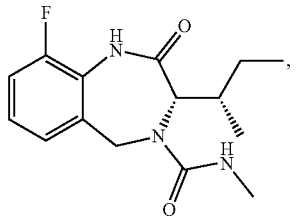
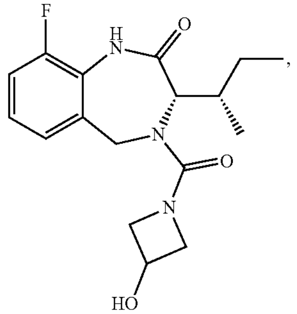
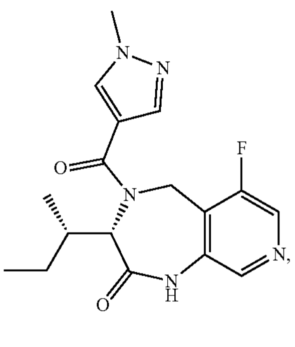
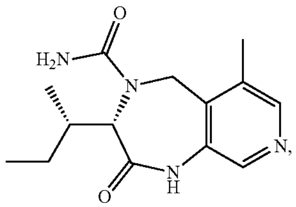
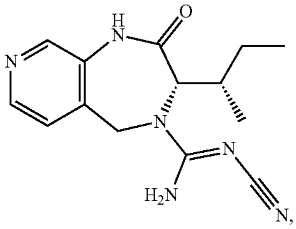
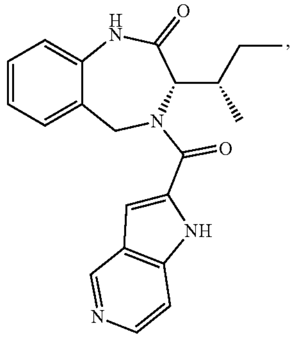
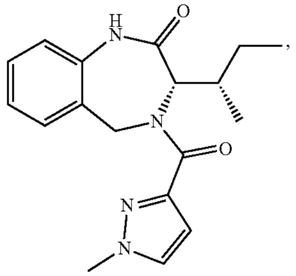
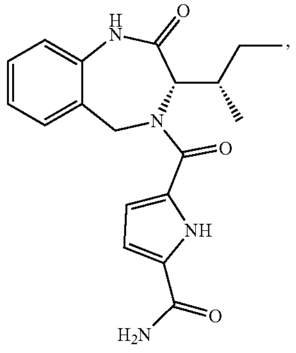
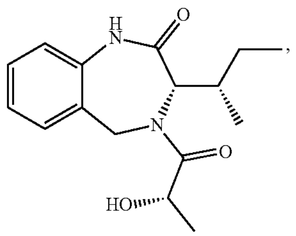

-continued
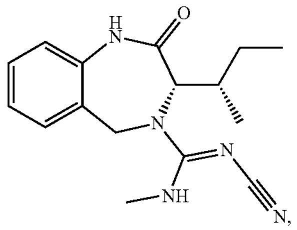
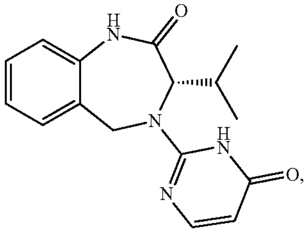
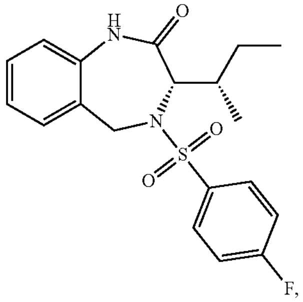
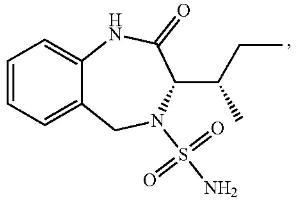
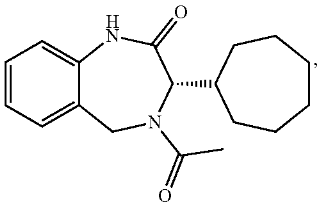
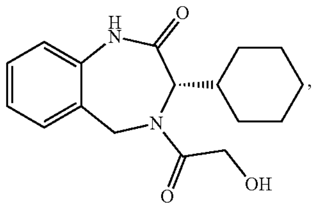
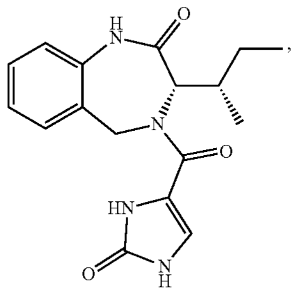
-continued
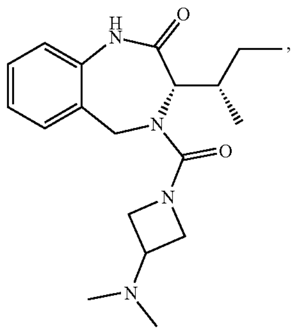
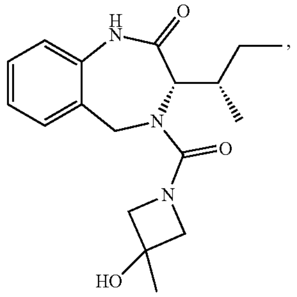
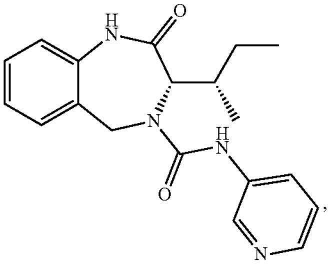
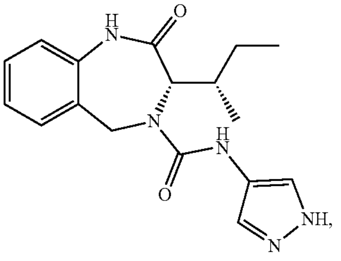
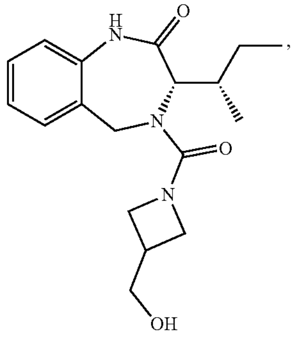 [SMILES: CC[C@H](C)[C@H]1C(=O)Nc2ccccc2CN1C(=O)N1CC(CO)C1]

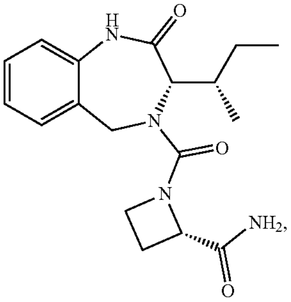
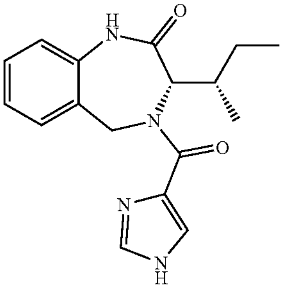
,
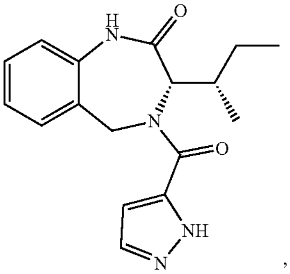
,
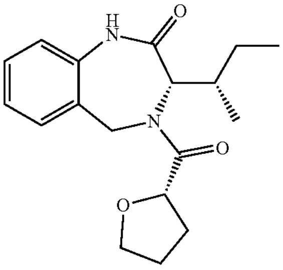
,
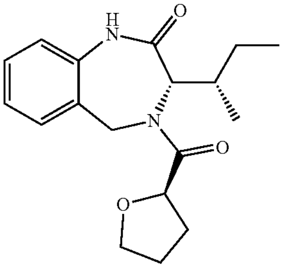
,
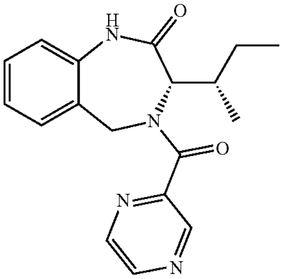
,
-continued
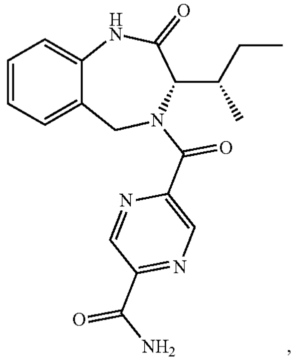
,
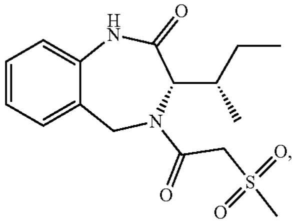
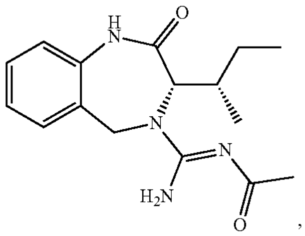
,
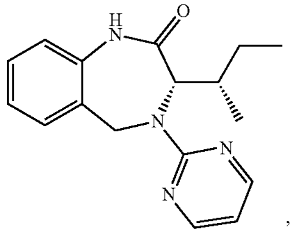
,
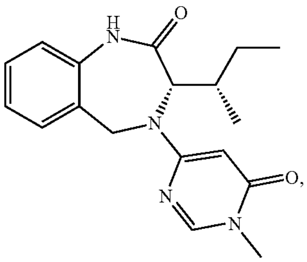
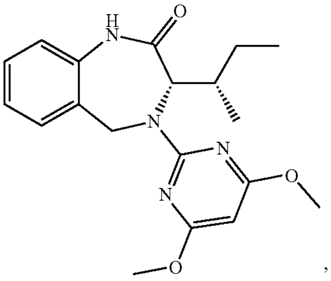
, -continued
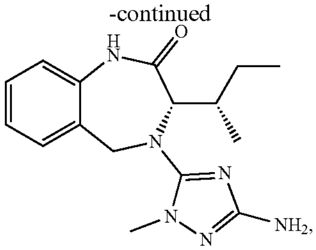
,
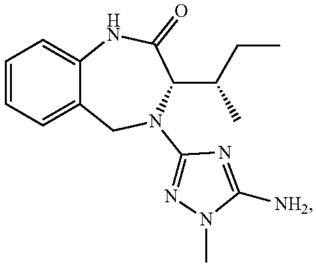
,
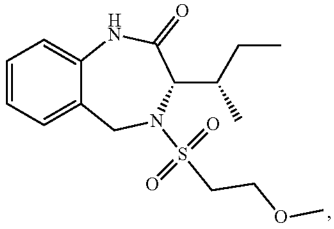
,
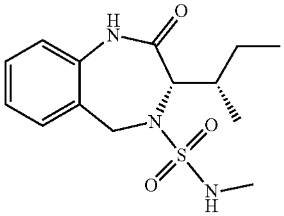
,
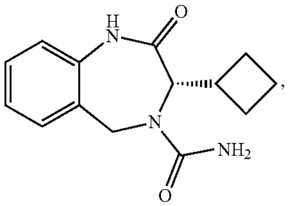
,
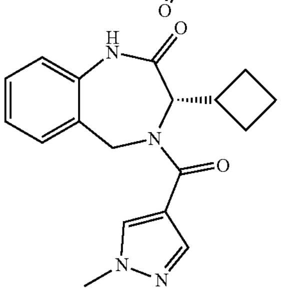
,
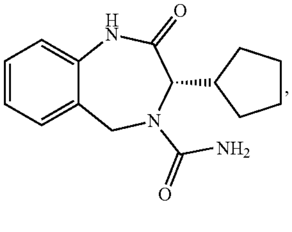
,
-continued
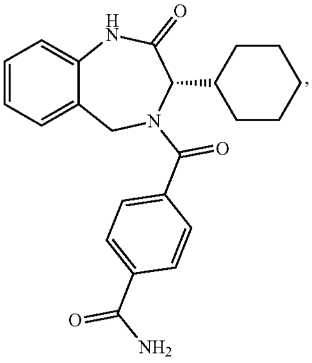
,
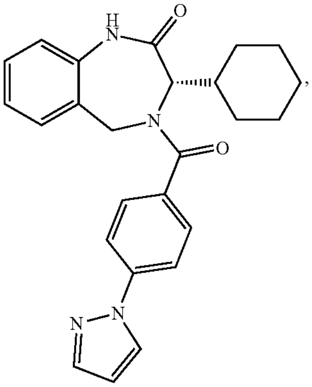
,
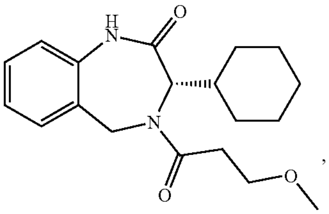
,
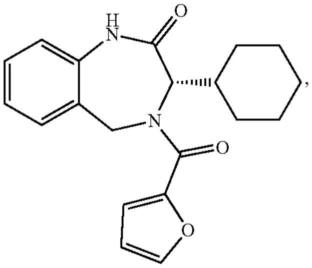
,
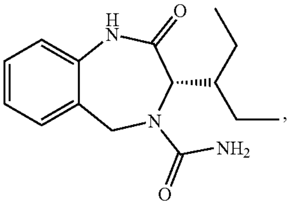
,
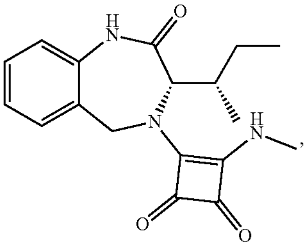
, -continued
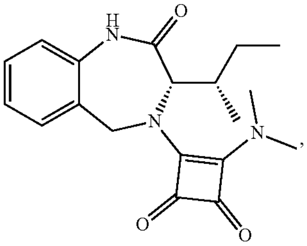
,
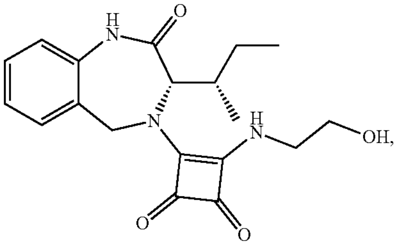
,
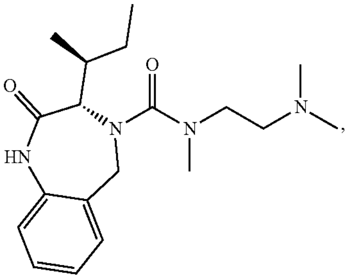
,
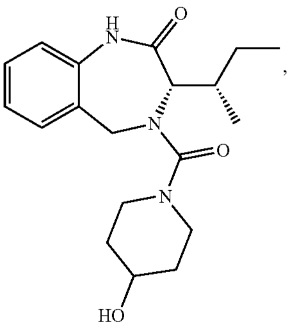
,
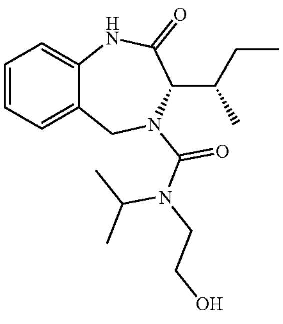
,
-continued
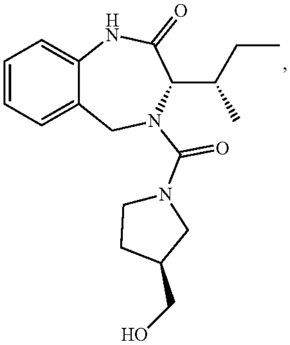
,
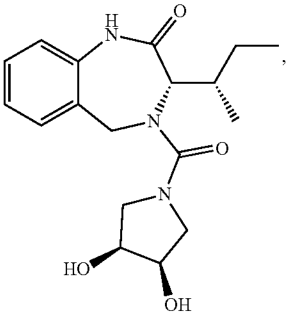
,
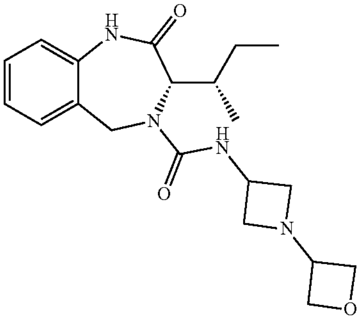
,
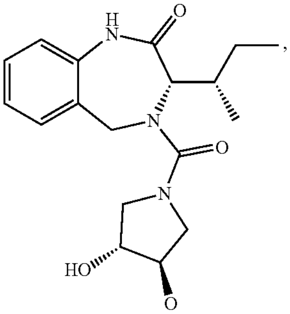
,
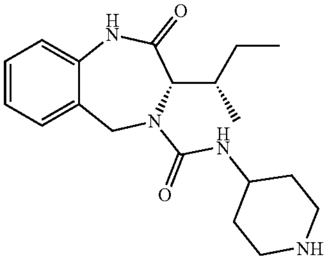
, -continued
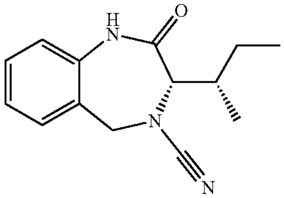
,
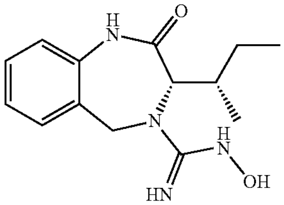
,
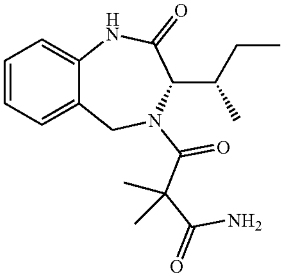
,
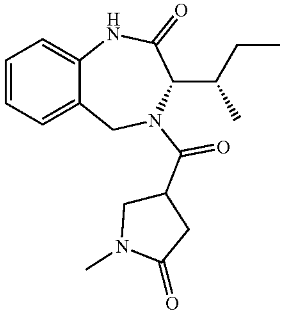
,
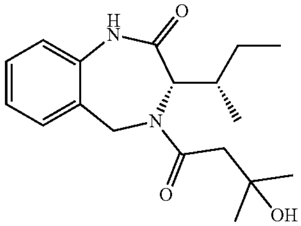
,
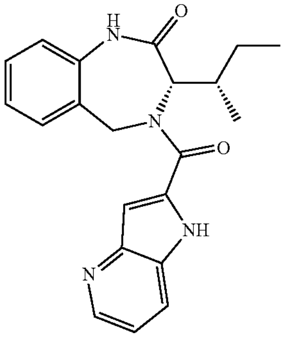
,
-continued
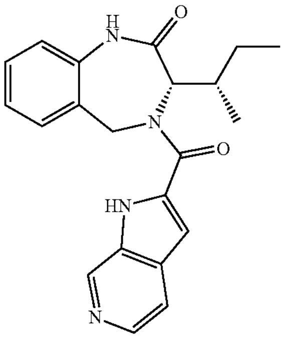
,
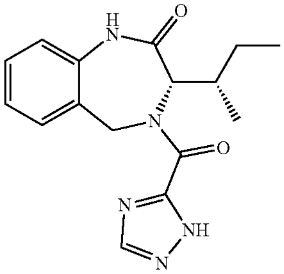
,
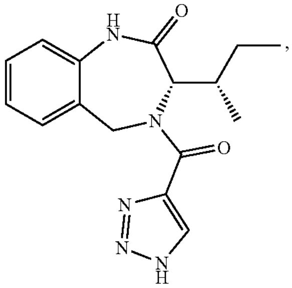
,
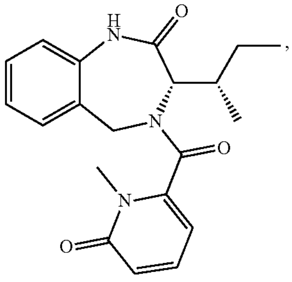
,
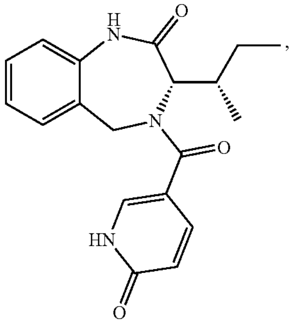
, -continued
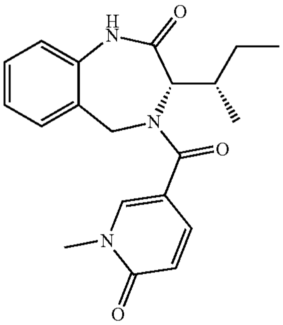,
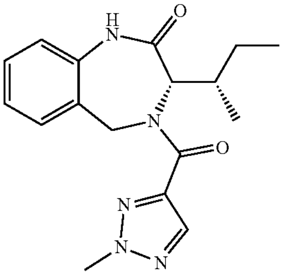,
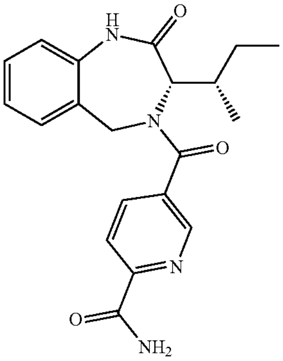,
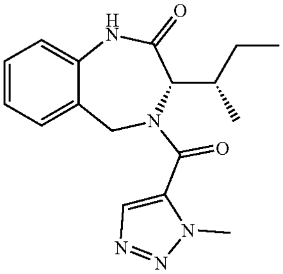,
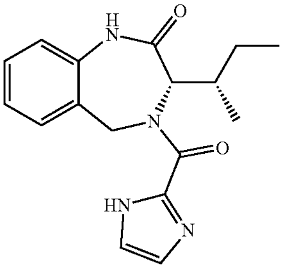,
-continued
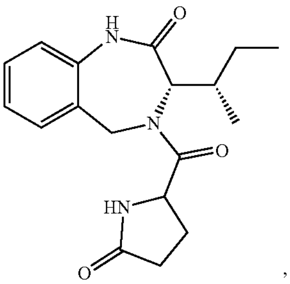,
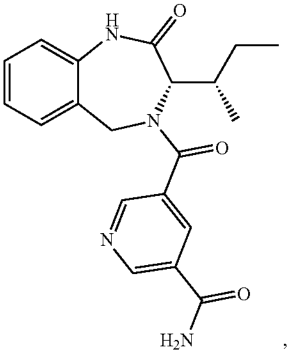,
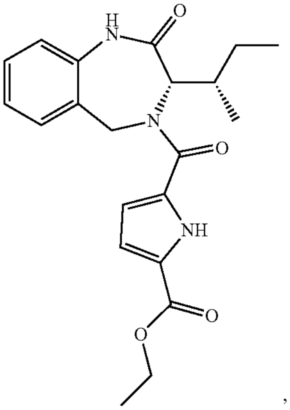,
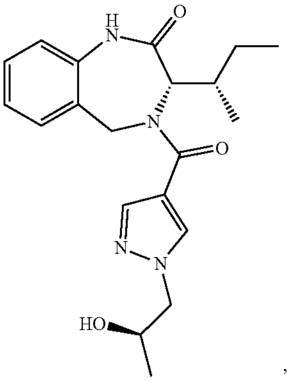, -continued
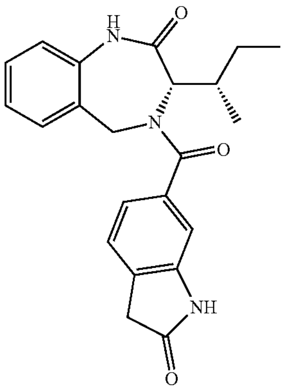
,
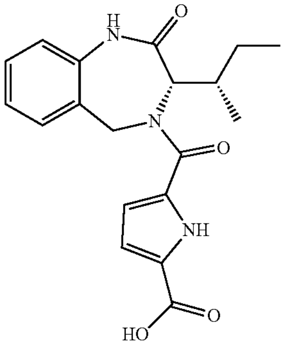
,
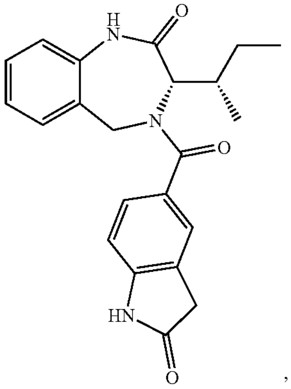
,
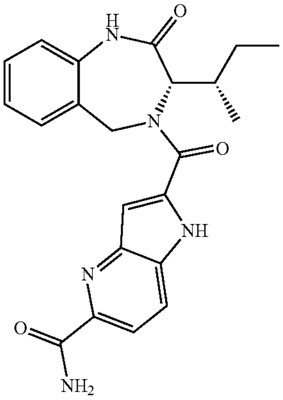
,
-continued
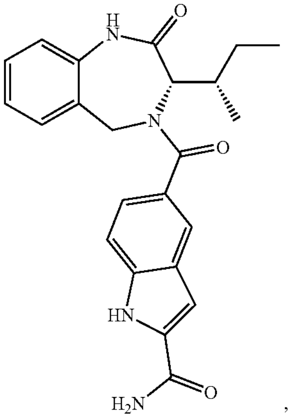
,
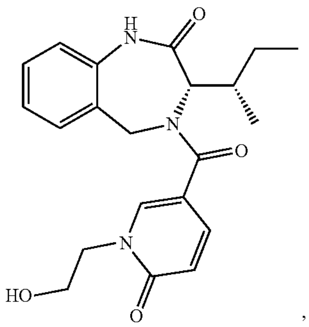
,
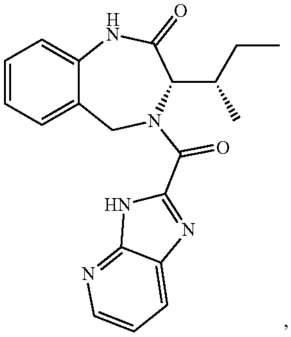
,
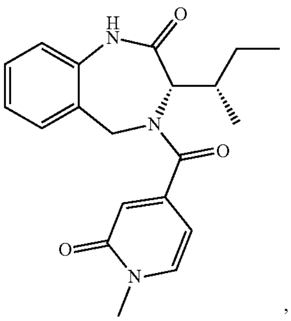
,

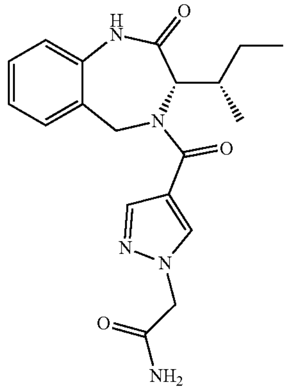
,
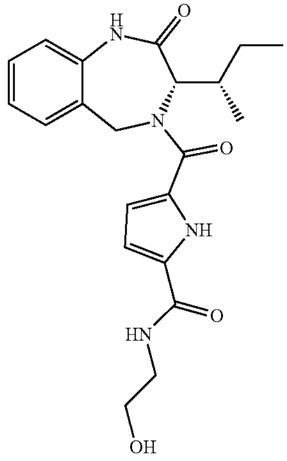
,
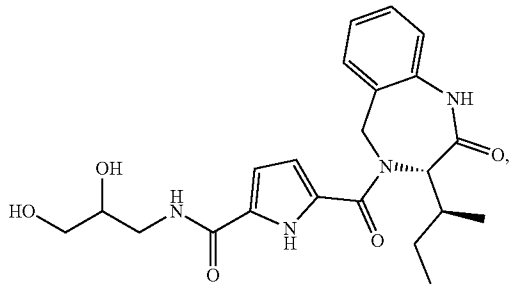
,
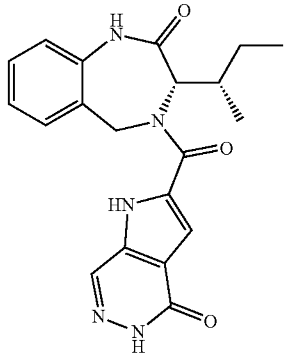
,
-continued
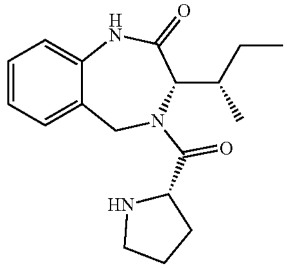
,
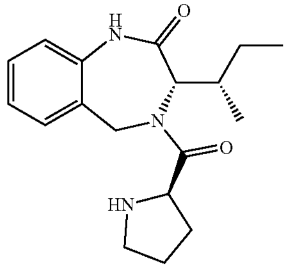
,
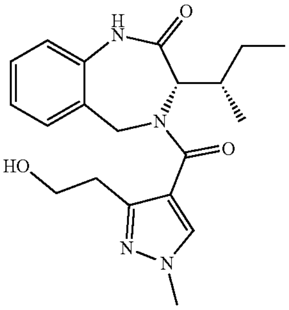
,
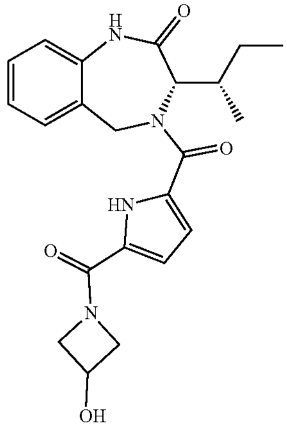
,
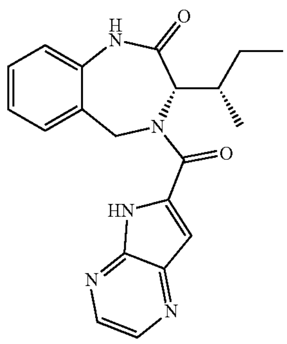
, -continued
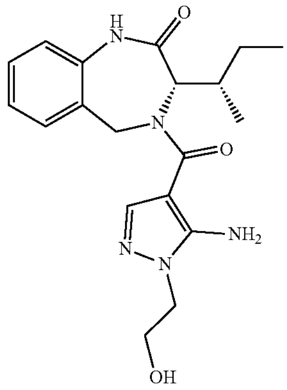
,
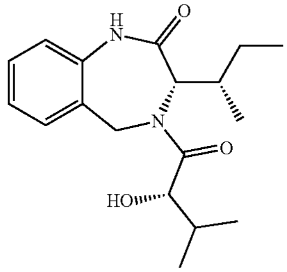
,
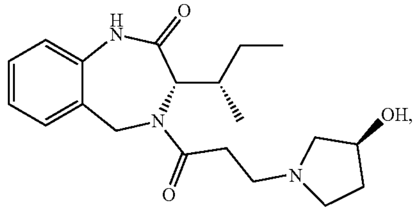
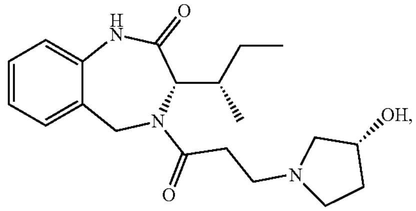
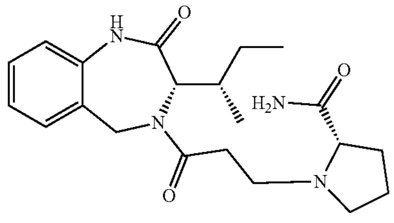
,
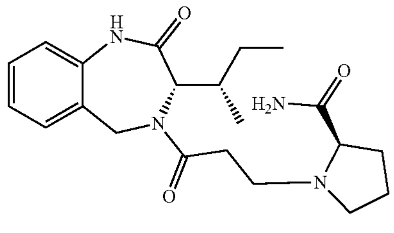
,
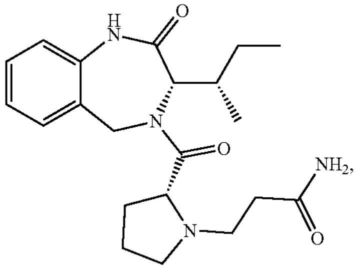
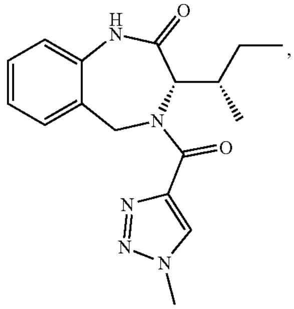
,
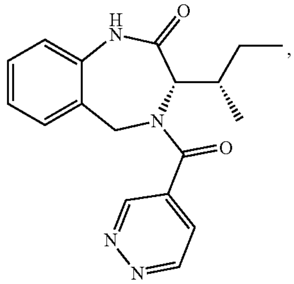
,
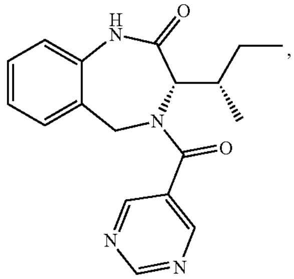
,
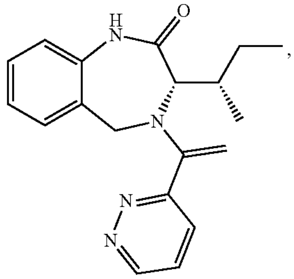
,
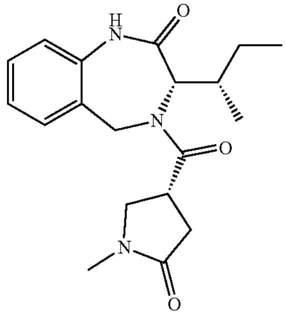

-continued
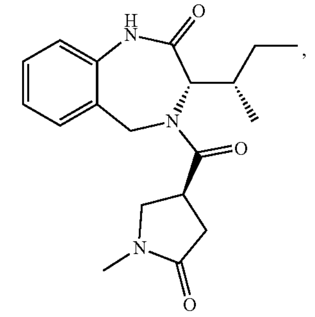
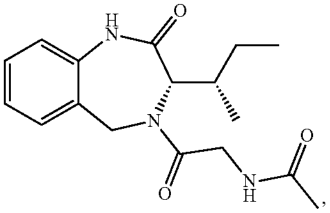
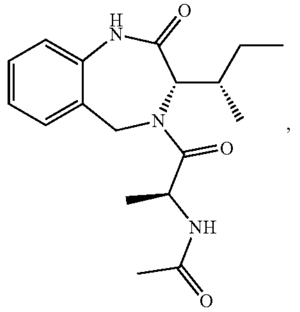
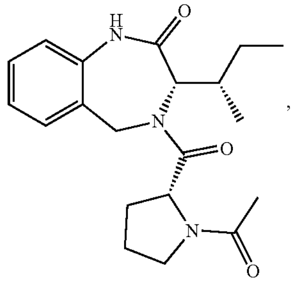
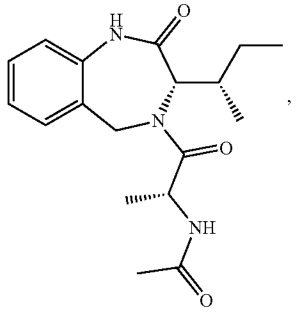
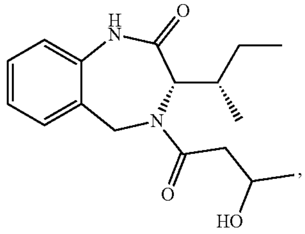
-continued
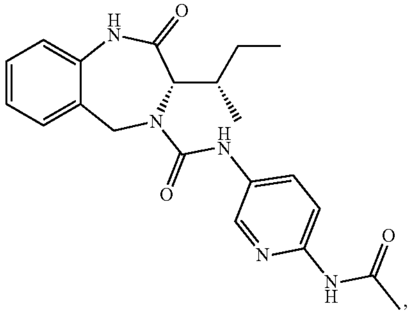
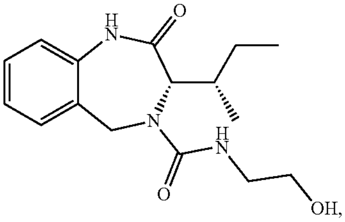
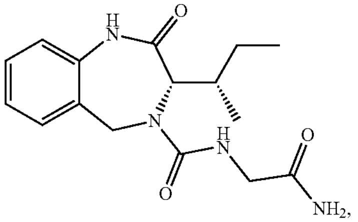
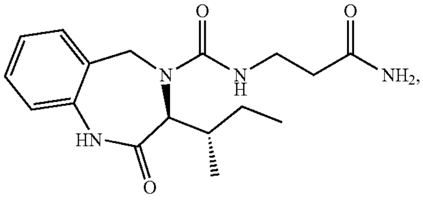
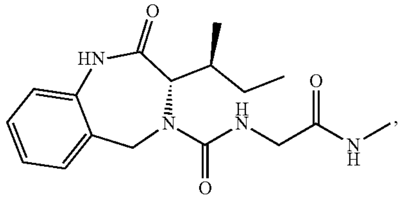
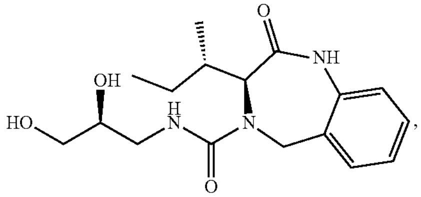
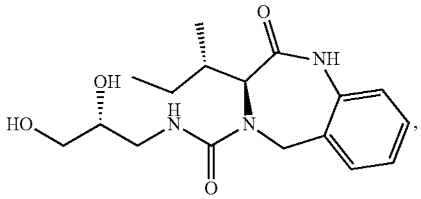

-continued
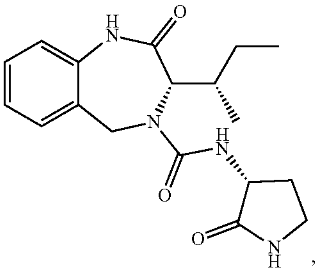
,
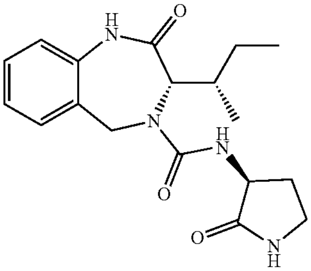
,
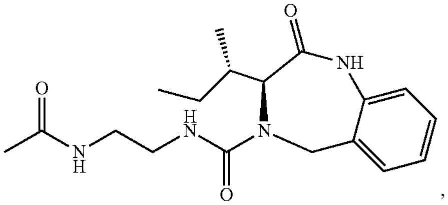
,
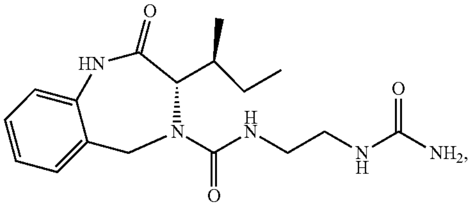
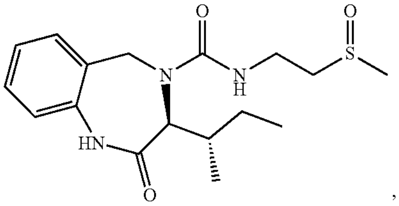
,
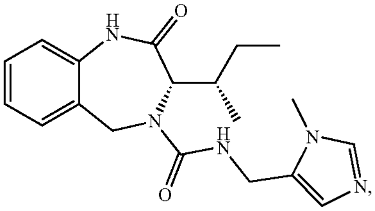
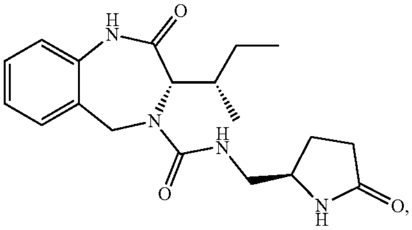
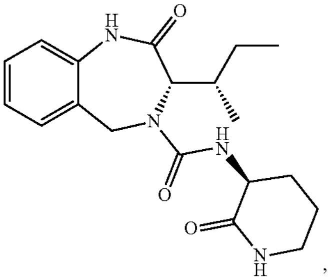
,
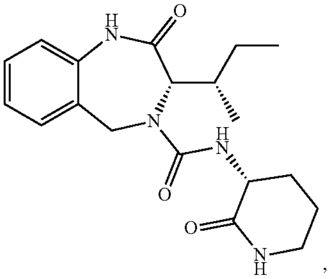
,
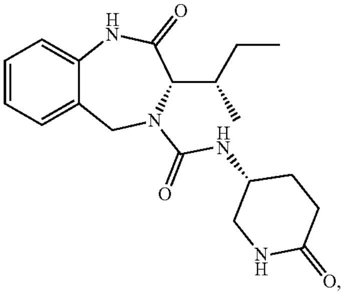
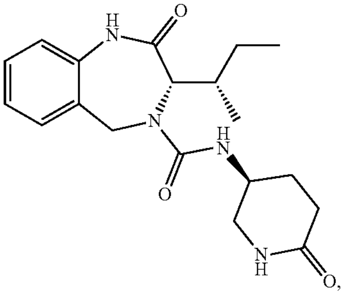
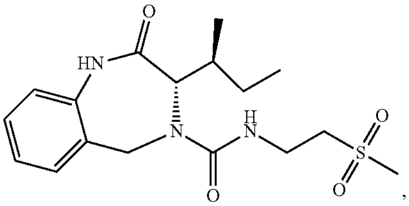
,
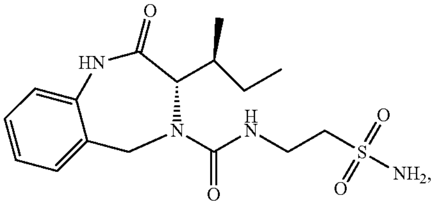

-continued
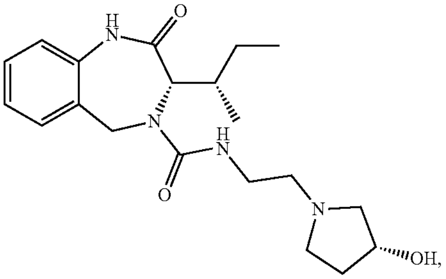
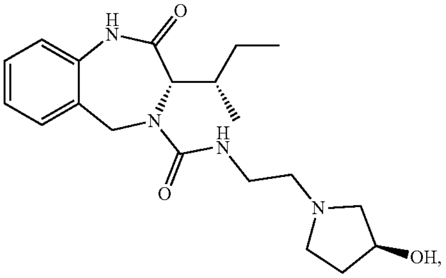
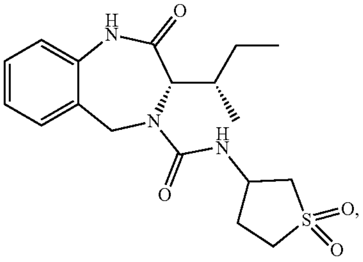
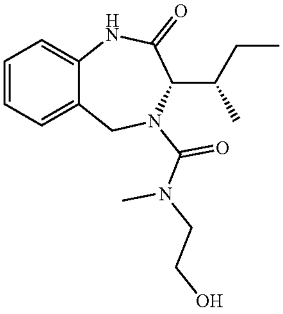
,
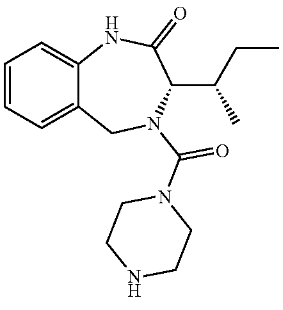
,
-continued
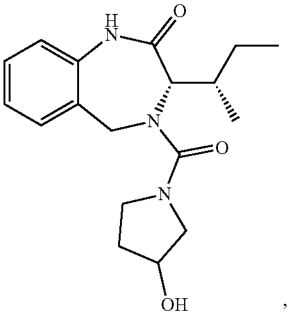
,
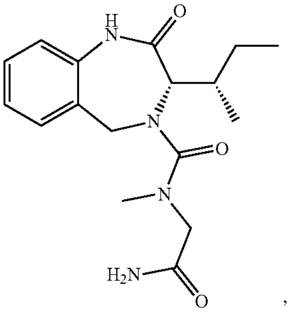
,
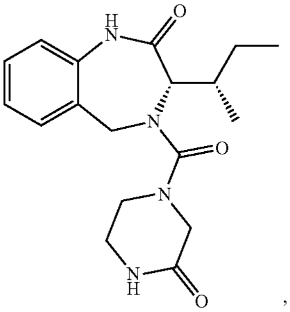
,
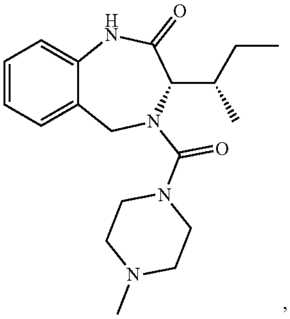
,
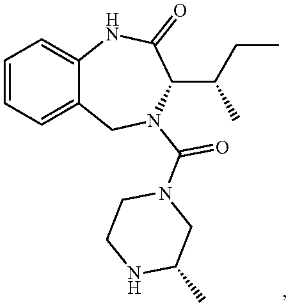
, -continued
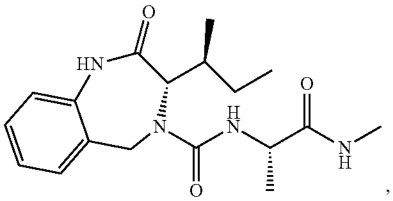
,
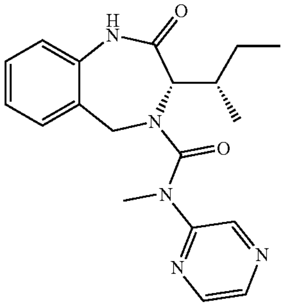
,
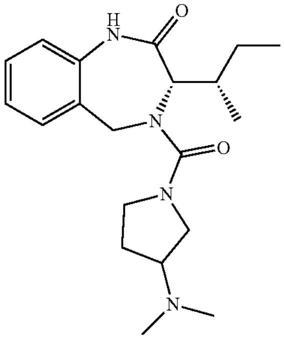
,
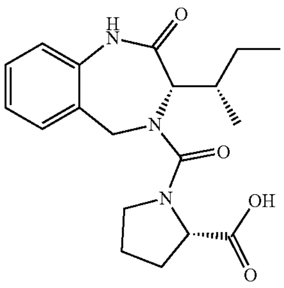
,
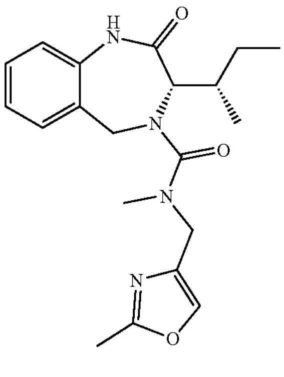
,
-continued
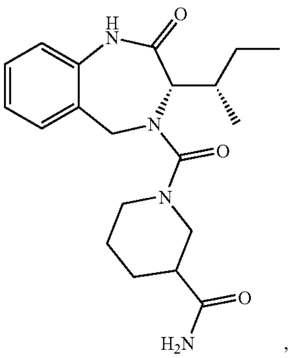
,
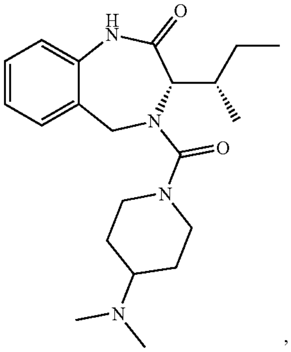
,
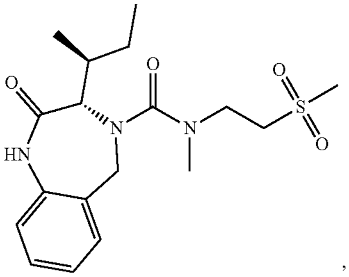
,
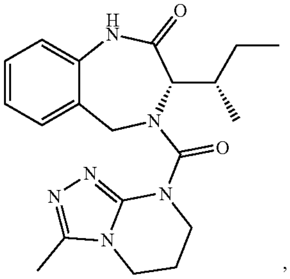
,
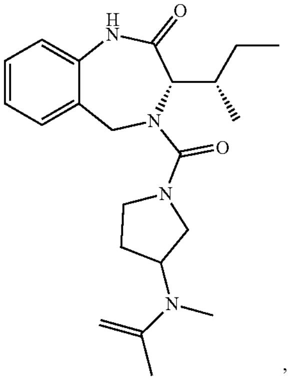
, -continued
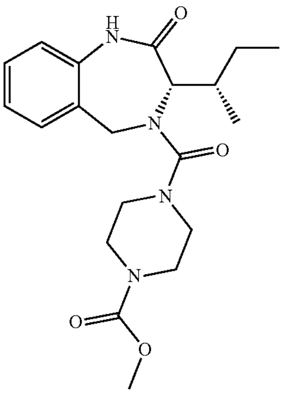
,
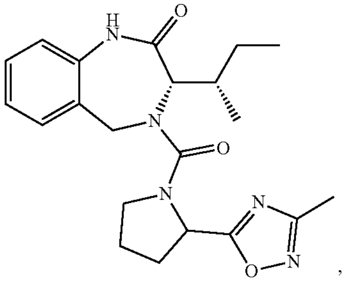
,
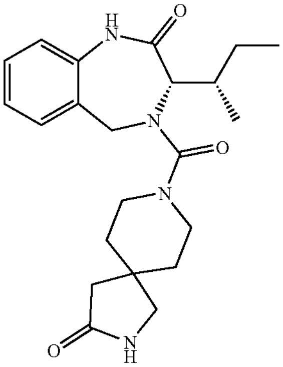
,
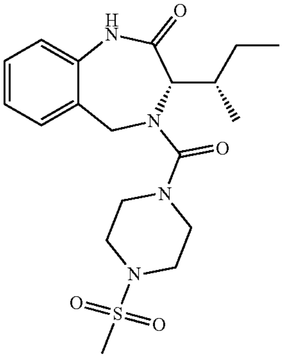
,
-continued
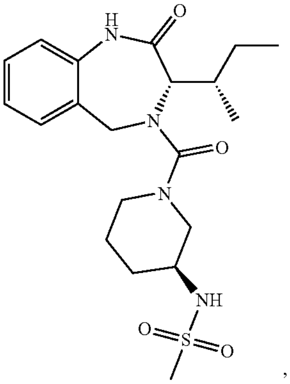
,
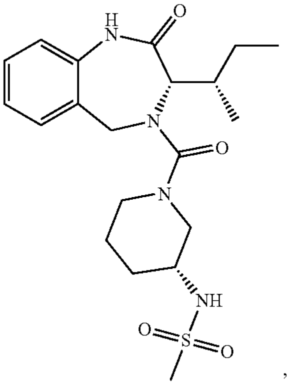
,
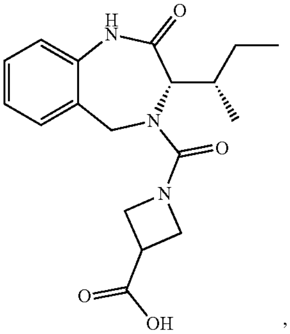
,
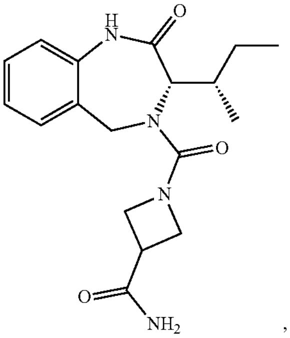
,
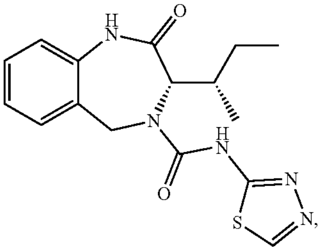

-continued
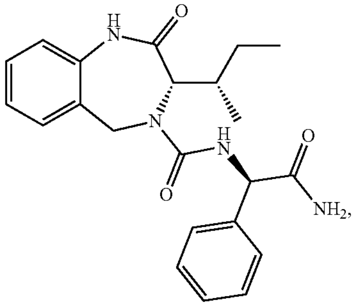
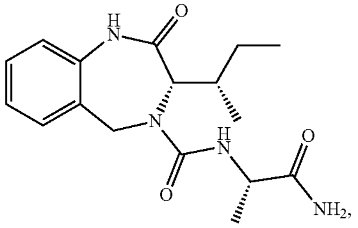
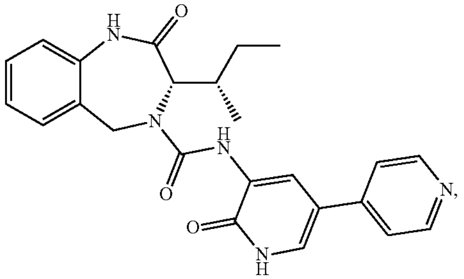
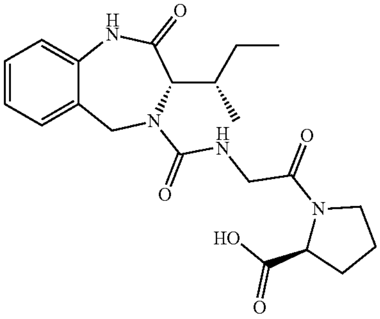
,
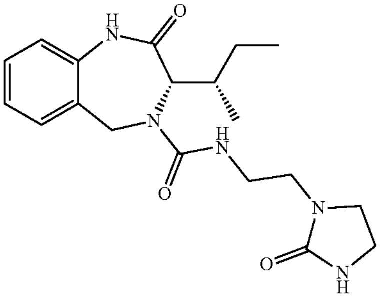
,
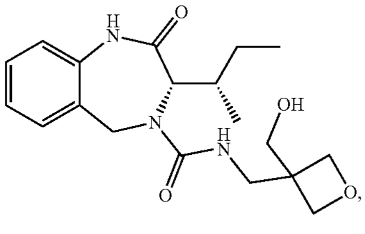
-continued
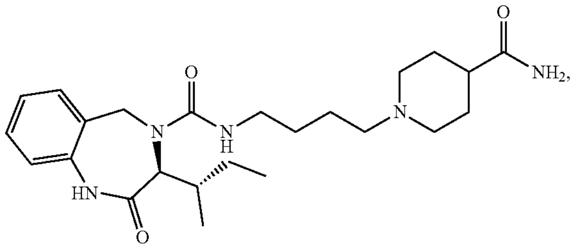
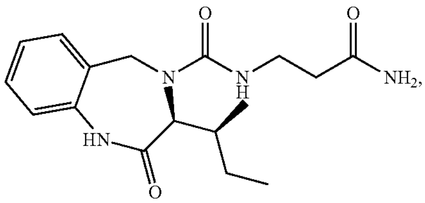
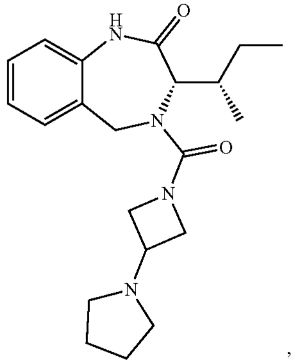
,
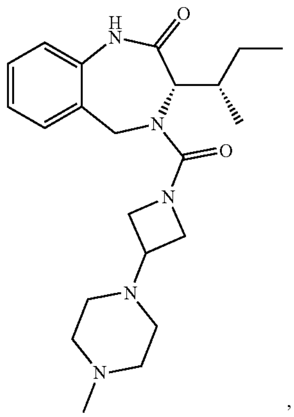
,
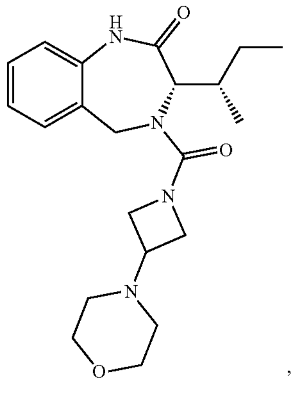
, -continued
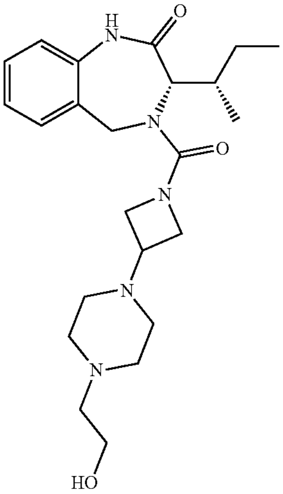
,
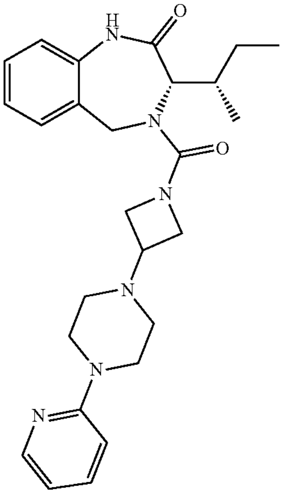
,
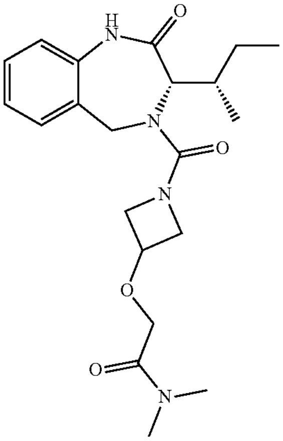
,
-continued
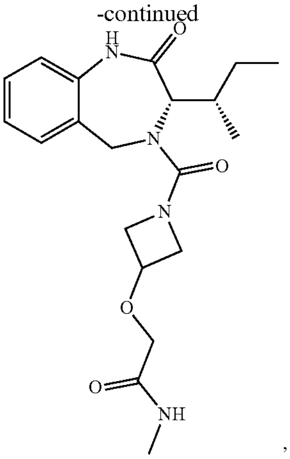
,
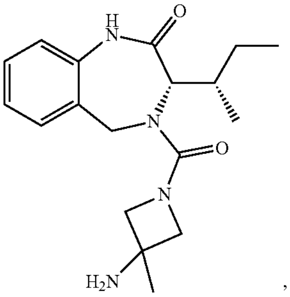
,
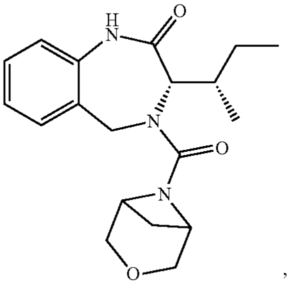
,
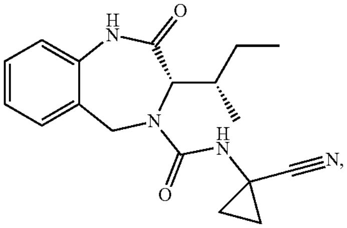
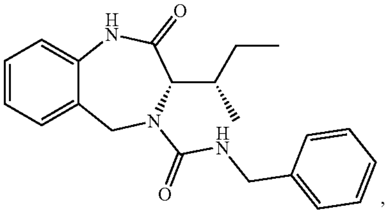
,
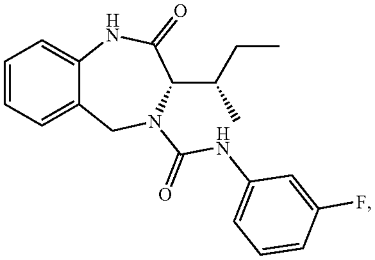

-continued
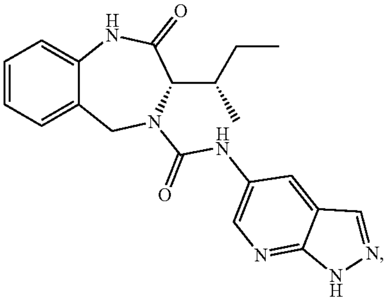
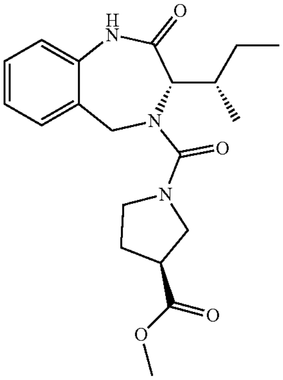
,
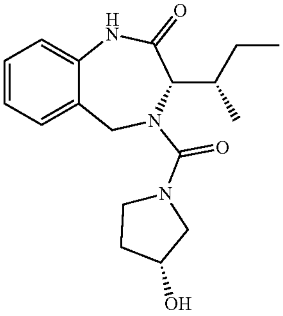
,
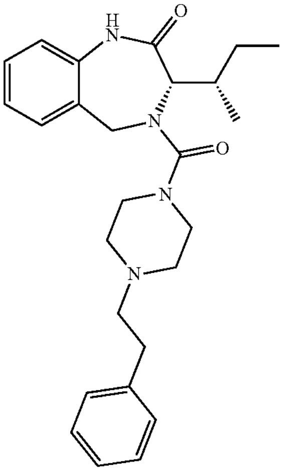
,
-continued
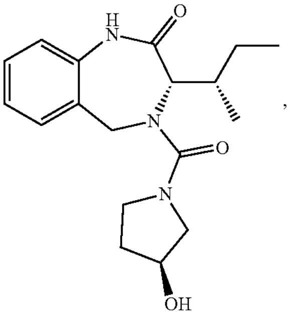
,
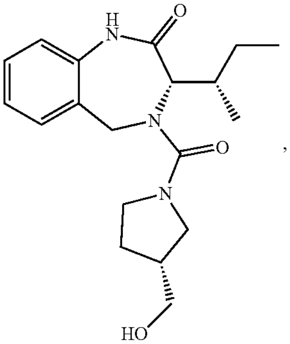
,
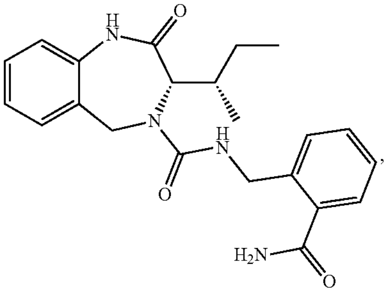
,
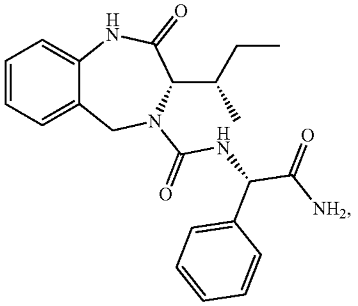
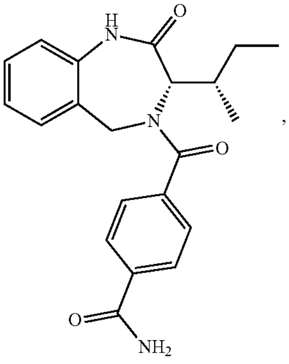
, -continued
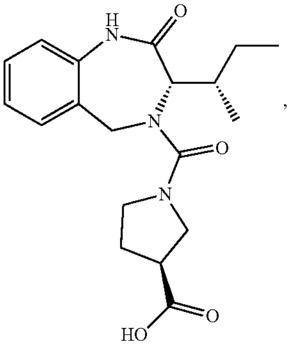
,
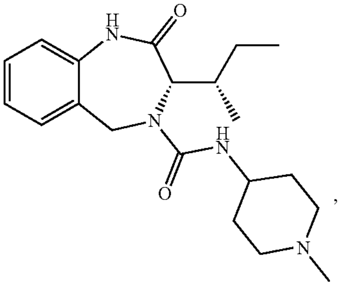
,
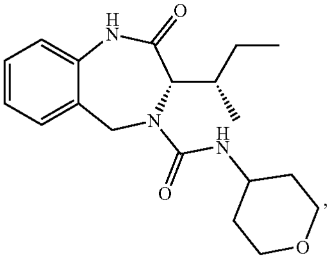
,
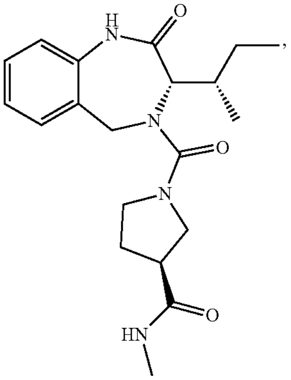
,
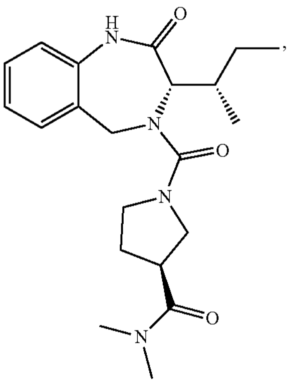
,
-continued
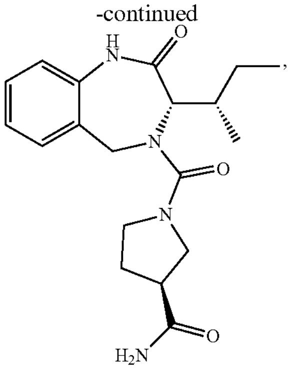
,
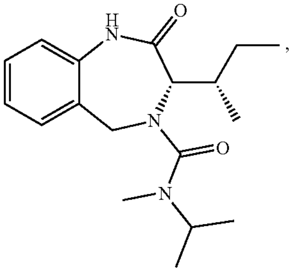
,
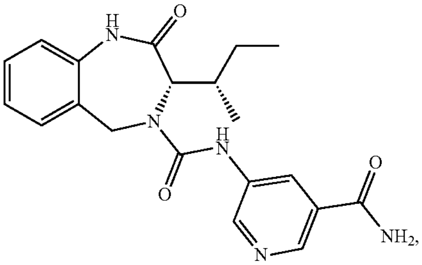
,
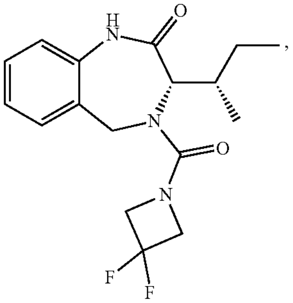
,
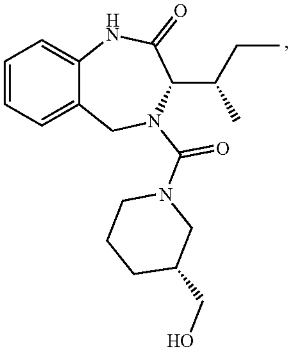
, -continued
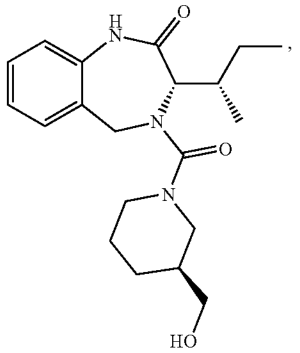
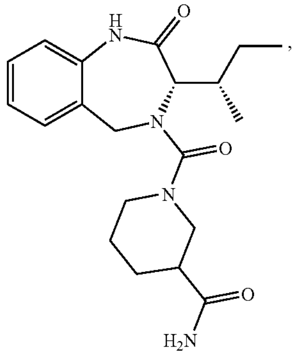
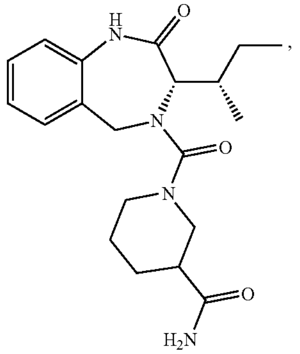
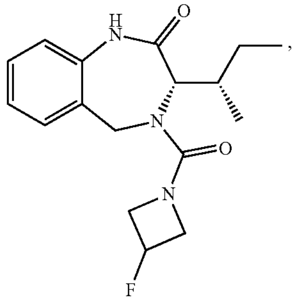
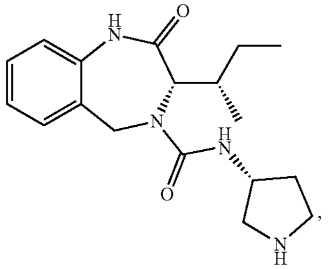
-continued
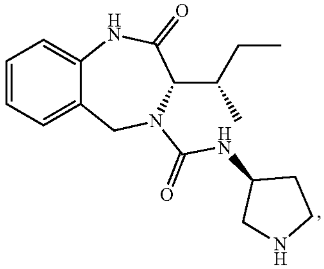
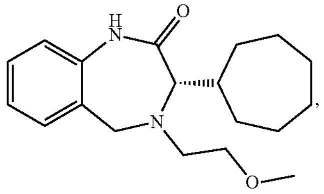
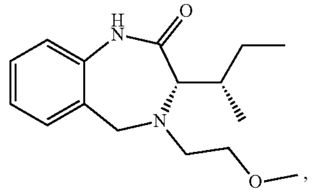
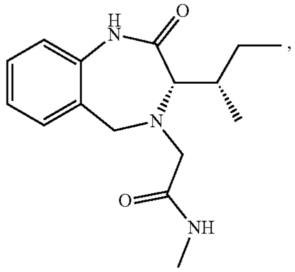
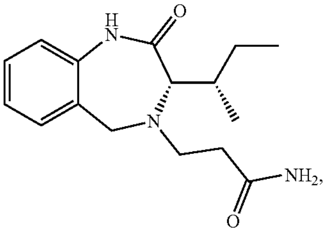
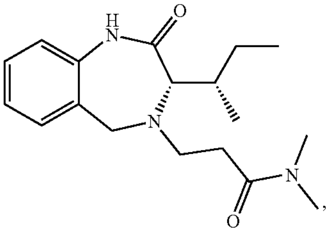
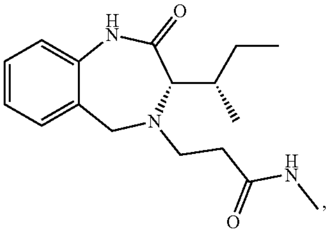

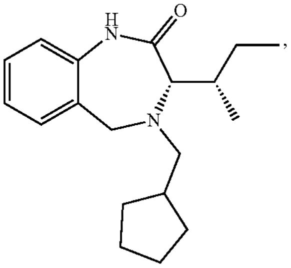
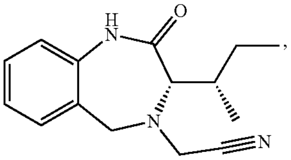
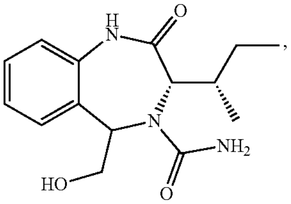
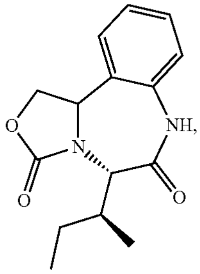
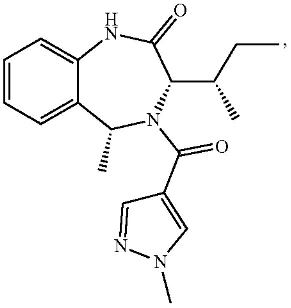
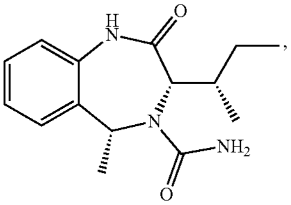
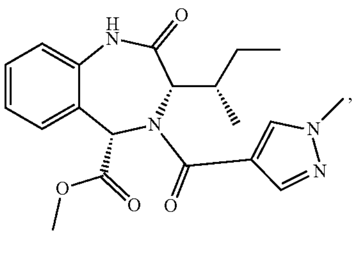
-continued
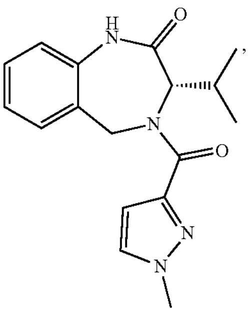
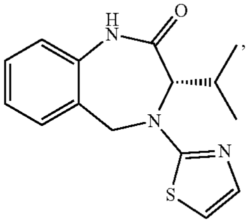
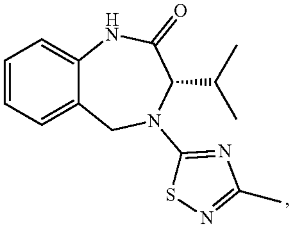
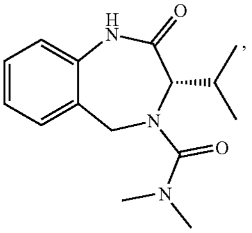
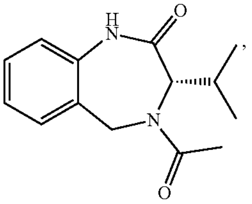
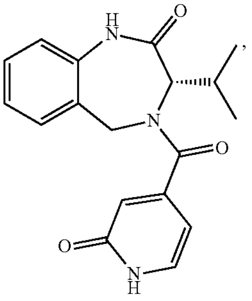

-continued
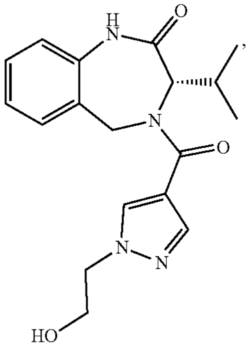
,
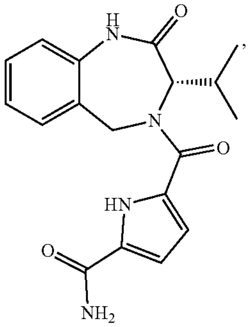
,
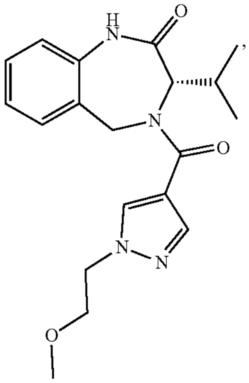
,
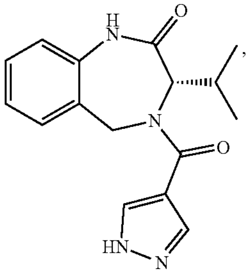
,
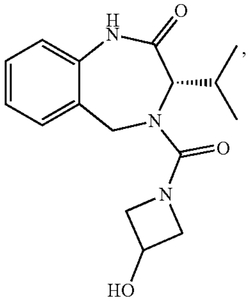
,
-continued
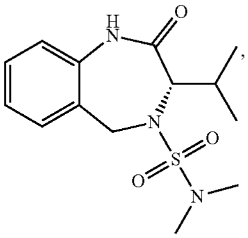
,
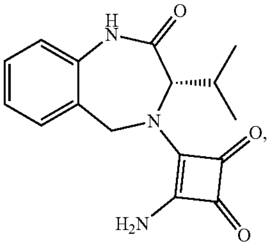
,
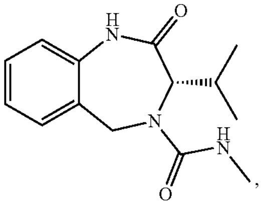
,
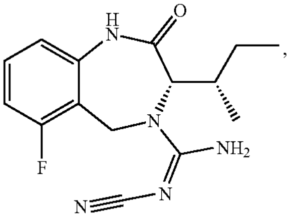
,
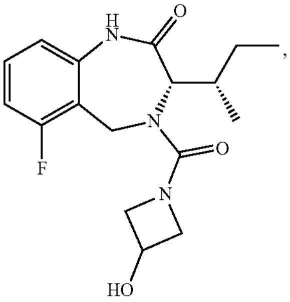
,
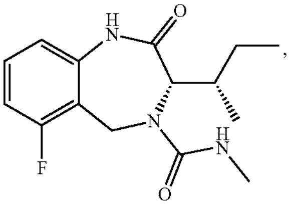
,
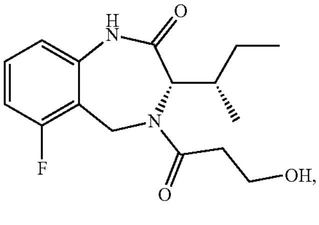
, -continued
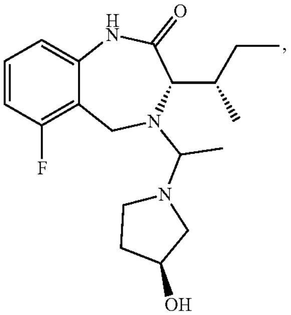
,
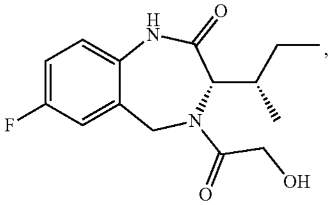
,
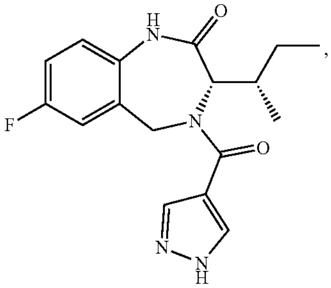
,
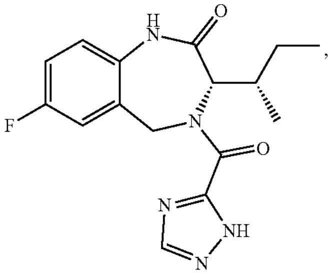
,
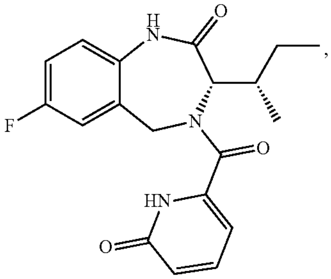
,
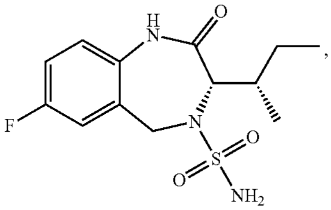
,
-continued
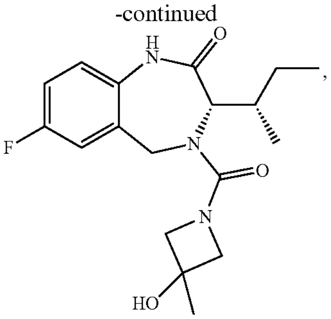
,
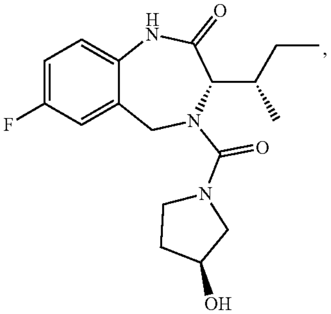
,
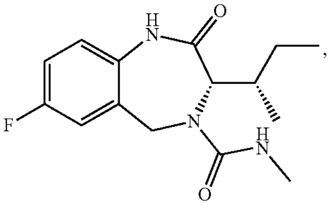
,
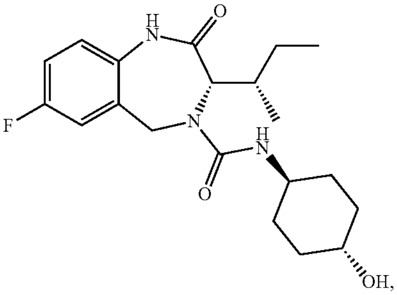
,
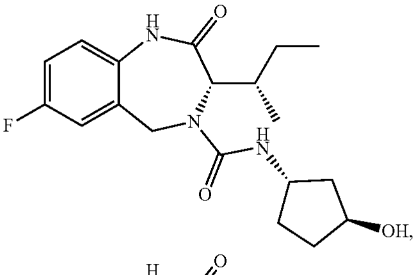
,
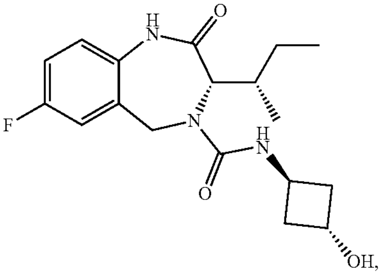
, -continued
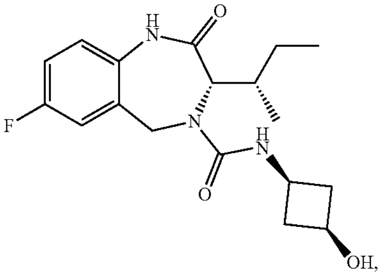
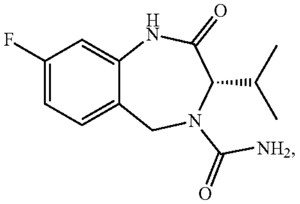
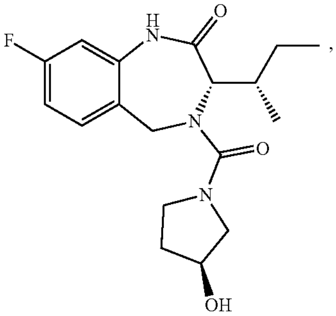
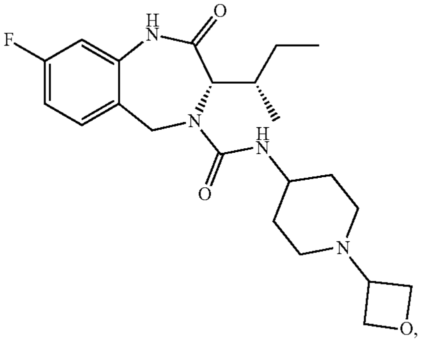
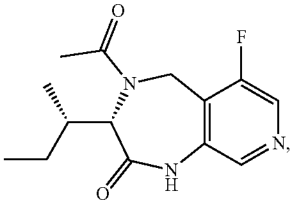
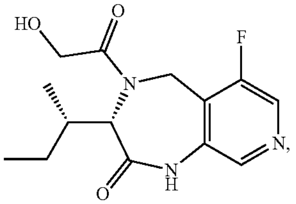
-continued
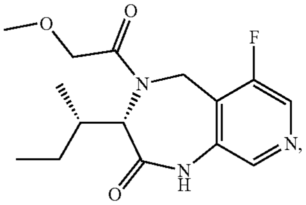
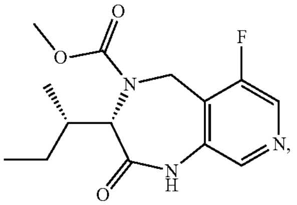
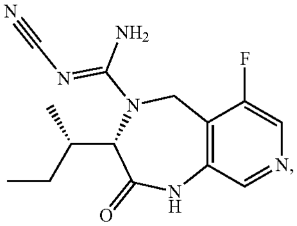
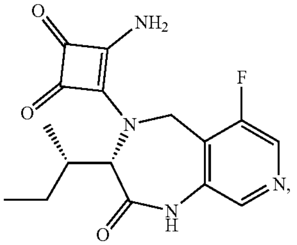
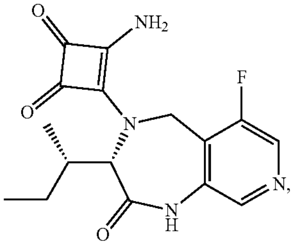
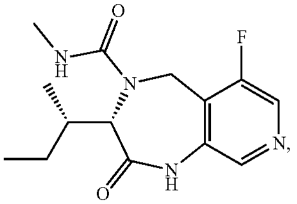
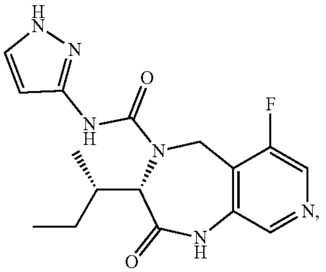

-continued
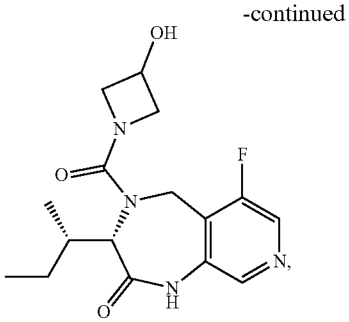
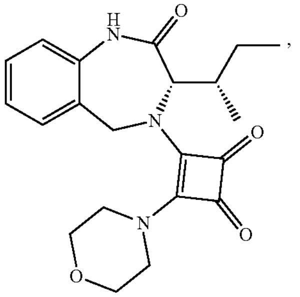
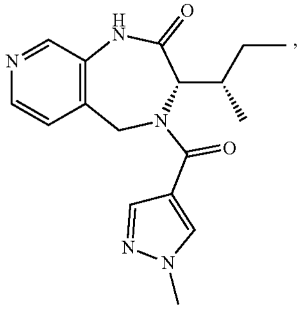
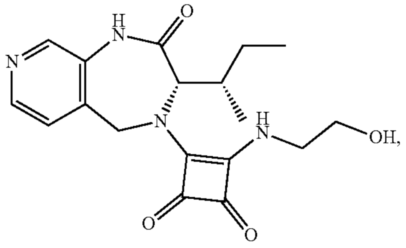
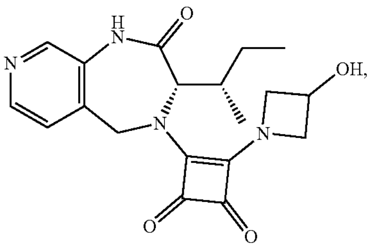
-continued
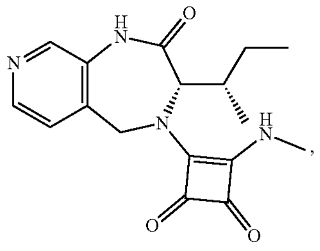
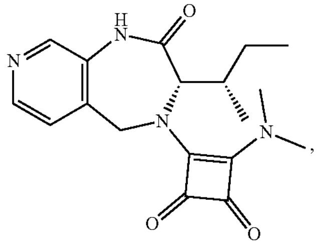
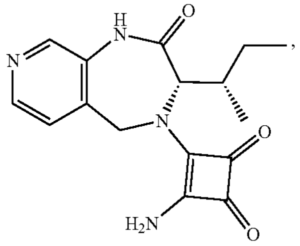
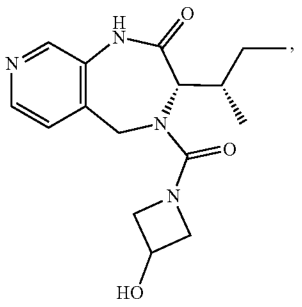
and
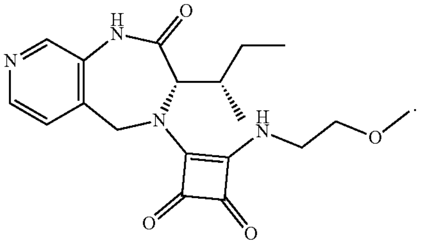
* * * * *